US012735490B2

(12) United States Patent
Simons et al.

(10) Patent No.: US 12,735,490 B2
(45) Date of Patent: Sep. 15, 2026

(54) HUMANIZED ANTI-HUMAN CD89 ANTIBODIES AND USES THEREOF

(71) Applicant: JJP Biologics SP. Z O.O., Warsaw (PL)

(72) Inventors: Petrus Johannes Simons, Hillegom (NL); Marcel Theodorus Den Hartog, Monnickendam (NL); Louis Boon, Badhoevedorp (NL)

(73) Assignee: JJP Biologics SP. Z O.O., Warsaw (PL)

( * ) Notice: Subject to any disclaimer, the term of this patent is extended or adjusted under 35 U.S.C. 154(b) by 752 days.

(21) Appl. No.: 17/996,465

(22) PCT Filed: Apr. 21, 2021

(86) PCT No.: PCT/NL2021/050259

§ 371 (c)(1),
(2) Date: Oct. 18, 2022

(87) PCT Pub. No.: WO2021/215919

PCT Pub. Date: Oct. 28, 2021

(65) Prior Publication Data

US 2023/0242646 A1 Aug. 3, 2023

(30) Foreign Application Priority Data

Apr. 21, 2020 (EP) .................................... 20170723

(51) Int. Cl.

| | |
|---|---|
| ***C07K 16/28*** | (2006.01) |
| ***A61K 39/00*** | (2006.01) |
| ***A61P 17/00*** | (2006.01) |
| ***A61P 37/06*** | (2006.01) |

(52) U.S. Cl.

CPC ............ *C07K 16/283* (2013.01); *A61P 17/00* (2018.01); *A61P 37/06* (2018.01); *A61K 2039/505* (2013.01); *C07K 2317/24* (2013.01); *C07K 2317/33* (2013.01); *C07K 2317/73* (2013.01); *C07K 2317/76* (2013.01); *C07K 2317/92* (2013.01)

(58) Field of Classification Search

None

See application file for complete search history.

(56) References Cited

U.S. PATENT DOCUMENTS 12,195,539 B2 * 1/2025 Simons ................ A61K 39/395

FOREIGN PATENT DOCUMENTS

| | | | |
|---|---|---|---|
| JP | 2005-507635 | A | 3/2005 |
| JP | 2008-056647 | A | 3/2008 |
| WO | 9823646 | A2 | 6/1998 |
| WO | 2009144279 | A1 | 12/2009 |
| WO | 2020084056 | A1 | 4/2020 |

OTHER PUBLICATIONS

Brown et al. Tolerance of single, but not multiple, amino acid replacements in antibody VH CDR 2: a means of minimizing B cell wastage from somatic hypermutation? J. Immuno. May 1996, 3285-91. (Year: 1996).*

Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*

Rabia et al. Understanding and overcoming trade-offs between antibody affinity, specificity, stability and solubility. Biochem Eng J. Sep. 15, 2018; 137: 365-374 (Year: 2018).*

Chae et al. Improvement of Biophysical Properties and Affinity of a Human Anti-L1CAM Therapeutic Antibody through Antibody Engineering Based on Computational Methods. Int. J. Mol. Sci. 2021, 22(13), 6696 (Year: 2021).*

Van Delft et al. Antagonizing FcαR1 (CD89) as treatment in IgA-mediated chronic inflammation and autoimmunity. Front Immunol. Apr. 4, 2023;14:1118539. (Year: 2023).*

Almagro et al. Humanization of antibodies, Frontiers in Bioscience Jan. 1, 2008, vol. 13pp.1619-1633, doi: 10.2741/2786.

Zhang et al.: "Neutrophil lactoferrin release induced by IgA immune . . . "Clinical and Experimental Immunology, Wileyblackwell Publishing Ltd, GB, vol. 121, No. 1, Jul. 1, 2000. XP009129865.

Shen L, "A Monoclonal Antibody Specific for Immunoglobulin a Receptor Triggers Polymorphonuclear Neutrophil Superoxide Release", Journal of Leukocyte Biology, Apr. 1, 1992 John Wiley & Sons Ltd, GB—ISSN 0741-5400, vol. 51, Nr:4, pp. 373-378. XP002066871.

* cited by examiner

*Primary Examiner* — Maher M Haddad

(74) *Attorney, Agent, or Firm* — Banner & Witcoff, Ltd.

(57) ABSTRACT

The disclosure describes a humanized antibody that can bind an extra-cellular part of human CD89 (human FcαRI) on human CD89 expressing cells that prevents binding of human IgA to human CD89 when the antibody is bound to said cells. The disclosure also describes the use of such antibodies in combating certain diseases.

26 Claims, 73 Drawing Sheets

Specification includes a Sequence Listing.

Fig. 2
A
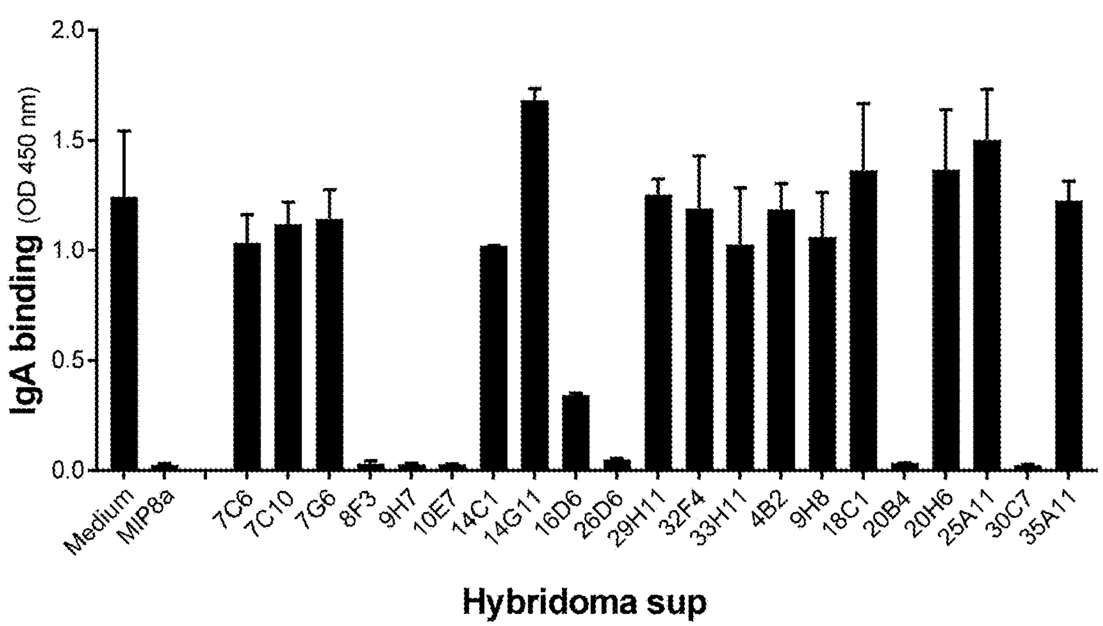
B
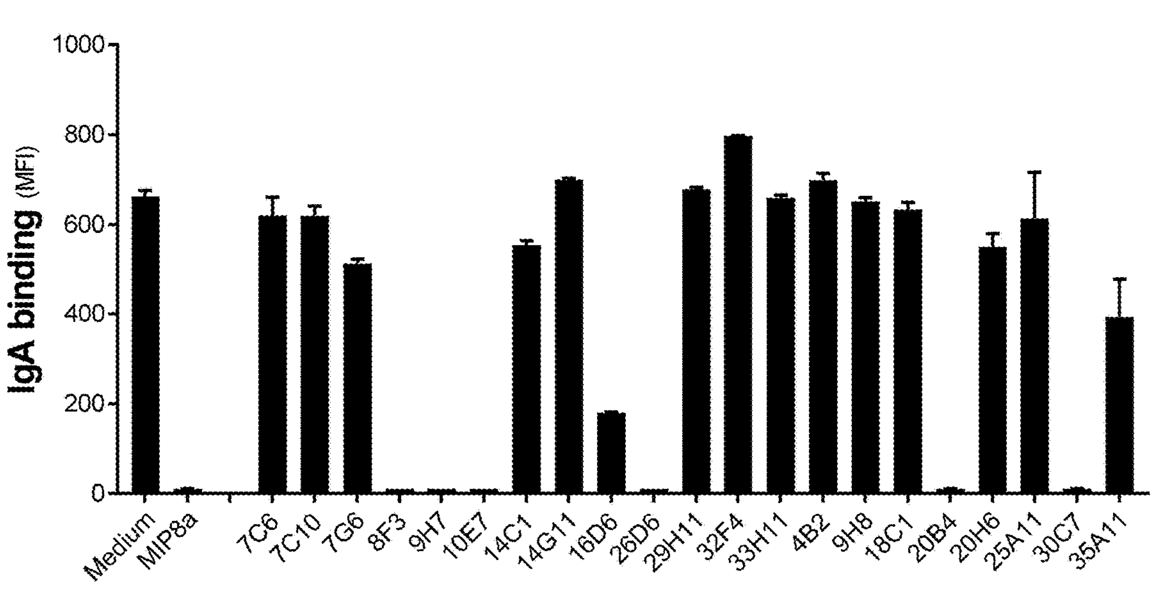

Fig. 3
A
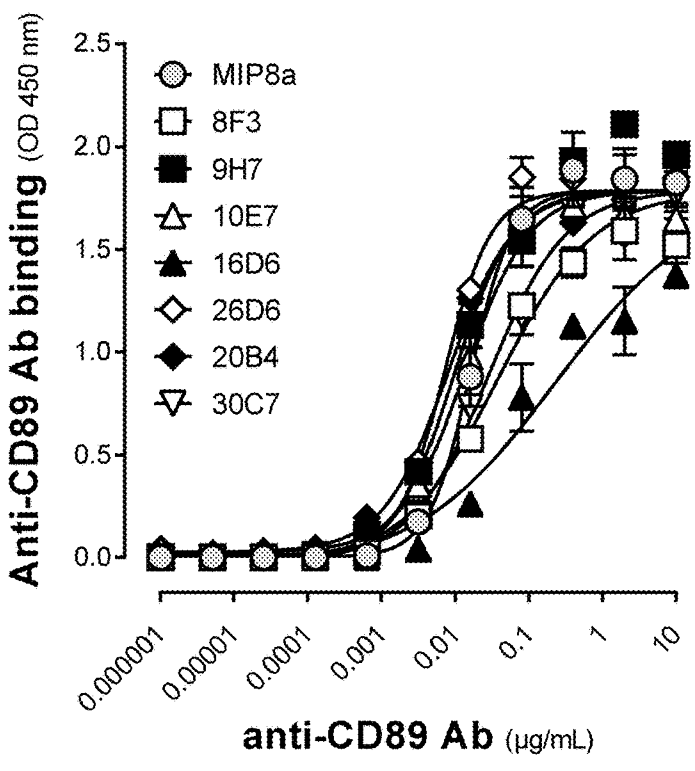
B
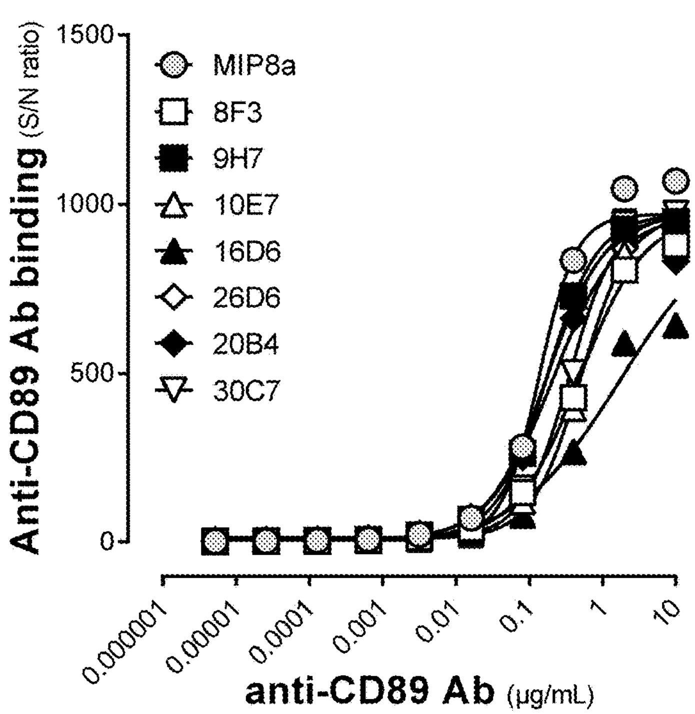

Fig. 4
A
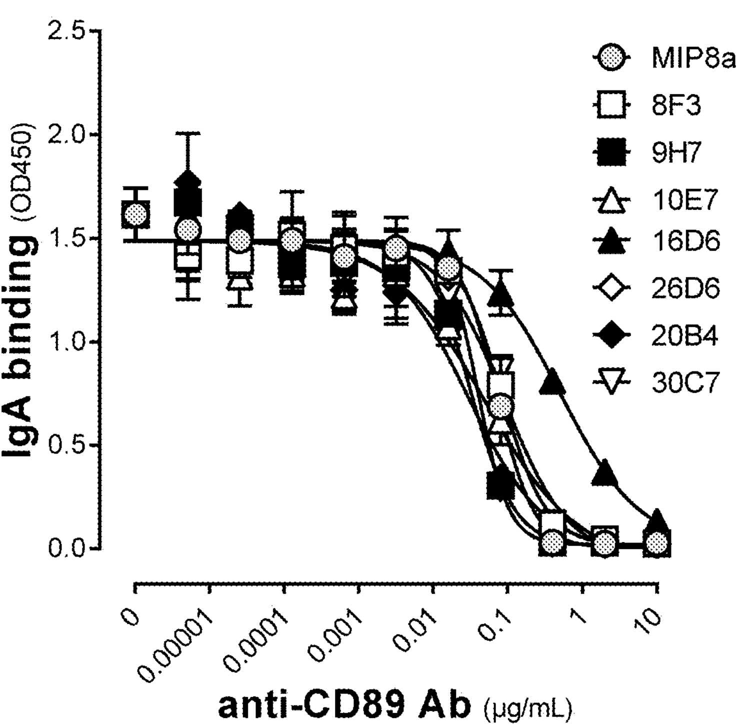
B
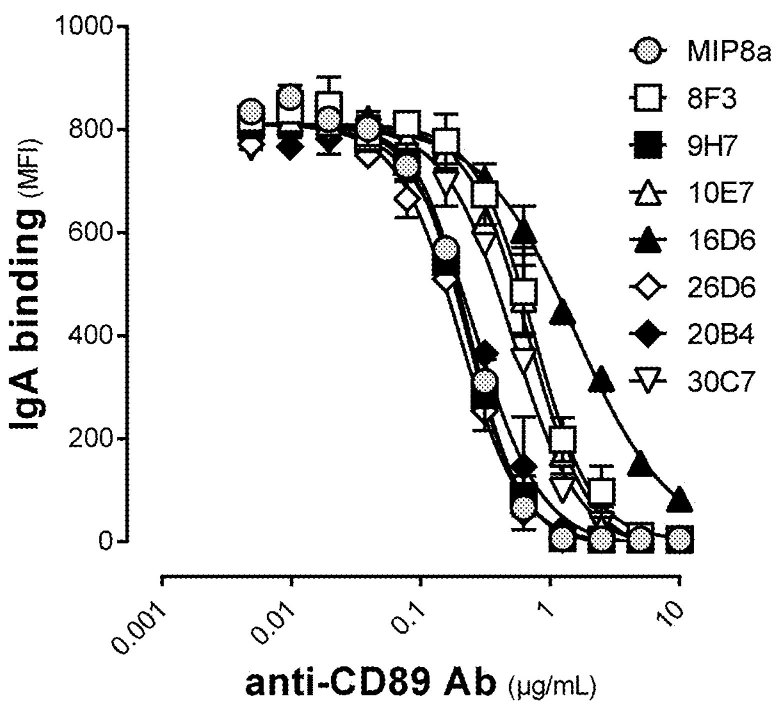

Fig. 5E
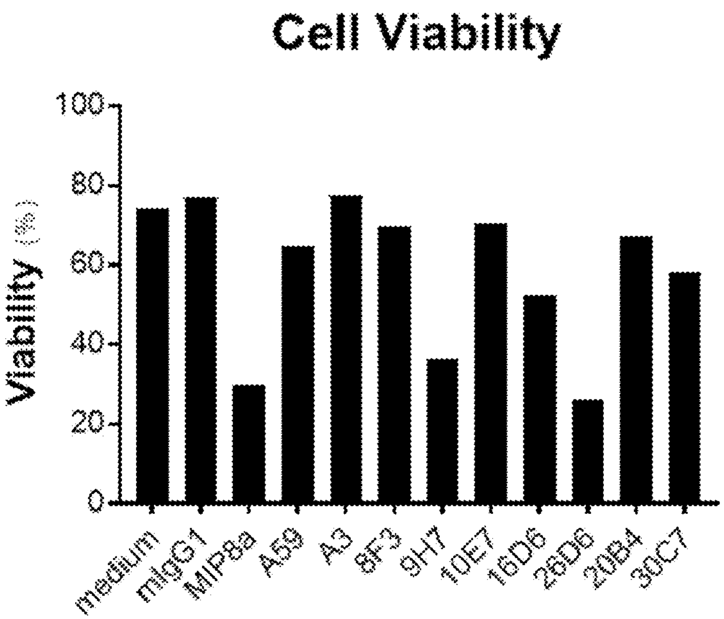
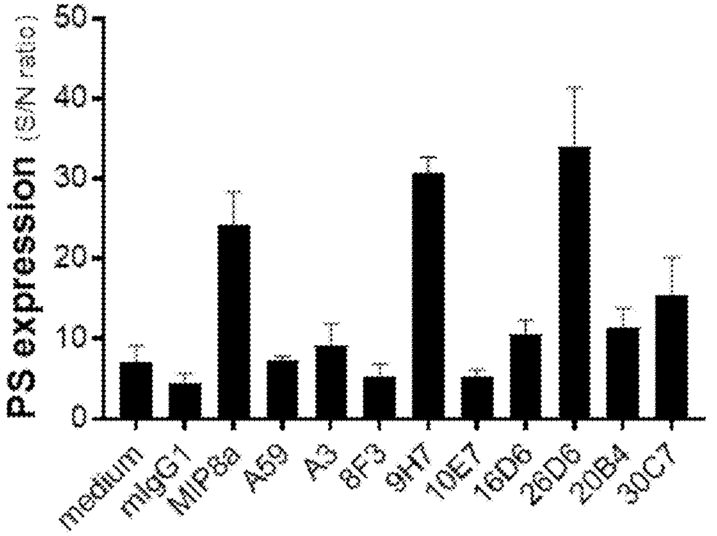

Fig. 6
A
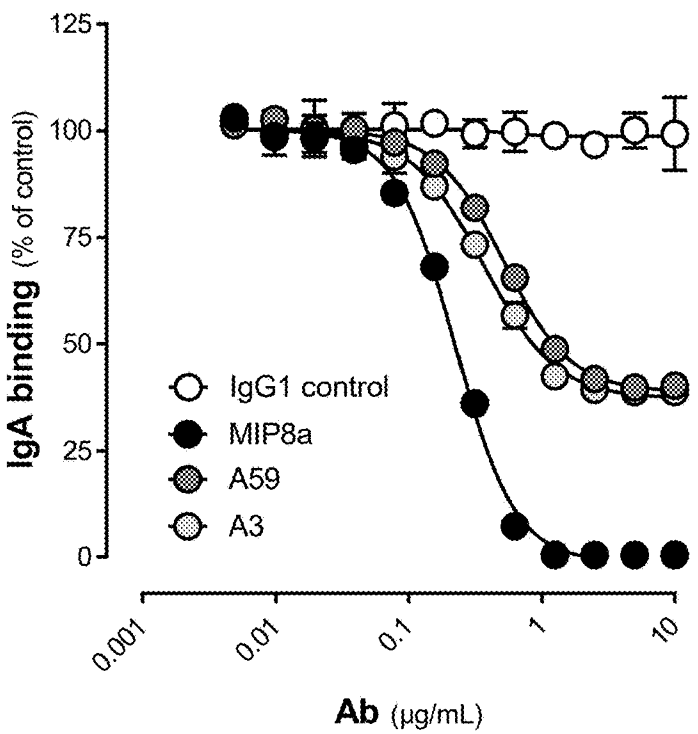
B
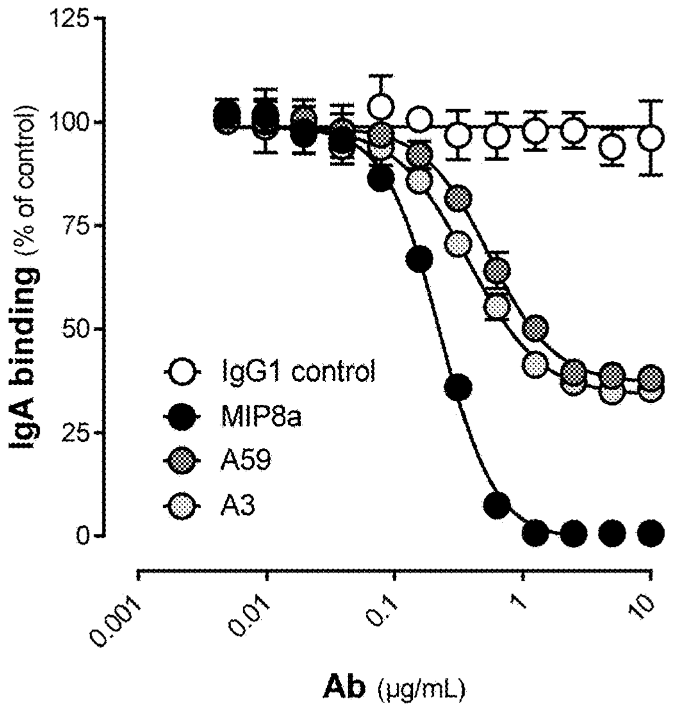

Fig. 7
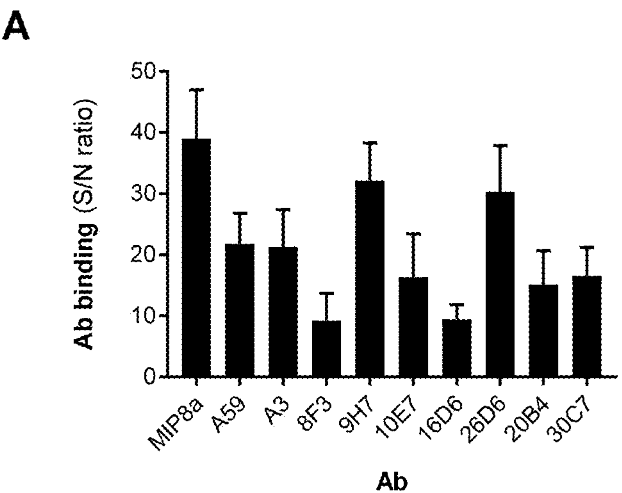
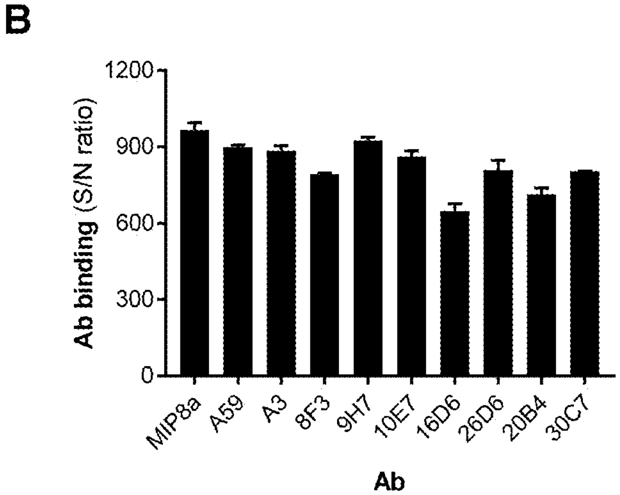
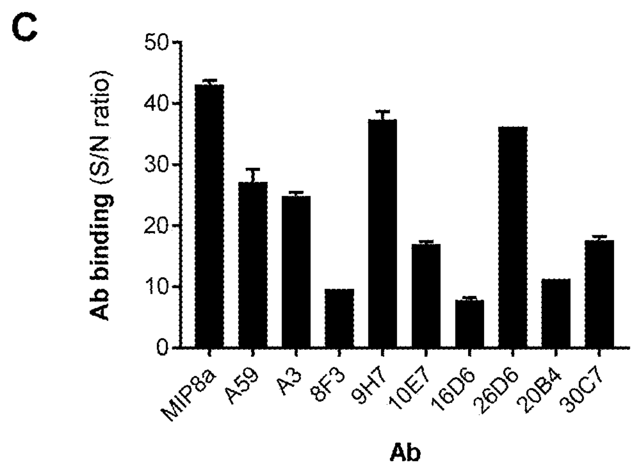

Fig. 8A (Donor 1)
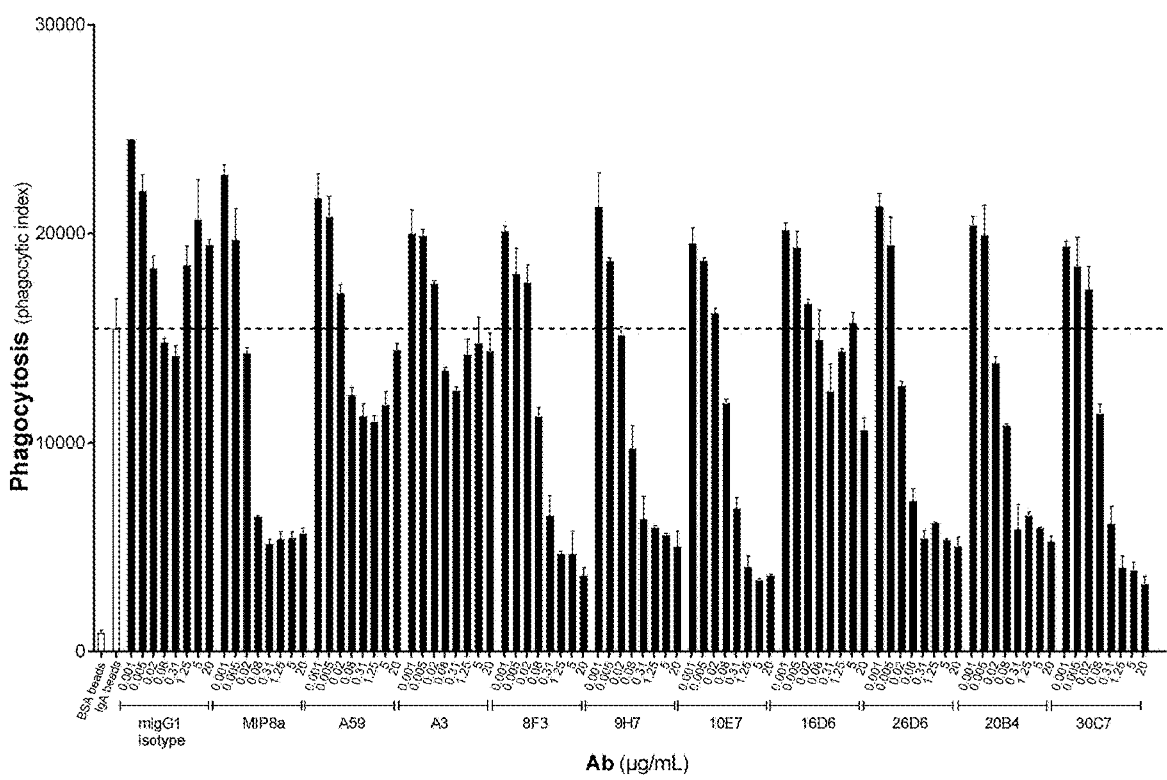

Fig. 8B (Donor 2)
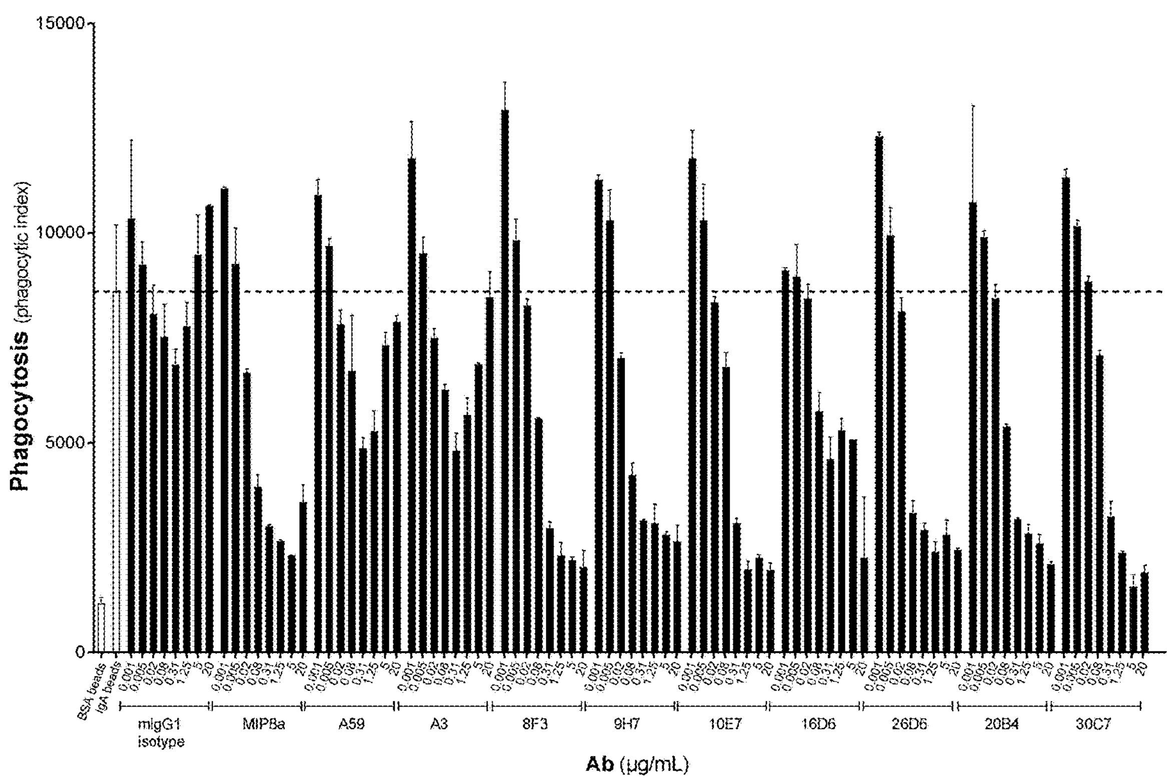

Fig. 8C (Donor 3)
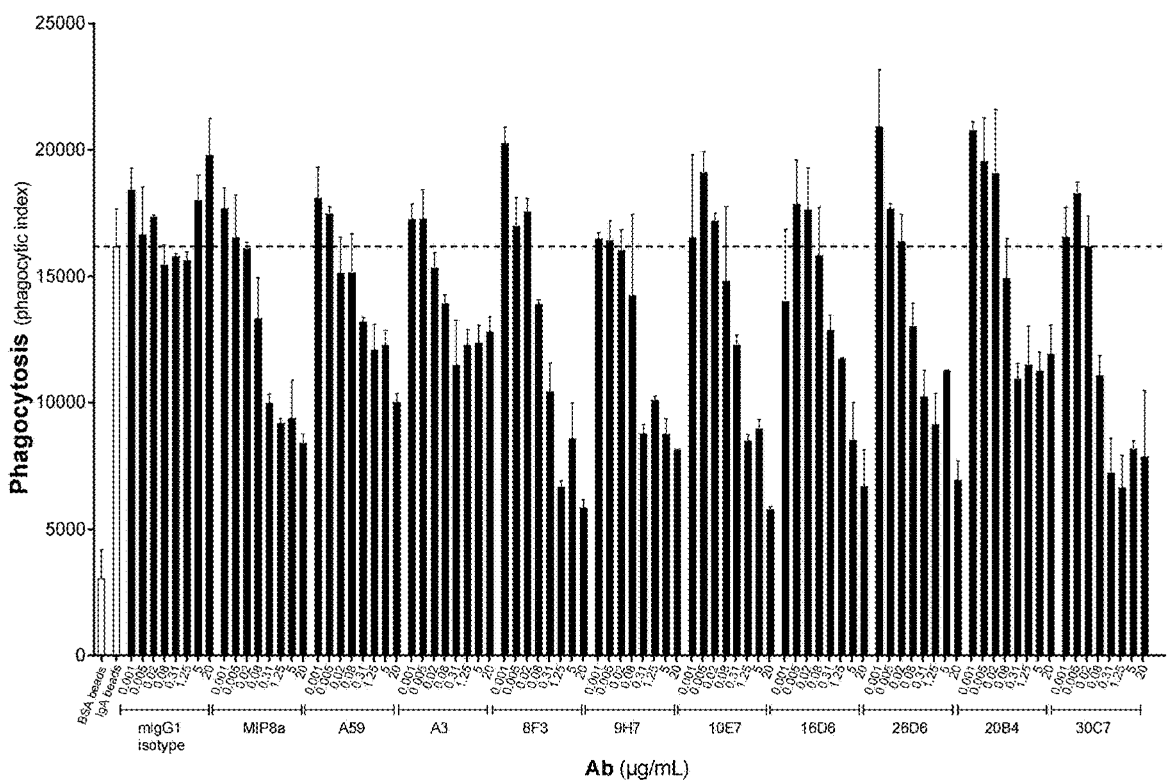

Fig. 9A (Donor 1)
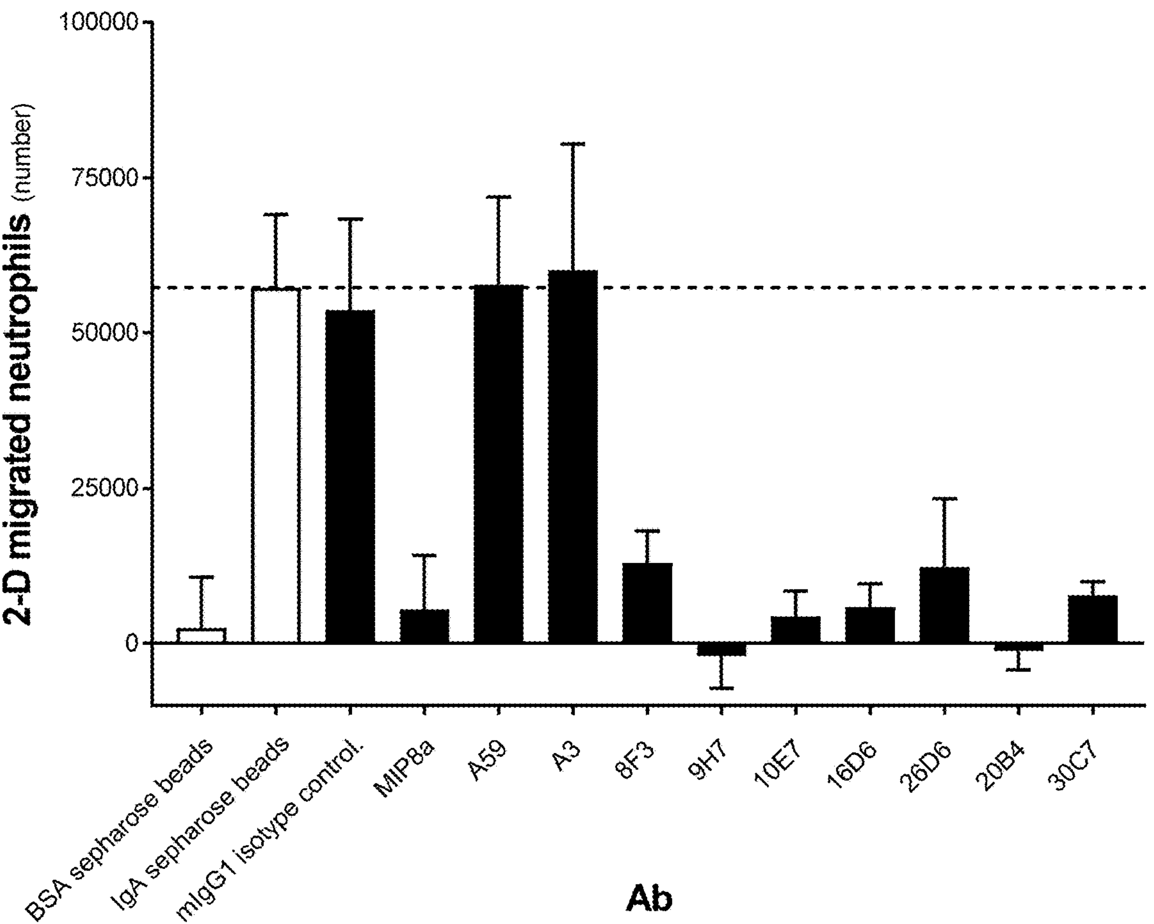

Fig. 9B (Donor 2)
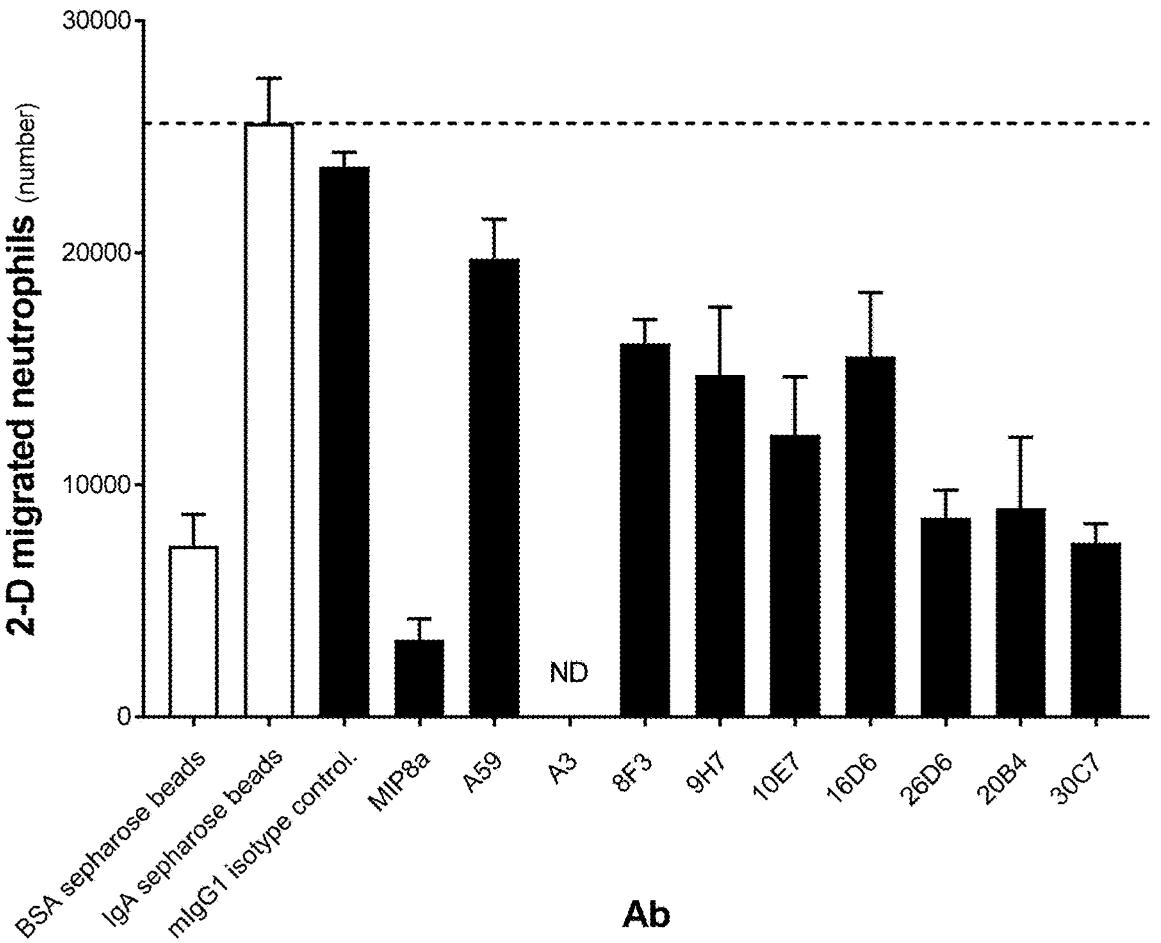

Fig. 9C (Donor 3)
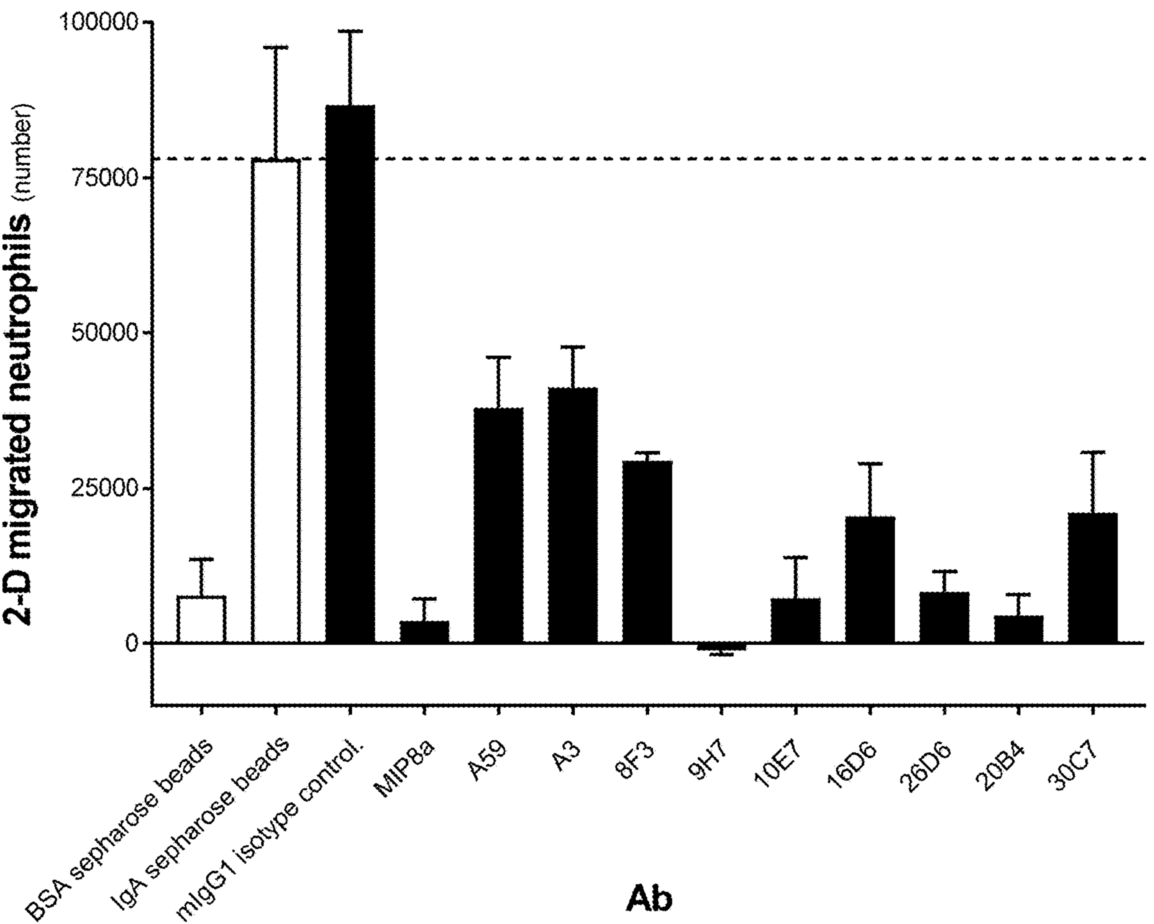

Fig. 9D (Donor 1)
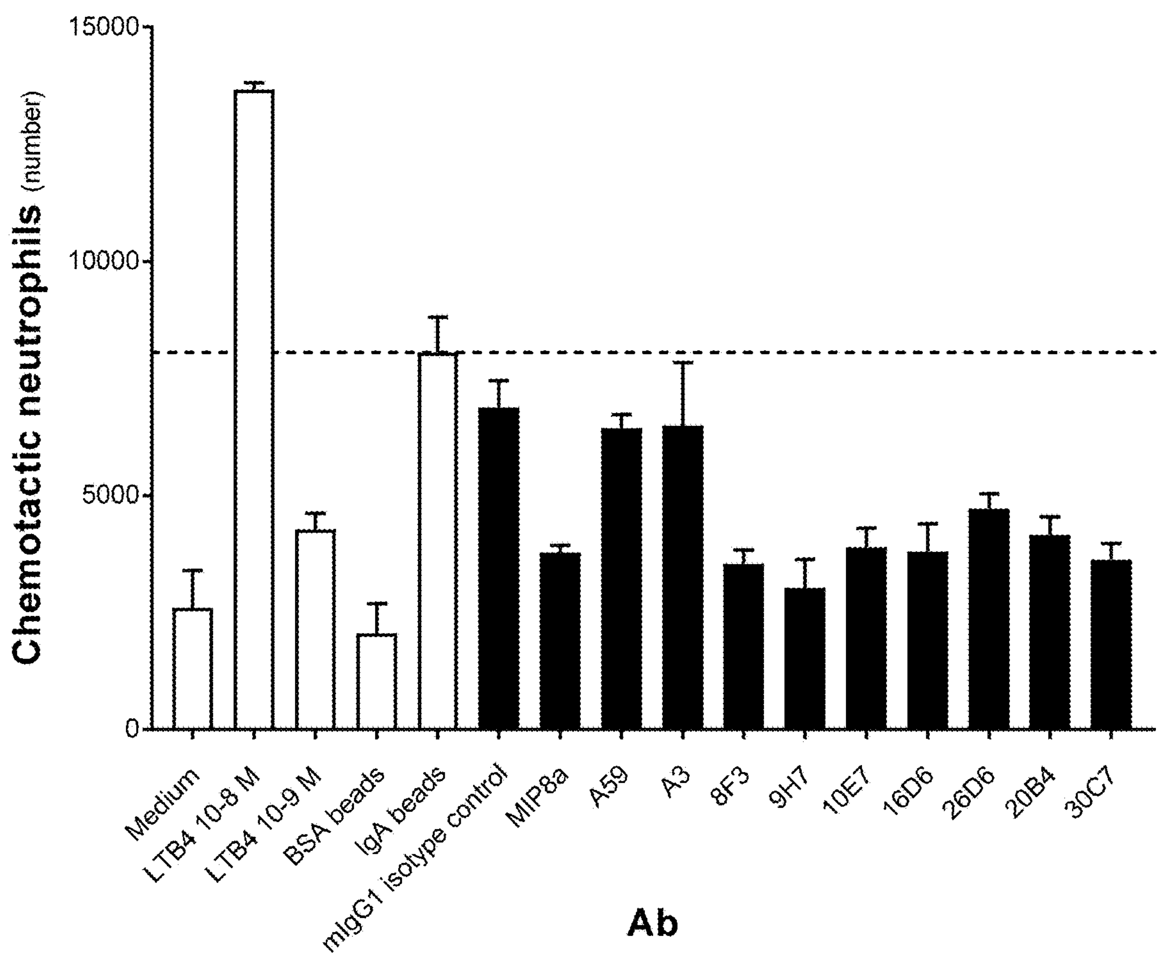

Fig. 9E (Donor 2)
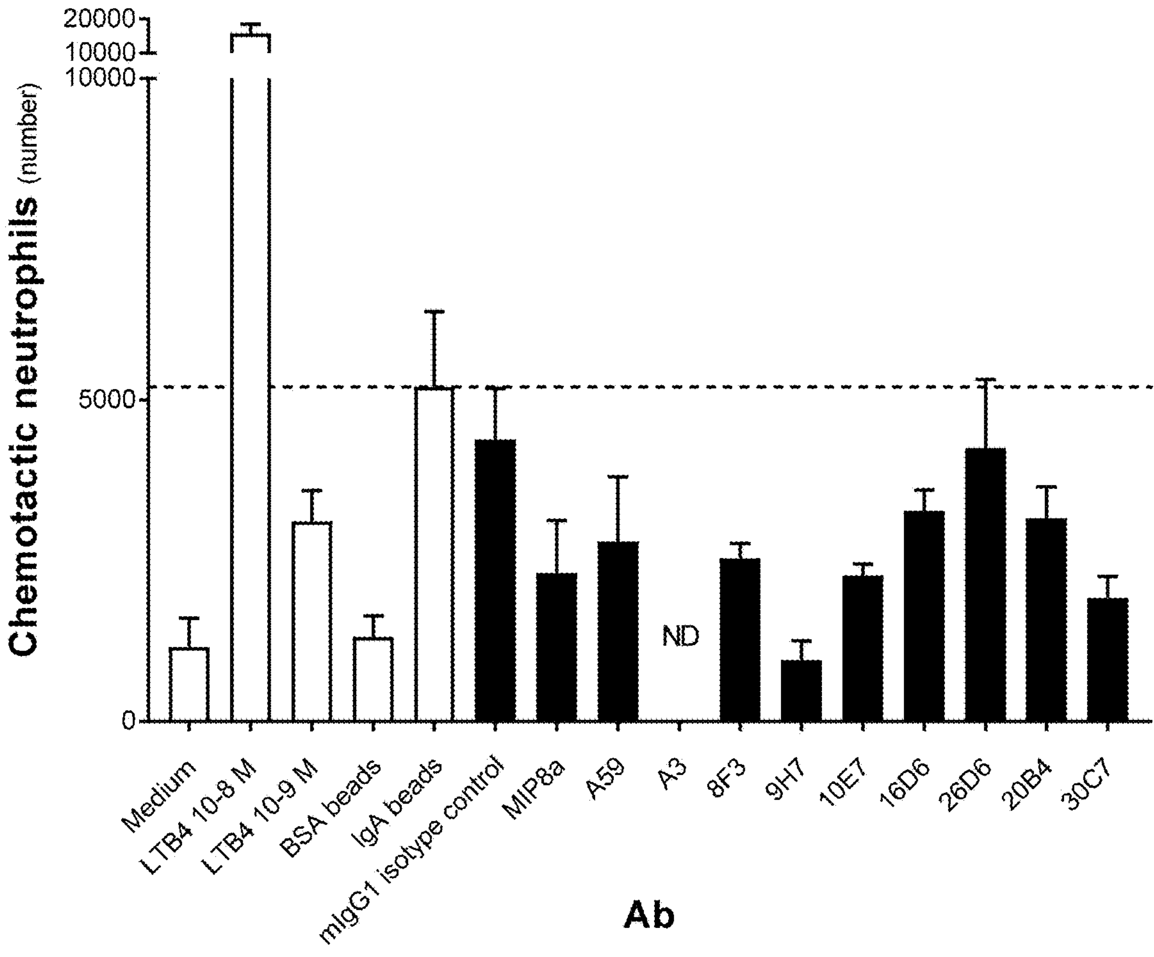

Fig. 9F (Donor 3)
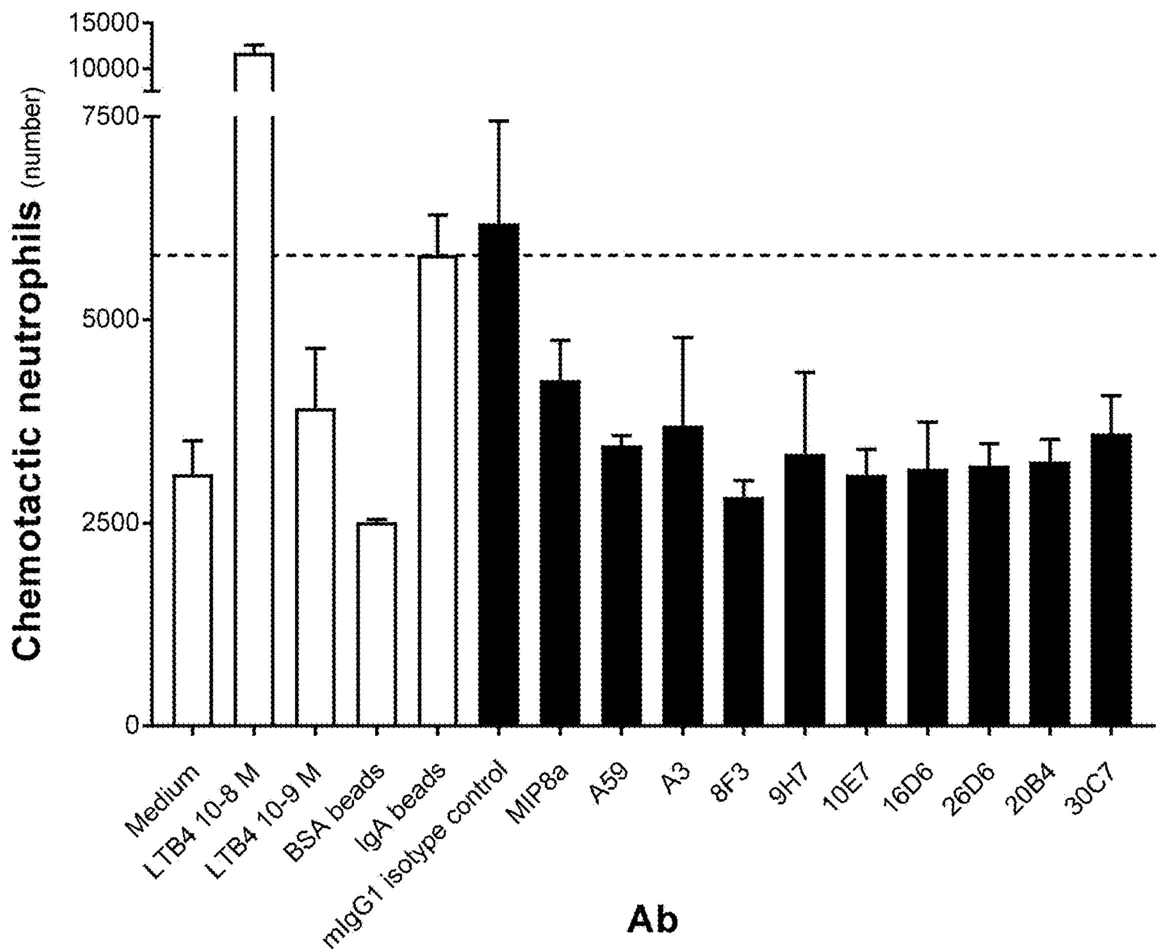

Fig. 9G (Donor 1)
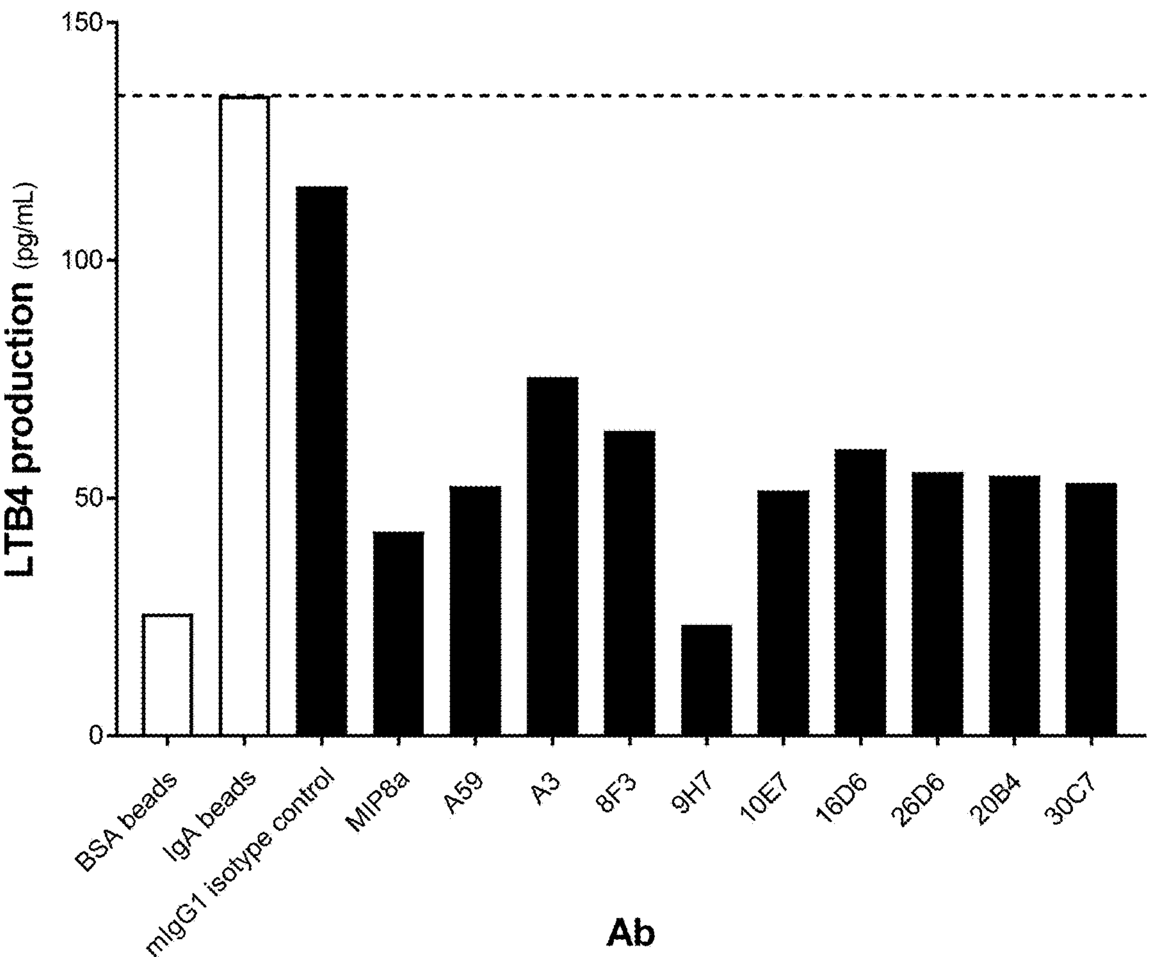

Fig. 9H (Donor 2)
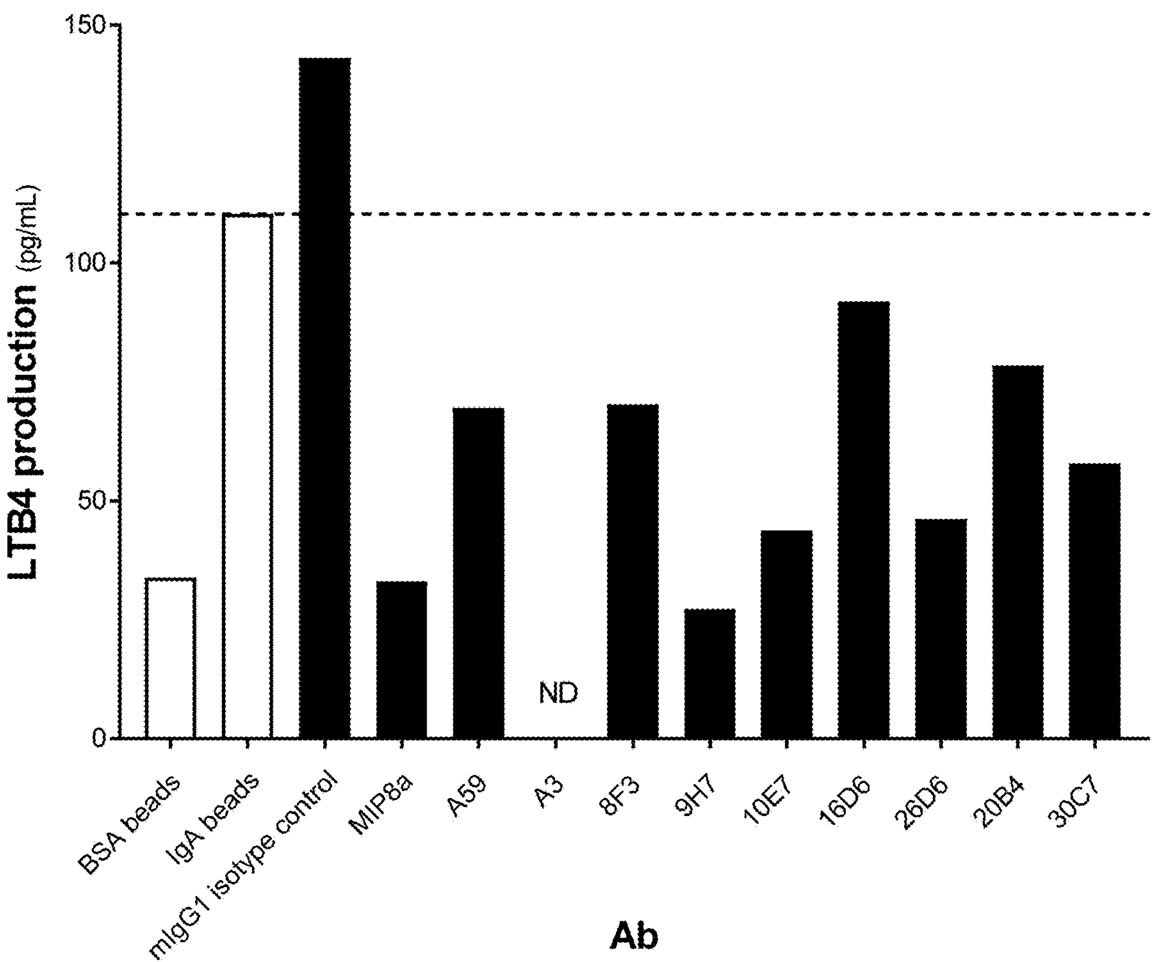

Fig. 9I (Donor 3)
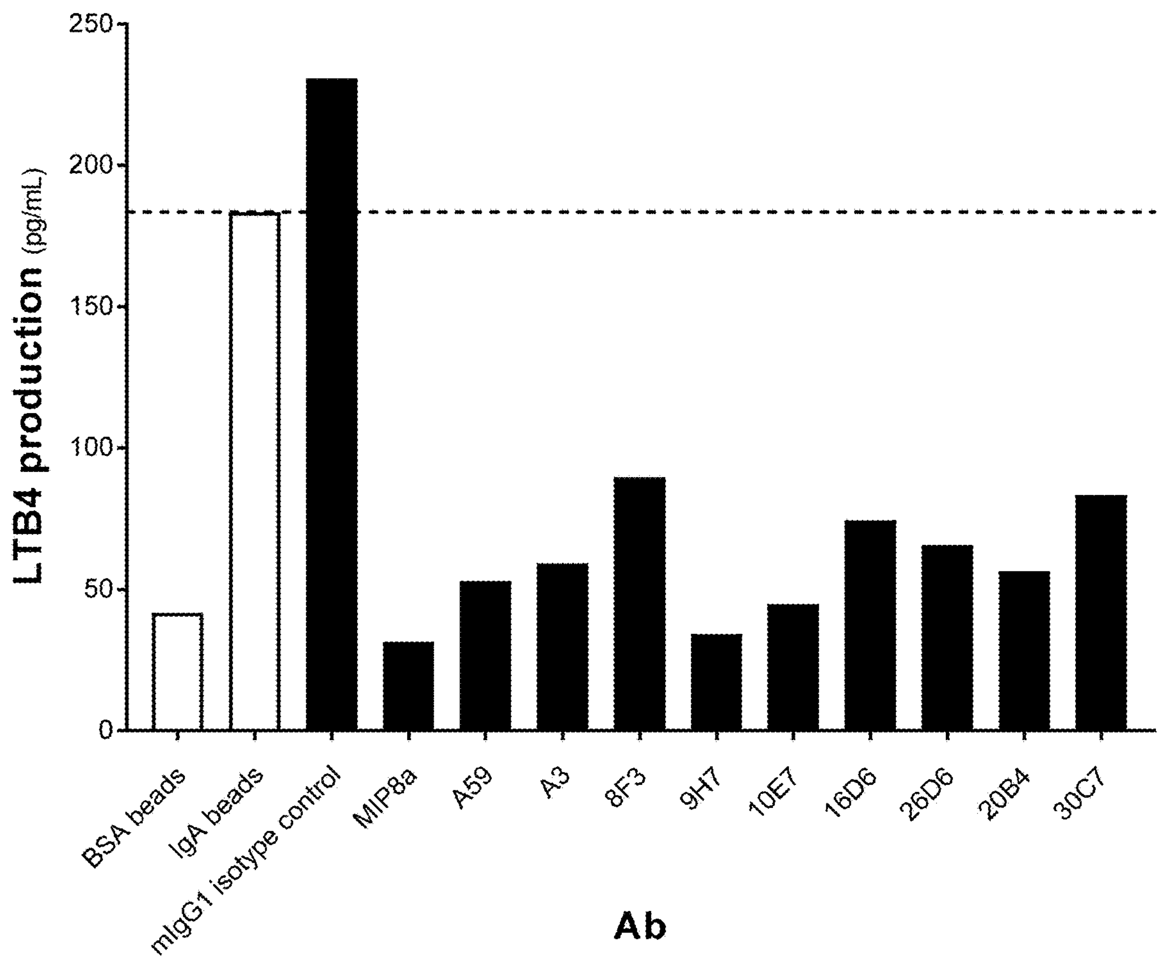

Fig. 10A (Donor 1)
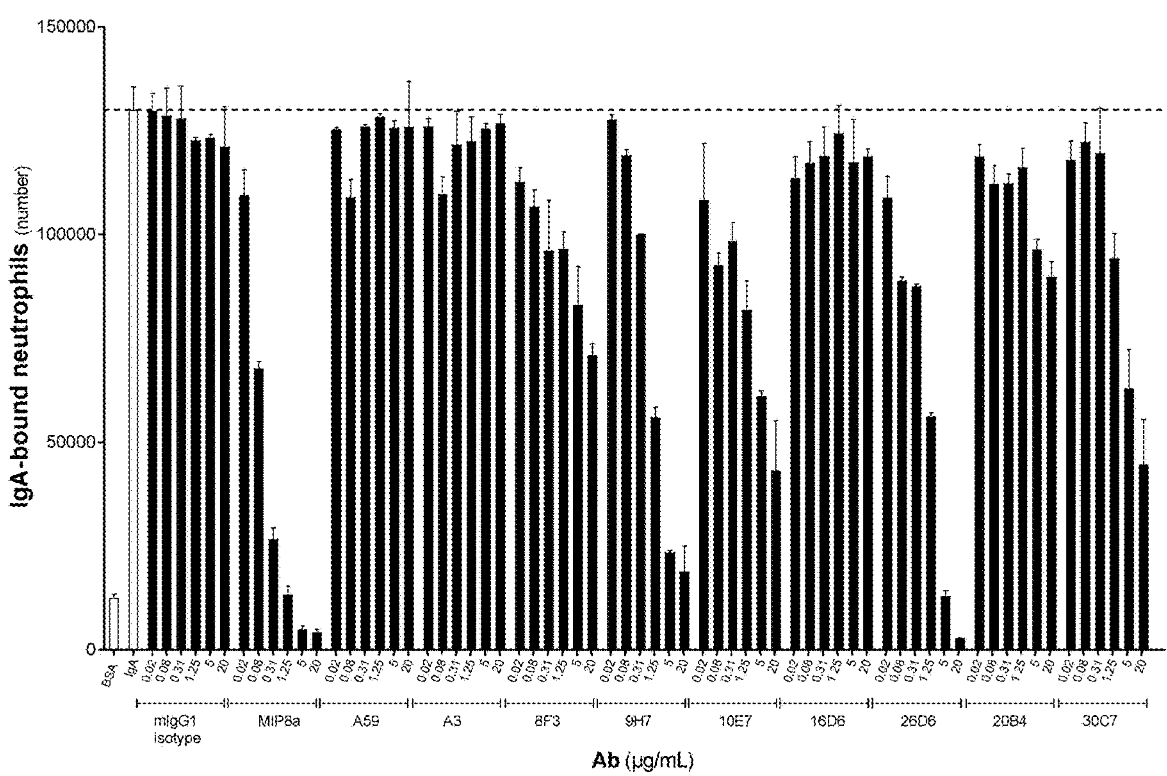

Fig. 10B (Donor 2)
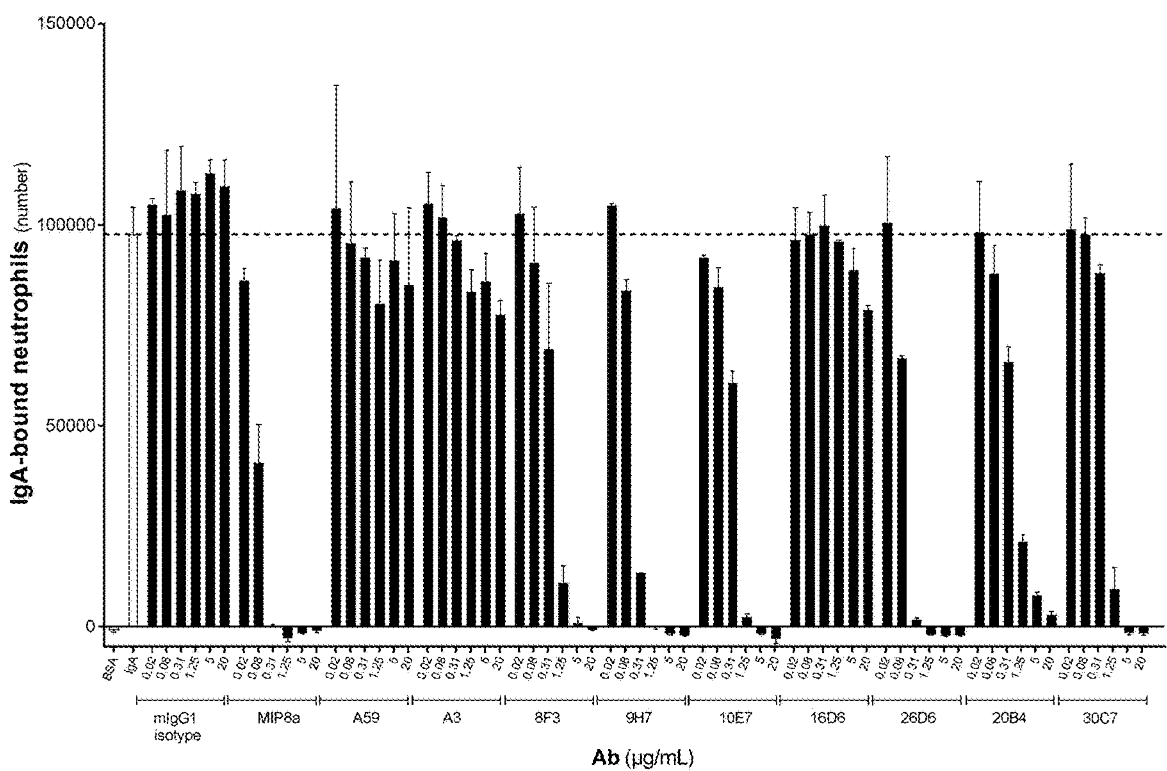

Fig. 10C (Donor 3)
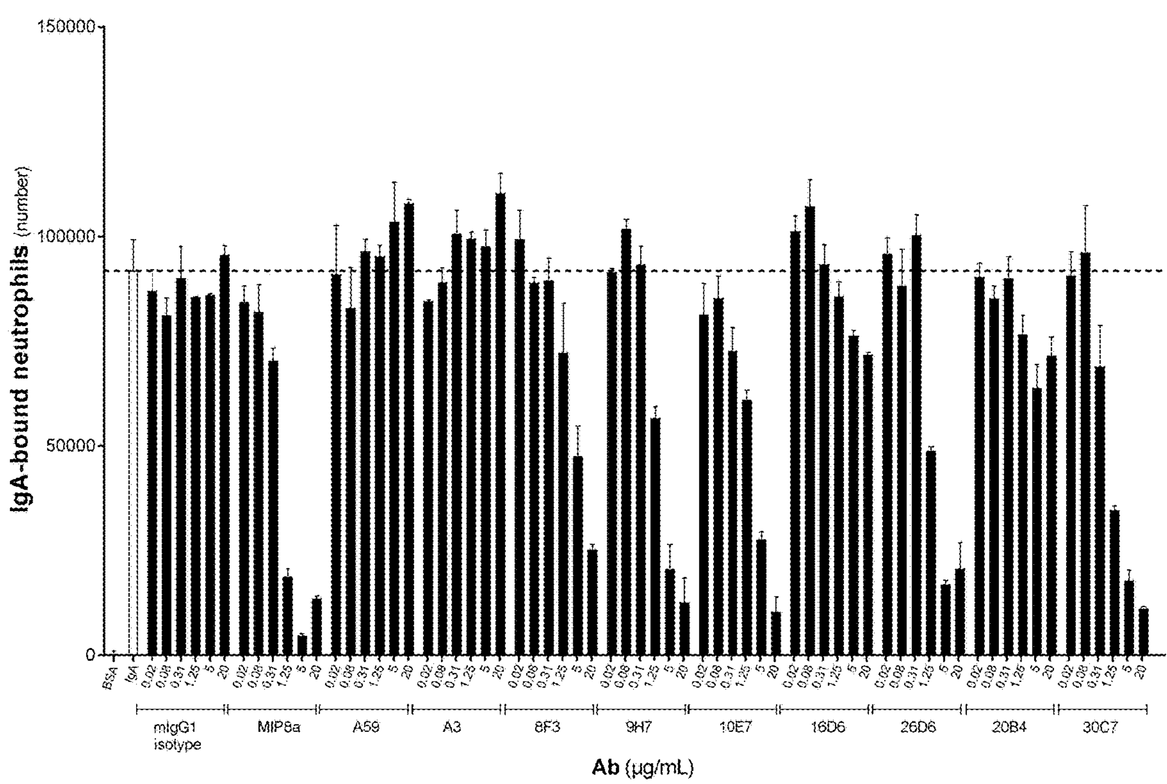

Fig. 10D (Donor 1)
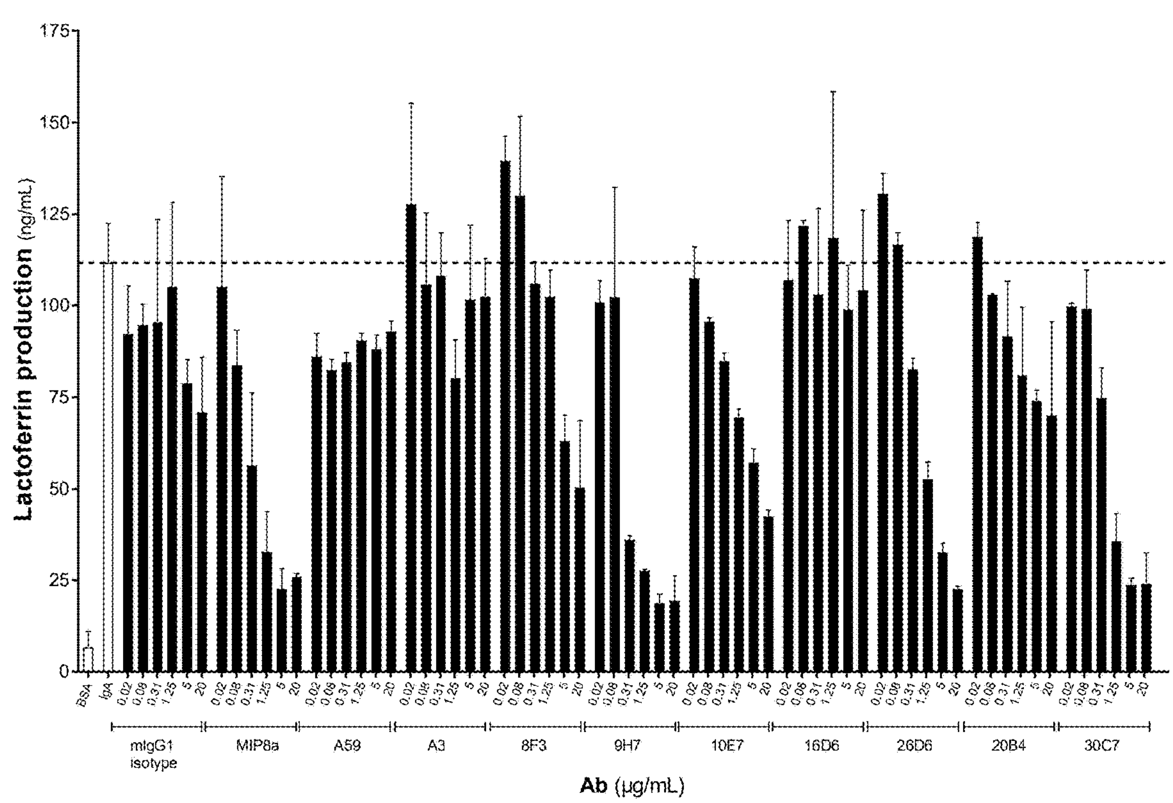

Fig. 10E (Donor 2)
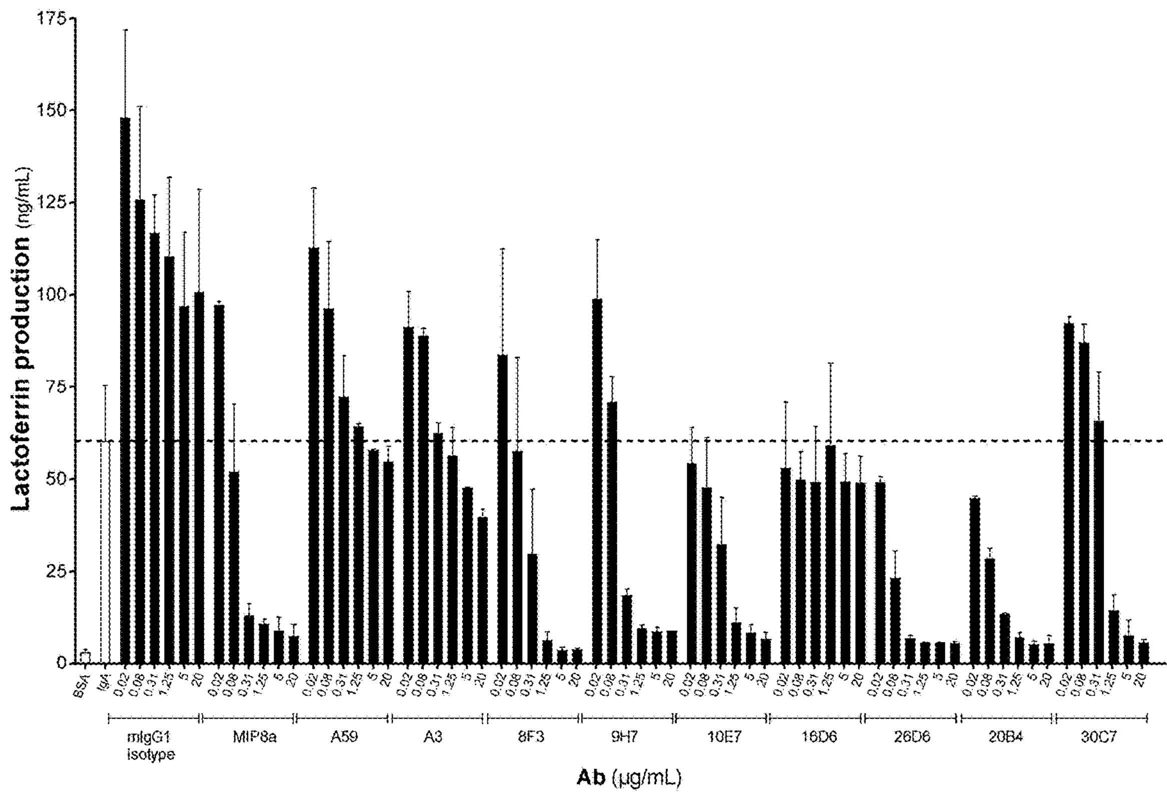

Fig. 10F (Donor 3)
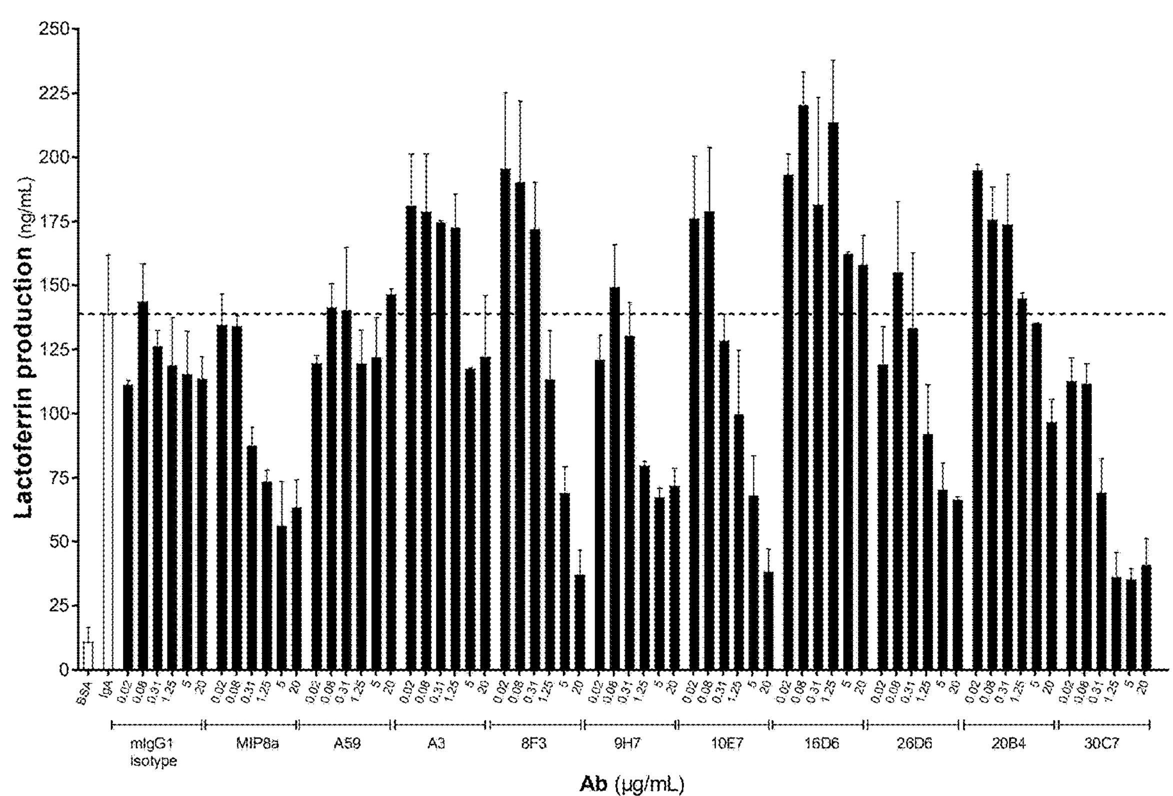

Fig. 11
A
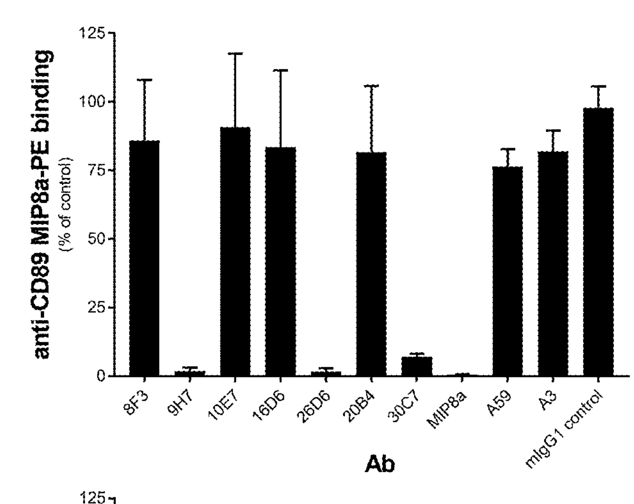
B
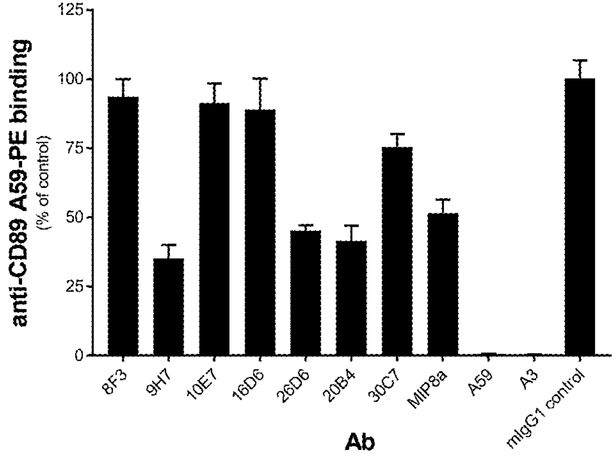
C
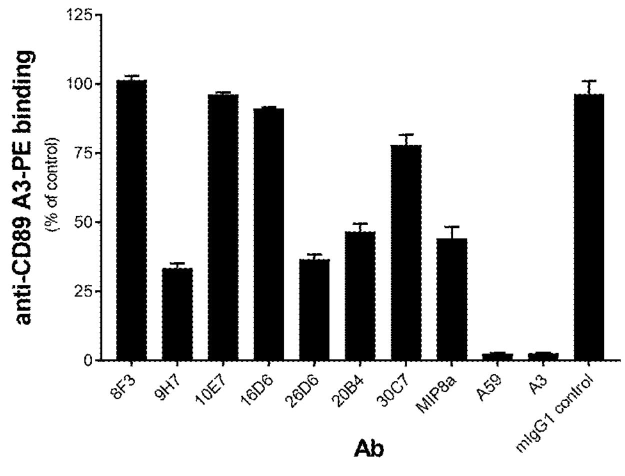

Fig. 12
A
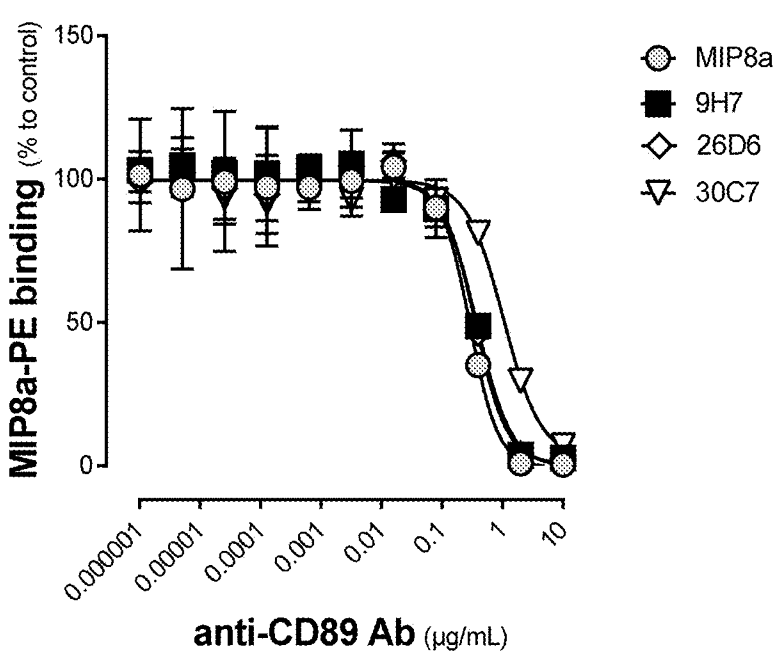
B
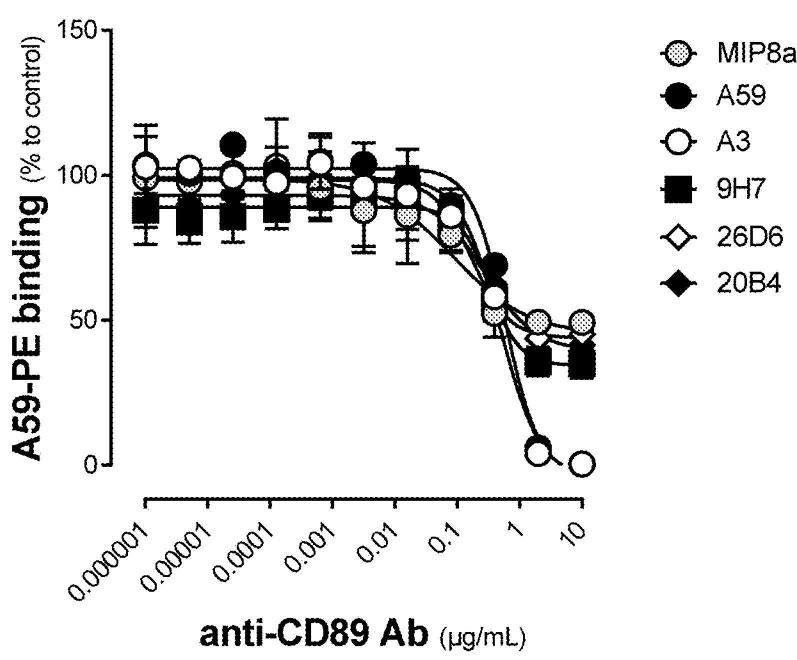

Mock

EC1 EC2

Ab binding (S/N ratio)

1000 100 10 1 0.1

MIP8a A59 A3 8F3 9H7 10E7 16D6 26D6 20B4 30C7

Ab

Fig. 14
A
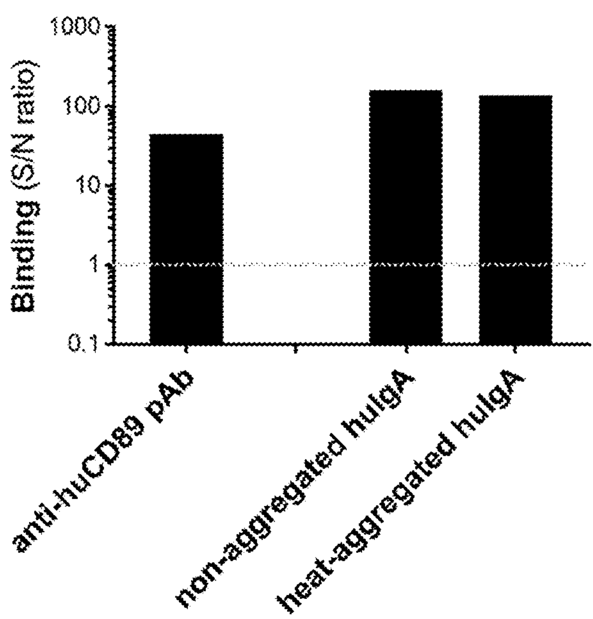
B
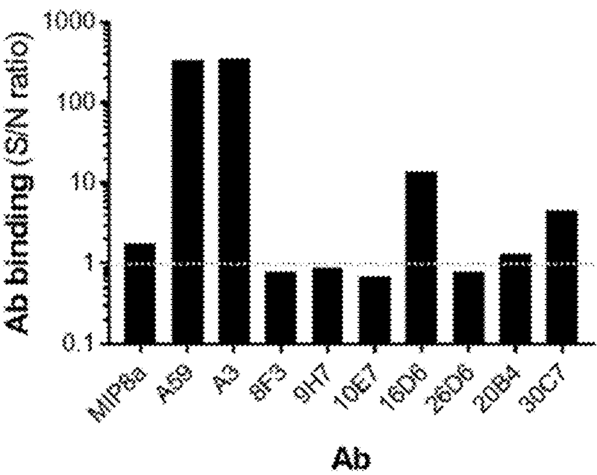

Fig. 16
A
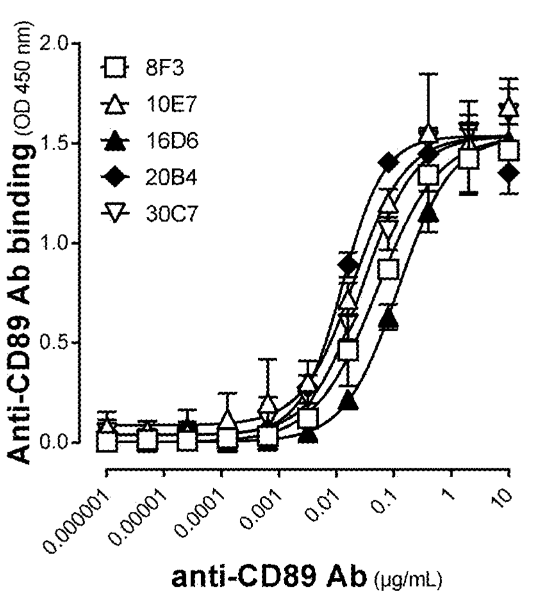
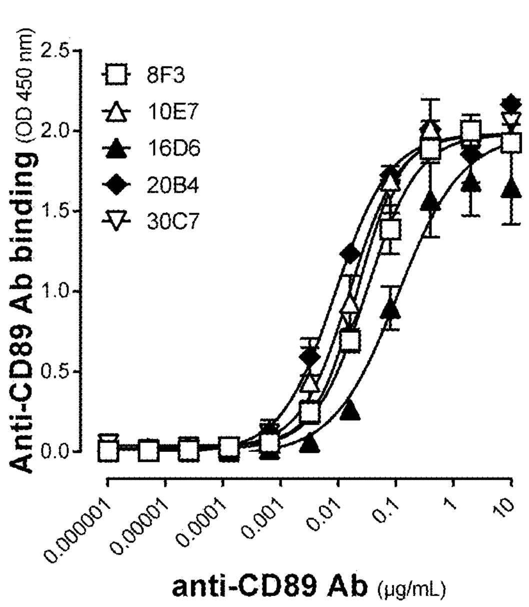
B
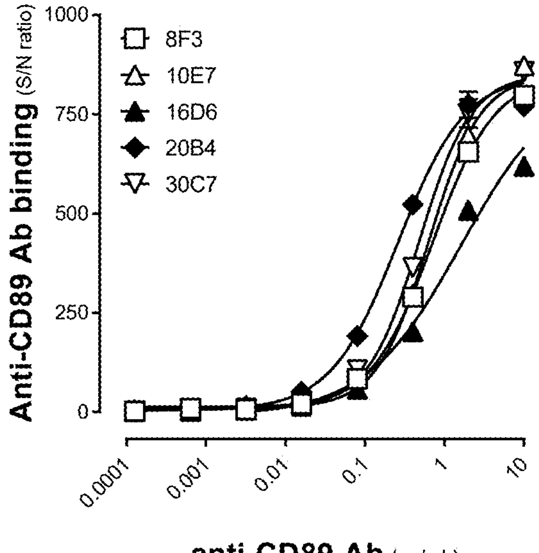
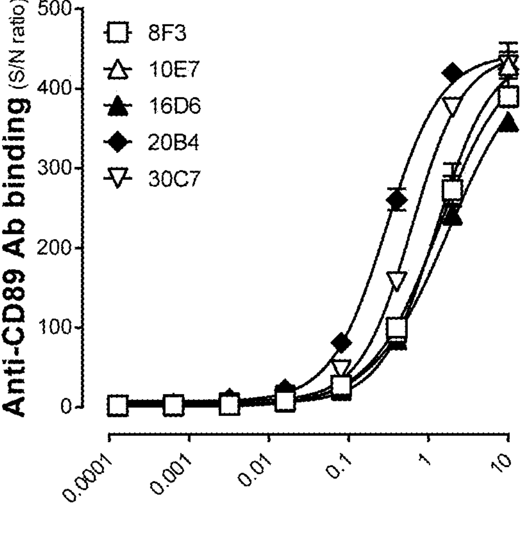

Fig. 17
A
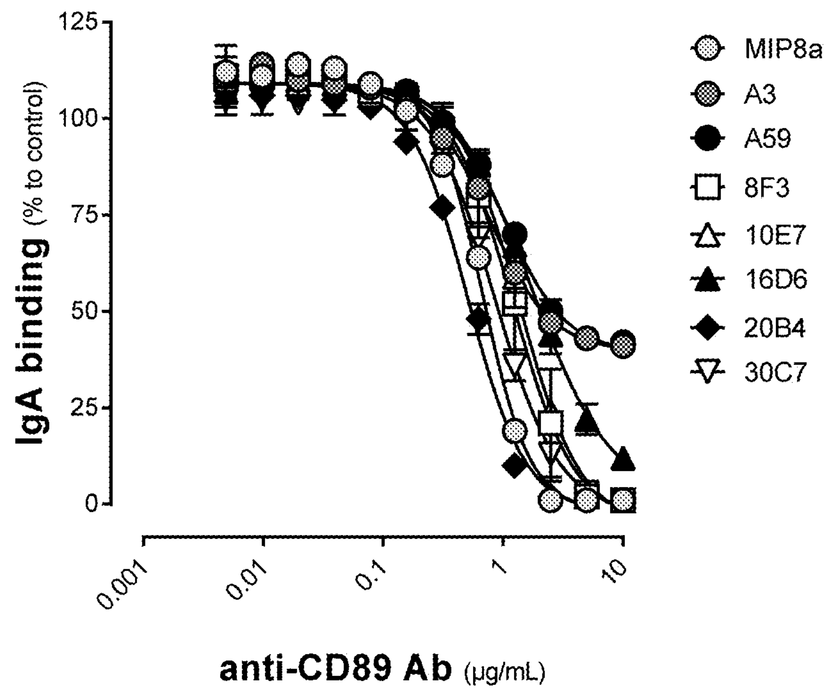
B
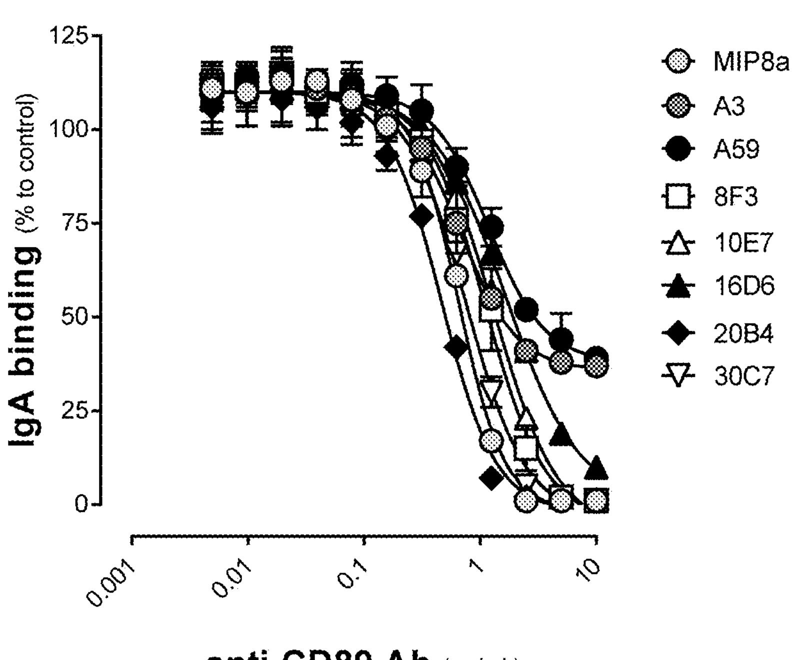

Fig. 19A (Donor 1)
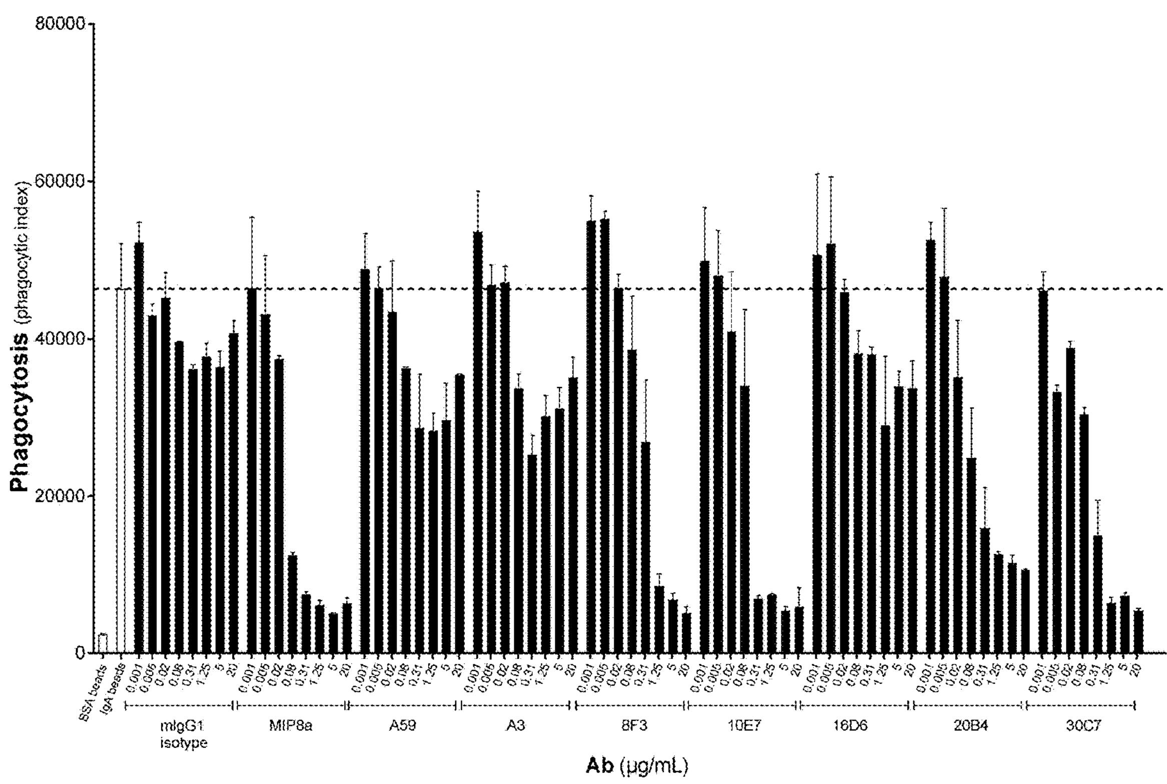

Fig. 19B (Donor 2)
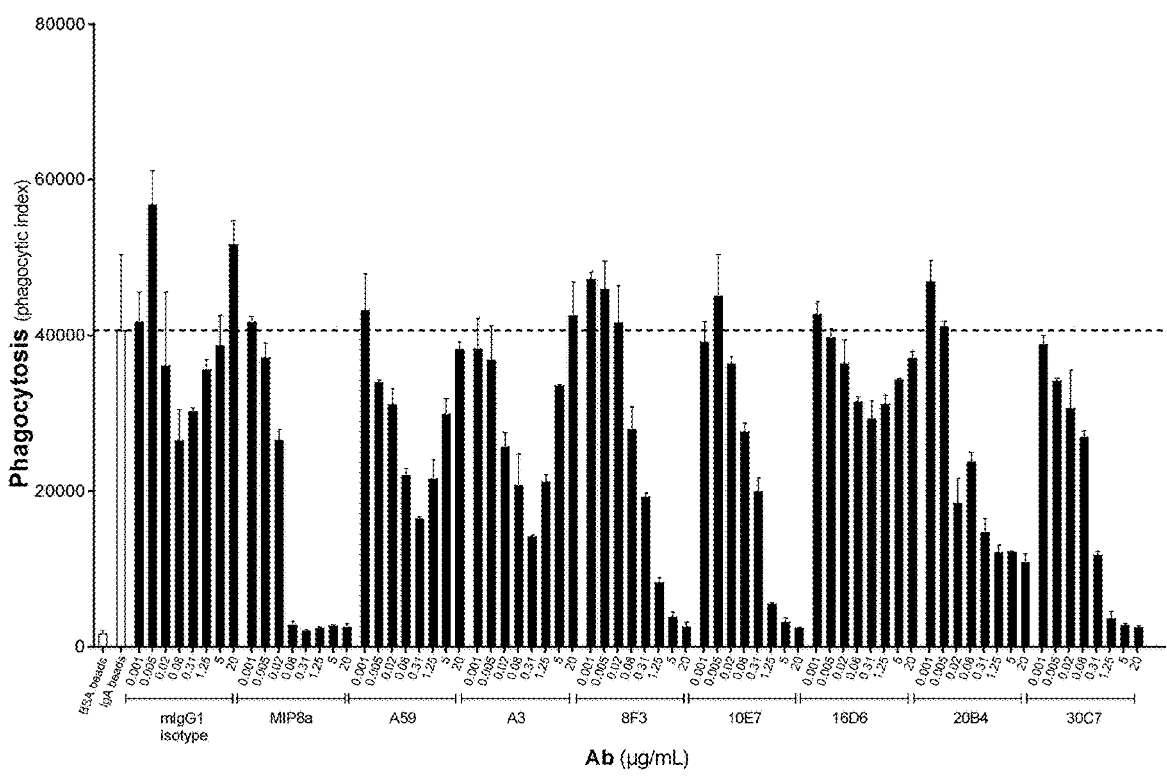

Fig. 19C (Donor 3)
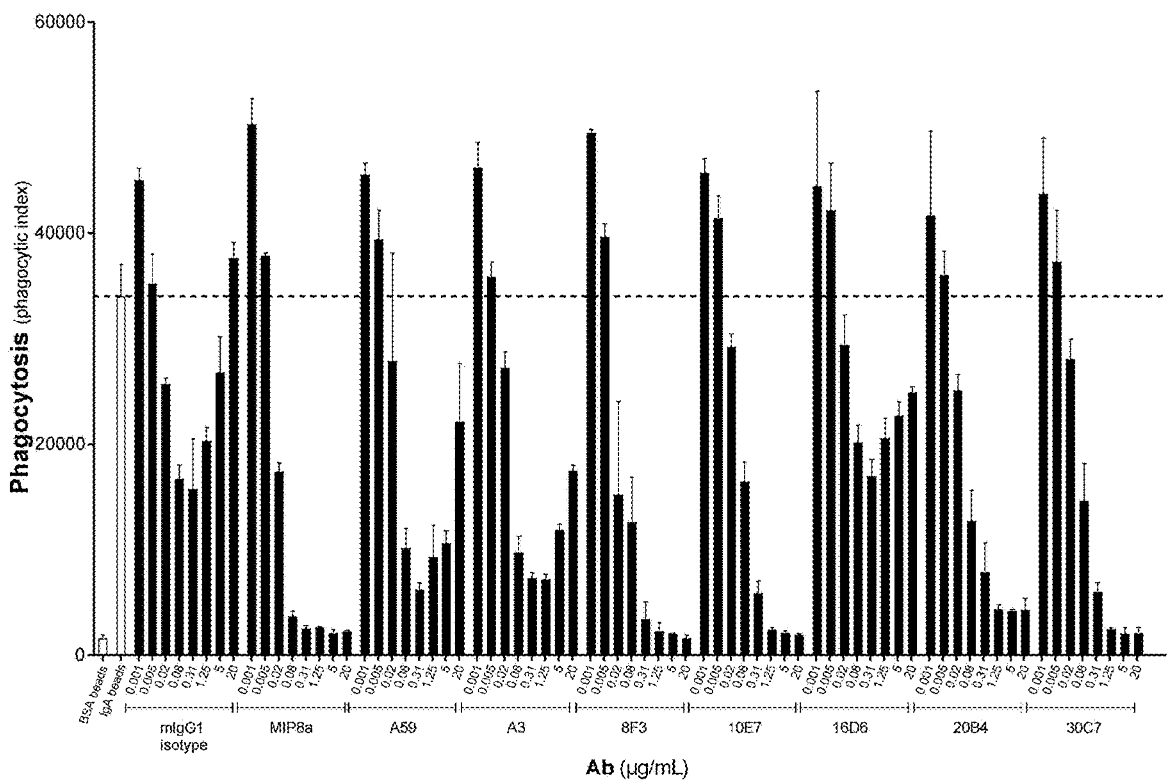

Fig. 20A (Donor 1)
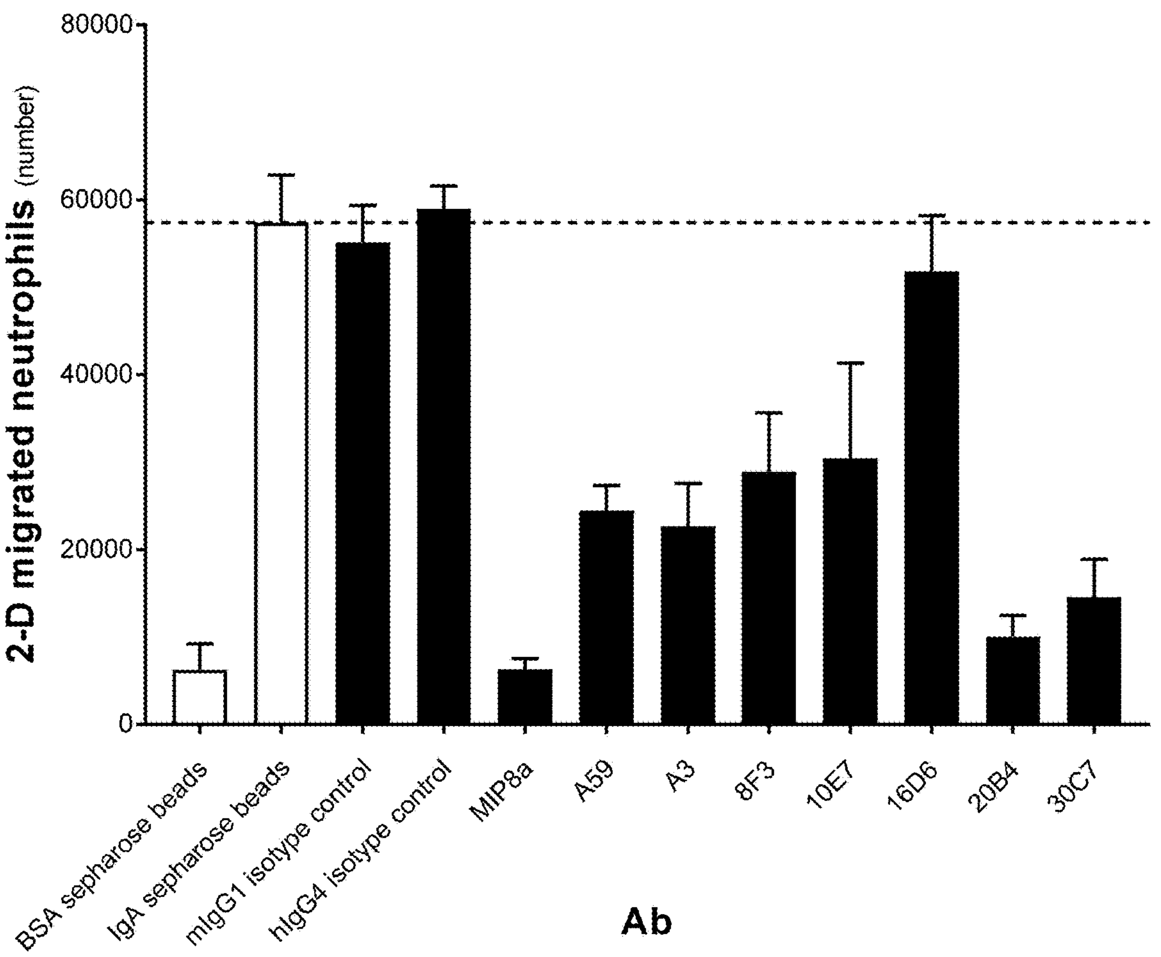

Fig. 20B (Donor 2)
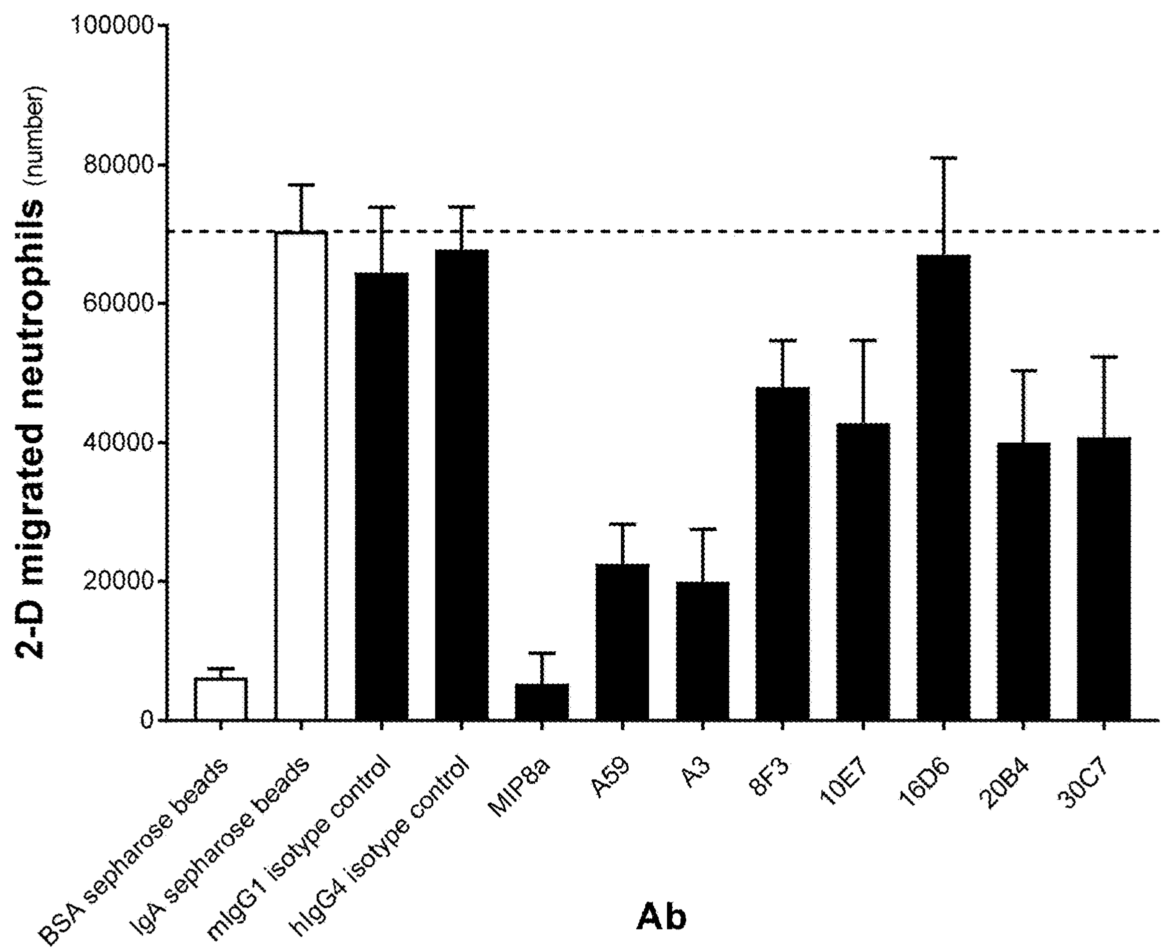

Fig. 20C (Donor 3)
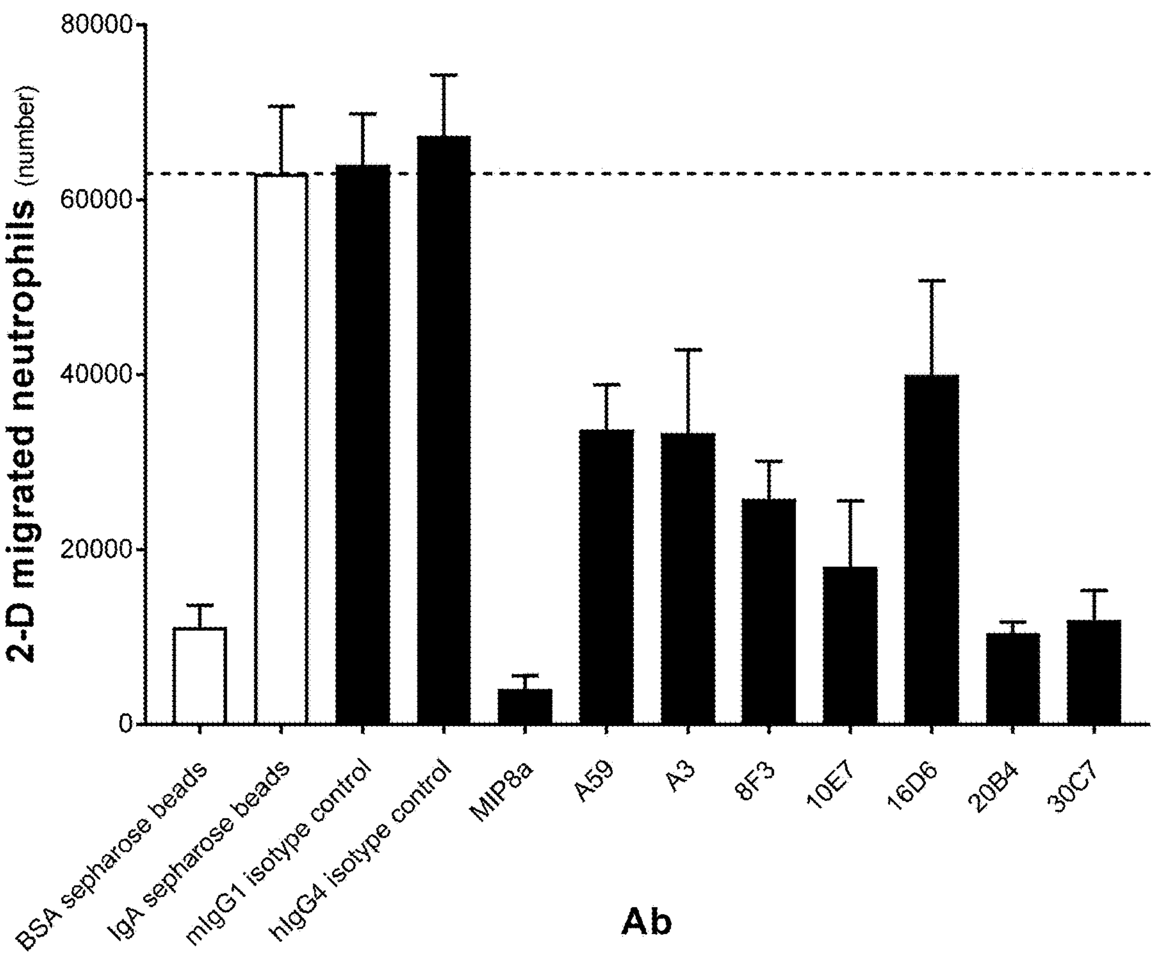

Fig. 20D (Donor 1)
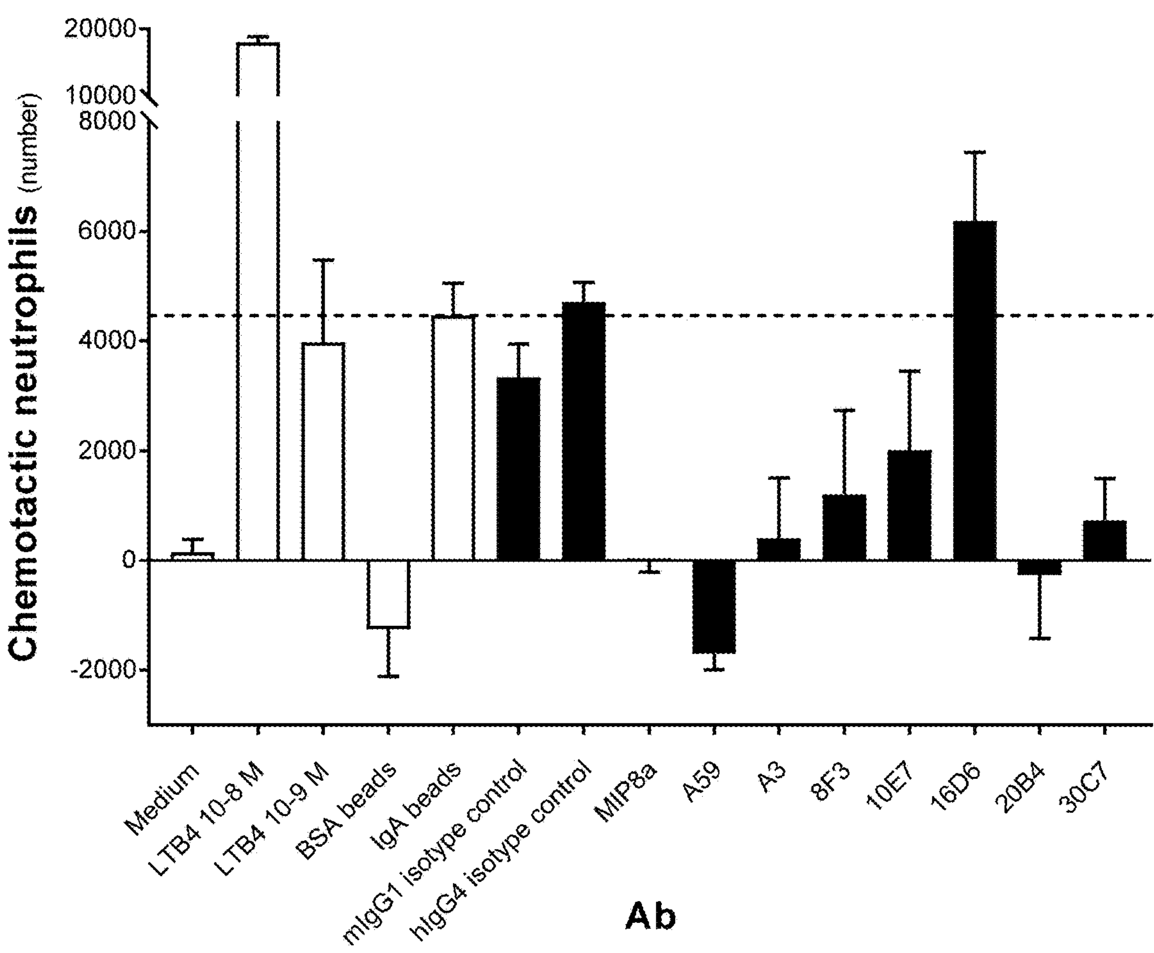

Fig. 20E (Donor 2)
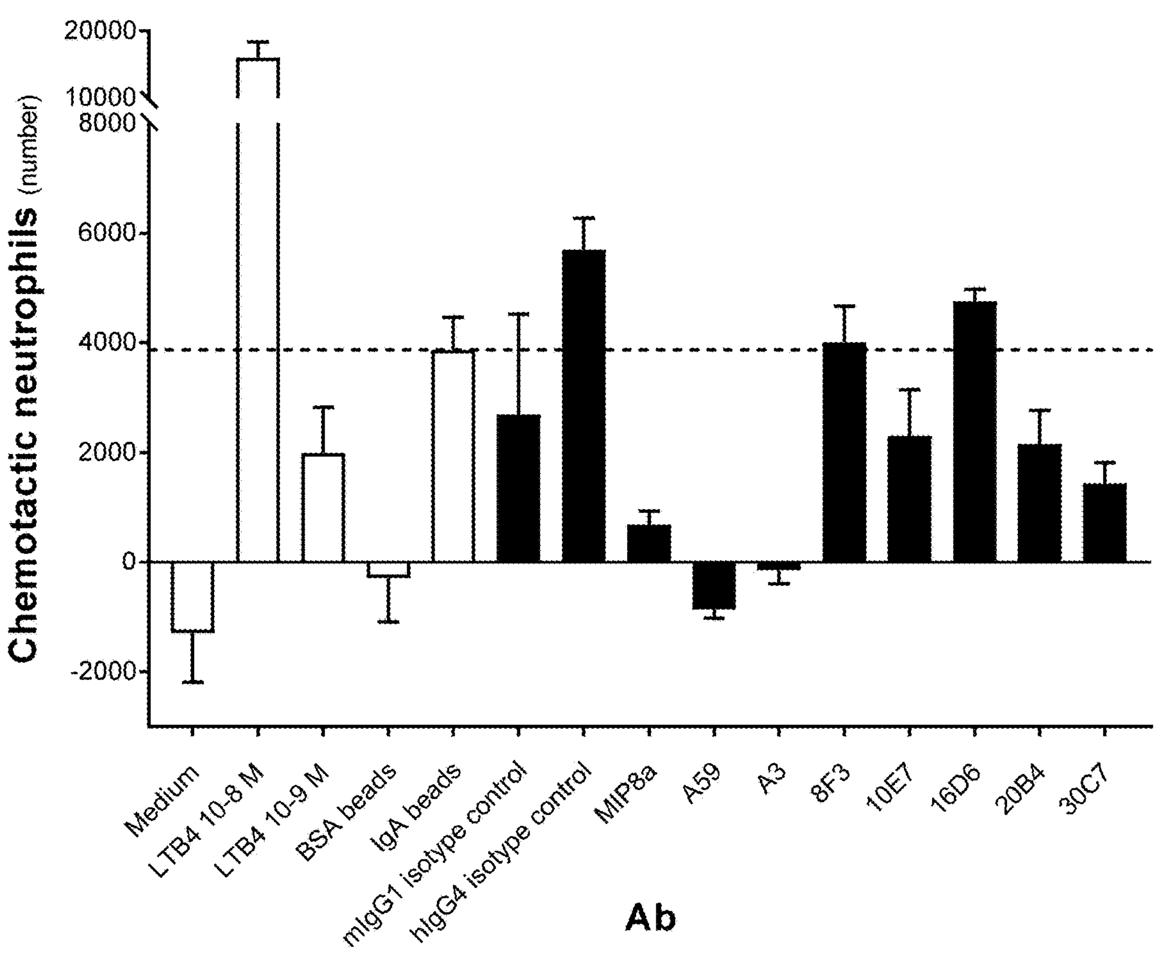

Fig. 20F (Donor 1)
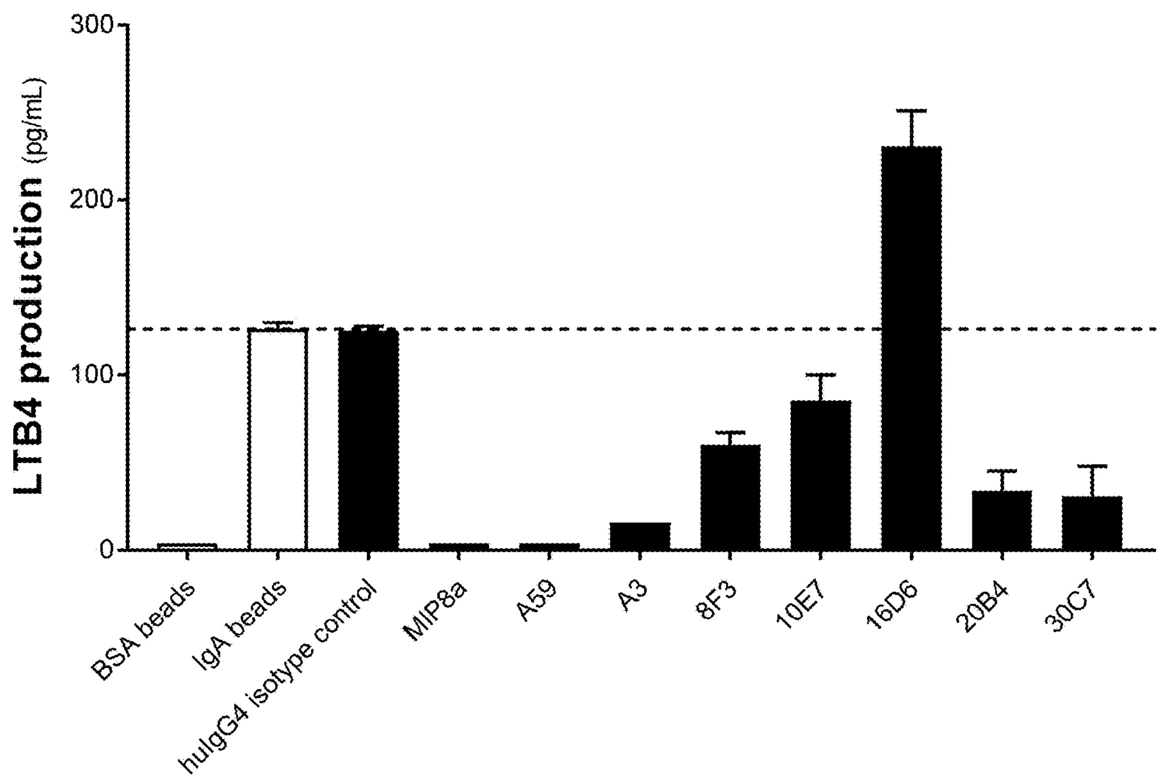

Fig. 20G (Donor 2)
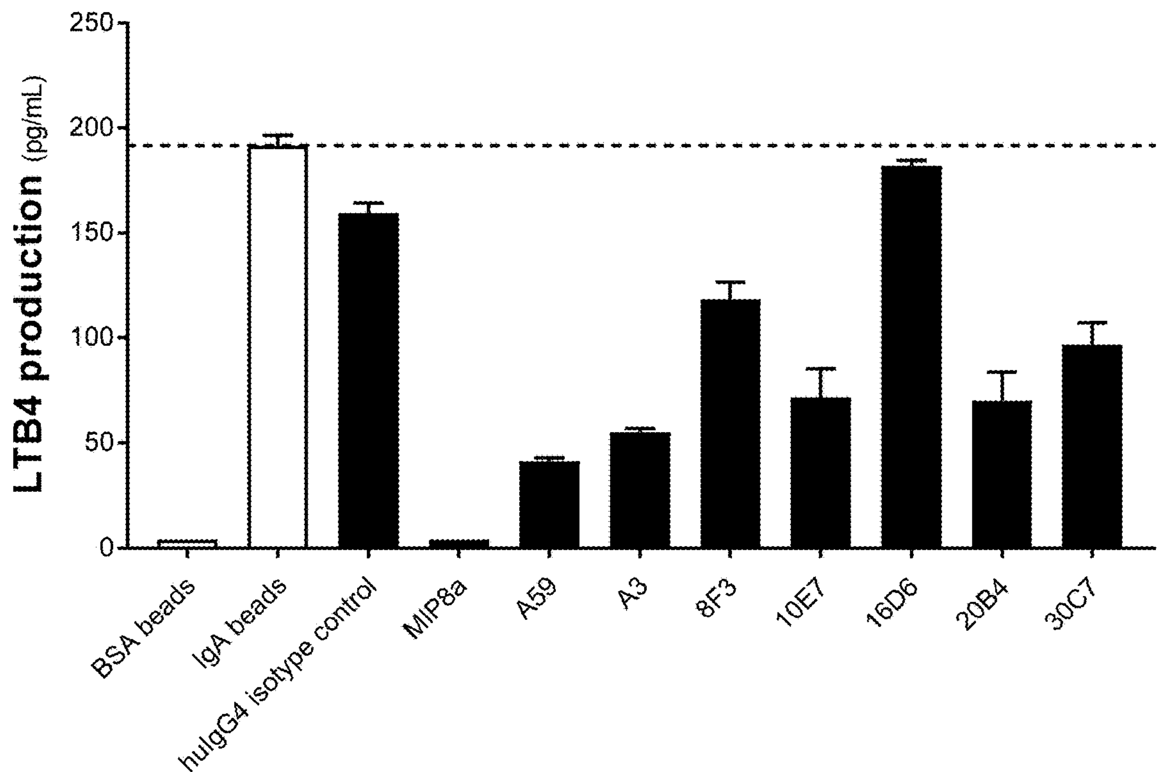

Fig.20H (Donor 3)
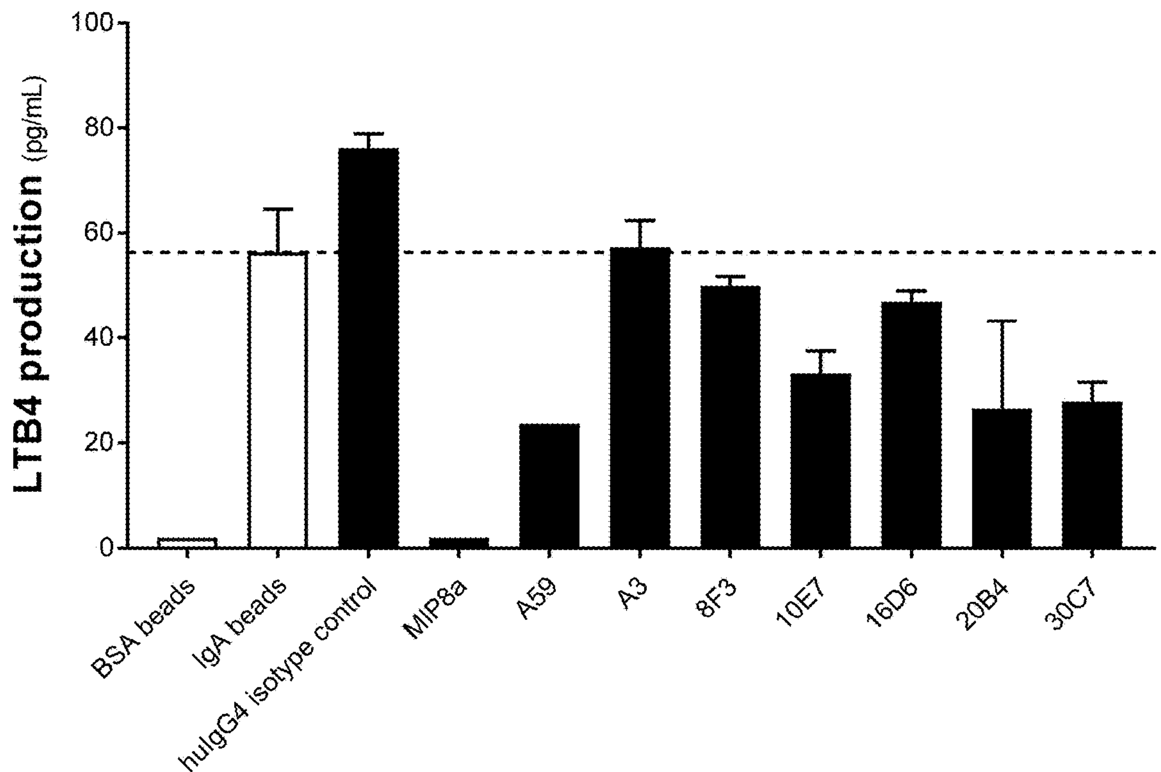

Fig. 21A (Donor 1)
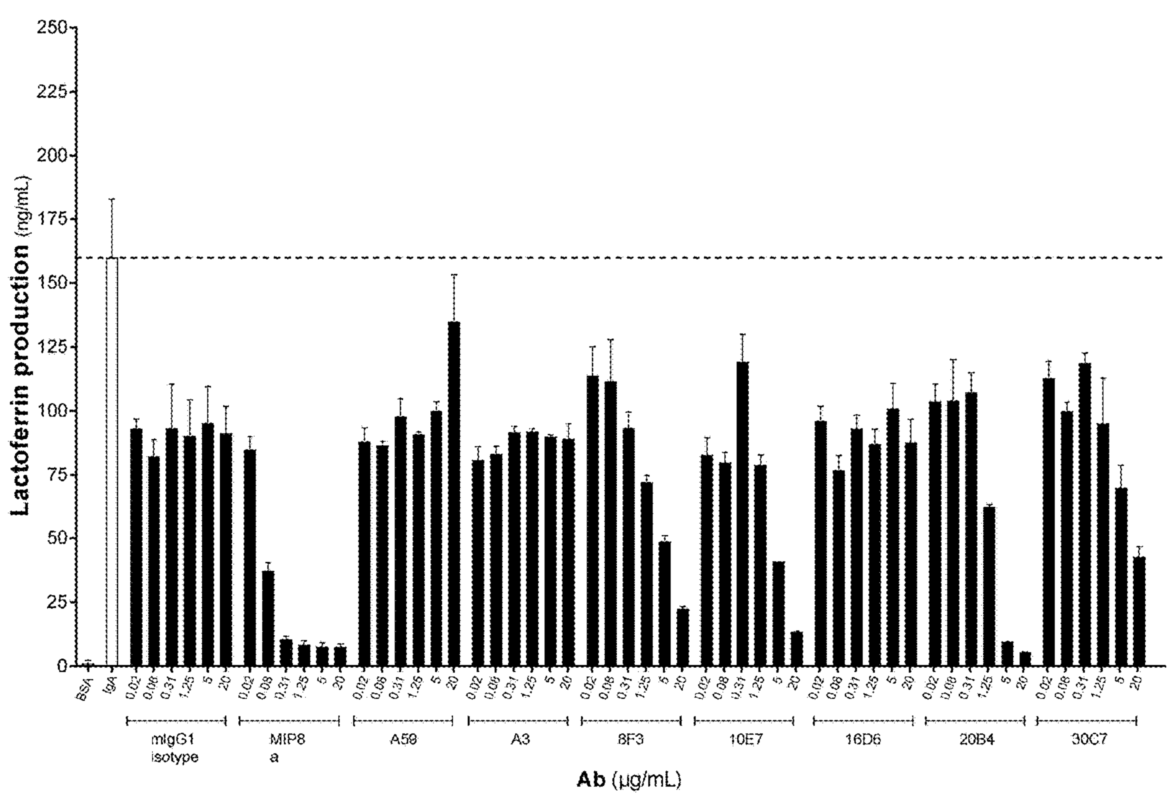

Fig. 21B (Donor 2)
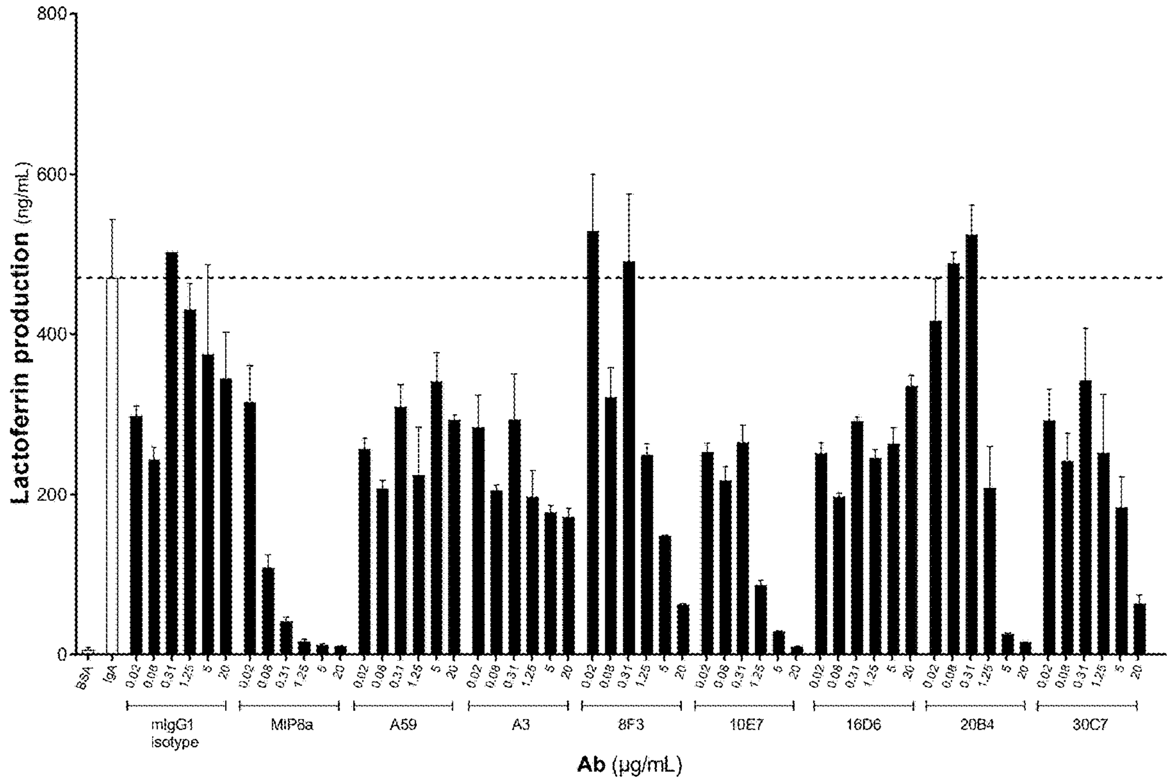
Fig. 22A (Budapest treaty deposit of the human CD89 expressing cells)
Fig. 22B (Budapest treaty deposit of the human CD89 expressing cells)

Fig. 26
A
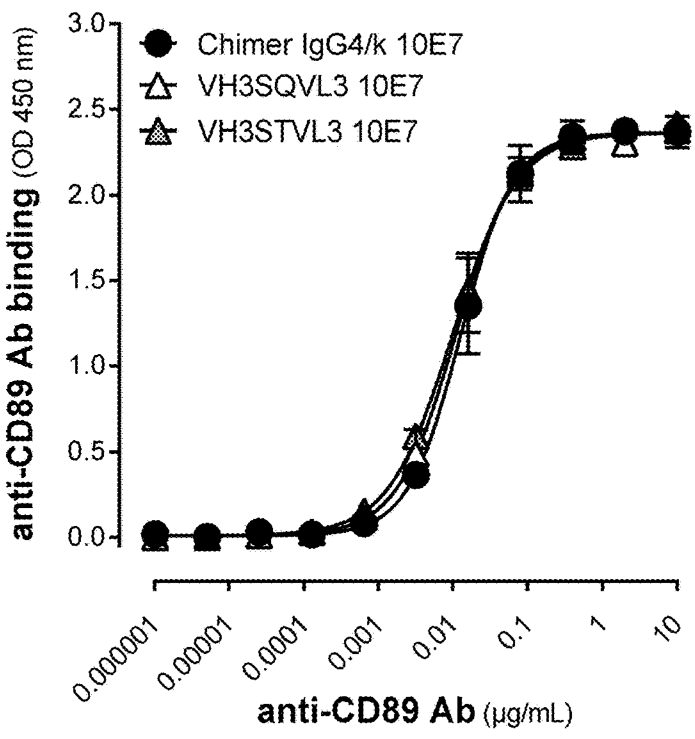
B
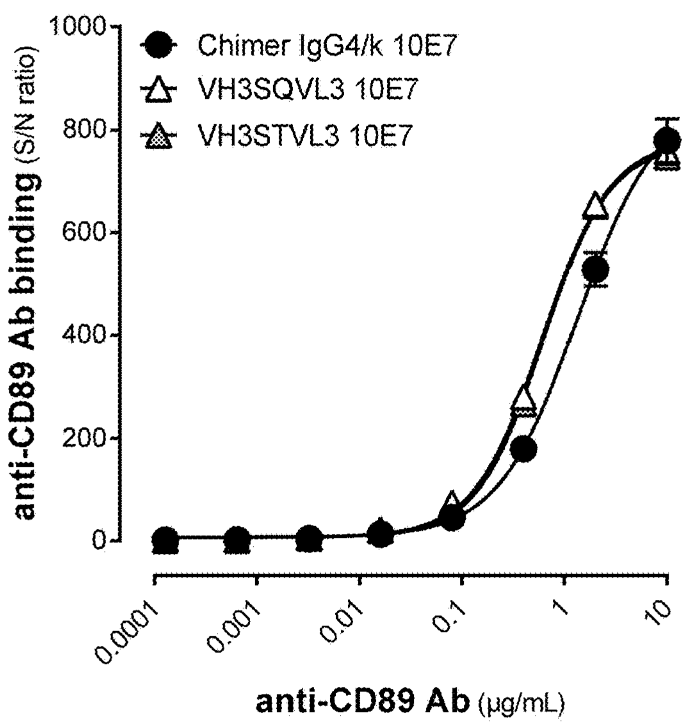

Fig. 27
A
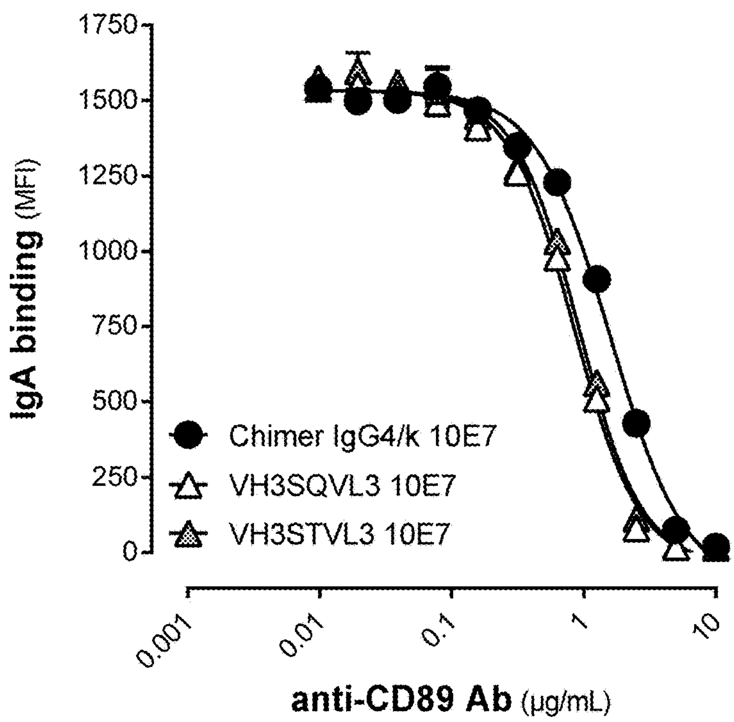
B
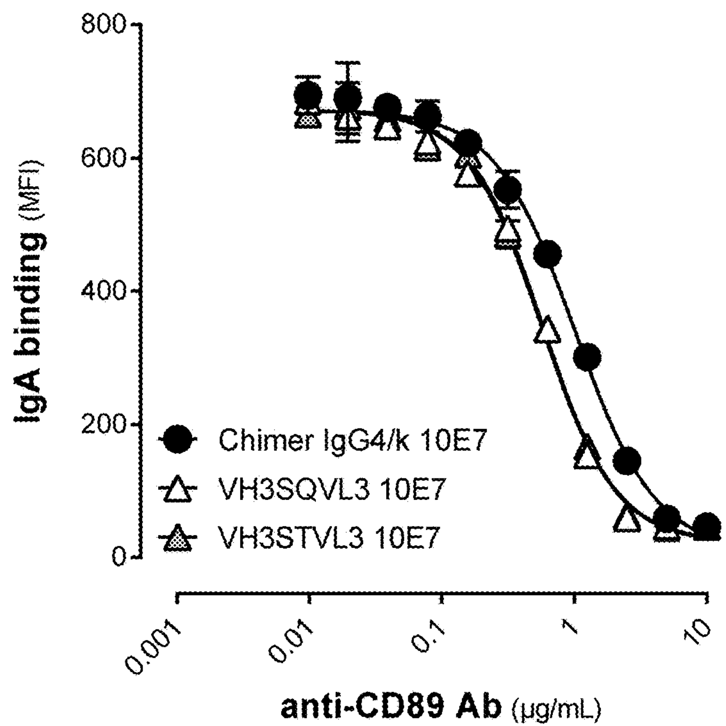

Fig. 29A (Donor 1)
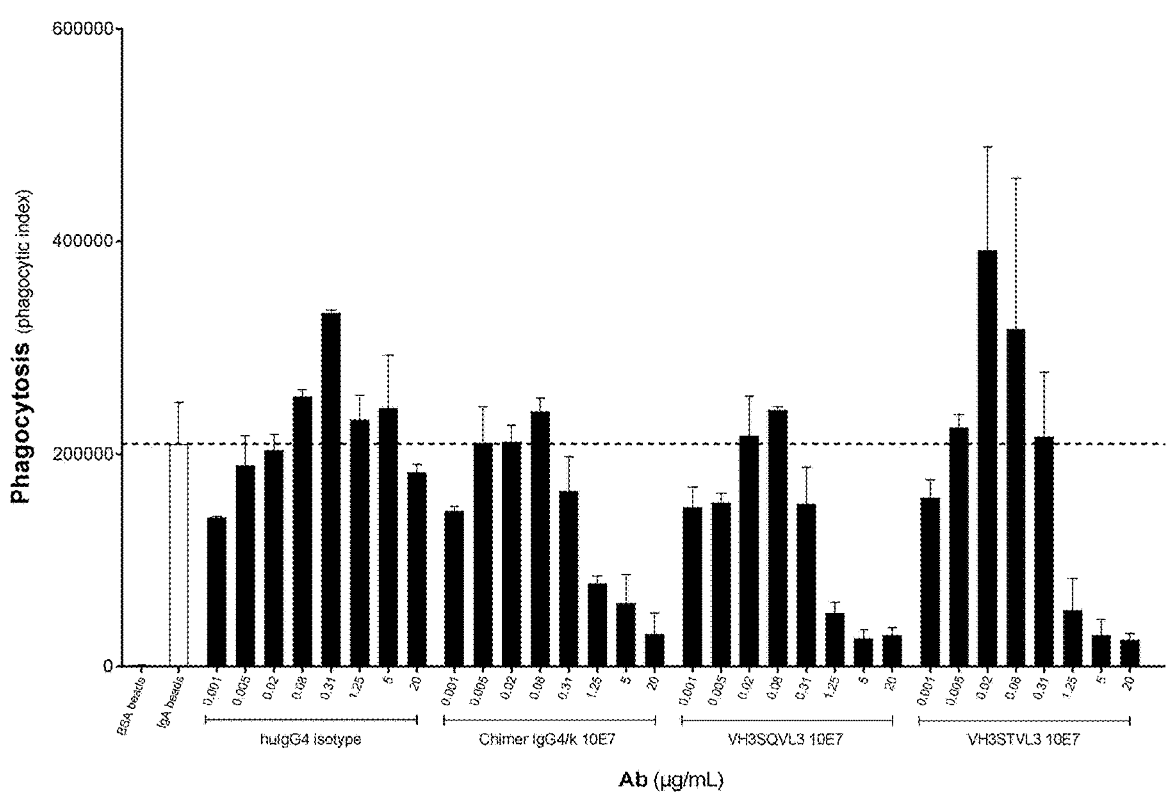

Fig. 29B (Donor 2)
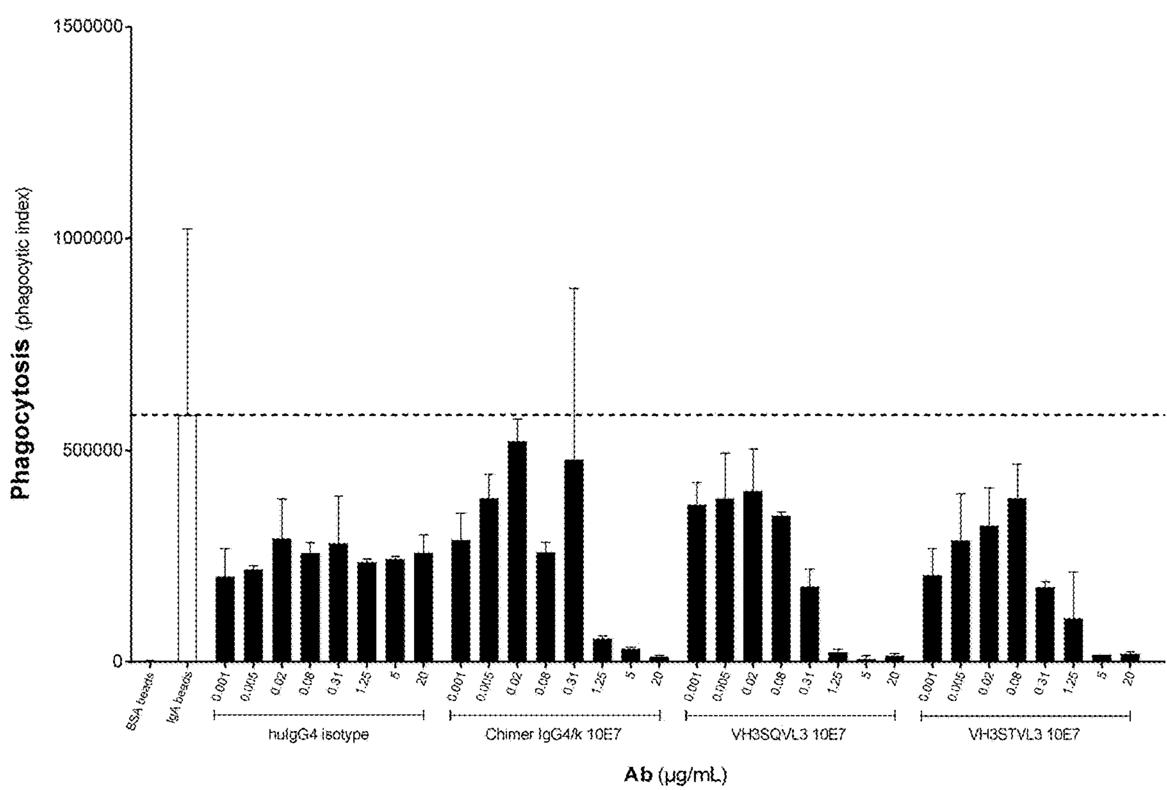

Fig. 29C (Donor 3)
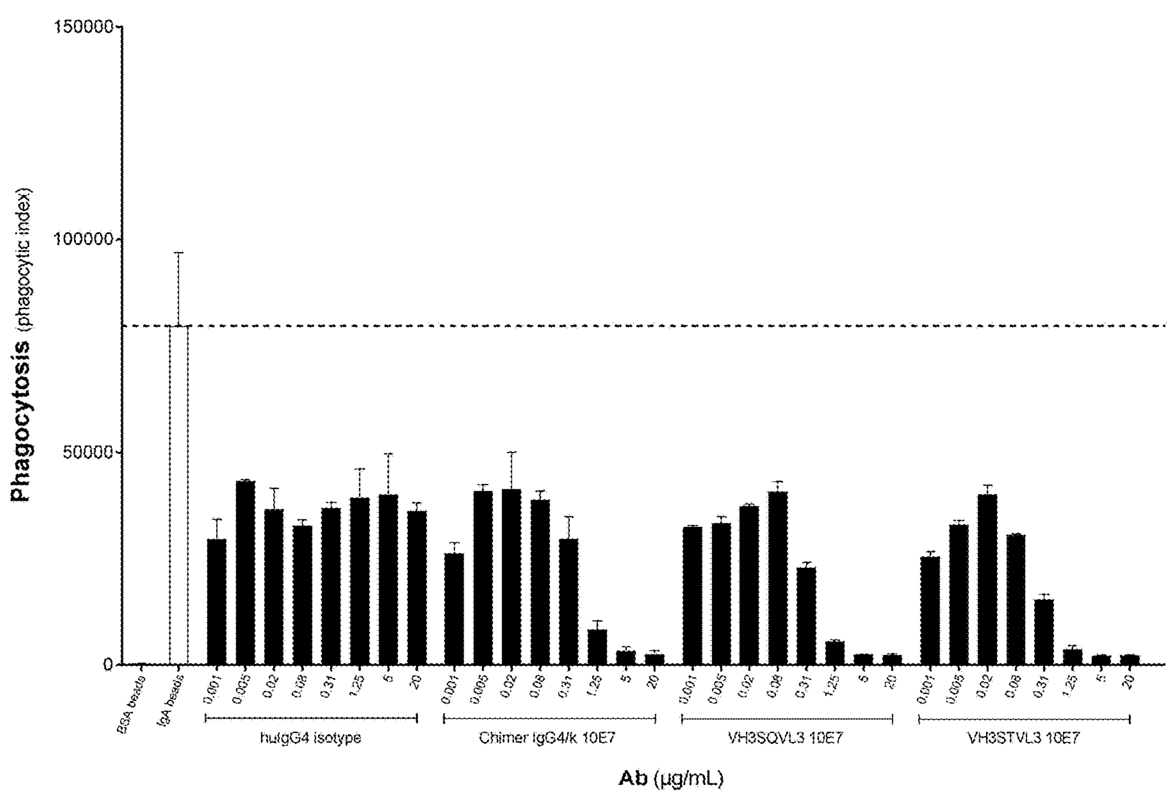

Fig. 30A (Donor 1)
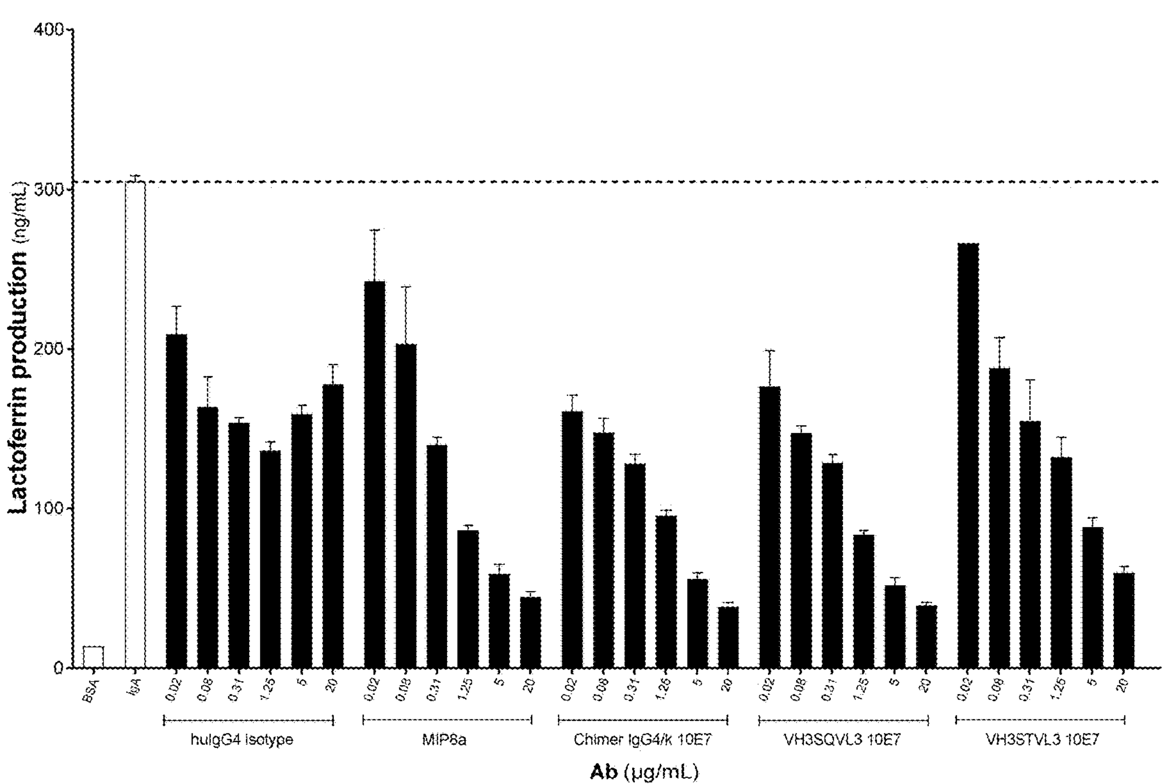

Fig. 30B (Donor 2)
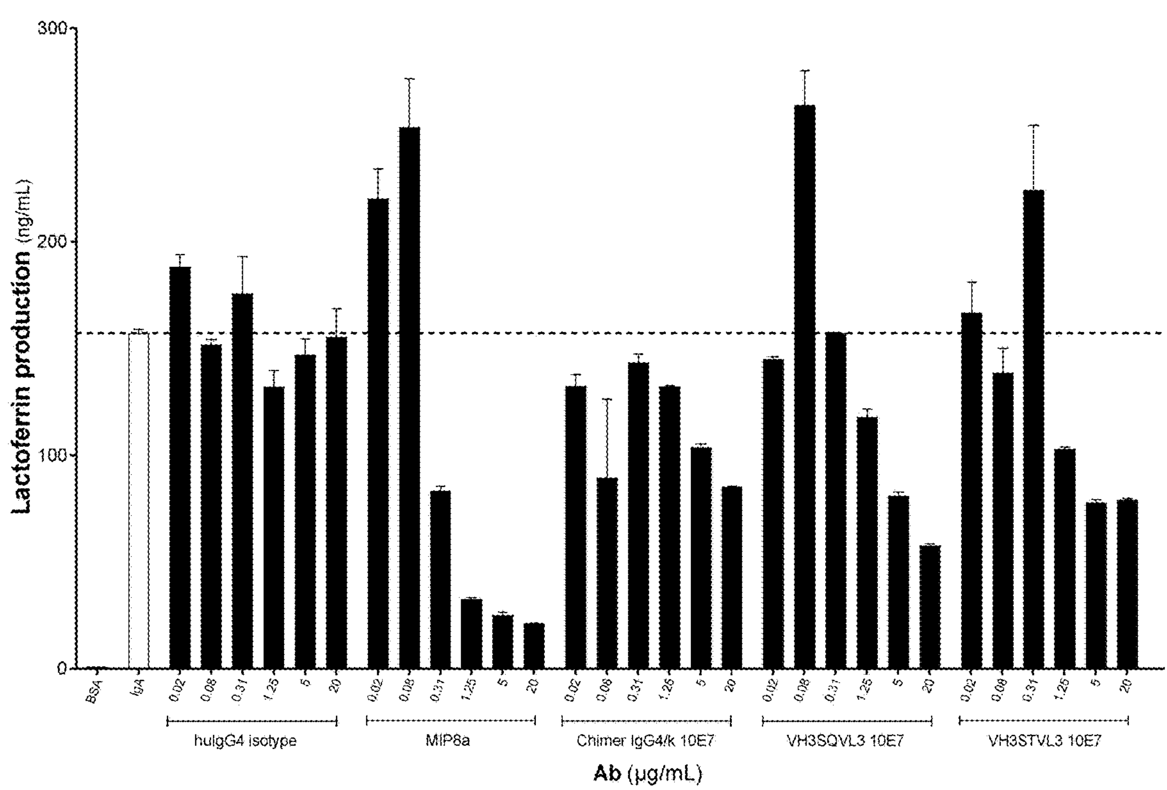

Fig. 30C (Donor 3)
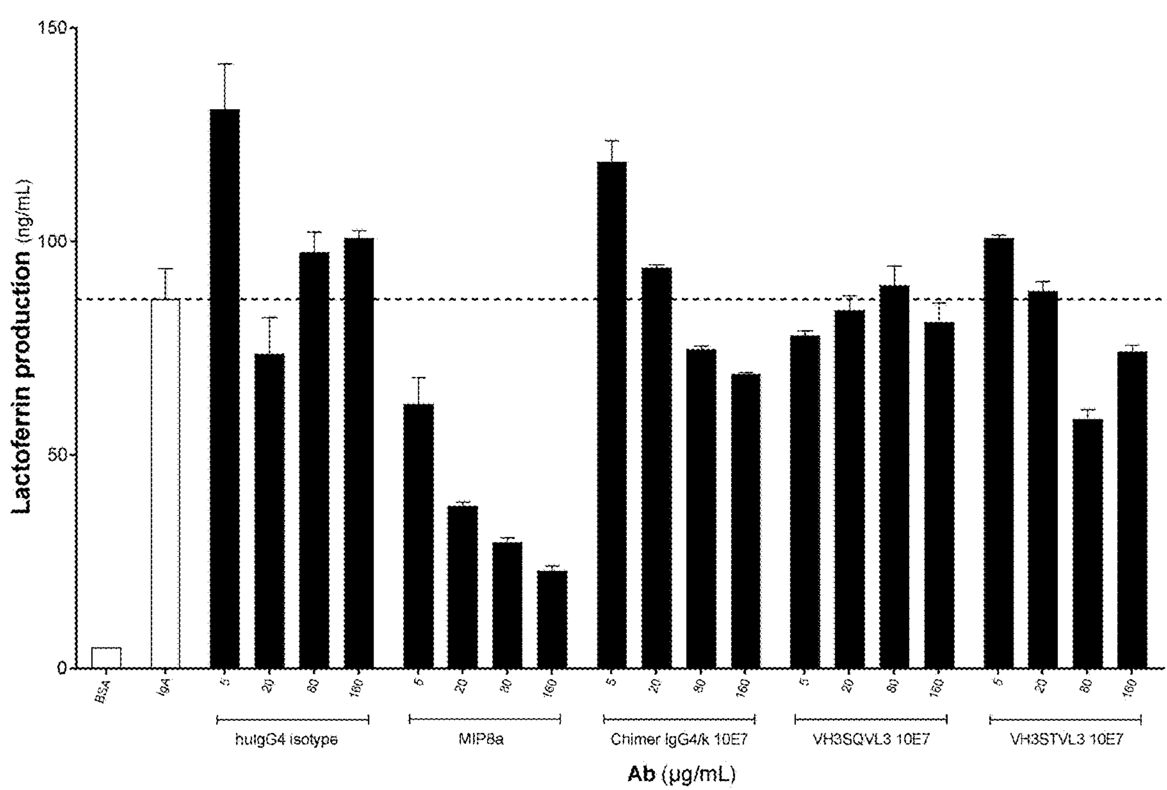

Fig. 30D (Donor 4)
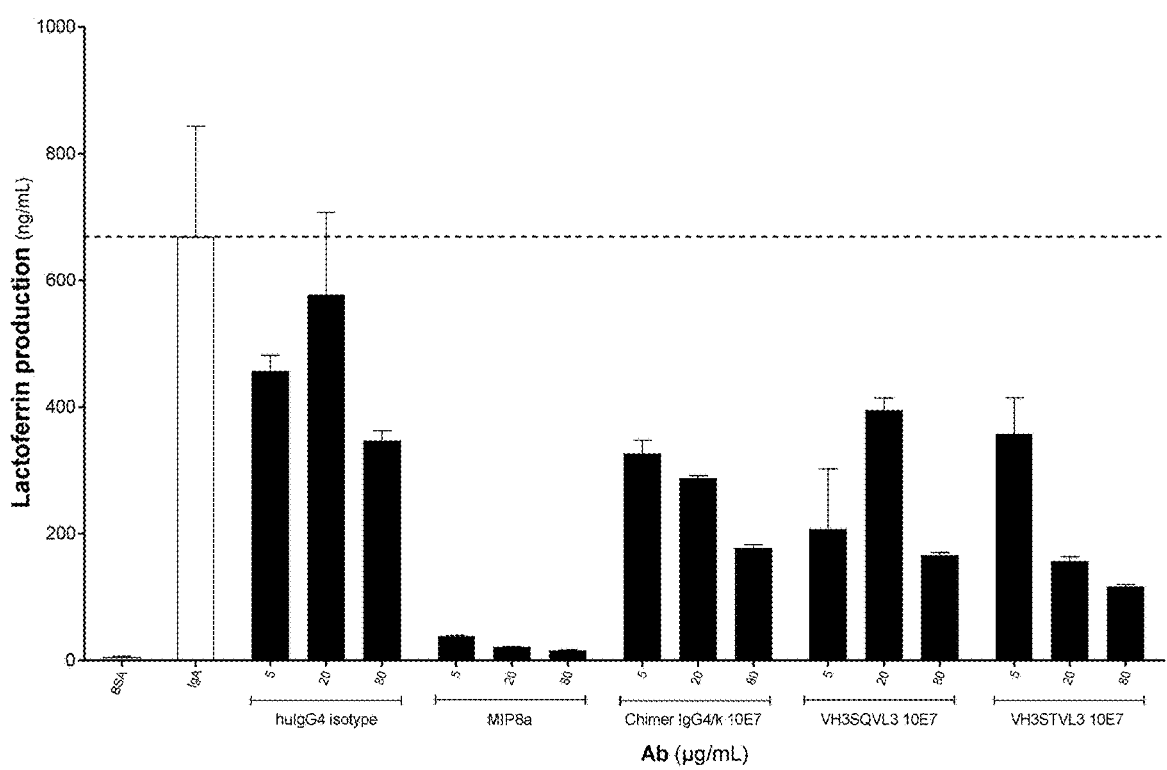

Fig. 30E (Donor 5)
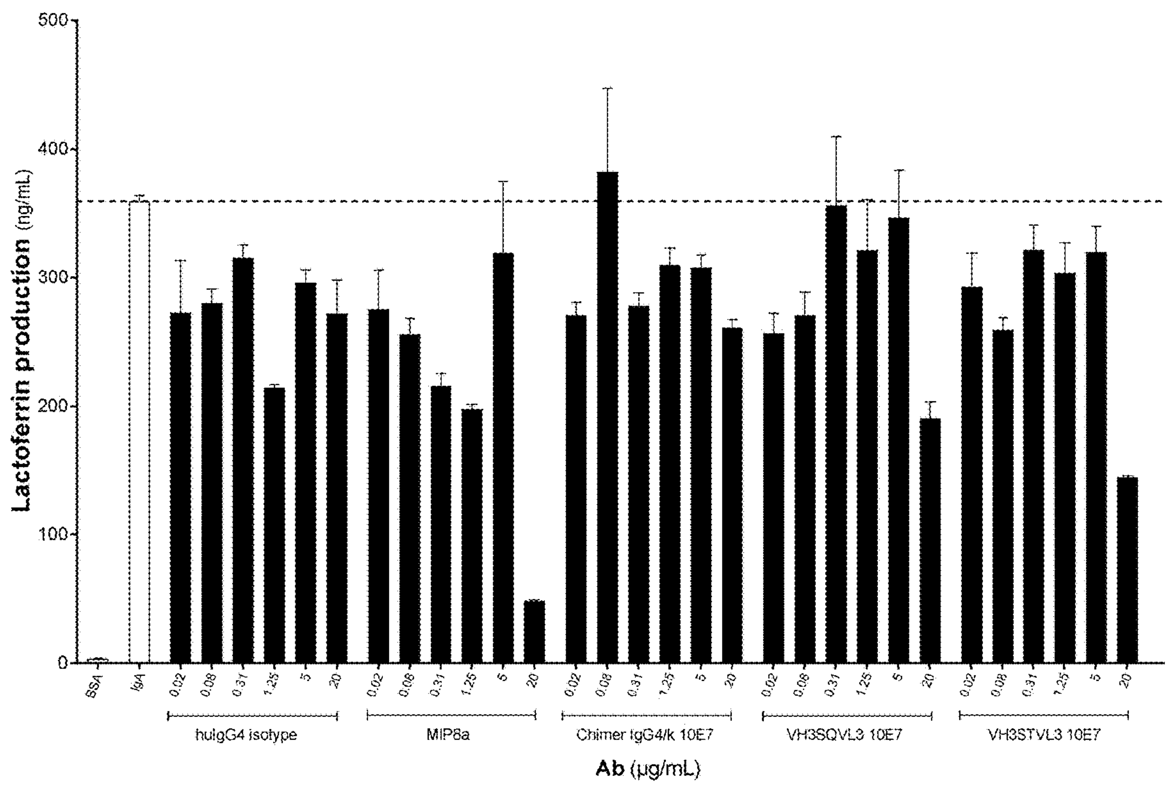

SEQUENCE LISTING

<160> NUMBER OF SEQ ID NOS: 150

<210> SEQ ID NO 1
<211> LENGTH: 287
<212> TYPE: PRT
<213> ORGANISM: Homo sapiens

<400> SEQUENCE: 1

```
Met Asp Pro Lys Gln Thr Thr Leu Leu Cys Leu Val Leu Cys Leu Gly
1               5                   10                  15

Gln Arg Ile Gln Ala Gln Glu Gly Asp Phe Pro Met Pro Phe Ile Ser
            20                  25                  30

Ala Lys Ser Ser Pro Val Ile Pro Leu Asp Gly Ser Val Lys Ile Gln
        35                  40                  45

Cys Gln Ala Ile Arg Glu Ala Tyr Leu Thr Gln Leu Met Ile Ile Lys
    50                  55                  60

Asn Ser Thr Tyr Arg Glu Ile Gly Arg Arg Leu Lys Phe Trp Asn Glu
65                  70                  75                  80

Thr Asp Pro Glu Phe Val Ile Asp His Met Asp Ala Asn Lys Ala Gly
                85                  90                  95

Arg Tyr Gln Cys Gln Tyr Arg Ile Gly His Tyr Arg Phe Arg Tyr Ser
            100                 105                 110

Asp Thr Leu Glu Leu Val Val Thr Gly Leu Tyr Gly Lys Pro Phe Leu
        115                 120                 125

Ser Ala Asp Arg Gly Leu Val Leu Met Pro Gly Glu Asn Ile Ser Leu
    130                 135                 140

Thr Cys Ser Ser Ala His Ile Pro Phe Asp Arg Phe Ser Leu Ala Lys
145                 150                 155                 160

Glu Gly Glu Leu Ser Leu Pro Gln His Gln Ser Gly Glu His Pro Ala
                165                 170                 175

Asn Phe Ser Leu Gly Pro Val Asp Leu Asn Val Ser Gly Ile Tyr Arg
            180                 185                 190

Cys Tyr Gly Trp Tyr Asn Arg Ser Pro Tyr Leu Trp Ser Phe Pro Ser
        195                 200                 205

Asn Ala Leu Glu Leu Val Val Thr Asp Ser Ile His Gln Asp Tyr Thr
    210                 215                 220

Thr Gln Asn Leu Ile Arg Met Ala Val Ala Gly Leu Val Leu Val Ala
225                 230                 235                 240

Leu Leu Ala Ile Leu Val Glu Asn Trp His Ser His Thr Ala Leu Asn
                245                 250                 255

Lys Glu Ala Ser Ala Asp Val Ala Glu Pro Ser Trp Ser Gln Gln Met
            260                 265                 270

Cys Gln Pro Gly Leu Thr Phe Ala Arg Thr Pro Ser Val Cys Lys
        275                 280                 285
```

<210> SEQ ID NO 2
<211> LENGTH: 861
<212> TYPE: DNA
<213> ORGANISM: Artificial Sequence
<220> FEATURE:
<223> OTHER INFORMATION: cDNA coding for human CD89

<400> SEQUENCE: 2

```
atggacccca agcagaccac cctgctgtgc ctggtgctgt gtctgggcca gagaatccag      60

gcccaggaag gcgacttccc catgcccttc atcagcgcca agagcagccc cgtgatcccc     120

ctggatggca gcgtgaagat ccagtgccag gccatcagag aggcctacct gacccagctg     180

atgatcatta agaacagcac ctaccgcgag atcggcagac ggctgaagtt ctggaacgag     240

acagaccccg agttcgtgat cgaccacatg gacgccaaca aggccggcag ataccagtgt     300

cagtaccgga tcggccacta ccggttccgg tacagcgaca ccctggaact ggtcgtgacc     360

ggcctgtacg gcaagccttt cctgagcgcc gatcggggac tggtgctgat gcccggcgag     420
```

```
aacatcagcc tgacctgtag cagcgcccac atccccttcg acagattcag cctggccaaa    480

gagggcgagc tgagcctgcc tcagcatcag tctggcgagc accccgccaa ctttagcctg    540

ggccctgtgg acctgaacgt gtccggcatc taccggtgct acggctggta caaccggtcc    600

ccctacctgt ggtccttccc cagcaacgct ctggaactgg tcgtgacaga cagcatccac    660

caggactaca ccacccagaa cctgatccgg atggccgtgg ctgggctggt gctggtggct    720

ctgctggcca ttctggtgga aaactggcac agccacaccg ccctgaacaa agaggccagc    780

gccgatgtgg ccgagccttc ttggagccag cagatgtgtc agcccggcct gaccttcgcc    840

agaacccctt ctgtgtgcaa g                                              861
```

```
<210> SEQ ID NO 3
<211> LENGTH: 266
<212> TYPE: PRT
<213> ORGANISM: Artificial Sequence
<220> FEATURE:
<223> OTHER INFORMATION: chimeric FcR protein

<400> SEQUENCE: 3

Met Asp Pro Lys Gln Thr Thr Leu Leu Cys Leu Val Leu Cys Leu Gly
1               5                   10                  15

Gln Arg Ile Gln Ala Gln Glu Gly Asp Phe Pro Met Pro Phe Ile Ser
            20                  25                  30

Ala Lys Ser Ser Pro Val Ile Pro Leu Asp Gly Ser Val Lys Ile Gln
        35                  40                  45

Cys Gln Ala Ile Arg Glu Ala Tyr Leu Thr Gln Leu Met Ile Ile Lys
    50                  55                  60

Asn Ser Thr Tyr Arg Glu Ile Gly Arg Arg Leu Lys Phe Trp Asn Glu
65                  70                  75                  80

Thr Asp Pro Glu Phe Val Ile Asp His Met Asp Ala Asn Lys Ala Gly
                85                  90                  95

Arg Tyr Gln Cys Gln Tyr Arg Ile Gly His Tyr Arg Phe Arg Tyr Ser
            100                 105                 110

Asp Thr Leu Glu Leu Val Val Thr Gly Glu Glu Pro Ala Gly Arg Leu
        115                 120                 125

Arg Asp Arg Pro Ser Leu Ser Val Arg Pro Ser Pro Ser Val Ala Pro
    130                 135                 140

Gly Glu Asn Val Thr Leu Leu Cys Gln Ser Gly Asn Arg Thr Asp Thr
145                 150                 155                 160

Phe Leu Leu Ser Lys Glu Gly Ala Ala His Arg Pro Leu Arg Leu Arg
                165                 170                 175

Ser Gln Asp Gln Asp Gly Trp Tyr Gln Ala Glu Phe Ser Leu Ser Pro
            180                 185                 190

Val Thr Ser Ala His Gly Gly Thr Tyr Arg Cys Tyr Arg Ser Leu Ser
        195                 200                 205

Thr Asn Pro Tyr Leu Leu Ser Gln Pro Ser Glu Pro Leu Ala Leu Leu
    210                 215                 220

Val Ala Asp Tyr Thr Met Gln Asn Leu Ile Arg Met Gly Leu Ala Ala
225                 230                 235                 240

Ser Val Leu Leu Leu Leu Gly Ile Leu Leu Cys Gln Ala Arg His Asp
                245                 250                 255

His Gly Gly Ala Arg Glu Ala Ala Arg Ser
            260                 265


<210> SEQ ID NO 4
```

<211> LENGTH: 292
<212> TYPE: PRT
<213> ORGANISM: Artificial Sequence
<220> FEATURE:
<223> OTHER INFORMATION: chimeric FcR protein

<400> SEQUENCE: 4

```
Met Asp Pro Lys Gln Thr Thr Leu Leu Cys Leu Val Leu Cys Leu Gly
1               5                   10                  15

Gln Arg Ile Gln Ala Gln Glu Gly Asp Phe Pro Met Pro Phe Ile Ser
            20                  25                  30

Ala Lys Ser Ser Pro Val Ile Pro Leu Asp Gly Ser Val Lys Ile Gln
        35                  40                  45

Cys Gln Ala Ile Arg Glu Ala Tyr Leu Thr Gln Leu Met Ile Ile Lys
    50                  55                  60

Asn Ser Thr Tyr Arg Glu Ile Gly Arg Arg Leu Lys Phe Trp Asn Glu
65                  70                  75                  80

Thr Asp Pro Glu Phe Val Ile Asp His Met Asp Ala Asn Lys Ala Gly
                85                  90                  95

Arg Tyr Gln Cys Gln Tyr Arg Ile Gly His Tyr Arg Phe Arg Tyr Ser
            100                 105                 110

Asp Thr Leu Glu Leu Val Val Thr Gly Glu Glu Pro Ala Gly Arg Leu
        115                 120                 125

Arg Asp Arg Pro Ser Leu Ser Val Arg Pro Ser Pro Ser Val Ala Pro
    130                 135                 140

Gly Glu Asn Val Thr Leu Leu Cys Gln Ser Gly Asn Arg Thr Asp Thr
145                 150                 155                 160

Phe Leu Leu Ser Lys Glu Gly Ala Ala His Arg Pro Leu Arg Leu Arg
                165                 170                 175

Ser Gln Asp Gln Asp Gly Trp Tyr Gln Ala Glu Phe Ser Leu Ser Pro
            180                 185                 190

Val Thr Ser Ala His Gly Gly Thr Tyr Arg Cys Tyr Arg Ser Leu Ser
        195                 200                 205

Thr Asn Pro Tyr Leu Leu Ser Gln Pro Ser Glu Pro Leu Ala Leu Leu
    210                 215                 220

Val Ala Asp Tyr Thr Met Gln Asn Leu Ile Arg Met Ala Val Ala Gly
225                 230                 235                 240

Leu Val Leu Val Ala Leu Leu Ala Ile Leu Val Glu Asn Trp His Ser
                245                 250                 255

His Thr Ala Leu Asn Lys Glu Ala Ser Ala Asp Val Ala Glu Pro Ser
            260                 265                 270

Trp Ser Gln Gln Met Cys Gln Pro Gly Leu Thr Phe Ala Arg Thr Pro
        275                 280                 285

Ser Val Cys Lys
    290
```

<210> SEQ ID NO 5
<211> LENGTH: 798
<212> TYPE: DNA
<213> ORGANISM: Artificial Sequence
<220> FEATURE:
<223> OTHER INFORMATION: cDNA coding for chimeric FcR

<400> SEQUENCE: 5

```
atggacccca agcagaccac actgctgtgc ctggtgctgt gtctcggcca gagaatccaa      60

gctcaagagg gcgacttccc catgcctttc atcagcgcca agagcagccc tgtgatccct     120
```

```
ctggatggca gcgtgaagat ccagtgccag gccatcagag aggcctacct gacacagctg    180

atgatcatta agaacagcac ctaccgcgag atcggcagac ggctgaagtt ctggaacgag    240

acagaccccg agttcgtgat cgaccacatg gacgccaaca aggccggcag ataccagtgt    300

cagtaccgga tcggccacta ccggttcaga tacagcgaca ccctggaact ggtggtcacc    360

ggcgaagaac ctgctggcag actgagagat agacccagcc tgtctgtgcg gccttctcct    420

tctgttgccc ctggcgagaa tgtgaccctg ctctgtcaga gcggcaaccg gaccgatacc    480

ttcctgctgt ctaaagaagg cgccgctcac agacccctga gactgagatc acaggaccag    540

gacggatggt atcaggccga gttctctctg agcccagtga catctgctca cggcggcacc    600

tacagatgct acagaagcct gagcacaaac ccctatctgc tgagccagcc tagcgagcct    660

ctggctctgc tggtggccga ttacaccatg cagaacctga tcagaatggg cctcgccgcc    720

tctgttctgc tgctgctggg aatcctgctg tgtcaagcca gacacgatca cggcggagcc    780

agagaagctg ccagatct                                                   798
```

<210> SEQ ID NO 6
<211> LENGTH: 876
<212> TYPE: DNA
<213> ORGANISM: Artificial Sequence
<220> FEATURE:
<223> OTHER INFORMATION: cDNA coding for chimeric FcR

<400> SEQUENCE: 6

```
atggacccca agcagaccac actgctgtgc ctggtgctgt gtctcggcca gagaatccaa     60

gctcaagagg gcgacttccc catgcctttc atcagcgcca agagcagccc tgtgatccct    120

ctggatggca gcgtgaagat ccagtgccag gccatcagag aggcctacct gacacagctg    180

atgatcatta agaacagcac ctaccgcgag atcggcagac ggctgaagtt ctggaacgag    240

acagaccccg agttcgtgat cgaccacatg gacgccaaca aggccggcag ataccagtgt    300

cagtaccgga tcggccacta ccggttcaga tacagcgaca ccctggaact ggtggtcacc    360

ggcgaagaac ctgctggcag actgagagat agacccagcc tgtctgtgcg gccttctcct    420

tctgttgccc ctggcgagaa tgtgaccctg ctctgtcaga gcggcaaccg gaccgatacc    480

ttcctgctgt ctaaagaagg cgccgctcac agacccctga gactgagatc acaggaccag    540

gacggatggt atcaggccga gttctctctg agcccagtga catctgctca cggcggcacc    600

tacagatgct acagaagcct gagcacaaac ccctatctgc tgagccagcc tagcgagcct    660

ctggctctgc tggtggccga ttacaccatg cagaacctga tcagaatggc cgtggccgga    720

ctggtgctgg ttgcactgct ggctatcctg gtggaaaact ggcacagcca cacagccctg    780

aacaaagagg cttctgccga cgtcgccgag ccttcttgga gtcagcagat gtgtcagccc    840

ggcctgacct tcgccagaac acctagcgtg tgcaag                               876
```

<210> SEQ ID NO 7
<211> LENGTH: 285
<212> TYPE: PRT
<213> ORGANISM: Artificial Sequence
<220> FEATURE:
<223> OTHER INFORMATION: chimeric FcR

<400> SEQUENCE: 7

```
Met Ala Pro Thr Leu Pro Ala Leu Leu Cys Leu Gly Leu Ser Val Gly
1               5                   10                  15

Leu Arg Thr Gln Val Gln Ala Gly Thr Phe Pro Lys Pro Ile Ile Trp
            20                  25                  30
```

```
Ala Glu Pro Ser Ser Val Val Pro Leu Gly Ser Ser Val Thr Ile Leu
        35                  40                  45

Cys Gln Gly Pro Pro Asn Thr Lys Ser Phe Ser Leu Asn Lys Glu Gly
    50                  55                  60

Asp Ser Thr Pro Trp Asn Ile His Pro Ser Leu Glu Pro Trp Asp Lys
65                  70                  75                  80

Ala Asn Phe Phe Ile Ser Asn Val Arg Glu Gln Gln Ala Gly Arg Tyr
                85                  90                  95

His Cys Ser His Phe Ile Gly Val Asn Trp Ser Glu Pro Ser Glu Pro
            100                 105                 110

Leu Asp Leu Leu Val Ala Gly Leu Tyr Gly Lys Pro Phe Leu Ser Ala
        115                 120                 125

Asp Arg Gly Leu Val Leu Met Pro Gly Glu Asn Ile Ser Leu Thr Cys
    130                 135                 140

Ser Ser Ala His Ile Pro Phe Asp Arg Phe Ser Leu Ala Lys Glu Gly
145                 150                 155                 160

Glu Leu Ser Leu Pro Gln His Gln Ser Gly Glu His Pro Ala Asn Phe
                165                 170                 175

Ser Leu Gly Pro Val Asp Leu Asn Val Ser Gly Ile Tyr Arg Cys Tyr
            180                 185                 190

Gly Trp Tyr Asn Arg Ser Pro Tyr Leu Trp Ser Phe Pro Ser Asn Ala
        195                 200                 205

Leu Glu Leu Val Val Thr Asp Ser Ile His Gln Asp Tyr Thr Thr Gln
    210                 215                 220

Asn Leu Ile Arg Met Ala Val Ala Gly Leu Val Leu Val Ala Leu Leu
225                 230                 235                 240

Ala Ile Leu Val Glu Asn Trp His Ser His Thr Ala Leu Asn Lys Glu
                245                 250                 255

Ala Ser Ala Asp Val Ala Glu Pro Ser Trp Ser Gln Gln Met Cys Gln
            260                 265                 270

Pro Gly Leu Thr Phe Ala Arg Thr Pro Ser Val Cys Lys
        275                 280                 285
```

<210> SEQ ID NO 8
<211> LENGTH: 855
<212> TYPE: DNA
<213> ORGANISM: Artificial Sequence
<220> FEATURE:
<223> OTHER INFORMATION: cDNA coding for chimeric FcR

<400> SEQUENCE: 8

```
atggccccta cactgcctgc tctgctgtgt ctgggactgt ctgtgggcct gagaacacag     60

gtgcaggccg gcacattccc caagcctatc atttgggccg agcctagctc tgtggtgcct    120

ctgggaagca gcgtgaccat cctgtgtcag ggccctccaa acaccaagag cttcagcctg    180

aacaaagagg gcgacagcac cccttggaac attcacccta gcctggaacc ttgggacaaa    240

gccaacttct tcatcagcaa cgtgcgcgag cagcaggccg gaagatacca ctgctctcac    300

ttcatcggag tgaattggag cgagcccagc gagcctctgg atctgcttgt ggctggcctg    360

tacggcaagc cttttctgtc tgccgataga ggcctggtgc tgatgcccgg cgagaatatc    420

agcctgacct gtagcagcgc tcacatcccc ttcgacagat tctccctggc caaagaaggc    480

gagctgagcc tgcctcagca tcagtctggc gaacaccccg ccaacttttc tctgggccct    540

gtggacctga acgtgtccgg catctacaga tgctacggct ggtacaatcg gagcccctac    600
```

```
ctgtggtctt tccccagcaa tgccctggaa ctggtggtca ccgatagcat ccaccaggac    660

tacaccacac agaacctgat cagaatggcc gtggccggac tggtgctggt tgcactgctg    720

gctattctgg tggaaaactg gcacagccac accgctctca acaaagaagc ctctgccgac    780

gtcgccgagc cttcttggag tcagcagatg tgtcagcccg gcctgacctt cgccagaaca    840

cctagcgtgt gcaag                                                     855


<210> SEQ ID NO 9
<211> LENGTH: 264
<212> TYPE: PRT
<213> ORGANISM: Bos taurus

<400> SEQUENCE: 9

Met Ala Pro Thr Leu Pro Ala Leu Leu Cys Leu Gly Leu Ser Val Gly
1               5                   10                  15

Leu Arg Thr Gln Val Gln Ala Gly Thr Phe Pro Lys Pro Ile Ile Trp
            20                  25                  30

Ala Glu Pro Ser Ser Val Val Pro Leu Gly Ser Ser Val Thr Ile Leu
        35                  40                  45

Cys Gln Gly Pro Pro Asn Thr Lys Ser Phe Ser Leu Asn Lys Glu Gly
    50                  55                  60

Asp Ser Thr Pro Trp Asn Ile His Pro Ser Leu Glu Pro Trp Asp Lys
65                  70                  75                  80

Ala Asn Phe Phe Ile Ser Asn Val Arg Glu Gln Gln Ala Gly Arg Tyr
                85                  90                  95

His Cys Ser His Phe Ile Gly Val Asn Trp Ser Glu Pro Ser Glu Pro
            100                 105                 110

Leu Asp Leu Leu Val Ala Gly Glu Glu Pro Ala Gly Arg Leu Arg Asp
        115                 120                 125

Arg Pro Ser Leu Ser Val Arg Pro Ser Pro Ser Val Ala Pro Gly Glu
    130                 135                 140

Asn Val Thr Leu Leu Cys Gln Ser Gly Asn Arg Thr Asp Thr Phe Leu
145                 150                 155                 160

Leu Ser Lys Glu Gly Ala Ala His Arg Pro Leu Arg Leu Arg Ser Gln
                165                 170                 175

Asp Gln Asp Gly Trp Tyr Gln Ala Glu Phe Ser Leu Ser Pro Val Thr
            180                 185                 190

Ser Ala His Gly Gly Thr Tyr Arg Cys Tyr Arg Ser Leu Ser Thr Asn
        195                 200                 205

Pro Tyr Leu Leu Ser Gln Pro Ser Glu Pro Leu Ala Leu Leu Val Ala
    210                 215                 220

Asp Tyr Thr Met Gln Asn Leu Ile Arg Met Gly Leu Ala Ala Ser Val
225                 230                 235                 240

Leu Leu Leu Leu Gly Ile Leu Leu Cys Gln Ala Arg His Asp His Gly
                245                 250                 255

Gly Ala Arg Glu Ala Ala Arg Ser
            260


<210> SEQ ID NO 10
<211> LENGTH: 792
<212> TYPE: DNA
<213> ORGANISM: Artificial Sequence
<220> FEATURE:
<223> OTHER INFORMATION: cDNA coding for bovine protein

<400> SEQUENCE: 10
```

-continued

```
atggccccta cactgcctgc tctgctgtgt ctgggactgt ctgtgggcct gagaacacag     60

gtgcaggccg gcacattccc caagcctatc atttgggccg agcctagctc tgtggtgcct    120

ctgggaagca gcgtgaccat cctgtgtcag ggccctccaa acaccaagag cttcagcctg    180

aacaaagagg gcgacagcac cccttggaac attcacccta gcctggaacc ttgggacaaa    240

gccaacttct tcatcagcaa cgtgcgcgag cagcaggccg gaagatacca ctgctctcac    300

ttcatcggag tgaattggag cgagcccagc gagcctctgg atctgcttgt tgctggcgaa    360

gaaccagccg gcagactgag agatagaccc tctctgagtg tgcggccctc tccttctgtt    420

gcccctggcg aaaatgtgac cctgctgtgc cagagcggca acaggaccga taccttcctg    480

ctgagcaaag aaggcgccgc tcacagaccc ctgagactga gatcacagga ccaggacgga    540

tggtatcagg ccgagttcag cctgtctcct gtgacatctg ctcacggcgg cacctacaga    600

tgctacagaa gcctgagcac aaacccctac ctgctgtccc agccttctga gcctttggct    660

ctgctggtgg ccgactacac catgcagaac ctgatcagaa tgggcctcgc cgcctctgtt    720

ctgctgctgc tgggaatcct gctctgtcag gccagacacg atcatggcgg agccagagaa    780

gccgccagat ct                                                        792
```

```
<210> SEQ ID NO 11
<211> LENGTH: 287
<212> TYPE: PRT
<213> ORGANISM: Macaca fascicularis

<400> SEQUENCE: 11

Met Asp Pro Lys Glu Thr Thr Leu Leu Cys Leu Val Leu Cys Leu Gly
1               5                   10                  15

Gln Arg Ile Gln Ala Gln Glu Gly Asn Phe Ser Thr Pro Phe Ile Ser
            20                  25                  30

Thr Arg Ser Ser Pro Val Val Pro Trp Gly Gly Ser Val Arg Ile Gln
        35                  40                  45

Cys Gln Ala Ile Pro Asp Ala Tyr Leu Ile Trp Leu Met Met Leu Lys
    50                  55                  60

Asn Ser Thr Tyr Glu Lys Arg Asp Glu Lys Leu Gly Phe Trp Asn Asp
65                  70                  75                  80

Thr Thr Pro Glu Phe Val Ile Asp His Met Asp Ala Asn Lys Ala Gly
                85                  90                  95

Arg Tyr Arg Cys Arg Tyr Arg Ile Gly Leu Ser Arg Phe Arg Tyr Ser
            100                 105                 110

Asp Thr Leu Glu Leu Val Val Thr Gly Leu Tyr Gly Lys Pro Ser Leu
        115                 120                 125

Ser Val Asp Arg Gly Pro Val Leu Met Pro Gly Glu Asn Ile Ser Val
    130                 135                 140

Thr Cys Ser Ser Ala His Ile Pro Phe Asp Arg Phe Ser Leu Ala Lys
145                 150                 155                 160

Glu Gly Glu Leu Ser Leu Pro Gln His Gln Ser Gly Glu His Pro Ala
                165                 170                 175

Asn Phe Ser Leu Gly Pro Val Asp Leu Asn Val Ser Gly Ser Tyr Arg
            180                 185                 190

Cys Tyr Gly Trp Tyr Asn Arg Ser Pro Tyr Leu Trp Ser Phe Pro Ser
        195                 200                 205

Asn Ala Leu Glu Leu Val Val Thr Asp Ser Ile Asn Arg Asp Tyr Thr
    210                 215                 220

Thr Gln Asn Leu Ile Arg Met Ala Met Ala Gly Leu Val Leu Val Ala
```

```
225                 230                 235                 240

Leu Leu Ala Ile Leu Val Glu Asn Trp His Ser His Lys Ala Leu Asn
                245                 250                 255

Lys Glu Ala Ser Ala Asp Val Ala Glu Pro Ser Trp Ser His Gln Met
            260                 265                 270

Cys Gln Pro Gly Trp Thr Phe Ala Arg Thr Pro Ser Val Cys Lys
        275                 280                 285


<210> SEQ ID NO 12
<211> LENGTH: 861
<212> TYPE: DNA
<213> ORGANISM: Artificial Sequence
<220> FEATURE:
<223> OTHER INFORMATION: cDNA coding for cynomolgus monkey CD89

<400> SEQUENCE: 12

atggacccca aagaaaccac cctgctgtgc ctggtgctgt gtctgggcca gagaatccag      60

gcccaggaag gcaacttcag cacccccttc atcagcacca gatccagccc cgtggtgcct     120

tggggaggct ctgtgcggat tcagtgccag gccatccccg acgcctacct gatctggctg     180

atgatgctga agaacagcac ctacgagaag cgggacgaga agctgggctt ctggaacgac     240

accacccccg agttcgtgat cgaccacatg gacgccaaca aggccggcag ataccggtgc     300

cggtacagaa tcggcctgag ccggttcaga tacagcgaca ccctggaact ggtcgtgacc     360

ggcctgtacg gcaagcctag cctgtccgtg gatagaggcc ccgtgctgat gcccggcgag     420

aacatcagcg tgacctgtag cagcgcccac atccccttcg acagattcag cctggccaaa     480

gagggcgagc tgagcctgcc tcagcatcag tctggcgagc accccgccaa ctttagcctg     540

ggccctgtgg acctgaacgt gtccggcagc tacagatgct acggctggta caaccggtcc     600

ccctacctgt ggtccttccc cagcaacgct ctggaactgg tcgtgacaga cagcatcaac     660

cgggactaca ccacccagaa cctgatccgg atggctatgg ccggactggt gctggtggcc     720

ctgctggcca tcctggtgga aaactggcac agccacaagg ccctgaacaa agaggccagc     780

gccgatgtgg ccgagccttc ttggagccac cagatgtgtc agcccggctg gaccttcgcc     840

agaacccctt ctgtgtgcaa g                                               861


<210> SEQ ID NO 13
<211> LENGTH: 287
<212> TYPE: PRT
<213> ORGANISM: Artificial Sequence
<220> FEATURE:
<223> OTHER INFORMATION: chimeric CD89

<400> SEQUENCE: 13

Met Asp Pro Lys Gln Thr Thr Leu Leu Cys Leu Val Leu Cys Leu Gly
1               5                   10                  15

Gln Arg Ile Gln Ala Gln Glu Gly Asn Phe Ser Thr Pro Phe Ile Ser
            20                  25                  30

Thr Arg Ser Ser Pro Val Val Pro Trp Gly Gly Ser Val Arg Ile Gln
        35                  40                  45

Cys Gln Ala Ile Arg Glu Ala Tyr Leu Thr Gln Leu Met Ile Ile Lys
    50                  55                  60

Asn Ser Thr Tyr Arg Glu Ile Gly Arg Arg Leu Lys Phe Trp Asn Glu
65                  70                  75                  80

Thr Asp Pro Glu Phe Val Ile Asp His Met Asp Ala Asn Lys Ala Gly
                85                  90                  95
```

-continued

```
Arg Tyr Gln Cys Gln Tyr Arg Ile Gly His Tyr Arg Phe Arg Tyr Ser
            100                 105                 110

Asp Thr Leu Glu Leu Val Val Thr Gly Leu Tyr Gly Lys Pro Phe Leu
        115                 120                 125

Ser Ala Asp Arg Gly Leu Val Leu Met Pro Gly Glu Asn Ile Ser Leu
    130                 135                 140

Thr Cys Ser Ser Ala His Ile Pro Phe Asp Arg Phe Ser Leu Ala Lys
145                 150                 155                 160

Glu Gly Glu Leu Ser Leu Pro Gln His Gln Ser Gly Glu His Pro Ala
                165                 170                 175

Asn Phe Ser Leu Gly Pro Val Asp Leu Asn Val Ser Gly Ile Tyr Arg
            180                 185                 190

Cys Tyr Gly Trp Tyr Asn Arg Ser Pro Tyr Leu Trp Ser Phe Pro Ser
        195                 200                 205

Asn Ala Leu Glu Leu Val Val Thr Asp Ser Ile His Gln Asp Tyr Thr
    210                 215                 220

Thr Gln Asn Leu Ile Arg Met Ala Val Ala Gly Leu Val Leu Val Ala
225                 230                 235                 240

Leu Leu Ala Ile Leu Val Glu Asn Trp His Ser His Thr Ala Leu Asn
                245                 250                 255

Lys Glu Ala Ser Ala Asp Val Ala Glu Pro Ser Trp Ser Gln Gln Met
            260                 265                 270

Cys Gln Pro Gly Leu Thr Phe Ala Arg Thr Pro Ser Val Cys Lys
        275                 280                 285
```

<210> SEQ ID NO 14
<211> LENGTH: 861
<212> TYPE: DNA
<213> ORGANISM: Artificial Sequence
<220> FEATURE:
<223> OTHER INFORMATION: cDNA coding for chimeric CD89

<400> SEQUENCE: 14

```
atggacccca agcagaccac actgctgtgc ctggtgctgt gtctcggcca gagaatccag      60

gctcaagagg gcaacttcag cacccctttc atcagcacca gatctagccc cgtggtgcct     120

tggggcggct ctgttagaat ccagtgccag gccatcagag aggcctacct gacacagctg     180

atgatcatta agaacagcac ctaccgcgag atcggcagac ggctgaagtt ctggaacgag     240

acagaccccg agttcgtgat cgaccacatg gacgccaaca aggccggcag ataccagtgt     300

cagtaccgga tcggccacta ccggttcaga tacagcgaca ccctggaact ggtggtcacc     360

ggcctgtacg gcaagccttt tctgagcgcc gatagaggcc tggtcctgat gcctggcgag     420

aacatcagcc tgacctgtag cagcgctcac atccccttcg acagattcag cctggccaaa     480

gagggcgagc tgtctctgcc tcagcatcag tctggcgagc accccgccaa tttttctctg     540

ggccctgtgg acctgaacgt gtccggcatc tacagatgct acggctggta caatcggagc     600

ccctacctgt ggtctttccc cagcaatgcc ctcgaactgg tcgtgaccga tagcatccac     660

caggactaca ccacacagaa cctgatcaga atggccgtgg ccggactggt gctggttgct     720

ctgctggcta ttctggtgga aaactggcac agccacacag ccctgaacaa agaggcttct     780

gccgacgtcg ccgagccttc ttggagtcag cagatgtgtc agcccggcct gaccttcgcc     840

agaacaccta gcgtgtgcaa g                                               861
```

<210> SEQ ID NO 15
<211> LENGTH: 287

```
<212> TYPE: PRT
<213> ORGANISM: Artificial Sequence
<220> FEATURE:
<223> OTHER INFORMATION: chimeric CD89

<400> SEQUENCE: 15

Met Asp Pro Lys Gln Thr Thr Leu Leu Cys Leu Val Leu Cys Leu Gly
1               5                   10                  15

Gln Arg Ile Gln Ala Gln Glu Gly Asp Phe Pro Met Pro Phe Ile Ser
            20                  25                  30

Ala Lys Ser Ser Pro Val Ile Pro Leu Asp Gly Ser Val Lys Ile Gln
        35                  40                  45

Cys Gln Ala Ile Pro Asp Ala Tyr Leu Ile Trp Leu Met Met Leu Lys
    50                  55                  60

Asn Ser Thr Tyr Glu Lys Arg Gly Arg Arg Leu Lys Phe Trp Asn Glu
65                  70                  75                  80

Thr Asp Pro Glu Phe Val Ile Asp His Met Asp Ala Asn Lys Ala Gly
                85                  90                  95

Arg Tyr Gln Cys Gln Tyr Arg Ile Gly His Tyr Arg Phe Arg Tyr Ser
            100                 105                 110

Asp Thr Leu Glu Leu Val Val Thr Gly Leu Tyr Gly Lys Pro Phe Leu
        115                 120                 125

Ser Ala Asp Arg Gly Leu Val Leu Met Pro Gly Glu Asn Ile Ser Leu
    130                 135                 140

Thr Cys Ser Ser Ala His Ile Pro Phe Asp Arg Phe Ser Leu Ala Lys
145                 150                 155                 160

Glu Gly Glu Leu Ser Leu Pro Gln His Gln Ser Gly Glu His Pro Ala
                165                 170                 175

Asn Phe Ser Leu Gly Pro Val Asp Leu Asn Val Ser Gly Ile Tyr Arg
            180                 185                 190

Cys Tyr Gly Trp Tyr Asn Arg Ser Pro Tyr Leu Trp Ser Phe Pro Ser
        195                 200                 205

Asn Ala Leu Glu Leu Val Val Thr Asp Ser Ile His Gln Asp Tyr Thr
    210                 215                 220

Thr Gln Asn Leu Ile Arg Met Ala Val Ala Gly Leu Val Leu Val Ala
225                 230                 235                 240

Leu Leu Ala Ile Leu Val Glu Asn Trp His Ser His Thr Ala Leu Asn
                245                 250                 255

Lys Glu Ala Ser Ala Asp Val Ala Glu Pro Ser Trp Ser Gln Gln Met
            260                 265                 270

Cys Gln Pro Gly Leu Thr Phe Ala Arg Thr Pro Ser Val Cys Lys
        275                 280                 285


<210> SEQ ID NO 16
<211> LENGTH: 861
<212> TYPE: DNA
<213> ORGANISM: Artificial Sequence
<220> FEATURE:
<223> OTHER INFORMATION: cDNA coding for chimeric CD89

<400> SEQUENCE: 16

atggacccca agcagaccac actgctgtgc ctggtgctgt gtctcggcca gagaatccaa      60

gctcaagagg gcgacttccc catgcctttc atcagcgcca agagcagccc tgtgatccct     120

ctggatggca gcgtgaagat ccagtgccag gccattcctg acgcctacct gatctggctg     180

atgatgctga agaacagcac ctacgagaag agaggcagac ggctgaagtt ctggaacgag     240
```

```
acagaccccg agttcgtgat cgaccacatg gacgccaaca aggccggcag ataccagtgt    300

cagtaccgga tcggccacta ccggttcaga tacagcgaca ccctggaact ggtggtcacc    360

ggcctgtacg gcaagccttt tctgtctgcc gatagaggac tggtgctgat gcccggcgag    420

aacatcagcc tgacctgtag ctctgctcac atccccttcg acagattcag cctggccaaa    480

gaaggcgagc tgagcctgcc tcagcatcag tctggcgaac accccgccaa cttttctctg    540

ggccctgtgg acctgaacgt gtccggcatc tacagatgct acggctggta caatcggagc    600

ccctacctgt ggtctttccc cagcaatgcc ctcgaactgg tcgtgaccga tagcatccac    660

caggactaca ccacacagaa cctgatcaga atggccgtgg ccggcctggt tctggttgct    720

ctgctggcta ttctggtgga aaactggcac agccacacag ccctgaacaa agaggcttct    780

gccgacgtcg ccgagccttc ttggagtcag cagatgtgtc agcccggcct gaccttcgcc    840

agaacaccta gcgtgtgcaa g                                              861
```

<210> SEQ ID NO 17
<211> LENGTH: 287
<212> TYPE: PRT
<213> ORGANISM: Artificial Sequence
<220> FEATURE:
<223> OTHER INFORMATION: chimeric CD89

<400> SEQUENCE: 17

```
Met Asp Pro Lys Gln Thr Thr Leu Leu Cys Leu Val Leu Cys Leu Gly
1               5                   10                  15

Gln Arg Ile Gln Ala Gln Glu Gly Asp Phe Pro Met Pro Phe Ile Ser
            20                  25                  30

Ala Lys Ser Ser Pro Val Ile Pro Leu Asp Gly Ser Val Lys Ile Gln
        35                  40                  45

Cys Gln Ala Ile Arg Glu Ala Tyr Leu Thr Gln Leu Met Ile Ile Lys
    50                  55                  60

Asn Ser Thr Tyr Arg Glu Ile Asp Glu Lys Leu Gly Phe Trp Asn Asp
65                  70                  75                  80

Thr Thr Pro Glu Phe Val Ile Asp His Met Asp Ala Asn Lys Ala Gly
                85                  90                  95

Arg Tyr Gln Cys Gln Tyr Arg Ile Gly His Tyr Arg Phe Arg Tyr Ser
            100                 105                 110

Asp Thr Leu Glu Leu Val Val Thr Gly Leu Tyr Gly Lys Pro Phe Leu
        115                 120                 125

Ser Ala Asp Arg Gly Leu Val Leu Met Pro Gly Glu Asn Ile Ser Leu
    130                 135                 140

Thr Cys Ser Ser Ala His Ile Pro Phe Asp Arg Phe Ser Leu Ala Lys
145                 150                 155                 160

Glu Gly Glu Leu Ser Leu Pro Gln His Gln Ser Gly Glu His Pro Ala
                165                 170                 175

Asn Phe Ser Leu Gly Pro Val Asp Leu Asn Val Ser Gly Ile Tyr Arg
            180                 185                 190

Cys Tyr Gly Trp Tyr Asn Arg Ser Pro Tyr Leu Trp Ser Phe Pro Ser
        195                 200                 205

Asn Ala Leu Glu Leu Val Val Thr Asp Ser Ile His Gln Asp Tyr Thr
    210                 215                 220

Thr Gln Asn Leu Ile Arg Met Ala Val Ala Gly Leu Val Leu Val Ala
225                 230                 235                 240

Leu Leu Ala Ile Leu Val Glu Asn Trp His Ser His Thr Ala Leu Asn
                245                 250                 255
```

```
Lys Glu Ala Ser Ala Asp Val Ala Glu Pro Ser Trp Ser Gln Gln Met
            260                 265                 270

Cys Gln Pro Gly Leu Thr Phe Ala Arg Thr Pro Ser Val Cys Lys
        275                 280                 285
```

<210> SEQ ID NO 18
<211> LENGTH: 861
<212> TYPE: DNA
<213> ORGANISM: Artificial Sequence
<220> FEATURE:
<223> OTHER INFORMATION: cDNA coding for chimeric CD89

<400> SEQUENCE: 18

```
atggacccca agcagaccac actgctgtgc ctggtgctgt gtctcggcca gagaatccaa      60

gctcaagagg gcgacttccc catgcctttc atcagcgcca agagcagccc tgtgatccct     120

ctggatggca gcgtgaagat ccagtgccag gccatcagag aggcctacct gacacagctg     180

atgatcatta agaacagcac ctaccgcgag atcgacgaga agctcggctt ctggaacgac     240

accacacctg agttcgtgat cgaccacatg gacgccaaca aggccggcag ataccagtgt     300

cagtaccgga tcggccacta ccggttcaga tacagcgaca ccctggaact ggtggtcacc     360

ggcctgtacg gcaagccttt tctgtctgcc gatagaggac tggtgctgat gcccggcgag     420

aacatcagcc tgacctgtag ctctgctcac atccccttcg acagattcag cctggccaaa     480

gaaggcgagc tgagcctgcc tcagcatcag tctggcgaac accccgccaa cttttctctg     540

ggccctgtgg acctgaacgt gtccggcatc tacagatgct acggctggta caatcggagc     600

cctacctgt ggtctttccc cagcaatgcc ctcgaactgg tcgtgaccga tagcatccac     660

caggactaca ccacacagaa cctgatcaga atggccgtgg ccggcctggt tctggttgct     720

ctgctggcta ttctggtgga aaactggcac agccacacag ccctgaacaa agaggcttct     780

gccgacgtcg ccgagccttc ttggagtcag cagatgtgtc agcccggcct gaccttcgcc     840

agaacaccta gcgtgtgcaa g                                               861
```

<210> SEQ ID NO 19
<211> LENGTH: 287
<212> TYPE: PRT
<213> ORGANISM: Artificial Sequence
<220> FEATURE:
<223> OTHER INFORMATION: chimeric CD89

<400> SEQUENCE: 19

```
Met Asp Pro Lys Gln Thr Thr Leu Leu Cys Leu Val Leu Cys Leu Gly
1               5                   10                  15

Gln Arg Ile Gln Ala Gln Glu Gly Asp Phe Pro Met Pro Phe Ile Ser
            20                  25                  30

Ala Lys Ser Ser Pro Val Ile Pro Leu Asp Gly Ser Val Lys Ile Gln
        35                  40                  45

Cys Gln Ala Ile Arg Glu Ala Tyr Leu Thr Gln Leu Met Ile Ile Lys
    50                  55                  60

Asn Ser Thr Tyr Arg Glu Ile Gly Arg Arg Leu Lys Phe Trp Asn Glu
65                  70                  75                  80

Thr Asp Pro Glu Phe Val Ile Asp His Met Asp Ala Asn Lys Ala Gly
                85                  90                  95

Arg Tyr Arg Cys Arg Tyr Arg Ile Gly Leu Ser Arg Phe Arg Tyr Ser
            100                 105                 110

Asp Thr Leu Glu Leu Val Val Thr Gly Leu Tyr Gly Lys Pro Phe Leu
```

```
        115                 120                 125

Ser Ala Asp Arg Gly Leu Val Leu Met Pro Gly Glu Asn Ile Ser Leu
    130                 135                 140

Thr Cys Ser Ser Ala His Ile Pro Phe Asp Arg Phe Ser Leu Ala Lys
145                 150                 155                 160

Glu Gly Glu Leu Ser Leu Pro Gln His Gln Ser Gly Glu His Pro Ala
                165                 170                 175

Asn Phe Ser Leu Gly Pro Val Asp Leu Asn Val Ser Gly Ile Tyr Arg
            180                 185                 190

Cys Tyr Gly Trp Tyr Asn Arg Ser Pro Tyr Leu Trp Ser Phe Pro Ser
        195                 200                 205

Asn Ala Leu Glu Leu Val Val Thr Asp Ser Ile His Gln Asp Tyr Thr
    210                 215                 220

Thr Gln Asn Leu Ile Arg Met Ala Val Ala Gly Leu Val Leu Val Ala
225                 230                 235                 240

Leu Leu Ala Ile Leu Val Glu Asn Trp His Ser His Thr Ala Leu Asn
                245                 250                 255

Lys Glu Ala Ser Ala Asp Val Ala Glu Pro Ser Trp Ser Gln Gln Met
            260                 265                 270

Cys Gln Pro Gly Leu Thr Phe Ala Arg Thr Pro Ser Val Cys Lys
        275                 280                 285
```

<210> SEQ ID NO 20
<211> LENGTH: 861
<212> TYPE: DNA
<213> ORGANISM: Artificial Sequence
<220> FEATURE:
<223> OTHER INFORMATION: cDNA coding for chimeric CD89

<400> SEQUENCE: 20

```
atggacccca agcagaccac actgctgtgc ctggtgctgt gtctcggcca gagaatccaa      60

gctcaagagg gcgacttccc catgcctttc atcagcgcca agagcagccc tgtgatccct     120

ctggatggca gcgtgaagat ccagtgccag gccatcagag aggcctacct gacacagctg     180

atgatcatta agaacagcac ctaccgcgag atcggcagac ggctgaagtt ctggaacgag     240

acagaccccg agttcgtgat cgaccacatg gacgccaaca aggccggcag ataccggtgc     300

agatacagaa tcggcctgag ccggttccgg tacagcgata cactggaact ggtggtcacc     360

ggcctgtacg gcaagccttt tctgagcgcc gatagaggac tggtgctgat gcccggcgag     420

aacatcagcc tgacctgtag ctctgctcac atccccttcg acagattcag cctggccaaa     480

gaaggcgagc tgagcctgcc tcagcatcag tctggcgaac accccgccaa cttttctctg     540

ggccctgtgg acctgaacgt gtccggcatc tacagatgct acggctggta caatcggagc     600

ccctacctgt ggtctttccc cagcaatgcc ctggaactcg tcgtgaccga tagcatccac     660

caggactaca ccacacagaa cctgatcaga atggccgtgg ccggcctggt tctggttgct     720

ctgctggcta ttctggtgga aaactggcac agccacacag ccctgaacaa agaggcttct     780

gccgacgtcg ccgagccttc ttggagtcag cagatgtgtc agcccggcct gaccttcgcc     840

agaacaccta gcgtgtgcaa g                                               861
```

<210> SEQ ID NO 21
<211> LENGTH: 287
<212> TYPE: PRT
<213> ORGANISM: Artificial Sequence
<220> FEATURE:
<223> OTHER INFORMATION: chimeric CD89

<400> SEQUENCE: 21

```
Met Asp Pro Lys Gln Thr Thr Leu Leu Cys Leu Val Leu Cys Leu Gly
1               5                   10                  15

Gln Arg Ile Gln Ala Gln Glu Gly Asp Phe Pro Met Pro Phe Ile Ser
            20                  25                  30

Ala Lys Ser Ser Pro Val Ile Pro Leu Asp Gly Ser Val Lys Ile Gln
        35                  40                  45

Cys Gln Ala Ile Arg Glu Ala Tyr Leu Ile Trp Leu Met Ile Ile Lys
    50                  55                  60

Asn Ser Thr Tyr Arg Glu Ile Gly Glu Lys Leu Gly Phe Trp Asn Glu
65                  70                  75                  80

Thr Asp Pro Glu Phe Val Ile Asp His Met Asp Ala Asn Lys Ala Gly
                85                  90                  95

Arg Tyr Gln Cys Gln Tyr Arg Ile Gly Leu Ser Arg Phe Arg Tyr Ser
            100                 105                 110

Asp Thr Leu Glu Leu Val Val Thr Gly Leu Tyr Gly Lys Pro Phe Leu
        115                 120                 125

Ser Ala Asp Arg Gly Leu Val Leu Met Pro Gly Glu Asn Ile Ser Leu
    130                 135                 140

Thr Cys Ser Ser Ala His Ile Pro Phe Asp Arg Phe Ser Leu Ala Lys
145                 150                 155                 160

Glu Gly Glu Leu Ser Leu Pro Gln His Gln Ser Gly Glu His Pro Ala
                165                 170                 175

Asn Phe Ser Leu Gly Pro Val Asp Leu Asn Val Ser Gly Ile Tyr Arg
            180                 185                 190

Cys Tyr Gly Trp Tyr Asn Arg Ser Pro Tyr Leu Trp Ser Phe Pro Ser
        195                 200                 205

Asn Ala Leu Glu Leu Val Val Thr Asp Ser Ile His Gln Asp Tyr Thr
    210                 215                 220

Thr Gln Asn Leu Ile Arg Met Ala Val Ala Gly Leu Val Leu Val Ala
225                 230                 235                 240

Leu Leu Ala Ile Leu Val Glu Asn Trp His Ser His Thr Ala Leu Asn
                245                 250                 255

Lys Glu Ala Ser Ala Asp Val Ala Glu Pro Ser Trp Ser Gln Gln Met
            260                 265                 270

Cys Gln Pro Gly Leu Thr Phe Ala Arg Thr Pro Ser Val Cys Lys
        275                 280                 285
```

<210> SEQ ID NO 22
<211> LENGTH: 861
<212> TYPE: DNA
<213> ORGANISM: Artificial Sequence
<220> FEATURE:
<223> OTHER INFORMATION: cDNA coding for chimeric CD89

<400> SEQUENCE: 22

```
atggacccca agcagaccac actgctgtgc ctggtgctgt gtctcggcca gagaatccaa      60

gctcaagagg gcgacttccc catgcctttc atcagcgcca agagcagccc tgtgatccct     120

ctggatggca gcgtgaagat ccagtgccag gccatcagag aggcctacct gatctggctg     180

atgatcatta agaacagcac ctaccgcgag atcggcgaga agctcggctt ctggaacgag     240

acagaccccg agttcgtgat cgaccacatg gacgccaaca aggccggcag ataccagtgt     300

cagtaccgga tcggcctgag ccggttcaga tacagcgata ccctggaact ggtggtcacc     360
```

```
ggcctgtacg gcaagccttt tctgtctgcc gatagaggac tggtgctgat gcccggcgag    420

aacatcagcc tgacctgtag ctctgctcac atccccttcg acagattcag cctggccaaa    480

gaaggcgagc tgagcctgcc tcagcatcag tctggcgaac accccgccaa cttttctctg    540

ggccctgtgg acctgaacgt gtccggcatc tacagatgct acggctggta caatcggagc    600

ccctacctgt ggtctttccc cagcaatgcc ctcgaactgg tcgtgaccga tagcatccac    660

caggactaca ccacacagaa cctgatcaga atggccgtgg ccggcctggt tctggttgct    720

ctgctggcta ttctggtgga aaactggcac agccacacag ccctgaacaa agaggcttct    780

gccgacgtcg ccgagccttc ttggagtcag cagatgtgtc agcccggcct gaccttcgcc    840

agaacaccta gcgtgtgcaa g                                              861


<210> SEQ ID NO 23
<211> LENGTH: 25
<212> TYPE: PRT
<213> ORGANISM: Homo sapiens

<400> SEQUENCE: 23

Gln Glu Gly Asp Phe Pro Met Pro Phe Ile Ser Ala Lys Ser Ser Pro
1               5                   10                  15

Val Ile Pro Leu Asp Gly Ser Val Lys
            20                  25


<210> SEQ ID NO 24
<211> LENGTH: 25
<212> TYPE: PRT
<213> ORGANISM: Homo sapiens

<400> SEQUENCE: 24

Ile Gln Cys Gln Ala Ile Arg Glu Ala Tyr Leu Thr Gln Leu Met Ile
1               5                   10                  15

Ile Lys Asn Ser Thr Tyr Arg Glu Ile
            20                  25


<210> SEQ ID NO 25
<211> LENGTH: 25
<212> TYPE: PRT
<213> ORGANISM: Homo sapiens

<400> SEQUENCE: 25

Gly Arg Arg Leu Lys Phe Trp Asn Glu Thr Asp Pro Glu Phe Val Ile
1               5                   10                  15

Asp His Met Asp Ala Asn Lys Ala Gly
            20                  25


<210> SEQ ID NO 26
<211> LENGTH: 25
<212> TYPE: PRT
<213> ORGANISM: Homo sapiens

<400> SEQUENCE: 26

Arg Tyr Gln Cys Gln Tyr Arg Ile Gly His Tyr Arg Phe Arg Tyr Ser
1               5                   10                  15

Asp Thr Leu Glu Leu Val Val Thr Gly
            20                  25


<210> SEQ ID NO 27
<211> LENGTH: 120
<212> TYPE: PRT
<213> ORGANISM: Artificial Sequence
```

```
<220> FEATURE:
<223> OTHER INFORMATION: Consensus amino acid sequence of heavy chain
      variable region of mouse anti-human CD89-specific antibody 8F3

<400> SEQUENCE: 27

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Lys Arg Leu Glu Trp Val
        35                  40                  45

Ala Thr Met His Ser Gly Gly Thr Tyr Thr Tyr Tyr Pro Asp Asn Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Met Tyr Tyr Cys
                85                  90                  95

Ala Arg Glu Thr Gly Leu Tyr Asp Gly Leu Phe Asp Phe Trp Gly Gln
            100                 105                 110

Gly Thr Thr Leu Thr Val Ser Ser
        115                 120


<210> SEQ ID NO 28
<211> LENGTH: 107
<212> TYPE: PRT
<213> ORGANISM: Artificial Sequence
<220> FEATURE:
<223> OTHER INFORMATION: Consensus amino acid sequence of light chain
      variable region of mouse anti-human CD89-specific antibody 8F3

<400> SEQUENCE: 28

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Thr Ile Ser Lys Tyr
            20                  25                  30

Leu Ala Trp Tyr Gln Glu Lys Pro Gly Lys Thr Asn Met Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Leu Ala Met Tyr Tyr Cys Gln Gln His Asp Glu Tyr Pro Trp
                85                  90                  95

Thr Phe Gly Gly Gly Thr Lys Leu Glu Ile Lys
            100                 105


<210> SEQ ID NO 29
<211> LENGTH: 5
<212> TYPE: PRT
<213> ORGANISM: Artificial Sequence
<220> FEATURE:
<223> OTHER INFORMATION: heavy chain CDR1 of 8F3

<400> SEQUENCE: 29

Asn Tyr Gly Met Ser
1               5


<210> SEQ ID NO 30
<211> LENGTH: 17
<212> TYPE: PRT
```

<213> ORGANISM: Artificial Sequence
<220> FEATURE:
<223> OTHER INFORMATION: heavy chain CDR2 of 8F3

<400> SEQUENCE: 30

Thr Met His Ser Gly Gly Thr Tyr Thr Tyr Tyr Pro Asp Asn Val Lys
1 5 10 15

Gly

<210> SEQ ID NO 31
<211> LENGTH: 11
<212> TYPE: PRT
<213> ORGANISM: Artificial Sequence
<220> FEATURE:
<223> OTHER INFORMATION: heavy chain CDR3 of 8F3

<400> SEQUENCE: 31

Glu Thr Gly Leu Tyr Asp Gly Leu Phe Asp Phe
1 5 10

<210> SEQ ID NO 32
<211> LENGTH: 11
<212> TYPE: PRT
<213> ORGANISM: Artificial Sequence
<220> FEATURE:
<223> OTHER INFORMATION: light chain CDR1 of 8F3

<400> SEQUENCE: 32

Arg Ala Ser Lys Thr Ile Ser Lys Tyr Leu Ala
1 5 10

<210> SEQ ID NO 33
<211> LENGTH: 7
<212> TYPE: PRT
<213> ORGANISM: Artificial Sequence
<220> FEATURE:
<223> OTHER INFORMATION: light chain CDR2 of 8F3

<400> SEQUENCE: 33

Ser Gly Ser Thr Leu Gln Ser
1 5

<210> SEQ ID NO 34
<211> LENGTH: 9
<212> TYPE: PRT
<213> ORGANISM: Artificial Sequence
<220> FEATURE:
<223> OTHER INFORMATION: light chain CDR3 of 8F3

<400> SEQUENCE: 34

Gln Gln His Asp Glu Tyr Pro Trp Thr
1 5

<210> SEQ ID NO 35
<211> LENGTH: 122
<212> TYPE: PRT
<213> ORGANISM: Artificial Sequence
<220> FEATURE:
<223> OTHER INFORMATION: Consensus amino acid sequence of heavy chain variable region of mouse anti-human CD89-specific antibody 9H7

<400> SEQUENCE: 35

Gln Ile Gln Leu Val Gln Ser Gly Pro Glu Leu Lys Lys Pro Gly Glu
1 5 10 15

Thr Val Lys Ile Ser Cys Lys Ala Ser Gly Tyr Thr Phe Lys Asn Tyr
20 25 30

```
Gly Met Asn Trp Val Lys Gln Ala Pro Gly Lys Gly Leu Lys Trp Met
        35                  40                  45

Ala Trp Ile Asn Thr Tyr Thr Gly Glu Pro Thr His Thr Asp Asp Phe
    50                  55                  60

Lys Gly Arg Phe Val Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Trp Gly Leu Gly Thr Thr Glu Glu Ala Ala Arg Asp Tyr Trp
            100                 105                 110

Gly Gln Gly Thr Thr Leu Thr Val Ser Ser
        115                 120


<210> SEQ ID NO 36
<211> LENGTH: 112
<212> TYPE: PRT
<213> ORGANISM: Artificial Sequence
<220> FEATURE:
<223> OTHER INFORMATION: Consensus amino acid sequence of light chain
      variable region of mouse anti-human CD89-specific antibody 9H7

<400> SEQUENCE: 36

Asp Val Val Met Thr Gln Thr Pro Leu Thr Leu Ser Val Thr Ile Gly
1               5                   10                  15

Gln Pro Ala Ser Met Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Ser Leu Ile Tyr Leu Val Ser Lys Gln Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110


<210> SEQ ID NO 37
<211> LENGTH: 5
<212> TYPE: PRT
<213> ORGANISM: Artificial Sequence
<220> FEATURE:
<223> OTHER INFORMATION: heavy chain CDR1 of 9H7

<400> SEQUENCE: 37

Asn Tyr Gly Met Asn
1               5


<210> SEQ ID NO 38
<211> LENGTH: 17
<212> TYPE: PRT
<213> ORGANISM: Artificial Sequence
<220> FEATURE:
<223> OTHER INFORMATION: heavy chain CDR2 of 9H7

<400> SEQUENCE: 38

Trp Ile Asn Thr Tyr Thr Gly Glu Pro Thr His Thr Asp Asp Phe Lys
1               5                   10                  15

Gly
```

```
<210> SEQ ID NO 39
<211> LENGTH: 13
<212> TYPE: PRT
<213> ORGANISM: Artificial Sequence
<220> FEATURE:
<223> OTHER INFORMATION: heavy chain CDR3 of 9H7

<400> SEQUENCE: 39

Trp Gly Leu Gly Thr Thr Glu Glu Ala Ala Arg Asp Tyr
1               5                   10


<210> SEQ ID NO 40
<211> LENGTH: 16
<212> TYPE: PRT
<213> ORGANISM: Artificial Sequence
<220> FEATURE:
<223> OTHER INFORMATION: light chain CDR1 of 9H7

<400> SEQUENCE: 40

Lys Ser Ser Gln Ser Leu Leu Asp Ser Asp Gly Lys Thr Tyr Leu Asn
1               5                   10                  15


<210> SEQ ID NO 41
<211> LENGTH: 7
<212> TYPE: PRT
<213> ORGANISM: Artificial Sequence
<220> FEATURE:
<223> OTHER INFORMATION: light chain CDR2 of 9H7

<400> SEQUENCE: 41

Leu Val Ser Lys Gln Asp Ser
1               5


<210> SEQ ID NO 42
<211> LENGTH: 9
<212> TYPE: PRT
<213> ORGANISM: Artificial Sequence
<220> FEATURE:
<223> OTHER INFORMATION: light chain CDR3 of 9H7

<400> SEQUENCE: 42

Trp Gln Gly Thr His Phe Pro Gln Thr
1               5


<210> SEQ ID NO 43
<211> LENGTH: 119
<212> TYPE: PRT
<213> ORGANISM: Artificial Sequence
<220> FEATURE:
<223> OTHER INFORMATION: Consensus amino acid sequence of heavy chain
      variable region of mouse anti-human CD89-specific antibody 10E7

<400> SEQUENCE: 43

Glu Val Gln Leu Val Glu Ser Gly Gly Gly Leu Val Gln Pro Gly Gly
1               5                   10                  15

Ser Leu Lys Leu Ser Cys Ala Ala Ser Gly Leu Thr Phe Ser Ser Tyr
            20                  25                  30

Gly Met Ser Trp Val Arg Gln Thr Pro Asp Lys Arg Leu Glu Leu Val
        35                  40                  45

Ala Thr Ile Asn Gly Asn Gly Asp Ile Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
```

```
                85                  90                  95

Ala Arg Asp Tyr Asp Tyr Asp Tyr Ala Met Asp Tyr Trp Gly Gln Gly
            100                 105                 110

Thr Ser Val Thr Val Ser Ser
        115


<210> SEQ ID NO 44
<211> LENGTH: 107
<212> TYPE: PRT
<213> ORGANISM: Artificial Sequence
<220> FEATURE:
<223> OTHER INFORMATION: Consensus amino acid sequence of light chain
      variable region of mouse anti-human CD89-specific antibody 10E7

<400> SEQUENCE: 44

Asp Ile Gln Met Thr Gln Ser Thr Ser Ser Leu Ser Ala Ser Leu Gly
1               5                   10                  15

Asp Ser Val Thr Ile Ser Cys Arg Ala Ser Gln Asp Ile Ile Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Glu Tyr Ser Leu Thr Val Ser Asn Leu Glu Lys
65                  70                  75                  80

Glu Asp Ile Ala Thr Tyr Phe Cys Gln Gln Gly Lys Thr Leu Pro Tyr
                85                  90                  95

Thr Phe Gly Gly Gly Thr Lys Leu Glu Ile Lys
            100                 105


<210> SEQ ID NO 45
<211> LENGTH: 5
<212> TYPE: PRT
<213> ORGANISM: Artificial Sequence
<220> FEATURE:
<223> OTHER INFORMATION: heavy chain CDR1 of 10E7

<400> SEQUENCE: 45

Ser Tyr Gly Met Ser
1               5


<210> SEQ ID NO 46
<211> LENGTH: 17
<212> TYPE: PRT
<213> ORGANISM: Artificial Sequence
<220> FEATURE:
<223> OTHER INFORMATION: heavy chain CDR2 of 10E7

<400> SEQUENCE: 46

Thr Ile Asn Gly Asn Gly Asp Ile Thr Tyr Tyr Pro Asp Ser Val Lys
1               5                   10                  15

Gly


<210> SEQ ID NO 47
<211> LENGTH: 10
<212> TYPE: PRT
<213> ORGANISM: Artificial Sequence
<220> FEATURE:
<223> OTHER INFORMATION: heavy chain CDR3 of 10E7

<400> SEQUENCE: 47

Asp Tyr Asp Tyr Asp Tyr Ala Met Asp Tyr
```

```
1               5                   10


<210> SEQ ID NO 48
<211> LENGTH: 11
<212> TYPE: PRT
<213> ORGANISM: Artificial Sequence
<220> FEATURE:
<223> OTHER INFORMATION: light chain CDR1 of 10E7

<400> SEQUENCE: 48

Arg Ala Ser Gln Asp Ile Ile Asn Tyr Leu Asn
1               5                   10


<210> SEQ ID NO 49
<211> LENGTH: 7
<212> TYPE: PRT
<213> ORGANISM: Artificial Sequence
<220> FEATURE:
<223> OTHER INFORMATION: light chain CDR2 of 10E7

<400> SEQUENCE: 49

Tyr Thr Ser Arg Leu His Ser
1               5


<210> SEQ ID NO 50
<211> LENGTH: 9
<212> TYPE: PRT
<213> ORGANISM: Artificial Sequence
<220> FEATURE:
<223> OTHER INFORMATION: light chain CDR3 of 10E7

<400> SEQUENCE: 50

Gln Gln Gly Lys Thr Leu Pro Tyr Thr
1               5


<210> SEQ ID NO 51
<211> LENGTH: 121
<212> TYPE: PRT
<213> ORGANISM: Artificial Sequence
<220> FEATURE:
<223> OTHER INFORMATION: Consensus amino acid sequence of heavy chain
      variable region of mouse anti-human CD89-specific antibody 16D6

<400> SEQUENCE: 51

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Thr Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Ala Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Phe Glu Asp Ser Ala Val Tyr Tyr Cys
                85                  90                  95

Ala Lys Gly Phe Gly Ser Pro Tyr Tyr Tyr Ala Met Asp Tyr Trp Gly
            100                 105                 110

Gln Gly Thr Ser Val Thr Val Ser Ser
        115                 120


<210> SEQ ID NO 52
<211> LENGTH: 108
```

```
<212> TYPE: PRT
<213> ORGANISM: Artificial Sequence
<220> FEATURE:
<223> OTHER INFORMATION: Consensus amino acid sequence of light chain
      variable region of mouse anti-human CD89-specific antibody 16D6

<400> SEQUENCE: 52

Glu Ile Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Asn Leu His Trp Tyr Gln Gln Lys Ser Glu Thr Ser Pro Lys Pro Trp
        35                  40                  45

Ile Tyr Gly Thr Ser Lys Leu Ala Ser Gly Val Pro Val Arg Phe Ser
    50                  55                  60

Gly Ser Gly Ser Gly Thr Ser Tyr Ser Leu Thr Ile Ser Asn Met Glu
65                  70                  75                  80

Ala Glu Asp Ala Ala Thr Tyr Tyr Cys Gln Gln Trp Ser Ser Phe Pro
                85                  90                  95

Leu Thr Phe Gly Gly Gly Thr Lys Leu Glu Ile Lys
            100                 105


<210> SEQ ID NO 53
<211> LENGTH: 5
<212> TYPE: PRT
<213> ORGANISM: Artificial Sequence
<220> FEATURE:
<223> OTHER INFORMATION: heavy chain CDR1 of 16D6

<400> SEQUENCE: 53

Thr Tyr Trp Ile Glu
1               5


<210> SEQ ID NO 54
<211> LENGTH: 17
<212> TYPE: PRT
<213> ORGANISM: Artificial Sequence
<220> FEATURE:
<223> OTHER INFORMATION: heavy chain CDR2 of 16D6

<400> SEQUENCE: 54

Glu Ile Leu Pro Gly Ser Gly Ser Ala Asn Tyr Asn Glu Lys Phe Lys
1               5                   10                  15

Gly


<210> SEQ ID NO 55
<211> LENGTH: 12
<212> TYPE: PRT
<213> ORGANISM: Artificial Sequence
<220> FEATURE:
<223> OTHER INFORMATION: heavy chain CDR3 of 16D6

<400> SEQUENCE: 55

Gly Phe Gly Ser Pro Tyr Tyr Tyr Ala Met Asp Tyr
1               5                   10


<210> SEQ ID NO 56
<211> LENGTH: 12
<212> TYPE: PRT
<213> ORGANISM: Artificial Sequence
<220> FEATURE:
<223> OTHER INFORMATION: light chain CDR1 of 16D6

<400> SEQUENCE: 56
```

```
Ser Val Ser Ser Ser Ile Ser Ser Ser Asn Leu His
1               5                   10


<210> SEQ ID NO 57
<211> LENGTH: 7
<212> TYPE: PRT
<213> ORGANISM: Artificial Sequence
<220> FEATURE:
<223> OTHER INFORMATION: light chain CDR2 of 16D6

<400> SEQUENCE: 57

Gly Thr Ser Lys Leu Ala Ser
1               5


<210> SEQ ID NO 58
<211> LENGTH: 9
<212> TYPE: PRT
<213> ORGANISM: Artificial Sequence
<220> FEATURE:
<223> OTHER INFORMATION: light chain CDR3 of 16D6

<400> SEQUENCE: 58

Gln Gln Trp Ser Ser Phe Pro Leu Thr
1               5


<210> SEQ ID NO 59
<211> LENGTH: 120
<212> TYPE: PRT
<213> ORGANISM: Artificial Sequence
<220> FEATURE:
<223> OTHER INFORMATION: Consensus amino acid sequence of heavy chain
      variable region of mouse anti-human CD89-specific antibody 26D6

<400> SEQUENCE: 59

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Leu Thr Lys Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Ser Leu Pro Leu Phe Gly Arg Asp Ser Phe Ala Tyr Trp Gly Gln
            100                 105                 110

Gly Thr Leu Val Thr Val Ser Ala
        115                 120


<210> SEQ ID NO 60
<211> LENGTH: 112
<212> TYPE: PRT
<213> ORGANISM: Artificial Sequence
<220> FEATURE:
<223> OTHER INFORMATION: Consensus amino acid sequence of light chain
      variable region of mouse anti-human CD89-specific antibody 26D6

<400> SEQUENCE: 60

Asp Val Val Met Thr Gln Thr Pro Leu Thr Leu Ser Val Thr Ile Gly
1               5                   10                  15
```

```
Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Val
                85                  90                  95

Thr His Phe Pro Gln Thr Phe Gly Gly Gly Thr Lys Leu Glu Ile Lys
            100                 105                 110


<210> SEQ ID NO 61
<211> LENGTH: 5
<212> TYPE: PRT
<213> ORGANISM: Artificial Sequence
<220> FEATURE:
<223> OTHER INFORMATION: heavy chain CDR1 of 26D6

<400> SEQUENCE: 61

Lys Tyr Gly Met Asn
1               5


<210> SEQ ID NO 62
<211> LENGTH: 17
<212> TYPE: PRT
<213> ORGANISM: Artificial Sequence
<220> FEATURE:
<223> OTHER INFORMATION: heavy chain CDR2 of 26D6

<400> SEQUENCE: 62

Trp Ile Asn Thr Tyr Thr Gly Glu Pro Thr Tyr Ala Asp Asp Phe Lys
1               5                   10                  15

Gly


<210> SEQ ID NO 63
<211> LENGTH: 11
<212> TYPE: PRT
<213> ORGANISM: Artificial Sequence
<220> FEATURE:
<223> OTHER INFORMATION: heavy chain CDR3 of 26D6

<400> SEQUENCE: 63

Leu Pro Leu Phe Gly Arg Asp Ser Phe Ala Tyr
1               5                   10


<210> SEQ ID NO 64
<211> LENGTH: 16
<212> TYPE: PRT
<213> ORGANISM: Artificial Sequence
<220> FEATURE:
<223> OTHER INFORMATION: light chain CDR1 of 26D6

<400> SEQUENCE: 64

Lys Ser Ser Gln Ser Leu Leu Asp Ser Asp Gly Lys Thr Tyr Leu Asn
1               5                   10                  15


<210> SEQ ID NO 65
<211> LENGTH: 7
<212> TYPE: PRT
<213> ORGANISM: Artificial Sequence
<220> FEATURE:
<223> OTHER INFORMATION: light chain CDR2 of 26D6
```

<400> SEQUENCE: 65

```
Leu Val Ser Lys Leu Asp Ser
1               5
```

<210> SEQ ID NO 66
<211> LENGTH: 9
<212> TYPE: PRT
<213> ORGANISM: Artificial Sequence
<220> FEATURE:
<223> OTHER INFORMATION: light chain CDR3 of 26D6

<400> SEQUENCE: 66

```
Trp Gln Val Thr His Phe Pro Gln Thr
1               5
```

<210> SEQ ID NO 67
<211> LENGTH: 116
<212> TYPE: PRT
<213> ORGANISM: Artificial Sequence
<220> FEATURE:
<223> OTHER INFORMATION: Consensus amino acid sequence of heavy chain variable region of mouse anti-human CD89-specific antibody 20B4

<400> SEQUENCE: 67

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Ile Ile Trp Ala Gly Gly Ser Thr Ser Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Asp His Tyr Asp Leu Phe Ala Tyr Trp Gly Gln Gly Thr Leu Val
            100                 105                 110

Thr Val Ser Ala
        115
```

<210> SEQ ID NO 68
<211> LENGTH: 107
<212> TYPE: PRT
<213> ORGANISM: Artificial Sequence
<220> FEATURE:
<223> OTHER INFORMATION: Consensus amino acid sequence of light chain variable region of mouse anti-human CD89-specific antibody 20B4

<400> SEQUENCE: 68

```
Asp Ile Leu Met Thr Gln Ser Pro Ser Ser Met Ser Val Ser Leu Gly
1               5                   10                  15

Asp Thr Val Ser Ile Thr Cys His Ala Ser Gln Asp Ile Ser Arg Asn
            20                  25                  30

Ile Gly Trp Leu Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Ala Asp Tyr Ser Leu Thr Ile Ser Ser Leu Glu Ser
65                  70                  75                  80
```

```
Glu Asp Phe Ala Asp Tyr Tyr Cys Val Gln Tyr Ala Gln Phe Pro Arg
                85                  90                  95

Thr Phe Gly Gly Gly Thr Lys Leu Glu Ile Lys
            100                 105


<210> SEQ ID NO 69
<211> LENGTH: 5
<212> TYPE: PRT
<213> ORGANISM: Artificial Sequence
<220> FEATURE:
<223> OTHER INFORMATION: heavy chain CDR1 of 20B4

<400> SEQUENCE: 69

Ser Tyr Gly Val His
1               5


<210> SEQ ID NO 70
<211> LENGTH: 16
<212> TYPE: PRT
<213> ORGANISM: Artificial Sequence
<220> FEATURE:
<223> OTHER INFORMATION: heavy chain CDR2 of 20B4

<400> SEQUENCE: 70

Ile Ile Trp Ala Gly Gly Ser Thr Ser Tyr Asn Ser Ala Leu Met Ser
1               5                   10                  15


<210> SEQ ID NO 71
<211> LENGTH: 8
<212> TYPE: PRT
<213> ORGANISM: Artificial Sequence
<220> FEATURE:
<223> OTHER INFORMATION: heavy chain CDR3 of 20B4

<400> SEQUENCE: 71

Asp His Tyr Asp Leu Phe Ala Tyr
1               5


<210> SEQ ID NO 72
<211> LENGTH: 11
<212> TYPE: PRT
<213> ORGANISM: Artificial Sequence
<220> FEATURE:
<223> OTHER INFORMATION: light chain CDR1 of 20B4

<400> SEQUENCE: 72

His Ala Ser Gln Asp Ile Ser Arg Asn Ile Gly
1               5                   10


<210> SEQ ID NO 73
<211> LENGTH: 7
<212> TYPE: PRT
<213> ORGANISM: Artificial Sequence
<220> FEATURE:
<223> OTHER INFORMATION: light chain CDR2 of 20B4

<400> SEQUENCE: 73

His Gly Thr Asn Leu Glu Asp
1               5


<210> SEQ ID NO 74
<211> LENGTH: 9
<212> TYPE: PRT
<213> ORGANISM: Artificial Sequence
<220> FEATURE:
<223> OTHER INFORMATION: light chain CDR3 of 20B4
```

<400> SEQUENCE: 74

```
Val Gln Tyr Ala Gln Phe Pro Arg Thr
1               5
```

<210> SEQ ID NO 75
<211> LENGTH: 118
<212> TYPE: PRT
<213> ORGANISM: Artificial Sequence
<220> FEATURE:
<223> OTHER INFORMATION: Consensus amino acid sequence of heavy chain variable region of mouse anti-human CD89-specific antibody 30C7

<400> SEQUENCE: 75

```
Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Val Met His Trp Val Lys Gln Ser His Ala Lys Ser Leu Glu Trp Ile
        35                  40                  45

Gly Val Ile Ser Thr Tyr Ser Gly Asn Thr Asn Tyr Asn Gln Lys Phe
    50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Glu Ser Asp Gly Tyr Tyr Phe Asp Tyr Trp Gly Gln Gly Thr
            100                 105                 110

Thr Leu Thr Val Ser Ser
        115
```

<210> SEQ ID NO 76
<211> LENGTH: 113
<212> TYPE: PRT
<213> ORGANISM: Artificial Sequence
<220> FEATURE:
<223> OTHER INFORMATION: Consensus amino acid sequence of light chain variable region of mouse anti-human CD89-specific antibody 30C7

<400> SEQUENCE: 76

```
Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Met Tyr Thr Phe Gly Gly Gly Thr Lys Leu Glu Ile
            100                 105                 110

Lys
```

<210> SEQ ID NO 77
<211> LENGTH: 5
<212> TYPE: PRT

<213> ORGANISM: Artificial Sequence
<220> FEATURE:
<223> OTHER INFORMATION: heavy chain CDR1 of 30C7

<400> SEQUENCE: 77

Asp Tyr Val Met His
1 5

<210> SEQ ID NO 78
<211> LENGTH: 17
<212> TYPE: PRT
<213> ORGANISM: Artificial Sequence
<220> FEATURE:
<223> OTHER INFORMATION: heavy chain CDR2 of 30C7

<400> SEQUENCE: 78

Val Ile Ser Thr Tyr Ser Gly Asn Thr Asn Tyr Asn Gln Lys Phe Lys
1 5 10 15

Gly

<210> SEQ ID NO 79
<211> LENGTH: 9
<212> TYPE: PRT
<213> ORGANISM: Artificial Sequence
<220> FEATURE:
<223> OTHER INFORMATION: heavy chain CDR3 of 30C7

<400> SEQUENCE: 79

Glu Ser Asp Gly Tyr Tyr Phe Asp Tyr
1 5

<210> SEQ ID NO 80
<211> LENGTH: 17
<212> TYPE: PRT
<213> ORGANISM: Artificial Sequence
<220> FEATURE:
<223> OTHER INFORMATION: light chain CDR1 of 30C7

<400> SEQUENCE: 80

Lys Ser Ser Gln Ser Leu Leu Asn Ser Arg Thr Arg Lys Asn Tyr Leu
1 5 10 15

Ala

<210> SEQ ID NO 81
<211> LENGTH: 7
<212> TYPE: PRT
<213> ORGANISM: Artificial Sequence
<220> FEATURE:
<223> OTHER INFORMATION: light chain CDR2 of 30C7

<400> SEQUENCE: 81

Trp Ala Ser Thr Arg Glu Ser
1 5

<210> SEQ ID NO 82
<211> LENGTH: 9
<212> TYPE: PRT
<213> ORGANISM: Artificial Sequence
<220> FEATURE:
<223> OTHER INFORMATION: light chain CDR3 of 30C7

<400> SEQUENCE: 82

Lys Gln Ser Tyr Asn Leu Met Tyr Thr
1 5

<210> SEQ ID NO 83
<211> LENGTH: 1398
<212> TYPE: DNA
<213> ORGANISM: Artificial Sequence
<220> FEATURE:
<223> OTHER INFORMATION: cDNA coding for chimeric mouse VH 8F3 human heavy IgG4 chain

<400> SEQUENCE: 83

```
atggagctgg gcctgagctg gatttttctg ctggccatcc tgaagggcgt gcagtgcgaa     60
gtgcagctgg ttgaatctgg cggcggactg gttaagcctg gcggatctct gaagctgagc    120
tgtgccgcca gcggcttcac cttcagcaat tacggcatga gctgggtccg acagacccct    180
gacaagagac tggaatgggt cgccacaatg cacagcggcg gcacctacac ctactatccc    240
gacaacgtga agggcagatt caccatcagc cgggacaacg ccaagaacaa cctgtacctg    300
cagatgagca gcctgcggag cgaggatacc gccatgtact actgcgccag agaaaccggc    360
ctgtacgacg gcctgttcga tttttggggc cagggcacca cactgaccgt gtctagcgcc    420
tctacaaagg gccctagcgt gttccctctg gctccttgta gcagaagcac cagcgagtct    480
acagccgctc tgggctgtct ggtcaaggac tactttcccg agcctgtgac agtgtcctgg    540
aactctggcg ctctgacaag cggcgtgcac acatttccag ccgtgctgca aagcagcggc    600
ctgtattctc tgagcagcgt ggtcacagtg cccagctcta gcctgggcac caagacctac    660
acatgcaatg tggaccacaa gcctagcaac accaaggtgg acaagcgcgt ggaatctaag    720
tacggccctc cttgtcctcc atgtcctgca cctgagtttc tcggcggacc ctccgtgttc    780
ctgtttcctc caaagcctaa ggacaccctg atgatcagca gaacccctga agtgacctgc    840
gtggtggtgg acgtttccca agaggaccct gaggtgcagt tcaattggta cgtggacggc    900
gtggaagtgc acaatgccaa gaccaagcct agagaggaac agttcaacag cacctacaga    960
gtggtgtccg tgctgacagt gctgcaccag gattggctga acggcaaaga gtacaagtgc   1020
aaggtgtcca acaagggcct gcctagcagc atcgagaaaa ccatcagcaa ggccaagggc   1080
cagccaagag aaccccaggt gtacacactg cctccaagcc aagaggaaat gaccaagaac   1140
caggtgtccc tgacctgcct ggttaagggc ttctacccct ccgatatcgc cgtggaatgg   1200
gagagcaatg gccagcctga gaacaactac aagaccacac ctcctgtgct ggacagcgac   1260
ggctcattct tcctgtacag caggctgacc gtggacaaga gcagatggca agagggcaac   1320
gtgttcagct gcagcgtgat gcacgaggcc ctgcacaacc actacaccca gaagtctctg   1380
agcctgtctc tgggcaag                                                 1398
```

<210> SEQ ID NO 84
<211> LENGTH: 1395
<212> TYPE: DNA
<213> ORGANISM: Artificial Sequence
<220> FEATURE:
<223> OTHER INFORMATION: cDNA coding for chimeric mouse VH 10E7 human heavy IgG4 chain

<400> SEQUENCE: 84

```
atggagctgg gcctgagctg gatttttctg ctggccatcc tgaagggcgt gcagtgcgaa     60
gtgcagctgg ttgaatctgg cggaggactg gttcagcctg gcggatctct gaagctgtct    120
tgtgccgcct ctggcctgac ctttagcagc tacggcatga gctgggtccg acagacccct    180
gacaagagac tggaactggt ggccacaatc aacggcaacg gcgacatcac ctactatccc    240
gacagcgtga agggcagatt caccatcagc cgggacaacg ccaagaacac cctgtacctg    300
```

-continued

```
cagatgagca gcctgaagtc cgaggacacc gccatgtact actgcgccag agactacgac    360

tacgattacg ctatggacta ctggggccag ggcaccagcg tgacagttag ctctgcctct    420

acaaagggcc ctagcgtgtt ccctctggct ccttgtagca gaagcaccag cgagtctaca    480

gccgctctgg gctgtctggt caaggactac tttcccgagc ctgtgaccgt gtcctggaat    540

tctggcgctc tgacaagcgg cgtgcacacc tttccagctg tgctgcaaag cagcggcctg    600

tactctctga gcagcgtggt cacagtgcct agctctagcc tgggcaccaa gacctacacc    660

tgtaatgtgg accacaagcc tagcaacacc aaggtggaca agcgcgtgga atctaagtac    720

ggccctcctt gtcctccatg tcctgctcca gagtttctcg gcggaccctc cgtgttcctg    780

tttcctccaa agcctaagga caccctgatg atcagcagaa cccctgaagt gacctgcgtg    840

gtggtggacg tttcccaaga ggaccctgag gtgcagttca attggtacgt ggacggcgtg    900

gaagtgcaca atgccaagac caagcctaga gaggaacagt tcaacagcac ctacagagtg    960

gtgtccgtgc tgaccgtgct gcaccaggat tggctgaacg gcaaagagta caagtgcaag   1020

gtgtccaaca agggcctgcc tagcagcatc gagaaaacca tcagcaaggc caagggccag   1080

ccaagagaac cccaggtgta cacactgcct ccaagccaag aggaaatgac caagaaccag   1140

gtgtccctga cctgcctggt taagggcttc tacccctccg atatcgccgt ggaatgggag   1200

agcaatggcc agcctgagaa caactacaag acaacccctc ctgtgctgga cagcgacggc   1260

tcattcttcc tgtacagcag actgaccgtg gacaagagca gatggcaaga gggcaacgtg   1320

ttcagctgca gcgtgatgca cgaggccctg cacaaccact acacccagaa gtctctgagc   1380

ctgtctctgg gcaag                                                    1395


<210> SEQ ID NO 85
<211> LENGTH: 1401
<212> TYPE: DNA
<213> ORGANISM: Artificial Sequence
<220> FEATURE:
<223> OTHER INFORMATION: cDNA coding for chimeric mouse VH 16D6 human
      heavy IgG4 chain

<400> SEQUENCE: 85

atggagctgg gcctgagctg gatttttctg ctggccatcc tgaagggcgt gcagtgtcag     60

gttcagctgc agcagtctgg cgccgagctt atgaagcctg gcgcctctgt gaagatcagc    120

tgcaaggcca ccggctacac cttcagcacc tactggatcg agtgggtcaa gcagaggcct    180

ggccacggac tggaatggat cggagagatc ctgcctggca gcggcagcgc caactacaac    240

gagaagttca agggcaaagc caccttcacc gccgacacca gcagcaacac agcctacatg    300

cagctgagca gcctgacctt cgaggacagc gccgtgtact actgcgccaa aggcttcggc    360

agcccctact actacgctat ggattactgg ggccagggca ccagcgtgac agtgtctagc    420

gcctctacaa agggccctag cgtgttccct ctggctcctt gtagcagaag caccagcgag    480

tctacagccg ctctgggctg tctggtcaag gactactttc ccgagcctgt gaccgtgtcc    540

tggaattctg gcgctctgac aagcggcgtg cacacctttc cagctgtgct gcaaagcagc    600

ggcctgtact ctctgagcag cgtggtcaca gtgcctagct ctagcctggg caccaagacc    660

tacacctgta atgtggacca caagcctagc aacaccaagg tggacaagcg cgtggaatct    720

aagtacggcc ctccttgtcc tccatgtcct gctccagagt ttctcggcgg accctccgtg    780

ttcctgtttc ctccaaagcc taaggacacc ctgatgatca gcagaacccc tgaagtgacc    840

tgcgtggtgg tggacgtttc ccaagaggac cctgaggtgc agttcaattg gtacgtggac    900
```

```
ggcgtggaag tgcacaacgc caagaccaag cctagagagg aacagttcaa ctccacctac    960

agagtggtgt ccgtgctgac cgtgctgcac caggattggc tgaacggcaa agagtacaag   1020

tgcaaggtgt ccaacaaggg cctgcctagc agcatcgaga aaaccatcag caaggccaag   1080

ggccagccaa gagaacccca ggtgtacaca ctgcctccaa gccaagagga aatgaccaag   1140

aaccaggtgt ccctgacctg cctcgtgaag ggcttctacc cttccgatat cgccgtggaa   1200

tgggagagca atggccagcc tgagaacaac tacaagacaa cccctcctgt gctggacagc   1260

gacggctcat tcttcctgta cagcagactg accgtggaca agagcagatg gcaagagggc   1320

aacgtgttct cctgcagcgt gatgcacgag gccctgcaca accactacac ccagaagtct   1380

ctgagcctgt ctctgggcaa g                                             1401
```

<210> SEQ ID NO 86
<211> LENGTH: 1386
<212> TYPE: DNA
<213> ORGANISM: Artificial Sequence
<220> FEATURE:
<223> OTHER INFORMATION: cDNA coding for chimeric mouse VH 20B4 human heavy IgG4 chain

<400> SEQUENCE: 86

```
atggagctgg gcctgagctg gatttttctg ctggccatcc tgaagggcgt gcagtgcaga     60

gtgcagctga aagagtctgg ccctggactg gtggccccaa gccagtctct gagcatcacc    120

tgtaccgtgt ccggcttcag cctgacaagc tatggcgtgc actgggtccg acagcctcca    180

ggcaaaggac tggaatggct gggcatcatt tgggctggcg gcagcaccag ctacaacagc    240

gctctgatga gccggctgag catctccaag gacaacagca agagccaggt gttcctgaag    300

atgaacagcc tgcagaccga cgacaccgcc atgtactact gcgccagaga tcactacgac    360

ctgttcgcct attggggcca gggcacactg gttacagtgt ccgccgcctc tacaaagggc    420

cctagtgtgt ttcctctggc tccctgcagc agaagcacca gcgaatctac agccgctctg    480

ggctgcctgg tcaaggacta ctttcctgag ccagtgaccg tgtcctggaa ctctggcgct    540

ctgacaagcg gcgtgcacac atttccagcc gtgctgcaaa gcagcggcct gtactctctg    600

tccagcgtgg tcacagtgcc tagctctagc ctgggcacca agacctacac ctgtaatgtg    660

gaccacaagc ctagcaacac caaggtggac aagcgcgtgg aatctaagta cggccctcct    720

tgtcctccat gtcctgcacc tgagtttctc ggcggaccct ccgtgttcct gtttcctcca    780

aagcctaagg acaccctgat gatcagcaga acccctgaag tgacctgcgt ggtggtggac    840

gtttcccaag aggaccctga ggtgcagttc aattggtacg tggacggcgt ggaagtgcac    900

aacgccaaga ccaagcctag agaggaacag ttcaacagca cctacagagt ggtgtccgtg    960

ctgacagtgc tgcaccagga ttggctgaac ggcaaagagt acaagtgcaa ggtgtccaac   1020

aagggcctgc ctagcagcat cgagaaaacc atcagcaagg ccaagggcca gccaagagaa   1080

ccccaggtgt acacactgcc tccaagccaa gaggaaatga ccaagaatca ggtgtccctg   1140

acctgcctcg tgaagggctt ctacccttcc gatatcgccg tggaatggga gagcaatggc   1200

cagcctgaga acaactacaa gacaacccct cctgtgctgg acagcgacgg ctcattcttc   1260

ctgtacagca gactgaccgt ggacaagagc agatggcaag agggcaacgt gttcagctgc   1320

tccgtgatgc acgaggccct gcacaaccac tacacccaga aaagcctgag cctgtctctg   1380

ggcaag                                                              1386
```

<210> SEQ ID NO 87

<211> LENGTH: 1392
<212> TYPE: DNA
<213> ORGANISM: Artificial Sequence
<220> FEATURE:
<223> OTHER INFORMATION: cDNA coding for chimeric mouse VH 30C7 human heavy IgG4 chain

<400> SEQUENCE: 87

```
atggagctgg gcctgagctg gatttttctg ctggccatcc tgaagggcgt gcagtgtcag     60
gttcagctgc agcagtctgg ccccgaactt gtcagacctg gcgtgtccgt gaagatcagc    120
tgtaaaggca gcggctacac cttcaccgac tacgtgatgc actgggtcaa gcagagccac    180
gccaagagcc tggaatggat cggcgtgatc agcacctaca gcggcaacac caactacaac    240
cagaagttca agggcaaagc caccatgacc gtggacaaga gcagcagcac cgcctacatg    300
gaactggcca ggctgacctc tgaggacagc gccatctact actgcgccag agagagcgac    360
ggctactact tcgattattg gggccagggc accacactga ccgtgtctag cgcctctaca    420
aagggcccta gcgtgttccc tctggctcct tgtagcagaa gcaccagcga gtctacagcc    480
gctctgggct gtctggtcaa ggactacttt cccgagcctg tgacagtgtc ctggaactct    540
ggcgctctga caagcggcgt gcacacattt ccagccgtgc tgcaaagcag cggcctgtac    600
tctctgagca gcgtggtcac agtgcctagc tctagcctgg gcaccaagac ctacacctgt    660
aatgtggacc acaagccttc caacaccaag gtggacaagc gcgtggaatc taagtacggc    720
cctccttgtc ctccatgtcc tgcacctgag tttctcggcg gaccctccgt gttcctgttt    780
cctccaaagc ctaaggacac cctgatgatc agcagaaccc ctgaagtgac ctgcgtggtg    840
gtggacgttt cccaagagga ccctgaggtg cagttcaatt ggtacgtgga cggcgtggaa    900
gtgcacaacg ccaagaccaa gcctagagag gaacagttca actccaccta cagagtggtg    960
tccgtgctga cagtgctgca ccaggattgg ctgaacggca aagagtacaa gtgcaaggtg   1020
tccaacaagg gcctgcctag cagcatcgag aaaaccatca gcaaggccaa gggccagcca   1080
agagaacccc aggtgtacac actgcctcca agccaagagg aaatgaccaa gaaccaggtg   1140
tccctgacct gcctcgtgaa gggcttctac ccttccgata tcgccgtgga atgggagagc   1200
aatggccagc ctgagaacaa ctacaagaca acccctcctg tgctggacag cgacggctca   1260
ttcttcctgt acagcagact gacagtggat aagagccggt ggcaagaggg caacgtgttc   1320
tcctgctctg tgatgcacga ggccctgcac aaccactaca cccagaaaag cctgagcctg   1380
tctctgggca ag                                                        1392
```

<210> SEQ ID NO 88
<211> LENGTH: 708
<212> TYPE: DNA
<213> ORGANISM: Artificial Sequence
<220> FEATURE:
<223> OTHER INFORMATION: cDNA coding for chimeric mouse VL 8F3 human light kappa chain

<400> SEQUENCE: 88

```
atggacatga gagttcccgc tcagctgctg ggactgctgc tgctttggtt tcctggcgct     60
agatgcgacg tgcagatcac acagagccct agctacctgg ctgcctctcc tggcgagaca    120
atcaccatca actgccgggc cagcaagacc atcagcaagt acctggcctg gtatcaagag    180
aagcccggca agaccaacat gctgctgatc tacagcggca gcacactgca gagcggagtg    240
cctagcagat tttccggctc tggcagcggc accgatttca ccctgaccat aagcagcctg    300
gaacctgagg acctggccat gtactactgc cagcagcacg acgagtaccc ctggacattt    360
```

```
ggcggaggca ccaagctgga aatcaagcgg acagtggccg ctcctagcgt gttcatcttt    420

ccacctagcg acgagcagct gaagtctggc acagcctctg tcgtgtgcct gctgaacaac    480

ttctacccca gagaagccaa ggtgcagtgg aaggtggaca acgccctgca gtccggcaat    540

agccaagaga gcgtgaccga gcaggacagc aaggactcta cctacagcct gagcagcacc    600

ctgacactga gcaaggccga ctacgagaag cacaaagtgt acgcctgcga agtgacccac    660

cagggccttt ctagccctgt gaccaagagc ttcaaccggg gcgaatgt                 708
```

<210> SEQ ID NO 89
<211> LENGTH: 708
<212> TYPE: DNA
<213> ORGANISM: Artificial Sequence
<220> FEATURE:
<223> OTHER INFORMATION: cDNA coding for chimeric mouse VL 10E7 human light kappa chain

<400> SEQUENCE: 89

```
atggacatga gagttcccgc tcagctgctg ggactgctgc tgctttggtt tcctggcgct     60

agatgcgaca tccagatgac ccagagcacc agcagcctgt ctgcctctct gggcgatagc    120

gtgaccatca gctgtagagc cagccaggac atcatcaact acctgaactg gtatcagcag    180

aaacccgacg gcaccgtgaa gctgctgatc tactacacca gcagactgca cagcggcgtg    240

cccagcagat tttctggctc tggaagcggc accgagtaca gcctgaccgt gtccaacctg    300

gaaaaagagg atatcgctac ctacttctgc cagcaaggca agaccctgcc ttacaccttt    360

ggcggaggca ccaagctgga aatcaagcgg acagtggccg ctcctagcgt gttcatcttt    420

ccacctagcg acgagcagct gaagtctggc acagcctctg tcgtgtgcct gctgaacaac    480

ttctacccca gagaagccaa ggtgcagtgg aaggtggaca acgccctgca gagcggcaat    540

agccaagaga gcgtgaccga gcaggacagc aaggactcta cctatagcct gagcagcacc    600

ctgacactga gcaaggccga ctacgagaag cacaaagtgt acgcctgcga agtgacccac    660

cagggccttt ctagccctgt gaccaagagc ttcaaccggg gcgaatgt                 708
```

<210> SEQ ID NO 90
<211> LENGTH: 711
<212> TYPE: DNA
<213> ORGANISM: Artificial Sequence
<220> FEATURE:
<223> OTHER INFORMATION: cDNA coding for chimeric mouse VL 16D6 human light kappa chain

<400> SEQUENCE: 90

```
atggacatga gagttcccgc tcagctgctg ggactgctgc tgctttggtt tcctggcgct     60

agatgcgaga tcgtgctgac acagagccct gctctgatgg ctgcttcccc tggcgagaaa    120

gtgaccatca cctgtagcgt gtccagcagc atcagcagct ccaacctgca ctggtatcag    180

cagaagtccg agacaagccc caagccttgg atctacggca caagcaaact ggccagcggc    240

gtgccagtca gattttctgg ctctggcagc ggcaccagct acagcctgac catcagcaac    300

atggaagccg aggatgccgc cacctactac tgccagcagt ggtccagctt tccactgacc    360

tttggcggag gcaccaagct ggaaatcaag cggacagtgg ccgctcctag cgtgttcatc    420

tttccaccta gcgacgagca gctgaagtct ggcacagcct ctgtcgtgtg cctgctgaac    480

aacttctacc ccagagaagc caaggtgcaa tggaaggtgg acaacgccct gcagagcggc    540

aatagccaag agagcgtgac cgagcaggac agcaaggact ccacctatag cctgagcagc    600
```

```
accctgacac tgagcaaggc cgactacgag aagcacaaag tgtacgcctg cgaagtgacc    660

caccagggcc tttctagccc tgtgaccaag agcttcaacc ggggcgaatg t             711


<210> SEQ ID NO 91
<211> LENGTH: 708
<212> TYPE: DNA
<213> ORGANISM: Artificial Sequence
<220> FEATURE:
<223> OTHER INFORMATION: cDNA coding for chimeric mouse VL 20B4 human
      light kappa chain

<400> SEQUENCE: 91

atggacatga gagttcccgc tcagctgctg ggactgctgc tgctttggtt tcctggcgct     60

agatgcgaca tcctgatgac acagagcccc agctccatgt ccgtgtctct gggcgatacc    120

gtgtccatca catgtcacgc cagccaggac atcagccgga atatcggatg gctgcagcag    180

aagcccggca agagctttaa gggcctgatc taccacggca ccaacctgga agatggcgtg    240

cccagcagat tttccggctc tggatctggc gccgactaca gcctgacaat cagcagcctg    300

gaaagcgagg acttcgccga ttactactgc gtgcagtacg cccagtttcc tcggacattt    360

ggcggaggca caaagctgga aatcaagcgg acagtggccg ctcctagcgt gttcatcttt    420

ccacctagcg acgagcagct gaagtctggc acagcctctg tcgtgtgcct gctgaacaac    480

ttctacccca gagaagccaa ggtgcagtgg aaggtggaca acgccctgca gagcggcaat    540

agccaagaga gcgtgaccga gcaggacagc aaggactcca cctatagcct gagcagcacc    600

ctgacactga gcaaggccga ctacgagaag cacaaagtgt acgcctgcga agtgacccac    660

cagggccttt ctagccctgt gaccaagagc ttcaaccggg gcgaatgt                 708


<210> SEQ ID NO 92
<211> LENGTH: 726
<212> TYPE: DNA
<213> ORGANISM: Artificial Sequence
<220> FEATURE:
<223> OTHER INFORMATION: cDNA coding for chimeric mouse VL 30C7 human
      light kappa chain

<400> SEQUENCE: 92

atggacatga gagttcccgc tcagctgctg ggactgctgc tgctttggtt tcctggcgct     60

agatgcgaca tcgtgatgtc tcagagccct agcagcctgg ctgtgtctgc cggcgagaaa    120

gtgaccatga gctgcaagag cagccagagc ctgctgaaca gccggaccag aaagaactac    180

ctggcctggt atcagcagaa gcccggacag tctcccaagc tgctgatcta ctgggccagc    240

accagagaaa gcggcgtgcc cgatagattc acaggcagcg gcagcggaac cgacttcacc    300

ctgacaatca gctctgtgca ggccgaggat ctggccgtgt actactgcaa gcagagctac    360

aacctgatgt acaccttcgg cggaggcacc aagctggaaa tcaagagaac agtggccgct    420

cctagcgtgt tcatcttccc accttccgac gagcagctga agtctggcac agcctctgtc    480

gtgtgcctgc tcaacaactt ctaccccaga gaagccaagg tgcagtggaa ggtggacaac    540

gccctgcaga gcggcaatag ccaagagagc gtgaccgagc aggacagcaa ggactctacc    600

tacagcctga gcagcacact gaccctgagc aaggccgact acgagaagca caaagtgtac    660

gcctgcgaag tgacccacca gggcctttct agccctgtga ccaagagctt caaccggggc    720

gaatgt                                                               726


<210> SEQ ID NO 93
<211> LENGTH: 466
```

```
<212> TYPE: PRT
<213> ORGANISM: Artificial Sequence
<220> FEATURE:
<223> OTHER INFORMATION: chimeric mouse VH 8F3 human heavy IgG4 chain

<400> SEQUENCE: 93

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asn Tyr Gly Met Ser Trp Val Arg Gln Thr Pro Asp Lys Arg Leu
    50                  55                  60

Glu Trp Val Ala Thr Met His Ser Gly Gly Thr Tyr Thr Tyr Tyr Pro
65                  70                  75                  80

Asp Asn Val Lys Gly Arg Phe Thr Ile Ser Arg Asp Asn Ala Lys Asn
                85                  90                  95

Asn Leu Tyr Leu Gln Met Ser Ser Leu Arg Ser Glu Asp Thr Ala Met
            100                 105                 110

Tyr Tyr Cys Ala Arg Glu Thr Gly Leu Tyr Asp Gly Leu Phe Asp Phe
        115                 120                 125

Trp Gly Gln Gly Thr Thr Leu Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Gln Glu Glu Met Thr Lys Asn Gln Val Ser Leu
    370                 375                 380
```

```
Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Lys
465


<210> SEQ ID NO 94
<211> LENGTH: 465
<212> TYPE: PRT
<213> ORGANISM: Artificial Sequence
<220> FEATURE:
<223> OTHER INFORMATION: chimeric mouse VH 10E7 human heavy IgG4 chain

<400> SEQUENCE: 94

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Lys Leu Ser Cys Ala Ala Ser Gly Leu Thr Phe
        35                  40                  45

Ser Ser Tyr Gly Met Ser Trp Val Arg Gln Thr Pro Asp Lys Arg Leu
    50                  55                  60

Glu Leu Val Ala Thr Ile Asn Gly Asn Gly Asp Ile Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Asp Tyr Asp Tyr Asp Tyr Ala Met Asp Tyr Trp
        115                 120                 125

Gly Gln Gly Thr Ser Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Leu Gly Gly Pro
                245                 250                 255

Ser Val Phe Leu Phe Pro Pro Lys Pro Lys Asp Thr Leu Met Ile Ser
            260                 265                 270
```

```
Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
    450                 455                 460

Lys
465


<210> SEQ ID NO 95
<211> LENGTH: 467
<212> TYPE: PRT
<213> ORGANISM: Artificial Sequence
<220> FEATURE:
<223> OTHER INFORMATION: chimeric mouse VH 16D6 human heavy IgG4 chain

<400> SEQUENCE: 95

Met Glu Leu Gly Leu Ser Trp Ile Phe Leu Leu Ala Ile Leu Lys Gly
1               5                   10                  15

Val Gln Cys Gln Val Gln Leu Gln Gln Ser Gly Ala Glu Leu Met Lys
            20                  25                  30

Pro Gly Ala Ser Val Lys Ile Ser Cys Lys Ala Thr Gly Tyr Thr Phe
        35                  40                  45

Ser Thr Tyr Trp Ile Glu Trp Val Lys Gln Arg Pro Gly His Gly Leu
    50                  55                  60

Glu Trp Ile Gly Glu Ile Leu Pro Gly Ser Gly Ser Ala Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Phe Glu Asp Ser Ala Val
            100                 105                 110

Tyr Tyr Cys Ala Lys Gly Phe Gly Ser Pro Tyr Tyr Tyr Ala Met Asp
        115                 120                 125

Tyr Trp Gly Gln Gly Thr Ser Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160
```

```
Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460

Leu Gly Lys
465
```

<210> SEQ ID NO 96
<211> LENGTH: 462
<212> TYPE: PRT
<213> ORGANISM: Artificial Sequence
<220> FEATURE:
<223> OTHER INFORMATION: chimeric mouse VH 20B4 human heavy IgG4 chain

<400> SEQUENCE: 96

```
Met Glu Leu Gly Leu Ser Trp Ile Phe Leu Leu Ala Ile Leu Lys Gly
1               5                   10                  15

Val Gln Cys Arg Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45
```

```
Thr Ser Tyr Gly Val His Trp Val Arg Gln Pro Pro Gly Lys Gly Leu
    50                  55                  60

Glu Trp Leu Gly Ile Ile Trp Ala Gly Gly Ser Thr Ser Tyr Asn Ser
65                  70                  75                  80

Ala Leu Met Ser Arg Leu Ser Ile Ser Lys Asp Asn Ser Lys Ser Gln
                85                  90                  95

Val Phe Leu Lys Met Asn Ser Leu Gln Thr Asp Asp Thr Ala Met Tyr
            100                 105                 110

Tyr Cys Ala Arg Asp His Tyr Asp Leu Phe Ala Tyr Trp Gly Gln Gly
        115                 120                 125

Thr Leu Val Thr Val Ser Ala Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Lys Thr Tyr Thr Cys Asn Val Asp His Lys Pro
    210                 215                 220

Ser Asn Thr Lys Val Asp Lys Arg Val Glu Ser Lys Tyr Gly Pro Pro
225                 230                 235                 240

Cys Pro Pro Cys Pro Ala Pro Glu Phe Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Gln Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Glu Gly Asn Val Phe Ser Cys Ser Val Met His Glu Ala Leu His
        435                 440                 445

Asn His Tyr Thr Gln Lys Ser Leu Ser Leu Ser Leu Gly Lys
    450                 455                 460
```

<210> SEQ ID NO 97
<211> LENGTH: 464
<212> TYPE: PRT
<213> ORGANISM: Artificial Sequence
<220> FEATURE:
<223> OTHER INFORMATION: chimeric mouse VH 30C7 human heavy IgG4 chain

<400> SEQUENCE: 97

```
Met Glu Leu Gly Leu Ser Trp Ile Phe Leu Leu Ala Ile Leu Lys Gly
1               5                   10                  15

Val Gln Cys Gln Val Gln Leu Gln Gln Ser Gly Pro Glu Leu Val Arg
            20                  25                  30

Pro Gly Val Ser Val Lys Ile Ser Cys Lys Gly Ser Gly Tyr Thr Phe
        35                  40                  45

Thr Asp Tyr Val Met His Trp Val Lys Gln Ser His Ala Lys Ser Leu
    50                  55                  60

Glu Trp Ile Gly Val Ile Ser Thr Tyr Ser Gly Asn Thr Asn Tyr Asn
65                  70                  75                  80

Gln Lys Phe Lys Gly Lys Ala Thr Met Thr Val Asp Lys Ser Ser Ser
                85                  90                  95

Thr Ala Tyr Met Glu Leu Ala Arg Leu Thr Ser Glu Asp Ser Ala Ile
            100                 105                 110

Tyr Tyr Cys Ala Arg Glu Ser Asp Gly Tyr Tyr Phe Asp Tyr Trp Gly
        115                 120                 125

Gln Gly Thr Thr Leu Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
```

```
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly Lys
    450                 455                 460


<210> SEQ ID NO 98
<211> LENGTH: 236
<212> TYPE: PRT
<213> ORGANISM: Artificial Sequence
<220> FEATURE:
<223> OTHER INFORMATION: chimeric mouse VL 8F3 human light kappa chain

<400> SEQUENCE: 98

Met Asp Met Arg Val Pro Ala Gln Leu Leu Gly Leu Leu Leu Leu Trp
1               5                   10                  15

Phe Pro Gly Ala Arg Cys Asp Val Gln Ile Thr Gln Ser Pro Ser Tyr
            20                  25                  30

Leu Ala Ala Ser Pro Gly Glu Thr Ile Thr Ile Asn Cys Arg Ala Ser
        35                  40                  45

Lys Thr Ile Ser Lys Tyr Leu Ala Trp Tyr Gln Glu Lys Pro Gly Lys
    50                  55                  60

Thr Asn Met Leu Leu Ile Tyr Ser Gly Ser Thr Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Glu Pro Glu Asp Leu Ala Met Tyr Tyr Cys Gln Gln
            100                 105                 110

His Asp Glu Tyr Pro Trp Thr Phe Gly Gly Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 99
<211> LENGTH: 236
<212> TYPE: PRT
<213> ORGANISM: Artificial Sequence
<220> FEATURE:
<223> OTHER INFORMATION: chimeric mouse VL 10E7 human light kappa chain
```

<400> SEQUENCE: 99

```
Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Thr Ser Ser
            20                  25                  30

Leu Ser Ala Ser Leu Gly Asp Ser Val Thr Ile Ser Cys Arg Ala Ser
        35                  40                  45

Gln Asp Ile Ile Asn Tyr Leu Asn Trp Tyr Gln Gln Lys Pro Asp Gly
    50                  55                  60

Thr Val Lys Leu Leu Ile Tyr Tyr Thr Ser Arg Leu His Ser Gly Val
65                  70                  75                  80

Pro Ser Arg Phe Ser Gly Ser Gly Ser Gly Thr Glu Tyr Ser Leu Thr
                85                  90                  95

Val Ser Asn Leu Glu Lys Glu Asp Ile Ala Thr Tyr Phe Cys Gln Gln
            100                 105                 110

Gly Lys Thr Leu Pro Tyr Thr Phe Gly Gly Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 100
<211> LENGTH: 237
<212> TYPE: PRT
<213> ORGANISM: Artificial Sequence
<220> FEATURE:
<223> OTHER INFORMATION: chimeric mouse VL 16D6 human light kappa chain

<400> SEQUENCE: 100

```
Met Asp Met Arg Val Pro Ala Gln Leu Leu Gly Leu Leu Leu Leu Trp
1               5                   10                  15

Phe Pro Gly Ala Arg Cys Glu Ile Val Leu Thr Gln Ser Pro Ala Leu
            20                  25                  30

Met Ala Ala Ser Pro Gly Glu Lys Val Thr Ile Thr Cys Ser Val Ser
        35                  40                  45

Ser Ser Ile Ser Ser Ser Asn Leu His Trp Tyr Gln Gln Lys Ser Glu
    50                  55                  60

Thr Ser Pro Lys Pro Trp Ile Tyr Gly Thr Ser Lys Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Asn Met Glu Ala Glu Asp Ala Ala Thr Tyr Tyr Cys Gln
            100                 105                 110
```

```
Gln Trp Ser Ser Phe Pro Leu Thr Phe Gly Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235


<210> SEQ ID NO 101
<211> LENGTH: 236
<212> TYPE: PRT
<213> ORGANISM: Artificial Sequence
<220> FEATURE:
<223> OTHER INFORMATION: chimeric mouse VL 20B4 human light kappa chain

<400> SEQUENCE: 101

Met Asp Met Arg Val Pro Ala Gln Leu Leu Gly Leu Leu Leu Leu Trp
1               5                   10                  15

Phe Pro Gly Ala Arg Cys Asp Ile Leu Met Thr Gln Ser Pro Ser Ser
            20                  25                  30

Met Ser Val Ser Leu Gly Asp Thr Val Ser Ile Thr Cys His Ala Ser
        35                  40                  45

Gln Asp Ile Ser Arg Asn Ile Gly Trp Leu Gln Gln Lys Pro Gly Lys
    50                  55                  60

Ser Phe Lys Gly Leu Ile Tyr His Gly Thr Asn Leu Glu Asp Gly Val
65                  70                  75                  80

Pro Ser Arg Phe Ser Gly Ser Gly Ser Gly Ala Asp Tyr Ser Leu Thr
                85                  90                  95

Ile Ser Ser Leu Glu Ser Glu Asp Phe Ala Asp Tyr Tyr Cys Val Gln
            100                 105                 110

Tyr Ala Gln Phe Pro Arg Thr Phe Gly Gly Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 102
<211> LENGTH: 242
<212> TYPE: PRT
<213> ORGANISM: Artificial Sequence
<220> FEATURE:
<223> OTHER INFORMATION: chimeric mouse VL 30C7 human light kappa chain

<400> SEQUENCE: 102

```
Met Asp Met Arg Val Pro Ala Gln Leu Leu Gly Leu Leu Leu Leu Trp
1               5                   10                  15

Phe Pro Gly Ala Arg Cys Asp Ile Val Met Ser Gln Ser Pro Ser Ser
            20                  25                  30

Leu Ala Val Ser Ala Gly Glu Lys Val Thr Met Ser Cys Lys Ser Ser
        35                  40                  45

Gln Ser Leu Leu Asn Ser Arg Thr Arg Lys Asn Tyr Leu Ala Trp Tyr
    50                  55                  60

Gln Gln Lys Pro Gly Gln Ser Pro Lys Leu Leu Ile Tyr Trp Ala Ser
65                  70                  75                  80

Thr Arg Glu Ser Gly Val Pro Asp Arg Phe Thr Gly Ser Gly Ser Gly
                85                  90                  95

Thr Asp Phe Thr Leu Thr Ile Ser Ser Val Gln Ala Glu Asp Leu Ala
            100                 105                 110

Val Tyr Tyr Cys Lys Gln Ser Tyr Asn Leu Met Tyr Thr Phe Gly Gly
        115                 120                 125

Gly Thr Lys Leu Glu Ile Lys Arg Thr Val Ala Ala Pro Ser Val Phe
    130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
225                 230                 235                 240

Glu Cys
```

<210> SEQ ID NO 103
<211> LENGTH: 30
<212> TYPE: DNA
<213> ORGANISM: Artificial Sequence
<220> FEATURE:
<223> OTHER INFORMATION: PCR primer

<400> SEQUENCE: 103

```
atgagtgtgc tcactcaggt cctggsgttg                                        30
```

<210> SEQ ID NO 104
<211> LENGTH: 33
<212> TYPE: DNA
<213> ORGANISM: Artificial Sequence
<220> FEATURE:
<223> OTHER INFORMATION: PCR primer

<400> SEQUENCE: 104
atgaggrccc ctgctcagwt tyttggmwtc ttg 33

<210> SEQ ID NO 105
<211> LENGTH: 30
<212> TYPE: DNA
<213> ORGANISM: Artificial Sequence
<220> FEATURE:
<223> OTHER INFORMATION: PCR primer

<400> SEQUENCE: 105
atggatttwc aggtgcagat twtcagcttc 30

<210> SEQ ID NO 106
<211> LENGTH: 24
<212> TYPE: DNA
<213> ORGANISM: Artificial Sequence
<220> FEATURE:
<223> OTHER INFORMATION: PCR primer

<400> SEQUENCE: 106
atgggcwtca aagatggagt caca 24

<210> SEQ ID NO 107
<211> LENGTH: 25
<212> TYPE: DNA
<213> ORGANISM: Artificial Sequence
<220> FEATURE:
<223> OTHER INFORMATION: PCR primer

<400> SEQUENCE: 107
atggtrtccw casctcagtt ccttg 25

<210> SEQ ID NO 108
<211> LENGTH: 20
<212> TYPE: DNA
<213> ORGANISM: Artificial Sequence
<220> FEATURE:
<223> OTHER INFORMATION: PCR primer

<400> SEQUENCE: 108
actggatggt gggaagatgg 20

<210> SEQ ID NO 109
<211> LENGTH: 26
<212> TYPE: DNA
<213> ORGANISM: Artificial Sequence
<220> FEATURE:
<223> OTHER INFORMATION: PCR primer

<400> SEQUENCE: 109
atgggatgga gctrtatcat sytctt 26

<210> SEQ ID NO 110
<211> LENGTH: 25
<212> TYPE: DNA
<213> ORGANISM: Artificial Sequence
<220> FEATURE:
<223> OTHER INFORMATION: PCR primer

<400> SEQUENCE: 110
atgractttg ggytcagctt grttt 25

<210> SEQ ID NO 111
<211> LENGTH: 29
<212> TYPE: DNA
<213> ORGANISM: Artificial Sequence
<220> FEATURE:
<223> OTHER INFORMATION: PCR primer

<400> SEQUENCE: 111
atggcttgtc yttrgsgctr ctcttctgc 29

<210> SEQ ID NO 112
<211> LENGTH: 26
<212> TYPE: DNA
<213> ORGANISM: Artificial Sequence
<220> FEATURE:
<223> OTHER INFORMATION: PCR primer

<400> SEQUENCE: 112
atggratgga gckgggtctt tmtctt 26

<210> SEQ ID NO 113
<211> LENGTH: 23
<212> TYPE: DNA
<213> ORGANISM: Artificial Sequence
<220> FEATURE:
<223> OTHER INFORMATION: PCR primer

<400> SEQUENCE: 113
atggmttggg tgtggamctt gct 23

<210> SEQ ID NO 114
<211> LENGTH: 21
<212> TYPE: DNA
<213> ORGANISM: Artificial Sequence
<220> FEATURE:
<223> OTHER INFORMATION: PCR primer

<400> SEQUENCE: 114
cagtggatag acagatgggg g 21

<210> SEQ ID NO 115
<211> LENGTH: 20
<212> TYPE: DNA
<213> ORGANISM: Artificial Sequence
<220> FEATURE:
<223> OTHER INFORMATION: PCR primer

<400> SEQUENCE: 115
aagatggata cagttggtgc 20

<210> SEQ ID NO 116
<211> LENGTH: 23
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (21)..(21)
<223> OTHER INFORMATION: /note="any nucleotide selected from c, g, a or t"

<400> SEQUENCE: 116
gasrthstga tgacccagac ncc 23

<210> SEQ ID NO 117
<211> LENGTH: 119
<212> TYPE: PRT
<213> ORGANISM: Artificial Sequence
<220> FEATURE:
<223> OTHER INFORMATION: 10E7 heavy chain variable region VH1

<400> SEQUENCE: 117

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Gly Met Ser Trp Val Arg Gln Ala Pro Gly Lys Gly Leu Glu Trp Val
        35                  40                  45

Ser Thr Ile Asn Gly Asn Gly Asp Ile Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Asp Tyr Asp Tyr Ala Met Asp Tyr Trp Gly Gln Gly
            100                 105                 110

Thr Leu Val Thr Val Ser Ser
        115
```

<210> SEQ ID NO 118
<211> LENGTH: 119
<212> TYPE: PRT
<213> ORGANISM: Artificial Sequence
<220> FEATURE:
<223> OTHER INFORMATION: 10E7 heavy chain variable region VH2

<400> SEQUENCE: 118

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Asn Gly Asn Gly Asp Ile Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Asp Tyr Asp Tyr Ala Met Asp Tyr Trp Gly Gln Gly
            100                 105                 110

Thr Leu Val Thr Val Ser Ser
        115
```

<210> SEQ ID NO 119
<211> LENGTH: 119
<212> TYPE: PRT
<213> ORGANISM: Artificial Sequence
<220> FEATURE:
<223> OTHER INFORMATION: 10E7 heavy chain variable region VH3

<400> SEQUENCE: 119

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Gly Met Ser Trp Val Arg Gln Ala Pro Gly Lys Gly Leu Glu Leu Val
        35                  40                  45
```

```
Ala Thr Ile Asn Gly Asn Gly Asp Ile Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Asp Tyr Asp Tyr Ala Met Asp Tyr Trp Gly Gln Gly
            100                 105                 110

Thr Leu Val Thr Val Ser Ser
        115


<210> SEQ ID NO 120
<211> LENGTH: 107
<212> TYPE: PRT
<213> ORGANISM: Artificial Sequence
<220> FEATURE:
<223> OTHER INFORMATION: 10E7 light chain variable region VL1

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ile Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Lys Thr Leu Pro Tyr
                85                  90                  95

Thr Phe Gly Gln Gly Thr Lys Leu Glu Ile Lys
            100                 105


<210> SEQ ID NO 121
<211> LENGTH: 107
<212> TYPE: PRT
<213> ORGANISM: Artificial Sequence
<220> FEATURE:
<223> OTHER INFORMATION: 10E7 light chain variable region VL2

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ile Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Lys Thr Leu Pro Tyr
                85                  90                  95

Thr Phe Gly Gln Gly Thr Lys Leu Glu Ile Lys
            100                 105
```

<210> SEQ ID NO 122
<211> LENGTH: 107
<212> TYPE: PRT
<213> ORGANISM: Artificial Sequence
<220> FEATURE:
<223> OTHER INFORMATION: 10E7 light chain variable region VL3

<400> SEQUENCE: 122

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ile Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Lys Thr Leu Pro Tyr
                85                  90                  95

Thr Phe Gly Gln Gly Thr Lys Leu Glu Ile Lys
            100                 105
```

<210> SEQ ID NO 123
<211> LENGTH: 107
<212> TYPE: PRT
<213> ORGANISM: Artificial Sequence
<220> FEATURE:
<223> OTHER INFORMATION: 10E7 light chain variable region VL4

<400> SEQUENCE: 123

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ile Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Lys Thr Leu Pro Tyr
                85                  90                  95

Thr Phe Gly Gln Gly Thr Lys Leu Glu Ile Lys
            100                 105
```

<210> SEQ ID NO 124
<211> LENGTH: 1392
<212> TYPE: DNA
<213> ORGANISM: Artificial Sequence
<220> FEATURE:
<223> OTHER INFORMATION: cDNA sequence coding for humanized IgG4 chain of anti-human-CD89 antibody 10E7 covering humanized VH1

<400> SEQUENCE: 124

```
atgaaatggg tcacctttat ctccctgctg ttcctgttct ccagcgccta ctctgaggtg     60

cagctgctgg aatctggcgg aggattggtt cagcctggcg gctctctgag actgtcttgt    120

gctgcttctg gcctgacctt ctcctcctac ggcatgtcct gggtccgaca ggctcctgga    180

aaaggcctgg aatgggtgtc caccatcaac ggcaacggcg acatcaccta ctatcccgac    240
```

```
tccgtgaagg gcagattcac catctctcgg gacaactcca agaacaccct gtacctgcag    300

atgaactccc tgagagccga ggacaccgcc gtgtactact gcgccagaga ctacgactac    360

gattacgcca tggactactg gggccagggc acactggtta ccgtgtcctc tgcttccacc    420

aagggaccct ctgtgttccc tctggctcct tgctccagat ccacctccga gtctacagct    480

gctctgggct gcctggtcaa ggactacttt cctgagcctg tgaccgtgtc ttggaactct    540

ggcgctctga catccggcgt gcacaccttt ccagctgtgc tgcaatccag cggcctgtac    600

tctctgtcct ccgtcgtgac cgtgccttct agctctctgg gcaccaagac ctacacctgt    660

aatgtggacc acaagccttc caacaccaag gtggacaagc gcgtggaatc taagtacggc    720

cctccttgtc ctccatgtcc tgctccagag tttctcggcg gaccttccgt gtttctgttc    780

cctccaaagc ctaaggacac cctgatgatc tctcggaccc ctgaagtgac ctgcgtggtg    840

gtggatgtgt cccaagagga cccagaggtg cagttcaatt ggtacgtgga cggcgtggaa    900

gtgcacaacg ccaagaccaa gcctagagag gaacagttca actccaccta cagagtggtg    960

tccgtgctga ccgtgctgca ccaggattgg ctgaacggaa aagagtacaa gtgcaaggtg   1020

tccaacaagg gcctgccttc cagcatcgaa aagaccatct ccaaggccaa gggccagcct   1080

agggaacccc aggtttacac cctgcctcca agccaagagg aaatgaccaa gaaccaggtg   1140

tccctgacct gcctcgtgaa gggattctac ccctccgata tcgccgtgga atgggagtct   1200

aatggccagc ctgagaacaa ctacaagaca acccctcctg tgctggactc cgacggcagc   1260

ttcttcctgt attcccgcct gaccgtggac aagtccagat ggcaagaggg caacgtgttc   1320

tcctgctccg tgatgcacga ggccctgcac aatcactaca cccagaagtc cctgtctctg   1380

tccctgggca ag                                                       1392


<210> SEQ ID NO 125
<211> LENGTH: 1392
<212> TYPE: DNA
<213> ORGANISM: Artificial Sequence
<220> FEATURE:
<223> OTHER INFORMATION: cDNA sequence coding for humanized IgG4 chain
      of anti-human-CD89 antibody 10E7 covering humanized VH2

<400> SEQUENCE: 125

atgaaatggg tcacctttat ctccctgctg ttcctgttct ccagcgccta ctctgaggtg     60

cagctgctgg aatctggcgg aggattggtt cagcctggcg gctctctgag actgtcttgt    120

gctgcttctg gcctgacctt ctcctcctac ggcatgtcct gggtccgaca ggctcctgga    180

aaaggcctgg aatgggtcgc caccatcaac ggcaacggcg acatcaccta ctatcccgac    240

tccgtgaagg gcagattcac catctctcgg gacaactcca agaacaccct gtacctgcag    300

atgaactccc tgagagccga ggacaccgcc gtgtactact gcgccagaga ctacgactac    360

gattacgcca tggactactg gggccagggc acactggtta ccgtgtcctc tgcttccacc    420

aagggaccct ctgtgttccc tctggctcct tgctccagat ccacctccga gtctacagct    480

gctctgggct gcctggtcaa ggactacttt cctgagcctg tgaccgtgtc ttggaactct    540

ggcgctctga catccggcgt gcacaccttt ccagctgtgc tgcaatccag cggcctgtac    600

tctctgtcct ccgtcgtgac cgtgccttct agctctctgg gcaccaagac ctacacctgt    660

aatgtggacc acaagccttc caacaccaag gtggacaagc gcgtggaatc taagtacggc    720

cctccttgtc ctccatgtcc tgctccagag tttctcggcg gaccttccgt gtttctgttc    780

cctccaaagc ctaaggacac cctgatgatc tctcggaccc ctgaagtgac ctgcgtggtg    840
```

```
gtggatgtgt cccaagagga cccagaggtg cagttcaatt ggtacgtgga cggcgtggaa    900

gtgcacaacg ccaagaccaa gcctagagag gaacagttca actccaccta cagagtggtg    960

tccgtgctga ccgtgctgca ccaggattgg ctgaacggaa aagagtacaa gtgcaaggtg   1020

tccaacaagg gcctgccttc cagcatcgaa aagaccatct ccaaggccaa gggccagcct   1080

agggaacccc aggtttacac cctgcctcca agccaagagg aaatgaccaa gaaccaggtg   1140

tccctgacct gcctcgtgaa gggattctac cctccgata  tcgccgtgga atgggagtct   1200

aatggccagc ctgagaacaa ctacaagaca acccctcctg tgctggactc cgacggcagc   1260

ttcttcctgt attcccgcct gaccgtggac aagtccagat ggcaagaggg caacgtgttc   1320

tcctgctccg tgatgcacga ggccctgcac aatcactaca cccagaagtc cctgtctctg   1380

tccctgggca ag                                                       1392
```

<210> SEQ ID NO 126
<211> LENGTH: 1392
<212> TYPE: DNA
<213> ORGANISM: Artificial Sequence
<220> FEATURE:
<223> OTHER INFORMATION: cDNA sequence coding for humanized IgG4 chain of anti-human-CD89 antibody 10E7 covering humanized VH3

<400> SEQUENCE: 126

```
atgaaatggg tcacctttat ctccctgctg ttcctgttct ccagcgccta ctctgaggtg     60

cagctgctgg aatctggcgg aggattggtt cagcctggcg gctctctgag actgtcttgt    120

gctgcttctg gcctgacctt ctcctcctac ggcatgtcct gggtccgaca ggctcctgga    180

aaaggcctgg aactggtggc taccatcaac ggcaacggcg acatcaccta ctatcccgac    240

tccgtgaagg gcagattcac catctctcgg gacaactcca agaacaccct gtacctgcag    300

atgaactccc tgagagccga ggacaccgcc gtgtactact gcgccagaga ctacgactac    360

gattacgcca tggactactg gggccagggc acactggtta ccgtgtcctc tgcttccacc    420

aagggaccct ctgtgttccc tctggctcct tgctccagat ccacctccga gtctacagct    480

gctctgggct gcctggtcaa ggactacttt cctgagcctg tgaccgtgtc ttggaactct    540

ggcgctctga catccggcgt gcacaccttt ccagctgtgc tgcaatccag cggcctgtac    600

tctctgtcct ccgtcgtgac cgtgccttct agctctctgg gcaccaagac ctacacctgt    660

aatgtggacc acaagccttc caacaccaag gtggacaagc gcgtggaatc taagtacggc    720

cctccttgtc ctccatgtcc tgctccagag tttctcggcg gaccttccgt gtttctgttc    780

cctccaaagc ctaaggacac cctgatgatc tctcggaccc ctgaagtgac ctgcgtggtg    840

gtggatgtgt cccaagagga cccagaggtg cagttcaatt ggtacgtgga cggcgtggaa    900

gtgcacaacg ccaagaccaa gcctagagag gaacagttca actccaccta cagagtggtg    960

tccgtgctga ccgtgctgca ccaggattgg ctgaacggaa aagagtacaa gtgcaaggtg   1020

tccaacaagg gcctgccttc cagcatcgaa aagaccatct ccaaggccaa gggccagcct   1080

agggaacccc aggtttacac cctgcctcca agccaagagg aaatgaccaa gaaccaggtg   1140

tccctgacct gcctcgtgaa gggattctac cctccgata  tcgccgtgga atgggagtct   1200

aatggccagc ctgagaacaa ctacaagaca acccctcctg tgctggactc cgacggcagc   1260

ttcttcctgt attcccgcct gaccgtggac aagtccagat ggcaagaggg caacgtgttc   1320

tcctgctccg tgatgcacga ggccctgcac aatcactaca cccagaagtc cctgtctctg   1380

tccctgggca ag                                                       1392
```

<210> SEQ ID NO 127
<211> LENGTH: 696
<212> TYPE: DNA
<213> ORGANISM: Artificial Sequence
<220> FEATURE:
<223> OTHER INFORMATION: cDNA sequence coding for humanized kappa chain of anti-human-CD89 antibody 10E7 covering humanized VL1

<400> SEQUENCE: 127

```
atgaaatggg tcacctttat ctccctgctg ttcctgttct cctccgccta ctccgacatc     60

cagatgaccc agtctccatc ctctctgtcc gcctctgtgg gcgacagagt gaccatcacc    120

tgtagagcca gccaggacat catcaactac ctgaactggt atcagcagaa gcccggcaag    180

gcccctaagc tgctgatcta ctacacctct cggctgcact ctggcgtgcc ctctagattt    240

tctggctccg gctctggcac cgactttacc ctgacaatct ccagcctgca gcctgaggac    300

ttcgccacct actattgcca gcagggcaag accctgcctt acacctttgg ccagggcacc    360

aagctggaaa tcaagcggac agtggccgct ccttccgtgt tcatcttccc accttccgac    420

gagcagctga agtccggcac agcttctgtc gtgtgcctgc tgaacaactt ctaccctcgg    480

gaagccaagg tgcagtggaa ggtggacaat gccctgcagt ccggcaactc ccaagagtct    540

gtgaccgagc aggactccaa ggacagcacc tacagcctgt cctccacact gaccctgtcc    600

aaggccgact acgagaagca caaggtgtac gcctgcgaag tgacccatca gggcctgtct    660

agccctgtga ccaagtcttt caaccggggc gagtgt                              696
```

<210> SEQ ID NO 128
<211> LENGTH: 696
<212> TYPE: DNA
<213> ORGANISM: Artificial Sequence
<220> FEATURE:
<223> OTHER INFORMATION: cDNA sequence coding for humanized kappa chain of anti-human-CD89 antibody 10E7 covering humanized VL2

<400> SEQUENCE: 128

```
atgaaatggg tcacctttat ctccctgctg ttcctgttct cctccgccta ctccgacatc     60

cagatgaccc agtctccatc ctctctgtcc gcctctgtgg gcgacagagt gaccatcacc    120

tgtagagcca gccaggacat catcaactac ctgaactggt atcagcagaa gcccggcaag    180

gcccctaagc tgctgatcta ctacacctct cggctgcact ctggcgtgcc ctctagattt    240

tctggctccg gctctggcac cgactatacc ctgacaatct ccagcctgca gcctgaggac    300

ttcgccacct actattgcca gcagggcaag accctgcctt acacctttgg ccagggcacc    360

aagctggaaa tcaagcggac agtggccgct ccttccgtgt tcatcttccc accttccgac    420

gagcagctga agtccggcac agcttctgtc gtgtgcctgc tgaacaactt ctaccctcgg    480

gaagccaagg tgcagtggaa ggtggacaat gccctgcagt ccggcaactc ccaagagtct    540

gtgaccgagc aggactccaa ggacagcacc tacagcctgt cctccacact gaccctgtcc    600

aaggccgact acgagaagca caaggtgtac gcctgcgaag tgacccatca gggcctgtct    660

agccctgtga ccaagtcttt caaccggggc gagtgt                              696
```

<210> SEQ ID NO 129
<211> LENGTH: 696
<212> TYPE: DNA
<213> ORGANISM: Artificial Sequence
<220> FEATURE:
<223> OTHER INFORMATION: cDNA sequence coding for humanized kappa chain of anti-human-CD89 antibody 10E7 covering humanized VL3

<400> SEQUENCE: 129

```
atgaaatggg tcacctttat ctccctgctg ttcctgttct cctccgccta ctccgacatc     60

cagatgaccc agtctccatc ctctctgtcc gcctctgtgg gcgacagagt gaccatcacc    120

tgtagagcca gccaggacat catcaactac ctgaactggt atcagcagaa acccggcaag    180

gccgtgaagc tgctgatcta ctacacctct cggctgcact ctggcgtgcc ctctagattt    240

tctggctccg gctctggcac cgactatacc ctgacaatct ccagcctgca gcctgaggac    300

ttcgccacct actattgcca gcagggcaag accctgcctt acacctttgg ccagggcacc    360

aagctggaaa tcaagcggac agtggccgct ccttccgtgt tcatcttccc accttccgac    420

gagcagctga agtccggcac agcttctgtc gtgtgcctgc tgaacaactt ctaccctcgg    480

gaagccaagg tgcagtggaa ggtggacaat gccctgcagt ccggcaactc ccaagagtct    540

gtgaccgagc aggactccaa ggacagcacc tacagcctgt cctccacact gaccctgtcc    600

aaggccgact acgagaagca caaggtgtac gcctgcgaag tgacccatca gggcctgtct    660

agccctgtga ccaagtcttt caaccggggc gagtgt                              696
```

<210> SEQ ID NO 130
<211> LENGTH: 696
<212> TYPE: DNA
<213> ORGANISM: Artificial Sequence
<220> FEATURE:
<223> OTHER INFORMATION: cDNA sequence coding for humanized kappa chain of anti-human-CD89 antibody 10E7 covering humanized VL4

<400> SEQUENCE: 130

```
atgaaatggg tcacctttat ctccctgctg ttcctgttct cctccgccta ctccgacatc     60

cagatgaccc agtctccatc ctctctgtcc gcctctgtgg gcgacagagt gaccatcacc    120

tgtagagcca gccaggacat catcaactac ctgaactggt atcagcagaa acccggcaag    180

accgtgaagc tgctgatcta ctacacctct cggctgcact ctggcgtgcc ctctagattt    240

tctggctccg gctctggcac cgactatacc ctgacaatct ccagcctgca gcctgaggac    300

ttcgctacct acttctgcca gcaaggcaag accctgcctt acacctttgg ccagggcacc    360

aagctggaaa tcaagcggac agtggccgct ccttccgtgt tcatcttccc accttccgac    420

gagcagctga agtccggcac agcttctgtc gtgtgcctgc tgaacaactt ctaccctcgg    480

gaagccaagg tgcagtggaa ggtggacaat gccctgcagt ccggcaactc ccaagagtct    540

gtgaccgagc aggactccaa ggacagcacc tacagcctgt cctccacact gaccctgtcc    600

aaggccgact acgagaagca caaggtgtac gcctgcgaag tgacccatca gggcctgtct    660

agccctgtga ccaagtcttt caaccggggc gagtgt                              696
```

<210> SEQ ID NO 131
<211> LENGTH: 464
<212> TYPE: PRT
<213> ORGANISM: Artificial Sequence
<220> FEATURE:
<223> OTHER INFORMATION: humanized IgG4 chain of anti-human-CD89 antibody 10E7 covering humanized VH1

<400> SEQUENCE: 131

```
Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Leu Val Gln Pro
            20                  25                  30
```

```
Gly Gly Ser Leu Arg Leu Ser Cys Ala Ala Ser Gly Leu Thr Phe Ser
        35                  40                  45

Ser Tyr Gly Met Ser Trp Val Arg Gln Ala Pro Gly Lys Gly Leu Glu
    50                  55                  60

Trp Val Ser Thr Ile Asn Gly Asn Gly Asp Ile Thr Tyr Tyr Pro Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Asp Tyr Asp Tyr Asp Tyr Ala Met Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly Lys
```

450 455 460

<210> SEQ ID NO 132
<211> LENGTH: 464
<212> TYPE: PRT
<213> ORGANISM: Artificial Sequence
<220> FEATURE:
<223> OTHER INFORMATION: humanized IgG4 chain of anti-human-CD89 antibody 10E7 covering humanized VH2

<400> SEQUENCE: 132

Met Lys Trp Val Thr Phe Ile Ser Leu Leu Phe Leu Phe Ser Ser Ala
1 5 10 15

Tyr Ser Glu Val Gln Leu Leu Glu Ser Gly Gly Gly Leu Val Gln Pro
20 25 30

Gly Gly Ser Leu Arg Leu Ser Cys Ala Ala Ser Gly Leu Thr Phe Ser
35 40 45

Ser Tyr Gly Met Ser Trp Val Arg Gln Ala Pro Gly Lys Gly Leu Glu
50 55 60

Trp Val Ala Thr Ile Asn Gly Asn Gly Asp Ile Thr Tyr Tyr Pro Asp
65 70 75 80

Ser Val Lys Gly Arg Phe Thr Ile Ser Arg Asp Asn Ser Lys Asn Thr
85 90 95

Leu Tyr Leu Gln Met Asn Ser Leu Arg Ala Glu Asp Thr Ala Val Tyr
100 105 110

Tyr Cys Ala Arg Asp Tyr Asp Tyr Asp Tyr Ala Met Asp Tyr Trp Gly
115 120 125

Gln Gly Thr Leu Val Thr Val Ser Ser Ala Ser Thr Lys Gly Pro Ser
130 135 140

Val Phe Pro Leu Ala Pro Cys Ser Arg Ser Thr Ser Glu Ser Thr Ala
145 150 155 160

Ala Leu Gly Cys Leu Val Lys Asp Tyr Phe Pro Glu Pro Val Thr Val
165 170 175

Ser Trp Asn Ser Gly Ala Leu Thr Ser Gly Val His Thr Phe Pro Ala
180 185 190

Val Leu Gln Ser Ser Gly Leu Tyr Ser Leu Ser Ser Val Val Thr Val
195 200 205

Pro Ser Ser Ser Leu Gly Thr Lys Thr Tyr Thr Cys Asn Val Asp His
210 215 220

Lys Pro Ser Asn Thr Lys Val Asp Lys Arg Val Glu Ser Lys Tyr Gly
225 230 235 240

Pro Pro Cys Pro Pro Cys Pro Ala Pro Glu Phe Leu Gly Gly Pro Ser
245 250 255

Val Phe Leu Phe Pro Pro Lys Pro Lys Asp Thr Leu Met Ile Ser Arg
260 265 270

Thr Pro Glu Val Thr Cys Val Val Val Asp Val Ser Gln Glu Asp Pro
275 280 285

Glu Val Gln Phe Asn Trp Tyr Val Asp Gly Val Glu Val His Asn Ala
290 295 300

Lys Thr Lys Pro Arg Glu Glu Gln Phe Asn Ser Thr Tyr Arg Val Val
305 310 315 320

Ser Val Leu Thr Val Leu His Gln Asp Trp Leu Asn Gly Lys Glu Tyr
325 330 335

Lys Cys Lys Val Ser Asn Lys Gly Leu Pro Ser Ser Ile Glu Lys Thr
340 345 350

```
Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly Lys
    450                 455                 460


<210> SEQ ID NO 133
<211> LENGTH: 464
<212> TYPE: PRT
<213> ORGANISM: Artificial Sequence
<220> FEATURE:
<223> OTHER INFORMATION: humanized IgG4 chain of anti-human-CD89
      antibody 10E7 covering humanized VH3

<400> SEQUENCE: 133

Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Leu Val Gln Pro
            20                  25                  30

Gly Gly Ser Leu Arg Leu Ser Cys Ala Ala Ser Gly Leu Thr Phe Ser
        35                  40                  45

Ser Tyr Gly Met Ser Trp Val Arg Gln Ala Pro Gly Lys Gly Leu Glu
    50                  55                  60

Leu Val Ala Thr Ile Asn Gly Asn Gly Asp Ile Thr Tyr Tyr Pro Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Asp Tyr Asp Tyr Asp Tyr Ala Met Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255
```

```
Val Phe Leu Phe Pro Pro Lys Pro Lys Asp Thr Leu Met Ile Ser Arg
        260                 265                 270

Thr Pro Glu Val Thr Cys Val Val Val Asp Val Ser Gln Glu Asp Pro
    275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly Lys
    450                 455                 460


<210> SEQ ID NO 134
<211> LENGTH: 232
<212> TYPE: PRT
<213> ORGANISM: Artificial Sequence
<220> FEATURE:
<223> OTHER INFORMATION: humanized kappa chain of anti-human-CD89
      antibody 10E7 covering humanized VL1

<400> SEQUENCE: 134

Met Lys Trp Val Thr Phe Ile Ser Leu Leu Phe Leu Phe Ser Ser Ala
1               5                   10                  15

Tyr Ser Asp Ile Gln Met Thr Gln Ser Pro Ser Ser Leu Ser Ala Ser
            20                  25                  30

Val Gly Asp Arg Val Thr Ile Thr Cys Arg Ala Ser Gln Asp Ile Ile
        35                  40                  45

Asn Tyr Leu Asn Trp Tyr Gln Gln Lys Pro Gly Lys Ala Pro Lys Leu
    50                  55                  60

Leu Ile Tyr Tyr Thr Ser Arg Leu His Ser Gly Val Pro Ser Arg Phe
65                  70                  75                  80

Ser Gly Ser Gly Ser Gly Thr Asp Phe Thr Leu Thr Ile Ser Ser Leu
                85                  90                  95

Gln Pro Glu Asp Phe Ala Thr Tyr Tyr Cys Gln Gln Gly Lys Thr Leu
            100                 105                 110

Pro Tyr Thr Phe Gly Gln Gly Thr Lys Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
```

```
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230


<210> SEQ ID NO 135
<211> LENGTH: 232
<212> TYPE: PRT
<213> ORGANISM: Artificial Sequence
<220> FEATURE:
<223> OTHER INFORMATION: humanized kappa chain of anti-human-CD89
      antibody 10E7 covering humanized VL2

<400> SEQUENCE: 135

Met Lys Trp Val Thr Phe Ile Ser Leu Leu Phe Leu Phe Ser Ser Ala
1               5                   10                  15

Tyr Ser Asp Ile Gln Met Thr Gln Ser Pro Ser Ser Leu Ser Ala Ser
            20                  25                  30

Val Gly Asp Arg Val Thr Ile Thr Cys Arg Ala Ser Gln Asp Ile Ile
        35                  40                  45

Asn Tyr Leu Asn Trp Tyr Gln Gln Lys Pro Gly Lys Ala Pro Lys Leu
    50                  55                  60

Leu Ile Tyr Tyr Thr Ser Arg Leu His Ser Gly Val Pro Ser Arg Phe
65                  70                  75                  80

Ser Gly Ser Gly Ser Gly Thr Asp Tyr Thr Leu Thr Ile Ser Ser Leu
                85                  90                  95

Gln Pro Glu Asp Phe Ala Thr Tyr Tyr Cys Gln Gln Gly Lys Thr Leu
            100                 105                 110

Pro Tyr Thr Phe Gly Gln Gly Thr Lys Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230


<210> SEQ ID NO 136
<211> LENGTH: 232
<212> TYPE: PRT
<213> ORGANISM: Artificial Sequence
<220> FEATURE:
```

```
<223> OTHER INFORMATION: humanized kappa chain of anti-human-CD89
      antibody 10E7 covering humanized VL3

<400> SEQUENCE: 136

Met Lys Trp Val Thr Phe Ile Ser Leu Leu Phe Leu Phe Ser Ser Ala
1               5                   10                  15

Tyr Ser Asp Ile Gln Met Thr Gln Ser Pro Ser Ser Leu Ser Ala Ser
            20                  25                  30

Val Gly Asp Arg Val Thr Ile Thr Cys Arg Ala Ser Gln Asp Ile Ile
        35                  40                  45

Asn Tyr Leu Asn Trp Tyr Gln Gln Lys Pro Gly Lys Ala Val Lys Leu
    50                  55                  60

Leu Ile Tyr Tyr Thr Ser Arg Leu His Ser Gly Val Pro Ser Arg Phe
65                  70                  75                  80

Ser Gly Ser Gly Ser Gly Thr Asp Tyr Thr Leu Thr Ile Ser Ser Leu
                85                  90                  95

Gln Pro Glu Asp Phe Ala Thr Tyr Tyr Cys Gln Gln Gly Lys Thr Leu
            100                 105                 110

Pro Tyr Thr Phe Gly Gln Gly Thr Lys Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230


<210> SEQ ID NO 137
<211> LENGTH: 232
<212> TYPE: PRT
<213> ORGANISM: Artificial Sequence
<220> FEATURE:
<223> OTHER INFORMATION: humanized kappa chain of anti-human-CD89
      antibody 10E7 covering humanized VL4

<400> SEQUENCE: 137

Met Lys Trp Val Thr Phe Ile Ser Leu Leu Phe Leu Phe Ser Ser Ala
1               5                   10                  15

Tyr Ser Asp Ile Gln Met Thr Gln Ser Pro Ser Ser Leu Ser Ala Ser
            20                  25                  30

Val Gly Asp Arg Val Thr Ile Thr Cys Arg Ala Ser Gln Asp Ile Ile
        35                  40                  45

Asn Tyr Leu Asn Trp Tyr Gln Gln Lys Pro Gly Lys Thr Val Lys Leu
    50                  55                  60

Leu Ile Tyr Tyr Thr Ser Arg Leu His Ser Gly Val Pro Ser Arg Phe
65                  70                  75                  80

Ser Gly Ser Gly Ser Gly Thr Asp Tyr Thr Leu Thr Ile Ser Ser Leu
                85                  90                  95
```

```
Gln Pro Glu Asp Phe Ala Thr Tyr Phe Cys Gln Gln Gly Lys Thr Leu
            100                 105                 110

Pro Tyr Thr Phe Gly Gln Gly Thr Lys Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230


<210> SEQ ID NO 138
<211> LENGTH: 119
<212> TYPE: PRT
<213> ORGANISM: Artificial Sequence
<220> FEATURE:
<223> OTHER INFORMATION: humanized 10E7 heavy chain variable region
      VH3SQ

<400> SEQUENCE: 138

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Gly Met Ser Trp Val Arg Gln Ala Pro Gly Lys Gly Leu Glu Leu Val
        35                  40                  45

Ala Thr Ile Ser Gly Gln Gly Asp Ile Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Asp Tyr Asp Tyr Ala Met Asp Tyr Trp Gly Gln Gly
            100                 105                 110

Thr Leu Val Thr Val Ser Ser
        115


<210> SEQ ID NO 139
<211> LENGTH: 119
<212> TYPE: PRT
<213> ORGANISM: Artificial Sequence
<220> FEATURE:
<223> OTHER INFORMATION: humanized 10E7 heavy chain variable region
      VH3ST

<400> SEQUENCE: 139

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30
```

```
Gly Met Ser Trp Val Arg Gln Ala Pro Gly Lys Gly Leu Glu Leu Val
        35                  40                  45

Ala Thr Ile Ser Gly Thr Gly Asp Ile Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Asp Tyr Asp Tyr Ala Met Asp Tyr Trp Gly Gln Gly
            100                 105                 110

Thr Leu Val Thr Val Ser Ser
        115


<210> SEQ ID NO 140
<211> LENGTH: 1392
<212> TYPE: DNA
<213> ORGANISM: Artificial Sequence
<220> FEATURE:
<223> OTHER INFORMATION: humanized IgG4 chain of anti-human-CD89
      antibody 10E7 covering humanized VH3SQ

<400> SEQUENCE: 140

atgaaatggg tcacctttat ctccctgctg ttcctgttct ccagcgccta ctctgaggtg     60

cagctgctgg aatctggcgg aggattggtt cagcctggcg gctctctgag actgtcttgt    120

gctgcttctg gcctgacctt ctcctcctac ggcatgtcct gggtccgaca ggctcctgga    180

aaaggcctgg aactggtggc taccatctct ggccagggcg acatcaccta ctatcccgac    240

tctgtgaagg gcagattcac catcagccgg gacaactcca agaacaccct gtacctgcag    300

atgaactccc tgagagccga ggacaccgcc gtgtactact gcgccagaga ctacgactac    360

gattacgcca tggactactg gggccagggc acactggtta ccgtgtcctc tgcttccacc    420

aagggaccct ctgtgttccc tctggctcct tgctccagat ccacctccga gtctacagct    480

gctctgggct gcctggtcaa ggactacttt cctgagcctg tgaccgtgtc ttggaactct    540

ggcgctctga catccggcgt gcacaccttt ccagctgtgc tgcaatccag cggcctgtac    600

tctctgtcct ccgtcgtgac cgtgccttct agctctctgg gcaccaagac ctacacctgt    660

aatgtggacc acaagccttc caacaccaag gtggacaagc gcgtggaatc taagtacggc    720

cctccttgtc ctccatgtcc tgctccagag tttctcggcg gaccttccgt gtttctgttc    780

cctccaaagc ctaaggacac cctgatgatc tctcggaccc ctgaagtgac ctgcgtggtg    840

gtggatgtgt cccaagagga cccagaggtg cagttcaatt ggtacgtgga cggcgtggaa    900

gtgcacaacg ccaagaccaa gcctagagag gaacagttca actccaccta cagagtggtg    960

tccgtgctga ccgtgctgca ccaggattgg ctgaacggaa aagagtacaa gtgcaaggtg   1020

tccaacaagg gcctgccttc cagcatcgaa aagaccatct ccaaggccaa gggccagcct   1080

agggaacccc aggtttacac cctgcctcca agccaagagg aaatgaccaa gaaccaggtg   1140

tccctgacct gcctcgtgaa gggcttctac ccttccgata tcgccgtgga atgggagagc   1200

aatggccagc ctgagaacaa ctacaagaca acccctcctg tgctggactc cgacggcagc   1260

ttcttcctgt attctcgcct gaccgtggac aagtccagat ggcaagaggg caacgtgttc   1320

tcctgctccg tgatgcacga ggccctgcac aatcactaca cccagaagtc cctgtctctg   1380

tccctgggca ag                                                        1392


<210> SEQ ID NO 141
```

<211> LENGTH: 1392
<212> TYPE: DNA
<213> ORGANISM: Artificial Sequence
<220> FEATURE:
<223> OTHER INFORMATION: humanized IgG4 chain of anti-human-CD89 antibody 10E7 covering humanized VH3ST

<400> SEQUENCE: 141

```
atgaaatggg tcacctttat ctccctgctg ttcctgttct ccagcgccta ctctgaggtg     60
cagctgctgg aatctggcgg aggattggtt cagcctggcg gctctctgag actgtcttgt    120
gctgcttctg gcctgacctt ctcctcctac ggcatgtcct gggtccgaca ggctcctgga    180
aaaggcctgg aactggtggc taccatctct ggcaccggcg acatcaccta ctatcccgac    240
tctgtgaagg gcagattcac catcagccgg gacaactcca agaacaccct gtacctgcag    300
atgaactccc tgagagccga ggacaccgcc gtgtactact gcgccagaga ctacgactac    360
gattacgcca tggactactg gggccagggc acactggtta ccgtgtcctc tgcttccacc    420
aagggaccct ctgtgttccc tctggctcct tgctccagat ccacctccga gtctacagct    480
gctctgggct gcctggtcaa ggactacttt cctgagcctg tgaccgtgtc ttggaactct    540
ggcgctctga catccggcgt gcacaccttt ccagctgtgc tgcaatccag cggcctgtac    600
tctctgtcct ccgtcgtgac cgtgccttct agctctctgg gcaccaagac ctacacctgt    660
aatgtggacc acaagccttc caacaccaag gtggacaagc gcgtggaatc taagtacggc    720
cctccttgtc ctccatgtcc tgctccagag tttctcggcg gaccttccgt gtttctgttc    780
cctccaaagc ctaaggacac cctgatgatc tctcggaccc ctgaagtgac ctgcgtggtg    840
gtggatgtgt cccaagagga cccagaggtg cagttcaatt ggtacgtgga cggcgtggaa    900
gtgcacaacg ccaagaccaa gcctagagag gaacagttca actccaccta cagagtggtg    960
tccgtgctga ccgtgctgca ccaggattgg ctgaacggaa aagagtacaa gtgcaaggtg   1020
tccaacaagg gcctgccttc cagcatcgaa aagaccatct ccaaggccaa gggccagcct   1080
agggaacccc aggtttacac cctgcctcca agccaagagg aaatgaccaa gaaccaggtg   1140
tccctgacct gcctcgtgaa gggcttctac ccttccgata tcgccgtgga atgggagagc   1200
aatggccagc ctgagaacaa ctacaagaca acccctcctg tgctggactc cgacggcagc   1260
ttcttcctgt attctcgcct gaccgtggac aagtccagat ggcaagaggg caacgtgttc   1320
tcctgctccg tgatgcacga ggccctgcac aatcactaca cccagaagtc cctgtctctg   1380
tccctgggca ag                                                       1392
```

<210> SEQ ID NO 142
<211> LENGTH: 464
<212> TYPE: PRT
<213> ORGANISM: Artificial Sequence
<220> FEATURE:
<223> OTHER INFORMATION: humanized IgG4 chain of anti-human-CD89 antibody 10E7 covering humanized VH3SQ

<400> SEQUENCE: 142

```
Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Leu Val Gln Pro
            20                  25                  30

Gly Gly Ser Leu Arg Leu Ser Cys Ala Ala Ser Gly Leu Thr Phe Ser
        35                  40                  45

Ser Tyr Gly Met Ser Trp Val Arg Gln Ala Pro Gly Lys Gly Leu Glu
    50                  55                  60
```

```
Leu Val Ala Thr Ile Ser Gly Gln Gly Asp Ile Thr Tyr Tyr Pro Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Asp Tyr Asp Tyr Asp Tyr Ala Met Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly Lys
    450                 455                 460
```

<210> SEQ ID NO 143
<211> LENGTH: 464

```
<212> TYPE: PRT
<213> ORGANISM: Artificial Sequence
<220> FEATURE:
<223> OTHER INFORMATION: humanized IgG4 chain of anti-human-CD89
      antibody 10E7 covering humanized VH3ST

<400> SEQUENCE: 143

Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Leu Val Gln Pro
            20                  25                  30

Gly Gly Ser Leu Arg Leu Ser Cys Ala Ala Ser Gly Leu Thr Phe Ser
        35                  40                  45

Ser Tyr Gly Met Ser Trp Val Arg Gln Ala Pro Gly Lys Gly Leu Glu
    50                  55                  60

Leu Val Ala Thr Ile Ser Gly Thr Gly Asp Ile Thr Tyr Tyr Pro Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Asp Tyr Asp Tyr Asp Tyr Ala Met Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
    370                 375                 380
```

```
Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly Lys
    450                 455                 460


<210> SEQ ID NO 144
<211> LENGTH: 119
<212> TYPE: PRT
<213> ORGANISM: Artificial Sequence
<220> FEATURE:
<223> OTHER INFORMATION: HC variable region
<220> FEATURE:
<221> NAME/KEY: MISC_FEATURE
<222> LOCATION: (47)..(47)
<223> OTHER INFORMATION: X is L or W
<220> FEATURE:
<221> NAME/KEY: MISC_FEATURE
<222> LOCATION: (49)..(49)
<223> OTHER INFORMATION: X is A or S
<220> FEATURE:
<221> NAME/KEY: MISC_FEATURE
<222> LOCATION: (52)..(52)
<223> OTHER INFORMATION: X is N or S
<220> FEATURE:
<221> NAME/KEY: MISC_FEATURE
<222> LOCATION: (54)..(54)
<223> OTHER INFORMATION: X is Q, T or N

<400> SEQUENCE: 144

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Gly Met Ser Trp Val Arg Gln Ala Pro Gly Lys Gly Leu Glu Xaa Val
        35                  40                  45

Xaa Thr Ile Xaa Gly Xaa Gly Asp Ile Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Asp Tyr Asp Tyr Ala Met Asp Tyr Trp Gly Gln Gly
            100                 105                 110

Thr Leu Val Thr Val Ser Ser
        115


<210> SEQ ID NO 145
<211> LENGTH: 107
<212> TYPE: PRT
<213> ORGANISM: Artificial Sequence
<220> FEATURE:
<223> OTHER INFORMATION: LC variable region
<220> FEATURE:
<221> NAME/KEY: MISC_FEATURE
<222> LOCATION: (43)..(43)
<223> OTHER INFORMATION: X is A or T
<220> FEATURE:
<221> NAME/KEY: MISC_FEATURE
```

```
<222> LOCATION: (44)..(44)
<223> OTHER INFORMATION: X is V or P
<220> FEATURE:
<221> NAME/KEY: MISC_FEATURE
<222> LOCATION: (71)..(71)
<223> OTHER INFORMATION: X is Y or F
<220> FEATURE:
<221> NAME/KEY: MISC_FEATURE
<222> LOCATION: (87)..(87)
<223> OTHER INFORMATION: X is Y or F

<400> SEQUENCE: 145

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ile Asn Tyr
            20                  25                  30

Leu Asn Trp Tyr Gln Gln Lys Pro Gly Lys Xaa Xaa Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Xaa Thr Leu Thr Ile Ser Ser Leu Gln Pro
65                  70                  75                  80

Glu Asp Phe Ala Thr Tyr Xaa Cys Gln Gln Gly Lys Thr Leu Pro Tyr
                85                  90                  95

Thr Phe Gly Gln Gly Thr Lys Leu Glu Ile Lys
            100                 105


<210> SEQ ID NO 146
<211> LENGTH: 119
<212> TYPE: PRT
<213> ORGANISM: Artificial Sequence
<220> FEATURE:
<223> OTHER INFORMATION: VH of anti-CD89 antibody
<220> FEATURE:
<221> NAME/KEY: MISC_FEATURE
<222> LOCATION: (52)..(52)
<223> OTHER INFORMATION: X is N or S
<220> FEATURE:
<221> NAME/KEY: MISC_FEATURE
<222> LOCATION: (54)..(54)
<223> OTHER INFORMATION: X is Q, T or N

<400> SEQUENCE: 146

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Gly Met Ser Trp Val Arg Gln Ala Pro Gly Lys Gly Leu Glu Leu Val
        35                  40                  45

Ala Thr Ile Xaa Gly Xaa Gly Asp Ile Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Asp Tyr Asp Tyr Ala Met Asp Tyr Trp Gly Gln Gly
            100                 105                 110

Thr Leu Val Thr Val Ser Ser
        115


<210> SEQ ID NO 147
<211> LENGTH: 17
```

<212> TYPE: PRT
<213> ORGANISM: Artificial Sequence
<220> FEATURE:
<223> OTHER INFORMATION: heavy chain CDR2 of 'CDR2 deamidation-repaired' 10E7

<400> SEQUENCE: 147

Thr Ile Ser Gly Gln Gly Asp Ile Thr Tyr Tyr Pro Asp Ser Val Lys
1               5                   10                  15

Gly

<210> SEQ ID NO 148
<211> LENGTH: 17
<212> TYPE: PRT
<213> ORGANISM: Artificial Sequence
<220> FEATURE:
<223> OTHER INFORMATION: heavy chain CDR2 of 'CDR2 deamidation-repaired' 10E7

<400> SEQUENCE: 148

Thr Ile Ser Gly Thr Gly Asp Ile Thr Tyr Tyr Pro Asp Ser Val Lys
1               5                   10                  15

Gly

<210> SEQ ID NO 149
<211> LENGTH: 119
<212> TYPE: PRT
<213> ORGANISM: Artificial Sequence
<220> FEATURE:
<223> OTHER INFORMATION: VH of anti-CD89 antibody
<220> FEATURE:
<221> NAME/KEY: MISC_FEATURE
<222> LOCATION: (54)..(54)
<223> OTHER INFORMATION: X is Q, T, or N

<400> SEQUENCE: 149

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Gly Met Ser Trp Val Arg Gln Ala Pro Gly Lys Gly Leu Glu Leu Val
        35                  40                  45

Ala Thr Ile Ser Gly Xaa Gly Asp Ile Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Asp Tyr Asp Tyr Ala Met Asp Tyr Trp Gly Gln Gly
            100                 105                 110

Thr Leu Val Thr Val Ser Ser
        115

<210> SEQ ID NO 150
<211> LENGTH: 119
<212> TYPE: PRT
<213> ORGANISM: Artificial Sequence
<220> FEATURE:
<223> OTHER INFORMATION: VH of anti-CD89 antibody
<220> FEATURE:
<221> NAME/KEY: MISC_FEATURE
<222> LOCATION: (54)..(54)
<223> OTHER INFORMATION: X is Q, T or N

```
<400> SEQUENCE: 150

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Gly Met Ser Trp Val Arg Gln Ala Pro Gly Lys Gly Leu Glu Leu Val
        35                  40                  45

Ala Thr Ile Asn Gly Xaa Gly Asp Ile Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Asp Tyr Asp Tyr Ala Met Asp Tyr Trp Gly Gln Gly
            100                 105                 110

Thr Leu Val Thr Val Ser Ser
        115
```

HUMANIZED ANTI-HUMAN CD89 ANTIBODIES AND USES THEREOF

RELATED APPLICATIONS

This application is a National Stage Application under 35 U.S.C. 371 of co-pending PCT application PCT/NL2021/050259 designating the United States and filed Apr. 21, 2021; which claims the benefit of EP application number 20170723.9 and filed Apr. 21, 2020, each of which are hereby incorporated by reference in their entireties.

FIELD OF THE INVENTION

The invention relates to the field of antibodies and the use of such antibodies. The antibodies are particularly useful to prevent binding of human IgA to human CD89. The antibodies are particularly useful to target human effector cells.

SEQUENCE LISTING

The instant application contains an updated Sequence Listing which has been submitted electronically in txt format and is hereby incorporated by reference in its entirety. Said txt copy, created on Oct. 17, 2025, is named "P126830US00_seqlist_ST25.txt" and is 180,224 bytes in size.

BACKGROUND OF THE INVENTION

Receptors for the Fc portions (FcR) of immunoglobulin are present on various types of immune cells and provide a link between humoral and cellular branches of the immune system. The interaction between antibodies and FcR provides the cells that express the FcR with antigen specific recognition properties. An interaction can initiate a variety of responses among which endocytosis, phagocytosis, transcytosis, exocytosis, superoxide generation, antibody-dependent cell cytotoxicity, and release of cytokine inflammatory mediators. The receptors for immunoglobulins and their role in immunological responses are extensively investigated.

Presently, five classes of antibody constant regions are recognized, namely IgG, IgA, IgD, IgE and IgM. IgA plays a role in the innate immune system. It is involved in preventing microorganisms and foreign proteins from penetrating the mucosal surfaces. IgA is also able to neutralizes toxins and infectious organisms. Furthermore, IgA has anti-inflammatory properties and is capable to inhibit functions such as IgG induced cytokine release and phagocytosis.

The different classes of antibody constant regions can interact with different Fc receptors. An Fc receptor that can bind IgA is CD89. Human CD89 is capable of binding to the heavy chain constant region of human IgA1 and human IgA2. CD89 is a glycosylated transmembrane receptor and is also known as FcαRI. CD89 has two extra-cellular domains, EC1 and EC2, a transmembrane domain and an intracellular domain. Interaction of CD89 with IgA is mediated by the EC1 extracellular domain. For a reference sequence we refer to NP_001991.1 (immunoglobulin alpha Fc receptor isoform a precursor). The reference is made solely to identify the human CD89 gene/protein. It is not intended to limit the human CD89 as described herein to the particular sequence of the database entry. Natural variants of human CD89 are within the scope of the invention. A recombinant human CD89 is also within the scope of the invention if it can bind IgA and can bind an antibody as described herein. CD89 is present on the cell surface of myeloid lineage cells including neutrophils, eosinophils, and most of the monocytes and macrophages. However, the receptor does not appear on mast cells and intestinal macrophages. CD89 expression is found to be constitutive and independent of the presence of IgA ligand.

CD89 can interact with monomeric IgA, polymeric IgA and IgA complexes. It is thought that monomeric IgA binds transiently to CD89, while polymeric IgA and IgA complexes bind avidly to CD89. CD89 can play a role in both pro- and anti-inflammatory responses. In order to respond to IgA binding the receptor has to associate with another factor, which is mostly a dimeric form of FcR γ-chain. Binding of ligand to CD89 can initiate a variety of biological processes. The cellular functions promoted by ligand binding to CD89 also depends on the associated FcR γ-chain.

Cross-linking of CD89 receptors on a cell can be achieved by binding of IgA antibodies, IgA immune complexes, or anti-CD89 antibodies. Cross-linking triggers an immunological response which can have positive and negative effects depending on the circumstances and particularly on the binding. CD89 specific antibodies can be used as a tool/medicament to modulate an immunological response. For example, an individual suffering from chronic inflammatory diseases can benefit from methods to inhibit immune responses. The CD89 receptor is expressed on various cell types, including neutrophils, eosinophils, monocytes and macrophages. Especially individuals suffering from diseases related to CD89 expressing cells and/or IgA related diseases may benefit from treatment with CD89 antibodies. Presently, there is no treatment known for diseases that are involved with neutrophils.

SUMMARY OF THE INVENTION

In one aspect the disclosure provides a humanized anti-human CD89 antibody that can bind an extra-cellular part of human CD89, comprising a heavy chain variable region comprising an amino acid sequence:

(SEQ ID NO: 144)
EVQLLESGGG LVQPGGSLRL SCAASGLTFS SYGMSWVRQA

PGKGLE$X_1$V$X_2$T I$X_3$G$X_4$GDITYY PDSVKGRFTI SRDNSKNTLY

TAVYYCARDY LQMNSLRAED DYDYAMDYWG QGTLVTVSS wherein:

$X_1$ is Lor W $X_2$ is A or S $X_3$ is Nor S $X_4$ is Q, T or N, wherein said heavy chain variable region comprises 0, 1, 2 or 3 amino acid variations, insertions, deletions, substitutions, additions with respect to the indicated amino acid sequence, or a combination thereof at positions other than $X_1$, $X_2$, $X_3$ and $X_4$, and a light chain variable region comprising an amino acid sequence:

(SEQ ID NO: 145)
DIQMTQSPSS LSASVGDRVT ITCRASQDII NYLNWYQQKP

GK$Z_1$$Z_2$KLLIYY TSRLHSGVPS RFSGSGSGTD $Z_3$TLTISSLQP

EDFATY$Z_4$CQQ GKTLPYTFGQ GTKLEIK, wherein:

$Z_1$ is A or T $Z_2$ is V or P $Z_3$ is Y or F $Z_4$ is Y or F, wherein said light chain variable region comprises 0, 1, 2 or 3 amino acid variations, insertions, deletions, substitutions, additions with respect to the indicated amino acid sequence, or a combination thereof at positions other than $Z_1$, $Z_2$, $Z_3$ and $Z_4$.

In a preferred embodiment $X_1$ is L, $X_2$ is A, $X_3$ is S, $X_4$ is T, $Z_1$ is A, $Z_2$ is V, $Z_3$ is Y and $Z_4$ is Y.

In another preferred embodiment $X_1$ is L, $X_2$ is A, $X_3$ is S, $X_4$ is Q, $Z_1$ is A, $Z_2$ is V, $Z_3$ is Y and $Z_4$ is Y.

In one aspect the disclosure provides an antibody that can bind an extra-cellular part of human CD89 comprising a heavy chain with the amino acid sequence of SEQ ID NO: 138 or 139 with 0, 1, 2, 3, 4, 5, 6, 7, 8, 9 or 10 amino acid insertions, deletions, substitutions or additions and a light chain with the amino acid sequence of SEQ ID NO: 122 with 0, 1, 2, 3, 4, 5, 6, 7 or 8 amino acid insertions, deletions, substitutions or additions.

An antibody as described herein can bind an extra-cellular part of human CD89 on human CD89 expressing cells and can prevent binding of human IgA to human CD89 when the antibody is bound to said cells.

In a further aspect an antibody as described herein can bind to an extra-cellular part of human CD89 on human CD89 expressing HEK293F cells. A Budapest treaty deposit of the human CD89 expressing HEK293F cells is deposited by Depositor Swiss Pharma International AG, Waldmannstr. 8, 8001 Zurich, Switzerland, under depositors reference 293F CG89 clone 2 at the Leibniz-Institut DSMZ-Deutsche Sammlung von Mikroorganismen und Zellkulturen GmbH (DSMZ), Braunschweig, Germany, having been assigned the accession number: DSM ACC3341.

In one aspect the disclosure provides a nucleic acid molecule or nucleic acid molecules encoding an antibody as disclosed herein or an antigen binding fragment thereof as disclosed herein. Also provided is a nucleic acid encoding a variable region as disclosed herein, preferably a heavy chain variable region and/or a light chain variable region of a humanized anti-human CD89 antibody as described herein.

In one aspect the disclosure provides a vector comprising a nucleic acid molecule as described herein. In one aspect the disclosure provides a cell (host cell) comprising an antibody, a nucleic acid molecule or molecules and/or a vector as disclosed herein. Preferably, the host cell is a mammalian, insect, plant, bacterial or yeast cell. More preferably, the host cell is a human cell. Preferably, the host cell is a hybridoma cell, a Chinese hamster ovary (CHO) cell, an NSO cell, or a PER-C6™ cell (European Collection of Cell Cultures (ECACC) 96022940; WO1997000326; Pau et al., 2001. Vaccine 19: 2716-2721).

In one aspect the disclosure provides a method of producing the antibody as disclosed herein. The method preferably includes harvesting of the antibody. Preferably, the antibodies are produced using a cell and are harvested from said cell. Preferably said cell is a hybridoma cell, a Chinese hamster ovary (CHO) cell, an NSO cell, or a PER-C6™ cell. In another preferred embodiment, the antibodies are produced synthetically.

One aspect of the disclosure provides a pharmaceutical composition comprising an antibody or antigen binding fragment thereof, nucleic acid and/or cell as disclosed. Preferably, the composition or antibody or antigen binding fragment thereof as disclosed herein are for use in the manufacture of a medicament. Preferably, the medicament is for the treatment or prophylaxis of chronic inflammatory diseases.

In one aspect the disclosure provides a method for the treatment of chronic inflammatory diseases in a subject comprising administering to the subject in need thereof a therapeutically effective amount of an antibody or antigen binding fragment thereof, a nucleic acid molecule or a vector or a pharmaceutical composition as disclosed herein.

In one aspect the disclosure provides an antibody or antigen binding fragment thereof for use in the treatment of chronic inflammatory diseases.

In one aspect the disclosure provides an antibody that can bind or binds an extra-cellular part of human CD89 on human CD89 expressing cells and that can prevent or prevents binding of human IgA to human CD89 when the antibody is bound to said cells and does not reduce the cell viability of said cells by more than 60% after overnight incubation at 37° C. The changes in viability or expression after overnight incubation at 37° C. as referred to herein preferable refer to changes relative to control values, preferably when incubated under the same conditions but without said antibody. Said viability experiments are preferably performed in a suitable medium, such as a serum free medium.

In a further aspect the disclosure provides an antibody that can bind an extra-cellular part of human CD89 on human CD89 expressing cells and that can prevent binding of human IgA to human CD89 when the antibody is bound to said cells and that does not increase phosphatidylserine expression of said cells by more than 20% after overnight incubation at 37° C., when compared to the same cells incubated under the same conditions but without said antibody.

In one aspect the disclosure provides an antibody that can bind an extra-cellular part of human CD89 on human CD89 expressing cells and that can prevent binding of human IgA to human CD89 when the antibody is bound to said cells at 37° C. in the absence of $NaN_3$, and that cannot displace monomeric human IgA or heat-aggregated IgA when bound to said cells at 4° C. in the presence of $NaN_3$.

In one aspect the disclosure provides, an antibody that can bind an extra-cellular part of human CD89 on human CD89 expressing cells and that can prevent binding of human IgA to human CD89 when the antibody is bound to said cells and that binds 20% or less to a recombinant human CD89 molecule wherein amino acids 22-46 of human CD89 are exchanged for amino acids 22-46 of cynomolgus CD89.

In one aspect the disclosure provides an antibody that can bind an extra-cellular part of human CD89 on human CD89 expressing cells and that can prevent binding of human IgA to human CD89 when the antibody is bound to said cells and that binds 20% or less to a chimeric CD89 molecule wherein amino acids 47-71 of human CD89 are exchanged for amino acids 47-71 of cynomolgus CD89.

In one aspect the disclosure provides an antibody that can bind an extra-cellular part of human CD89 on human CD89 expressing cells and that can prevent binding of human IgA to human CD89 when the antibody is bound to said cells and that binds 20% or less to a chimeric CD89 molecule wherein amino acids 72-96 of human CD89 are exchanged for amino acids 72-96 of cynomolgus CD89.

In one aspect the disclosure provides, an antibody that can bind an extra-cellular part of human CD89 on human CD89 expressing cells and that can prevent binding of human IgA to human CD89 when the antibody is bound to said cells and of which binding is not reduced by 20% or less to a chimeric CD89 molecule wherein amino acids 97-121 of human CD89 are exchanged for amino acids 97-121 of cynomolgus CD89.

In one aspect the disclosure provides an antibody that can bind an extra-cellular part of human CD89 on human CD89 expressing cells and that can prevent binding of human IgA to human CD89 when the antibody is bound to said cells and that binds 20% or less to a chimeric CD89 molecule wherein amino acids 58; 59; 73; 74; 76; 106 and 107 of human CD89 are exchanged for amino acids 58; 59; 73; 74; 76; 106 and 107 respectively of cynomolgus CD89.

In one aspect the disclosure provides an antibody that can bind an extra-cellular part of human CD89 comprising a heavy chain variable region with the CDR1, CDR2 and CDR3 sequence of SEQ ID NO: 29-31 with 0, 1 or 2 amino acid insertions, deletions, substitutions or additions and a light chain variable region with the CDR1, CDR2 and CDR3 sequence of SEQ ID NO: 32-34 with 0, 1 or 2 amino acid insertions, deletions, substitutions or additions.

In a further aspect the disclosure provides an antibody that can bind an extra-cellular part of human CD89 comprising a heavy chain variable region with the amino acid sequence of SEQ ID NO: 27 with 0, 1, 2, 3, 4, 5, 6, 7, 8, 9 or 10 amino acid insertions, deletions, substitutions or additions and a light chain variable region with the amino acid sequence of SEQ ID NO: 28 with 0, 1, 2, 3, 4, 5, 6, 7, 8, 9 or 10 amino acid insertions, deletions, substitutions or additions.

In one aspect the disclosure provides an antibody that can bind an extra-cellular part of human CD89 comprising a heavy chain variable region with the CDR1, CDR2 and CDR3 sequence of SEQ ID NO: 45-47 with 0, 1 or 2 amino acid insertions, deletions, substitutions or additions and a light chain variable region with the CDR1, CDR2 and CDR3 sequence of SEQ ID NO: 48-50 with 0, 1 or 2 amino acid insertions, deletions, substitutions or additions.

In a further aspect the disclosure provides an antibody that can bind an extra-cellular part of human CD89 comprising a heavy chain variable region with the amino acid sequence of SEQ ID NO: 43 with 0, 1, 2, 3, 4, 5, 6, 7, 8, 9 or 10 amino acid insertions, deletions, substitutions or additions and a light chain variable region with the amino acid sequence of SEQ ID NO: 44 with 0, 1, 2, 3, 4, 5, 6, 7, 8, 9 or 10 amino acid insertions, deletions, substitutions or additions.

In one aspect the disclosure provides an antibody that can bind an extra-cellular part of human CD89 comprising a heavy chain variable region with the CDR1, CDR2 and CDR3 sequence of SEQ ID NO: 69-71 with 0, 1 or 2 amino acid insertions, deletions, substitutions or additions and a light chain variable region with the CDR1, CDR2 and CDR3 sequence of SEQ ID NO: 72-74 with 0, 1 or 2 amino acid insertions, deletions, substitutions or additions.

In a further aspect the disclosure provides an antibody that can bind an extra-cellular part of human CD89 comprising a heavy chain variable region with the amino acid sequence of SEQ ID NO: 67 with 0, 1, 2, 3, 4, 5, 6, 7, 8, 9 or 10 amino acid insertions, deletions, substitutions or additions and a light chain variable region with the amino acid sequence of SEQ ID NO: 68 with 0, 1, 2, 3, 4, 5, 6, 7, 8, 9 or 10 amino acid insertions, deletions, substitutions or additions.

In one aspect the disclosure provides an antibody that can bind an extra-cellular part of human CD89 comprising a heavy chain variable region with the CDR1, CDR2 and CDR3 sequence of SEQ ID NO: 77-79 with 0, 1 or 2 amino acid insertions, deletions, substitutions or additions and a light chain variable region with the CDR1, CDR2 and CDR3 sequence of SEQ ID NO: 80-82 with 0, 1 or 2 amino acid insertions, deletions, substitutions or additions.

In a further aspect the disclosure provides an antibody that can bind an extra-cellular part of human CD89 comprising a heavy chain variable region with the amino acid sequence of SEQ ID NO: 75 with 0, 1, 2, 3, 4, 5, 6, 7, 8, 9 or 10 amino acid insertions, deletions, substitutions or additions and a light chain variable region with the amino acid sequence of SEQ ID NO: 76 with 0, 1, 2, 3, 4, 5, 6, 7, 8, 9 or 10 amino acid insertions, deletions, substitutions or additions.

In one aspect the disclosure provides an antibody that can bind an extra-cellular part of human CD89 comprising a heavy chain variable region with the CDR1, CDR2 and CDR3 sequence of SEQ ID NO: 53-55 with 0, 1 or 2 amino acid insertions, deletions, substitutions or additions and a light chain variable region with the CDR1, CDR2 and CDR3 sequence of SEQ ID NO: 56-58 with 0, 1 or 2 amino acid insertions, deletions, substitutions or additions.

In a further aspect the disclosure provides an antibody that can bind an extra-cellular part of human CD89 comprising a heavy chain variable region with the amino acid sequence of SEQ ID NO: 51 with 0, 1, 2, 3, 4, 5, 6, 7, 8, 9 or 10 amino acid insertions, deletions, substitutions or additions and a light chain variable region with the amino acid sequence of SEQ ID NO: 52 with 0, 1, 2, 3, 4, 5, 6, 7, 8, 9 or 10 amino acid insertions, deletions, substitutions or additions.

In one aspect the disclosure provides an antibody that can bind an extra-cellular part of human CD89, preferably the antibody can bind the EC1 extra-cellular domain of CD89.

BRIEF DESCRIPTION OF THE DRAWINGS

FIG. 2. Effect of mouse anti-human CD89 antibodies (supernatants) on binding of serum human IgA to rhuCD89 (A, ELISA) or to membrane-bound human CD89 (B, FACS) on HEK293F cells. Mean±SD (n=2) are shown.

FIG. 3. Binding characteristics of purified CD89/IgA blocking mouse anti-human CD89 antibodies to rhuCD89 (A, ELISA) or to membrane-bound human CD89 (B, FACS) on HEK293F cells. Mean±SD (n=2) are shown.

FIG. 6. Effect of prototypic commercial mouse anti-human CD89 antibodies clone MIP8a, clone A59 and clone A3 on prevention/inhibition of non-aggregated (A) or heat-aggregated (B) serum human IgA binding to membrane-bound human CD89 on HEK293F cells. Mean±SD (n=2) are shown.

FIG. 7. Binding of purified CD89/IgA blocking mouse anti-human CD89 antibodies (at 10 μg/mL) to membrane-bound human CD89 on ex vivo human neutrophilic granulocytes (A; Mean±SD from 5 different healthy donors), on HEK293F cells (B; mean±SD (n=2)), and on monocytic U937 cells (C; mean±SD (n=2)).

FIG. 8. Effect of purified CD89/IgA blocking mouse anti-human CD89 antibodies on phagocytosis of serum human IgA-coated latex beads by human CD89 expressing ex vivo primary human neutrophilic granulocytes. FIGS. 8A, 8B, and 8C represent healthy donors 1, 2, and 3, respectively. Dashed line represents phagocytosis of IgA-coated beads only (i.e., without addition of antibodies). Mean±SD (n=2) are shown.

FIG. 9. Effect of purified CD89/IgA blocking mouse anti-human CD89 antibodies (at 20 μg/mL) on (A-C; mean±SD (n=3)) serum human IgA-coated Sepharose beads-induced 2-dimensional migration of, and on (D-F; mean±SD (n=3)) their corresponding supernatant-derived chemotactic activity on and (G-I; n=1) their corresponding supernatant-derived chemoattractive LTB4 levels from human CD89 expressing ex vivo primary human neutrophilic granulocytes. FIGS. 9A, 9D, and 9G represent healthy donor 1; FIGS. 9B, 9E, and 9H represent healthy donor 2; and FIGS. 9C, 9F, and 9I represent healthy donor 3. Dashed lines represent (A-C) 2-dimensional granulocyte migration, (D-F) granulocyte chemotaxis, and (G-I) granulocyte LTB4 production induced by IgA-coated Sepharose beads only (i.e., without addition of antibodies). ND=not determined.

FIG. 10. Effect of purified CD89/IgA blocking mouse anti-human CD89 antibodies on (A-C) serum human IgA binding to, and on (D-F) their corresponding serum human IgA-mediated lactoferrin production (a degranulation marker) from human CD89 expressing ex vivo primary human neutrophilic granulocytes. FIGS. 10A and 10D represent healthy donor 1; FIGS. 10B and 10E represent healthy donor 2; and FIGS. 10C and 10F represent healthy donor 3. Dashed lines represent (A-C) granulocytes binding to, and (D-F) their corresponding lactoferrin production induced by IgA-coated plates only (i.e., without addition of antibodies). Mean±SD (n=2) are shown.

FIG. 11. Cross-competition of non-labeled purified CD89/IgA blocking mouse anti-human CD89 antibodies (at 10 μg/mL) with PE-conjugated commercial mouse anti-CD89 antibodies clone MIP8a (A; CD89/IgA blocker), clone A59 (B; CD89/IgA non-blocker), and clone A3 (C; CD89/IgA non-blocker) to membrane-bound human CD89 on HEK293F cells. Mean±SD (at least n=2) are shown.

FIG. 14. (A) Binding of rabbit anti-human CD89 polyclonal antibodies, and of non-aggregated or heat-aggregated serum human IgA to membrane-bound cynomolgus monkey full-length CD89. (B) Binding of purified CD89/IgA blocking mouse anti-human CD89 antibodies to membrane-bound cynomolgus monkey full-length CD89. Dotted grey lines represent background (i.e., no binding of mouse anti-human CD89 antibodies).

FIG. 16. Binding characteristics of purified CD89/IgA blocking chimeric mouse/human anti-human CD89 antibodies to rhuCD89 (A, ELISA) or to membrane-bound human CD89 (B, FACS) on HEK293F cells. Mean±SD (n=2) are shown.

FIG. 19. Effect of purified CD89/IgA blocking chimeric mouse/human anti-human CD89 antibodies on phagocytosis of serum human IgA-coated latex beads by human CD89 expressing ex vivo primary human neutrophilic granulocytes. FIGS. 19A, 19B, and 19C represent healthy donors 1, 2, and 3, respectively. Dashed line represents phagocytosis of IgA-coated beads only (i.e., without addition of antibodies). Mean±SD (n=2) are shown.

FIG. 20. Effect of purified CD89/IgA blocking chimeric mouse/human anti-human CD89 antibodies (at 20 μg/mL) on (A-C; mean±SD (n=3)) serum human IgA-coated Sepharose beads-induced 2-dimensional migration of, and on (D-E; mean±SD (n=3)) their corresponding supernatant-derived chemotactic activity on and (F-H; mean±SD (n=2)) their corresponding supernatant-derived chemoattractive LTB4 levels from human CD89 expressing ex vivo primary human neutrophilic granulocytes. FIGS. 20A, 20D, and 20F represent healthy donor 1; FIGS. 20B, 20E, and 20G represent healthy donor 2; and FIGS. 20C and 20H represent healthy donor 3. Dashed lines represent (A-C) 2-dimensional granulocyte migration, (D-E) granulocyte chemotaxis, and (F-H) granulocyte LTB4 production induced by IgA-coated Sepharose beads only (i.e., without addition of antibodies).

FIG. 21. Effect of purified CD89/IgA blocking chimeric mouse/human anti-human CD89 antibodies on serum human IgA-mediated lactoferrin production (a degranulation marker) from human CD89 expressing ex vivo primary human neutrophilic granulocytes. Dashed line represents lactoferrin production induced by IgA-coated plates only (i.e., without addition of antibodies). Mean±SD (n=2) are shown from 2 healthy donors (1 and 2).

FIG. 22: A Budapest treaty deposit of the human CD89 expressing HEK293F cells is are deposited under accession number: DSM ACC3341 and identification reference: 293F CD89 clone 2. Deposit forms: (A) Receipt in the case of an original deposit (B) Viability statement.

FIG. 26: Binding of characteristics of purified CD89/IgA blocking 'CDR2 deamidation-repaired' (i.e., VH3SQVL3 10E7 and VH3STVL3 10E7) humanized anti-human CD89 antibody 10E7 versions VH3SQVL3 and VH3STVL3 (i.e., humanized VH3 and VL3 versions derived from CD89/IgA blocking mouse anti-human antibody 10E7 VH and VL regions combined with human constant IgG4K regions) to rhuCD89 (A, ELISA) and to membrane-bound human CD89 (B, FACS) on HEK293F cells. CD89/IgA blocking chimeric anti-human CD89 antibody 10E7 (i.e., chimer IgG4/K 10E7) was used as reference. Mean±SD (n=2) are shown.

FIG. 27: Effect of purified CD89/IgA blocking 'CDR2 deamidation-repaired' (i.e., VH3SQVL3 10E7 and VH3STVL3 10E7) humanized anti-human CD89 antibody 10E7 versions VH3SQVL3 and VH3STVL3 (i.e., humanized VH3 and VL3 versions derived from CD89/IgA blocking mouse anti-human antibody 10E7 VH and VL regions combined with human constant IgG4K regions) on binding of serum human IgA (A) and secretory human IgA (B) to membrane-bound human CD89 on HEK293F cells. CD89/IgA blocking chimeric anti-human CD89 antibody 10E7 (i.e., chimer IgG4/K 10E7) was used as reference. Mean±SD (n=2) are shown.

FIG. 29: Effect of purified CD89/IgA blocking 'CDR2 deamidation-repaired' humanized IgG4/kappa anti-human CD89 monoclonal antibody 10E7 versions VH3SQVL3 and VH3STVL3 on phagocytosis of serum human IgA-coated latex beads by human CD89 expressing ex vivo primary human neutrophilic granulocytes. FIGS. 29A, 29B, and 29C represent healthy donors 1, 2, and 3, respectively. Dashed line represents phagocytosis of IgA-coated beads only (i.e., without addition of antibodies). Mean±SD (n=2) are shown.

FIG. 30: Effect of purified CD89/IgA blocking 'CDR2 deamidation-repaired' humanized IgG4/kappa anti-human CD89 monoclonal antibody 10E7 versions VH3SQVL3 and VH3STVL3 on serum human IgA-mediated lactoferrin production (a degranulation marker) from human CD89 expressing ex vivo primary human neutrophilic granulocytes. FIGS. 30A-30E represent healthy donors 1-5, respectively. Dashed line represents lactoferrin production induced by IgA-coated plates only (i.e., without addition of antibodies). Mean±SD (n=2) are shown.

DETAILED DESCRIPTION OF THE DISCLOSED EMBODIMENTS

Figure 1:
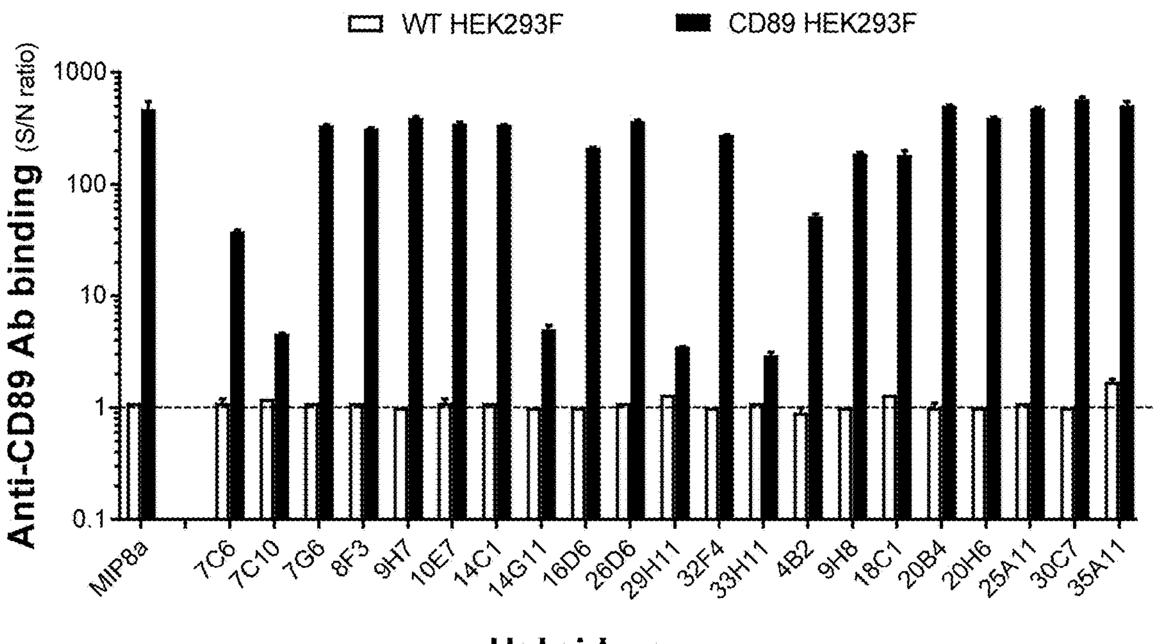
FIG. 1. Binding of mouse anti-human CD89 antibodies (supernatants) to membrane-bound full-length human CD89 on HEK293F cells using flow cytometry. Dashed line represents background (i.e., no binding of mouse anti-human CD89 antibodies). Mean±SD (n=2) are shown.

The disclosure describes antibodies that can bind an extra-cellular part of human CD89 (human FcαRI) on human CD89 expressing cells. An antibody as described herein is useful to prevent binding of human IgA to human CD89 when the antibody is bound to said cells. Several antibodies have been generated that can bind to the CD89 receptor. It is thought that monoclonal antibodies that bind to the EC1 domain of CD89 can block IgA binding, while antibodies that bind the EC2 domain do not prevent IgA binding to the receptor. Antibodies that specifically interfere with the IgA-binding site on CD89 are known in the art. For example, the antibodies MIP8a, 2D11 or MY43 as described in Morton et al., J. Exp. Med. 1999 Jun. 7; 189(11):1715-22 and Shen L. A., J Leukoc Biol. 1992 April; 51 (4):373-8. MIP8a is a mouse monoclonal antibody that binds to human CD89 and has a mouse IgG1 constant region. Antibodies that can bind CD89, for example MIP8a, can induce neutrophil death (Wehrli et al., J Immunol. 2014 Dec. 1; 193(11):5649-59).

In one aspect the invention provides new humanized antibodies that can bind an extra-cellular part of human CD89 (human FcαRI) on human CD89 expressing cells and that can prevent binding of human IgA to human CD89 when the antibody is bound to the cells.

In one aspect the invention provides new antibodies that can bind an extra-cellular part of human CD89 (human FcαRI) on human CD89 expressing cells and that can prevent binding of human IgA to human CD89 when the antibody is bound to the cells and that induce less cell death to the human CD89 expressing cells compared to the antibody MIP8a.

The term "antibody" refers to an immunoglobulin molecule that is typically composed of two identical pairs of polypeptide chains, each pair having one "heavy" (H) chain and one "light" (L) chain. Human light chains are classified as kappa (κ) and lambda (λ). Heavy chains are classified as mu, delta, gamma, alpha, or epsilon, and define the antibody's isotype as IgM, IgD, IgG, IgA, and IgE, respectively. Each heavy chain is comprised of a heavy chain variable region (abbreviated herein as HCVR or VH) and a heavy chain constant region. The heavy chain constant regions of IgD, IgG, and IgA are comprised of three domains, CH1, CH2 and CH3, and the heavy chain constant regions of IgM and IgE are comprised of four domains, CH1, CH2, CH3, and CH4. Each light chain is comprised of a light chain variable region (abbreviated herein as LCVR or VL) and a light chain constant region. The light chain constant region is comprised of one domain, CL. The constant regions of the antibodies may mediate the binding of the immunoglobulin to host tissues or factors, including various cells of the immune system (e.g., effector cells). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from the amino-terminus to carboxy-terminus in the following order: FR1, CDR1, FR2, CDR2, FR3, CDR3, FR4. The variable regions of the light and heavy chain together form the antibody binding site and defines the specificity for the epitope. Various methods are known in the art to assign amino acids to a region or domain in an antibody. Well known methods include the Kabat method and the Chothia method (Kabat Sequences of Proteins of Immunological Interest (National Institutes of Health, Bethesda, Md. (1987 and 1991); Chothia et al. Conformations of immunoglobulin hypervariable regions in Nature 1989; 342(6252):877-83). The assignment of the amino acids to each region or domain of this disclosure is in accordance with the definitions of Kabat.

The term "antibody" encompasses murine, humanized, deimmunized, human and chimeric antibodies, and an antibody that is a multimeric form of antibodies, such as dimers, trimers, or higher-order multimers of monomeric antibodies. Antibody also encompasses monospecific, bispecific or multispecific antibodies, and any other modified configuration of the immunoglobulin molecule that comprises an antigen recognition site of the required specificity. It also encompasses an antibody that is linked or attached to a non-antibody moiety. Further, the term "antibody" is not limited by any particular method of producing the antibody. For example, it includes monoclonal antibodies, recombinant antibodies and polyclonal antibodies. The invention provides an antibody as described herein. Furthermore, the invention provides a part, derivative and/or analogue of an antibody as disclosed herein. The part, derivative and/or analogue retains the antigen binding property of the antibody in kind, not necessarily in amount. Non-limiting examples of a part and/or derivative include a part of an antibody is an antigen binding part and typically contains one or more variable domains of the antibody. Non-limiting examples are the various Fab fragments. Apart can also be a so-called single domain antibody fragment. A single-domain antibody fragment (sdAb, called Nanobody by Ablynx, the developer) is an antibody fragment with a single monomeric variable antibody domain. Like a whole antibody, it is able to bind selectively to a specific antigen. With a molecular weight of only 12-15 kDa, single-domain antibody fragments are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable regions, one from a light and one from a heavy chain). Single-domain antibodies by themselves are not much smaller than normal antibodies (being typically 90-100 kDa). Single-domain antibody fragments are mostly engineered from heavy-chain antibodies found in camelids; these are called VHH fragments (Nanobodies®). Some fishes also have heavy-chain only antibodies (IgNAR, 'immunoglobulin new antigen receptor'), from which single-domain antibody fragments called VNAR fragments can be obtained. An alternative approach is to split the dimeric variable domains from common immunoglobulin G (IgG) from humans or mice into monomers. Although most research into single-domain antibodies is currently based on heavy chain variable domains, nanobodies derived from light chains have also been shown to bind specifically to target epitopes. A non-limiting example of an antibody part contains a variable domain of a heavy chain and/or a light chain of an antibody or an equivalent thereof. Non-limiting examples of such parts are VHH, Human Domain Antibodies (dAbs) and Unibodies. Preferred antibody parts or derivatives have at least a variable domain of a heavy chain and a light chain of an antibody as described herein. Non-limiting examples of a derivative or a part is are a F(ab)-fragment and a single chain Fv fragment. A functional part of a bispecific antibody comprises the antigen binding parts of the bispecific antibody, or a derivative and/or analogue of the binding parts.

A "single-chain antibody" (scFv) has a single polypeptide chain comprising a VL domain linked to a VH domain wherein VL domain and VH domain are paired to form a monovalent molecule. Single chain antibody can be prepared according to method known in the art (see, for example, Bird et al., (1988) Science 242:423-426 and Huston et al., (1988) Proc. Natl. Acad. Sci. USA 85:5879-5883). A "diabody" has two chains, each chain comprising a heavy chain variable region connected to a light chain variable region on the same polypeptide chain connected by a short peptide linker, wherein the two regions on the same chain do not pair with each other but with complementary domains on the other chain to form a bispecific molecule. Methods of preparing diabodies are known in the art (See, e.g., Holliger P. et al., (1993) Proc. Natl. Acad. Sci. USA 90:6444-6448, and Poljak R. J. et al., (1994) Structure 2:1121-1123). Domain antibodies (dAbs) are small functional binding units of antibodies, corresponding to the variable regions of either the heavy or light chains of antibodies. Domain antibodies are well expressed in bacterial, yeast, and mammalian cell systems. Further details of domain antibodies and methods of production thereof are known in the art (see, for example, U.S. Pat. Nos. 6,291,158; 6,582,915; 6,593,081; WO04/003019 and WO03/002609). Nanobodies are derived from the heavy chains of an antibody. A nanobody typically comprises a single variable domain and two constant domains (CH2 and CH3) and retains antigen-binding capacity of the original antibody. Nanobodies can be prepared by methods known in the art (see e.g., U.S. Pat. Nos. 6,765,087, 6,838,254, WO 06/079372). Unibodies have one light chain and one heavy chain of an IgG4 antibody. Unibodies may be made by the removal of the hinge region of IgG4 antibodies. Further details of unibodies and methods of preparing them may be found in WO2007/059782.

The list of analogues to antibodies is increasing every year. With the sequence of the variable domains and the presently extensive knowledge of the 3D structure of many different antibodies the skilled person can convert an antibody of the invention to one or the other antibody analogue, part or derivative.

In addition to the binding molecule, the molecules of the invention may further comprise a moiety for increasing the in vivo half-life of the molecule, such as but not limited to polyethylene glycol (PEG), human serum albumin, glycosylation groups, fatty acids and dextran. Such further moieties may be conjugated or otherwise combined with the binding moiety using methods well known in the art.

Also provided are chimeric antigen receptors (CAR) comprising a variable domain of an antibody as described herein. CAR are engineered receptors that combine a new specificity (typically an antigen binding part of an antibody or a derivative thereof) with an immune cell to target cells. The receptors are called chimeric because they are fused of parts from different sources (T lymphocytes genetically modified to express one or more chimeric antigen receptors (CARs; see, e.g., Eshhar, U.S. Pat. No. 7,741,465; Eshhar, U.S. Patent Application Publication No. 2012/0093842). In some embodiments, the antibodies as disclosed herein can be coupled to an active compound for example a toxin. Furthermore, the antibodies or antigen binding fragments as disclosed may be coupled to a label, e.g. a fluorescent protein, chemical label, organic dye, coloured particle or enzyme. The antibodies as disclosed herein can be coupled to a drug to form an antibody-drug conjugate (ADC). The invention provides antibody analogues, antibody parts and antibody derivatives, also when these molecules are coupled to other molecules or incorporated.

In some embodiments an antibody as disclosed herein is a chimeric antibody. The term "chimeric antibody" refers to an antibody that comprises amino acid sequences derived from two different species such as human and mouse, typically a combination of mouse variable (from heavy and light chains) regions and human constant (heavy and light chains) regions. A non-limiting example of generating such a chimeric antibody is described in the working examples (Example 6). In this chimeric antibody the mouse IgG1/kappa constant region is exchanged for a human IgG/kappa constant domain.

In a preferred embodiment an antibody as disclosed herein is a humanized antibody. The term "humanized antibody" refers to an antibody that contains some or all of the CDRs from a non-human animal antibody while the framework and constant regions of the antibody contain amino acid residues derived from human antibody sequences. Humanized antibodies are typically produced by grafting CDRs from a mouse antibody into human framework sequences followed by back substitution of certain human framework residues for the corresponding mouse residues from the source antibody. Humanized antibodies can also be generated in silico using the amino acid sequence of an antibody of non-human origin and Protein Design Lab (PDL) Technology (U.S. Pat. Nos. 569,376, 5,693,671, 5,585,089). An advantage of humanized antibodies is their increased in vivo tolerability compared to murine counterparts.

The term "deimmunized antibody" also refers to an antibody of non-human origin in which, typically in one or more variable regions, one or more epitopes have been removed, that have a high propensity of constituting a human T-cell and/or B-cell epitope, for purposes of reducing immunogenicity. The amino acid sequence of the epitope can be removed in full or in part. However, typically the amino acid sequence is altered by substituting one or more of the amino acids constituting the epitope for one or more other amino acids, thereby changing the amino acid sequence into a sequence that does not constitute a human T-cell and/or B-cell epitope. The amino acids are substituted by amino acids that are present at the corresponding position(s) in a corresponding human variable heavy or variable light chain as the case may be.

In a preferred embodiment, an anti-CD89 antibody as disclosed herein is humanized.

Where herein reference is made to an "deamidation repaired" amino acid sequence it is intended to refer to an amino acid sequence wherein an amino acid that is prone to deamidation is replaced with an amino acid that is less or not prone to deamidation. Deamidation is a chemical reaction in which an amide functional group in the side chain of the amino acids asparagine or glutamine is removed or converted to another functional group. Typically, asparagine (Asn) is converted to aspartic acid or isoaspartic acid. Glutamine (Gln) can be converted to glutamic acid or pyroglutamic acid. Asn-Gly sites are most prone to deamidation, and asparagine is more readily deamidated compared to glutamine. The deamidation of asparagine and/or glutamine may alter the structure of the antibody as well as its stability and/or function. In an antibody, this reaction is not desirable because it may alter antibody structure, stability or function (i.e., antibody-antigen binding), and may lead to antibody degradation. Amino acids in antibody variable regions that are prone to deamidation can be predicted (Sydow et al. PLoS ONE 2014; 9(6): e100736). Thus, residues that are at risk of deamidation are identified, and these sites can then be repaired by replacing the amino acid prone to deamidation with an amino acid that is less prone to deamidation.

In a preferred embodiment, a humanized anti-CD89 antibody as disclosed herein is deamidation-repaired. In one preferred embodiment, an asparagine prone to deamidation is replaced with a serine (S), threonine (T) or a glutamine (Q) amino acid.

In some embodiments, an antibody as disclosed herein is a human antibody. The term "human antibody" refers to an antibody consisting of amino acid sequences of human immunoglobulin sequences only. A human antibody may contain murine carbohydrate chains if produced in a mouse, in a mouse cell or in a hybridoma derived from a mouse cell. Human antibodies may be prepared in a variety of ways known in the art. Chimeric, humanized, deimmunized and human antibodies are within the scope of the invention.

An antibody that can bind human CD89 binds to the receptor under conditions that are normally used for antibody binding. When the antibody and the human CD89 receptor are contacted with each other under conditions suitable for antibody binding, the antibody will bind to the human CD89 receptor. The antibody binds to membrane bound human CD89 expressed on the HEK293F cells as deposited under number DSM ACC3341, while the antibody does not bind significantly to HEK293F cells that do not express human CD89 on their cell membrane. Binding of the antibody to a human CD89 expressing cell can be detected by methods known to the person skilled in the art. For example, by using a secondary antibody carrying a fluorescent label and measure labelled cells using flow cytometry (FACS).

CD89 is an Fc receptor that can bind IgA. The receptor is also known as FcαRI. Human CD89 is capable of binding to the heavy chain constant region of human IgA1 and human IgA2. CD89 is a glycosylated transmembrane receptor and has two extra-cellular domains, EC1 and EC2, a transmembrane domain and an intracellular domain. Interaction of CD89 with IgA is mediated by the EC1 extracellular domain. For a reference sequence we refer to NP_001991.1 (immunoglobulin alpha Fe receptor isoform a precursor). The reference is made solely to identify a human CD89 gene/protein. It is not intended to limit the human CD89 as described herein to the particular sequence of the database entry. Natural variants of human CD89 that can bind IgA and can be bound by an antibody as described herein are within the scope of the invention. A recombinant human CD89 is also within the scope of the invention if it can bind IgA and can bind an antibody as described herein.

CD89 is present on the cell surface of myeloid lineage cells including neutrophils, eosinophils, and most of the monocytes and macrophages. The receptor does not appear on mast cells and intestinal macrophages. CD89 expression is found to be constitutive and independent of the presence of IgA ligand. The term "human CD89 expressing cells" refers to a cell that expresses human CD89. Exemplary cells are neutrophils, eosinophils, monocytes and/or macrophages.

Cross-linking of CD89 receptors on a cell can be achieved by binding of IgA antibodies, IgA immune complexes, or anti-CD89 antibodies. Binding of IgA can trigger an immunological response which can have positive and negative effects.

The term "extra-cellular" literally means outside the cells. The term "extra-cellular part" refers to a part of a molecule that is on the outer side of the cell membrane. This part of the molecule can be available for interactions with other molecules outside the cell. The human CD89 receptor has 2 extra-cellular domains, namely EC1 and EC2. These domains may interact with molecules outside the cell, for example IgA antibodies. IgA is known to bind to the EC1 domain of the human CD89 receptor.

Human CD89 expressing cells are cells that express the human CD89 molecule. Preferably, the molecule is present on the cell membrane of the cell. Examples of cell expressing human CD89 are, but are not limited to neutrophils, eosinophils, monocytes and/or macrophages. Furthermore, a modified HEK293F cell line expressing human CD89 on the cell membrane is deposited under number: DSM ACC3341

The term "to prevent binding" refers to the ability of the antibody or antigen binding fragment thereof as disclosed herein to prevent IgA from interacting with the human CD89 receptor. If the anti-CD89 antibody or antibody fragment thereof is bound to the human CD89 receptor, IgA can no longer bind to the human CD89 receptor. Preferably, binding of the anti-CD89 antibody as disclosed herein blocks or reduces the ability of IgA binding to the human CD89 receptor for at least 50%, preferably at least 60%, at least 70%, at least 80% or at least 90%. Prevention or blocking or reduction of binding of IgA to CD89 is preferably measured with a method described in the examples. Preferably CD89 expressing cell are used. Preferably, said cells are stably expressing human CD89. An antibody of interest is titrated on CD89 expressing cells. Subsequently, the cells are incubated with IgA. After washing the IgA bound to the cells was detected using a labelled antibody against the IgA, preferably a fluorescent labeled antibody. Binding of IgA on the membrane of the human CD89 expressing cells can be measured using a flow cytometer (FACS). The amount of bound IgA indicates the blocking capabilities of the titrated antibody. Less binding of IgA at a certain antibody concentration indicates a stronger blocking capacity of the antibody. A preferred method is described in the examples of which the results are depicted in FIG. 4a and FIG. 4b. A test antibody is preferably titrated on human CD89 coated wells or on CD89 expressing HEK293F cells. Blocking capacity is then readily determined by comparing the titration curve with curves obtained with a positive control such as MIP8a. Blocking percentages are typically given as a percentage when compared to the blocking of MIP8a under otherwise identical conditions. Comparison of the percentage of binding of the test antibody and the control antibody MIP8a is preferably done at a concentration of antibody where the test antibody has just reached at least 90% of its blocking capacity. In FIG. 4b this is around the 1 μg/ml antibody concentration. The percentage blocking of antibody 8F3 is calculated to be about $((800-200)/800)\times 100$=about 75% in this example. The percentage blocking of antibody 16D6 is calculated to be about $((800-450)/800)\times 100$=about 45%. A control IgG1 that does not bind CD89 typically does not prevent binding of IgA to CD89.

Immunoglobulin A is an antibody isotype that is found, among others in the blood and in sero-mucosal secretions. Human IgA has two subclasses namely IgA1 and IgA2 and can be produced in monomeric and dimeric form. The dimeric form is the most prevalent form. The secreted form of dimeric IgA is also referred to as secretory IgA. The secreted form of IgA is partially sterically hindered in its binding to FcαRI. This is because some of sIgA's FcαRI binding sites are obscured by a section of the cleaved polymeric Ig receptor (called secretory component after cleavage) that aided sIgA's secretion into the gut lumen. Prior to binding to the polymeric receptor dimeric IgA (dIgA), binds to FcαRI with approximately the same affinity as monomeric IgA. The term "heat aggregated IgA" refers to complexes of IgA formed by heating IgA. These aggregates can mimic immune complexes, for example circulating immune complexes. The heat-aggregated IgA complexes can be produced by any method known to the person skilled in the art.

The term "cell death" refers to the event of a biological cell ceasing to carry out its functions. Cell death may result from various causes, for example apoptosis, programmed cell death, mitotic catastrophe, ischemic cell death and/or immunogenic cell death. The term "cell viability" relates to the capacity of the cell to perform certain functions, such as metabolism, growth, reproduction, some form of responsiveness, and adaptability. Cell death and cell viability can be evaluated by a number of suitable assays known to the skilled person, e.g. the MultiTox-Glo or MultiTox-Fluor multiplex cytotoxicity assay (Promega, Madison, Wisconsin), or the Live and Dead Cell Assay (Abcam; Cambridge, Massachusetts). Dye exclusion methods are frequently used as a measure to determine dead cells. Dyes as trypan blue do not easily pass the membrane of living cells but will enter dead cells as these are not able to maintain the integrity of their cell membrane. A suitable method for determining the viability of cells is described in the example section.

Antibodies that specifically interfere with the IgA-binding site on CD89 are known in the art. For example, the antibodies MIP8a, 2D11 or MY43 as described in Morton et al., J. Exp. Med. 1999 Jun. 7; 189(11):1715-22 and Shen L. A., J Leukoc Biol. 1992 April; 51 (4):373-8. MIP8a is a mouse monoclonal antibody that binds to human CD89 and has a mouse IgG1 constant region. MIP8a is shown to induce neutrophil death as described in Wehrli et al., J Immunol. 2014 Dec. 1; 193(11):5649-59.

In one aspect the disclosure provides a humanized anti-human CD89 antibody that can bind an extra-cellular part of human CD89, comprising a heavy chain variable region comprising an amino acid sequence:

(SEQ ID NO: 144)

EVQLLESGGG LVQPGGSLRL SCAASGLTFS SYGMSWVRQA

PGKGLEX$_1$VX$_2$T IX$_3$GX$_4$GDITYY PDSVKGRFTI SRDNSKNTLY

TAVYYCARDY LQMNSLRAED DYDYAMDYWG QGTLVTVSS wherein:

$X_1$ is Lor W $X_2$ is A or S $X_3$ is Nor S $X_4$ is Q, T or N, wherein said heavy chain variable region comprises preferably 0-3, preferably 0-2, preferably 0-1 and preferably 0 amino acid variations, insertions, deletions, substitutions, additions with respect to the indicated amino acid sequence, or a combination thereof at positions other than $X_1$, $X_2$, $X_3$ and $X_4$, and a light chain variable region comprising an amino acid sequence:

(SEQ ID NO: 145)

DIQMTQSPSS LSASVGDRVT ITCRASQDII NYLNWYQQKP

GKZ$_1$Z$_2$KLLIYY TSRLHSGVPS RFSGSGSGTD Z$_3$TLTISSLQP

EDFATYZ$_4$CQQ GKTLPYTFGQ GTKLEIK wherein:

$Z_1$ is A or T $Z_2$ is V or P $Z_3$ is Y or F $Z_4$ is Y or F, wherein said light chain variable region comprises preferably 0-3, preferably 0-2, preferably 0-1 and preferably 0 amino acid variations, insertions, deletions, substitutions, additions with respect to the indicated amino acid sequence, or a combination thereof at positions other than $Z_1$, $Z_2$, $Z_3$ and $Z_4$.

In some embodiments $X_1$, $X_2$, $X_3$ and $X_4$ are L, A, S and T, or L, A, S and Q, or L, A, N and N, or W, A, N and N, or W, S, N and N, and $Z_1$, $Z_2$, $Z_3$ and $Z_4$ are A, V, Y and Y.

In other embodiments $X_1$, $X_2$, $X_3$ and $X_4$ are L, A, N and N, or W, A, N and N, or W, S, N and N, and $Z_1$, $Z_2$, $Z_3$ and $Z_4$ are A, P, F and Y, In further embodiments $X_1$, $X_2$, $X_3$ and $X_4$ are L, A, N and N, or W, A, N and N, or W, S, N and N, and $Z_1$, $Z_2$, $Z_3$ and $Z_4$ are A, P, Y and Y, In further embodiments $X_1$, $X_2$, $X_3$ and $X_4$ are L, A, N and N, or W, A, N and N, or W, S, N and N, and $Z_1$, $Z_2$, $Z_3$ and $Z_4$ are T, V, Y and F, In a preferred embodiment $X_1$, $X_2$, $X_3$ and $X_4$ are L, A, S and T, and $Z_1$, $Z_2$, $Z_3$ and $Z_4$ are A, V, Y and Y. In another preferred embodiment $X_1$, $X_2$, $X_3$ and $X_4$ are L, A, S and Q, and $Z_1$, $Z_2$, $Z_3$ and $Z_4$ are A, V, Y and Y.

In a preferred embodiment an anti-human CD89 antibody as disclosed herein comprises the amino acid sequence EVQLLESGGG LVQPGGSLRL SCAASGLTFS SYGMSWVRQA PGKGLELVAT IX$_3$GX$_4$GDITYY PDSVKGRFTI SRDNSKNTLY LQMNSLRAED TAVYYCARDY DYDYAMDYWG QGTLVTVSS (SEQ ID NO: 146)

wherein said heavy chain variable region comprises preferably 0-3, preferably 0-2, preferably 0-1 and preferably 0 amino acid variations, insertions, deletions, substitutions, additions with respect to the indicated amino acid sequence, or a combination thereof at positions other than $X_3$ and $X_4$, and a light chain variable region comprising the amino acid sequence of SEQ ID NO: 122 comprising 0, 1, 2 or 3 amino acid insertions, deletions, substitutions or additions.

In a preferred embodiment $X_3$ is S and $X_4$ is T.

In another preferred embodiment $X_3$ is S and $X_4$ is Q.

A heavy chain as disclosed herein comprises 10, preferably 9, preferably 8, preferably 7, preferably 6, preferably 5, preferably 4, preferably 3, preferably 2, preferably 1, preferably 0 amino acid insertions, deletions, substitutions or additions. Of said 0-10 amino acid insertions, deletions, substitutions or additions no more than 3 are present in the heavy chain variable region. A heavy chain variable region as disclosed herein comprises 3, preferably 2, preferably 1, preferably 0 amino acid insertions, deletions, substitutions or additions. In a preferred embodiment, said 0-3 amino acid insertions, deletions, substitutions are present at positions other than $X_1$, $X_2$, $X_3$ and $X_4$, and an amino acid insertion, deletion, substitution or addition in a heavy chain variable region, when present is in a framework region. An amino acid insertion, deletion, substitution or addition in a heavy chain variable region, when present is preferably not an amino acid insertion, deletion, substitution or addition selected from a leucine (L) at position 5, an arginine (R) at position 19, an alanine (A) at position 40, a glycine (G) at position 42, a glycine (G) at position 44, a serine (S) at position 75, an asparagine (N) at position 84, an arginine (R) at position 87, an alanine (A) at position 88, a valine (V) at position 93, and a leucine (L) at position 114 of the heavy chain variable region.

A light chain as disclosed herein comprises 8, preferably 7, preferably 6, preferably 5, preferably 4, preferably 3, preferably 2, preferably 1, preferably 0 amino acid insertions, deletions, substitutions or additions. Of said 0-8 amino acid insertions, deletions, substitutions or additions no more than 5 are present in the light chain constant region and no more than 3 are present in the light chain variable region. A light chain variable region as disclosed herein comprises 3, preferably 2, preferably 1, preferably 0 amino acid insertions, deletions, substitutions or additions. In a preferred embodiment, said 0-3 amino acid insertions, deletions, substitutions or additions are present at positions other than $Z_1$, $Z_2$, $Z_3$ and $Z_4$, and an amino acid insertion, deletion, substitution or addition in a light chain variable region, when present is in a framework region. An amino acid insertion, deletion, substitution or addition in a light chain variable region, when present is preferably not an amino acid insertion, deletion, substitution or addition selected from a proline (P) at position 8, a valine (V) at position 15, an arginine (R) at position 18, a threonine (T) at position 22, a glycine (G) at position 41, a lysine (K) at position 42, an aspartic acid (D) at position 70, a threonine (T) at position 72, an isoleucine (I) at position 75, a serine (S) at position 77, a glutamine (Q) at position 79, a glutamine (Q) at position 80, a threonine (T) at position 83, and a glutamine (Q) at position 100 of the light chain variable region.

In one aspect the disclosure provides a humanized antibody binding human CD89 comprising a heavy chain variable region with the amino acid sequence of SEQ ID NO: 138 with 0, 1, 2 or 3 amino acid insertions, deletions, substitutions or additions and a light chain variable region with the amino acid sequence of SEQ ID NO: 122 with 0, 1, 2 or 3 amino acid insertions, deletions, substitutions or additions.

In a further aspect the disclosure provides a humanized antibody binding CD89, wherein the antibody comprises a heavy chain with the amino acid sequence of SEQ ID NO: 142 with 0, 1, 2, 3, 4, 5, 6, 7, 8, 9 or 10 amino acid insertions, deletions, substitutions or additions, wherein no more than 3, preferably no more than 2, preferably no more than 1, preferably 0 amino acid insertions, deletions, substitutions or additions are present in the variable region of the heavy chain, and a light chain with the amino acid sequence of SEQ ID NO: 136 with 0, 1, 2, 3, 4, 5, 6, 7 or 8 amino acid insertions, deletions, substitutions or additions, wherein no more than 3, preferably no more than 2, preferably no more than 1, preferably 0 amino acid insertions, deletions, substitutions or additions are present in the variable region of the light chain. Preferably, said humanized antibody that can bind an extra-cellular part of human CD89 comprises a heavy chain with the amino acid sequence of SEQ ID NO: 142 and a light chain variable region with the amino acid sequence of SEQ ID NO: 136. An exemplary antibody with these characteristics is antibody 10E7 VH3STVL3.

In one aspect the disclosure provides a humanized antibody binding human CD89 comprising a heavy chain variable region with the amino acid sequence of SEQ ID NO: 139 with 0, 1, 2 or 3 amino acid insertions, deletions, substitutions or additions and a light chain variable region with the amino acid sequence of SEQ ID NO: 122 with 0, 1, 2 or 3 amino acid insertions, deletions, substitutions or additions.

In a further aspect the disclosure provides a humanized antibody binding CD89, wherein the antibody comprises a heavy chain with the amino acid sequence of SEQ ID NO: 143 with 0, 1, 2, 3, 4, 5, 6, 7, 8, 9 or 10 amino acid insertions, deletions, substitutions or additions, wherein no more than 3, preferably no more than 2, preferably no more than 1, preferably 0 amino acid insertions, deletions, substitutions or additions are present in the variable region of the heavy chain, and a light chain with the amino acid sequence of SEQ ID NO: 136 with 0, 1, 2, 3, 4, 5, 6, 7 or 8 amino acid insertions, deletions, substitutions or additions, wherein no more than 3, preferably no more than 2, preferably no more than 1, preferably 0 amino acid insertions, deletions, substitutions or additions are present in the variable region of the light chain. Preferably, said humanized antibody that can bind an extra-cellular part of human CD89 comprises a heavy chain with the amino acid sequence of SEQ ID NO: 143 and a light chain variable region with the amino acid sequence of SEQ ID NO: 136. An exemplary antibody with these characteristics is antibody 10E7 VH3SQVL3.

In one the disclosure provides a humanized antibody binding human CD89 comprising a heavy chain variable region with the amino acid sequence of SEQ ID NO: 119 with 0, 1, 2 or 3 amino acid insertions, deletions, substitutions or additions and a light chain variable region with the amino acid sequence of SEQ ID NO: 122 with 0, 1, 2 or 3 amino acid insertions, deletions, substitutions or additions.

In a further aspect the disclosure provides a humanized antibody binding CD89, wherein the antibody comprises a heavy chain with the amino acid sequence of SEQ ID NO: 133 with 0, 1, 2, 3, 4, 5, 6, 7, 8, 9 or 10 amino acid insertions, deletions, substitutions or additions, wherein no more than 3, preferably no more than 2, preferably no more than 1, preferably 0 amino acid insertions, deletions, substitutions or additions are present in the variable region of the heavy chain, and a light chain with the amino acid sequence of SEQ ID NO: 136 with 0, 1, 2, 3, 4, 5, 6, 7 or 8 amino acid insertions, deletions, substitutions or additions, wherein no more than 3, preferably no more than 2, preferably no more than 1, preferably 0 amino acid insertions, deletions, substitutions or additions are present in the variable region of the light chain. Preferably, said humanized antibody that can bind an extra-cellular part of human CD89 comprises a heavy chain with the amino acid sequence of SEQ ID NO: 133 and a light chain variable region with the amino acid sequence of SEQ ID NO: 136. An exemplary antibody with these characteristics is antibody 10E7 VH3VL3.

In one aspect the disclosure provides a humanized antibody binding human CD89 comprising a heavy chain variable region with the amino acid sequence of SEQ ID NO: 119 with 0, 1, 2 or 3 amino acid insertions, deletions, substitutions or additions and a light chain variable region with the amino acid sequence of SEQ ID NO: 123 with 0, 1, 2 or 3 amino acid insertions, deletions, substitutions or additions.

In a further aspect the disclosure provides a humanized antibody binding CD89, wherein the antibody comprises a heavy chain with the amino acid sequence of SEQ ID NO: 133 with 0, 1, 2, 3, 4, 5, 6, 7, 8, 9 or 10 amino acid insertions, deletions, substitutions or additions, wherein no more than 3, preferably no more than 2, preferably no more than 1, preferably 0 amino acid insertions, deletions, substitutions or additions are present in the variable region of the heavy chain, and a light chain with the amino acid sequence of SEQ ID NO: 137 with 0, 1, 2, 3, 4, 5, 6, 7 or 8 amino acid insertions, deletions, substitutions or additions, wherein no more than 3, preferably no more than 2, preferably no more than 1, preferably 0 amino acid insertions, deletions, substitutions or additions are present in the variable region of the light chain. Preferably, said humanized antibody that can bind an extra-cellular part of human CD89 comprises a heavy chain with the amino acid sequence of SEQ ID NO: 133 and a light chain variable region with the amino acid sequence of SEQ ID NO: 137. An exemplary antibody with these characteristics is antibody 10E7 VH3VL4.

In one aspect the disclosure provides a humanized antibody binding human CD89 comprising a heavy chain variable region with the amino acid sequence of SEQ ID NO: 117 with 0, 1, 2 or 3 amino acid insertions, deletions, substitutions or additions and a light chain variable region with the amino acid sequence of SEQ ID NO: 120 with 0, 1, 2 or 3 amino acid insertions, deletions, substitutions or additions.

In a further aspect the disclosure provides a humanized antibody binding CD89, wherein the antibody comprises a heavy chain with the amino acid sequence of SEQ ID NO: 131 with 0, 1, 2, 3, 4, 5, 6, 7, 8, 9 or 10 amino acid insertions, deletions, substitutions or additions, wherein no more than 3, preferably no more than 2, preferably no more than 1, preferably 0 amino acid insertions, deletions, substitutions or additions are present in the variable region of the heavy chain, and a light chain with the amino acid sequence of SEQ ID NO: 134 with 0, 1, 2, 3, 4, 5, 6, 7 or 8 amino acid insertions, deletions, substitutions or additions, wherein no more than 3, preferably no more than 2, preferably no more than 1, preferably 0 amino acid insertions, deletions, substitutions or additions are present in the variable region of the light chain. Preferably, said humanized antibody that can bind an extra-cellular part of human CD89 comprises a heavy chain with the amino acid sequence of SEQ ID NO: 131 and a light chain variable region with the amino acid sequence of SEQ ID NO: 134. An exemplary antibody with these characteristics is antibody 10E7 VH1VL1.

In one aspect the disclosure provides a humanized antibody binding human CD89 comprising a heavy chain variable region with the amino acid sequence of SEQ ID NO: 117 with 0, 1, 2 or 3 amino acid insertions, deletions, substitutions or additions and a light chain variable region with the amino acid sequence of SEQ ID NO: 121 with 0, 1, 2 or 3 amino acid insertions, deletions, substitutions or additions.

In a further aspect the disclosure provides a humanized antibody binding CD89, wherein the antibody comprises a heavy chain with the amino acid sequence of SEQ ID NO: 131 with 0, 1, 2, 3, 4, 5, 6, 7, 8, 9 or 10 amino acid insertions, deletions, substitutions or additions, wherein no more than 3, preferably no more than 2, preferably no more than 1, preferably 0 amino acid insertions, deletions, substitutions or additions are present in the variable region of the heavy chain, and a light chain with the amino acid sequence of SEQ ID NO: 135 with 0, 1, 2, 3, 4, 5, 6, 7 or 8 amino acid insertions, deletions, substitutions or additions, wherein no more than 3, preferably no more than 2, preferably no more than 1, preferably 0 amino acid insertions, deletions, substitutions or additions are present in the variable region of the light chain. Preferably, said humanized antibody that can bind an extra-cellular part of human CD89 comprises a heavy chain with the amino acid sequence of SEQ ID NO: 131 and a light chain variable region with the amino acid sequence of SEQ ID NO: 135. An exemplary antibody with these characteristics is antibody 10E7 VH1VL2.

In one aspect the disclosure provides a humanized antibody binding human CD89 comprising a heavy chain variable region with the amino acid sequence of SEQ ID NO: 117 with 0, 1, 2 or 3 amino acid insertions, deletions, substitutions or additions and a light chain variable region with the amino acid sequence of SEQ ID NO: 122 with 0, 1, 2 or 3 amino acid insertions, deletions, substitutions or additions.

In a further aspect the disclosure provides a humanized antibody binding CD89, wherein the antibody comprises a heavy chain with the amino acid sequence of SEQ ID NO: 131 with 0, 1, 2, 3, 4, 5, 6, 7, 8, 9 or 10 amino acid insertions, deletions, substitutions or additions, wherein no more than 3, preferably no more than 2, preferably no more than 1, preferably 0 amino acid insertions, deletions, substitutions or additions are present in the variable region of the heavy chain, and a light chain with the amino acid sequence of SEQ ID NO: 136 with 0, 1, 2, 3, 4, 5, 6, 7 or 8 amino acid insertions, deletions, substitutions or additions, wherein no more than 3, preferably no more than 2, preferably no more than 1, preferably 0 amino acid insertions, deletions, substitutions or additions are present in the variable region of the light chain. Preferably, said humanized antibody that can bind an extra-cellular part of human CD89 comprises a heavy chain with the amino acid sequence of SEQ ID NO: 131 and a light chain variable region with the amino acid sequence of SEQ ID NO: 136. An exemplary antibody with these characteristics is antibody 10E7 VH1VL3.

In one aspect the disclosure provides a humanized antibody binding human CD89 comprising a heavy chain variable region with the amino acid sequence of SEQ ID NO: 117 with 0, 1, 2 or 3 amino acid insertions, deletions, substitutions or additions and a light chain variable region with the amino acid sequence of SEQ ID NO: 123 with 0, 1, 2 or 3 amino acid insertions, deletions, substitutions or additions.

In a further aspect the disclosure provides a humanized antibody binding CD89, wherein the antibody comprises a heavy chain with the amino acid sequence of SEQ ID NO: 131 with 0, 1, 2, 3, 4, 5, 6, 7, 8, 9 or 10 amino acid insertions, deletions, substitutions or additions, wherein no more than 3, preferably no more than 2, preferably no more than 1, preferably 0 amino acid insertions, deletions, substitutions or additions are present in the variable region of the heavy chain, and a light chain with the amino acid sequence of SEQ ID NO: 137 with 0, 1, 2, 3, 4, 5, 6, 7 or 8 amino acid insertions, deletions, substitutions or additions, wherein no more than 3, preferably no more than 2, preferably no more than 1, preferably 0 amino acid insertions, deletions, substitutions or additions are present in the variable region of the light chain. Preferably, said humanized antibody that can bind an extra-cellular part of human CD89 comprises a heavy chain with the amino acid sequence of SEQ ID NO: 131 and a light chain variable region with the amino acid sequence of SEQ ID NO: 137. An exemplary antibody with these characteristics is antibody 10E7 VH1VL4.

In one aspect the disclosure provides a humanized antibody binding human CD89 comprising a heavy chain variable region with the amino acid sequence of SEQ ID NO: 118 with 0, 1, 2 or 3 amino acid insertions, deletions, substitutions or additions and a light chain variable region with the amino acid sequence of SEQ ID NO: 120 with 0, 1, 2 or 3 amino acid insertions, deletions, substitutions or additions.

In a further aspect the disclosure provides a humanized antibody binding CD89, wherein the antibody comprises a heavy chain with the amino acid sequence of SEQ ID NO: 132 with 0, 1, 2, 3, 4, 5, 6, 7, 8, 9 or 10 amino acid insertions, deletions, substitutions or additions, wherein no more than 3, preferably no more than 2, preferably no more than 1, preferably 0 amino acid insertions, deletions, substitutions or additions are present in the variable region of the heavy chain, and a light chain with the amino acid sequence of SEQ ID NO: 134 with 0, 1, 2, 3, 4, 5, 6, 7 or 8 amino acid insertions, deletions, substitutions or additions, wherein no more than 3, preferably no more than 2, preferably no more than 1, preferably 0 amino acid insertions, deletions, substitutions or additions are present in the variable region of the light chain. Preferably, said humanized antibody that can bind an extra-cellular part of human CD89 comprises a heavy chain with the amino acid sequence of SEQ ID NO: 132 and a light chain variable region with the amino acid sequence of SEQ ID NO: 134. An exemplary antibody with these characteristics is antibody 10E7 VH2VL1.

In one aspect the disclosure provides a humanized antibody binding human CD89 comprising a heavy chain variable region with the amino acid sequence of SEQ ID NO: 118 with 0, 1, 2 or 3 amino acid insertions, deletions, substitutions or additions and a light chain variable region with the amino acid sequence of SEQ ID NO: 121 with 0, 1, 2 or 3 amino acid insertions, deletions, substitutions or additions.

In a further aspect the disclosure provides a humanized antibody binding CD89, wherein the antibody comprises a heavy chain with the amino acid sequence of SEQ ID NO: 132 with 0, 1, 2, 3, 4, 5, 6, 7, 8, 9 or 10 amino acid insertions, deletions, substitutions or additions, wherein no more than 3, preferably no more than 2, preferably no more than 1, preferably 0 amino acid insertions, deletions, substitutions or additions are present in the variable region of the heavy chain, and a light chain with the amino acid sequence of SEQ ID NO: 135 with 0, 1, 2, 3, 4, 5, 6, 7 or 8 amino acid insertions, deletions, substitutions or additions, wherein no more than 3, preferably no more than 2, preferably no more than 1, preferably 0 amino acid insertions, deletions, substitutions or additions are present in the variable region of the light chain. Preferably, said humanized antibody that can bind an extra-cellular part of human CD89 comprises a heavy chain with the amino acid sequence of SEQ ID NO: 132 and a light chain variable region with the amino acid sequence of SEQ ID NO: 135. An exemplary antibody with these characteristics is antibody 10E7 VH2VL2.

In one aspect the disclosure provides a humanized antibody binding human CD89 comprising a heavy chain variable region with the amino acid sequence of SEQ ID NO: 118 with 0, 1, 2 or 3 amino acid insertions, deletions, substitutions or additions and a light chain variable region with the amino acid sequence of SEQ ID NO: 122 with 0, 1, 2 or 3 amino acid insertions, deletions, substitutions or additions.

In a further aspect the disclosure provides a humanized antibody binding CD89, wherein the antibody comprises a heavy chain with the amino acid sequence of SEQ ID NO: 132 with 0, 1, 2, 3, 4, 5, 6, 7, 8, 9 or 10 amino acid insertions, deletions, substitutions or additions, wherein no more than 3, preferably no more than 2, preferably no more than 1, preferably 0 amino acid insertions, deletions, substitutions or additions are present in the variable region of the heavy chain, and a light chain with the amino acid sequence of SEQ ID NO: 136 with 0, 1, 2, 3, 4, 5, 6, 7 or 8 amino acid insertions, deletions, substitutions or additions, wherein no more than 3, preferably no more than 2, preferably no more than 1, preferably 0 amino acid insertions, deletions, substitutions or additions are present in the variable region of the light chain. Preferably, said humanized antibody that can bind an extra-cellular part of human CD89 comprises a heavy chain with the amino acid sequence of SEQ ID NO: 132 and a light chain variable region with the amino acid sequence of SEQ ID NO: 136. An exemplary antibody with these characteristics is antibody 10E7 VH2VL3.

In one aspect the disclosure provides a humanized antibody binding human CD89 comprising a heavy chain variable region with the amino acid sequence of SEQ ID NO: 118 with 0, 1, 2 or 3 amino acid insertions, deletions, substitutions or additions and a light chain variable region with the amino acid sequence of SEQ ID NO: 123 with 0, 1, 2 or 3 amino acid insertions, deletions, substitutions or additions.

In a further aspect the disclosure provides a humanized antibody binding CD89, wherein the antibody comprises a heavy chain with the amino acid sequence of SEQ ID NO: 132 with 0, 1, 2, 3, 4, 5, 6, 7, 8, 9 or 10 amino acid insertions, deletions, substitutions or additions, wherein no more than 3, preferably no more than 2, preferably no more than 1, preferably 0 amino acid insertions, deletions, substitutions or additions are present in the variable region of the heavy chain, and a light chain with the amino acid sequence of SEQ ID NO: 137 with 0, 1, 2, 3, 4, 5, 6, 7 or 8 amino acid insertions, deletions, substitutions or additions, wherein no more than 3, preferably no more than 2, preferably no more than 1, preferably 0 amino acid insertions, deletions, substitutions or additions are present in the variable region of the light chain. Preferably, said humanized antibody that can bind an extra-cellular part of human CD89 comprises a heavy chain with the amino acid sequence of SEQ ID NO: 132 and a light chain variable region with the amino acid sequence of SEQ ID NO: 137. An exemplary antibody with these characteristics is antibody 10E7 VH2VL4.

In one aspect the disclosure provides a humanized antibody binding human CD89 comprising a heavy chain variable region with the amino acid sequence of SEQ ID NO: 119 with 0, 1, 2 or 3 amino acid insertions, deletions, substitutions or additions and a light chain variable region with the amino acid sequence of SEQ ID NO: 120 with 0, 1, 2 or 3 amino acid insertions, deletions, substitutions or additions.

In a further aspect the disclosure provides a humanized antibody binding CD89, wherein the antibody comprises a heavy chain with the amino acid sequence of SEQ ID NO: 133 with 0, 1, 2, 3, 4, 5, 6, 7, 8, 9 or 10 amino acid insertions, deletions, substitutions or additions, wherein no more than 3, preferably no more than 2, preferably no more than 1, preferably 0 amino acid insertions, deletions, substitutions or additions are present in the variable region of the heavy chain, and a light chain with the amino acid sequence of SEQ ID NO: 134 with 0, 1, 2, 3, 4, 5, 6, 7 or 8 amino acid insertions, deletions, substitutions or additions, wherein no more than 3, preferably no more than 2, preferably no more than 1, preferably 0 amino acid insertions, deletions, substitutions or additions are present in the variable region of the light chain. Preferably, said humanized antibody that can bind an extra-cellular part of human CD89 comprises a heavy chain with the amino acid sequence of SEQ ID NO: 133 and a light chain variable region with the amino acid sequence of SEQ ID NO: 134. An exemplary antibody with these characteristics is antibody 10E7 VH3VL1.

In one aspect the disclosure provides a humanized antibody binding human CD89 comprising a heavy chain variable region with the amino acid sequence of SEQ ID NO: 119 with 0, 1, 2 or 3 amino acid insertions, deletions, substitutions or additions and a light chain variable region with the amino acid sequence of SEQ ID NO: 121 with 0, 1, 2 or 3 amino acid insertions, deletions, substitutions or additions.

In a further aspect the disclosure provides a humanized antibody binding CD89, wherein the antibody comprises a heavy chain with the amino acid sequence of SEQ ID NO: 133 with 0, 1, 2, 3, 4, 5, 6, 7, 8, 9 or 10 amino acid insertions, deletions, substitutions or additions, wherein no more than 3, preferably no more than 2, preferably no more than 1, preferably 0 amino acid insertions, deletions, substitutions or additions are present in the variable region of the heavy chain, and a light chain with the amino acid sequence of SEQ ID NO: 135 with 0, 1, 2, 3, 4, 5, 6, 7 or 8 amino acid insertions, deletions, substitutions or additions, wherein no more than 3, preferably no more than 2, preferably no more than 1, preferably 0 amino acid insertions, deletions, substitutions or additions are present in the variable region of the light chain. Preferably, said humanized antibody that can bind an extra-cellular part of human CD89 comprises a heavy chain with the amino acid sequence of SEQ ID NO: 133 and a light chain variable region with the amino acid sequence of SEQ ID NO: 135. An exemplary antibody with these characteristics is antibody 10E7 VH3VL2.

In one aspect a humanized antibody as disclosed herein has a higher affinity for the extracellular part of human CD89 compared to a chimeric antibody comprising a heavy chain with the amino acid sequence of SEQ ID NO: 94 and a light chain with the amino acid sequence of SEQ ID NO: 99.

In one aspect the invention provides an antibody that can bind an extra-cellular part of human CD89 (human FcαRI) on human CD89 expressing cells and that can prevent binding of human IgA to human CD89 when the antibody is bound to the cells and that induces less cell death in the human CD89 expressing cells compared to the antibody MIP8a. Preferably, the antibody induces 10% less cell death compared to the antibody MIP8a. More preferably, the antibody induces 20% less cell death compared to the antibody MIP8a. More preferably, the antibody induces 40% less cell death compared to the antibody MIP8a. A cell death inducing property of the antibody is preferably determined using the human CD89 expressing HEK293F cells deposited under number: DSM ACC3341.

Targeted effector cells can be lysed after binding of anti-human CD89 antibodies. An antibody as disclosed herein is useful to target cells expressing human CD89, without triggering extensive cell death or lysis of the target cells. Such characteristics are useful to maintain the target cells alive. Surviving cells can respond to the binding of the CD89 antibody, possibly by altered signalling. Surviving CD89 expressing cells can respond to the lack of IgA binding to CD89 due to the blocking properties of an antibody as disclosed herein. A cell that has an antibody as disclosed herein can be available to respond to other stimuli, pathogens, and/or immune actions independent of IgA.

In some embodiments, the disclosure provides an antibody that can bind an extra-cellular part of human CD89 on human CD89 expressing cells and that can prevent binding of human IgA to human CD89 when the antibody is bound to said cells and does not reduce the cell viability of said cells by more than 60% after overnight incubation at 37° C. Preferably, binding of the antibody to said cells does not reduce the cell viability of said cells after overnight incubation by more than 50%, or more than 40%, or more than 30%, or more than 20%, or more than 10% or less. A cell viability protecting property of the antibody is preferably determined using the human CD89 expressing HEK293F cells deposited under number: DSM ACC3341.

Cells are usually cultured at 37° C. Effects of stimuli on cells may be visible directly or after an incubation period. Some stimuli require cell signalling before the effect is visible. The term "overnight incubation at 37° C." recites that the cells are incubated with the stimuli overnight. Overnight can mean for example 12-16 hours or 8-24 hours, after which the characteristics of the cells are measured, for example the cell viability or phosphatidylserine expression.

In some embodiments, the disclosure provides an antibody that can bind an extra-cellular part of human CD89 on human CD89 expressing cells and that can prevent binding of human IgA to human CD89 when the antibody is bound to said cells and that does not increase phosphatidylserine expression of said cells by more than 20% after overnight incubation at 37° C. Preferably, binding of the antibody to said cells does not increase phosphatidylserine expression of said cells after overnight incubation at 37° C. by more than 20%, more preferably not by more than 10%, more preferably not by more than 5%. An effect of the antibody on phosphatidylserine expression is preferably determined using the human CD89 expressing HEK293F cells deposited under number: DSM ACC3341.

Phosphatidylserine is a phospholipid and is a component of the cell membrane. It has a role in cell signalling, and is correlated with cell death and apoptosis. The expression of phosphatidylserine in the membrane of cells may be used as a marker for cell death. The expression of phosphatidylserine in the membrane of cells may be measured by methods known to the skilled person. Phosphatidylserine is actively held facing the cytosolic (inner) side of the cell membrane. However, when a cell undergoes apoptosis, phosphatidylserine is no longer restricted to the cytosolic side. Instead it is rapidly exchanged between the two sides. Phosphatidylserine expression is typically determined by detecting phosphatidylserine on the outward directed surface of the cell membrane. The levels of phosphatidylserine may be compared to control cells, for example untreated cells. An exemplary method is described in detail in the example section.

The expression of phosphatidylserine may be determined by incubation the cells with an anti-phosphatidylserine antibody. In parallel, cells may be incubated with a negative control, for example anti-human CD19 antibody. After washing and fixing the cells the membrane phosphatidylserine expression can be measured using a flow cytometer (FACS).

In some embodiments, an antibody is provided that: can bind an extra-cellular part of human CD89 on human CD89 expressing cells; that can prevent binding of human IgA to human CD89 when the antibody is bound to said cells at 37° C. in the absence of $NaN_3$; and that cannot displace monomeric human IgA or heat-aggregated IgA when bound to said cells by more than 90% at 4° C. in the presence of $NaN_3$. An effect of the antibody on IgA displacement is preferably determined using the human CD89 expressing HEK293F cells deposited under number: DSM ACC3341.

In a preferred embodiment, said antibody is a humanized antibody.

Sodium azide in combination with a low temperature of 4° C. is used to inhibit the metabolic activity of cells. Sodium azide is a reversible inhibitor of mitochondrial respiration. Inhibition of the metabolic activity of the cells refers to less mitochondrial respiration of the cell. In some embodiments an antibody as disclosed herein cannot displace human IgA by more than 90% on cells with an inhibited metabolism.

In one embodiment, the disclosure provides an antibody that binds 20% or less to a recombinant human CD89 molecule wherein amino acids 22-46 of human CD89 are exchanged for amino acids 22-46 of cynomolgus CD89, while the antibody can bind an extra-cellular part of human CD89 on human CD89 expressing cells and that can prevent binding of human IgA to human CD89 when the antibody is bound to the cells. Preferably, the antibody binds 10% or less to said recombinant human CD89 molecule. An exemplary antibody with these characteristics is antibody 20B4. The amino acids Gln22-Lys46 substituted in this CD89 molecule are part of the EC1 domain of CD89 (SEQ ID NO:23). In some embodiments, binding of said antibody to said cell induces less cell death in human CD89 expressing cells when compared to MIP8a. In some embodiments, binding of said antibody to said cell does not reduce the cell viability of said cells by more than 60% after overnight incubation at 37° C. In some embodiment, binding of said antibody to said cell does not increase phosphatidylserine expression of said cells by more than 20% after overnight incubation at 37° C.

The IgA system differs between various species including human, mouse and rabbit. For example, there is no mouse homologue identified of the human CD89 gene. CD89 homologues have been identified in rats and cattle. The present disclosure includes working examples of antibodies binding to CD89 on human cells expressing human CD89 and human cells expressing chimeric CD89 molecules. A human/cynomolgus chimeric CD89 molecule has a part of a human CD89 molecule and a part of the cynomolgus CD89. The parts are combined such that the general protein structure is kept intact.

A cynomolgus (*Macaca fascicularis*) monkey CD89 gene has a similar intron/exon structure as human CD89 and exhibits 86% on homology to human gene (Rogers et al. 2004, Immunology). Substitutions of amino acids of human CD89 with the corresponding amino acids of cynomolgus CD89 can be used to test the specificity and cross-reactivity of the antibodies. Substitutions with cynomolgus CD89 can contribute identifying the epitope of the anti-human CD89 antibody.

In one embodiment, the disclosure provides an antibody that binds 20% or less to a chimeric CD89 molecule wherein amino acids 47-71 of human CD89 are exchanged for amino acids 47-71 of cynomolgus CD89, while the antibody can bind an extra-cellular part of human CD89 on human CD89 expressing cells and that can prevent binding of human IgA to human CD89 when the antibody is bound to said cells. Preferably, the antibody binds 10% or less to said recombinant human CD89 molecule. Preferably, the antibody binds 5% or less to said recombinant human CD89 molecule. Exemplary antibodies with these characteristics are antibodies 20B4, 8F3, 30C7 and 16D6. Amino acids Ile47-Ile71 are part of the EC1 domain of CD89 (SEQ ID NO:24). IgA can bind to this part of the CD89 receptor. Therefore, antibodies that bind to this part of the CD89 receptor potentially interfere with the interaction of IgA with CD89.

In one embodiment, the disclosure provides an antibody that binds 20% or less to a chimeric CD89 molecule wherein amino acids 72-96 of human CD89 are exchanged for amino acids 72-96 of cynomolgus CD89, while the antibody can bind an extra-cellular part of human CD89 on human CD89 expressing cells and that can prevent binding of human IgA to human CD89 when the antibody is bound to said cells. Preferably, the antibody binds 10% or less to said recombinant human CD89 molecule. Preferably, the antibody binds 5% or less to said recombinant human CD89 molecule. Exemplary antibodies with these characteristics are antibodies 8F3, 10E7 and 16D6. Amino acids Gly72-Gly96 are part of the EC1 domain of CD89 (SEQ ID NO:25). This part of the EC1 domain is thought to comprise an F-G loop, which is predicted to be located at the bottom of EC1 in a position close to the cell membrane.

In one embodiment, the disclosure provides an antibody of which binding is not reduced by 20% or less to a chimeric CD89 molecule wherein amino acids 97-121 of human CD89 are exchanged for amino acids 97-121 of cynomolgus CD89, and the antibody can bind an extra-cellular part of human CD89 on human CD89 expressing cells and that can prevent binding of human IgA to human CD89 when the antibody is bound to said cells. Preferably, binding of the antibody to said recombinant human CD89 molecule is not reduced by 10% or less. Exemplary antibodies with these characteristics are antibodies 20B4, 8F3, 30C7, 10E7 and 16D6. Amino acids Arg97-Gly121 are part of the EC1 domain of CD89 (SEQ ID NO: 26). For example, the MIP8a antibody can bind to this part of the EC1 domain.

In one embodiment, the disclosure provides an antibody that binds 20% or less to a chimeric CD89 molecule wherein amino acids 58; 59; 73; 74; 76; 106 and 107 of human CD89 are exchanged for amino acids 58; 59; 73; 74; 76; 106 and 107 respectively of cynomolgus CD89, while the antibody can bind an extra-cellular part of human CD89 on human CD89 expressing cells and that can prevent binding of human IgA to human CD89 when the antibody is bound to said cells. Preferably, the antibody binds 10% or less to said recombinant human CD89 molecule. Preferably, the antibody binds 5% or less to said recombinant human CD89 molecule. Exemplary antibodies with these characteristics are Antibody 8F3, 10E7 and 16D6. Amino acids Thr58 and Gln59 are thought to be relevant for human IgA-CD89 binding.

In some embodiments, binding of said antibody to said cell does induce less cell death in human CD89 expressing cells when compared to MIP8a. In some embodiments, binding of said antibody to said cell does not reduce the cell viability of said cells by more than 60% after overnight incubation at 37° C. In some embodiment, binding of said antibody to said cell does not increase phosphatidylserine expression of said cells by more than 20% after overnight incubation at 37° C.

An antibody as described herein can bind to an extra-cellular part of human CD89 on human CD89 expressing HEK293F cells. Exemplary HEK293F cells that express membrane-bound human CD89 are deposited under number: DSM ACC3341 in accordance to the Budapest treaty. These HEK293F cells are stably expressing human CD89 on their cells surface. Preferably, using these cells allows to compare the effect of different antibodies targeting human CD89. Preferably, to study the percentage of cells undergoing cell death after binding of the CD89 antibody. Using a cell line stably expressing human CD89 typically reduces the difference in expression between the cells and allows better comparison of the experimental conditions, when compared to transiently transfected cells.

One aspect of the disclosure provides an antibody binding human CD89 comprising a heavy chain variable region with the CDR1, CDR2 and CDR3 sequence of SEQ ID NO: 29-31 with 0, 1 or 2 amino acid insertions, deletions, substitutions or additions and a light chain variable region with the CDR1, CDR2 and CDR3 sequence of SEQ ID NO: 32-34 with 0, 1 or 2 amino acid insertions, deletions, substitutions or additions. Preferably, the antibody that can bind an extra-cellular part of human CD89 comprises a heavy chain variable region with the CDR1, CDR2 and CDR3 sequence of SEQ ID NO: 29-31 and a light chain variable region with the CDR1, CDR2 and CDR3 sequence of SEQ ID NO: 32-34.

In a further aspect the disclosure provides an antibody binding human CD89 comprising a heavy chain variable region with the amino acid sequence of SEQ ID NO: 27 with 0, 1, 2, 3, 4, 5, 6, 7, 8, 9 or 10 amino acid insertions, deletions, substitutions or additions and a light chain variable region with the amino acid sequence of SEQ ID NO: 28 with 0, 1, 2, 3, 4, 5, 6, 7, 8, 9 or 10 amino acid insertions, deletions, substitutions or additions. In a preferred embodiment, the 0, 1, 2, 3, 4, 5, 6, 7, 8, 9 or 10 amino acid insertions, deletions, substitutions or additions are located in the framework regions of the light and/or heavy chain variable region. Preferably, the antibody that can bind an extra-cellular part of human CD89 comprises a heavy chain variable region with the amino acid sequence of SEQ ID NO: 27 and a light chain variable region with the amino acid sequence of SEQ ID NO: 28. An exemplary antibody with these characteristics is Antibody 8F3. An antibody having these CDRs can bind to an epitope in the EC1 domain of CD89, particularly to a part of the sequences of SEQ ID NO:24 and SEQ ID NO:25.

In one aspect the disclosure provides an antibody binding human CD89 comprising a heavy chain variable region with the CDR1, CDR2 and CDR3 sequence of SEQ ID NO: 45-47 with 0, 1 or 2 amino acid insertions, deletions, substitutions or additions and a light chain variable region with the CDR1, CDR2 and CDR3 sequence of SEQ ID NO: 48-50 with 0, 1 or 2 amino acid insertions, deletions, substitutions or additions. Preferably, the antibody that can bind an extra-cellular part of human CD89 comprises a heavy chain variable region with the CDR1, CDR2 and CDR3 sequence of SEQ ID NO: 45-47 and a light chain variable region with the CDR1, CDR2 and CDR3 sequence of SEQ ID NO: 48-50.

In a further aspect the disclosure provides an antibody binding human CD89 comprising a heavy chain variable region with the amino acid sequence of SEQ ID NO: 43 with 0, 1, 2, 3, 4, 5, 6, 7, 8, 9 or 10 amino acid insertions, deletions, substitutions or additions and a light chain variable region with the amino acid sequence of SEQ ID NO: 44 with 0, 1, 2, 3, 4, 5, 6, 7, 8, 9 or 10 amino acid insertions, deletions, substitutions or additions. In a preferred embodiment, the 0, 1, 2, 3, 4, 5, 6, 7, 8, 9 or 10 amino acid insertions, deletions, substitutions or additions are located in the framework regions of the light and/or heavy chain variable region. Preferably, the antibody that can bind an extra-cellular part of human CD89 comprises a heavy chain variable region with the amino acid sequence of SEQ ID NO: 43 and a light chain variable region with the amino acid sequence of SEQ ID NO: 44. An exemplary antibody with these characteristics is Antibody 10E7. An antibody having these CDRs can bind to an epitope in the EC1 domain of CD89, particularly to a part of the sequence of SEQ ID NO:25.

In one aspect the disclosure provides an antibody binding human CD89 comprising a heavy chain variable region with the CDR1, CDR2 and CDR3 sequence of SEQ ID NO: 69-71 with 0, 1 or 2 amino acid insertions, deletions, substitutions or additions and a light chain variable region with the CDR1, CDR2 and CDR3 sequence of SEQ ID NO: 72-74 with 0, 1 or 2 amino acid insertions, deletions, substitutions or additions. Preferably, the antibody that can bind an extra-cellular part of human CD89 comprises a heavy chain variable region with the CDR1, CDR2 and CDR3 sequence of SEQ ID NO: 69-71 and a light chain variable region with the CDR1, CDR2 and CDR3 sequence of SEQ ID NO: 72-74.

In a further aspect the disclosure provides an antibody binding human CD89 comprising a heavy chain variable region with the amino acid sequence of SEQ ID NO: 67 with 0, 1, 2, 3, 4, 5, 6, 7, 8, 9 or 10 amino acid insertions, deletions, substitutions or additions and a light chain variable region with the amino acid sequence of SEQ ID NO: 68 with 0, 1, 2, 3, 4, 5, 6, 7, 8, 9 or 10 amino acid insertions, deletions, substitutions or additions. In a preferred embodiment, the 0, 1, 2, 3, 4, 5, 6, 7, 8, 9 or 10 amino acid insertions, deletions, substitutions or additions are located in the framework regions of the light and/or heavy chain variable region. Preferably, the antibody that can bind an extra-cellular part of human CD89 comprises a heavy chain variable region with the amino acid sequence of SEQ ID NO: 67 and a light chain variable region with the amino acid sequence of SEQ ID NO: 68. An exemplary antibody with these characteristics is Antibody 20B4. An antibody having these CDRs can bind to an epitope in the EC1 domain of CD89, particularly to a part of the sequences of SEQ ID NO:23 and SEQ ID NO:24.

In one aspect the disclosure provides an antibody binding human CD89 comprising a heavy chain variable region with the CDR1, CDR2 and CDR3 sequence of SEQ ID NO: 77-79 with 0, 1 or 2 amino acid insertions, deletions, substitutions or additions and a light chain variable region with the CDR1, CDR2 and CDR3 sequence of SEQ ID NO: 80-82 with 0, 1 or 2 amino acid insertions, deletions, substitutions or additions. Preferably, the antibody that can bind an extra-cellular part of human CD89 comprises a heavy chain variable region with the CDR1, CDR2 and CDR3 sequence of SEQ ID NO: 77-79 and a light chain variable region with the CDR1, CDR2 and CDR3 sequence of SEQ ID NO: 80-82.

In a further aspect the disclosure provides an antibody binding human CD89 comprising a heavy chain variable region with the amino acid sequence of SEQ ID NO: 75 with 0, 1, 2, 3, 4, 5, 6, 7, 8, 9 or 10 amino acid insertions, deletions, substitutions or additions and a light chain variable region with the amino acid sequence of SEQ ID NO: 76 with 0, 1, 2, 3, 4, 5, 6, 7, 8, 9 or 10 amino acid insertions, deletions, substitutions or additions. In a preferred embodiment, the 0, 1, 2, 3, 4, 5, 6, 7, 8, 9 or 10 amino acid insertions, deletions, substitutions or additions are located in the framework regions of the light and/or heavy chain variable region. Preferably, the antibody that can bind an extra-cellular part of human CD89 comprises a heavy chain variable region with the amino acid sequence of SEQ ID NO: 75 and a light chain variable region with the amino acid sequence of SEQ ID NO: 76. An exemplary antibody with these characteristics is Antibody 30C7. An antibody having these CDRs can bind to an epitope in the EC1 domain of CD89, particularly to a part of the sequence of SEQ ID NO:24.

In one aspect the disclosure provides an antibody binding human CD89 comprising a heavy chain variable region with the CDR1, CDR2 and CDR3 sequence of SEQ ID NO: 53-55 with 0, 1 or 2 amino acid insertions, deletions, substitutions or additions and a light chain variable region with the CDR1, CDR2 and CDR3 sequence of SEQ ID NO: 56-58 with 0, 1 or 2 amino acid insertions, deletions, substitutions or additions. Preferably, the antibody that can bind an extra-cellular part of human CD89 comprises a heavy chain variable region with the CDR1, CDR2 and CDR3 sequence of SEQ ID NO: 53-55 and a light chain variable region with the CDR1, CDR2 and CDR3 sequence of SEQ ID NO: 56-58.

In a further aspect the disclosure provides an antibody binding human CD89 comprising a heavy chain variable region with the amino acid sequence of SEQ ID NO: 51 with 0, 1, 2, 3, 4, 5, 6, 7, 8, 9 or 10 amino acid insertions, deletions, substitutions or additions and a light chain variable region with the amino acid sequence of SEQ ID NO: 52 with 0, 1, 2, 3, 4, 5, 6, 7, 8, 9 or 10 amino acid insertions, deletions, substitutions or additions. In a preferred embodiment, the 0, 1, 2, 3, 4, 5, 6, 7, 8, 9 or 10 amino acid insertions, deletions, substitutions or additions are located in the framework regions of the light and/or heavy chain variable region. Preferably, the antibody that can bind an extra-cellular part of human CD89 comprises a heavy chain variable region with the amino acid sequence of SEQ ID NO: 51 and a light chain variable region with the amino acid sequence of SEQ ID NO: 52. An exemplary antibody with these characteristics is Antibody 16D6. An antibody having these CDRs can bind to an epitope in the EC1 domain of CD89, particularly to a part of the sequences of SEQ ID NO:24 and SEQ ID NO:25.

Binding of an antibody referred to herein by sequence to a cell can induce less cell death in human CD89 expressing cells when compared to MIP8a. In some embodiments, binding of said antibody to said cell does not reduce the cell viability of said cells by more than 60% after overnight incubation at 37° C. In some embodiment, binding of said antibody to said cell does not increase phosphatidylserine expression of said cells by more than 20% after overnight incubation at 37° C.

Also provided is an antibody binding human CD89 comprising a heavy chain variable region with the CDR1, CDR2 and CDR3 sequence of SEQ ID NO: 37-39 with 0, 1 or 2 amino acid insertions, deletions, substitutions or additions and a light chain variable region with the CDR1, CDR2 and CDR3 sequence of SEQ ID NO: 40-42 with 0, 1 or 2 amino acid insertions, deletions, substitutions or additions.

A preferred embodiment provides an antibody binding human CD89 comprising a heavy chain variable region with the amino acid sequence of SEQ ID NO: 35 with 0, 1, 2, 3, 4, 5, 6, 7, 8, 9 or 10 amino acid insertions, deletions, substitutions or additions and a light chain variable region with the amino acid sequence of SEQ ID NO: 36 with 0, 1, 2, 3, 4, 5, 6, 7, 8, 9 or 10 amino acid insertions, deletions, substitutions or additions. In a preferred embodiment the amino acid insertions, deletions, substitutions or additions are located in the framework regions of the light and/or heavy chain variable region. An exemplary antibody with these characteristics is Antibody 9H7.

One embodiment provides an antibody binding human CD89 comprising a heavy chain variable region with the CDR1, CDR2 and CDR3 sequence of SEQ ID NO: 61-63 with 0, 1 or 2 amino acid insertions, deletions, substitutions or additions and a light chain variable region with the CDR1, CDR2 and CDR3 sequence of SEQ ID NO: 64-66 with 0, 1 or 2 amino acid insertions, deletions, substitutions or additions.

A preferred embodiment provides an antibody binding human CD89 comprising a heavy chain variable region with the amino acid sequence of SEQ ID NO: 59 with 0, 1, 2, 3, 4, 5, 6, 7, 8, 9 or 10 amino acid insertions, deletions, substitutions or additions and a light chain variable region with the amino acid sequence of SEQ ID NO: 60 with 0, 1, 2, 3, 4, 5, 6, 7, 8, 9 or 10 amino acid insertions, deletions, substitutions or additions. In a preferred embodiment, the amino acid insertions, deletions, substitutions or additions are located in the framework regions of the light and/or heavy chain variable region. An exemplary antibody with these characteristics is Antibody 26D6.

An anti-human-CD89 antibody or antigen binding fragment thereof of the disclosure preferably comprises a heavy chain variable region and a light chain variable region as described herein. Such an antibody has good characteristics. It is of course possible to generate variants of such an original antibody by modifying one or more amino acids therein. Many of such variants will behave more or less similar when compared to said original. Such variants are also included in the scope of the disclosure.

Variants can have amino acid substitutions, insertions, deletions, or additions with respect to the sequence of the original antibody. An amino acid substitution is the replacement of an amino acid with another amino acid. Preferably, the amino acid is preplaced by an amino acid having similar chemical properties, which is often called conservative substitution. Amino acid deletions result in the deletion of one or multiple amino acids from the sequence. Amino acid insertions result in one or more additional amino acids in the sequence. Amino acid addition results in one or more amino acids at the start or end of the amino acid sequence.

A non-limiting example of such a modification is an antibody comprising a pyro-glutamate instead of a glutamate. Other non-limiting examples of such modifications are an insertion, deletion, inversion and/or substitution of one or more amino acids when compared to said original antibody. Preferably amino acid substitutions, insertions, deletions, or additions are outside the CDR's of the variable domain. Preferably amino acid substitutions, insertions, deletions, or additions are within the framework regions of the variable region and/or in the constant region of the antibody. CD89 binding of variants can be tested as described herein.

In some embodiments, the constant region of an antibody of the invention is the constant region of an IgG, IgA, IgD, IgE or IgM antibody, such as IgG1, IgG2, IgG3 or IgG4 antibody. The constant regions may comprise modifications such as amino acid substitutions to confer specific properties to the constant regions. For instance, mutation of the IgG4 hinge region to render the antibody more stable towards the exchange of half-molecules. Other modifications affect half-life of the antibody, add or remove a glycosylation site, improve production, improve the homogeneity of the antibody product produced in large scale fermenters etc.

An antibody of the invention is preferably a murine IgG1, a human IgG1 mutated in the constant region to reduce or prevent complement activation or Fc receptor interactions, or a human IgG4, or a human IgG4 mutated to prevent the exchange of half-molecules with other IgG4 molecules. In a preferred embodiment an antibody disclosed herein is a humanized IgG4, or a humanized IgG4 mutated to prevent the exchange of half-molecules with other IgG4 molecules, or a humanized IgG1 mutated in the constant region to reduce or prevent complement activation or Fc receptor interactions.

Some variations in the constant region of an antibody as disclosed herein is allowed. Typically, between about 0-10 amino acid substitutions are allowed in the constant region. Often more amino acid changes than 10 are allowed. An antibody of the invention can have a heavy chain constant region (CH1-CH2-CH3) with 0-15, preferably 0-10, more preferably 0-5, more preferably 5, 4, 3, 2, 1, or 0 amino acid substitutions with respect to a naturally occurring heavy chain constant region (CH1-CH2-CH3). Such an antibody can have a light chain constant region with 0-5, preferably 5, 4, 3, 2, 1, or 0 amino acid substitutions with respect to a naturally occurring light chain constant region.

Some variation in IgG4 occurs in nature and/or is allowed without changing the immunological properties of the resulting antibody. An antibody with an IgG4 constant region or a mutated IgG1 constant region has at least most of the pharmacological properties of an antibody but does not bind complement, and will thus not induce depletion of the cells its binds to in vivo. Preferably said constant region is a constant region of a human antibody (chimeric).

Preferably, said constant region is a region that is deficient in complement activation, preferably a human IgG4 constant region or a mutated human $IgG_1$ constant region. In a preferred embodiment, said a humanized antibody as disclosed herein has an IgG4 or IgG1 isotype.

CD89 binding by an antibody and antigen binding fragments thereof disclosed herein can be confirmed in a number of suitable assays known to the skilled person. Such assays include, e.g., affinity assays, e.g., western blots, radioimmunoassay, FACS, and ELISA (enzyme-linked immunosorbent assay). The examples (e.g. Example 2 (a)) describe in detail some of the many assays which can be used to measure CD89 binding, as well as a method to determine the relative binding affinity of an antibody for human CD89.

The term "binding molecule" encompasses (1) an antibody, (2) an antigen-binding fragment of an antibody, and (3) a derivative of an antibody, each as defined herein. The term "binds to CD89" or "can bind (to) CD89" or "binding to CD89" refers to the binding of a binding molecule, as defined herein, to the human CD89 receptor in an in vitro assay, such as BIAcore™ (surface plasmon resonance) or Octet® (bio-layer interferometry). The binding molecule has a binding affinity ($K_D$) of about $1\times10^{-6}$ M or less, about $1\times10^{-7}$ M or less, about $1\times10^{-8}$ M or less, about $1\times10^{-9}$ M or less, about $1\times10^{-10}$ M or less, about $1\times10^{-11}$ M or less, or about $1\times10^{-12}$ M or less. Said binding preferably is specific, meaning that CD89, or an epitope thereof, is specifically bound by the binding molecule. The affinity is a measure for the strength of binding to a particular antigen or epitope. Specific binding, or "specifically recognizing" is defined herein as binding with affinities ($K_D$) at most $1\times10E^{-6}$ M, preferably at most $1\times10E^{-7}$ M, $1\times10E^{-8}$ M or, most preferably, at most $1\times10E^{-9}$ M.

As described herein below, the $K_D$ of a humanized anti-human CD89 antibody as described herein preferably is less than 1.5 nM, such as less than 1.4 nM, less than 1.3 nM, less than 1.2 nM, less than 1.1 nM, or less than 1 nM. This $K_D$ is surprisingly less when compared to the $K_D$ of the parental mouse antibody, which is about 1.7 nM.

The term "$K_D$" refers to the equilibrium dissociation constant of a particular antibody-antigen interaction and is used to describe the binding affinity between a ligand (such as an antibody) and a protein (such as CD89). The smaller the equilibrium dissociation constant, the more tightly bound the ligand is, or the higher the affinity between ligand and protein. A $K_D$ can be measured by surface plasmon resonance- and bio-layer interferometry-based assays. The term "anti-CD89 antibody" refers to an antibody, as defined herein, capable of binding to CD89, preferably human CD89.

The terms "$K_{on}$" and "$K_{off}$" refer to the rate constants of ligand (such as an antibody) association to (on-rate) and dissociation from (off-rate), respectively, its target protein (such as CD89). "$K_{on}$" characterizes how fast a ligand (such as an antibody) binds to its target protein (such as CD89), and "$K_{off}$" characterizes how fast a ligand (such as an antibody) dissociates from its target protein (such as CD89).

The ability to block the interaction of IgA with the CD89 receptor of an antibody and antigen binding fragment thereof as disclosed herein can be confirmed in a number of suitable assays known to the skilled person. Such assays include, e.g. affinity assays ELISA and FACS. The presented examples (e.g. Example 2 (b)) describe in detail two of the many assays, FACS and ELISA, which can be used to test the ability of anti-CD89 antibodies to block the binding of IgA to the CD89 receptor.

To test the IgA blocking characteristics of an antibody with an ELISA assay, recombinant CD89 is coated on plates. Subsequently, the coated plate is blocked using a blocking buffer to prevent non-specific binding. The plates with recombinant CD89 are incubated with the antibody and/or hybridoma supernatant of interest. Subsequently, IgA is added to the wells with CD89. After washing the amount of bound IgA is measured using ELISA techniques. The amount of bound IgA indicates the blocking capabilities of the tested antibody, whereby less binding of IgA indicates a stronger blocking capacity of the antibody. Also, CD89 expressing cell can be used to test the IgA blocking characteristics of an antibody with a FACS assay. Preferably, said cells are stably expressing human CD89. CD89 expressing cells are incubated with the antibody of interest or hybridoma supernatant of interest. Subsequently, the cells are incubated with IgA. After washing the IgA bound to the cells was labeled using a secondary antibody against the IgA, preferably a fluorescent secondary antibody. Binding of IgA on the membrane of the human CD89 expressing cells can be measured using a flow cytometer (FACS). The amount of bound IgA indicates the blocking capabilities of the tested antibody, whereby less binding of IgA indicates a stronger blocking capacity of the antibody.

In order to analyze whether purified anti-human CD89 antibodies as disclosed herein are able to displace previously saturated IgA to human CD89, the skilled person can use a number of known suitable assays. One of the suitable test methods is disclosed in the example section. In this assay IgA is allowed to bind to CD89 expressing cells. Thereafter, an anti-CD89 antibody is added to the cells. The amount of IgA still bound on the cell can be measured with FACS analysis. The assay is described in detail in Example 2. This and other assays can be used to measure human IgA displacement by anti-human CD89 antibodies. Displacement can be measured using metabolically active cells (for instance incubated overnight at 37° C.) or using metabolically inactive cells (for instance incubated at 4° C. in the presence of sodium-azide)

In a further aspect, the disclosure provides a nucleic acid molecule or nucleic acid molecules encoding an antibody as disclosed herein or an antigen binding fragment thereof as disclosed herein. Also provided is a nucleic acid molecule encoding a variable region as disclosed herein. A nucleic acid as used in the disclosure is typically but not exclusively a ribonucleic acid (RNA) or a deoxyribonucleic acid (DNA). Based on the genetic code, a skilled person can determine the nucleic acid sequence which encode an antibody variant as disclosed herein. Based on the degeneracy of the genetic code, sixty-four codons may be used to encode twenty amino acids and translational terminal signal. As is known to a skilled person, codon usage bias in different organisms can affect gene expression level. Various computational tools are available to the skilled person in order to optimize codon usage depending on which organisms the desired nucleic acid will be expressed.

In a further aspect, the disclosure provides a vector comprising a nucleic acid sequence molecule as described herein. The term "vector" as used herein refers to a nucleic acid molecule, such as a plasmid, bacteriophage or animal virus, capable of introducing a heterologous nucleic acid sequence into a host cell. A vector according to the invention allows the expression or production of an antibody of the invention encoded by the heterologous nucleic acid sequence in a host cell. A vector used in accordance with the invention is for instance derived from an animal virus, examples of which include, but not limited to, vaccinia virus (including attenuated derivatives such as the Modified Vaccinia virus Ankara, MVA), Newcastle Disease virus (NDV), adenovirus or retrovirus. A vector according to the invention preferably comprises an expression cassette comprising a promoter that is suitable for initiation of transcription of an antibody according to the invention in the selected host cells. Examples of suitable promoters for expression of polypeptides according to the invention in eukaryotic host cells include, but are not limited to, beta-actin promoter, immunoglobin promoter, 5S RNA promoter, or virus derived promoters such as cytomegalovirus (CMV), Rous sarcoma virus (RSV) and Simian virus 40 (SV40) promoters for mammalian hosts.

When a nucleic acid molecule or nucleic acid molecules as disclosed herein is/are expressed in a cell, the cell may produce an antibody according to the disclosure. Therefore, in one embodiment, a cell is provided comprising an antibody, a nucleic acid molecule or molecules and/or a vector according to the disclosure. The host cells may be a mammalian, insect, plant, bacterial or yeast cell. Said cell is preferably an animal cell, preferably a mammalian cell, most preferably a human cell. Examples of mammalian cell lines suitable as host cells include a hybridoma cell, a Chinese hamster ovary (CHO) cell, an NSO cell, or a PER-C6™ cell. For the purpose of the disclosure a suitable cell is any cell capable of comprising and preferably of producing said antibodies and/or said nucleic acids. The disclosure further encloses cell cultures that comprise said cells.

The term "host cell" refers to a cell into which an expression vector expressing an anti-human CD89 antibody as described herein has been introduced. The term encompasses not only the particular subject cell but also the progeny of such a cell. Because certain modifications may occur in successive generations due to either environmental influences or mutation, such progeny may not be identical to the parent cell but are still included within the scope of the term "host cell."

An antibody as disclosed herein can be produced by any method known to a skilled person. In a preferred embodiment, the antibodies are produced using a cell, preferably wherein the cell is a hybridoma cell, a CHO cell, an NSO cell or a PER-C6™ cell. In a particular preferred embodiment said cell is a CHO cell, preferably said cell is cultured in serum free medium. This includes harvesting said antibody form said culture. The antibody is preferably purified form the medium, preferably said antibody is affinity purified. Alternatively, said antibodies can be generated synthetically.

Various institutions and companies have developed cell lines for the large-scale production of antibodies, for instance for clinical use. These cells are also used for other purposes such as the production of proteins. Cell lines developed for industrial scale production of proteins and antibodies are herein further referred to as industrial cell lines. Thus, a preferred embodiment of the disclosure provides the use of a cell line developed for the large-scale production of said antibodies.

An antibody according to the invention exhibits a number of activities that can be advantageously used in therapeutic and non-therapeutic uses. In particular, antibodies according to the invention are useful for the treatment of an individual. Preferably, the antibodies according to the invention are useful for the treatment of immune related diseases or prevention against immune related diseases. In some embodiments, an antibody according to the invention is preferably used in therapy, preferably human therapy. In some embodiments, an antibody as disclosed herein may be used for research purposes. For example, in in vitro experiments, cell culture, organotypic culture and in vivo models.

Also described are methods for treatment or prophylaxis of chronic inflammatory diseases (CIDs). Examples of CIDs are e.g. inflammatory bowel disease (IBD) such as ulcerative colitis or Crohn's disease, chronic obstructive lung disease (COPD), asthma, allergic and non-allergic rhinitis, food allergies such as Celiac disease, and skin diseases such as linear IgA bullous disease or dermatitis herpetiformis. One of the common features that contributes to tissue destruction observed in CIDs is local accumulation of polymorphonuclear cells, more in particular neutrophils and/or eosinophils. Polymorphonuclear cells are white blood cells characterized by the presence of granules in their cytoplasm.

Binding of IgA to its receptor CD89 can trigger a cascade of events including the activation of immune cells that eventually leads to migration, accumulation and infiltration of polymorphonuclear cells. Because cross-linking of CD89 by IgA-immune complexes potently recruits and activates neutrophils, the presence of aberrant IgA might result in aggravated pro-inflammatory responses, leading to tissue damage. This might play a role in different CIDs that are characterized by an increase in serum (auto-) IgA levels, such as IgA nephropathy, Henoch-Schönlein purpura, ankylosing spondylitis, Sjögren's syndrome, alcoholic liver cirrhosis, celiac disease, asthma, IBD, rheumatoid arthritis, linear IgA bullous disease and dermatitis herpetiformis (Aleyd et al. Immunol Rev 2015; 268: 123-138). Interfering with the binding between IgA and its receptor CD89 may inhibit the signaling cascade and the accumulation of polymorphonuclear cells. Therefore, CIDs may be treated or prevented by administering an effective amount of an antibody of the invention to a patient in need of such a treatment. Blocking the interaction between IgA and the receptor on the polymorphonuclear cells, such as neutrophils, may cease the inflammatory reaction. Therefore, CID patient may benefit from treatment using an antibody as disclosed herein.

The invention provides a method for the treatment of a subject suffering from inflammatory diseases comprising administering to said subject a therapeutically effective amount of an antibody as disclosed herein. Also provided is a method for the preparation of a medicament for the treatment of a subject suffering from inflammatory diseases. The disclosure describes methods for preventing the activation of immune cells by blocking the binding between IgA and CD89.

The disclosure further comprises a pharmaceutical composition comprising an antibody or antigen binding fragment thereof as disclosed herein, or a nucleic acid encoding same, or a cell comprising an antibody or antigen binding fragment thereof as disclosed herein, or a nucleic acid encoding same. Provided are pharmaceutical compositions comprising a polypeptide according to the invention or a pharmaceutically acceptable salt thereof, and at least one pharmaceutically acceptable carrier, diluent and/or excipient. Such compositions are especially suited for use as a medicament. The compositions may be in any suitable forms, such as liquid, semi-solid and solid dosage forms. The dosage and scheduling for the formulation, which is selected can be determined by standard procedures, well known by a skilled person. Such procedures involve extrapolating and estimating dosing schedule form animal models, and then determining the optimal dosage in a human clinical dose ranging study. The dosage in pharmaceutical compositions will vary depending upon an number of factors, such as the desired release and pharmacodynamic characteristics.

As used herein, an "subject" is a human or an animal. Subjects include, but are not limited to, mammals such as humans, pigs, ferrets, seals, rabbits, cats, dogs, cows and horses, and birds such as chickens, ducks, geese and turkeys.

In a preferred embodiment of the invention, a subject is a mammal. In a particularly preferred embodiment, the subject is a human.

The term "antigen-binding fragment" of an antibody refers to one or more portions of a full-length antibody that retain the ability to bind to the same antigen (i.e., human CD89) that the antibody binds to. The term "antigen-binding fragment" also encompasses a portion of an antibody that is part of a larger molecule formed by non-covalent or covalent association or of the antibody portion with one or more additional molecular entities. Examples of additional molecular entities include amino acids, peptides, or proteins, such as the streptavidin core region, which may be used to make a tetrameric scFv molecule (Kipriyanov et al. Hum Antibodies Hybridomas 1995; 6(3): 93-101). An exemplary antigen-binding fragment is a VH and/or a VL of an antibody. Antigen-binding fragments include Fab, F(ab'), $F(ab')_2$, complementarity determining region (CDR) fragments, single-chain antibodies (scFv), bivalent single-chain antibodies, and other antigen recognizing immunoglobulin fragments. In some instances, the term "antibody" as used herein can be understood to also include an antigen binding fragment thereof.

The term "human antibody" refers to an antibody consisting of amino acid sequences of human immunoglobulin sequences only. A human antibody may contain murine carbohydrate chains if produced in a mouse, in a mouse cell or in a hybridoma derived from a mouse cell. Human antibodies may be prepared in a variety of ways known in the art.

The term "epitope" refers to the part of an antigen that is capable of specific binding to an antibody, or T-cell receptor or otherwise interacting with a molecule. "Epitope" is also referred to in the art as the "antigenic determinant". An epitope generally consists of chemically active surface groupings of molecules such as amino acids or carbohydrate or sugar side chains. An epitope may be "linear" or "non-linear/conformational". Once a desired epitope is determined (e.g., by epitope mapping), antibodies to that epitope can be generated. The generation and characterization of antibodies may also provide information about desirable epitopes. From this information, it is then possible to screen antibodies for those which bind to the same epitope e.g. by conducting cross-competition studies to find antibodies that competitively bind with one another, i.e., the antibodies compete for binding to the antigen.

As used herein, "to comprise" and its conjugations is used in its non-limiting sense to mean that items following the word are included, but items not specifically mentioned are not excluded. In addition, the verb "to consist" may be replaced by "to consist essentially of" meaning that a compound or adjunct compound as defined herein may comprise additional component(s) than the ones specifically identified, said additional component(s) not altering the unique characteristic of the invention.

The articles "a" and "an" are used herein to refer to one or to more than one (i.e., to at least one) of the grammatical object of the article. By way of example, "an element" means one element or more than one element.

The word "approximately" or "about" when used in association with a numerical value (approximately 10, about 10) preferably means that the value may be the given value of 10 more or less 1% of the value.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

For the purpose of clarity and a concise description features are described herein as part of the same or separate embodiments. However, it will be appreciated that the scope of the invention may include embodiments having combinations of all or some of the features described.

All patent and literature references cited in the present specification are hereby incorporated by reference in their entirety.

The invention is further explained in the following examples. These examples do not limit the scope of the invention, but merely serve to clarify the invention.

EXAMPLES

Example 1. Generation of CD89/IgA Blocking Mouse Anti-Human CD89 Monoclonal Antibodies (a). Generation of HEK293F Cells Transiently Expressing Surface Human CD89 for Immunization cDNA encoding for human full-length CD89 protein (Swiss-Prot no. P24071.1; see SEQ ID NO: 1) was optimized for mammalian expression and synthesized by GENEART, Regensburg, Germany (see SEQ ID NO: 2). This cDNA was subcloned in a pcDNA3.1-derived expression plasmid. This full-length human CD89 plasmid was transiently transfected in FreeStyle™ 293F cells (Life Technologies) using the FreeStyle™ 293 Expression System (Life Technologies). After 2 days, these HEK293F cells were harvested, washed with sterile phosphate-buffered saline solution (PBS), and aliquoted at ~$20.0\times10^6$ viable cells/mL in PBS and stored at −80° C. to obtain cell lysates. Prior to storage, human CD89 surface expression on transfected HEK293F cells was flow cytometrically confirmed using 1:20 diluted phycoerythrin (PE)-conjugated mouse anti-human CD89 antibody (clone MIP8a; BioRad).

(b). Generation of HEK293F Cells Stably Expressing Surface Human CD89 for Screening cDNA encoding for human full-length CD89 protein (Swiss-Prot no. P24071.1; see SEQ ID NO: 1) was optimized for mammalian expression and synthesized by GENEART, Regensburg, Germany (see SEQ ID NO: 2). This cDNA was subcloned in a pcDNA3.1-derived expression plasmid. This full-length human CD89 plasmid was transfected in FreeStyle™ 293F cells (Life Technologies) using the FreeStyle™ 293 Expression System (Life Technologies). Stable human full-length CD89-transfected HEK293F clone no. 2 was selected using 125 μg/mL G418/Geneticin (Gibco). Human CD89 surface expression on transfected HEK293F cells was flow cytometrically confirmed using 1:20 diluted PE-conjugated mouse anti-human CD89 antibody (clone MIP8a; BioRad).

(c). Immunization and Generation of Mouse Anti-Human CD89 Monoclonal Antibodies

Four BALB/c mice (females, 6-8 weeks of age; Charles River Laboratories) were subcutaneously injected with ~500 μL recombinant C-terminal polyhistidine-tagged human extracellular CD89 domain (NCBI Ref SEQ NP_001991.1; Sino Biological Inc) and human CD89 transiently transfected HEK293F cell lysate (see Example 1 (a) above) in oil-in-water emulsified Sigma Adjuvant System® (SAS; Sigma) on Day 0; each mouse was injected with 25 μg recombinant human CD89 and human CD89-transfected HEK293F cell lysate (prepared from $5\times10^6$ viable membrane-bound CD89 expressing cells) in 250 μL PBS mixed with 250 μL SAS. On Day 14 and on Day 28, antibody responses in these four mice were boosted by subcutaneous injections with recombinant human CD89 and human CD89 transiently transfected HEK293F cell lysate in oil-in-water emulsified SAS; each mouse was injected with 25 μg recombinant human CD89 and human CD89-transfected HEK293F cell lysate (prepared from $5\times10^6$ viable membrane-bound CD89 expressing cells) in 250 μL PBS mixed with 250 μL SAS. Finally, two mice (mouse no. 3 and no. 4) were intraperitoneally injected with recombinant human CD89 and human CD89 transiently transfected HEK293F cell lysate without adjuvant on Day 42 and on Day 43; each mouse was injected with 20 μg recombinant human CD89 and human CD89-transfected HEK293F cell lysate (prepared from $4\times10^6$ viable membrane-bound CD89 expressing cells) in 200 μL PBS. Additionally, two mice (mouse no. 1 and no. 2) were intraperitoneally injected with recombinant human CD89 and human CD89 transiently transfected HEK293F cell lysate without adjuvant on Day 77 and on Day 78; each mouse was injected with 20 μg recombinant human CD89 and human CD89-transfected HEK293F cell lysate (prepared from $4\times10^6$ viable membrane-bound CD89 expressing cells) in 200 μL PBS. On Day 46 (for fusion I; mouse no. 3 and no. 4) or on Day 81 (for fusion II; mouse no. 1 and no. 2), splenocytes from these immunized mice were fused with SP2/0-Ag14 myeloma cells (DSMZ) using standard hybridoma technology (originally described by Köhler and Milstein in Nature 1975, 256: 495) as described below. Briefly, immunized mice were sacrificed. Splenocytes were teased from spleens, and washed in serum-free opti-MEM® I with GlutaMax medium (SF medium; Invitrogen). Logarithmically growing SP2/0-Ag14 myeloma cells were washed in SF medium, and added to the splenocytes yielding a 5:1 ratio of splenocytes-to-myeloma cells. The cells were then pelleted, and the supernatant was removed. One ml of a 37% (v/v) solution of polyethylene glycol 4000 (Merck) was then added dropwise over a 60-seconds period, after which the cells were incubated for another 60-seconds at 37° C. Eight ml SF medium, followed by 5 ml opti-MEM® I with GlutaMax/10% (v/v) fetal calf serum (FCS; Bodinco), was then slowly added with gentle agitation. After 30 minutes at room temperature (RT), the cells were pelleted, washed in opti-MEM® I with GlutaMax/10% FCS to remove residual polyethylene glycol, and finally plated at a concentration of $0.1\times10^6$ cells/200 μL per well in aminopterin selection medium, i.e., opti-MEM® I with GlutaMax/10% FCS that was supplemented with 50× Hybri-Max™ aminopterin (a de novo DNA synthesis inhibitor; Sigma). From Day 7, aminopterin selection medium was replenished every 2-3 days, and on Day 12-14, aminopterin selection medium was replaced by opti-MEM I with GlutaMax/10% FCS.

(d). Screening for the Presence of Mouse Anti-Human CD89 Monoclonal Antibodies

From Day 12-14 after each fusion, supernatants from growing hybridomas were screened for the presence of mouse anti-human CD89 antibodies of IgG class (i.e., 'high affinity' IgGs, as opposed to 'low affinity' IgMs) using an ELISA with recombinant C-terminal polyhistidine-tagged human (extracellular) CD89 (rhuCD89; Sino Biological) as target protein. To this end, rhuCD89 was coated at 0.5 μg/mL in PBS (25 ng/50 μL/well) using half-area 96-wells EIA plates (Corning) during 16-24 hours at 4-8° C. After extensive washing with PBS/0.05% Tween 20, plates were blocked with PBS/0.05% Tween 20/1% bovine serum albumin (BSA; Roche) for 1 hour at RT. Subsequently, plates were incubated with 50 μL undiluted hybridoma supernatant/well for 1 hour at RT. In parallel, 50 μL culture medium (opti-MEM® I with GlutaMax/10% FCS) and 50 μL mouse anti-human CD89 antibody clone MIP8a (BioRad) at 10 μg/mL (diluted in culture medium) were run as negative and positive controls, respectively. After extensive washing in PBS/0.05% Tween 20, binding of antibodies on rhuCD89 was determined with 1:5,000 diluted horseradish peroxidase (HRP)-conjugated goat anti-mouse IgG Fey-specific antibodies (Jackson ImmunoResearch) for 1 hour at RT, followed by a ready-to-use solution of TMB substrate (Invitrogen) for colorimetric detection. After adding 1 M $H_2SO_4$, binding (optical density) of antibodies on rhuCD89 was measured at wavelength of 450 nm (reference wavelength of 655 nm) using a microplate reader (iMark; BioRad).

From Day 12-14 after fusion, supernatants from growing hybridomas were also screened and confirmed for mouse anti-human CD89 antibodies of IgG class (i.e., 'high affinity' IgGs, as opposed to 'low affinity' IgMs) production using FACS with membrane-bound human CD89 as target protein. To this end, stable human full-length CD89-transfected HEK293F cells (clone no. 2; see above Example 1 (b) above) were put at $10\times10^6$ cells/mL in ice-chilled PBS containing 0.1% BSA (Sigma)/0.05% $NaN_3$ (PBS/BSA/$NaN_3$) supplemented with 50 μg/mL human IgGs (blocking possible Fcγ receptors; Sigma) for 10 minutes at 4° C. Then, 10 μL/tube (i.e., $0.1\times10^6$ cells) of these cells were incubated with 100 μL undiluted hybridoma supernatant/tube for 30 minutes at 4° C. In parallel, 100 μL culture medium (opti-MEM® I with GlutaMax/10% FCS), 100 μL mouse IgG1 isotype control (BD Biosciences) at 10 μg/mL (diluted in culture medium), and 100 μL mouse IgG2a isotype control (BD Biosciences) at 10 μg/mL (diluted in culture medium) were run as negative controls, and 100 μL mouse anti-human CD89 antibody clone MIP8a (BioRad) at 10 μg/mL (diluted in culture medium) was run as a positive control. Non-transfected (i.e., negative for membrane-bound human CD89 expression) wild type (WT) HEK293F cells were also run as negative control cells to determine antibody specificity. After extensive washing in PBS/BSA/$NaN_3$, cells were subsequently incubated with 1:200 diluted PE-conjugated goat anti-mouse IgG Fey-specific antibodies (Jackson ImmunoResearch) for 30 minutes at 4° C. After extensive washing in PBS/BSA/$NaN_3$, cells were fixed in 2% formaldehyde in PBS/BSA/$NaN_3$ for 30 minutes at 4° C. Binding (geo-mean fluorescence intensity) of antibodies on membrane human CD89 was measured using a flow cytometer (FACSCalibur; BD Biosciences).

Double CD89 positive (i.e., rhuCD89+ in ELISA (data not shown) and membrane CD89+ HEK293F cells in FACS (FIG. 1)) hybridomas were expanded and cryopreserved. Supernatants from these double CD89 positive hybridomas showed no reactivity with non-transfected WT HEK293F cells (i.e., negative for membrane-bound human CD89 expression). As shown in FIG. 1, this approach yielded 21 mouse anti-human CD89-specific antibody-producing hybridomas. Subsequently, supernatants of these mouse anti-human CD89-specific antibody-producing hybridomas were tested for their ability to block the binding of serum human IgA on its receptor CD89 (see Example 1 (e) below).

(e). Screening for the Presence of CD89/IgA Blocking Mouse Anti-Human CD89 Monoclonal Antibodies In order to analyze the effect of mouse anti-human CD89 antibodies on binding of serum human IgA to human CD89, the ability of mouse anti-human CD89 antibodies to sterically hinder the interaction of serum human IgA with human CD89 was determined by using ELISA and FACS analysis.

ELISA: rhuCD89 (Sino Biological) was coated at 0.5 μg/mL in PBS (25 ng/50 μL/well) using half-area 96-wells EIA plates (Corning) during 16-24 hours at 4-8° C. After extensive washing with PBS/0.05% Tween 20, plates were blocked with PBS/0.05% Tween 20/1% BSA (Roche) for 1 hour at RT. Subsequently, plates were incubated with 25 μL undiluted hybridoma supernatant/well for 30 minutes at RT. In parallel, 25 μL culture medium (opti-MEM® I with GlutaMax/10% FCS) and 25 μL mouse anti-human CD89 antibody clone MIP8a (BioRad) at 20 μg/mL (diluted in culture medium) were run as negative and positive controls, respectively. After this (i.e., without washing), 25 μL purified human (serum-derived) IgA (Bethyl Laboratories) at 2 μg/mL (diluted in culture medium) was added to these wells, and incubated for another 30 minutes at RT. After extensive washing in PBS/0.05% Tween 20, binding of serum human IgA on rhuCD89 was determined with biotin-conjugated F(ab')2 fragment goat anti-human serum IgA α chain-specific antibodies (Jackson ImmunoResearch) at 1 μg/mL for 1 hour at RT. After extensive washing in PBS/0.05% Tween 20, 1:10,000 diluted HRP-conjugated streptavidin (Jackson ImmunoResearch) was added, and incubated for 1 hour at RT, followed by a ready-to-use solution of TMB substrate (Invitrogen) for colorimetric detection. After adding 1 M $H_2SO_4$, binding (optical density) of serum human IgA on rhuCD89 was measured at wavelength of 450 nm (reference wavelength of 655 nm) using a microplate reader (iMark; BioRad).

FACS: stable human full-length CD89-transfected HEK293F cells (clone no. 2; see above Example 1 (b) above) were put at $10\times10^6$ cells/mL in ice-chilled PBS containing 0.1% BSA (Sigma)/0.05% $NaN_3$ (PBS/BSA/$NaN_3$). Then, 10 μL/tube (i.e., $0.1\times10^6$ cells) of these cells were incubated with 50 μL undiluted hybridoma supernatant/tube for 30 minutes at 4° C. In parallel, 50 μL culture medium (opti-MEM® I with GlutaMax/10% FCS), 50 μL mouse IgG1 isotype control (BD Biosciences) at 20 μg/mL (diluted in culture medium), and 50 μL mouse IgG2a isotype control (BD Biosciences) at 20 μg/mL (diluted in culture medium) were run as negative controls, and 50 μL mouse anti-human CD89 antibody clone MIP8a (BioRad) at 20 μg/mL (diluted in culture medium) was run as a positive control. After this (i.e., without washing), 50 μL purified human (serum-derived) IgA (Bethyl Laboratories) at 20 μg/mL (diluted in culture medium) was added to these cells, and incubated for another 30 minutes at 4° C. After extensive washing in PBS/BSA/$NaN_3$, binding of serum human IgA on membrane human CD89 was determined with biotin-conjugated F(ab')2 fragment goat anti-human serum IgA α chain-specific antibodies (Jackson ImmunoResearch) at 5 μg/mL for 30 minutes at 4° C. After extensive washing in PBS/BSA/$NaN_3$, 1:200 diluted PE-conjugated streptavidin (Jackson ImmunoResearch) was added, and incubated for 30 minutes at 4° C. After extensive washing in PBS/BSA/$NaN_3$, cells were fixed in 2% formaldehyde in PBS/BSA/$NaN_3$ for 30 minutes at 4° C. Binding (geo-mean fluorescence intensity) of serum human IgA on membrane human CD89 was measured using a flow cytometer (FACSCalibur; BD Biosciences).

As shown in FIG. 2A, 6 out of the 21 examined supernatants from mouse anti-human CD89-specific antibody-producing hybridomas (i.e., 8F3, 9H7, 10E7, 26D6, 20B4, and 30C7) showed strong/complete blocking of the binding of serum human IgA to rhuCD89, whereas 1 out of the 21 examined supernatants from mouse anti-human CD89-specific antibody-producing hybridomas (i.e., 16D6) showed intermediate/partial blocking of the binding of serum human IgA to rhuCD89. For reference purposes, purified mouse anti-human CD89 antibody clone MIP8a, a well-known CD89/IgA blocker (Zhang et al. Clin Exp Immunol 2000; 121: 106-111), was run in parallel, and showed strong/complete blocking of the binding of serum human IgA to rhuCD89.

As shown in FIG. 2B, 6 out of the 21 examined supernatants from mouse anti-human CD89-specific antibody-producing hybridomas (i.e., 8F3, 9H7, 10E7, 26D6, 20B4, and 30C7) showed strong/complete blocking of the binding of serum human IgA to membrane-bound human CD89, whereas 1 out of the 21 examined supernatants from mouse anti-human CD89-specific antibody-producing hybridomas (i.e., 16D6) showed intermediate/partial blocking of the binding of serum human IgA to membrane-bound human CD89. For reference purposes, purified mouse anti-human CD89 antibody clone MIP8a (BioRad), a well-known CD89/IgA blocker (Zhang et al. Clin Exp Immunol 2000; 121: 106-111), was run in parallel, and showed strong/complete blocking of the binding of serum human IgA to membrane-bound human CD89.

Mouse antibodies were purified from above-mentioned CD89/IgA blocking mouse anti-human CD89-specific antibody-producing hybridoma supernatants using protein G columns (GE Healthcare). Heavy and light chains were typed for isotype class using the IsoStrip™ Mouse Monoclonal Antibody Isotyping kit (Roche), and all purified CD89/IgA blocking mouse anti-human CD89-specific antibodies (i.e., 8F3, 9H7, 10E7, 16D6, 26D6, 20B4, and 30C7) were found to be IgG1/κ. In addition, LPS levels were determined using the LAL chromogenic endpoint assay (Hycult Biotech), and all purified CD89/IgA blocking mouse anti-human CD89-specific antibodies (i.e., 8F3, 9H7, 10E7, 16D6, 26D6, 20B4, and 30C7) contained <0.005 EU LPS/μg mouse IgG. Subsequently, these purified CD89/IgA blocking mouse anti-human CD89-specific antibodies were tested in detail for their relative binding affinity for human CD89, for their blocking effect on the binding of serum human IgA to human CD89, and for their blocking effect on serum human IgA-mediated phagocytosis by and on serum human IgA-mediated migration of human CD89 expressing primary human neutrophilic granulocytes, as described in Example 2 and 3. In addition, the fine specificity of these purified CD89/IgA blocking mouse anti-human CD89-specific antibodies was examined by cross-competition with known commercial CD89/IgA blocking and non-blocking mouse anti-human CD89-specific antibodies, by human CD89/bovine Fcγ2R domain mapping, by cross-species binding on cynomolgus monkey CD89, and by human/cynomolgus monkey CD89 epitope mapping, as described in Example 4.

Example 2. Binding Characterization of CD89/IgA Blocking Mouse Anti-Human CD89 Monoclonal Antibodies

(a). Relative Binding Affinity of CD89/IgA Blocking Mouse Anti-Human CD89 Antibodies for Human CD89

In order to determine the relative binding affinity of purified CD89/IgA blocking mouse anti-human CD89 antibodies for human CD89, ELISA and FACS analysis were used.

ELISA: rhuCD89 (Sino Biological) was coated at 0.5 μg/mL in PBS (25 ng/50 μL/well) using half-area 96-wells EIA plates (Corning) during 16-24 hours at 4-8° C. After extensive washing with PBS/0.05% Tween 20, plates were blocked with PBS/0.05% Tween 20/1% BSA (Roche) for 1 hour at RT. Subsequently, plates were incubated with 50 μL titrated (in block buffer) purified mouse anti-human CD89 antibody/well for 1 hour at RT. In parallel, 50 μL titrated (in block buffer) purified mouse anti-human CD89 antibody clone MIP8a (BioRad) was run as a positive control. After extensive washing in PBS/0.05% Tween 20, binding of antibodies on rhuCD89 was determined with 1:5,000 diluted horseradish peroxidase (HRP)-conjugated goat anti-mouse IgG Fcγ-specific antibodies (Jackson ImmunoResearch) for 1 hour at RT, followed by a ready-to-use solution of TMB substrate (Invitrogen) for colorimetric detection. After adding 1 M $H_2SO_4$, binding (optical density) of antibodies on rhuCD89 was measured at wavelength of 450 nm (reference wavelength of 655 nm) using a microplate reader (iMark; BioRad).

FACS: stable human full-length CD89-transfected HEK293F cells (clone no. 2; see above Example 1(b) above) were put at $10\times10^6$ cells/mL in ice-chilled PBS containing 0.1% BSA (Sigma)/0.05% $NaN_3$ (PBS/BSA/$NaN_3$) supplemented with 50 μg/mL human IgGs (blocking possible Fcγ receptors; Sigma) for 10 minutes at 4° C. Then, 10 μL/tube (i.e., $0.1\times10^6$ cells) of these cells were incubated with 100 μL titrated (in PBS/BSA/$NaN_3$) purified mouse anti-human CD89 antibody/tube for 30 minutes at 4° C. In parallel, 100 μL titrated (in PBS/BSA/$NaN_3$) purified mouse IgG1 isotype control (BD Biosciences) and 100 μL titrated (in PBS/BSA/$NaN_3$) purified mouse anti-human CD89 antibody clone MIP8a (BioRad) were run as negative and positive controls, respectively. After extensive washing in PBS/BSA/$NaN_3$, cells were subsequently incubated with 1:200 diluted PE-conjugated goat anti-mouse IgG Fcγ-specific antibodies (Jackson ImmunoResearch) for 30 minutes at 4° C. After extensive washing in PBS/BSA/$NaN_3$, cells were fixed in 2% formaldehyde in PBS/BSA/$NaN_3$ for 30 minutes at 4° C. Binding (geo-mean fluorescence intensity) of antibodies on membrane human CD89 was measured using a flow cytometer (FACSCalibur; BD Biosciences).

As shown in FIG. 3A, all purified CD89/IgA blocking mouse anti-human CD89-specific antibodies dose-dependently bound to rhuCD89. Based on their binding profile, the following relative affinity ranking was found (from high to lower affinity): 9H7=26D6=20B4>8F3=10E7=30C7 (=MIP8a)>16D6. For reference purposes, purified mouse anti-human CD89 antibody clone MIP8a, a well-known CD89/IgA blocker (Zhang et al. Clin Exp Immunol 2000; 121: 106-111), was run in parallel, and also showed dose dependent binding to rhuCD89.

As shown in FIG. 3B, all purified CD89/IgA blocking mouse anti-human CD89-specific antibodies dose-dependently bound to membrane human CD89. Based on their binding profile, the following relative affinity ranking was found (from high to lower affinity): 9H7=26D6=20B4 (=MIP8a)>8F3=10E7=30C7>16D6, which was in agreement with the relative affinity ranking found in ELISA. For reference purposes, purified mouse anti-human CD89 antibody clone MIP8a, a well-known CD89/IgA blocker (Zhang et al. Clin Exp Immunol 2000; 121: 106-111), was run in parallel, and also showed dose dependent binding to membrane human CD89.

(b). Degree of CD89/IgA Blocking Capacity of CD89/IgA Blocking Mouse Anti-Human CD89 Antibodies In order to analyze the degree of CD89/IgA blocking of purified mouse anti-human CD89 antibodies, the ability of purified CD89/IgA blocking mouse anti-human CD89 antibodies to sterically hinder the interaction of human IgA with human CD89 was determined by using ELISA and FACS analysis.

ELISA: rhuCD89 (Sino Biological) was coated at 0.5 μg/mL in PBS (25 ng/50 μL/well) using half-area 96-wells EIA plates (Corning) during 16-24 hours at 4-8° C. After extensive washing with PBS/0.05% Tween 20, plates were blocked with PBS/0.05% Tween 20/1% BSA (Roche) for 1 hour at RT. Subsequently, plates were incubated with 25 μL titrated (in block buffer) purified mouse anti-human CD89 antibody/well for 30 minutes at RT. In parallel, 25 μL titrated (in block buffer) purified mouse anti-human CD89 antibody clone MIP8a (BioRad) was run as positive controls. After this (i.e., without washing), 25 μL purified human (serum-derived) IgA (Bethyl Laboratories) at 2 μg/mL (diluted in block buffer) was added to these wells, and incubated for another 30 minutes at RT. After extensive washing in PBS/0.05% Tween 20, binding of serum human IgA on rhuCD89 was determined with biotin-conjugated F(ab')2 fragment goat anti-human serum IgA α chain-specific antibodies (Jackson ImmunoResearch) at 1 μg/mL for 1 hour at RT. After extensive washing in PBS/0.05% Tween 20, 1:10,000 diluted HRP-conjugated streptavidin (Jackson ImmunoResearch) was added, and incubated for 1 hour at RT, followed by a ready-to-use solution of TMB substrate (Invitrogen) for colorimetric detection. After adding 1 M $H_2SO_4$, binding (optical density) of serum human IgA on rhuCD89 was measured at wavelength of 450 nm (reference wavelength of 655 nm) using a microplate reader (iMark; BioRad).

FACS: stable human full-length CD89-transfected HEK293F cells (clone no. 2; see above Example 1 (b) above) were put at $10\times10^6$ cells/mL in ice-chilled PBS containing 0.1% BSA (Sigma)/0.05% $NaN_3$ (PBS/BSA/$NaN_3$) supplemented with 50 μg/mL human IgGs (blocking possible Fcγ receptors; Sigma) for 10 minutes at 4° C. Then, 10 μL/tube (i.e., $0.1\times10^6$ cells) of these cells were incubated with 50 μL titrated (in PBS/BSA/$NaN_3$) purified mouse anti-human CD89 antibody/tube for 30 minutes at 4° C. In parallel, 50 μL titrated (in PBS/BSA/$NaN_3$) purified mouse IgG1 isotype control (BD Biosciences) and 50 μL titrated (in PBS/BSA/$NaN_3$) purified mouse anti-human CD89 antibody clone MIP8a (BioRad) were run as negative and positive controls, respectively. After this (i.e., without washing), 50 μL purified human (serum-derived) IgA (Bethyl Laboratories) at 20 μg/mL (diluted in PBS/BSA/$NaN_3$) was added to these cells, and incubated for another 30 minutes at 4° C. After extensive washing in PBS/BSA/$NaN_3$, binding of serum human IgA on membrane human CD89 was determined with biotin-conjugated F(ab')2 fragment goat anti-human serum IgA α chain-specific antibodies (Jackson ImmunoResearch) at 5 μg/mL for 30 minutes at 4° C. After extensive washing in PBS/BSA/$NaN_3$, 1:200 diluted PE-conjugated streptavidin (Jackson ImmunoResearch) was added, and incubated for 30 minutes at 4° C. After extensive washing in PBS/BSA/$NaN_3$, cells were fixed in 2% formaldehyde in PBS/BSA/$NaN_3$ for 30 minutes at 4° C. Binding (geo-mean fluorescence intensity) of serum human IgA on membrane human CD89 was measured using a flow cytometer (FACSCalibur; BD Biosciences).

As shown in FIG. 4A, all purified CD89/IgA blocking mouse anti-human CD89-specific antibodies dose-dependently prevented serum human IgA binding to rhuCD89. Based on their CD89/IgA blocking profile, the following ranking was found (from a strong to a weaker CD89/IgA blocking degree): 9H7=26D6=20B4>8F3=10E7=30C7 (=MIP8a)>16D6. Interestingly, there seemed to be a strong positive relationship between the degree of these examined purified mouse anti-human CD89 antibodies to sterically block serum human IgA binding to rhuCD89 (this example) and their respective relative binding affinity for rhuCD89 (see Example 2 (a) above). For reference purposes, purified mouse anti-human CD89 antibody clone MIP8a, a well-known CD89/IgA blocker (Zhang et al. Clin Exp Immunol 2000; 121: 106-111), was run in parallel, and also showed dose dependent blocking of the binding of serum human IgA to rhuCD89.

As shown in FIG. 4B, all purified CD89/IgA blocking mouse anti-human CD89-specific antibodies dose-dependently prevented serum human IgA binding to membrane human CD89. Based on their CD89/IgA blocking profile, the following ranking was found (from a strong to a lower CD89/IgA blocking degree): 9H7=26D6=20B4 (=MIP8a)>8F3=10E7=30C7>16D6, which was in agreement with the CD89/IgA blocking degree found in ELISA. Interestingly, there seemed to be a strong positive relationship between the degree of these examined purified mouse anti-human CD89 antibodies to sterically block serum human IgA binding to membrane human CD89 (this example) and their respective relative binding affinity for membrane human CD89 (see Example 2 (a) above). For reference purposes, purified mouse anti-human CD89 antibody clone MIP8a, a well-known CD89/IgA blocker (Zhang et al. Clin Exp Immunol 2000; 121: 106-111), was run in parallel, and also showed dose dependent blocking of the binding of serum human IgA to membrane human CD89.

In order to analyze the degree of CD89/IgA blocking of purified mouse anti-human CD89 antibodies, the ability of purified CD89/IgA blocking mouse anti-human CD89 antibodies to sterically hinder the interaction of secretory human IgA with human CD89 was determined by using FACS analysis.

Stable human full-length CD89-transfected HEK293F cells (clone no. 2; see above Example 1 (b) above) were put at $10\times10^6$ cells/mL in ice-chilled PBS containing 0.1% BSA (Sigma)/0.05% $NaN_3$ (PBS/BSA/$NaN_3$). Then, 10 μL/tube (i.e., $0.1\times10^6$ cells) of these cells were incubated with or without 50 μL titrated (in PBS/BSA/$NaN_3$) purified mouse anti-human CD89 antibody/tube for 30 minutes at 4° C. In parallel, 50 μL titrated (in PBS/BSA/$NaN_3$) purified mouse anti-human CD89 antibody clone MIP8a (BioRad) was run as a positive control. After this (i.e., without washing), 50 μL purified human (colostrum-derived) IgA (BioRad) at 0.16 μM (diluted in PBS/BSA/$NaN_3$) was added to these cells, and incubated for another 30 minutes at 4° C. After extensive washing in PBS/BSA/$NaN_3$, binding of secretory human IgA on membrane human CD89 was determined with biotin-conjugated F(ab')2 fragment goat anti-human serum IgA α chain-specific antibodies (Jackson ImmunoResearch) at 5 μg/mL for 30 minutes at 4° C. After extensive washing in PBS/BSA/$NaN_3$, 1:200 diluted PE-conjugated streptavidin (Jackson ImmunoResearch) was added, and incubated for 30 minutes at 4° C. After extensive washing in PBS/BSA/$NaN_3$, cells were fixed in 4% formaldehyde in PBS/BSA/$NaN_3$ for 30 minutes at 4° C. Binding (geo-mean fluorescence intensity) of secretory human IgA on membrane human CD89 was measured using a flow cytometer (FACSCalibur; BD Biosciences).

Figure 4C:
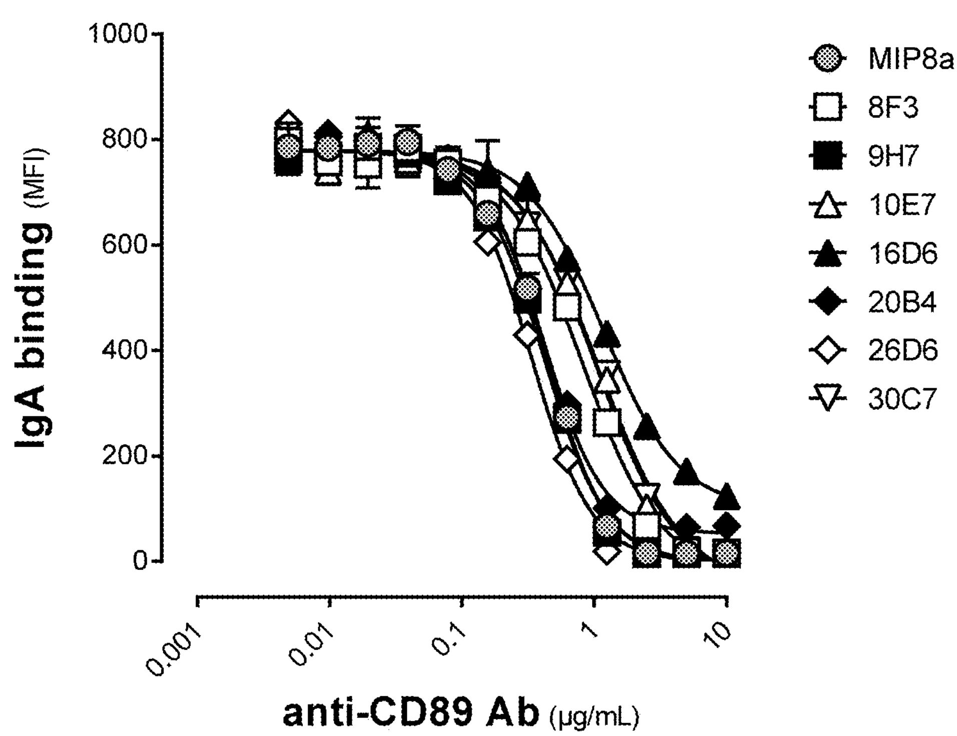
FIG. 4. Effect of purified CD89/IgA blocking mouse anti-human CD89 antibodies on binding of serum human IgA to rhuCD89 (A, ELISA) or to membrane-bound human CD89 (B, FACS) on HEK293F cells. Effect of purified CD89/IgA blocking mouse anti-human CD89 antibodies on binding of secretory human IgA to membrane-bound human CD89 (C) on HEK293F cells. Mean±SD (n=2) are shown.

As shown in FIG. 4C, all purified CD89/IgA blocking mouse anti-human CD89-specific antibodies dose-dependently prevented secretory human IgA binding to membrane human CD89. Based on their CD89/IgA blocking profile, the following ranking was found (from a strong to a lower CD89/IgA blocking degree): 9H7=26D6=20B4(=MIP8a) >8F3=10E7=30C7>16D6, which was in agreement with the CD89/IgA blocking degree using serum human IgA found in FACS (see FIG. 4B). Interestingly, there seemed to be a strong positive relationship between the degree of these examined purified mouse anti-human CD89 antibodies to sterically block secretory human IgA binding to membrane human CD89 (this example) and their respective relative binding affinity for membrane human CD89 (see Example 2 (a) above). For reference purposes, purified mouse anti-human CD89 antibody clone MIP8a, a well-known CD89/IgA blocker (Zhang et al. Clin Exp Immunol 2000; 121: 106-111), was run in parallel, and also showed dose dependent blocking of the binding of secretory human IgA to membrane human CD89.

Human CD89 is described to be a receptor with low/moderate affinity for monomeric human IgA (Ka≈106 $M^{-1}$), while human IgA immune complexes bind avidly to human CD89 (Bakema et al. Immunol Rev 2011; 4: 612-624). To mimic human IgA immune complexes, human (serum-derived) IgA (Bethyl Laboratories) was heated at 63° C. for 30 minutes, and cooled down to RT followed by centrifugation at 4° C. 12000×g for 2 minutes to remove any insoluble protein precipitation. This heat-aggregated (serum-derived) human IgA was compared to non-aggregated (serum-derived) human IgA using size exclusion chromatography analysis, and demonstrated that heat-aggregated human IgA consisted of ~40% monomeric, ~15% dimeric, and ~45% tetrameric or higher-order of multimeric human IgA, whereas non-aggregated human IgA consisted of ~70% monomeric, ~20% dimeric, and ~10% trimeric human IgA. Then, the ability of our purified CD89/IgA blocking mouse anti-human CD89 antibodies to sterically hinder the interaction of this heat-aggregated serum human IgA versus non-aggregated serum human IgA with membrane-bound human CD89 was determined by using FACS analysis (see below).

Stable human full-length CD89-transfected HEK293F cells (clone no. 2; see above Example 1 (b) above) were put at $10\times10^6$ cells/mL in ice-chilled PBS containing 0.1% BSA (Sigma)/0.05% $NaN_3$ (PBS/BSA/$NaN_3$) supplemented with 50 μg/mL human IgGs (blocking possible Fcγ receptors; Sigma) for 10 minutes at 4° C. Then, 10 μL/tube (i.e., $0.1\times10^6$ cells) of these cells were incubated with or without 50 μL purified mouse anti-human CD89 antibody at 20 μg/mL (in PBS/BSA/$NaN_3$) for 30 minutes at 4° C. In parallel, 50 μL purified mouse IgG1 isotype control (BD Biosciences) at 20 μg/mL (in PBS/BSA/$NaN_3$) and 50 μL purified mouse anti-human CD89 antibody clone MIP8a (a well-known CD89/IgA blocker (Zhang et al. Clin Exp Immunol 2000; 121: 106-111); BioRad) at 20 μg/mL (in PBS/BSA/$NaN_3$) were run as negative and positive controls, respectively. Moreover, 50 μL purified mouse anti-human CD89 antibody clone A59 (a well-known CD89/IgA non-blocker (Monteiro et al. J Immunol 1992; 148: 1764-1770); BD Biosciences) at 20 μg/mL (in PBS/BSA/$NaN_3$) and 50 μL purified mouse anti-human CD89 antibody clone A3 (a well-known CD89/IgA non-blocker (Monteiro et al. J Immunol 1992; 148: 1764-1770); Santa Cruz Biotechnology) at 20 μg/mL (in PBS/BSA/$NaN_3$) were run as additional negative controls. After this (i.e., without washing), 50 μL purified non-aggregated or heat-aggregated human (serum-derived) IgA (Bethyl Laboratories) at 20 μg/mL (diluted in PBS/BSA/$NaN_3$) was added to these cells, and incubated for another 30 minutes at 4° C. After extensive washing in PBS/BSA/$NaN_3$, binding of non-aggregated or heat-aggregated serum human IgA on membrane human CD89 was determined with biotin-conjugated F(ab')2 fragment goat anti-human serum IgA α chain-specific antibodies (Jackson ImmunoResearch) at 5 μg/mL for 30 minutes at 4° C. After extensive washing in PBS/BSA/$NaN_3$, 1:200 diluted PE-conjugated streptavidin (Jackson ImmunoResearch) was added, and incubated for 30 minutes at 4° C. After extensive washing in PBS/BSA/$NaN_3$, cells were fixed in 2% formaldehyde in PBS/BSA/$NaN_3$ for 30 minutes at 4° C. Binding (geo-mean fluorescence intensity) of non-aggregated or heat-aggregated serum human IgA on membrane human CD89 was measured using a flow cytometer (FACSCalibur; BD Biosciences).

Figure 5A:
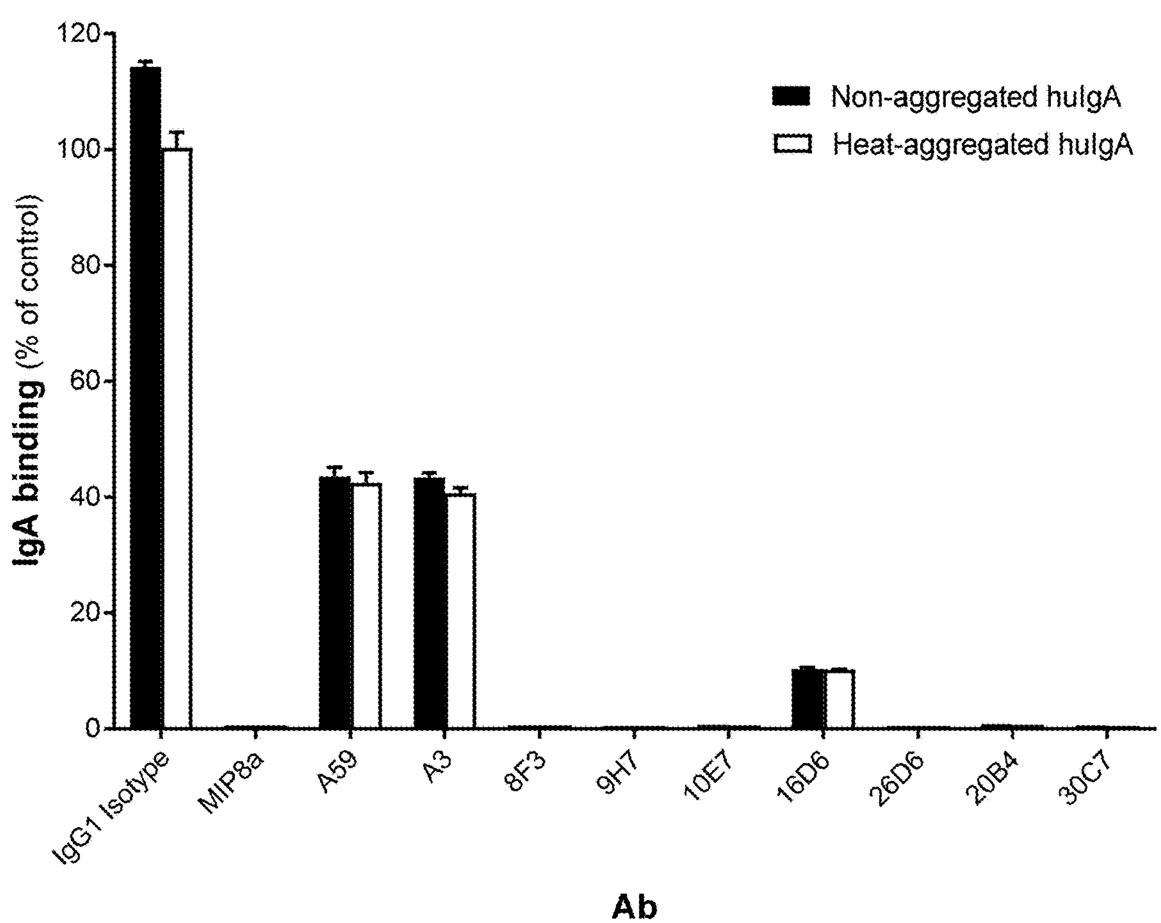
FIG. 5. Effect of purified CD89/IgA blocking mouse anti-human CD89 antibodies (at 10 μg/mL) on (A, C) prevention of non-aggregated or heat-aggregated serum human IgA binding to, on (B, D) displacement of previously saturated non-aggregated or heat-aggregated serum human IgA to, and on (E) induction of cell death (cell viability and phosphatidylserine expression) in membrane-bound human CD89 expressing HEK293F cells. Effects of CD89/IgA blocking mouse anti-human CD89 antibodies were examined (A, B) under metabolic inactive conditions (i.e., in the presence of $NaN_3$ and at a cold ambient temperature (4° C.)) and (C, D, E) under metabolic active conditions (i.e., in the absence of $NaN_3$ and at a physiologic ambient temperature (37° C.)). Mean±SD (n=2) are shown.

As shown in FIG. 5A, all our purified CD89/IgA blocking mouse anti-human CD89-specific antibodies prevented heat-aggregated serum human IgA binding to membrane human CD89 to a similar extent as found with non-aggregated serum human IgA. For reference purposes, purified mouse anti-human CD89 antibody clone MIP8a, a well-known CD89/IgA blocker (Zhang et al. Clin Exp Immunol 2000; 121: 106-111), was run in parallel, and also showed blocking of the binding of heat-aggregated serum human IgA binding to membrane human CD89 to a similar extent as found with non-aggregated serum human IgA. Surprisingly, purified mouse anti-human CD89 antibody clone A59 and clone A3—both well-known CD89/IgA non-blockers (Monteiro et al. J Immunol 1992; 148: 1764-1770)—showed partial (~60%) blocking of the binding of heat-aggregated serum human IgA binding to membrane human CD89 to a similar extent as found with non-aggregated serum human IgA.

Collectively, these results demonstrated that CD89/IgA blocking mouse anti-human CD89-specific antibody 8F3, 9H7, 10E7, 16D6, 26D6, 20B4, and 30C7 prevented the binding of monomeric, dimeric, trimeric, tetrameric or higher-order of multimeric serum human IgA (i.e., non-aggregated and heat-aggregated IgA) and dimeric secretory human IgA to membrane human CD89. For summary, see Table 1A (i.e., serum human IgA blocking).

(c). Serum Human IgA Displacement by CD89/IgA Blocking Mouse Anti-Human CD89 Antibodies In order to analyze whether purified CD89/IgA blocking mouse anti-human CD89 antibodies were able to displace previously saturated serum human IgA to human CD89, the effect of purified mouse anti-human CD89 antibodies on serum human IgA displacement to membrane-bound human CD89 on HEK293F cells was determined by using FACS analysis.

Stable human full-length CD89-transfected HEK293F cells (clone no. 2; see above Example 1 (b) above) were put at $10\times10^6$ cells/mL in ice-chilled PBS containing 0.1% BSA (Sigma)/0.05% $NaN_3$ (PBS/BSA/$NaN_3$) supplemented with 50 μg/mL human IgGs (blocking possible Fcγ receptors; Sigma) for 10 minutes at 4° C. Then, 10 μL/tube (i.e., $0.1\times10^6$ cells) of these cells were incubated with 50 μL purified non-aggregated or heat-aggregated human (serum-derived) IgA (Bethyl Laboratories) at 20 μg/mL (diluted in PBS/BSA/$NaN_3$) for 30 minutes at 4° C. After this (i.e., without washing), 50 μL purified mouse anti-human CD89 antibody at 20 μg/mL (in PBS/BSA/$NaN_3$) was added to these cells, and incubated for another 30 minutes at 4° C. In parallel, 50 μL purified mouse IgG1 isotype control (BD Biosciences) at 20 μg/mL (in PBS/BSA/$NaN_3$) and 50 μL purified mouse anti-human CD89 antibody clone MIP8a (a well-known CD89/IgA blocker (Zhang et al. Clin Exp Immunol 2000; 121: 106-111); BioRad) at 20 μg/mL (in PBS/BSA/$NaN_3$) were run as negative and positive controls, respectively. Moreover, 50 μL purified mouse anti-human CD89 antibody clone A59 (a well-known CD89/IgA non-blocker (Monteiro et al. J Immunol 1992; 148: 1764-1770); BD Biosciences) at 20 μg/mL (in PBS/BSA/$NaN_3$) and 50 μL purified mouse anti-human CD89 antibody clone A3 (a well-known CD89/IgA non-blocker (Monteiro et al. J Immunol 1992; 148: 1764-1770); Santa Cruz Biotechnology) at 20 μg/mL (in PBS/BSA/$NaN_3$) were run as additional negative controls. After extensive washing in PBS/BSA/$NaN_3$, binding of non-aggregated or heat-aggregated serum human IgA on membrane human CD89 was determined with biotin-conjugated F(ab')2 fragment goat anti-human serum IgA α chain-specific antibodies (Jackson ImmunoResearch) at 5 μg/mL for 30 minutes at 4° C. After extensive washing in PBS/BSA/$NaN_3$, 1:200 diluted PE-conjugated streptavidin (Jackson ImmunoResearch) was added, and incubated for 30 minutes at 4° C. After extensive washing in PBS/BSA/$NaN_3$, cells were fixed in 2% formaldehyde in PBS/BSA/$NaN_3$ for 30 minutes at 4° C. Binding (geo-mean fluorescence intensity) of non-aggregated or heat-aggregated serum human IgA on membrane human CD89 was measured using a flow cytometer (FACSCalibur; BD Biosciences).

Figure 5B:
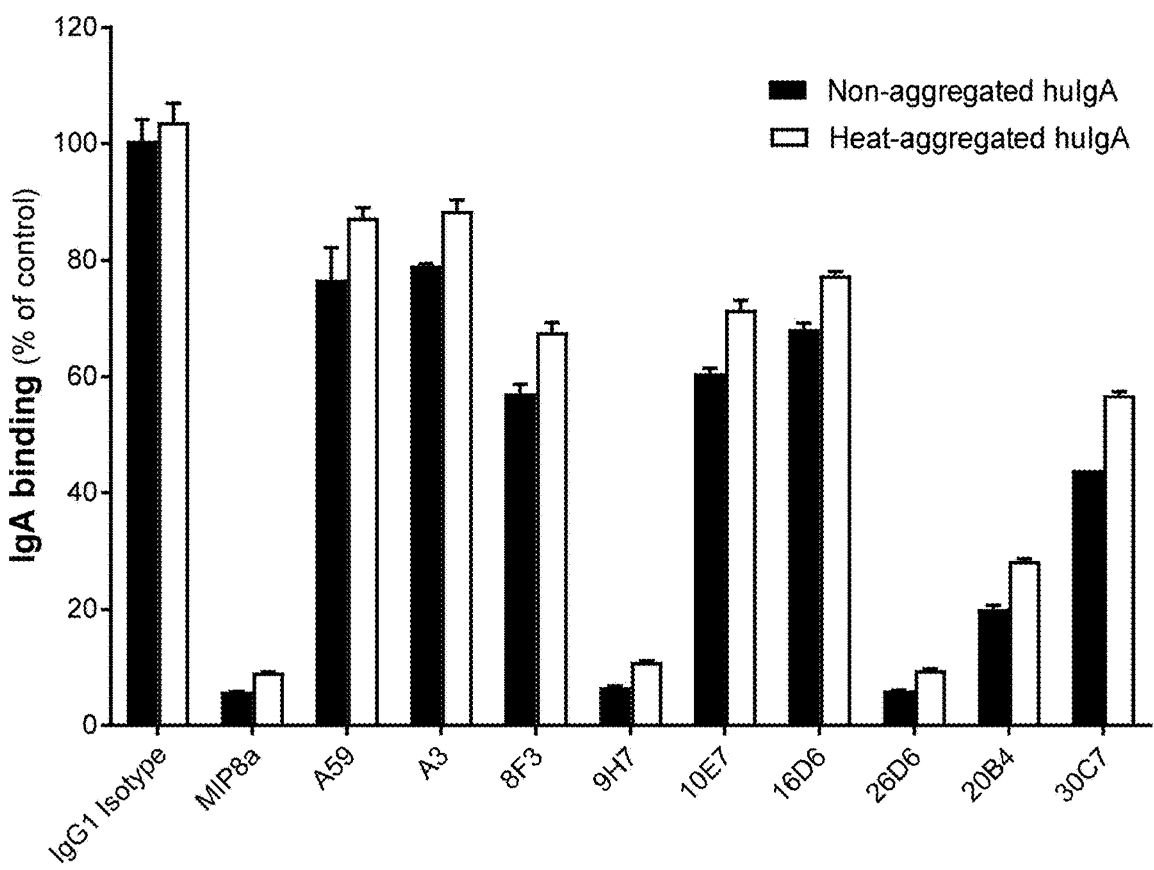

As shown in FIG. 5B, all our purified CD89/IgA blocking mouse anti-human CD89-specific antibodies displaced non-aggregated serum human IgA on previously saturated membrane human CD89 to a variable degree. Based on their degree of serum human IgA displacement, the following ranking was found (from a strong to a weaker human IgA displacement degree): 9H7=26D6 (=MIP8a)>20B4>30C7>8F3=10E7>16D6. For reference purposes, purified mouse anti-human CD89 antibody clone MIP8a, a well-known CD89/IgA blocker (Zhang et al. Clin Exp Immunol 2000; 121: 106-111), was run in parallel, and also displaced non-aggregated serum human IgA on previously saturated membrane human CD89. In contrast, purified mouse anti-human CD89 antibody clone A59 and clone A3—both well-known CD89/IgA non-blockers (Monteiro et al. J Immunol 1992; 148: 1764-1770)—did not displace non-aggregated serum human IgA on previously saturated membrane human CD89.

As shown in FIG. 5B, all our purified CD89/IgA blocking mouse anti-human CD89-specific antibodies (except for 16D6) also displaced heat-aggregated serum human IgA on previously saturated membrane human CD89 to a variable degree and to a slightly lesser extent as found with non-aggregated serum human IgA. Based on their degree of serum human IgA displacement, the following ranking was found (from a strong to a weaker human IgA displacement degree): 9H7=26D6(=MIP8a)>20B4>30C7>8F3=10E7. For reference purposes, purified mouse anti-human CD89 antibody clone MIP8a, a well-known CD89/IgA blocker (Zhang et al. Clin Exp Immunol 2000; 121: 106-111), was run in parallel, and also displaced non-aggregated serum human IgA on previously saturated membrane human CD89 although to a slightly lesser extent as found with non-aggregated serum human IgA. In contrast, purified mouse anti-human CD89 antibody clone A59 and clone A3—both well-known CD89/IgA non-blockers (Monteiro et al. J Immunol 1992; 148: 1764-1770)—did not displace heat-aggregated serum human IgA on previously saturated membrane human CD89.

These results demonstrated that CD89/IgA blocking mouse anti-human CD89-specific antibody 8F3, 9H7, 10E7, (16D6), 26D6, 20B4, and 30C7 showed displacement of monomeric, dimeric and trimeric serum human IgA (i.e., non-aggregated IgA), and, to a slightly lesser extent, of tetrameric or higher-order of multimeric serum human IgA (i.e., heat-aggregated IgA) on previously saturated membrane human CD89. For summary, see Table 1A.

TABLE 1A

IgA blocking and IgA displacement profiles of purified CD89/IgA blocking mouse anti-human CD89-specific antibodies at saturated concentration (i.e., 10 μg/mL) on membrane human CD89 under flow-cytometric and metabolic inactive conditions (i.e., in the presence of $NaN_3$ and at a cold ambient temperature (4° C.)). IgA blocking or IgA displacement by mouse anti-human CD89 antibodies

| | IgA blocking ($1^{st}$ Ab & $2^{nd}$ IgA) | | IgA displacement ($1^{st}$ IgA & $2^{nd}$ Ab) | |
|---|---|---|---|---|
| Anti-CD89 Ab | Non-aggr IgA | Heat-aggr IgA | Non-aggr IgA | Heat-aggr IgA |
| 8F3 | +++ | +++ | + | + |
| 9H7 | +++ | +++ | +++ | +++ |
| 10E7 | +++ | +++ | + | + |
| 16D6 | +++ | +++ | + | − |
| 26D6 | +++ | +++ | +++ | +++ |
| 20B4 | +++ | +++ | +++ | ++ |
| 30C7 | +++ | +++ | ++ | + |
| mIgG1 control | − | − | − | − |
| MIP8a | +++ | +++ | +++ | +++ |
| A59 | ++ | ++ | − | − |
| A3 | ++ | ++ | − | − |

− = no blocking of IgA binding or no IgA displacement on membrane human CD89 by mouse anti-CD89 antibodies (76-125% IgA binding in FIGS. 5A and 5B),
+ = weak blocking of IgA binding or weak IgA displacement on membrane human CD89 by mouse anti-CD89 antibodies (51-75% IgA binding in FIGS. 5A and 5B),
++ = intermediate blocking of IgA binding or intermediate IgA displacement on membrane human CD89 by mouse anti-CD89 antibodies (26-50% IgA binding in FIGS. 5A and 5B),
+++ = strong blocking of IgA binding or strong IgA displacement on membrane human CD89 by mouse anti-CD89 antibodies (0-25% IgA binding in FIGS. 5A and 5B).
Aggr = aggregated.

Since all above-described experiments (see Example 2 (b) and Example 2 (c) above) were performed under (flow-cytometric) metabolic inactive conditions (i.e., at a cold ambient temperature (4° C.), and by the presence of $NaN_3$, a reversible inhibitor of mitochondrial respiration, which prevents capping, shedding, and internalization of an antibody-antigen complex after the antibodies bind to receptors), we also examined the ability of our purified CD89/IgA blocking mouse anti-human CD89 antibodies to sterically hinder the interaction of non-aggregated and heat-aggregated serum human IgA with membrane-bound human CD89 under metabolic (active) conditions as follows:

Human IgA blocking setup: stable human full-length CD89-transfected HEK293F cells (clone no. 2; see above Example 1 (b) above) were put at $1.70\times10^6$ cells/mL in FreeStyle™ 293 culture medium (Life Technologies) supplemented with 125 μg/mL G418/Geneticin (Gibco) at 4° C. Then, 400 μL/tube (i.e., $0.7\times10^6$ cells) of these cells were incubated with or without 50 μL purified mouse anti-human CD89 antibody at 100 μg/mL (in FreeStyle™ 293 culture medium) for 30 minutes at 4° C. In parallel, 50 μL purified mouse IgG1 isotype control (BD Biosciences) at 100 μg/mL (in FreeStyle™ 293 culture medium) and 50 μL purified mouse anti-human CD89 antibody clone MIP8a (a well-known CD89/IgA blocker (Zhang et al. Clin Exp Immunol 2000; 121: 106-111); BioRad) at 100 μg/mL (in FreeStyle™ 293 culture medium) were run as negative and positive controls, respectively. Moreover, 50 μL purified mouse anti-human CD89 antibody clone A59 (a well-known CD89/IgA non-blocker (Monteiro et al. J Immunol 1992; 148: 1764-1770); BD Biosciences) at 100 μg/mL (in FreeStyle™ 293 culture medium) and 50 μL purified mouse anti-human CD89 antibody clone A3 (a well-known CD89/IgA non-blocker (Monteiro et al. J Immunol 1992; 148: 1764-1770); Santa Cruz Biotechnology) at 100 μg/mL (in PBS/BSA/$NaN_3$) were run as additional negative controls. After this (i.e., without washing), 50 μL purified non-aggregated or heat-aggregated human (serum-derived) IgA (Bethyl Laboratories) at 100 μg/mL (in FreeStyle™ 293 culture medium) was added to these cells, and incubated for another 24 hours in a 5% $CO_2$-incubator at 37° C. After extensive washing in PBS/BSA/$NaN_3$, binding of non-aggregated or heat-aggregated serum human IgA on membrane human CD89 was determined with biotin-conjugated F(ab')2 fragment goat anti-human serum IgA α chain-specific antibodies (Jackson ImmunoResearch) at 5 μg/mL for 30 minutes at 4° C. After extensive washing in PBS/BSA/$NaN_3$, 1:200 diluted PE-conjugated streptavidin (Jackson ImmunoResearch) was added, and incubated for 30 minutes at 4° C. After extensive washing in PBS/BSA/$NaN_3$, cells were fixed in 2% formaldehyde in PBS/BSA/$NaN_3$ for 30 minutes at 4° C. Binding (geo-mean fluorescence intensity) of non-aggregated or heat-aggregated serum human IgA on membrane human CD89 was measured using a flow cytometer (FACSCalibur; BD Biosciences).

Human IgA displacement setup: stable human full-length CD89-transfected HEK293F cells (clone no. 2; see above Example 1 (b) above) were put at $1.70\times10^6$ cells/mL in FreeStyle™ 293 culture medium (Life Technologies) supplemented with 125 μg/mL G418/Geneticin (Gibco) at 4° C. Then, 400 μL/tube (i.e., $0.7\times10^6$ cells) of these cells were incubated with 50 μL purified non-aggregated or heat-aggregated human (serum-derived) IgA (Bethyl Laboratories) at 100 μg/mL (in FreeStyle™ 293 culture medium) for 30 minutes at 4° C. After this (i.e., without washing), 50 μL purified mouse anti-human CD89 antibody at 100 μg/mL (in FreeStyle™ 293 culture medium) was added to these cells, and incubated for another 24 hours in a 5% $CO_2$-incubator at 37° C. In parallel, 50 μL purified mouse IgG1 isotype control (BD Biosciences) at 100 μg/mL (in FreeStyle™ 293 culture medium) and 50 μL purified mouse anti-human CD89 antibody clone MIP8a (a well-known CD89/IgA blocker (Zhang et al. Clin Exp Immunol 2000; 121: 106-111); BioRad) at 100 μg/mL (in FreeStyle™ 293 culture medium) were run as negative and positive controls, respectively. Moreover, 50 μL purified mouse anti-human CD89 antibody clone A59 (a well-known CD89/IgA non-blocker (Monteiro et al. J Immunol 1992; 148: 1764-1770); BD Biosciences) at 100 μg/mL (in FreeStyle™ 293 culture medium) and 50 μL purified mouse anti-human CD89 antibody clone A3 (a well-known CD89/IgA non-blocker (Monteiro et al. J Immunol 1992; 148: 1764-1770); Santa Cruz Biotechnology) at 100 μg/mL (in PBS/BSA/$NaN_3$) were run as additional negative controls. After extensive washing in PBS/BSA/$NaN_3$, binding of non-aggregated or heat-aggregated serum human IgA on membrane human CD89 was determined with biotin-conjugated F(ab')2 fragment goat anti-human serum IgA α chain-specific antibodies (Jackson ImmunoResearch) at 5 μg/mL for 30 minutes at 4° C. After extensive washing in PBS/BSA/$NaN_3$, 1:200 diluted PE-conjugated streptavidin (Jackson ImmunoResearch) was added, and incubated for 30 minutes at 4° C. After extensive washing in PBS/BSA/$NaN_3$, cells were fixed in 2% formaldehyde in PBS/BSA/$NaN_3$ for 30 minutes at 4° C. Binding (geo-mean fluorescence intensity) of non-aggregated or heat-aggregated serum human IgA on membrane human CD89 was measured using a flow cytometer (FACSCalibur; BD Biosciences).

Figure 5C:
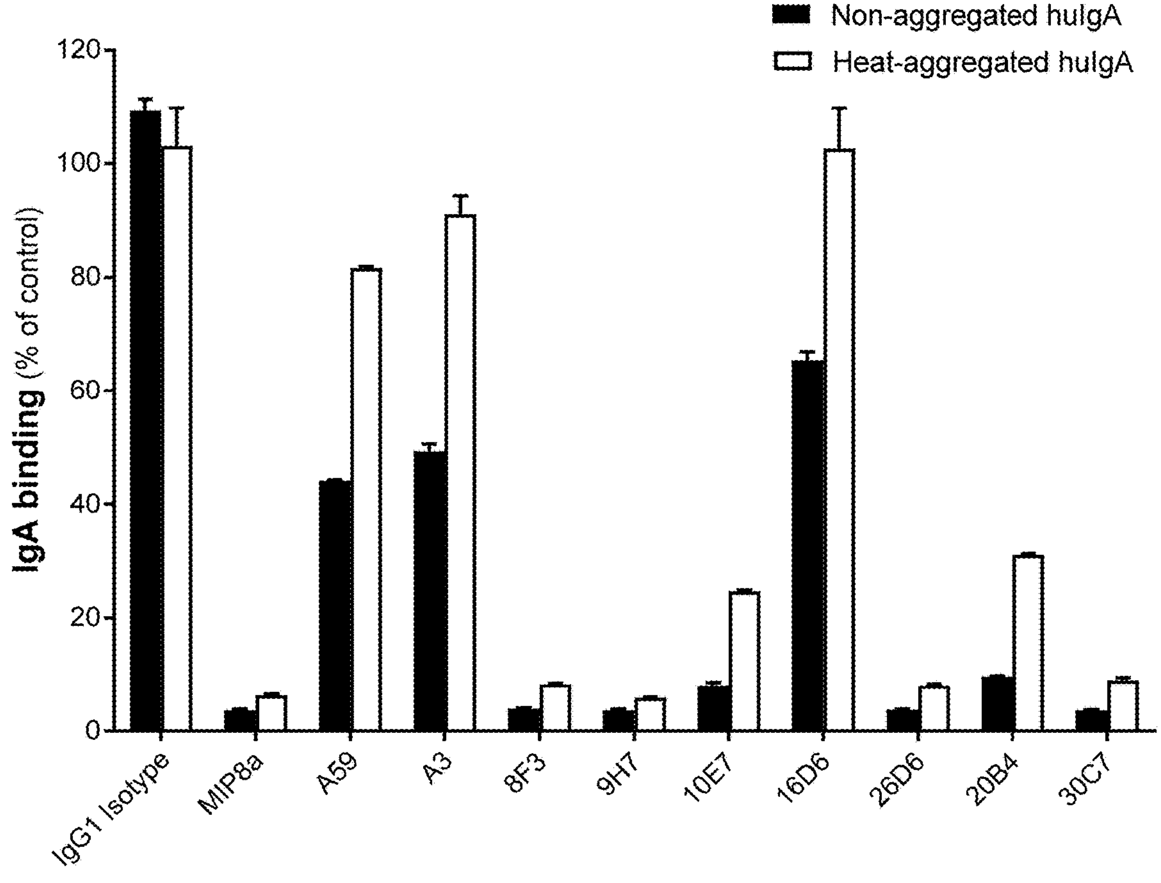

As shown in FIG. 5C, purified CD89/IgA blocking mouse anti-human CD89-specific antibodies 8F3, 9H7, 10E7, 26B6, 20B4, and 30C7 strongly inhibited non-aggregated and heat-aggregated serum human IgA binding to membrane human CD89 under metabolic active conditions. Purified CD89/IgA blocking mouse anti-human CD89-specific antibody 16D6 showed partial blocking of the binding of non-aggregated serum human IgA binding to membrane human CD89, whereas mouse anti-human CD89 antibody 16D6 was unable to block the binding of heat-aggregated serum human IgA binding to membrane human CD89 under metabolic active conditions. For reference purposes, purified mouse anti-human CD89 antibody clone MIP8a, a well-known CD89/IgA blocker (Zhang et al. Clin Exp Immunol 2000; 121: 106-111), was run in parallel, and also showed strong blocking of the binding of non-aggregated and heat-aggregated serum human IgA binding to membrane human CD89 under metabolic active conditions. Surprisingly, purified mouse anti-human CD89 antibody clone A59 and clone A3—both well-known CD89/IgA non-blockers (Monteiro et al. J Immunol 1992; 148: 1764-1770)—showed partial blocking of the binding of non-aggregated serum human IgA binding to membrane human CD89, whereas mouse anti-human CD89 antibody clone A59 and clone A3 were unable to block the binding of heat-aggregated serum human IgA binding to membrane human CD89 under metabolic active conditions.

Figure 5D:
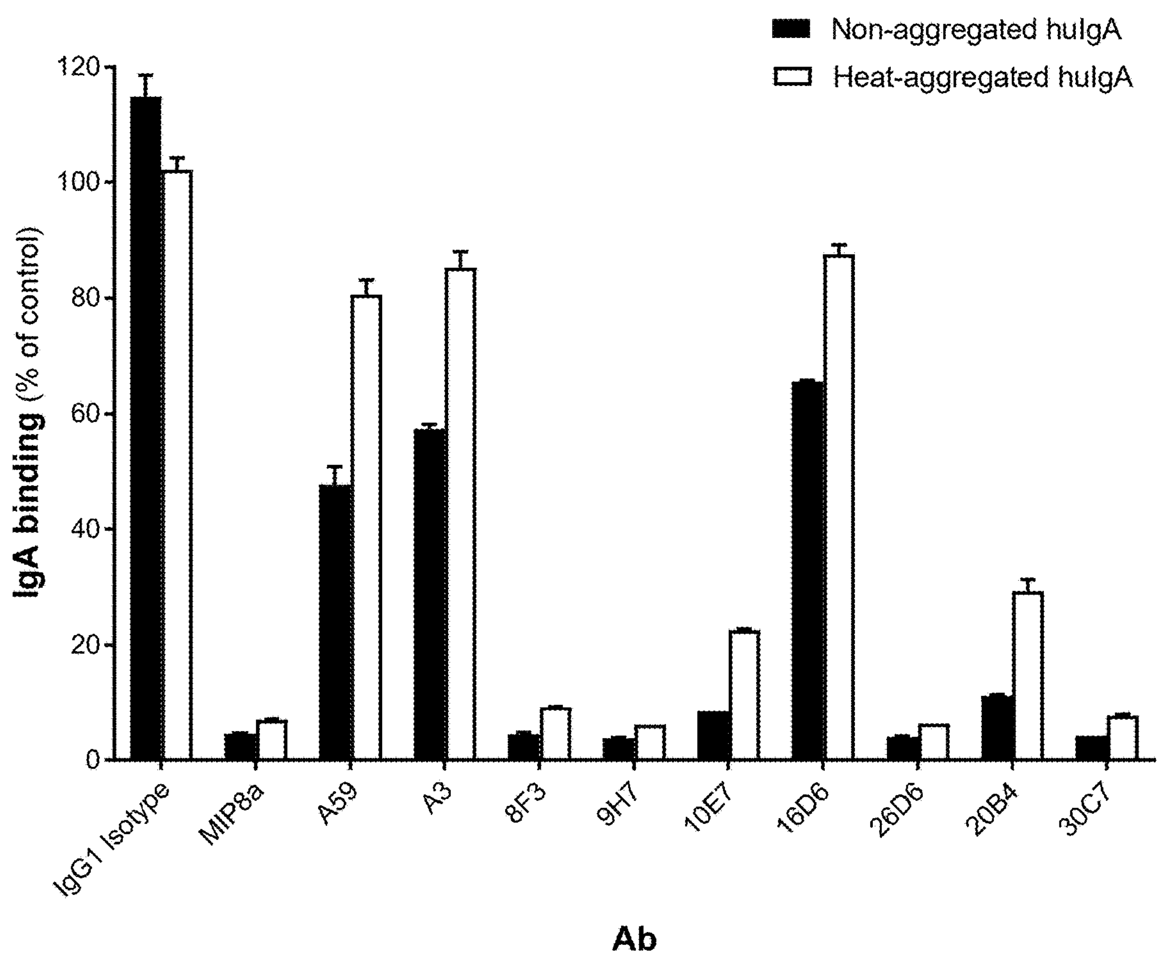

As shown in FIG. 5D, purified CD89/IgA blocking mouse anti-human CD89-specific antibodies 8F3, 9H7, 10E7, 26B6, 20B4, and 30C7 strongly displaced non-aggregated and heat-aggregated serum human IgA on previously saturated membrane human CD89 under metabolic active conditions. Purified CD89/IgA blocking mouse anti-human CD89-specific antibody 16D6 could partially displace non-aggregated serum human IgA on previously saturated membrane human CD89, whereas mouse anti-human CD89 antibody 16D6 was unable to displace heat-aggregated serum human IgA on previously saturated membrane human CD89 under metabolic active conditions. For reference purposes, purified mouse anti-human CD89 antibody clone MIP8a, a well-known CD89/IgA blocker (Zhang et al. Clin Exp Immunol 2000; 121: 106-111), was run in parallel, and could also strongly displace non-aggregated and heat-aggregated serum human IgA on previously saturated membrane human CD89 under metabolic active conditions. Surprisingly, purified mouse anti-human CD89 antibody clone A59 and clone A3—both well-known CD89/IgA non-blockers (Monteiro et al. J Immunol 1992; 148: 1764-1770)—could partially displace non-aggregated serum human IgA on previously saturated membrane human CD89, whereas mouse anti-human CD89 antibody clone A59 and clone A3 were unable to displace heat-aggregated serum human IgA on previously saturated membrane human CD89 under metabolic active conditions These results demonstrated that CD89/IgA blocking mouse anti-human CD89-specific antibody 8F3, 9H7, 10E7, 26D6, 20B4, and 30C7 inhibited the binding of monomeric, dimeric and trimeric serum human IgA (i.e., non-aggregated IgA), and of tetrameric or higher-order of multimeric serum human IgA (i.e., heat-aggregated IgA) on membrane human CD89 under metabolic active conditions. In addition, CD89/IgA blocking mouse anti-human CD89-specific antibody 8F3, 9H7, 10E7, 26D6, 20B4, and 30C7 also displaced monomeric, dimeric and trimeric serum human IgA (i.e., non-aggregated IgA), and tetrameric or higher-order of multimeric serum human IgA (i.e., heat-aggregated IgA) on previously saturated membrane human CD89 under metabolic active conditions. For summary, see Table 1B.

TABLE 1B

IgA blocking and IgA displacement profiles of purified CD89/IgA blocking mouse anti-human CD89-specific antibodies at saturated concentration (i.e., 10 μg/mL) on membrane human CD89 after 24 hours under metabolic (active) conditions (i.e., in the absence of $NaN_3$ and at a physiologic ambient temperature (37° C.)). IgA blocking or IgA displacement by mouse anti-human CD89 antibodies

| | IgA blocking ($1^{st}$ Ab & $2^{nd}$ IgA) | | IgA displacement ($1^{st}$ IgA & $2^{nd}$ Ab) | |
|---|---|---|---|---|
| Anti-CD89 Ab | Non-aggr IgA | Heat-aggr IgA | Non-aggr IgA | Heat-aggr IgA |
| 8F3 | +++ | +++ | +++ | +++ |
| 9H7 | +++ | +++ | +++ | +++ |
| 10E7 | +++ | +++ | +++ | +++ |
| 16D6 | + | − | + | − |
| 26D6 | +++ | +++ | +++ | +++ |
| 20B4 | +++ | ++ | +++ | ++ |
| 30C7 | +++ | +++ | +++ | +++ |
| mIgG1 control | − | − | − | − |
| MIP8a | +++ | +++ | +++ | +++ |
| A59 | ++ | − | ++ | − |
| A3 | ++ | − | + | − |

− = no blocking of IgA binding or no IgA displacement on membrane human CD89 by mouse anti-CD89 antibodies (76-125% IgA binding in FIGS. 5C and 5D),
+ = weak blocking of IgA binding or weak IgA displacement on membrane human CD89 by mouse anti-CD89 antibodies (51-75% IgA binding in FIGS. 5C and 5D),
++ = intermediate blocking of IgA binding or intermediate IgA displacement on membrane human CD89 by mouse anti-CD89 antibodies (26-50% IgA binding in FIGS. 5C and 5D),
+++ = strong blocking of IgA binding or strong IgA displacement on membrane human CD89 by mouse anti-CD89 antibodies (0-25% IgA binding in FIGS. 5C and 5D).
Aggr = aggregated.

CD89/IgA blocking mouse anti-human CD89 antibody clone MIP8a has been described to induce human cell death in CD89 expressing human neutrophilic granulocytes (Wehrli et al. J Immunol 2014, 193: 5649-5659). Depending on the inflammatory microenvironment, caspase-dependent (typically observed during apoptosis) or caspase-independent (non-apoptotic) cell death was induced in these human neutrophilic granulocytes by exposure to bivalent mouse anti-human CD89 antibody clone MIP8a. Therefore, the effect of our generated CD89/IgA blocking mouse anti-human CD89 antibodies 8F3, 9H7, 10E7, 16D6, 26D6, 20B4, and 30C7 on human CD89-mediated cell death was examined using stable human full-length CD89-transfected HEK293F cells as target cells.

Stable human full-length CD89-transfected HEK293F cells (clone no. 2; see above Example 1 (b) above) were put at $1.25\times10^6$ cells/mL in FreeStyle™ 293 culture medium (Life Technologies) supplemented with 125 μg/mL G418/Geneticin (Gibco) at 4° C. Then, 400 Li/tube (i.e., $0.5\times10^6$ cells) of these cells were incubated with or without 50 μL purified mouse anti-human CD89 antibody at 100 μg/mL (in FreeStyle™ 293 culture medium) for 30 minutes at 4° C. In parallel, 50 μL purified mouse IgG1 isotype control (BD Biosciences) at 100 μg/mL (in FreeStyle™ 293 culture medium) and 50 μL purified mouse anti-human CD89 antibody clone MIP8a (a well-known CD89/IgA blocker (Zhang et al. Clin Exp Immunol 2000; 121: 106-111); BioRad) at 100 μg/mL (in FreeStyle™ 293 culture medium) were run as negative and positive cell death inducing controls, respectively. Moreover, 50 μL purified mouse anti-human CD89 antibody clone A59 (a well-known CD89/IgA non-blocker (Monteiro et al. J Immunol 1992; 148: 1764-1770); BD Biosciences) at 100 μg/mL (in FreeStyle™ 293 culture medium) and 50 μL purified mouse anti-human CD89 antibody clone A3 (a well-known CD89/IgA non-blocker (Monteiro et al. J Immunol 1992; 148: 1764-1770); Santa Cruz Biotechnology) at 100 μg/mL (in PBS/BSA/$NaN_3$) were run as additional controls. Subsequently (i.e., without washing), 50 μL FreeStyle™ 293 culture medium was added to these cells, and incubated for another 24 hours in a 5% $CO_2$-incubator at 37° C. After this 24-hours incubation, cells were stained with 0.02% trypan blue (Sigma-Aldrich) to distinguish between live and dead cells. For this, the percentage of viable cells were counted using a Bürker haemocytometer. In addition, and after extensive washing in PBS/BSA/$NaN_3$, expression of phospholipid phosphatidylserine in the membrane of cells, which is known as a marker for apoptosis or cell death, was determined with Alexa Fluor®488-conjugated mouse anti-phosphatidylserine antibody (Merck Millipore) at 10 μg/mL (in PBS/BSA/$NaN_3$) for 30 minutes at 4° C. In parallel, Alexa Fluor®488-conjugated mouse anti-human CD19 antibody (BD Biosciences) was run as a negative control. After extensive washing in PBS/BSA/$NaN_3$, cells were fixed in 2% formaldehyde in PBS/BSA/$NaN_3$ for 30 minutes at 4° C. Membrane phosphatidylserine expression (geo-mean fluorescence intensity) was measured using a flow cytometer (FACSCalibur; BD Biosciences).

As shown in FIG. 5E, purified CD89/IgA blocking mouse anti-human CD89-specific antibodies 9H7 and 26B6 triggered cell death in human CD89 expressing HEK293F cells, which was exemplified by decreased cell viability (measured by trypan blue exclusion assay) and by increased phosphatidylserine expression levels after treatment with both mouse anti-human CD89-specific antibodies. As expected, commercial CD89/IgA blocking mouse anti-human CD89 antibody clone MIP8a also induced cell death in these human CD89 expressing HEK293F cells, and this cell death induction was comparable to that was found with mouse anti-human CD89-specific antibodies 9H7 and 26B6. Surprisingly, purified CD89/IgA blocking mouse anti-human CD89-specific antibodies 8F3, 10E7, 16D6, 20B4, and 30C7 did not induced significant cell death in these human CD89 expressing HEK293F cells, nor did commercial CD89/IgA non-blocking mouse anti-human CD89 antibody clone A59 and clone A3.

These results demonstrated that CD89/IgA blocking mouse anti-human CD89-specific antibodies 9H7 and 26B6 induced cell death in membrane human CD89 expressing cells, whereas CD89/IgA blocking mouse anti-human CD89-specific antibodies 8F3, 10E7, 16D6, 20B4, and 30C7 did not induce cell death in membrane human CD89 expressing cells.

(d). Degree of CD89/IgA Blocking Capacity of Commercial Prototypic Mouse Anti-Human CD89 Antibodies Human CD89 consists of a short cytoplasmic tail, a transmembrane region, and two extracellular (EC) Ig-like domains. By a short interdomain hinge region, these two Ig-like EC domains are folded with an angle of about 90° to each other (Ding et al. J Biol Chem 2003; 278:27966-27970). The binding site of human IgA on human CD89 is in the membrane-distal Ig-like EC1 domain and is not in the membrane-proximal Ig-like EC2 domain (Wines et al. J Immunol 1999; 162: 2146-2153; Morton J Exp Med 1999; 189:1715-1722; Lu et al. Protein Sci 2014; 23: 378-386). Consequently, it is generally accepted that mouse anti-human CD89 antibodies that bind to the EC1 domain of human CD89 can block human IgA binding on human CD89, whereas mouse anti-human CD89 antibodies that bind to the EC2 domain of human CD89 are not able to block human IgA binding on human CD89 (Morton et al. Arch Immunol Ther Exp 2001; 49: 217-229; Bakema et al. Immunol Rev 2011; 4: 612-624). More specifically, prototypic CD89/IgA blocking mouse anti-human CD89 antibody clone MIP8a recognizes an epitope within the EC1 domain of human CD89 (Lu et al. Protein Sci 2014; 23: 378-386), while prototypic CD89/IgA non-blocking mouse anti-human CD89 antibody clone A59 and A3 recognize an epitope within the EC2 domain of human CD89 (Morton J Exp Med 1999; 189:1715-1722) and within the border of EC1-EC2 domains of human CD89 (Morton J Exp Med 1999; 189: 1715-1722), respectively.

Surprisingly, purified well-known CD89/IgA non-blockers (Monteiro et al. J Immunol 1992; 148: 1764-1770) mouse anti-human CD89 antibody clone A59 and clone A3 (when examined at 10 μg/mL) showed partial but significant (~60%) blocking of the binding of both non-aggregated and heat-aggregated serum human IgA binding to membrane human CD89 (see Example 2 (b) above). Therefore, mouse anti-human CD89 antibody clone A59 and clone A3 were investigated in more detail to sterically hinder the interaction of serum human IgA with membrane-bound human CD89 by using FACS analysis.

Stable human full-length CD89-transfected HEK293F cells (clone no. 2; see above Example 1 (b) above) were put at $10\times10^6$ cells/mL in ice-chilled PBS containing 0.1% BSA (Sigma)/0.05% $NaN_3$ (PBS/BSA/$NaN_3$) supplemented with 50 μg/mL human IgGs (blocking possible Fcγ receptors; Sigma) for 10 minutes at 4° C. Then, 10 μL/tube (i.e., $0.1\times10^6$ cells) of these cells were incubated with or without 50 μL titrated (in PBS/BSA/$NaN_3$) purified mouse anti-human CD89 antibody clone A59 (BD Biosciences) and clone A3 (Santa Cruz Biotechnology) for 30 minutes at 4° C. In parallel, 50 μL titrated (in PBS/BSA/$NaN_3$) purified mouse IgG1 isotype control (BD Biosciences) and 50 μL purified (in PBS/BSA/$NaN_3$) mouse anti-human CD89 antibody clone MIP8a (BioRad) were run as negative and positive controls, respectively. After this (i.e., without washing), 50 μL purified non-aggregated or heat-aggregated human (serum-derived) IgA (Bethyl Laboratories) at 20 μg/mL (diluted in PBS/BSA/$NaN_3$) was added to these cells, and incubated for another 30 minutes at 4° C. After extensive washing in PBS/BSA/$NaN_3$, binding of non-aggregated or heat-aggregated serum human IgA on membrane human CD89 was determined with biotin-conjugated F(ab')2 fragment goat anti-human serum IgA α chain-specific antibodies (Jackson ImmunoResearch) at 5 μg/mL for 30 minutes at 4° C. After extensive washing in PBS/BSA/$NaN_3$, 1:200 diluted PE-conjugated streptavidin (Jackson ImmunoResearch) was added, and incubated for 30 minutes at 4° C. After extensive washing in PBS/BSA/$NaN_3$, cells were fixed in 2% formaldehyde in PBS/BSA/$NaN_3$ for 30 minutes at 4° C. Binding (geo-mean fluorescence intensity) of non-aggregated or heat-aggregated serum human IgA on membrane human CD89 was measured using a flow cytometer (FACSCalibur; BD Biosciences).

As shown in FIGS. 6A and 6B, both mouse anti-human CD89-specific antibodies clone 59 and A3 dose-dependently and partially inhibited (i.e., ~60% maximum inhibition) non-aggregated and heat-aggregated serum human IgA binding to membrane human CD89, whereas their corresponding mouse IgG1 isotype control lacks any effect on non-aggregated and heat-aggregated serum human IgA binding to membrane human CD89, demonstrating that the inhibitory effect of mouse anti-human CD89-specific antibodies clone 59 and A3 on the CD89/IgA interaction was specific. For reference purposes, purified mouse anti-human CD89 antibody clone MIP8a, a well-known CD89/IgA blocker (Zhang et al. Clin Exp Immunol 2000; 121: 106-111), was run in parallel, and showed dose dependent and complete prevention of the binding of non-aggregated and heat-aggregated serum human IgA to membrane human CD89.

These results demonstrated that mouse anti-human CD89-specific antibodies clone 59 and A3, prototypic antibodies which recognize epitopes within the EC2 domain of human CD89 (Morton J Exp Med 1999; 189:1715-1722) and within the border of EC1-EC2 domains of human CD89 (Morton J Exp Med 1999; 189:1715-1722), respectively, are able to specifically and partially inhibit the binding of monomeric, dimeric, trimeric, tetrameric or higher-order of multimeric serum human IgA (i.e., non-aggregated and heat-aggregated IgA) to membrane human CD89. Most likely, mouse anti-human CD89-specific antibodies clone 59 and A3 can change the folding of membrane human CD89—after binding to the EC2 domain or EC1-EC2 border—in such a manner that the binding of serum human IgA to human CD89 becomes less 'favourable' or optimal (as opposed to steric hinderance by anti-human CD89 antibodies, which recognize the IgA binding site (i.e., EC1 domain) on human CD89).

Example 3. Biological Characterization of CD89/IgA Blocking Mouse Anti-Human CD89 Monoclonal Antibodies Using Ex Vivo Human CD89 Expressing Primary Human Neutrophilic Granulocytes (a). Binding of CD89/IgA Blocking Mouse Anti-Human CD89 Antibodies on Human CD89 Expressing Primary Human Neutrophilic Granulocytes In order to determine the binding of purified CD89/IgA blocking mouse anti-human CD89 antibodies on human CD89 expressing primary human neutrophilic granulocytes, FACS analysis was used.

Primary human neutrophilic granulocytes were isolated from healthy donor (after informed consent) peripheral blood using Lymphoprep™ (Axis-Shield) gradient centrifugation followed by lysis of erythrocytes in a $NH_4Cl$ lysis buffer solution—For comparison purposes, stable human full-length CD89-transfected HEK293F cells (clone no. 2; see above Example 1 (b) above) and the human CD89 expressing monocytic U937 cell line (a generous gift from Dr. RT Urbanus, Department of Haematology, University Medical Centre Utrecht, NL) were examined in parallel. After washing in PBS, granulocytes were put at $10\times10^6$ cells/mL in ice-chilled PBS containing 0.1% BSA (Sigma-Aldrich; PBS/BSA) supplemented with 50 μg/mL human IgGs (blocking possible Fcγ receptors; Sigma-Aldrich) for 10 minutes at 4° C. Then, 10 Li/tube (i.e., $0.1\times10^6$ cells) of these cells were incubated with 100 μL purified mouse anti-human CD89 antibody at 10 μg/mL (in PBS/BSA) for 30 minutes at 4° C. In parallel, 100 μL purified mouse IgG1 isotype control (Biolegend) at 10 μg/mL (in PBS/BSA) was run as a negative control, and 100 μL purified mouse anti-human CD89 antibody clone MIP8a (BioRad) at 10 μg/mL (in PBS/BSA), clone A59 (BD Biosciences) at 10 μg/mL (in PBS/BSA), and clone A3 (Santa Cruz Biotechnology) at 10 μg/mL (in PBS/BSA) were run as positive controls. After extensive washing in PBS/BSA, cells were subsequently incubated with 1:200 diluted PE-conjugated goat anti-mouse IgG Fey-specific antibodies (Jackson ImmunoResearch) for 30 minutes at 4° C. After extensive washing in PBS/BSA, cells were fixed in 2% formaldehyde in PBS/BSA for 30 minutes at 4° C. Binding (geo-mean fluorescence intensity) of antibodies on membrane human CD89 from ex vivo human neutrophilic granulocytes was measured using a flow cytometer (Cyan; BeckmanCoulter).

As shown in FIG. 7A, all our purified CD89/IgA blocking mouse anti-human CD89-specific antibodies (at 10 μg/mL) bound to membrane human CD89 from ex vivo human neutrophilic granulocytes isolated from multiple donors (n=5). Based on their binding profile on neutrophilic granulocytes, the following ranking was found (from high to lower binding intensity): 9H7=26D6(=MIP8a) >10E7=30C7=20B4(=A59=A3)>8F3=16D6, which was unexpectedly significantly different than the binding ranking found with these purified CD89/IgA blocking mouse anti-human CD89-specific antibodies (at 10 μg/mL) to membrane full-length human CD89 from HEK293F cells (see FIG. 7B), i.e., 8F3=9H7=10E7=26D6=20B4=30C7 (=MIP8a=A59=A3)>16D6. In addition, the binding ranking found with purified CD89/IgA blocking mouse anti-human CD89-specific antibodies (at 10 μg/mL) to membrane human CD89 from monocytic U937 cells (see FIG. 7C), i.e., 9H7=26D6 (=MIP8a)>10E7=30C7(=A59=A3)>8F3=16D6=20B4, seems to be similar (except for 20B4) to the aforementioned binding ranking found with purified CD89/IgA blocking mouse anti-human CD89-specific antibodies (at 10 μg/mL) to membrane human CD89 from ex vivo human neutrophilic granulocytes.

These results demonstrated that CD89/IgA blocking mouse anti-human CD89-specific antibody 8F3, 9H7, 10E7, 16D6, 26D6, 20B4, and 30C7 recognized epitopes on membrane human CD89 from ex vivo human neutrophilic granulocytes, on membrane human full-length CD89 from HEK293F cells and on membrane human CD89 from monocytic U937 cells. However, the binding ranking found with these CD89/IgA blocking mouse anti-human CD89-specific antibodies was significantly different when ex vivo human CD89 expressing human neutrophilic granulocytes (from high to lower binding intensity; 9H7=26D6 (=MIP8a)>10E7=30C7=20B4(=A59=A3)>8F3=16D6) versus human full-length CD89 expressing HEK293F cells (from high to lower binding intensity; 8F3=9H7=10E7=26D6=20B4=30C7(=MIP8a=A59=A3)>16D6) were used as target cells in this comparative study, which suggested possible (lack of) recognition of multiple membrane human CD89 isoforms on these cells. Indeed, primary human neutrophilic granulocytes and monocytes are known to express—apart from the full-length CD89 (also called FcαRIa.1)—two alternative splice variant transcripts of human CD89 (Patry at al. J Immunol 1996; 156: 4442-4448; Pleass et al. Biochem J 1996; 318: 771-777; Togo et al. FEBS Letters 2003; 535:20-209), which lack (1) part of the EC2 domain (Gly195-Thr216; Swiss-Prot no. P24071.2) of human CD89 (called FcαRIa.2 or Δ66EC2) or (2) the entire EC2 domain (Gly121-Thr216; Swiss-Prot no. P24071.3) of human CD89 (called FcαRIa.3 or ΔEC2). Since mouse anti-human CD89-specific antibody 8F3, 9H7, 10E7, 16D6, 26D6, 20B4, and 30C7 at 10 μg/mL bound to HEK293F cells (expressing the full-length human CD89 version only) to a similar degree (except for low affinity antibody 16D6; see also Example 2 (a) above), whereas the binding of mouse anti-human CD89-specific antibody 8F3, 10E7, 16D6, 20B4, and 30C7 at 10 μg/mL (like human IgA non-blockers clone A59 and A3 that recognize an epitope within the EC2 domain of human CD89 (Morton J Exp Med 1999; 189:1715-1722) and within the border of EC1-EC2 domains of human CD89 (Morton J Exp Med 1999; 189:1715-1722), respectively) was significantly lower than the binding of mouse anti-human CD89-specific antibody 9H7 and 26D6 at 10 μg/mL (like human IgA blocker MIP8a that recognizes an epitope within the EC1 domain of human CD89 (Lu et al. Protein Sci 2014; 23: 378-386)) to primary human neutrophilic granulocytes (expressing the full-length human CD89, ΔEC2, and, to a lesser extent, Δ66EC2 versions), suggests that (1) mouse anti-human CD89-specific antibody 8F3, 10E7, 16D6, 20B4, and 30C7 recognize either epitopes within the EC2 domain or the border of EC1-EC2 domains of human CD89 (like human IgA non-blockers clone A59 and A3, which are not able to bind to alternative splice variant FcαRIa.3, because it lacks the EC2 domain) or recognize epitopes within the EC1 domain, which are not accessible in alternative splice variants (i.e., FcαRIa.2 and/or FcαRIa.3) of human CD89 due to 'aberrant' protein folding (as opposed to 'normal' protein folding of full-length human CD89/FcαRIa.1) of these alternative splice variants, and (2) mouse anti-human CD89-specific antibody 9H7 and 26D6 recognize epitopes within the EC1 domain of human CD89 (like human IgA blocker MIP8a). Interestingly, alternative splice variant FcαRIa.3 (or ΔEC2) lacks binding to serum-derived human IgA, although the entire EC1 domain (i.e., the IgA binding site on human CD89) is present on this splice variant, which indicates 'aberrant' protein folding (as opposed to 'normal' protein folding of full-length human CD89/FcαRIa.1) of this alternative splice variant FcαRIa.3. Furthermore, full-length human CD89 are likely to form two different conformations, i.e., an inactive versus an active status of human CD89, due to inside-out signalling (Brandsma et al. Immunol Rev 2015, 268: 74-87). As a result, inactive human CD89 shows low affinity binding for human IgA, whereas active human CD89 shows high affinity binding for human IgA (Bracke et al. Blood 2001; 97: 3478-3483). Thus, the conformational change/status of full-length human CD89 (upon inside-out signalling) could also lead to differential binding of our generated CD89/IgA blocking mouse anti-human CD89-specific antibodies to full-length human CD89 on ex vivo human neutrophilic granulocytes.

In concordance, the binding of mouse anti-human CD89-specific antibody 8F3, 10E7, 16D6, 20B4, and 30C7 at 10 μg/mL (like non-blockers clone A59 and A3 that recognize an epitope within the EC2 domain of human CD89 (Morton J Exp Med 1999; 189:1715-1722) and within the border of EC1-EC2 domains of human CD89 (Morton J Exp Med 1999; 189:1715-1722), respectively) was significantly lower than the binding of mouse anti-human CD89-specific antibody 9H7 and 26D6 at 10 μg/mL (like blocker MIP8a that recognizes an epitope within the EC1 domain of human CD89 (Lu et al. Protein Sci 2014; 23: 378-386)) to monocytic U937 cells, which are also known to express the full-length human CD89, ΔEC2 and A66EC2 versions (Patry at al. J Immunol 1996; 156: 4442-4448; Togo et al. FEBS Letters 2003; 535:20-209).

These results also demonstrated that CD89/IgA blocking mouse anti-human CD89-specific antibody 8F3, 9H7, 10E7, 16D6, 26D6, 20B4, and 30C7 recognized non-polymorphic epitopes on membrane human CD89 from ex vivo human neutrophilic granulocytes, because these antibodies unambiguously bound to human neutrophilic granulocytes isolated from all 5 examined donors.

(b). Blocking Serum Human IgA-Mediated Phagocytosis by Human CD89 Expressing Primary Human Neutrophilic Granulocytes Using CD89/IgA Blocking Mouse Anti-Human CD89 Monoclonal Antibodies In order to analyze the biological activity of purified CD89/IgA blocking mouse anti-human CD89 antibodies, the ability of generated CD89/IgA blocking mouse anti-human CD89 antibodies to inhibit phagocytosis of serum human IgA-coated latex beads by human CD89 expressing primary human neutrophilic granulocytes was determined.

Primary human neutrophilic granulocytes were isolated from healthy donors (after informed consent) peripheral blood using Lymphoprep™ (Axis-Shield) gradient centrifugation followed by lysis of erythrocytes in a $NH_4Cl$ lysis buffer solution. After washing in PBS, granulocytes were resuspended at $2.0\times10^6$ cells/mL in RPMI 1640 (Gibco) supplemented with 10% heat-inactivated FCS (Sigma-Aldrich). Then, 100 μL/well (i.e., $0.2\times10^6$ cells in 96-wells flat-bottom plates; Greiner) of these cells were incubated with titrated (in RPMI/10% FCS) purified mouse anti-human CD89 antibody for 20 minutes at 4° C. In parallel, titrated (in RPMI/10% FCS) purified mouse IgG1 isotype control (Biolegend) was run as a negative control, and titrated (in RPMI/1% FCS) purified mouse anti-human CD89 antibody clone MIP8a (BioRad), clone A59 (BD Biosciences) and clone A3 (Santa Cruz Biotechnology) were run as controls. After this (i.e., without washing), 1.2 μL purified human (serum-derived) IgA (MP Biomedicals)-coated fluorescent latex beads (1 μm-sized and carboxylate-modified polystyrene; Sigma-Aldrich) at a cell-to-bead ratio of 1:60 were added to these cells (preparation IgA-beads, see Aleyd et al. J Immunol 2014; 192: 2374-2383), and incubated for another 30 minutes at 37° C. In parallel, BSA (Sigma-Aldrich)-coated fluorescent latex beads at a cell-to-bead ratio of 1:60 were run as a negative control (preparation BSA-beads, see Aleyd et al. J Immunol 2014; 192: 2374-2383). After washing in RPMI/10% FCS and resuspension in PBS/0.1% BSA (Sigma-Aldrich), serum human IgA-mediated phagocytosis of fluorescent latex beads (geo-mean fluorescence intensity used to calculate phagocytic index according to Aleyd et al. J Immunol 2014; 192: 2374-2383) by membrane human CD89 on ex vivo human neutrophilic granulocytes was measured using a flow cytometer (Cyan; Beckman Coulter).

As shown in FIG. 8, all purified CD89/IgA blocking mouse anti-human CD89-specific antibodies dose-dependently inhibited serum human IgA-mediated phagocytosis in membrane human CD89 expressing ex vivo primary human neutrophilic granulocytes isolated from three healthy individuals, although some donor-to-donor variation was observed. Based on their degree of serum human IgA-mediated phagocytosis inhibition, the following ranking was found (from a strong to a lower IgA-mediated phagocytosis inhibitory degree): 8F3=9H7=10E7=26D6=30C7(=MIP8a)>20B4>16D16. For reference purposes, purified mouse anti-human CD89 antibody clone MIP8a, a well-known CD89/IgA blocker (Zhang et al. Clin Exp Immunol 2000; 121: 106-111), was run in parallel, and also showed dose dependent inhibition of serum human IgA-mediated phagocytosis in membrane human CD89 expressing ex vivo primary human neutrophilic granulocytes isolated from three healthy individuals, although some donor-to-donor variation was observed. In contrast, purified mouse anti-human CD89 antibody clone A59 and clone A3—both well-known CD89/IgA non-blockers (Monteiro et al. J Immunol 1992; 148: 1764-1770)—showed no, hardly any, or weak inhibition of serum human IgA-mediated phagocytosis in membrane human CD89 expressing ex vivo primary human neutrophilic granulocytes isolated from three healthy individuals.

These results demonstrated that CD89/IgA blocking mouse anti-human CD89-specific antibody 8F3, 9H7, 10E7, 16D6, 26D6, 20B4, and 30C7 inhibited serum human IgA-mediated phagocytotic activity of membrane human CD89 expressing ex vivo primary human neutrophilic granulocytes. For summary, see Table 2.

TABLE 2

Blocking effect of purified CD89/IgA blocking mouse anti-human CD89-specific antibodies on phagocytosis of serum human IgA-coated latex beads by human CD89 expressing ex vivo primary human neutrophilic granulocytes.
Blocking phagocytosis of IgA-coated latex beads by mouse anti-human CD89 antibodies

| Anti-CD89 Ab | Donor 1 | Donor 2 | Donor 3 |
|---|---|---|---|
| 8F3 | +++ | +++ | ++ |
| 9H7 | +++ | +++ | ++ |
| 10E7 | +++ | +++ | ++ |
| 16D6 | −/+ | +/++ | ++ |
| 26D6 | +++ | +++ | ++ |
| 20B4 | +++ | +++ | + |
| 30C7 | +++ | +++ | ++ |
| mIgG1 control | − | − | − |
| MIP8a | +++ | +++ | ++ |
| A59 | −/+ | −/+ | + |
| A3 | − | −/+ | + |

− = no blocking of IgA-coated latex bead phagocytosis via membrane human CD89 by mouse anti-CD89 antibodies,
+ = weak blocking of IgA-coated latex bead phagocytosis via membrane human CD89 by mouse anti-CD89 antibodies,
++ = intermediate blocking of IgA-coated latex bead phagocytosis via membrane human CD89 by mouse anti-CD89 antibodies,
+++ = strong blocking of IgA-coated latex bead phagocytosis via membrane human CD89 by mouse anti-CD89 antibodies.

(c). Blocking Serum Human IgA-Mediated Migration of, Serum Human IgA-Mediated Chemotaxis of, and Serum Human IgA-Mediated Leukotriene B4 Production from Human CD89 Expressing Primary Human Neutrophilic Granulocytes Using CD89/IgA Blocking Mouse Anti-Human CD89 Monoclonal Antibodies In order to analyze the biological activity of purified CD89/IgA blocking mouse anti-human CD89 antibodies, the ability of generated CD89/IgA blocking mouse anti-human CD89 antibodies to inhibit (1) serum human IgA-mediated migration of, (2) serum human IgA-mediated chemotaxis of, and (3) serum human IgA-mediated neutrophil-chemoattractant leukotriene B4 (LTB4) production from human CD89 expressing primary human neutrophilic granulocytes were determined.

Two-dimensional (2-D) migration assay: primary human neutrophilic granulocytes were isolated from healthy donors (after informed consent) peripheral blood using Lymphoprep™ (Axis-Shield) gradient centrifugation followed by lysis of erythrocytes in a $NH_4Cl$ lysis buffer solution. Then, these primary human neutrophilic granulocytes were labeled with 1 μM fluorescent calcein-AM (Molecular Probes) for 30 minutes at 37° C. After washing, these calcein AM-labeled granulocytes were resuspended at $2.5\times10^6$ cells/mL in RPMI 1640 (Gibco) supplemented with 10% heat-inactivated FCS (Sigma-Aldrich), and subsequently 100 μL calcein AM-labeled granulocytes (i.e., $0.25\times10^6$ cells/well in 96-wells flat-bottom plates; Greiner) were incubated with 20 μg/mL (in RPMI/10% FCS) purified mouse anti-human CD89 antibody for 20 minutes at 4° C. In parallel, 20 μg/mL (in RPMI/10% FCS) purified mouse IgG1 isotype control (Biolegend) was run as a negative control, and 20 μg/mL (in RPMI/10% FCS) purified mouse anti-human CD89 antibody clone MIP8a (BioRad), clone A59 (BD Biosciences) and clone A3 (Santa Cruz Biotechnology) were run as controls. After this, 150 μL RPMI/10% FCS per well was added, and cells were left for 10 minutes to become monolayers again. After this (i.e., without washing), 10 μL purified human (serum-derived) IgA (MP Biomedicals)-coated Sepharose 4B beads (90 μm-sized and cyanogen bromide-activated; GE Healthcare) were gently added to these monolayers of cells (preparation 3 μg/mL IgA-beads, see Van der Steen et al. Gastroentorol 2009; 137: 2018-2029), and incubated for another 40 minutes at 37° C. In parallel, BSA (Sigma-Aldrich)-coated Sepharose 4B beads were run as a negative control (preparation 3 μg/mL BSA-beads, see Van der Steen et al. Gastroentorol 2009; 137: 2018-2029). Then, supernatants were collected and used for the chemotaxis assay and LBT4 ELISA (see below), and Sepharose beads were washed to remove non-bound/non-migrated calcein AM-labeled granulocytes. Subsequently, granulocytes were lysed in a 0.2% (w/v) hexadecyltrimethylammonium bromide (Sigma-Aldrich) buffer for 30 minutes at RT, and released calcein AM (reflecting the number of IgA-bound/migrated granulocytes) was measured in 96-wells flat-bottom plates (Greiner) using a fluorometer (FLUOstar/POLARstar; BMG Labtech). The number of IgA-bound/migrated ex vivo human neutrophilic granulocytes was quantified by using a standard curve with known numbers of lysed calcein AM-labeled granulocytes (i.e., 0-$0.3\times10^6$ cells/well).

Chemotaxis assay: primary human neutrophilic granulocytes were isolated from healthy donors (after informed consent) peripheral blood using Lymphoprep™ (Axis-Shield) gradient centrifugation followed by lysis of erythrocytes in a $NH_4Cl$ lysis buffer solution. Then, these primary human neutrophilic granulocytes were labeled with 1 M fluorescent calcein-AM (Molecular Probes) for 30 minutes at 37° C. After washing, these calcein AM-labeled granulocytes were resuspended at $1.0\times10^6$ cells/mL in RPMI 1640 (Gibco) supplemented with 10% heat-inactivated FCS (Sigma-Aldrich). To measure chemotaxis, wells of the lower compartment of the Boyden chamber (Neuro Probe) were filled with 29 μL of supernatants from IgA-coated Sepharose bead-stimulated primary human neutrophilic granulocytes (i.e., from another healthy donor, see above). In parallel, RPMI/10% FCS medium only and purified 1 or 10 nM LTB4 (in RPMI; Sigma-Aldrich) were run as negative and positive controls, respectively. Subsequently, the lower compartment was covered with a 3 m pore-sized polyvinylpyrrolidone-coated polycarbonate filter (Neuro Probe), followed by assembly of the upper compartment onto the lower compartment of the Boyden chamber. After this, 50 μL calcein AM-labeled granulocytes (i.e., $0.05\times10^6$ cells/well) was added in wells of the upper compartment. After incubation for 40 minutes at 37° C., chemotaxis of ex vivo human neutrophilic granulocytes from the upper compartment towards wells of the lower compartment was determined. For this, granulocytes in the lower compartment were lysed in a 0.1% (w/v) hexadecyltrimethylammonium bromide (Sigma-Aldrich) buffer for 30 minutes at RT, and released calcein AM (reflecting the number of chemotactic granulocytes) was measured in 96-wells flat-bottom plates (Greiner) using a fluorometer (FLUOstar/POLARstar; BMG Labtech). The number of IgA-coated Sepharose bead-induced chemotactic ex vivo human neutrophilic granulocytes was quantified by using a standard curve with known numbers of lysed calcein AM-labeled granulocytes (i.e., 0-$0.05\times10^6$ cells/well).

LTB4 ELISA: LTB4 levels were measured in supernatants from IgA-coated Sepharose bead-stimulated ex vivo human neutrophilic granulocytes (see above). To this end, a commercially available LTB4 competitive ELISA kit (R&D Systems) was used according to manufacturer's instructions.

As shown in FIGS. 9A-C, all our purified CD89/IgA blocking mouse anti-human CD89-specific antibodies at 20 μg/mL inhibited of serum human IgA-coated Sepharose beads-mediated migration of membrane human CD89 expressing ex vivo primary human neutrophilic granulocytes isolated from three healthy individuals, although some donor-to-donor variation was observed. For reference purposes, purified mouse anti-human CD89 antibody clone MIP8a, a well-known CD89/IgA blocker (Zhang et al. Clin Exp Immunol 2000; 121: 106-111), was run in parallel, and also showed inhibition of serum human IgA-coated Sepharose beads-mediated migration of membrane human CD89 expressing ex vivo primary human neutrophilic granulocytes isolated from three healthy individuals, although some donor-to-donor variation was observed. In contrast, purified mouse anti-human CD89 antibody clone A59 and clone A3—both well-known CD89/IgA non-blockers (Monteiro et al. J Immunol 1992; 148: 1764-1770)—showed highly variable (i.e., no, weak, or intermediate) inhibition serum human IgA-coated Sepharose beads-mediated migration of membrane human CD89 expressing ex vivo primary human neutrophilic granulocytes.

As shown in FIGS. 9D-F, all our purified CD89/IgA blocking mouse anti-human CD89-specific antibodies at 20 μg/mL inhibited of serum human IgA-coated Sepharose beads-mediated chemotaxis of membrane human CD89 expressing ex vivo primary human neutrophilic granulocytes isolated from three healthy individuals, although some donor-to-donor variation was observed. For reference purposes, purified mouse anti-human CD89 antibody clone MIP8a, a well-known CD89/IgA blocker (Zhang et al. Clin Exp Immunol 2000; 121: 106-111), was run in parallel, and also showed inhibition of serum human IgA-coated Sepharose beads-mediated chemotaxis of membrane human CD89 expressing ex vivo primary human neutrophilic granulocytes isolated from three healthy individuals, although some donor-to-donor variation was observed. In contrast, purified mouse anti-human CD89 antibody clone A59 and clone A3—both well-known CD89/IgA non-blockers (Monteiro et al. J Immunol 1992; 148: 1764-1770)—showed highly variable (i.e., no, intermediate, or strong) inhibition serum human IgA-coated Sepharose beads-mediated chemotaxis of membrane human CD89 expressing ex vivo primary human neutrophilic granulocytes.

As shown in FIGS. 9G-I, all our purified CD89/IgA blocking mouse anti-human CD89-specific antibodies at 20 μg/mL inhibited of serum human IgA-coated Sepharose beads-mediated chemoattractive LTB4 production by membrane human CD89 expressing ex vivo primary human neutrophilic granulocytes isolated from three healthy individuals, although some donor-to-donor variation was observed. For reference purposes, purified mouse anti-human CD89 antibody clone MIP8a, a well-known CD89/IgA blocker (Zhang et al. Clin Exp Immunol 2000; 121: 106-111), was run in parallel, and also showed inhibition of serum human IgA-coated Sepharose beads-mediated chemoattractive LTB4 production by membrane human CD89 expressing ex vivo primary human neutrophilic granulocytes isolated from three healthy individuals, although some donor-to-donor variation was observed. Surprisingly, purified mouse anti-human CD89 antibody clone A59 and clone A3—both well-known CD89/IgA non-blockers (Monteiro et al. J Immunol 1992; 148: 1764-1770)—also showed inhibition of serum human IgA-coated Sepharose beads-mediated chemoattractive LTB4 production by membrane human CD89 expressing ex vivo primary human neutrophilic granulocytes.

These results demonstrated that CD89/IgA blocking mouse anti-human CD89-specific antibody 8F3, 9H7, 10E7, 16D6, 26D6, 20B4, and 30C7 inhibited serum human IgA-mediated migration of, chemotaxis of, and chemoattractive LTB4 release from membrane human CD89 expressing ex vivo primary human neutrophilic granulocytes. For summary, see Tables 3 and 4.

TABLE 3

Blocking effect of purified CD89/IgA blocking mouse anti-human CD89-specific antibodies on serum human IgA-coated Sepharose beads-induced 2-D migration of human CD89 expressing ex vivo primary human neutrophilic granulocytes.
Blocking of IgA-coated Sepharose beads-induced 2-D migration by mouse anti-human CD89 antibodies

| Anti-CD89 Ab | Donor 1 | Donor 2 | Donor 3 |
|---|---|---|---|
| 8F3 | +++ | ++ | ++/+++ |
| 9H7 | +++ | ++ | +++ |
| 10E7 | +++ | ++/+++ | +++ |
| 16D6 | +++ | ++ | ++/+++ |
| 26D6 | +++ | +++ | +++ |
| 20B4 | +++ | +++ | +++ |
| 30C7 | +++ | +++ | ++/+++ |
| mIgG1 control | − | − | − |
| MIP8a | +++ | +++ | +++ |
| A59 | − | + | ++ |
| A3 | − | ND | ++ |

− = no blocking of IgA-coated Sepharose beads-induced 2-D migration via membrane human CD89 by mouse anti-CD89 antibodies,
+ = weak blocking of IgA-coated Sepharose beads-induced 2-D migration via membrane human CD89 by mouse anti-CD89 antibodies,
++ = intermediate blocking of IgA-coated Sepharose beads-induced 2-D migration via membrane human CD89 by mouse anti-CD89 antibodies,
+++ = strong blocking of IgA-coated Sepharose beads-induced 2-D migration via membrane human CD89 by mouse anti-CD89 antibodies.
ND = not determined.

TABLE 4

Blocking effect of purified CD89/IgA blocking mouse anti-human CD89-specific antibodies on serum human IgA-coated Sepharose beads-induced (1) chemotaxis of, and (2) LTB4 production by human CD89 expressing ex vivo primary human neutrophilic granulocytes.
Blocking of IgA-coated Sepharose beads-induced chemotaxis and LTB4 production by mouse anti-human CD89 antibodies

| | Donor 1 | | Donor 2 | | Donor 3 | |
|---|---|---|---|---|---|---|
| Anti-CD89 Ab | Chemotaxis | LTB4 | Chemotaxis | LTB4 | Chemotaxis | LTB4 |
| 8F3 | ++/+++ | ++/+++ | ++ | ++ | +++ | ++/+++ |
| 9H7 | +++ | +++ | +++ | +++ | +++ | +++ |
| 10E7 | ++/+++ | ++/+++ | ++/+++ | +++ | +++ | +++ |
| 16D6 | ++/+++ | ++/+++ | ++ | + | +++ | ++/+++ |
| 26D6 | ++ | ++/+++ | − | +++ | +++ | +++ |
| 20B4 | ++/+++ | ++/+++ | ++ | ++ | +++ | +++ |
| 30C7 | ++/+++ | ++/+++ | ++/+++ | ++/+++ | +++ | ++/+++ |

TABLE 4-continued

Blocking effect of purified CD89/IgA blocking mouse anti-human CD89-specific antibodies on serum human IgA-coated Sepharose beads-induced (1) chemotaxis of, and (2) LTB4 production by human CD89 expressing ex vivo primary human neutrophilic granulocytes. Blocking of IgA-coated Sepharose beads-induced chemotaxis and LTB4 production by mouse anti-human CD89 antibodies

| | Donor 1 | | Donor 2 | | Donor 3 | |
|---|---|---|---|---|---|---|
| Anti-CD89 Ab | Chemotaxis | LTB4 | Chemotaxis | LTB4 | Chemotaxis | LTB4 |
| mIgG1 control | – | – | – | – | – | – |
| MIP8a | ++/++ | ++/+++ | ++/+++ | +++ | ++ | +++ |
| A59 | – | ++/+++ | ++ | ++ | +++ | +++ |
| A3 | – | ++ | ND | ND | +++ | +++ |

– = no blocking of IgA-coated Sepharose beads-induced chemotaxis and LTB4 production via membrane human CD89 by mouse anti-CD89 antibodies,
+ = weak blocking of IgA-coated Sepharose beads-induced chemotaxis and LTB4 production via membrane human CD89 by mouse anti-CD89 antibodies,
++ = intermediate blocking of IgA-coated Sepharose beads-induced chemotaxis and LTB4 production via membrane human CD89 by mouse anti-CD89 antibodies,
+++ = strong blocking of IgA-coated Sepharose beads-induced chemotaxis and LTB4 production via membrane human CD89 by mouse anti-CD89 antibodies.
ND = not determined.

(d). Blocking Serum Human IgA Binding on and Serum Human IgA-Mediated Lactoferrin Production from Human CD89 Expressing Primary Human Neutrophilic Granulocytes Using CD89/IgA Blocking Mouse Anti-Human CD89 Monoclonal Antibodies In order to analyze the biological activity of purified CD89/IgA blocking mouse anti-human CD89 antibodies, the ability of generated CD89/IgA blocking mouse anti-human CD89 antibodies to (1) sterically hinder the interaction of serum human IgA with, and (2) inhibit serum human IgA-mediated lactoferrin production from human CD89 expressing primary human neutrophilic granulocytes were determined.

Primary human neutrophilic granulocytes were isolated from healthy donors (after informed consent) peripheral blood using Lymphoprep™ (Axis-Shield) gradient centrifugation followed by lysis of erythrocytes in a $NH_4Cl$ lysis buffer solution. Then, these primary human neutrophilic granulocytes were labeled with 1 M fluorescent calcein-AM (Molecular Probes) for 30 minutes at 37° C. After washing, these calcein AM-labeled granulocytes were resuspended at $2.0\times10^6$ cells/mL in RPMI 1640 (Gibco) supplemented with 10% heat-inactivated FCS (Sigma-Aldrich), and subsequently 100 μL calcein AM-labeled granulocytes (i.e., $0.2\times10^6$ cells/well) were incubated with titrated (in RPMI/10% FCS) purified mouse anti-human CD89 antibody for 20 minutes at 4° C. In parallel, titrated (in RPMI/10% FCS) purified mouse IgG1 isotype control (Biolegend) was run as a negative control, and titrated (in RPMI/10% FCS) purified mouse anti-human CD89 antibody clone MIP8a (BioRad), clone A59 (BD Biosciences) and clone A3 (Santa Cruz Biotechnology) were run as controls. After this (i.e., without washing), 100 μL these cells (i.e., $0.2\times10^6$ cells/well) were added to 96-wells flat-bottom ELISA plates (Nunc-Immuno MaxiSorp), which were previously coated with either 100 μL/well purified human (serum-derived) IgA (MP Biomedicals) at 10 μg/mL or with 100 μL/well BSA (used as a negative control; Sigma-Aldrich) at 10 μg/mL. After incubation for 30 minutes at 37° C., supernatants (180 μL/well) were harvested to remove non-bound granulocytes, and these supernatants were used (after several centrifugal clearance steps) to measure lactoferrin production levels (used as a degranulation marker; see below). After washing the plates, granulocytes were lysed in a 0.2% (w/v) hexadecyltrimethylammonium bromide (Sigma-Aldrich) buffer for 30 minutes at RT, and released calcein AM (reflecting the number of IgA-bound granulocytes) was measured in 96-wells flat-bottom plates (Greiner) using a fluorometer (FLUOstar/POLARstar; BMG Labtech). The number of IgA-bound ex vivo human neutrophilic granulocytes was quantified by using a standard curve with known numbers of lysed calcein AM-labeled granulocytes (i.e., 0-$0.3\times10^6$ cells/well).

Lactoferrin production was measured in the supernatants of primary human neutrophilic granulocytes (representing the degree of degranulation), which were stimulated with plate-bound serum human IgA (see above). For this, 96-wells flat-bottom ELISA plates (Nunc-Immuno MaxiSorp) were coated with 100 μL/well rabbit anti-human lactoferrin antibodies (1:5000; Sigma-Aldrich) during 16-24 hours at 4-8° C. After extensive washing in PBS/0.05% Tween 20, plates were blocked with 200 μL/well PBS/0.05% Tween 20/0.5% BSA (Sigma-Aldrich) for 1 hour at RT. Plates were then incubated with 100 μL/well supernatant at a 1;2 dilution (in block buffer) for 1 hour at 37° C. After extensive washing in PBS/0.05% Tween 20, plates were incubated with alkaline phosphatase-labeled rabbit anti-human lactoferrin detection antibodies (1:2500; MP Biomedicals) for 1 hour at 37° C. After adding P-nitrophenyl phosphate (Sigma-Aldrich), optical density was measured at wavelength of 405 nm with a microplate reader (iMArk; Bio-Rad). Purified human lactoferrin (Sigma-Aldrich) was used as a standard to calculate the amount of lactoferrin released by serum human IgA-stimulated ex vivo human neutrophilic granulocytes.

As shown in FIGS. 10A-C, all our purified CD89/IgA blocking mouse anti-human CD89-specific antibodies (except for 16D6) dose-dependently inhibited the binding of human CD89 expressing ex vivo primary human neutrophilic granulocytes isolated from three healthy individuals to serum human IgA, although some donor-to-donor variation was observed. Based on their degree of inhibition, the following ranking was found (from a strong to a lower inhibitory degree): 9H7=10E7=26D6=30C7(=MIP8a)>8F3>20B4. For reference purposes, purified mouse anti-human CD89 antibody clone MIP8a, a well-known CD89/IgA blocker (Zhang et al. Clin Exp Immunol 2000; 121: 106-111), was run in parallel, and also showed dose dependent inhibition on the binding of human CD89 expressing ex vivo primary human neutrophilic granulocytes isolated from three healthy individuals to serum human IgA, although some donor-to-donor variation was observed. In contrast, purified mouse anti-human CD89 antibody clone A59 and clone A3—both well-known CD89/IgA non-blockers (Monteiro et al. J Immunol 1992; 148: 1764-1770)—showed no inhibition on the binding of human CD89 expressing ex vivo primary human neutrophilic granulocytes isolated from three healthy individuals to serum human IgA.

As shown in FIGS. 10D-F, all our purified CD89/IgA blocking mouse anti-human CD89-specific antibodies (except for 16D6) dose-dependently inhibited serum human IgA-mediated lactoferrin production by human CD89 expressing ex vivo primary human neutrophilic granulocytes isolated from three healthy individuals, although some donor-to-donor variation was observed. Based on their degree of inhibition, the following ranking was found (from a strong to a lower inhibitory degree): 9H7=10E7=26D6=30C7(=MIP8a)>8F3>20B4. Interestingly, the degree of these examined purified mouse anti-human CD89 antibodies to inhibit serum human IgA-mediated lactoferrin production by human neutrophilic granulocytes mirrored their respective degree of inhibition on the binding of human CD89 expressing human neutrophilic granulocytes to serum human IgA (compare FIGS. 10D-F with FIGS. 10A-C). For reference purposes, purified mouse anti-human CD89 antibody clone MIP8a, a well-known CD89/IgA blocker (Zhang et al. Clin Exp Immunol 2000; 121: 106-111), was run in parallel, and also showed dose dependent inhibition of IgA-mediated lactoferrin production by human CD89 expressing ex vivo primary human neutrophilic granulocytes isolated from three healthy individuals, although some donor-to-donor variation was observed. In contrast, purified mouse anti-human CD89 antibody clone A59 and clone A3—both well-known CD89/IgA non-blockers (Monteiro et al. J Immunol 1992; 148: 1764-1770)—showed no inhibition of IgA-mediated lactoferrin production by human CD89 expressing ex vivo primary human neutrophilic granulocytes isolated from three healthy individuals.

These results demonstrated that CD89/IgA blocking mouse anti-human CD89-specific antibody 8F3, 9H7, 10E7, 26D6, 20B4, and 30C7 inhibited the binding of human CD89 expressing ex vivo primary human neutrophilic granulocytes to serum human IgA, and on their corresponding IgA-mediated lactoferrin production (a degranulation marker). For summary, see Table 5.

TABLE 5

Blocking effect of purified CD89/IgA blocking mouse anti-human CD89-specific antibodies on (1) binding of human CD89 expressing ex vivo neutrophilic granulocytes to IgA-coated plates, and on (2) their primary human corresponding IgA-mediated lactoferrin production. Blocking IgA binding and corresponding IgA-mediated lactoferrin production by mouse anti-human CD89 antibodies

| | Donor 1 | | Donor 2 | | Donor 3 | |
|---|---|---|---|---|---|---|
| Anti-CD89 Ab | IgA binding | Lacto-ferrin | IgA binding | Lacto-ferrin | IgA binding | Lacto-ferrin |
| 8F3 | + | ++ | +++ | +++ | ++ | +++ |
| 9H7 | +++ | +++ | +++ | +++ | +++ | ++ |
| 10E7 | ++ | ++ | +++ | +++ | +++ | +++ |
| 16D6 | – | – | – | – | + | – |
| 26D6 | +++ | +++ | +++ | +++ | +++ | ++ |
| 20B4 | + | + | +++ | +++ | + | + |
| 30C7 | ++ | +++ | +++ | +++ | +++ | +++ |
| mIgG1 control | – | – | – | – | – | – |
| MIP8a | +++ | +++ | +++ | +++ | +++ | ++ |
| A59 | – | – | – | – | – | – |
| A3 | – | – | – | – | – | – |

– = no blocking of binding of human CD89 expressing granulocytes to IgA-coated plates and on their corresponding IgA-mediated lactoferrin production by mouse anti-CD89 antibodies,
+ = weak blocking of binding of human CD89 expressing granulocytes to IgA-coated plates and on their corresponding IgA-mediated lactoferrin production by mouse anti-CD89 antibodies,
++ = intermediate blocking of binding of human CD89 expressing granulocytes to IgA-coated plates and on their corresponding IgA-mediated lactoferrin production by mouse anti-CD89 antibodies,
+++ = strong blocking of binding of human CD89 expressing granulocytes to IgA-coated plates and on their corresponding IgA-mediated lactoferrin production by mouse anti-CD89 antibodies.

(e). Blocking Serum Human IgA-Mediated Neutrophil Extracellular Traps (NETs) Release from Human CD89 Expressing Primary Human Neutrophilic Granulocytes Using CD89/IgA Blocking Mouse Anti-Human CD89 Monoclonal Antibodies In order to analyze the biological activity of purified CD89/IgA blocking mouse anti-human CD89 antibodies, the ability of generated CD89/IgA blocking mouse anti-human CD89 antibodies to inhibit serum human IgA-mediated NETs release from human CD89 expressing primary human neutrophilic granulocytes was determined.

Primary human neutrophilic granulocytes were isolated from multiple healthy donors (after informed consent) peripheral blood using Lymphoprep™ (Axis-Shield) gradient centrifugation followed by lysis of erythrocytes in a $NH_4Cl$ lysis buffer solution. After washing in PBS, granulocytes were resuspended at $0.5\times10^6$ cells/mL in RPMI 1640 (Gibco) supplemented with 10% heat-inactivated FCS (Sigma-Aldrich). Then, $1.0\times10^5$ cells/200 μL/well (in 96-wells U-bottom plates (Greiner)) were incubated with 20 μg/mL purified mouse anti-human CD89 antibody for 20 minutes at 4° C. In parallel, purified mouse IgG1 isotype control (Biolegend) was run as a negative control. After this (i.e., without washing), 3.0 μL purified human (serum-derived) IgA (MP Biomedicals)-coated non-fluorescent latex beads (0.9 μm-sized and carboxylate-modified polystyrene; Sigma-Aldrich) at a cell-to-bead ratio of 1:300 were added to these cells (preparation IgA-beads, see Aleyd et al. J Immunol 2014; 192: 2374-2383), and incubated for another 30 minutes at 37° C. In parallel, BSA (Sigma-Aldrich)-coated non-fluorescent latex beads at a cell-to-bead ratio of 1:300 were run as a negative control (preparation BSA-beads, see Aleyd et al. J Immunol 2014; 192: 2374-2383). After this, cells were washed twice with in RPMI 1640 (Gibco) supplemented with 10% heat-inactivated FCS (Sigma-Aldrich), and subsequently these cells were transferred to 96-wells flat-bottom black plates (FLUOTRAC™ 200; Greiner) at $1.0\times10^5$ cells/200 μL/well and incubated for another 3 hours at 37° C. When indicated, 100 μg/mL DNAse I was added. Then, release of extracellular DNA was examined by adding 2.5 μg/mL SYTOX® Green (Invitrogen). Fluorescence intensity was measured using a fluorometer (FLUOstar/POLARstar; BMG Labtech).

Figure 23:
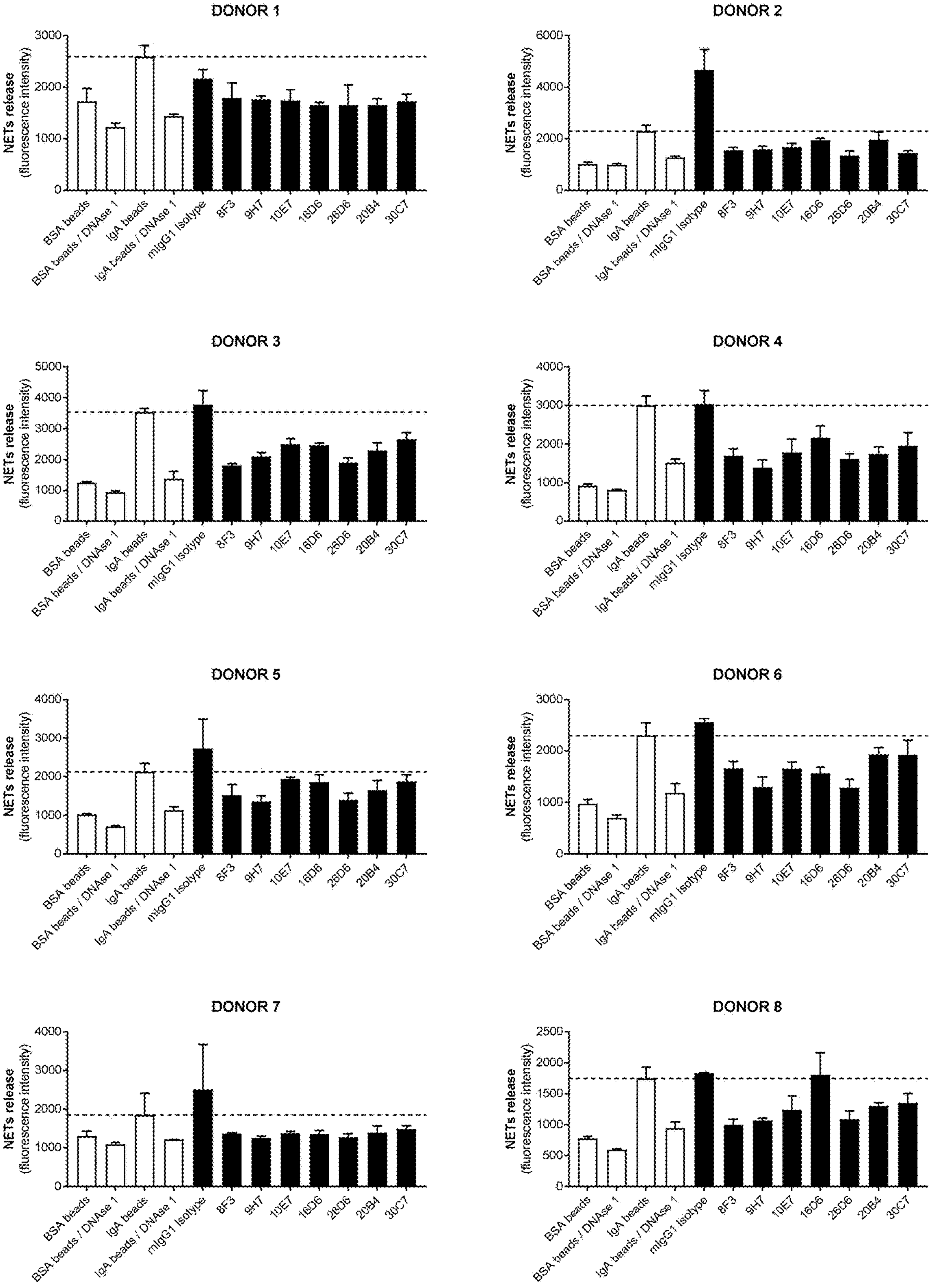
FIG. 23: Effect of purified CD89/IgA blocking mouse anti-human CD89 antibodies on serum human IgA-coated latex beads-induced NETs release by human CD89 expressing ex vivo primary human neutrophilic granulocytes. Dashed line represents NETs release induced by IgA-coated beads only (i.e., without addition of antibodies). Mean±SD (n=3) are shown from 8 different healthy donors (1-8).

As shown in FIG. 23, all our purified CD89/IgA blocking mouse anti-human CD89-specific antibodies inhibited serum human IgA-mediated NETs release from human CD89 expressing ex vivo primary human neutrophilic granulocytes isolated from eight healthy individuals, although some donor-to-donor variation was observed.

These results demonstrated that CD89/IgA blocking mouse anti-human CD89-specific antibody 8F3, 9H7, 10E7, 16D6, 26D6, 20B4, and 30C7 inhibited serum human IgA-mediated NETs release from human CD89 expressing ex vivo primary human neutrophilic granulocytes.

(f). Induction of Cell Death in Human CD89 Expressing Primary Human Neutrophilic Granulocytes Using CD89/IgA Blocking Mouse Anti-Human CD89 Monoclonal Antibodies CD89/IgA blocking mouse anti-human CD89 antibody clone MIP8a has been described to induce human cell death in CD89 expressing human neutrophilic granulocytes (Wehrli et al. J Immunol 2014, 193: 5649-5659). Depending on the inflammatory microenvironment, caspase-dependent (typically observed during apoptosis) or caspase-independent (non-apoptotic) cell death was induced in these human neutrophilic granulocytes by exposure to bivalent mouse anti-human CD89 antibody clone MIP8a. Therefore, the effect of our generated CD89/IgA blocking mouse anti-human CD89 antibodies 8F3, 9H7, 10E7, 16D6, 26D6, 20B4, and 30C7 on human CD89-mediated cell death was examined using non-primed (to mimic a non-inflammatory condition) and LPS-primed (to mimic an inflammatory condition) human CD89 expressing primary human neutrophilic granulocytes as target cells.

Primary human neutrophilic granulocytes were isolated from multiple healthy donors (after informed consent) peripheral blood using Lymphoprep™ (Axis-Shield) gradient centrifugation followed by lysis of erythrocytes in a $NH_4Cl$ lysis buffer solution. After washing in PBS, granulocytes were resuspended at $2.0\times10^6$ cells/mL in RPMI 1640 (Gibco) supplemented with 10% heat-inactivated FCS (Sigma-Aldrich). Then, these cells were non-primed or LPS-primed (100 ng/mL Ultrapure LPS from *E. coli* 0111: B4; Invivogen) for 5 minutes at 37° C. After washing, these granulocytes were resuspended at $2.0\times10^6$ cells/mL in RPMI 1640 (Gibco) supplemented with 10% heat-inactivated FCS (Sigma-Aldrich), and subsequently 250 μL granulocytes (i.e., $0.5\times10^6$ cells/well in 96-wells flat-bottom plates; Falcon) were incubated with 10 μg/mL purified mouse anti-human CD89 antibody in combination with 10 μg/mL cross-linking goat anti-mouse IgG-specific antibodies (Southern Biotech) for 5 hours at 37° C. In parallel, purified mouse IgG1 isotype control (Biolegend) and purified mouse anti-human CD89 antibody clone MIP8a (BioRad) were run as negative and positive controls, respectively. After extensive washing in ice-chilled PBS containing 0.1% BSA (Sigma-Aldrich; PBS/BSA), granulocytes were stained with 3 μM red-fluorescent DNA counterstain propidium iodide for 30-60 minutes at 4° C. After extensive washing in PBS/BSA, cells were fixed in 2% formaldehyde in PBS/BSA for 30 minutes at 4° C. Percentage cell death (based on propidium iodide staining) in ex vivo human neutrophilic granulocytes was determined using a flow cytometer (FACSCalibur or Fortessa; BD Biosciences).

Figure 24:
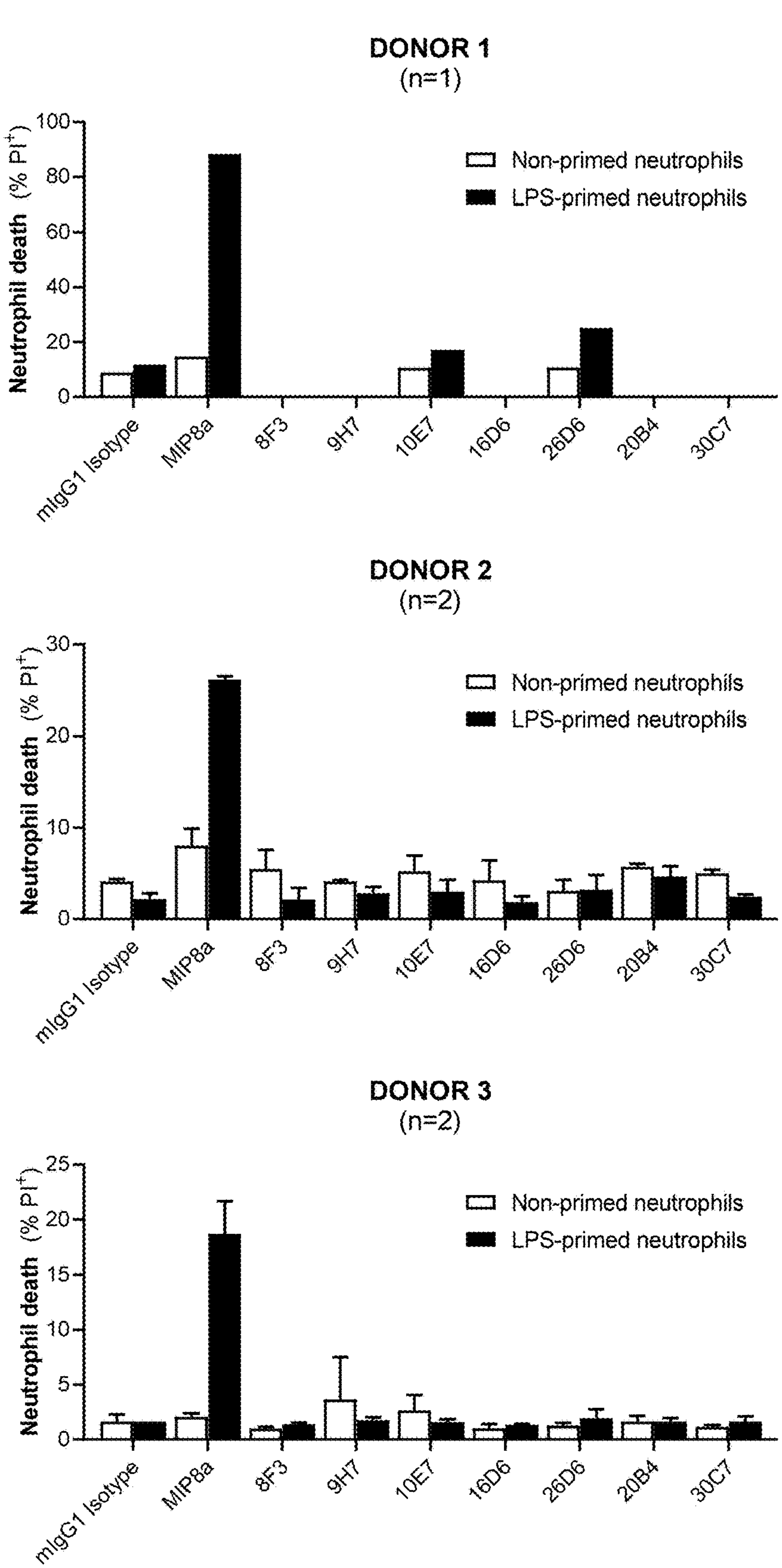
FIG. 24: Effect of purified CD89/IgA blocking mouse anti-human CD89 antibodies on induction of cell death (percentage propidium iodide (PI)) in non-primed and LPS-primed membrane-bound human CD89 expressing ex vivo primary human neutrophilic granulocytes. Mean±SD (n=1 or 2) are shown from 3 healthy donors (1, 2, and 3).

As shown in FIG. 24, all our purified CD89/IgA blocking mouse anti-human CD89-specific antibodies and commercial CD89/IgA blocking mouse anti-human CD89 antibody clone MIP8a did not trigger cell death in non-primed human CD89 expressing ex vivo primary human neutrophilic granulocytes isolated from three healthy individuals. In contrast, commercial CD89/IgA blocking mouse anti-human CD89 antibody clone MIP8a induced significant cell death in LPS-primed human CD89 expressing ex vivo primary human neutrophilic granulocytes, although some donor-to-donor variation was observed, whereas all our purified CD89/IgA blocking mouse anti-human CD89-specific antibodies did not trigger cell death in these LPS-primed human CD89 expressing ex vivo primary human neutrophilic granulocytes.

These results demonstrated that CD89/IgA blocking mouse anti-human CD89-specific antibodies 8F3, 9H7, 10E7, 16D6, 26D6, 20B4, and 30C7 did not induce cell death in human CD89 expressing ex vivo primary human neutrophilic granulocytes under non-inflammatory (i.e., after non-priming) and inflammatory (i.e., after LPS priming) conditions.

(g). Blocking Experimentally Induced Human IgA-Mediated Autoimmune Skin Disorder Linear IgA Bullous Disease Using CD89/IgA Blocking Mouse Anti-Human CD89 Monoclonal Antibody 10E7

In order to analyze the biological activity of purified CD89/IgA blocking mouse anti-human CD89 antibody 10E7, the ability of generated CD89/IgA blocking mouse anti-human CD89 antibody 10E7 to inhibit experimentally induced human IgA-mediated autoimmune skin disorder linear IgA bullous disease (LABD) was determined.

LABD is a chronic skin disease associated with IgA autoantibodies, which is characterized by sub-epidermal blisters with dense inflammatory infiltrates that are dominated by CD89 expressing neutrophilic granulocytes (Van der Steen et al. J Immunol 2012; 189: 1594-1601). In LABD patients, linear IgA deposition is typically found at the dermo-epidermal junction, and these IgA autoantibodies are mainly directed against the transmembrane hemidesmosomal antigen BP180/collagen XVII (Otten et al. Curr mol Med 2014; 14: 69-95), which induce sustained neutrophilic granulocyte recruitment through cross-linking of human CD89. As a consequence, constant activation (i.e., by reactive oxygen species and pro-inflammatory cytokine production) and infiltration (i.e., by local chemoattractant LTB4 release) of CD89 expressing neutrophilic granulocytes cause severe tissue damage and aggravation of symptoms in LABD patients.

Figure 31A:
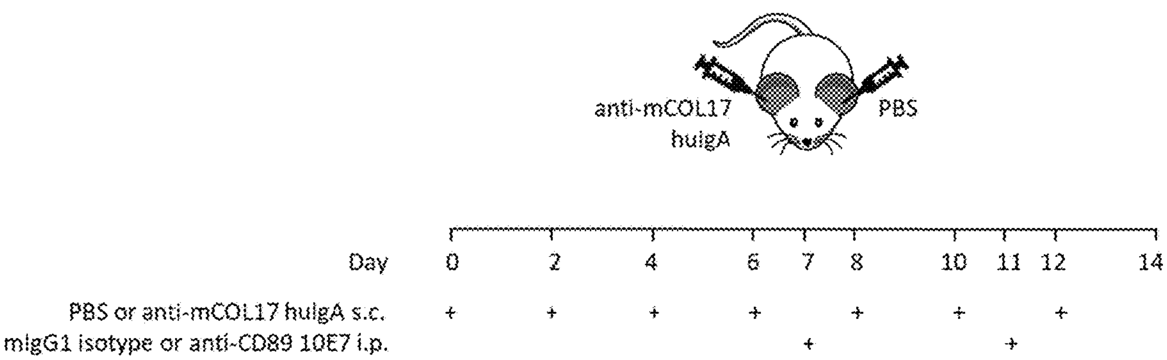
FIG. 31: (A) Experimental setup of in vivo LABD mouse model and treatment regimen with CD89/IgA blocking mouse anti-human CD89 antibody 10E7. (B) In vivo effect of purified CD89/IgA blocking mouse anti-human CD89 antibody 10E7 on anti-mouse collagen XVII human IgA antibody-induced human CD89 expressing mouse neutrophilic granulocyte influx at the injection site. Mean±SD are shown. Black circles and black squares represent PBS injections in left ears and anti-mouse collagen XVII human IgA injections in right ears of each individual mouse, respectively. *P<0.05 (two-tailed unpaired Student's t-test); ns=not significant.

In vivo LABD mouse model: In double transgenic human CD89/human IgA (Tg huCD89/huIgA) mice, which lack the mouse CD89 homologue, human CD89 expression, regulation, interaction with human IgA, and function mimic the human situation (Van Egmond et al, Blood 1999; 93: 4387-4394). These Tg huCD89/huIgA (equally distributed female and male) mice, which express membrane human CD89 on their circulating mouse neutrophilic granulocytes (Van Egmond et al, Blood 1999; 93: 4387-4394), were subcutaneously injected with 10 μL anti-mouse collagen XVII human IgA (auto)antibodies at 7 mg/mL (Prof. Dr. M. van Egmond, Dept Molecular Cell Biology and Immunology, VUmc, Amsterdam, NL) in right ears or 10 μL PBS in left ears on Day 0, 2, 4, 6, 8, 10, and 12. Human CD89 expressing mouse neutrophilic granulocyte influx at the injection sites was monitored with and without purified CD89/IgA blocking mouse anti-human CD89 antibody 10E7 treatment. To this end, 100 μL purified CD89/IgA blocking mouse anti-human CD89 antibody 10E7 at 1.5 mg/mL was intraperitoneally injected on Day 7 and 11 (for treatment regimen, see FIG. 31A). In parallel, 100 μL mouse IgG1 isotype control (Biolegend) at 1.5 mg/mL was run as a negative control. On Day 14, mice were sacrificed, and ears were excised and subsequently snap-frozen in liquid nitrogen. These ear tissue specimens were cryosectioned (6 μm) and fixed in acetone for 10 minutes at RT. Then, these air-dried cryosections were incubated with 1:400 diluted Alexa Fluor® 488-conjugated rat anti-mouse Ly-6G (GR-1 staining, a neutrophilic granulocyte marker; eBioscience) for 1 hour at RT. After washing in PBS, nuclei were counterstained using DAPI (Invitrogen) at 1 μg/mL for 5 minutes at RT. Tile scanning to obtain an image of the whole ear was performed using the Vectra Polaris microscope with the following settings: DAPI MSI 0.43 ms, FITC 81.70 ms and a 20 times magnification. The GR-1 staining of cryosections was analysed using ImageJ/Fiji software. The total area ($\mu m^2$) of mice ears and the area of the specific GR-1 staining ($\mu m^2$) was measured. Quantification was calculated as the GR-1 area ($\mu m^2$) divided by the total area ($\mu m^2$). The following formula was used to determine the GR-1/total area ratio:

$$\frac{GR-1 \text{ Area } (\mu m^2)}{\text{Total area } (\mu m^2)/10{,}000(\mu m^2)}.$$

Figure 31B:
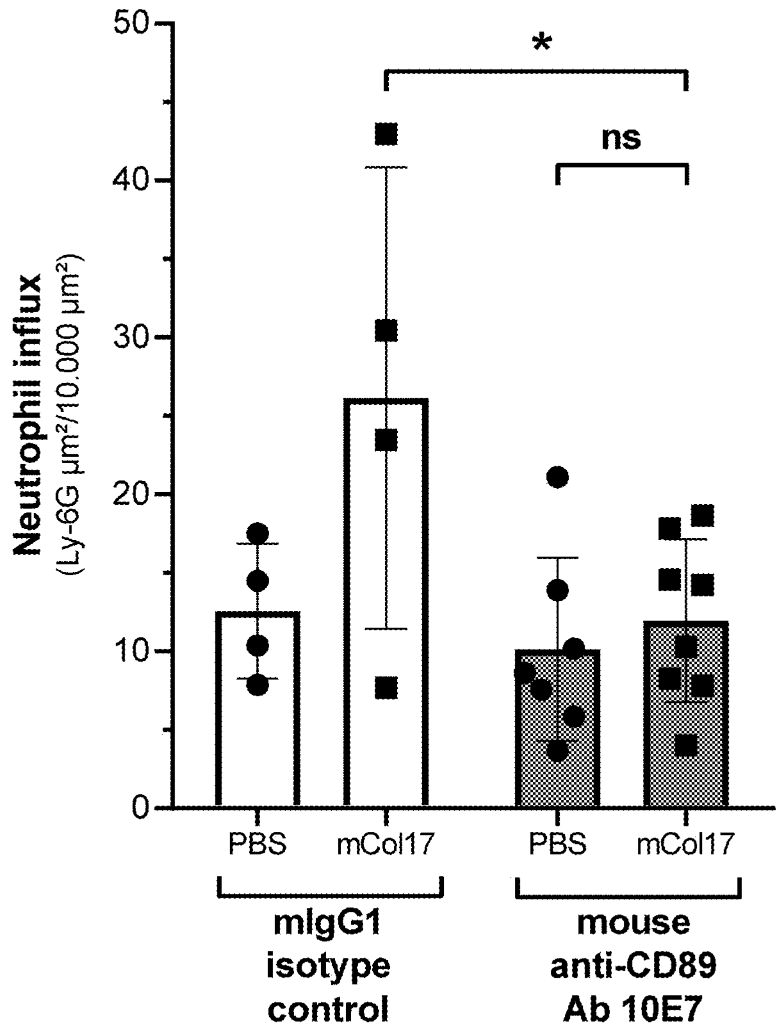

As shown in FIG. 31B, purified CD89/IgA blocking mouse anti-human CD89-specific antibody 10E7 significantly ($P<0.05$) inhibited anti-mouse collagen XVII human IgA antibody-induced human CD89 expressing mouse neutrophilic granulocyte influx at the injection site.

These results demonstrated that CD89/IgA blocking mouse anti-human CD89-specific antibody 10E7 inhibited experimentally induced in vivo human IgA-mediated human CD89 expressing mouse neutrophilic granulocyte influxes in Tg huCD89/huIgA mice.

Example 4. Characterization of Human CD89 Epitopes and CD89 Domains Recognized by CD89/IgA Blocking Mouse Anti-Human CD89 Monoclonal Antibodies (a). Cross-Competition of Non-Labeled CD89/IgA Blocking Mouse Anti-Human CD89 Antibodies with PE-Conjugated Commercial Mouse Anti-CD89 Antibodies Clone MIP8a (CD89/IgA Blocker), Clone A59 (CD89/IgA Non-Blocker) and Clone A3 (CD89/IgA Non-Blocker) to Human CD89

In order to analyze the fine specificity of purified CD89/IgA blocking mouse anti-human CD89 antibodies, the location of epitope(s) recognized by the generated CD89/IgA blocking mouse anti-human CD89 antibodies was determined by cross-competition with purified mouse anti-human CD89 antibody clone MIP8a, a well-known CD89/IgA blocker (Zhang et al. Clin Exp Immunol 2000; 121: 106-111), with purified mouse anti-human CD89 antibody clone A59, a well-known CD89/IgA non-blocker (Monteiro et al. J Immunol 1992; 148: 1764-1770), and with purified mouse anti-human CD89 antibody clone A3, a well-known CD89/IgA non-blocker (Monteiro et al. J Immunol 1992; 148: 1764-1770).

Human CD89 consists of a short cytoplasmic tail, a transmembrane region, and two extracellular (EC) Ig-like domains. By a short interdomain hinge region, these two Ig-like EC domains are folded with an angle of about 90° to each other (Ding et al. J Biol Chem 2003; 278:27966-27970). The binding site of human IgA on human CD89 is in the membrane-distal Ig-like EC1 domain and is not in the membrane-proximal Ig-like EC2 domain (Wines et al. J Immunol 1999; 162: 2146-2153; Morton J Exp Med 1999; 189:1715-1722; Lu et al. Protein Sci 2014; 23: 378-386). Consequently, it is generally accepted that mouse anti-human CD89 antibodies that bind to the EC1 domain of human CD89 can block human IgA binding on human CD89, whereas mouse anti-human CD89 antibodies that bind to the EC2 domain of human CD89 are not able to block human IgA binding on human CD89 (Morton et al. Arch Immunol Ther Exp 2001; 49: 217-229; Bakema et al. Immunol Rev 2011; 4: 612-624). More specifically, prototypic CD89/IgA blocking mouse anti-human CD89 antibody clone MIP8a recognizes an epitope within the EC1 domain of human CD89 (Lu et al. Protein Sci 2014; 23: 378-386), while prototypic CD89/IgA non-blocking mouse anti-human CD89 antibody clone A59 and A3 recognize an epitope within the EC2 domain of human CD89 (Morton J Exp Med 1999; 189:1715-1722) and within the border of EC1-EC2 domains of human CD89 (Morton J Exp Med 1999; 189: 1715-1722), respectively. The ability of generated purified CD89/IgA blocking mouse anti-human CD89 antibodies to compete with well-known CD89/IgA blocking and non-blocking mouse anti-human CD89 antibodies (i.e., clone MIP8a, clone A59, and clone A3) on membrane human CD89 was determined by FACS analysis.

Stable human full-length CD89-transfected HEK293F cells (clone no. 2; see Example 1 (b) above) were put at $10\times10^6$ cells/mL in ice-chilled PBS containing 0.1% BSA (Sigma)/0.05% $NaN_3$ (PBS/BSA/$NaN_3$) supplemented with 50 μg/mL human IgGs (blocking possible Fcγ receptors; Sigma) for 10 minutes at 4° C. Then, 10 μL/tube (i.e., $0.1\times10^6$ cells) of these cells were incubated with or without 100 μL purified mouse anti-human CD89 antibody at 10 μg/mL (in PBS/BSA/$NaN_3$) for 30 minutes at 4° C. In parallel, 100 μL purified mouse IgG1 isotype control (BD Biosciences) at 10 μg/mL (in PBS/BSA/$NaN_3$) was run as a negative control, and 100 μL purified mouse anti-human CD89 antibody clone MIP8a (BioRad) at 10 μg/mL (in PBS/BSA/$NaN_3$), clone A59 (BD Biosciences) at 10 μg/mL (in PBS/BSA/$NaN_3$), and clone A3 (Santa Cruz Biotechnology) at 10 μg/mL (in PBS/BSA/$NaN_3$) were run as positive controls. After this (i.e., without washing), 5 μL undiluted PE-conjugated mouse anti-human CD89 antibody clone MIP8a (BioRad), clone A59 (BD Biosciences), and clone A3 (Santa Cruz Biotechnology) was added to these cells, and incubated for another 30 minutes at 4° C. After extensive washing in PBS/BSA/$NaN_3$, cells were fixed in 2% formaldehyde in PBS/BSA/$NaN_3$ for 30 minutes at 4° C. Binding (geo-mean fluorescence intensity) of PE-conjugated mouse anti-human CD89 antibody clone MIP8a, clone A59, and clone A3 on membrane human CD89 was measured using a flow cytometer (FACSCalibur; BD Biosciences).

As shown in FIG. 11A, pre-incubation with non-labeled purified CD89/IgA blocking mouse anti-human CD89-specific antibody 9H7, 26D6, and 30C7 at 10 μg/mL completely (>90%) blocked the subsequent binding of commercial PE-conjugated CD89/IgA blocking mouse anti-human CD89 antibody clone MIP8a on membrane human CD89, whereas pre-incubation with non-labeled purified CD89/IgA blocking mouse anti-human CD89-specific antibody 8F3, 10E7, 16D6 and 20B4 at 10 μg/mL did not block (<25%) the subsequent binding of commercial PE-conjugated CD89/IgA blocking mouse anti-human CD89 antibody clone MIP8a on membrane human CD89. For reference purposes, pre-incubation with non-labeled purified CD89/IgA blocking mouse anti-human CD89 antibody clone MIP8a at 10 μg/mL also completely (>90%) blocked the subsequent binding of its PE-conjugated antibody counterpart on membrane human CD89, whereas pre-incubation with non-labeled purified well-known CD89/IgA non-blocking mouse anti-human CD89 antibody clone A59 and A3 at 10 μg/mL did not block (<25%) the subsequent binding of commercial PE-conjugated CD89/IgA blocking mouse anti-human CD89 antibody clone MIP8a on membrane human CD89.

As shown in FIG. 11B, pre-incubation with non-labeled purified CD89/IgA blocking mouse anti-human CD89-specific antibody 9H7, 26D6, and 20B4 at 10 μg/mL partially (~55-65%) blocked the subsequent binding of commercial PE-conjugated CD89/IgA non-blocking mouse anti-human CD89 antibody clone A59 on membrane human CD89, whereas pre-incubation with non-labeled purified CD89/IgA blocking mouse anti-human CD89-specific antibody 8F3, 10E7, 16D6 and 30C7 at 10 μg/mL did not block (<25%) the subsequent binding of commercial PE-conjugated CD89/IgA non-blocking mouse anti-human CD89 antibody clone A59 on membrane human CD89. For reference purposes, pre-incubation with non-labeled purified CD89/IgA non-blocking mouse anti-human CD89 antibody clone A59 at 10 μg/mL completely (>90%) blocked the subsequent binding of its PE-conjugated antibody counterpart on membrane human CD89. Moreover, pre-incubation with non-labeled purified well-known CD89/IgA non-blocking mouse anti-human CD89 antibody clone A3 at 10 g/mL also completely (>90%) blocked the subsequent binding of commercial PE-conjugated CD89/IgA non-blocking mouse anti-human CD89 antibody clone A59 on membrane human CD89, whereas pre-incubation with non-labeled purified well-known CD89/IgA blocking mouse anti-human CD89 antibody clone MIP8a at 10 g/mL partially blocked (~50%) the subsequent binding of commercial PE-conjugated CD89/IgA non-blocking mouse anti-human CD89 antibody clone A59 on membrane human CD89.

As shown in FIG. 11C, pre-incubation with non-labeled purified CD89/IgA blocking mouse anti-human CD89-specific antibody 9H7, 26D6, and 20B4 at 10 μg/mL partially (~55-65%) blocked the subsequent binding of commercial PE-conjugated CD89/IgA non-blocking mouse anti-human CD89 antibody clone A3 on membrane human CD89, whereas pre-incubation with non-labeled purified CD89/IgA blocking mouse anti-human CD89-specific antibody 8F3, 10E7, 16D6 and 30C7 at 10 μg/mL did not block (<25%) the subsequent binding of commercial PE-conjugated CD89/IgA non-blocking mouse anti-human CD89 antibody clone A3 on membrane human CD89. For reference purposes, pre-incubation with non-labeled purified CD89/IgA non-blocking mouse anti-human CD89 antibody clone A3 at 10 μg/mL completely (>90%) blocked the subsequent binding of its PE-conjugated antibody counterpart on membrane human CD89. Moreover, pre-incubation with non-labeled purified well-known CD89/IgA non-blocking mouse anti-human CD89 antibody clone A59 at 10 μg/mL also completely (>90%) blocked the subsequent binding of commercial PE-conjugated CD89/IgA non-blocking mouse anti-human CD89 antibody clone A3 on membrane human CD89, whereas pre-incubation with non-labeled purified well-known CD89/IgA blocking mouse anti-human CD89 antibody clone MIP8a at 10 μg/mL partially blocked (~55%) the subsequent binding of commercial PE-conjugated CD89/IgA non-blocking mouse anti-human CD89 antibody clone A3 on membrane human CD89.

In order to analyze the degree of above-described cross-competition, pre-incubation with titrated (as opposed to using 10 μg/mL only) cross-competing non-labeled purified CD89/IgA blocking mouse anti-human CD89-specific antibodies was also performed followed by incubation with PE-conjugated mouse anti-human CD89 antibody clone MIP8a, clone A59, and clone A3 using stable human full-length CD89-transfected HEK293F cells (clone no. 2; see Example 1 (b) above).

As shown in FIG. 12A, all 'MIP8a' cross-competing non-labeled purified CD89/IgA blocking mouse anti-human CD89-specific antibodies (i.e., 9H7, 26D6, and 30C7) dose-dependently blocked the binding of commercial PE-conjugated CD89/IgA blocking mouse anti-human CD89 antibody clone MIP8a on membrane human CD89. Based on their 'MIP8a' cross-competition profile, the following ranking was found (from a strong to a lower 'MIP8a-PE' blocking degree): 9H7=26D6(=MIP8a)>30C7. For summary, see Table 6.

As shown in FIG. 12B, all 'A59' cross-competing non-labeled purified CD89/IgA blocking mouse anti-human CD89-specific antibodies (i.e., 9H7, 26D6, and 20B4) dose-dependently blocked the binding of commercial PE-conjugated CD89/IgA non-blocking mouse anti-human CD89 antibody clone A59 on membrane human CD89. Based on their 'A59' cross-competition profile, the following ranking was found (from a strong to a weaker 'A59-PE' blocking degree): (A59=A3)>9H7=26D6=20B4(=MIP8a). For summary, see Table 6.

Figure 12C:
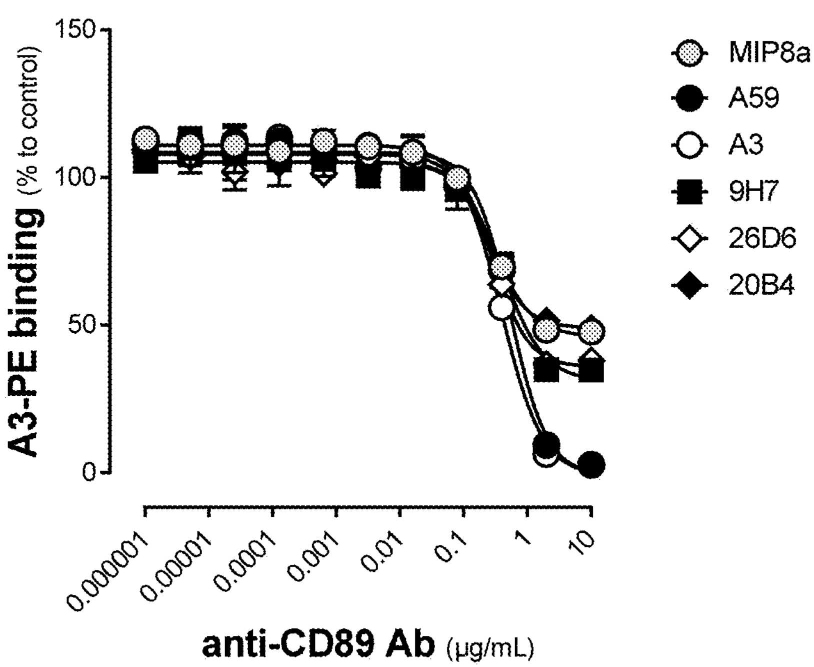
FIG. 12. Detailed analysis of cross-competing non-labeled purified CD89/IgA blocking mouse anti-human CD89 antibodies with PE-conjugated commercial mouse anti-CD89 antibodies clone MIP8a (A; CD89/IgA blocker), clone A59 (B; CD89/IgA non-blocker), and clone A3 (C: CD89/IgA non-blocker) to membrane-bound human CD89 on HEK293F cells. Mean±SD (at least n=2) are shown.

As shown in FIG. 12C, all 'A3' cross-competing non-labeled purified CD89/IgA blocking mouse anti-human CD89-specific antibodies (i.e., 9H7, 26D6, and 20B4) dose-dependently blocked the binding of commercial PE-conjugated CD89/IgA non-blocking mouse anti-human CD89 antibody clone A3 on membrane human CD89. Based on their 'A3' cross-competition profile, the following ranking was found (from a strong to a weaker 'A3-PE' blocking degree): (A59=A3)>9H7=26D6=20B4(=MIP8a). For summary, see Table 6.

TABLE 6

Cross-competition profiles of non-labeled purified CD89/IgA blocking mouse anti -human CD89-specific antibodies with PE-conjugated commercial mouse anti-CD89 antibodies clone MIP8a (CD89/IgA blocker), clone A59 (CD89/IgA non-blocker) and clone A3 (CD89/IgA non-blocker) on membrane human CD89.

| | Cross-competition | | |
|---|---|---|---|
| Anti-CD89 Ab | MIP8a-PE | A59-PE | A3-PE |
| 8F3 | − | − | − |
| 9H7 | ++ | + | + |
| 10E7 | − | − | − |
| 16D6 | − | − | − |
| 26D6 | ++ | + | + |
| 20B4 | − | + | + |
| 30C7 | +/++ | − | − |
| mIgG1 control | − | − | − |
| MIP8a | ++ | + | + |
| A59 | − | ++ | ++ |
| A3 | − | ++ | ++ |

− = no blocking of binding of PE-conjugated commercial mouse anti-CD89 antibodies clone MIP8a (CD89/IgA blocker), clone A59 (CD89/IgA non-blocker) or clone A3 (CD89/IgA non-blocker) on membrane human CD89 ,
\+ = weak blocking of binding of PE-conjugated commercial mouse anti-CD89 antibodies clone MIP8a (CD89/IgA blocker), clone A59 (CD89/IgA non-blocker) or clone A3 (CD89/IgA non-blocker) on membrane human CD89,
++ = strong blocking of of binding of PE-conjugated commercial mouse anti-CD89 antibodies clone MIP8a (CD89/IgA blocker), clone A59 (CD89/IgA non-blocker) or clone A3 (CD89/IgA non-blocker) on membrane human CD89.

These results demonstrated that CD89/IgA blocking mouse anti-human CD89-specific antibody 8F3, 10E7, 16D6, 20B4, and 30C7 bound to human CD89 epitopes, which were different from the human CD89 epitopes recognized by commercial mouse anti-human CD89 antibody clone MIP8a, clone A59 or clone A3, because their cross-competition profiles were significantly different from cross-competition profiles obtained with these commercial mouse anti-human CD89 antibodies. Moreover, these results demonstrated that CD89/IgA blocking mouse anti-human CD89-specific antibody 8F3, 10E7, and 16D6 as a group (three antibodies with identical cross-competition profiles) versus CD89/IgA blocking mouse anti-human CD89-specific antibody 9H7 and 26B6 as a group (both antibodies with identical cross-competition profiles) versus CD89/IgA blocking mouse anti-human CD89-specific antibody 20B4 versus CD89/IgA blocking mouse anti-human CD89-specific antibody 30C7 bound to non-identical CD89 epitopes, because their cross-competition profiles were significantly different. In addition, these results demonstrated that CD89/IgA blocking mouse anti-human CD89-specific antibody 9H7 and 26B6 as a group (both antibodies with identical cross-competition profiles) versus commercial mouse anti-human CD89 antibody clone MIP8a seemed to bind to a similar CD89 epitope, because their cross-competition profiles were identical. These results also demonstrated that CD89/IgA blocking mouse anti-human CD89-specific antibody 8F3, 10E7, and 16D6 seemed to bind to a similar CD89 epitope, because their cross-competition profiles were identical. Finally, these results demonstrated that CD89/IgA blocking mouse anti-human CD89-specific antibody 9H7 and 26B6 seemed to bind to a similar CD89 epitope, because their cross-competition profiles were identical.

(b). Binding of CD89/IgA Blocking Mouse Anti-Human CD89 Antibodies to Membrane Full-Length Human CD89 and Various Membrane Chimeric Human CD89/Bovine Fcγ2R Constructs (EC1 Versus EC2 Domain Mapping of Human CD89)

In order to analyze the fine specificity of purified CD89/IgA blocking mouse anti-human CD89 antibodies, the location of epitope(s) recognized by the generated CD89/IgA blocking mouse anti-human CD89 antibodies was determined by domain mapping. The ability of CD89/IgA blocking mouse anti-human CD89 antibodies to bind to the EC1 domain or to the EC2 domain of human CD89, expressed on the surface of HEK293F cells, was determined by FACS analysis.

Figure 13A:
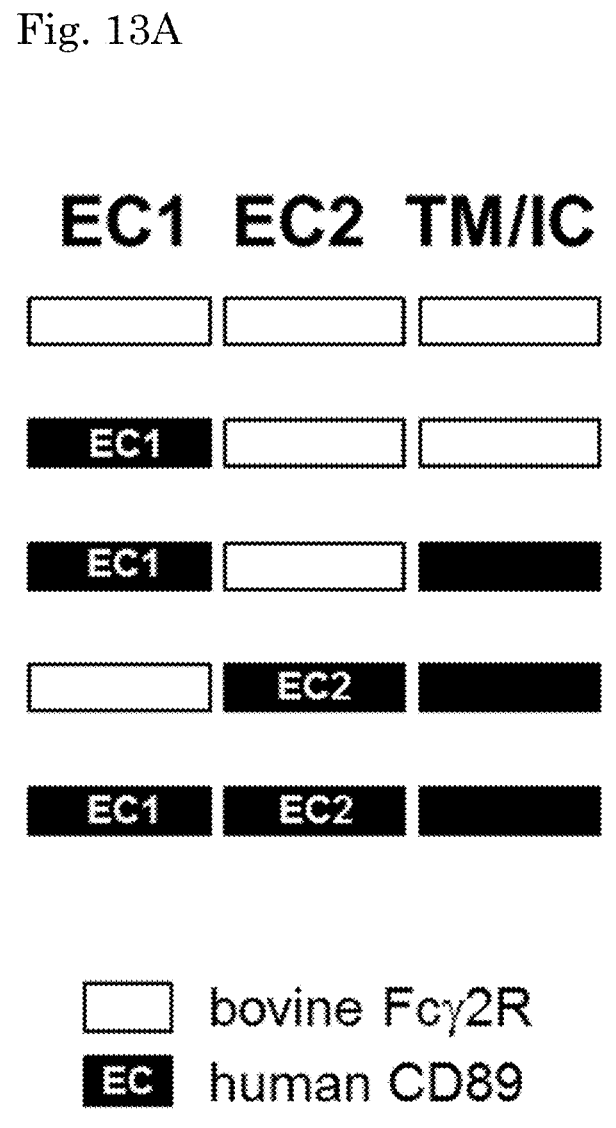

Structurally, human CD89 and bovine Fcγ2R are highly homologous and are closely related to each other (Ravetch et al. Annu Rev Immunol 1991; 9: 457-492; Zhang et al. J Immunol 1995; 155: 1534-1541). Therefore, chimeric human/bovine receptors were designed by exchanging Ig-like EC1 and EC2 domains between these two receptor proteins (see also FIG. 13A). Functionally, human CD89 and bovine Fcγ2R are completely distinct in that human CD89 binds human IgA but not bovine IgG2, whereas bovine Fcγ2R binds bovine IgG2 and not human IgA. The following human CD89 constructs were generated and transiently expressed: (1) membrane full-length human CD89 construct, which contained both Ig-like EC1 and Ig-like EC2 domains of human CD89 (see SEQ ID NO: 1), and therefore denoted as 'human EC1-EC2-CD89', (2) membrane chimeric Ig-like EC1 domain of human CD89 combined with Ig-like EC2 domain of bovine Fcγ2R construct (see SEQ ID NO: 3 and NO: 4, i.e., combined with bovine transmembrane-intracellular region or with human transmembrane-intracellular region, respectively), and therefore denoted as 'human EC1-CD89', and (3) membrane chimeric Ig-like EC1 domain of bovine Fcγ2R combined with Ig-like EC2 domain of human CD89 construct (see SEQ ID NO: 7), and therefore denoted as 'human EC2-CD89'. In addition, membrane full-length bovine Fcγ2R construct was also generated, which contained both Ig-like EC1 and Ig-like EC2 domains of bovine Fcγ2R (see SEQ ID NO: 9), and therefore denoted as 'bovine Fcγ2R'. cDNAs encoding for above-described 'human EC1-EC2-D89', 'human EC1-CD89', 'human EC2-CD89', and 'bovine Fcγ2R' constructs were optimized for mammalian expression and synthesized by GENEART, Regensburg, Germany (see SEQ ID NO: 2, NO: 5, NO: 6, NO: 8, and NO: 10, respectively). These cDNAs were subcloned in pcDNA3.1-derived expression plasmids.

Using the FreeStyle™ 293 Expression System (Invitrogen), FreeStyle™ 293F cells (Invitrogen) were transiently transfected with 'human CD89', 'human EC1-CD89', 'human EC2-CD89', and 'bovine Fcγ2R' constructs. After 48 hours and/or 72 hours, the binding of CD89/IgA blocking mouse anti-human CD89 antibodies to aforementioned chimeric human/bovine receptors on transfected cells was analyzed by FACS analysis. To this end, transient transfected HEK293F cells were put at $10\times10^6$ cells/mL in ice-chilled phosphate-buffered saline containing 0.1% BSA (Sigma)/0.05% $NaN_3$ (PBS/BSA/$NaN_3$) supplemented with 50 μg/mL human IgGs (blocking Fcγ receptors; Sigma) for 10 minutes at 4° C. Then, 10 Li/tube (i.e., $0.1\times10^6$ cells) of these cells were incubated with or without 100 μL purified mouse anti-human CD89 antibody at 10 μg/mL (in PBS/BSA/$NaN_3$) for 30 minutes at 4° C. In parallel, 100 μL purified mouse IgG1 isotype control (BD Biosciences) at 10 μg/mL (in PBS/BSA/$NaN_3$) was run as a negative control, and 100 μL at 10 μg/mL (in PBS/BSA/$NaN_3$) purified mouse anti-human CD89 antibody clone MIP8a (BioRad), clone A59 (BD Biosciences), and clone A3 (Santa Cruz Biotechnology) were run as positive controls. After extensive washing in PBS/BSA/$NaN_3$, cells were subsequently incubated with 1:200 diluted PE-conjugated goat anti-mouse IgG Fey-specific antibodies (Jackson ImmunoResearch) for 30 minutes at 4° C. After extensive washing in PBS/BSA/$NaN_3$, cells were fixed in 2% formaldehyde in PBS/BSA/$NaN_3$ for 30 minutes at 4° C. Binding of antibodies was measured using a flow cytometer (model FACSCalibur; BD Biosciences).

Apart from above-described binding of CD89/IgA blocking mouse anti-human CD89 antibodies to chimeric human/bovine receptors, (1) membrane surface expression levels and (2) proper folding of these chimeric human/bovine receptors were also examined on these transiently transfected cells. For this, transient transfected HEK293F cells were put at $10\times10^6$ cells/mL in ice-chilled phosphate-buffered saline containing 0.1% BSA (Sigma)/0.05% $NaN_3$ (PBS/BSA/$NaN_3$) supplemented with 50 μg/mL human IgGs (blocking Fcγ receptors; Sigma) for 10 minutes at 4° C. Then, 10 μL/tube (i.e., $0.1\times10^6$ cells) of these cells were incubated (1) with or without 100 μL purified rabbit anti-human CD89 polyclonal antibodies (Sino Biological) at 2.5 μg/mL (in PBS/BSA/$NaN_3$), and (2) with or without 100 μL purified non-aggregated or heat-aggregated human (serum-derived; see Example 2 (b) above) IgA (Bethyl Laboratories) at 10 μg/mL (diluted in PBS/BSA/$NaN_3$) for 30 minutes at 4° C. After extensive washing in PBS/BSA/$NaN_3$, binding of (1) rabbit anti-human CD89 polyclonal antibodies and of (2) non-aggregated or heat-aggregated serum human IgA on membrane human CD89 was determined with 1:200 diluted FITC-conjugated F(ab')2 fragment goat anti-rabbit IgG heavy/light chains-specific antibodies (Jackson ImmunoResearch) and with biotin-conjugated F(ab')2 fragment goat anti-human serum IgA α chain-specific antibodies (Jackson ImmunoResearch) at 5 μg/mL for 30 minutes at 4° C., respectively. After extensive washing in PBS/BSA/$NaN_3$, 1:200 diluted PE-conjugated streptavidin (Jackson ImmunoResearch) was added, and incubated for 30 minutes at 4° C. After extensive washing in PBS/BSA/$NaN_3$, cells were fixed in 2% formaldehyde in PBS/BSA/$NaN_3$ for 30 minutes at 4° C. Binding of (1) rabbit anti-human CD89 polyclonal antibodies and of (2) non-aggregated or heat-aggregated serum human IgA on membrane chimeric human/bovine receptors were measured using a flow cytometer (model FACSCalibur; BD Biosciences).

Figure 13B:
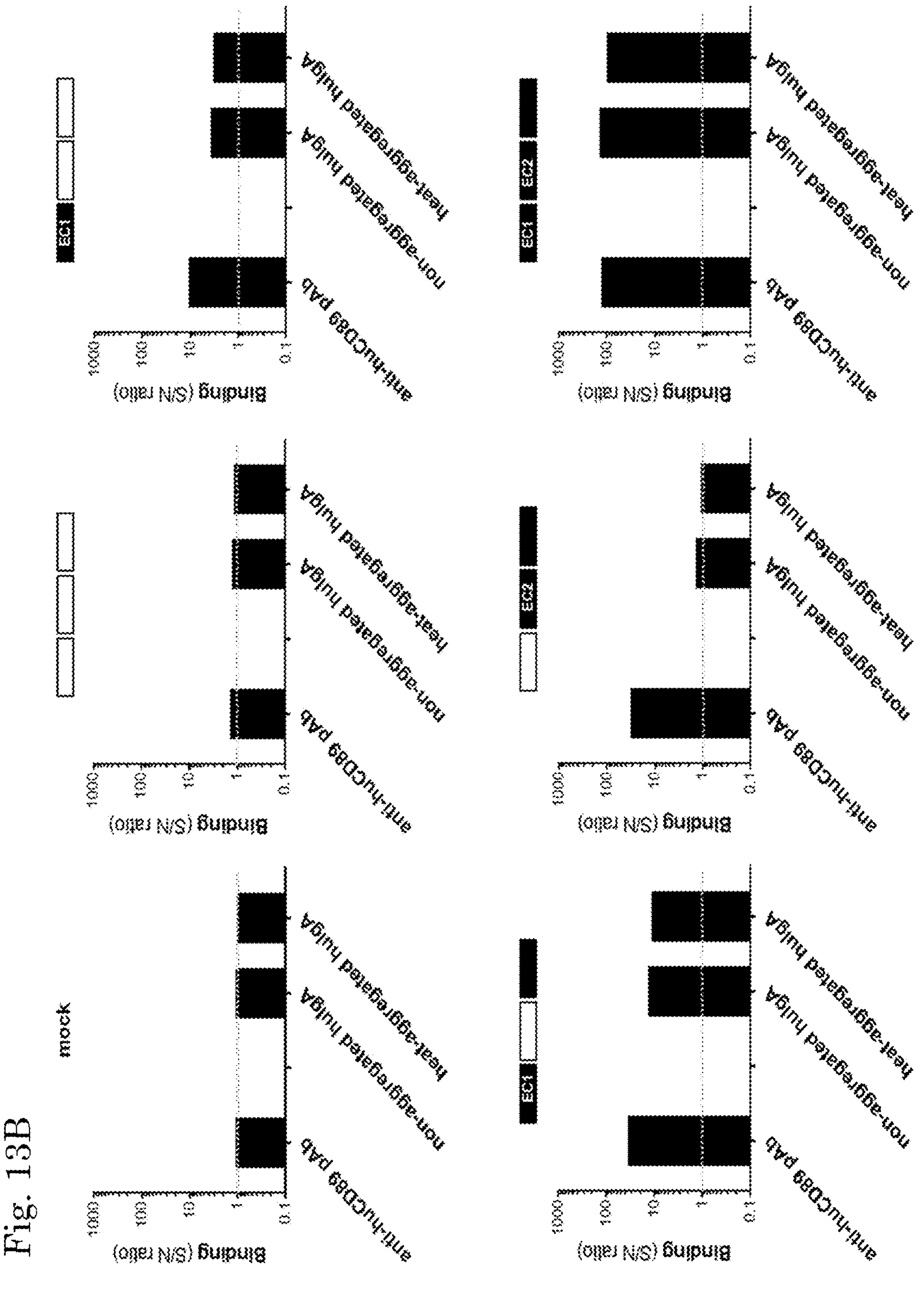
FIG. 13. (A) Schematic representation of wild type human CD89, wild type bovine Fcγ2R, and their derived chimeric human/bovine FcR constructs. (B) Binding (n=1) of rabbit anti-human CD89 polyclonal antibodies, and of non-aggregated or heat-aggregated serum human IgA to membrane-bound human full-length CD89 ('human EC1-EC2-CD89'; i.e. ■■■, to membrane-bound chimeric human EC1-CD89/bovine EC2-Fcγ2R ('human EC1-CD89', i.e., ■□□ and ■□■), to membrane-bound chimeric bovine EC1-Fcγ2R/human EC2-CD89 ('human EC2-CD89'; i.e., □■■), and to membrane-bound bovine full-length Fcγ2R ('bovine Fcγ2R', i.e., □□□) on HEK293F cells. (C) Binding (n=1) of purified CD89/IgA blocking mouse anti-human CD89 antibodies to membrane-bound human full-length CD89 ('human EC1-EC2-CD89'), to membrane-bound chimeric human EC1-CD89/bovine EC2-Fcγ2R ('human EC1-CD89'), to membrane-bound chimeric bovine EC1-Fcγ2R/human EC2-CD89 ('human EC2-CD89'), and to membrane-bound bovine full-length Fcγ2R ('bovine Fcγ2R') on HEK293F cells. Dotted grey lines represent background (i.e., no binding of mouse anti-human CD89 antibodies).

As shown in FIG. 13B, all chimeric human CD89/bovine Fcγ2R receptors (i.e., two versions of 'human EC1-CD89', and 'human EC2-CD89') and full-length human CD89 were expressed on the membrane surface of transiently transfected cells as evidenced by the binding of rabbit anti-human CD89 polyclonal antibodies on these cells. Furthermore, these membrane-expressed chimeric human CD89/bovine Fcγ2R receptors (i.e., two versions of 'human EC1-CD89') and full-length human CD89 seemed to show a proper protein folding as evidenced by the binding of both non-aggregated and heat-aggregated serum human IgA. As expected, the chimeric human CD89/bovine Fcγ2R receptor 'human EC2-CD89', which lacks the EC1 domain (i.e., the IgA binding site on human CD89), did not bind to non-aggregated and heat-aggregated serum human IgA. As expected, rabbit anti-human CD89 polyclonal antibodies, and non-aggregated and heat-aggregated serum human IgA did not bind to mock-transfected cells nor to full-length bovine Fcγ2R transfected cells.

Figure 13C:
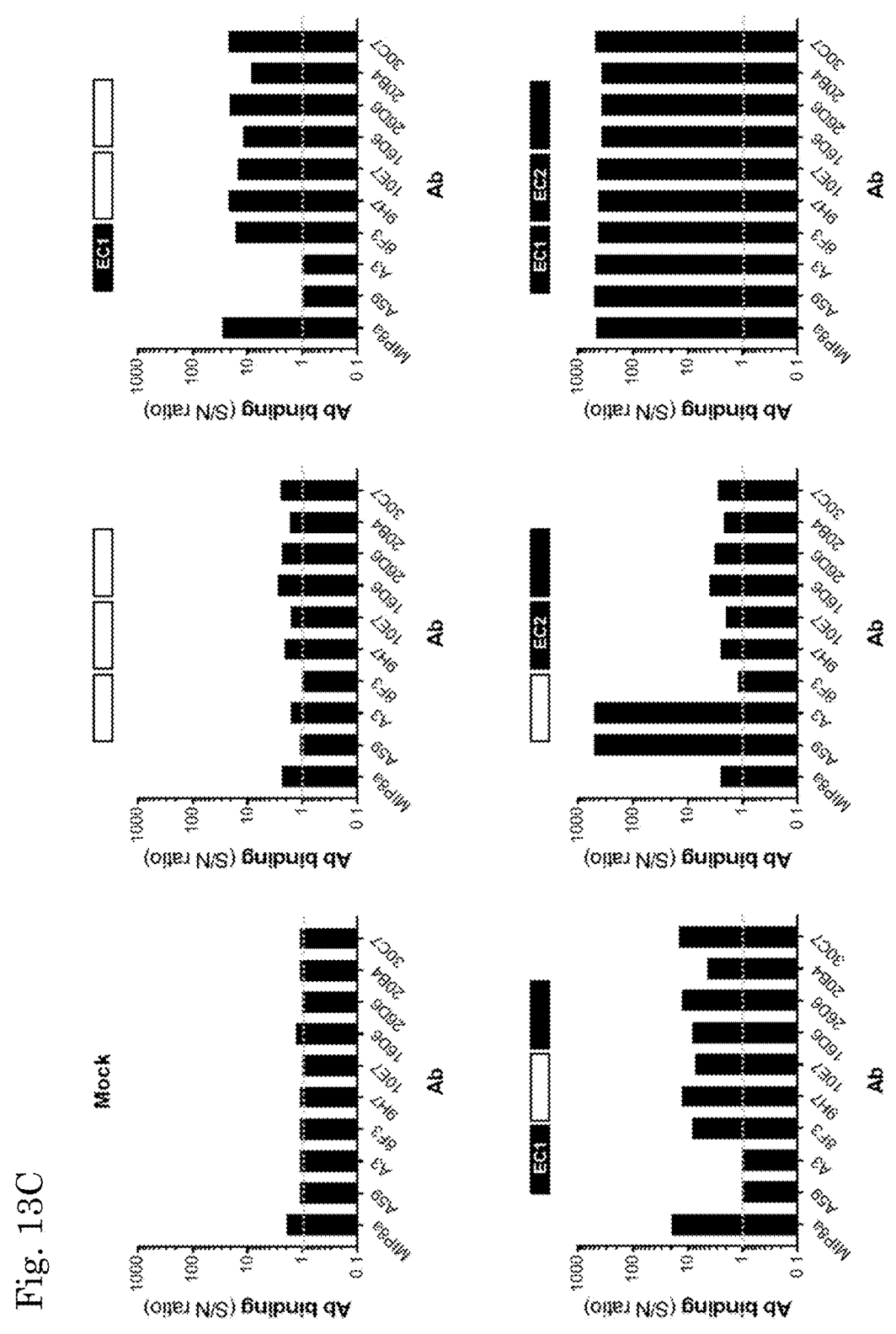

As shown in FIG. 13C, all our purified CD89/IgA blocking mouse anti-human CD89-specific antibodies (i.e., 8F3, 9H7, 10E7, 16D6, 26D6, 20B4, and 30C7) showed binding to both versions of 'human EC1-CD89' and not to 'human EC2-CD89' on transfected 293F cells. Moreover, all our purified CD89/IgA blocking mouse anti-human CD89-specific antibodies (i.e., 8F3, 9H7, 10E7, 16D6, 26D6, 20B4, and 30C7) showed binding to full-length human CD89 'human EC1-EC2-CD89) transfected cells but showed no binding to mock-transfected cells nor to full-length bovine Fcγ2R transfected cells. As expected, purified well-known CD89/IgA blocking mouse anti-human CD89 antibody clone MIP8a, which recognizes an epitope within the EC1 domain of human CD89 (Lu et al. Protein Sci 2014; 23: 378-386), showed binding to both versions of 'human EC1-CD89' and not to 'human EC2-CD89', whereas purified well-known CD89/IgA non-blocking mouse anti-human CD89 antibody clone A59, which recognizes an epitope within the EC2 domain of human CD89 (Morton J Exp Med 1999; 189:1715-1722), showed binding to 'human EC2-CD89' and not to 'human EC1-CD89'. Surprisingly, purified well-known CD89/IgA non-blocking mouse anti-human CD89 antibody clone A3, which recognizes an epitope depending on parts of both EC1 and EC2 domains of human CD89 (Morton J Exp Med 1999; 189:1715-1722), did bind to 'human EC2-CD89' and not to 'human EC1-CD89'. Finally, all these examined commercial mouse anti-human CD89-specific antibodies showed binding to full-length human CD89 'human EC1-EC2-CD89) transfected cells but showed no binding to mock-transfected cells nor to full-length bovine Fcγ2R transfected cells.

These results demonstrated that all our CD89/IgA blocking mouse anti-human CD89 antibodies 8F3, 9H7, 10E7, 16D6, 26D6, 20B4, and 30C7 seemed to recognize linear and/or non-linear/conformational epitopes within the EC1 domain (i.e., Gln22-Gly121; Swiss-Prot no. P24071.1) of human full-length CD89.

(c). Binding of CD89/IgA Blocking Mouse Anti-Human CD89 Antibodies to Membrane Cynomolgus Monkey CD89

In order to analyze the multispecies cross-reactivity of our purified CD89/IgA blocking mouse anti-human CD89 antibodies, the ability of generated CD89/IgA blocking mouse anti-human CD89 antibodies to bind to the full-length cynomolgus monkey CD89, expressed on the surface of HEK293F cells, was determined by FACS analysis.

cDNA encoding for cynomolgus monkey CD89 protein (see SEQ ID NO: 11; NCBI Reference Sequence XP_005590398.1) was optimized for mammalian expression and synthesized by GENEART, Regensburg, Germany (see SEQ ID NO: 12). This cDNA was subcloned in a pcDNA3.1-derived expression plasmid.

Using the FreeStyle™ 293 Expression System (Invitrogen), FreeStyle™ 293F cells (Invitrogen) were transiently transfected with cynomolgus monkey full-length CD89. After 48 hours and/or 72 hours, the cross-reactivity of CD89/IgA blocking mouse anti-human CD89 antibodies to surface cynomolgus monkey CD89 on transfected cells was analyzed by FACS analysis. To this end, transient transfected HEK293F cells were put at $10\times10^6$ cells/mL in ice-chilled phosphate-buffered saline containing 0.1% BSA (Sigma)/0.05% $NaN_3$ (PBS/BSA/$NaN_3$) supplemented with 50 μg/mL human IgGs (blocking Fcγ receptors; Sigma) for 10 minutes at 4° C. Then, 10 μL/tube (i.e., $0.1\times10^6$ cells) of these cells were incubated with or without 100 μL purified mouse anti-human CD89 antibody at 10 μg/mL (in PBS/BSA/$NaN_3$) for 30 minutes at 4° C. In parallel, 100 μL purified mouse IgG1 isotype control (BD Biosciences) at 10 μg/mL (in PBS/BSA/$NaN_3$) was run as a negative control, and 100 μL at 10 μg/mL (in PBS/BSA/$NaN_3$) purified mouse anti-human CD89 antibody clone MIP8a (BioRad), clone A59 (BD Biosciences), and clone A3 (Santa Cruz Biotechnology) were run as positive controls. After extensive washing in PBS/BSA/$NaN_3$, cells were subsequently incubated with 1:200 diluted PE-conjugated goat anti-mouse IgG Fey-specific antibodies (Jackson ImmunoResearch) for 30 minutes at 4° C. After extensive washing in PBS/BSA/$NaN_3$, cells were fixed in 2% formaldehyde in PBS/BSA/$NaN_3$ for 30 minutes at 4° C. Binding of antibodies was measured using a flow cytometer (model FACSCalibur; BD Biosciences).

Apart from above-described binding of CD89/IgA blocking mouse anti-human CD89 antibodies to cynomolgus monkey full-length CD89, (1) membrane surface expression levels and (2) proper folding of cynomolgus monkey full-length CD89 were also examined on these transiently transfected cells. For this, transient transfected HEK293F cells were put at $10\times10^6$ cells/mL in ice-chilled phosphate-buffered saline containing 0.1% BSA (Sigma)/0.05% $NaN_3$ (PBS/BSA/$NaN_3$) supplemented with 50 μg/mL human IgGs (blocking Fcγ receptors; Sigma) for 10 minutes at 4° C. Then, 10 Li/tube (i.e., $0.1\times10^6$ cells) of these cells were incubated (1) with or without 100 μL purified rabbit anti-human CD89 polyclonal antibodies (Sino Biological) at 2.5 μg/mL (in PBS/BSA/$NaN_3$), and (2) with or without 100 μL purified non-aggregated or heat-aggregated human (serum-derived; see Example 2 (b) above) IgA (Bethyl Laboratories) at 10 μg/mL (diluted in PBS/BSA/$NaN_3$) for 30 minutes at 4° C. After extensive washing in PBS/BSA/$NaN_3$, binding of (1) rabbit anti-human CD89 polyclonal antibodies and of (2) non-aggregated or heat-aggregated serum human IgA on membrane cynomolgus monkey CD89 was determined with 1:200 diluted FITC-conjugated F(ab')2 fragment goat anti-rabbit IgG heavy/light chains-specific antibodies (Jackson ImmunoResearch) and with biotin-conjugated F(ab')2 fragment goat anti-human serum IgA α chain-specific antibodies (Jackson ImmunoResearch) at 5 μg/mL for 30 minutes at 4° C., respectively. After extensive washing in PBS/BSA/$NaN_3$, 1:200 diluted PE-conjugated streptavidin (Jackson ImmunoResearch) was added, and incubated for 30 minutes at 4° C. After extensive washing in PBS/BSA/$NaN_3$, cells were fixed in 2% formaldehyde in PBS/BSA/$NaN_3$ for 30 minutes at 4° C. Binding of (1) rabbit anti-human CD89 polyclonal antibodies and of (2) non-aggregated or heat-aggregated serum human IgA on membrane cynomolgus monkey CD89 were measured using a flow cytometer (model FACSCalibur; BD Biosciences).

As shown in FIG. 14A, full-length cynomolgus monkey CD89 was expressed on the membrane surface of transiently transfected cells as evidenced by the binding of cross-reacting rabbit anti-human CD89 polyclonal antibodies on these cells. Furthermore, this membrane-expressed full-length cynomolgus monkey CD89 seemed to show a proper protein folding as evidenced by the binding of both cross-reactive non-aggregated and heat-aggregated serum human IgA.

As shown in FIG. 14B, purified CD89/IgA blocking mouse anti-human CD89-specific antibodies 16D6 and 30C7 showed intermediate/weak cross-reactivity against cynomolgus monkey full-length CD89 on transfected 293F cells. Purified CD89/IgA blocking mouse anti-human CD89 antibodies 8F3, 9H7, 10E7, 26D6, and 20B4, did not recognize cynomolgus monkey full-length CD89 on transfected 293F cells. Commercial purified mouse anti-human CD89-specific antibodies clone A59 and clone A3 showed strong cross-reactivity against cynomolgus monkey full-length CD89 on transfected 293F cells, whereas commercial purified mouse anti-human CD89-specific antibody clone MIP8a did not any binding on cynomolgus monkey full-length CD89.

These results demonstrated that mouse anti-human CD89 antibodies 16D6 and 30C7 seemed to recognize linear and/or non-linear/conformational epitopes in, most likely, the EC1 domain of cynomolgus monkey full-length CD89.

Predicted amino acid sequence of full-length cynomolgus monkey CD89 protein (i.e., Met1-Lys287; NCBI Reference Sequence: XP_005590398.1) shows 86% homology with amino acid sequence of full-length human CD89 protein (i.e., Met1-Lys287; Swiss-Prot no. P24071.1), and predicted amino acid sequence of extracellular region of cynomolgus monkey CD89 (i.e., Gln22-Asn227; NCBI Reference Sequence: XP_005590398.1) shows 83% homology with amino acid sequence of extracellular region human CD89 protein (i.e., Gln22-Asn227; Swiss-Prot no. P24071.1). In more detail, predicted amino acid sequence of the EC1 domain (i.e., Gln22-Gly121; NCBI Reference Sequence: XP_005590398.1), of the short hinge region (i.e., Leu122-Lys125), of the EC2 domain (i.e., Pro126-Asn220), and of the membrane proximal ‘linker’ region (i.e., Arg221-Asn227) of cynomolgus monkey CD89 protein shows 72%, 100%, 93%, and 85% homology with amino acid sequence of their corresponding counterparts of human CD89 protein, respectively.

Considering that our generated CD89/IgA blocking mouse anti-human CD89 antibodies 8F3, 9H7, 10E7, 16D6, 26D6, 20B4, and 30C7 seemed to recognize linear and/or non-linear/conformational epitopes within the EC1 domain (i.e., Gln22-Gly121; Swiss-Prot no. P24071.1) of human full-length CD89 (see Example 4 (b) above), it not surprising that the majority our CD89/IgA blocking mouse anti-human CD89 antibodies (i.e., 8F3, 9H7, 10E7, 26D6, and 20B4) did not cross-react with the low-homologous (i.e., 72% amino acid sequence) EC1 domain (i.e., Gln22-Gly121; NCBI Reference Sequence: XP_005590398.1) of full-length cynomolgus monkey CD89 on transfected 293F cells.

(d). Binding of CD89/IgA Blocking Mouse Anti-Human CD89 Antibodies to Various Membrane Chimeric Human CD89/Cynomolgus Monkey CD89 Constructs (Epitope Mapping within the EC1 Domain of Human CD89)

In order to analyze the fine specificity of purified CD89/IgA blocking mouse anti-human CD89 antibodies, the epitope(s) recognized by the generated CD89/IgA blocking mouse anti-human CD89 antibodies was determined by epitope mapping. The ability of CD89/IgA blocking mouse anti-human CD89 antibodies to bind to epitopes within the EC1 domain of human CD89 expressed on the surface of HEK293F cells, was determined by FACS analysis.

Figure 15A:
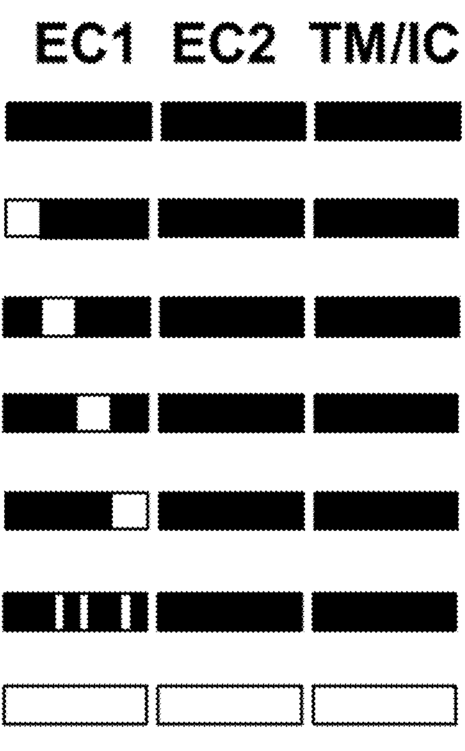
FIG. 15. (A) Schematic representation of wild type human CD89, wild type cynomolgus monkey CD89, and their derived chimeric human/cynomolgus monkey CD89 constructs. (B) Binding (n=1) of rabbit anti-human CD89 polyclonal antibodies, and of non-aggregated or heat-aggregated serum human IgA to membrane-bound human full-length CD89 ('human EC1-CD89'; i.e., ■■■), to membrane-bound chimeric human/cynomolgus monkey CD89-hotspots ('ΔThr58, Gln59; ΔArg73, Arg74, Lys76; ΔHis106, Tyr107 human EC1-CD89', i.e., ■■■), to membrane-bound chimeric human/cynomolgus monkey CD89-I ('ΔGln22-Lys46 human EC1-CD89', i.e., □■■), to membrane-bound chimeric human/cynomolgus monkey CD89-II ('ΔIle47-Ile71 human EC1-CD89', i.e., ■□■■), to membrane-bound chimeric human/cynomolgus monkey CD89-III ('AGly72-Gly96 human EC1-CD89', i.e., ■□■■), to membrane-bound chimeric human/cynomolgus monkey CD89-IV ('ΔArg97-Gly121 human EC1-CD89', i.e., ■□■), and to membrane-bound chimeric cynomolgus monkey full-length CD89 ('cynomolgus EC1-CD89', i.e., □□□) on HEK293F cells. (C) Binding (n=1) of purified CD89/IgA blocking mouse anti-human CD89 antibodies to membrane-bound human full-length CD89 ('human EC1-CD89), to membrane-bound chimeric human/cynomolgus monkey CD89-hotspots ('ΔThr58, Gln59; ΔArg73, Arg74, Lys76; ΔHis106, Tyr107 human EC1-CD89'), to membrane-bound chimeric human/cynomolgus monkey CD89-I ('ΔGln22-Lys46 human EC1-CD89'), to membrane-bound chimeric human/cynomolgus monkey CD89-II ('ΔIle47-Ile71 human EC1-CD89'), to membrane-bound chimeric human/cynomolgus monkey CD89-III ('ΔGly72-Gly96 human EC1-CD89'), to membrane-bound chimeric human/cynomolgus monkey CD89-IV ('ΔArg97-Gly121 human EC1-CD89'), and to membrane-bound chimeric cynomolgus monkey full-length CD89 ('cynomolgus EC1-CD89') on HEK293F cells. Dashed grey lines represent background (i.e., no binding of mouse anti-human CD89 antibodies).

Structurally, full-length human CD89 and full-length cynomolgus monkey CD89 are highly homologous (i.e., amino acid sequence; see also Example 4 (c) above) and are closely related to each other (Rogers et al. Immunol 2004; 113: 178-186). However, our generated CD89/IgA blocking mouse anti-human CD89 antibodies, which all recognized epitopes with the EC1 domain of human CD89 (see Example 4 (b) above), showed either no (i.e., 8F3, 9H7, 10E7, 26D6, and 20B4), weak (i.e., 30C7) or intermediate (i.e., 16D6) cross-species reactivity with the EC1 domain of cynomolgus monkey CD89 (see Example 4 (c) above). Therefore, chimeric human CD89/cynomolgus monkey CD89 receptors were designed by exchanging parts (i.e., peptides of 25 amino acids in length) from the EC1 domain of human CD89 with reciprocal counterparts from the EC1 domain of cynomolgus monkey CD89 (see also FIG. 15A) to determine the critical regions within the EC1 domain of human CD89, which are recognized by our generated CD89/IgA blocking mouse anti-human CD89 antibodies. Functionally, human CD89 and cynomolgus monkey CD89 are similar in that both human CD89 and cynomolgus monkey CD89 bind serum human IgA (see Example 4 (c) above). The following human CD89 constructs were generated and transiently expressed: (1) membrane full-length human CD89 construct, which contained the full-length EC1 domain of human CD89 (see SEQ ID NO: 1), and therefore denoted as ‘human EC1-CD89’, (2) membrane chimeric human CD89/cynomolgus monkey CD89 construct (I) consisting of Gln22-Lys46 from the EC1 domain of human CD89 exchanged for reciprocal Gln22-Arg46 from the EC1 domain of cynomolgus monkey CD89 (see SEQ ID NO: 13), and therefore denoted as ‘ΔGln22-Lys46 human EC1-CD89’, (3) membrane chimeric human CD89/cynomolgus monkey CD89 construct (II) consisting of Ile47-Ile71 from the EC1 domain of human CD89 exchanged for reciprocal Ile47-Arg71 from the EC1 domain of cynomolgus monkey CD89 (see SEQ ID NO: 15), and therefore denoted as ‘ΔIle47-Ile71 human EC1-CD89’, (4) membrane chimeric human CD89/cynomolgus monkey CD89 construct (III) consisting of Gly72-Gly96 from the EC1 domain of human CD89 exchanged for reciprocal Asp72-Gly96 from the EC1 domain of cynomolgus monkey CD89 (see SEQ ID NO: 17), and therefore denoted as ‘ΔGly72-Gly96 human EC1-CD89’, and (5) membrane chimeric human CD89/cynomolgus monkey CD89 construct (IV) consisting of Arg97-Gly121 from the EC1 domain of human CD89 exchanged for reciprocal Arg97-Gly121 from the EC1 domain of cynomolgus monkey CD89 (see SEQ ID NO: 19), and therefore denoted as ‘ΔArg97-Gly121 human EC1-CD89’. In addition, membrane full-length cynomolgus monkey CD89 construct, which contained the full-length EC1 domain of human cynomolgus monkey CD89 (see SEQ ID NO: 11), and therefore denoted as ‘cynomolgus EC1-CD89’.

In addition to exchanging EC1 domain parts of consecutive peptides of 25 amino acids in length (i.e., constructs I-IV, see above), the human IgA contacting amino acid residues (hotspots) on human CD89 (according to Herr et al, Nature 2003; 423: 614-620; Bakema et al. Immunol Rev 2011; 4: 612-624; Lu et al. Protein Sci 2014; 23: 378-386) were also exchanged for reciprocal amino acids from the EC1 domain of cynomolgus monkey CD89 (see also FIG. 15A). To this end, the following chimeric human CD89/cynomolgus monkey CD89 construct was generated and transiently expressed: membrane chimeric human CD89/cynomolgus monkey CD89 construct consisting of Thr58, Gln59, Arg73, Arg74, Lys76, His106, and Tyr107 from the EC1 domain of human CD89 exchanged for reciprocal Ile58, Trp59, Glu73, Lys74, Gly76, Leu106, and Ser107 from the EC1 domain of cynomolgus monkey CD89 (see SEQ ID NO: 21), and therefore denoted as 'ΔThr58, Gln59; ΔArg73, Arg74, Lys76; ΔHis106, Tyr107 human EC1-CD89' (hotspots).

cDNAs encoding for above-described 'human EC1-CD89', 'ΔGln22-Lys46 human EC1-CD89', 'ΔIle47-Ile71 human EC1-CD89', 'ΔGly72-Gly96 human EC1-CD89', 'ΔArg97-Gly121 human EC1-CD89', 'ΔThr58, Gln59; ΔArg73, Arg74, Lys76; ΔHis106, Tyr107 human EC1-CD89' (hotspots), and 'cynomolgus EC1-CD89' constructs were optimized for mammalian expression and synthesized by GENEART, Regensburg, Germany (see SEQ ID NO: 2, NO: 14, NO: 16, NO: 18, NO: 20, NO: 22, and NO: 12, respectively). These cDNAs were subcloned in pcDNA3.1-derived expression plasmids.

Using the FreeStyle™ 293 Expression System (Invitrogen), FreeStyle™ 293F cells (Invitrogen) were transiently transfected with 'human EC1-CD89', 'ΔGln22-Lys46 human EC1-CD89', 'ΔIle47-Ile71 human EC1-CD89', 'ΔGly72-Gly96 human EC1-CD89', 'ΔArg97-Gly121 human EC1-CD89', 'ΔThr58, Gln59; ΔArg73, Arg74, Lys76; ΔHis106, Tyr107 human EC1-CD89' (hotspots), and 'cynomolgus EC1-CD89' constructs. After 48 hours, the binding of CD89/IgA blocking mouse anti-human CD89 antibodies to aforementioned chimeric human CD89/cynomolgus monkey CD89 constructs on transfected cells was analyzed by FACS analysis. To this end, transient transfected HEK293F cells were put at $10\times10^6$ cells/mL in ice-chilled phosphate-buffered saline containing 0.1% BSA (Sigma)/0.05% $NaN_3$ (PBS/BSA/$NaN_3$) supplemented with 50 μg/mL human IgGs (blocking Fcγ receptors; Sigma) for 10 minutes at 4° C. Then, 10 μL/tube (i.e., $0.1\times10^6$ cells) of these cells were incubated with or without 100 μL purified mouse anti-human CD89 antibody at 10 μg/mL (in PBS/BSA/$NaN_3$) for 30 minutes at 4° C. In parallel, 100 μL purified mouse IgG1 isotype control (BD Biosciences) at 10 μg/mL (in PBS/BSA/$NaN_3$) was run as a negative control, and 100 μL at 10 μg/mL (in PBS/BSA/$NaN_3$) purified mouse anti-human CD89 antibody clone MIP8a (BioRad), clone A59 (BD Biosciences), and clone A3 (Santa Cruz Biotechnology) were run as positive controls. After extensive washing in PBS/BSA/$NaN_3$, cells were subsequently incubated with 1:200 diluted PE-conjugated goat anti-mouse IgG Fcγ-specific antibodies (Jackson ImmunoResearch) for 30 minutes at 4° C. After extensive washing in PBS/BSA/$NaN_3$, cells were fixed in 2% formaldehyde in PBS/BSA/$NaN_3$ for 30 minutes at 4° C. Binding of antibodies was measured using a flow cytometer (model FACSCalibur; BD Biosciences).

Apart from above-described binding of CD89/IgA blocking mouse anti-human CD89 antibodies to chimeric human CD89/cynomolgus monkey CD89 constructs, (1) membrane surface expression levels and (2) proper folding of these chimeric human CD89/cynomolgus monkey CD89 constructs were also examined on these transiently transfected cells. For this, transient transfected HEK293F cells were put at $10\times10^6$ cells/mL in ice-chilled phosphate-buffered saline containing 0.1% BSA (Sigma)/0.05% $NaN_3$ (PBS/BSA/$NaN_3$) supplemented with 50 μg/mL human IgGs (blocking Fcγ receptors; Sigma) for 10 minutes at 4° C. Then, 10 Li/tube (i.e., $0.1\times10^6$ cells) of these cells were incubated (1) with or without 100 μL purified rabbit anti-human CD89 polyclonal antibodies (Sino Biological) at 2.5 μg/mL (in PBS/BSA/$NaN_3$), and (2) with or without 100 μL purified non-aggregated or heat-aggregated human (serum-derived; see Example 2 (b) above) IgA (Bethyl Laboratories) at 10 μg/mL (diluted in PBS/BSA/$NaN_3$) for 30 minutes at 4° C. After extensive washing in PBS/BSA/$NaN_3$, binding of (1) rabbit anti-human CD89 polyclonal antibodies and of (2) non-aggregated or heat-aggregated serum human IgA on membrane human CD89 was determined with 1:200 diluted FITC-conjugated F(ab')2 fragment goat anti-rabbit IgG heavy/light chains-specific antibodies (Jackson ImmunoResearch) and with biotin-conjugated F(ab')2 fragment goat anti-human serum IgA α chain-specific antibodies (Jackson ImmunoResearch) at 5 μg/mL for 30 minutes at 4° C., respectively. After extensive washing in PBS/BSA/$NaN_3$, 1:200 diluted PE-conjugated streptavidin (Jackson ImmunoResearch) was added, and incubated for 30 minutes at 4° C. After extensive washing in PBS/BSA/$NaN_3$, cells were fixed in 2% formaldehyde in PBS/BSA/$NaN_3$ for 30 minutes at 4° C. Binding of (1) rabbit anti-human CD89 polyclonal antibodies and of (2) non-aggregated or heat-aggregated serum human IgA on membrane chimeric human CD89/cynomolgus monkey CD89 constructs were measured using a flow cytometer (model FACSCalibur; BD Biosciences).

Figure 15B:
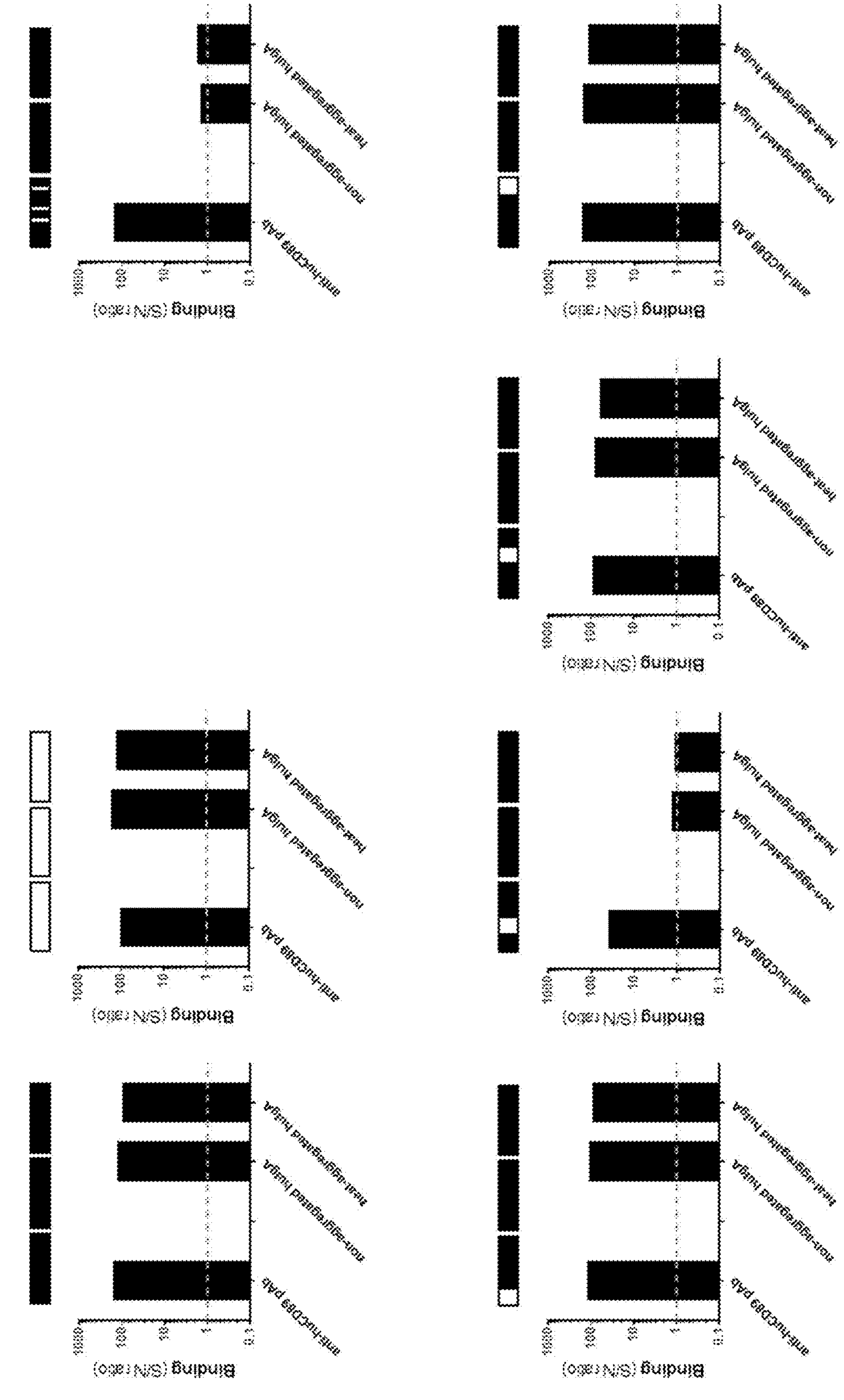

As shown in FIG. 15B, all chimeric human CD89/cynomolgus monkey CD89 constructs (i.e., 'ΔGln22-Lys46 human EC1-CD89', 'ΔIle47-Ile71 human EC1-CD89', 'ΔGly72-Gly96 human EC1-CD89', 'ΔArg97-Gly121 human EC1-CD89', and 'ΔThr58, Gln59; ΔArg73, Arg74, Lys76; ΔHis106, Tyr107 human EC1-CD89' (hotspots)), and full-length human CD89 and full-length cynomolgus monkey CD89 were expressed on the membrane surface of transiently transfected cells as evidenced by the binding of rabbit anti-human CD89 polyclonal antibodies on these cells. Furthermore, membrane-expressed chimeric human CD89/cynomolgus monkey CD89 constructs 'ΔGln22-Lys46 human EC1-CD89', 'ΔGly72-Gly96 human EC1-CD89', and 'ΔArg97-Gly121 human EC1-CD89', and full-length human CD89 and full-length cynomolgus monkey CD89 bound to both non-aggregated and heat-aggregated serum human IgA. In contrast, membrane-expressed chimeric human CD89/cynomolgus monkey CD89 constructs 'ΔIle47-Ile71 human EC1-CD89' and 'ΔThr58, Gln59; ΔArg73, Arg74, Lys76; ΔHis106, Tyr107 human EC1-CD89' (hotspots) did not show any binding to non-aggregated and to heat-aggregated serum human IgA.

These results demonstrated that serum human IgA bound to the amino acid sequence Ile47-Ile71 (i.e., IQCQAIREAYLTQLMIIKNSTYREI; see SEQ ID NO: 24) within the EC1 domain of human CD89, and that amino acid residues Thr58 and Gln59 within this Ile47-Ile71 amino acid sequence seemed critical for this serum human IgA/human CD89 interaction, since serum human IgA showed no binding to the 'ΔThr58, Gln59; ΔArg73, Arg74, Lys76; ΔHis106, Tyr107 human EC1-CD89' (hotspots) construct. For summary, see Table 7.

Figure 15C:
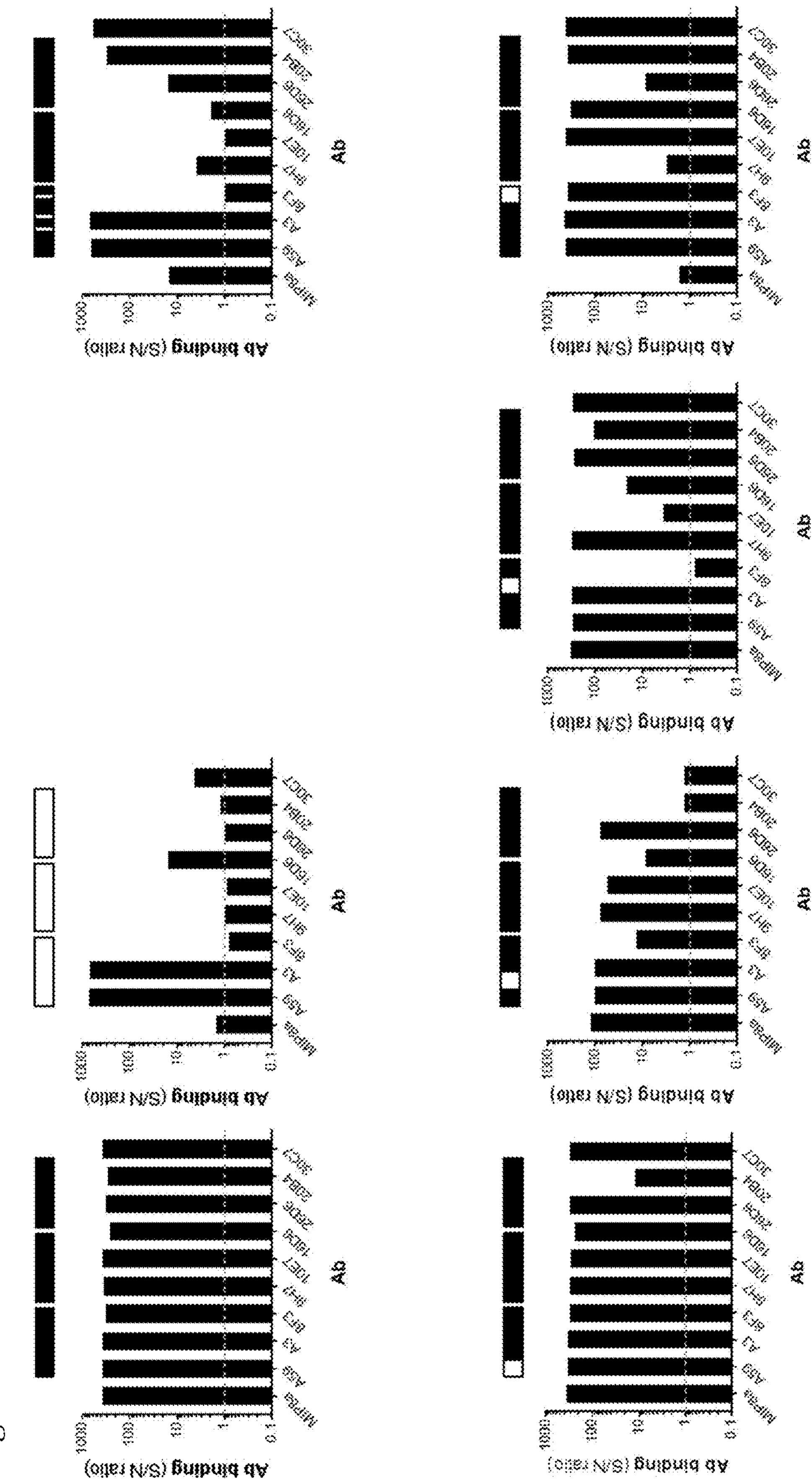

As shown in FIG. 15C, and as expected (see Example 4 (c) above), all our purified CD89/IgA blocking mouse anti-human CD89-specific antibodies (i.e., 8F3, 9H7, 10E7, 16D6, 26D6, 20B4, and 30C7) showed strong binding to full-length human CD89, but showed no (i.e., 8F3, 9H7, 10E7, 26D6, and 20B4), weak (i.e., 30C7), or intermediate (i.e., 16D6) binding to full-length cynomolgus monkey CD89. As expected (see Example 4 (c) above), commercial mouse anti-human CD89 antibody clone MIP8a also showed strong binding to full-length human CD89, but no binding to full-length cynomolgus monkey CD89. As expected (see Example 4 (c) above), commercial mouse anti-human CD89 antibody clone A59 and clone A3 showed strong binding to both full-length human CD89 and full-length cynomolgus monkey CD89. For summary, see Table 7.

As shown in FIG. 15C, our purified CD89/IgA blocking mouse anti-human CD89-specific antibody 8F3, showed strong binding to 'ΔGln22-Lys46 human EC1-CD89' and 'ΔArg97-Gly121 human EC1-CD89' constructs, but showed intermediate or no binding to 'ΔIle47-Ile71 human EC1-CD89' and 'ΔGly72-Gly96 human EC1-CD89' constructs, respectively, which indicated that mouse anti-human CD89 antibody 8F3 recognized a linear or non-linear/conformational epitope in amino acid sequences Ile47-Ile71 and Gly72-Gly96 within the EC1 domain (i.e., IQCQAIREAYLTQLMIIKNSTYREI and GRRLKFWNETDPEFVIDHMDANKAG, respectively; see SEQ ID NO: 24 and 25) of human CD89. Amino acid residues Thr58, Gln59, Arg73, Arg74, and Lys76 within these amino acid sequences Ile47-Ile71 and Gly72-Gly96 seemed critical for binding of mouse anti-human CD89 antibody 8F3 to 10 human CD89 since mouse anti-human CD89 antibody 8F3 showed no binding to the 'ΔThr58, Gln59; ΔArg73, Arg74, Lys76; ΔHis106, Tyr107 human EC1-CD89' (hotspots) construct. For summary, see Table 7.

As shown in FIG. 15C, our purified CD89/IgA blocking mouse anti-human CD89-specific antibody 9H7, showed strong binding to 'ΔGln22-Lys46 human EC1-CD89', 'ΔIle47-Ile71 human EC1-CD89', and 'ΔGly72-Gly96 human EC1-CD89' constructs, but showed weak binding to the 'ΔArg97-Gly121 human EC1-CD89' construct, which indicated that mouse anti-human CD89 antibody 9H7 recognized a linear or non-linear/conformational epitope in amino acid sequence Arg97-Gly121 (i.e., RYQCQYRIGHYRFRYSDTLELVVTG; see SEQ ID NO: 26) within the EC1 domain of human CD89. Amino acid residues His106 and Tyr107 within this amino acid sequence Arg97-Gly121 seemed critical for binding of mouse anti-human CD89 antibody 9H7 to human CD89 since mouse anti-human CD89 antibody 9H7 showed weak binding to the 'ΔThr58, Gln59; ΔArg73, Arg74, Lys76; ΔHis106, Tyr107 human EC1-CD89' (hotspots) construct. For summary, see Table 7.

As shown in FIG. 15C, our purified CD89/IgA blocking mouse anti-human CD89-specific antibody 10E7, showed strong binding to 'ΔGln22-Lys46 human EC1-CD89', 'ΔIle47-Ile71 human EC1-CD89', and 'ΔArg97-Gly121 human EC1-CD89' constructs, but showed weak binding to the 'ΔGly72-Gly96 human EC1-CD89' construct, which indicated that mouse anti-human CD89 antibody 10E7 recognized a linear or non-linear/conformational epitope in amino acid sequence Gly72-Gly96 (i.e., GRRLKFWNETDPEFVIDHMDANKAG; see SEQ ID NO: 25) within the EC1 domain of human CD89. Amino acid residues Arg73, Arg74, and Lys76 within this amino acid sequence Giy72-Gly96 seemed critical for binding of mouse anti-human CD89 antibody 10E7 to human CD89 since mouse anti-human CD89 antibody 10E7 showed no binding to the 'ΔThr58, Gln59; ΔArg73, Arg74, Lys76; ΔHis106, Tyr107 human EC1-CD89' (hotspots) construct. For summary, see Table 7.

As shown in FIG. 15C, our purified CD89/IgA blocking mouse anti-human CD89-specific antibody 16D6, showed strong binding to 'ΔGln22-Lys46 human EC1-CD89' and 'ΔArg97-Gly121 human EC1-CD89' constructs, but showed weak or intermediate binding to 'ΔIle47-Ile71 human EC1-CD89' and 'ΔGly72-Gly96 human EC1-CD89' constructs, respectively, which indicated that mouse anti-human CD89 antibody 16D6 recognized a linear or non-linear/conformational epitope in amino acid sequences Ile47-Ile71 and Gly72-Gly96 within the EC1 domain (i.e., IQCQAIREAYLTQLMIIKNSTYREI and GRRLKFWNETDPEFVIDHMDANKAG, respectively; see SEQ ID NO: 24 and 25) of human CD89. Amino acid residues Thr58, Gln59, Arg73, Arg74, and Lys76 within these amino acid sequences Ile47-Ile71 and Gly72-Gly96 seemed critical for binding of mouse anti-human CD89 antibody 16D6 to human CD89 since mouse anti-human CD89 antibody 16D6 showed no binding to the 'ΔThr58, Gln59; ΔArg73, Arg74, Lys76; ΔHis106, Tyr107 human EC1-CD89' (hotspots) construct. For summary, see Table 7.

As shown in FIG. 15C, our purified CD89/IgA blocking mouse anti-human CD89-specific antibody 26D6, showed strong binding to 'ΔGln22-Lys46 human EC1-CD89', 'ΔIle47-Ile71 human EC1-CD89', and 'ΔGly72-Gly96 human EC1-CD89' constructs, but showed weak binding to the 'ΔArg97-Gly121 human EC1-CD89' construct, which indicated that mouse anti-human CD89 antibody 26D6 recognized a linear or non-linear/conformational epitope in amino acid sequence Arg97-Gly121 (i.e., RYQCQYRIGHYRFRYSDTLELVVTG; see SEQ ID NO: 26) within the EC1 domain of human CD89. Amino acid residues His106 and Tyr107 within this amino acid sequence Arg97-Gly121 seemed critical for binding of mouse anti-human CD89 antibody 26D6 to human CD89 since mouse anti-human CD89 antibody 26D6 showed intermediate binding to the 'ΔThr58, Gln59; ΔArg73, Arg74, Lys76; ΔHis106, Tyr107 human EC1-CD89' (hotspots) construct. For summary, see Table 7.

As shown in FIG. 15C, our purified CD89/IgA blocking mouse anti-human CD89-specific antibody 20B4, showed strong binding to 'ΔGly72-Gly96 human EC1-CD89' and 'ΔArg97-Gly121 human EC1-CD89' constructs, but showed intermediate or no binding to 'ΔGln22-Lys46 human EC1-CD89' and 'ΔIle47-Ile71 human EC1-CD89' constructs, respectively, which indicated that mouse anti-human CD89 antibody 20B4 recognized a linear or non-linear/conformational epitope in amino acid sequences Gln22-Lys46 and Ile47-Ile71 within the EC1 domain (i.e., QEGDFPMPFISAKSSPVIPLDGSVK and IQCQAIREAYLTQLMIIKNSTYREI, respectively; see SEQ ID NO: 23 and 24) of human CD89. Amino acid residues Thr58 and Gln59 within the amino acid sequence Ile47-Ile71 seemed non-critical for binding of mouse anti-human CD89 antibody 20B4 to human CD89 since mouse anti-human CD89 antibody 20B4 showed strong binding to the 'ΔThr58, Gln59; ΔArg73, Arg74, Lys76; ΔHis106, Tyr107 human EC1-CD89' (hotspots) construct. For summary, see Table 7.

As shown in FIG. 15C, our purified CD89/IgA blocking mouse anti-human CD89-specific antibody 30C7, showed strong binding to 'ΔGln22-Lys46 human EC1-CD89', 'ΔGly72-Gly96 human EC1-CD89' and 'ΔArg97-Gly121 human EC1-CD89' constructs, but showed no binding to the 'ΔIle47-Ile71 human EC1-CD89' construct, which indicated that mouse anti-human CD89 antibody 30C7 recognized a linear or non-linear/conformational epitope in amino acid sequence Ile47-Ile71 within the EC1 domain (i.e., IQCQAIREAYLTQLMIIKNSTYREI, respectively; see SEQ ID NO: 24) of human CD89. Amino acid residues Thr58 and Gln59 within this amino acid sequence Ile47-Ile71 seemed non-critical for binding of mouse anti-human CD89 antibody 30C7 to human CD89 since mouse anti-human CD89 antibody 30C7 showed strong binding to the 'ΔThr58, Gln59; ΔArg73, Arg74, Lys76; ΔHis106, Tyr107 human EC1-CD89' (hotspots) construct. For summary, see Table 7.

As shown in FIG. 15C, purified well-known CD89/IgA blocking mouse anti-human CD89 antibody clone MIP8a showed strong binding to 'ΔGln22-Lys46 human EC1-CD89', 'ΔIle47-Ile71 human EC1-CD89', and 'ΔGly72-Gly96 human EC1-CD89' constructs, but showed no binding to the 'ΔArg97-Gly121 human EC1-CD89' construct, which indicated that mouse anti-human CD89 antibody clone MIP8a recognized a linear or non-linear/conformational epitope in amino acid sequence Arg97-Gly121 (i.e., RYQCQYRIGHYRFRYSDTLELVVTG; see SEQ ID NO: 26) within the EC1 domain of human CD89. Amino acid residues His106 and Tyr107 within this amino acid sequence Arg97-Gly121 seemed critical for binding of mouse anti-human CD89 antibody clone MIP8a to human CD89 since mouse anti-human CD89 antibody clone MIP8a showed intermediate binding to the 'ΔThr58, Gln59; ΔArg73, Arg74, Lys76; ΔHis106, Tyr107 human EC1-CD89' (hotspots) construct. For summary, see Table 7.

As shown in FIG. 15C, and as expected, purified well-known CD89/IgA non-blocking mouse anti-human CD89 antibody clone A59 and clone A3, which both recognize epitopes within the EC2 domain of human CD89 (see Example 4 (b) above), showed strong binding to all examined chimeric human CD89/cynomolgus monkey CD89 constructs since the human EC2 domain was not changed in any of these constructs. For summary, see Table 7.

TABLE 7

Binding of purified CD89/IgA blocking mouse anti-human CD89-specific antibodies and serum human IgA to membrane-bound chimeric human CD89/cynomolgus monkey CD89 constructs on HEK cells.
Binding of mouse anti-human CD89 antibodies and human IgA to chimeric humanCD89/cynoCD89 constructs

| | | Human CD89 exchanged for EC1 parts from cynoCD89 | | | | | |
|---|---|---|---|---|---|---|---|
| Anti-CD89 Ab | huCD89 | I (22-46) | II (47-71) | III (72-96) | IV (97-121) | hotspots | cynoCD89 |
| 8F3 | ++ | ++ | + | − | ++ | − | − |
| 9H7 | ++ | ++ | ++ | ++ | −/+ | −/+ | − |
| 10E7 | ++ | ++ | ++ | −/+ | ++ | − | − |
| 16D6 | ++ | ++ | −/+ | + | ++ | − | + |
| 26D6 | ++ | ++ | ++ | ++ | −/+ | + | − |
| 20B4 | ++ | + | − | ++ | ++ | ++ | − |
| 30C7 | ++ | ++ | − | ++ | ++ | ++ | −/+ |
| MIP8a | ++ | ++ | ++ | ++ | ++ | − | − |
| A59 | ++ | ++ | ++ | ++ | ++ | ++ | ++ |
| A3 | ++ | ++ | ++ | ++ | ++ | ++ | ++ |
| huIgA | ++ | ++ | − | ++ | ++ | − | ++ |

− = no binding of mouse anti-CD89 antibodies or human IgA to membrane chimeric humanCD89/cynoCD89 constructs,
−/+ = weak binding of mouse anti-CD89 antibodies or human IgA to membrane chimeric humanCD89/cynoCD89 constructs,
\+ = intermediate binding of mouse anti-CD89 antibodies or human IgA to membrane chimeric humanCD89/cynoCD89 constructs,
++ = strong binding of mouse anti-CD89 antibodies or human IgA to membrane chimeric humanCD89/cynoCD89 constructs.

Example 5. Molecular Genetic Characterization of CD89/IgA Blocking Mouse Anti-Human CD89 Monoclonal Antibodies Hybridoma cells producing CD89/IgA blocking mouse anti-human CD89-specific antibody 8F3, 9H7, 10E7, 16D6, 26D6, 20B4, and 30C7 were washed with PBS, and aliquoted in microvials containing $5\times10^6$ cells, and stored as pellets at −80° C. These cell pellets were used to isolate RNA by using RNeasy Mini Isolation Kit (QIAGEN). RNA concentration was determined (A260 nm), and RNA was stored at −80° C. By reverse transcriptase, cDNA was synthesized from 2 μg of RNA using the RevertAid™ H Minus First Strand cDNA Synthesis Kit (Fermentas), and stored at −80° C. Based on the isotype mouse IgG1/kappa, primers as shown in Table 8 were designed to amplify the variable (V) regions of mouse anti-human CD89-specific antibody 8F3, 9H7, 10E7, 16D6, 26D6, 20B4, and 30C7.

TABLE 8

PCR primers used to amplify cDNA of mouse anti-human CD89-specific antibody 8F3, 9H7, 10E7, 16D6, 26D6, 20B4, and 30C7.

| No.* | Sequence | s/as | Gene |
|---|---|---|---|
| 385 | ATGAGTGTGCTCACTCAGGTCCTGGSGTTG (SEQ ID NO: 103) | s | VL |
| 386 | ATGAGGRCCCCTGCTCAGWTTYTTGGMWTCTTG (SEQ ID NO: 104) | s | VL |

TABLE 8-continued

PCR primers used to amplify cDNA of mouse anti-human CD89-specific antibody 8F3, 9H7, 10E7, 16D6, 26D6, 20B4, and 30C7.

| No.* | Sequence | s/as | Gene |
|---|---|---|---|
| 387 | ATGGATTTWCAGGTGCAGATTWTCAGCTTC (SEQ ID NO: 105) | s | VL |
| 389 | ATGGGCWTCAAAGATGGAGTCACA (SEQ ID NO: 106) | s | VL |
| 391 | ATGGTRTCCWCASCTCAGTTCCTTG (SEQ ID NO: 107) | s | VL |
| 394 | ACTGGATGGTGGGAAGATGG (SEQ ID NO: 108) | as | Ck |
| 405 | ATGGGATGGAGCTRTATCATSYTCTT (SEQ ID NO: 109) | s | VH |
| 407 | ATGRACTTTGGGYTCAGCTTGRTTT (SEQ ID NO: 110) | s | VH |
| 409 | ATGGCTTGTCYTTRGSGCTRCTCTTCTGC (SEQ ID NO: 111) | s | VH |
| 410 | ATGGRATGGAGCKGGGTCTTTMTCTT (SEQ ID NO: 112) | s | VH |
| 412 | ATGGMTTGGGTGTGGAMCTTGCT (SEQ ID NO: 113) | s | VH |
| 416 | CAGTGGATAGACAGATGGGGG (SEQ ID NO: 114) | as | CH |
| 605 | AAGATGGATACAGTTGGTGC (SEQ ID NO: 115) | as | Ck |
| 609 | GASRTHSTGATGACCCAGACNCC (SEQ ID NO: 116) | s | VL |

s = sense;
as = antisense;
VL = variable light chain region;
VH = variable heavy chain region;
Ck = constant kappa (K) light chain region;
CH = constant IgG1 heavy chain region;
*Numbering according to Bioceros BV internal coding system; degenerated primers: K = G or T, S = G or C, R = A or G, M = A or C, W = A or T, Y = C or T, H = A or C or T, and N = any base.

Primers 385, 386, 387, 389, and 391 are sense primers designed to anneal with the signal peptide of the light chain of a mouse antibody; primers 394 and 605 are antisense primers annealing with the constant region of mouse κ light chain. Primer 609 is a degenerated primer annealing with mouse framework 1 (FR1) of mouse VL region. Primers 405, 407, 409, 410 and 412 are sense primers annealing with the signal peptide of the heavy chain of a mouse antibody; primer 416 is antisense primer designed to anneal with the constant region of heavy chain IgG1. Various PCRs were done using primer combinations shown in Table 8. Generated PCR products were subcloned in pCR™-Blunt II-TOPO® vector. Subsequently, cloned inserts were sequenced.

A total of 4 and 5 informative sequences from the heavy chain and light chain sequence reactions, respectively, were obtained of CD89/IgA blocking mouse anti-human CD89-specific antibody 8F3. Based on this information, consensus amino acid sequences of VH and VL regions of mouse anti-human CD89 antibody 8F3 were determined, and are set forth in SEQ ID NO: 27 and 28, respectively. The amino acid sequences of the CDRs of VH and VL regions of mouse anti-human CD89 antibody 8F3 are set forth in SEQ ID NO: 29-31 and 32-34, respectively.

A total of 4 informative sequences from both the heavy chain and light chain sequence reactions were obtained of CD89/IgA blocking mouse anti-human CD89-specific antibody 9H7. Based on this information, consensus amino acid sequences of VH and VL regions of mouse anti-human CD89 antibody 9H7 were determined, and are set forth in SEQ ID NO: 35 and 36, respectively. The amino acid sequences of the CDRs of VH and VL regions of mouse anti-human CD89 antibody 9H7 are set forth in SEQ ID NO: 37-39 and 40-42, respectively.

A total of 4 informative sequences from both the heavy chain and light chain sequence reactions were obtained of CD89/IgA blocking mouse anti-human CD89-specific antibody 10E7. Based on this information, consensus amino acid sequences of VH and VL regions of mouse anti-human CD89 antibody 10E7 were determined, and are set forth in SEQ ID NO: 43 and 44, respectively. The amino acid sequences of the CDRs of VH and VL regions of mouse anti-human CD89 antibody 10E7 are set forth in SEQ ID NO:45-47 and 48-50, respectively.

A total of 4 informative sequences from both the heavy chain and light chain sequence reactions were obtained of CD89/IgA blocking mouse anti-human CD89-specific antibody 16D6. Based on this information, consensus amino acid sequences of VH and VL regions of mouse anti-human CD89 antibody 16D6 were determined, and are set forth in SEQ ID NO: 51 and 52, respectively. The amino acid sequences of the CDRs of VH and VL regions of mouse anti-human CD89 antibody 16D6 are set forth in SEQ ID NO: 53-55 and 56-58, respectively.

A total of 4 informative sequences of both the heavy chain and light chain sequence reactions were obtained from CD89/IgA blocking mouse anti-human CD89-specific antibody 26D6. Based on this information, consensus amino acid sequences of VH and VL regions of mouse anti-human CD89 antibody 26D6 were determined, and are set forth in SEQ ID NO: 59 and 60, respectively. The amino acid sequences of the CDRs of VH and VL regions of mouse anti-human CD89 antibody 26D6 are set forth in SEQ ID NO: 61-63 and 64-66, respectively.

A total of 4 and 6 informative sequences from the heavy chain and light chain sequence reactions, respectively, were obtained of CD89/IgA blocking mouse anti-human CD89-specific antibody 20B4. Based on this information, consensus amino acid sequences of VH and VL regions of mouse anti-human CD89 antibody 20B4 were determined, and are set forth in SEQ ID NO: 67 and 68, respectively. The amino acid sequences of the CDRs of VH and VL regions of mouse anti-human CD89 antibody 20B4 are set forth in SEQ ID NO: 69-71 and 72-74, respectively.

A total of 4 informative sequences from both the heavy chain and light chain sequence reactions were obtained of CD89/IgA blocking mouse anti-human CD89-specific antibody 30C7. Based on this information, consensus amino acid sequences of VH and VL regions of mouse anti-human CD89 antibody 30C7 were determined, and are set forth in SEQ ID NO: 75 and 76, respectively. The amino acid sequences of the CDRs of VH and VL regions of mouse anti-human CD89 antibody 30C7 are set forth in SEQ ID NO: 77-79 and 80-82, respectively.

Example 6. Generation of CD89/IgA Blocking Chimeric Mouse/Human IgG4/Kappa (i.e., Exchanging Mouse Constant IgG1/Kappa Domains for Constant Human IgG4/Kappa Domains) Anti-Human CD89 Monoclonal Antibodies Based on determined mouse V-regions (see Example 5 above) of CD89/IgA blocking mouse anti-human CD89 antibodies, a design was made to generate CD89/IgA blocking chimeric mouse/human anti-human CD89 antibody versions. To this end, *Cricetulus griseus*-optimized cDNA sequences, SEQ ID NO: 83 (coding for chimeric mouse/human heavy IgG4 chain 8F3), NO: 84 (coding for chimeric mouse/human heavy IgG4 chain 10E7), NO: 85 (coding for chimeric mouse/human heavy IgG4 chain 16D6), NO: 86 (coding for chimeric mouse/human heavy IgG4 chain 20B4), and NO: 87 (coding for chimeric mouse/human heavy IgG4 chain 30C7), and SEQ ID NO: 88 (coding for chimeric mouse/human light κ chain 8F3), NO: 89 (coding for chimeric mouse/human light κ chain 10E7), NO: 90 (coding for chimeric mouse/human light κ chain 16D6), NO: 91 (coding for chimeric mouse/human light κ chain 20B4), and NO: 92 (coding for chimeric mouse/human light κ chain 30C7), were ordered at GENEART (Regensburg, Germany), which encoded a human signal peptide followed by either the mouse VH chain linked to the human stabilized (i.e., S239P; according Angal et al in Mol. Immunol., Vol. 30, No. 1, pp. 105-108, 1993) IgG4 constant region, or followed by the mouse VL chain linked to the human kappa constant region. Using suitable restriction enzymes, generated cDNAs were subcloned in pcDNA3.1-derived expression plasmids. Chimeric antibodies were subsequently transiently expressed in 293-F cells (Invitrogen) using the FreeStyle™ 293 Expression System (Invitrogen). Expressed CD89/IgA blocking chimeric anti-human CD89 antibodies were purified from supernatants using conventional affinity chromatography protein A columns. After this, LPS levels were determined using the LAL chromogenic endpoint assay (Hycult Biotech), and all our purified CD89/IgA blocking chimeric mouse/human anti-human CD89-specific antibodies (i.e., 8F3, 10E7, 16D6, 20B4, and 30C7) contained <0.001 EU LPS/μg chimeric IgG.

For chimeric amino acid sequences, see SEQ ID NO: 93 (chimeric mouse/human heavy IgG4 chain 8F3), SEQ ID NO: 94 (chimeric mouse/human heavy IgG4 chain 10E7), SEQ ID NO: 95 (chimeric mouse/human heavy IgG4 chain 16D6), SEQ ID NO: 96 (chimeric mouse/human heavy IgG4 chain 20B4), SEQ ID NO: 97 (chimeric mouse/human heavy IgG4 chain 30C7), SEQ ID NO: 98 (chimeric mouse/human light κ chain 8F3), SEQ ID NO: 99 (chimeric mouse/human light κ chain 10E7), SEQ ID NO: 100 (chimeric mouse/human light κ chain 16D6), SEQ ID NO: 101 (chimeric mouse/human light κ chain 20B4), and SEQ ID NO: 102 (chimeric mouse/human light κ chain 30C7).

Example 7. Binding Characterization of CD89/IgA Blocking Chimeric Mouse/Human Anti-Human CD89 Antibodies (a). Relative Binding Affinity of CD89/IgA Blocking Chimeric Mouse/Human Anti-Human CD89 Antibodies for Human CD89

In order to determine the relative binding affinity of purified CD89/IgA blocking chimeric mouse/human anti-human CD89 antibodies for human CD89, ELISA and FACS analysis were used.

ELISA: rhuCD89 (Sino Biological) was coated at 0.5 μg/mL in PBS (25 ng/50 μL/well) using half-area 96-wells EIA plates (Corning) during 16-24 hours at 4-8° C. After extensive washing with PBS/0.05% Tween 20, plates were blocked with PBS/0.05% Tween 20/1% BSA (Roche) for 1 hour at RT. Subsequently, plates were incubated with and without 50 μL titrated (in block buffer) purified chimeric mouse/human anti-human CD89 antibody/well for 1 hour at RT. After extensive washing in PBS/0.05% Tween 20, binding of antibodies on rhuCD89 was determined with 1:5,000 diluted horseradish peroxidase (HRP)-conjugated goat anti-human IgG Fcγ-specific antibodies (Jackson ImmunoResearch) for 1 hour at RT, followed by a ready-to-use solution of TMB substrate (Invitrogen) for colorimetric detection. After adding 1 M $H_2SO_4$, binding (optical density) of antibodies on rhuCD89 was measured at wavelength of 450 nm (reference wavelength of 655 nm) using a microplate reader (iMark; BioRad). For comparison, mouse anti-human CD89 antibody counterparts were run in parallel, and their binding was monitored as described in Example 2 (a).

FACS: stable human full-length CD89-transfected HEK293F cells (clone no. 2; see above Example 1(b) above) were put at $10\times10^6$ cells/mL in ice-chilled PBS containing 0.1% BSA (Sigma)/0.05% $NaN_3$ (PBS/BSA/$NaN_3$) supplemented with 50 μg/mL human IgGs (blocking possible Fcγ receptors; Sigma) for 10 minutes at 4° C. Then, 10 μL/tube (i.e., $0.1\times10^6$ cells) of these cells were incubated with or without 100 μL titrated (in PBS/BSA/$NaN_3$) purified chimeric mouse/human anti-human CD89 antibody/tube for 30 minutes at 4° C. In parallel, 100 μL purified human IgG4 isotype control antibody (Opdivo®; Bristol-Myers Squibb) at 10 μg/mL (in PBS/BSA/$NaN_3$) was run as a negative control. After extensive washing in PBS/BSA/$NaN_3$, cells were subsequently incubated with 1:200 diluted PE-conjugated goat anti-human IgG Fey-specific antibodies (Jackson ImmunoResearch) for 30 minutes at 4° C. After extensive washing in PBS/BSA/$NaN_3$, cells were fixed in 2% formaldehyde in PBS/BSA/$NaN_3$ for 30 minutes at 4° C. Binding (geo-mean fluorescence intensity) of antibodies on membrane human CD89 was measured using a flow cytometer (FACSCalibur; BD Biosciences). For comparison, mouse anti-human CD89 antibody counterparts were run in parallel, and their binding was monitored as described in Example 2 (a).

As shown in FIG. 16A, all purified CD89/IgA blocking chimeric mouse/human anti-human CD89-specific antibodies dose-dependently bound to rhuCD89. Based on their binding profile, the following relative affinity ranking was found (from high to lower affinity): 20B4>8F3=10E7=30C7>16D6. For comparison and in agreement, their mouse anti-human CD89 antibody counterparts showed a similar relative affinity ranking, i.e., 20B4>8F3=10E7=30C7>16D6. More specifically, chimeric mouse/human anti-human CD89 antibody 20B4, 8F3, 10E7, 30C7, and 16D6 resulted in the following relative affinities (i.e., half-maximum binding EC50) of 9, 31, 16, 22, and 108 ng/mL, respectively, while corresponding mouse anti-human CD89 antibody 20B4, 8F3, 10E7, 30C7, and 16D6 resulted in relative affinities of 13, 52, 20, 29, and 119 ng/mL, respectively, which indicated that binding affinities of chimeric mouse/human anti-human CD89 antibody 20B4, 8F3, 10E7, 30C7, and 16D6 against rhuCD89 seemed to remain unaltered during the chimerization process.

As shown in FIG. 16B, all purified CD89/IgA blocking chimeric mouse/human anti-human CD89-specific antibodies dose-dependently bound to membrane human CD89. Based on their binding profile, the following relative affinity ranking was found (from high to lower affinity): 20B4>30C7>8F3=10E7>16D6. For comparison, their mouse anti-human CD89 antibody counterparts showed a slightly different relative affinity ranking, i.e., 20B4>8F3=10E7=30C7>16D6. More specifically, chimeric mouse/human anti-human CD89 antibody 20B4, 8F3, 10E7, 30C7, and 16D6 resulted in the following relative affinities (i.e., half-maximum binding EC50) of 296, 1321, 1251, 615, and 1789 ng/mL, respectively, while corresponding mouse anti-human CD89 antibody 20B4, 8F3, 10E7, 30C7, and 16D6 resulted in relative affinities of 260, 714, 637, 484, and 1622 ng/mL, respectively, which indicated (1) that binding affinities of chimeric mouse/human mouse anti-human CD89 antibody 20B4, 30C7, and 16D6 against membrane-bound CD89 seemed to remain unaltered during the chimerization process, and (2) that binding affinities of chimeric mouse/human mouse anti-human CD89 antibody 8F3 and 10E7 against membrane-bound CD89 seemed to be slightly decreased during the chimerization process.

(b). Degree of CD89/IgA Blocking Capacity of CD89/IgA Blocking Chimeric Mouse/Human Anti-Human CD89 Antibodies In order to analyze the degree of CD89/IgA blocking of purified chimeric mouse/human anti-human CD89 antibodies, the ability of purified CD89/IgA blocking chimeric mouse/human anti-human CD89 antibodies to sterically hinder the interaction of serum human IgA with human CD89 was determined by using FACS analysis.

Stable human full-length CD89-transfected HEK293F cells (clone no. 2; see above Example 1 (b) above) were put at $10\times10^6$ cells/mL in ice-chilled PBS containing 0.1% BSA (Sigma)/0.05% $NaN_3$ (PBS/BSA/$NaN_3$) supplemented with 50 μg/mL human IgGs (blocking possible Fcγ receptors; Sigma) for 10 minutes at 4° C. Then, 10 μL/tube (i.e., $0.1\times10^6$ cells) of these cells were incubated with 50 μL titrated (in PBS/BSA/$NaN_3$) purified chimeric mouse/human anti-human CD89 antibody/tube for 30 minutes at 4° C. In parallel, 50 μL titrated (in PBS/BSA/$NaN_3$) purified mouse anti-human CD89 antibody clone MIP8a (a well-known CD89/IgA blocker (Zhang et al. Clin Exp Immunol 2000; 121: 106-111), BioRad) was run as a positive control. Moreover, 50 μL purified mouse anti-human CD89 antibody clone A59 (a well-known CD89/IgA non-blocker (Monteiro et al. J Immunol 1992; 148: 1764-1770); BD Biosciences) at 20 μg/mL (in PBS/BSA/$NaN_3$) and 50 μL purified mouse anti-human CD89 antibody clone A3 (a well-known CD89/IgA non-blocker (Monteiro et al. J Immunol 1992; 148: 1764-1770); Santa Cruz Biotechnology) at 20 μg/mL (in PBS/BSA/$NaN_3$) were run as negative controls. After this (i.e., without washing), 50 μL purified non-aggregated or heat-aggregated ((see Example 2 (b) above) human (serum-derived) IgA (Bethyl Laboratories) at 20 μg/mL (diluted in PBS/BSA/$NaN_3$) was added to these cells, and incubated for another 30 minutes at 4° C. After extensive washing in PBS/BSA/$NaN_3$, binding of serum human IgA on membrane human CD89 was determined with biotin-conjugated F(ab')2 fragment goat anti-human serum IgA α chain-specific antibodies (Jackson ImmunoResearch) at 5 μg/mL for 30 minutes at 4° C. After extensive washing in PBS/BSA/$NaN_3$, 1:200 diluted PE-conjugated streptavidin (Jackson ImmunoResearch) was added, and incubated for 30 minutes at 4° C. After extensive washing in PBS/BSA/$NaN_3$, cells were fixed in 2% formaldehyde in PBS/BSA/$NaN_3$ for 30 minutes at 4° C. Binding (geo-mean fluorescence intensity) of non-aggregated or heat-aggregated serum human IgA on membrane human CD89 was measured using a flow cytometer (FACSCalibur; BD Biosciences).

As shown in FIGS. 17A and 17B, all purified CD89/IgA blocking chimeric mouse/human anti-human CD89-specific antibodies dose-dependently prevented non-aggregated and heat-aggregated serum human IgA binding to membrane human CD89. Based on their CD89/IgA blocking profile, the following ranking was found (from a strong to a lower CD89/IgA blocking degree): 20B4>30C7>8F3=10E7>16D6. Interestingly, there seemed to be a strong positive relationship between the degree of these examined chimeric mouse/human anti-human CD89 antibodies to sterically block serum human IgA binding to membrane human CD89 (this example) and their respective relative binding affinity for membrane human CD89 (see Example 7 (a) above). For reference purposes, mouse anti-human CD89 antibody clone MIP8a, a well-known CD89/IgA blocker (Zhang et al. Clin Exp Immunol 2000; 121: 106-111), was run in parallel, and also showed dose dependent blocking of the binding of serum human IgA to membrane human CD89. In addition, mouse anti-human CD89-specific antibodies clone 59 and A3 dose-dependently and partially inhibited (i.e., ~60% maximum inhibition) non-aggregated and heat-aggregated serum human IgA binding to membrane human CD89, which confirmed our previous results using these two well-known CD89/IgA non-blockers (see Examples 2 (d) above).

In order to analyze the degree of CD89/IgA blocking of purified chimeric mouse/human anti-human CD89 antibodies, the ability of purified CD89/IgA blocking chimeric mouse/human anti-human CD89 antibodies to sterically hinder the interaction of secretory human IgA with human CD89 was determined by using FACS analysis.

Stable human full-length CD89-transfected HEK293F cells (clone no. 2; see above Example 1 (b) above) were put at $10\times10^6$ cells/mL in ice-chilled PBS containing 0.1% BSA (Sigma)/0.05% $NaN_3$ (PBS/BSA/$NaN_3$). Then, 10 μL/tube (i.e., $0.1\times10^6$ cells) of these cells were incubated with or without 50 μL titrated (in PBS/BSA/$NaN_3$) purified chimeric mouse/human anti-human CD89 antibody/tube for 30 minutes at 4° C. In parallel, 50 μL titrated (in PBS/BSA/$NaN_3$) purified mouse anti-human CD89 antibody clone MIP8a (BioRad) was run as a positive control. After this (i.e., without washing), 50 μL purified human (colostrum-derived) IgA (BioRad) at 0.20 μM (diluted in PBS/BSA/$NaN_3$) was added to these cells, and incubated for another 30 minutes at 4° C. After extensive washing in PBS/BSA/$NaN_3$, binding of secretory human IgA on membrane human CD89 was determined with biotin-conjugated F(ab')2 fragment goat anti-human serum IgA α chain-specific antibodies (Jackson ImmunoResearch) at 5 μg/mL for 30 minutes at 4° C. After extensive washing in PBS/BSA/$NaN_3$, 1:200 diluted PE-conjugated streptavidin (Jackson ImmunoResearch) was added, and incubated for 30 minutes at 4° C. After extensive washing in PBS/BSA/$NaN_3$, cells were fixed in 4% formaldehyde in PBS/BSA/$NaN_3$ for 30 minutes at 4° C. Binding (geo-mean fluorescence intensity) of secretory human IgA on membrane human CD89 was measured using a flow cytometer (FACSCalibur; BD Biosciences).

Figure 17C:
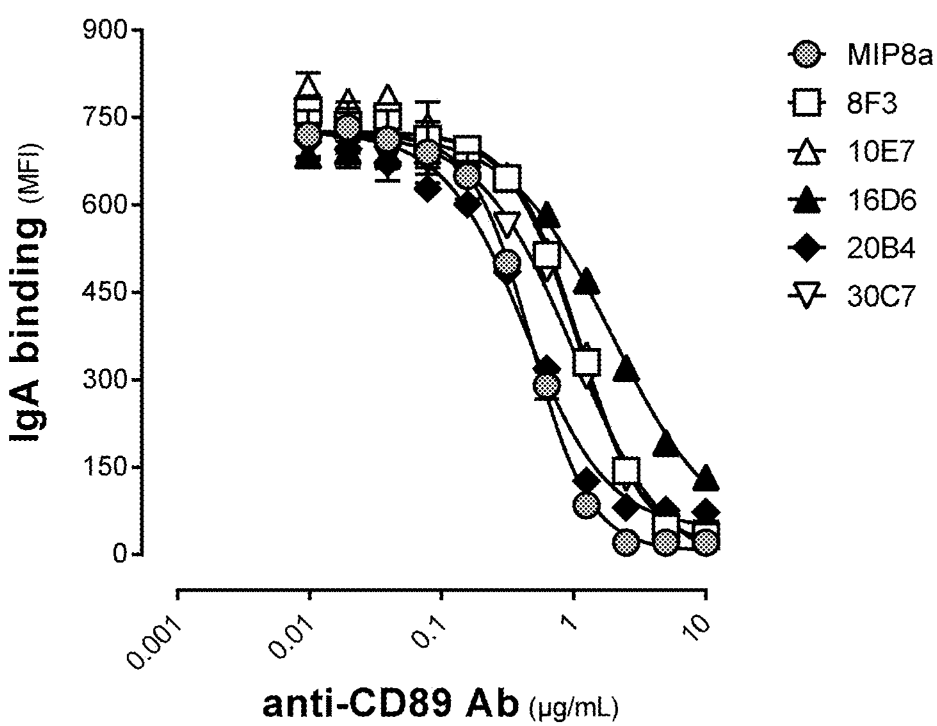
FIG. 17. Effect of purified CD89/IgA blocking chimeric mouse/human anti-human CD89 antibodies on binding of non-aggregated (A) or heat-aggregated (B) serum human IgA to membrane-bound human CD89 on HEK293F cells. Effect of purified CD89/IgA blocking chimeric mouse/human anti-human CD89 antibodies on binding of secretory human IgA to membrane-bound human CD89 (C) on HEK293F cells. Mean f SD (n=2) are shown.

As shown in FIG. 17C, all purified CD89/IgA blocking chimeric mouse/human anti-human CD89-specific antibodies dose-dependently prevented secretory human IgA binding to membrane human CD89. Based on their CD89/IgA blocking profile, the following ranking was found (from a strong to a lower CD89/IgA blocking degree): 20B4>30C7>8F3=10E7>16D6, which was in agreement with the CD89/IgA blocking degree using serum human IgA found in FACS (see FIGS. 17A and 17B). Interestingly, there seemed to be a strong positive relationship between the degree of these examined purified mouse anti-human CD89 antibodies to sterically block secretory human IgA binding to membrane human CD89 (this example) and their respective relative binding affinity for membrane human CD89 (see Example 7 (a) above). For reference purposes, purified mouse anti-human CD89 antibody clone MIP8a, a well-known CD89/IgA blocker (Zhang et al. Clin Exp Immunol 2000; 121: 106-111), was run in parallel, and also showed dose dependent blocking of the binding of secretory human IgA to membrane human CD89.

Collectively, these results demonstrated that CD89/IgA blocking chimeric mouse/human anti-human CD89-specific antibody 8F3, 10E7, 16D6, 20B4, and 30C7 prevented the binding of monomeric, dimeric, trimeric, tetrameric or higher-order of multimeric serum human IgA (i.e., non-aggregated and heat-aggregated IgA) and dimeric secretory human IgA to membrane human CD89.

Example 8. Biological Characterization of CD89/IgA Blocking Chimeric Mouse/Human Anti-Human CD89 Monoclonal Antibodies Using Ex Vivo Human CD89 Expressing Primary Human Neutrophilic Granulocytes (a). Binding of CD89/IgA Blocking Chimeric Mouse/Human Anti-Human CD89 Antibodies on Human CD89 Expressing Primary Human Neutrophilic Granulocytes In order to determine the binding of purified CD89/IgA blocking chimeric mouse/human anti-human CD89 antibodies on human CD89 expressing primary human neutrophilic granulocytes, FACS analysis was used.

Primary human neutrophilic granulocytes were isolated from healthy donor (after informed consent) peripheral blood using Lymphoprep™ (Axis-Shield) gradient centrifugation followed by lysis of erythrocytes in a $NH_4Cl$ lysis buffer solution—After washing in PBS, granulocytes were put at $10\times10^6$ cells/mL in ice-chilled PBS containing 0.1% BSA (Sigma-Aldrich; PBS/BSA) supplemented with 50 μg/mL human IgGs (blocking possible Fcγ receptors; Sigma-Aldrich) for 10 minutes at 4° C. Then, 10 Li/tube (i.e., $0.1\times10^6$ cells) of these cells were incubated with or without 100 μL chimeric mouse/human anti-human CD89-specific antibody (i.e., 8F3, 10E7, 16D6, 20B4, and 30C7) at 10 μg/mL (in PBS/BSA) for 30 minutes at 4° C. In parallel, 100 μL purified human IgG4 isotype control antibody (Opdivo®; Bristol-Myers Squibb) at 10 μg/mL (in PBS/BSA) was run as a negative control. After extensive washing in PBS/BSA, cells were subsequently incubated with 1:100 diluted fluorescein isothiocyanate-conjugated mouse anti-human IgG4-specific antibodies (Sigma-Aldrich) for 30 minutes at 4° C. After extensive washing in PBS/BSA, cells were fixed in 2% formaldehyde in PBS/BSA for 30 minutes at 4° C. Binding (geo-mean fluorescence intensity) of antibodies on membrane human CD89 from ex vivo human neutrophilic granulocytes was measured using a flow cytometer (Cyan; BeckmanCoulter).

Figure 18:
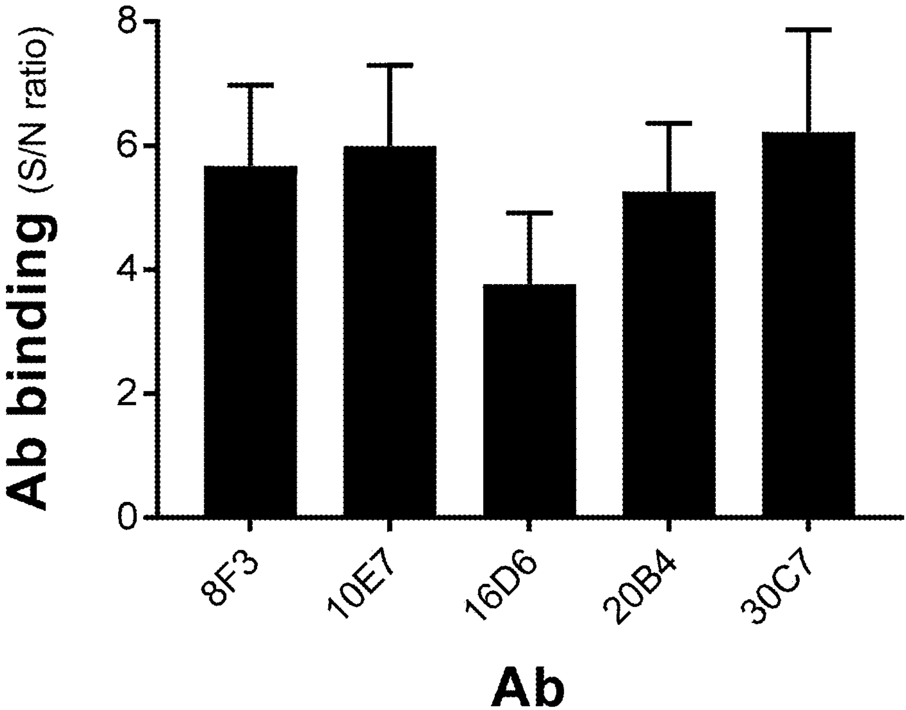
FIG. 18. Binding of purified CD89/IgA blocking chimeric mouse/human anti-human CD89 antibodies (at 10 μg/mL) to membrane-bound human CD89 on ex vivo human neutrophilic granulocytes (Mean±SD from 3 different healthy donors).

As shown in FIG. 18, all our purified CD89/IgA blocking chimeric mouse/human anti-human CD89 antibodies (at 10 μg/mL) bound to membrane human CD89 from ex vivo human neutrophilic granulocytes isolated from multiple donors (n=3). Based on their binding profile on neutrophilic granulocytes, the following ranking was found (from high to lower binding intensity): 8F3=10E7=30C7=20B4>16D6

These results also demonstrated that our CD89/IgA blocking chimeric mouse/human anti-human CD89 antibody 8F3, 10E7, 16D6, 20B4, and 30C7 recognized non-polymorphic epitopes on membrane human CD89 from ex vivo human neutrophilic granulocytes, because these antibodies unambiguously bound to human neutrophilic granulocytes isolated from all 3 examined donors.

(b). Blocking Serum Human IgA-Mediated Phagocytosis by Human CD89 Expressing Primary Human Neutrophilic Granulocytes Using CD89/IgA Blocking Chimeric Mouse/Human Anti-Human CD89 Monoclonal Antibodies In order to analyze the biological activity of purified CD89/IgA blocking chimeric mouse/human anti-human CD89 antibodies, the ability of generated CD89/IgA blocking chimeric mouse/human anti-human CD89 antibodies to inhibit phagocytosis of serum human IgA-coated latex beads by human CD89 expressing primary human neutrophilic granulocytes was determined.

Primary human neutrophilic granulocytes were isolated from healthy donors (after informed consent) peripheral blood using Lymphoprep™ (Axis-Shield) gradient centrifugation followed by lysis of erythrocytes in a $NH_4Cl$ lysis buffer solution. After washing in PBS, granulocytes were resuspended at $2.0\times10^6$ cells/mL in RPMI 1640 (Gibco) supplemented with 10% heat-inactivated FCS (Sigma-Aldrich). Then, 100 μL/well (i.e., $0.2\times10^6$ cells in 96-wells flat-bottom plates; Greiner) of these cells were incubated with titrated (in RPMI/10% FCS) purified chimeric mouse/human anti-human CD89 antibody (i.e., 8F3, 10E7, 16D6, 20B4, and 30C7) for 20 minutes at 4° C. After this (i.e., without washing), 1.2 μL purified human (serum-derived)

IgA (MP Biomedicals)-coated fluorescent latex beads (1 μm-sized and carboxylate-modified polystyrene; Sigma-Aldrich) at a cell-to-bead ratio of 1:60 were added to these cells (preparation IgA-beads, see Aleyd et al. J Immunol 2014; 192: 2374-2383), and incubated for another 30 minutes at 37° C. In parallel, BSA (Sigma-Aldrich)-coated fluorescent latex beads at a cell-to-bead ratio of 1:60 were run as a negative control (preparation BSA-beads, see Aleyd et al. J Immunol 2014; 192: 2374-2383). After washing in RPMI/10% FCS and resuspension in PBS/0.1% BSA (Sigma-Aldrich), serum human IgA-mediated phagocytosis of fluorescent latex beads (geo-mean fluorescence intensity used to calculate phagocytic index according to Aleyd et al. J Immunol 2014; 192: 2374-2383) by membrane human CD89 on ex vivo human neutrophilic granulocytes was measured using a flow cytometer (Cyan; Beckman Coulter). For comparison, commercial mouse anti-human CD89 antibodies clone MIP8a, clone A59 and clone A3 were run in parallel, like described in Example 3 (b).

As shown in FIG. 19, all purified CD89/IgA blocking chimeric mouse/human anti-human CD89-specific antibodies dose-dependently inhibited serum human IgA-mediated phagocytosis in membrane human CD89 expressing ex vivo primary human neutrophilic granulocytes isolated from three healthy individuals, although some donor-to-donor variation was observed. Based on their degree of serum human IgA-mediated phagocytosis inhibition, the following ranking was found (from a strong to a lower IgA-mediated phagocytosis inhibitory degree): 8F3=10E7=30C7>20B4>16D16.

These results demonstrated that CD89/IgA blocking chimeric mouse/human anti-human CD89-specific antibody 8F3, 10E7, 16D6, 20B4, and 30C7 inhibited serum human IgA-mediated phagocytotic activity of membrane human CD89 expressing ex vivo primary human neutrophilic granulocytes.

(c). Blocking Serum Human IgA-Mediated Migration of, Serum Human IgA-Mediated Chemotaxis of, and Serum Human IgA-Mediated Leukotriene B4 Production from Human CD89 Expressing Primary Human Neutrophilic Granulocytes Using CD89/IgA Blocking Chimeric Mouse/Human Anti-Human CD89 Monoclonal Antibodies In order to analyze the biological activity of purified CD89/IgA blocking chimeric mouse/human anti-human CD89 antibodies, the ability of generated CD89/IgA blocking chimeric mouse/human anti-human CD89 antibodies to inhibit (1) serum human IgA-mediated migration of, (2) serum human IgA-mediated chemotaxis of, and (3) serum human IgA-mediated neutrophil-chemoattractant leukotriene B4 (LTB4) production from human CD89 expressing primary human neutrophilic granulocytes were determined.

Two-dimensional (2-D) migration assay: primary human neutrophilic granulocytes were isolated from healthy donors (after informed consent) peripheral blood using Lymphoprep™ (Axis-Shield) gradient centrifugation followed by lysis of erythrocytes in a $NH_4Cl$ lysis buffer solution. Then, these primary human neutrophilic granulocytes were labeled with 1 μM fluorescent calcein-AM (Molecular Probes) for 30 minutes at 37° C. After washing, these calcein AM-labeled granulocytes were resuspended at $2.5\times10^6$ cells/mL in RPMI 1640 (Gibco) supplemented with 10% heat-inactivated FCS (Sigma-Aldrich), and subsequently 100 μL calcein AM-labeled granulocytes (i.e., $0.25\times10^6$ cells/well in 96-wells flat-bottom plates; Greiner) were incubated with 20 μg/mL (in RPMI/10% FCS) purified chimeric mouse/human anti-human CD89 antibody (i.e., 8F3, 10E7, 16D6, 20B4, and 30C7) for 20 minutes at 4° C. In parallel, 20 μg/mL (in RPMI/10% FCS) purified human IgG4 isotype control (Sigma-Aldrich) was run as a negative control. After this, 150 μL RPMI/10% FCS per well was added, and cells were left for 10 minutes to become monolayers again. After this (i.e., without washing), 10 μL purified human (serum-derived) IgA (MP Biomedicals)-coated Sepharose 4B beads (90 m-sized and cyanogen bromide-activated; GE Healthcare) were gently added to these monolayers of cells (preparation 3 μg/mL IgA-beads, see Van der Steen et al. Gastroentorol 2009; 137: 2018-2029), and incubated for another 40 minutes at 37° C. In parallel, BSA (Sigma-Aldrich)-coated Sepharose 4B beads were run as a negative control (preparation 3 μg/mL BSA-beads, see Van der Steen et al. Gastroentorol 2009; 137: 2018-2029). Then, supernatants were collected and used for the chemotaxis assay and LBT4 ELISA (see below), and Sepharose beads were washed to remove non-bound/non-migrated calcein AM-labeled granulocytes. Subsequently, granulocytes were lysed in a 0.2% (w/v) hexadecyltrimethylammonium bromide (Sigma-Aldrich) buffer for 30 minutes at RT, and released calcein AM (reflecting the number of IgA-bound/migrated granulocytes) was measured in 96-wells flat-bottom plates (Greiner) using a fluorometer (FLUOstar/POLARstar; BMG Labtech). The number of IgA-bound/migrated ex vivo human neutrophilic granulocytes was quantified by using a standard curve with known numbers of lysed calcein AM-labeled granulocytes (i.e., 0-$0.3\times10^6$ cells/well). For comparison, commercial mouse anti-human CD89 antibodies clone MIP8a, clone A59 and clone A3 were run in parallel, like described in Example 3 (c).

Chemotaxis assay: primary human neutrophilic granulocytes were isolated from healthy donors (after informed consent) peripheral blood using Lymphoprep™ (Axis-Shield) gradient centrifugation followed by lysis of erythrocytes in a $NH_4Cl$ lysis buffer solution. Then, these primary human neutrophilic granulocytes were labeled with 1 μM fluorescent calcein-AM (Molecular Probes) for 30 minutes at 37° C. After washing, these calcein AM-labeled granulocytes were resuspended at $1.0\times10^6$ cells/mL in RPMI 1640 (Gibco) supplemented with 10% heat-inactivated FCS (Sigma-Aldrich). To measure chemotaxis, wells of the lower compartment of the Boyden chamber (Neuro Probe) were filled with 29 μL of supernatants from IgA-coated Sepharose bead-stimulated primary human neutrophilic granulocytes (i.e., from another healthy donor, see above). In parallel, RPMI/10% FCS medium only and purified 1 or 10 nM LTB4 (in RPMI; Sigma-Aldrich) were run as negative and positive controls, respectively. Subsequently, the lower compartment was covered with a 3 m pore-sized polyvinylpyrrolidone-coated polycarbonate filter (Neuro Probe), followed by assembly of the upper compartment onto the lower compartment of the Boyden chamber. After this, 50 μL calcein AM-labeled granulocytes (i.e., $0.05\times10^6$ cells/well) was added in wells of the upper compartment. After incubation for 40 minutes at 37° C., chemotaxis of ex vivo human neutrophilic granulocytes from the upper compartment towards wells of the lower compartment was determined. For this, granulocytes in the lower compartment were lysed in a 0.1% (w/v) hexadecyltrimethylammonium bromide (Sigma-Aldrich) buffer for 30 minutes at RT, and released calcein AM (reflecting the number of chemotactic granulocytes) was measured in 96-wells flat-bottom plates (Greiner) using a fluorometer (FLUOstar/POLARstar; BMG Labtech). The number of IgA-coated Sepharose bead-induced chemotactic ex vivo human neutrophilic granulocytes was quantified by using a standard curve with known numbers of lysed calcein AM-labeled granulocytes (i.e., 0-0.05×10$^6$ cells/well).

LTB4 ELISA: LTB4 levels were measured in supernatants from IgA-coated Sepharose bead-stimulated ex vivo human neutrophilic granulocytes (see above). To this end, a commercially available LTB4 competitive ELISA kit (R&D Systems) was used according to manufacturer's instructions.

As shown in FIGS. 20A-C, all our purified CD89/IgA blocking chimeric mouse/human anti-human CD89-specific antibodies (except for 16D6) at 20 μg/mL inhibited of serum human IgA-coated Sepharose beads-mediated migration of membrane human CD89 expressing ex vivo primary human neutrophilic granulocytes isolated from three healthy individuals, although some donor-to-donor variation was observed.

As shown in FIGS. 20D-E, all our purified CD89/IgA blocking chimeric mouse/human anti-human CD89-specific antibodies (except for 16D6) at 20 μg/mL inhibited of serum human IgA-coated Sepharose beads-mediated chemotaxis of membrane human CD89 expressing ex vivo primary human neutrophilic granulocytes isolated from two healthy individuals, although some donor-to-donor variation was observed.

As shown in FIGS. 20F-H, all our purified CD89/IgA blocking chimeric mouse/human anti-human CD89-specific antibodies (except for 16D6) at 20 μg/mL inhibited of serum human IgA-coated Sepharose beads-mediated chemoattractive LTB4 production by membrane human CD89 expressing ex vivo primary human neutrophilic granulocytes isolated from three healthy individuals, although some donor-to-donor variation was observed.

These results demonstrated that CD89/IgA blocking chimeric mouse/human anti-human CD89-specific antibody 8F3, 10E7, 20B4, and 30C7 inhibited serum human IgA-mediated migration of, chemotaxis of, and chemoattractive LTB4 release from membrane human CD89 expressing ex vivo primary human neutrophilic granulocytes.

(d). Blocking Serum Human IgA-Mediated Lactoferrin Production from Human CD89 Expressing Primary Human Neutrophilic Granulocytes Using CD89/IgA Blocking Chimeric Mouse/Human Anti-Human CD89 Monoclonal Antibodies In order to analyze the biological activity of purified CD89/IgA blocking chimeric mouse/human anti-human CD89 antibodies, the ability of generated CD89/IgA blocking chimeric mouse/human anti-human CD89 antibodies to inhibit serum human IgA-mediated lactoferrin production from human CD89 expressing primary human neutrophilic granulocytes were determined.

Primary human neutrophilic granulocytes were isolated from healthy donors (after informed consent) peripheral blood using Lymphoprep™ (Axis-Shield) gradient centrifugation followed by lysis of erythrocytes in a $NH_4Cl$ lysis buffer solution. Then, these primary human neutrophilic granulocytes were labeled with 1 M fluorescent calcein-AM (Molecular Probes) for 30 minutes at 37° C. After washing, these calcein AM-labeled granulocytes were resuspended at 2.0×10$^6$ cells/mL in RPMI 1640 (Gibco) supplemented with 10% heat-inactivated FCS (Sigma-Aldrich), and subsequently 100 μL calcein AM-labeled granulocytes (i.e., 0.2×10$^6$ cells/well) were incubated with titrated (in RPMI/10% FCS) purified chimeric mouse/human anti-human CD89 antibody (i.e., 8F3, 10E7, 16D6, 20B4, and 30C7) for 20 minutes at 4° C. After this (i.e., without washing), 100 μL these cells (i.e., 0.2×10$^6$ cells/well) were added to 96-wells flat-bottom ELISA plates (Nunc-Immuno MaxiSorp), which were previously coated with either 100 μL/well purified human (serum-derived) IgA (MP Biomedicals) at 10 μg/mL or with 100 μL/well BSA (used as a negative control; Sigma-Aldrich) at 10 μg/mL. After incubation for 30 minutes at 37° C., supernatants (180 μL/well) were harvested to remove non-bound granulocytes, and these supernatants were used (after several centrifugal clearance steps) to measure lactoferrin production levels (used as a degranulation marker; see below). For comparison, commercial mouse anti-human CD89 antibodies clone MIP8a, clone A59 and clone A3 were run in parallel, like described in Example 3 (d).

Lactoferrin production was measured in the supernatants of primary human neutrophilic granulocytes (representing the degree of degranulation), which were stimulated with plate-bound serum human IgA (see above). For this, 96-wells flat-bottom ELISA plates (Nunc-Immuno MaxiSorp) were coated with 100 μL/well rabbit anti-human lactoferrin antibodies (1:5000; Sigma-Aldrich) during 16-24 hours at 4-8° C. After extensive washing in PBS/0.05% Tween 20, plates were blocked with 200 μL/well PBS/0.05% Tween 20/0.5% BSA (Sigma-Aldrich) for 1 hour at RT. Plates were then incubated with 100 μL/well supernatant at a 1;2 dilution (in block buffer) for 1 hour at 37° C. After extensive washing in PBS/0.05% Tween 20, plates were incubated with alkaline phosphatase-labeled rabbit anti-human lactoferrin detection antibodies (1:2500; MP Biomedicals) for 1 hour at 37° C. After adding P-nitrophenyl phosphate (Sigma-Aldrich), optical density was measured at wavelength of 405 nm with a microplate reader (iMArk; Bio-Rad). Purified human lactoferrin (Sigma-Aldrich) was used as a standard to calculate the amount of lactoferrin released by serum human IgA-stimulated ex vivo human neutrophilic granulocytes.

As shown in FIG. 21, all our purified CD89/IgA blocking chimeric mouse/human anti-human CD89-specific antibodies (except for 16D6) dose-dependently inhibited serum human IgA-mediated lactoferrin production by human CD89 expressing ex vivo primary human neutrophilic granulocytes isolated from two healthy individuals, although some donor-to-donor variation was observed These results demonstrated that CD89/IgA blocking chimeric mouse/human anti-human CD89-specific antibody 8F3, 10E7, 20B4, and 30C7 inhibited IgA-mediated lactoferrin production (a degranulation marker) by human CD89 expressing ex vivo primary human neutrophilic granulocytes.

Example 9. Generation of CD89/IgA Blocking Humanized IgG4/Kappa Anti-Human CD89 Monoclonal Antibody 10E7

Based on determined mouse V-regions (see Example 5 above) of CD89/IgA blocking mouse anti-human CD89 antibody 10E7, CD89/IgA blocking humanized anti-human CD89 antibody 10E7 versions were generated.

In silico humanized variable heavy chain sequences (3) and humanized variable light chain sequences (4) of CD89/IgA blocking mouse anti-human CD89 antibody 10E7 were obtained using PDL technology (performed by Panorama Research Institute, Sunnyvale, CA, USA). For humanized variable heavy chain and variable light chain amino acid sequences of CD89/IgA blocking mouse anti-human CD89 antibody 10E7, see SEQ ID NO: 117 (VH1), 118 (VH2), 119 (VH3), 120 (VL1), 121 (VL2), 122 (VL3), and 123 (VL4).

After this design, *Cricetulus griseus*-optimized cDNA sequences, SEQ ID NO: 124, 125, 126 (coding for full length humanized heavy IgG4 chain 10E7 versions, i.e., VH1, VH2, VH3, respectively) and SEQ ID NO: 127, 128, 129, 130 (coding for full length humanized light κ chain 10E7 versions, i.e., VL1, VL2, VL3, VL4, respectively), were ordered at GENEART (Regensburg, Germany), which encoded a human signal peptide followed by either the humanized variable heavy chain linked to the human stabilized (i.e., S239P; according Angal et al in Mol. Immunol., Vol. 30, No. 1, pp. 105-108, 1993) IgG4 constant region, or followed by the humanized variable light chain linked to the human kappa constant region. Using suitable restriction enzymes, generated cDNAs were subcloned in pcDNA3.1-derived expression plasmids. CD89/IgA blocking humanized anti-human CD89 antibody 10E7 versions were subsequently transiently expressed in 293-F cells (Invitrogen) using the FreeStyle™ 293 Expression System (Invitrogen). Supernatants containing these expressed CD89/IgA blocking humanized anti-human CD89 antibody 10E7 versions were examined for their binding against rhuCD89 and membrane-bound human CD89 using conventional ELISA and flow cytometry (Example 10, see below), respectively.

In this manner, twelve humanized versions of CD89/IgA blocking humanized anti-human CD89 antibody 10E7 were generated, i.e., VH1VL1, VH1VL2, VH1VL3, VH1VL4, VH2VL1, VH2VL2, VH2VL3, VH2VL4, VH3VL1, VH3VL2, VH3VL3, and VH3VL4.

For humanized amino acid sequences of CD89/IgA blocking humanized anti-human CD89 antibody 10E7, see SEQ ID NO: 131, 132, 133 (coding for full length humanized heavy IgG4 chain 10E7 versions, i.e., VH1, VH2, VH3, respectively), and SEQ ID NO: 134, 135, 136, 137 (coding for full length humanized light κ chain 10E7 versions, i.e., VL1, VL2, VL3, VL4, respectively).

Example 10. Binding Characterization of CD89/IgA Blocking Humanized IgG4/Kappa Anti-Human CD89 Monoclonal Antibody 10E7

(a). Relative Binding Affinity of CD89/IgA Blocking Humanized IgG4/Kappa Anti-Human CD89 Monoclonal Antibody 10E7 Versions for Human CD89

In order to determine the relative binding affinity of CD89/IgA blocking humanized IgG4/kappa anti-human CD89 monoclonal antibody 10E7 versions for human CD89, ELISA and FACS analysis were used.

ELISA: rhuCD89 (Sino Biological) was coated at 0.5 μg/mL in PBS (50 ng/100 μL/well) using 96-wells MaxiSorp plates (NUNC) during 16-24 hours at 4-8° C. After extensive washing with PBS/0.05% Tween 20, plates were blocked with PBS/0.05% Tween 20/1% BSA (Roche) for 1 hour at RT. Subsequently, plates were incubated with and without 100 μL titrated (in FreeStyle™ 293 Expression medium (Invitrogen); antibody concentrations in supernatants (see Example 9) were pre-determined against an internal human IgG4K standard by using a bio-layer interferometry Octet® apparatus in combination with protein A biosensor tips) humanized anti-human CD89 antibody 10E7/well for 1 hour at RT. Chimeric anti-human CD89 antibody 10E7 (see Example 6) was run in parallel for reference purposes. After extensive washing in PBS/0.05% Tween 20, binding of antibodies on rhuCD89 was determined with 1:5,000 diluted horseradish peroxidase (HRP)-conjugated goat anti-human IgG Fcγ-specific antibodies (Jackson ImmunoResearch) for 1 hour at RT, followed by a ready-to-use solution of TMB substrate (Invitrogen) for colorimetric detection. After adding 1 M HCL, binding (optical density) of antibodies on rhuCD89 was measured at wavelength of 450 nm (reference wavelength of 655 nm) using a microplate reader (Synergy HTX; BioTek).

FACS: stable human full-length CD89-transfected HEK293F cells (clone no. 2; see above Example 1(b) above) were put at $10\times10^6$ cells/mL in ice-chilled PBS containing 0.1% BSA (Sigma)/0.05% $NaN_3$ (PBS/BSA/$NaN_3$) supplemented with 50 μg/mL human IgGs (blocking possible Fcγ receptors; Sigma) for 10 minutes at 4° C. Then, 10 μL/tube (i.e., $0.1\times10^6$ cells) of these cells were incubated with and without 100 μL titrated (in FreeStyle™ 293 Expression medium (Invitrogen); antibody concentrations in supernatants (see Example 9) were pre-determined against an internal human IgG4K standard by using a bio-layer interferometry Octet® apparatus in combination with protein A biosensor tips) humanized anti-human CD89 antibody 10E7/tube for 30 minutes at 4° C. Chimeric anti-human CD89 antibody 10E7 (see Example 6) was run in parallel for reference. After extensive washing in PBS/BSA/$NaN_3$, cells were subsequently incubated with 1:200 diluted PE-conjugated goat anti-human IgG Fcγ-specific antibodies (Jackson ImmunoResearch) for 30 minutes at 4° C. After extensive washing in PBS/BSA/$NaN_3$, cells were fixed in 4% formaldehyde in PBS/BSA/$NaN_3$ for 30 minutes at 4° C. Binding (geo-mean fluorescence intensity) of antibodies on membrane human CD89 was measured using a flow cytometer (FACSCalibur; BD Biosciences).

Figure 25:
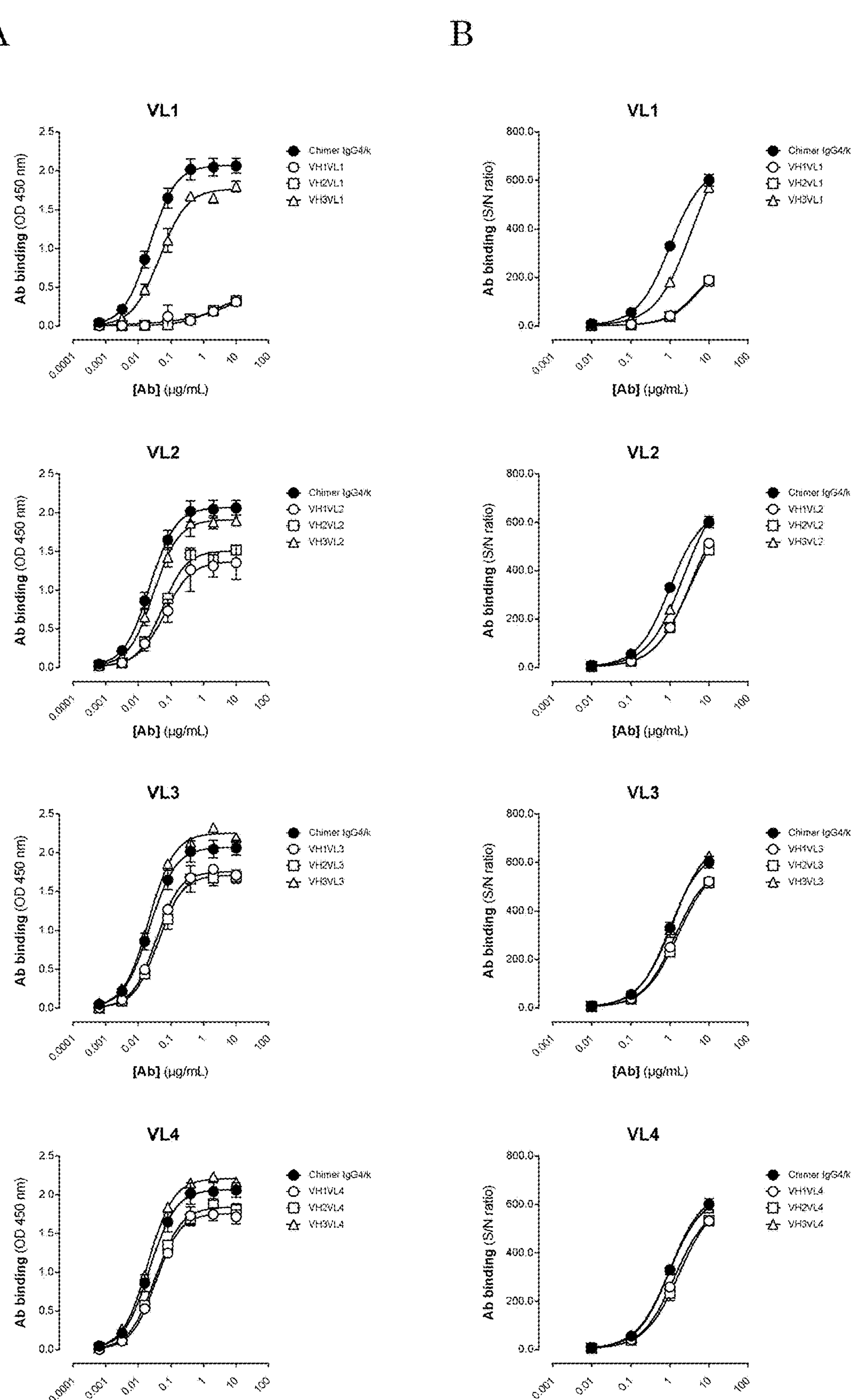
FIG. 25: Binding of characteristics of (supernatants of) CD89/IgA blocking humanized anti-human CD89 antibody 10E7 (i.e., humanized VH1, 2, 3 and VL1, 2, 3, 4 versions derived from CD89/IgA blocking mouse anti-human antibody 10E7 VH and VL regions combined with human constant IgG4/K regions) to rhuCD89 (A, ELISA) and to membrane-bound human CD89 (B, FACS) on HEK293F cells. CD89/IgA blocking chimeric anti-human CD89 antibody 10E7 (i.e., chimer IgG4/K) was used as reference. Mean±SD (n=2) are shown.

As shown in FIG. 25A, all CD89/IgA blocking humanized IgG4/kappa anti-human CD89 monoclonal antibody 10E7 versions (i.e., VH1VL1, VH1VL2, VH1VL3, VH1VL4, VH2VL1, VH2VL2, VH2VL3, VH2VL4, VH3VL1, VH3VL2, VH3VL3, and VH3VL4) and CD89/IgA blocking chimeric IgG4/kappa anti-human CD89 monoclonal antibody 10E7 dose-dependently bound to rhuCD89. CD89/IgA blocking chimeric IgG4/kappa anti-human CD89 monoclonal antibody 10E7 (i.e., reference) and CD89/IgA blocking humanized IgG4/kappa anti-human CD89 monoclonal antibody 10E7 versions VH3VL3 and VH3VL4 showed similar S-shaped titration curves, which indicated that their binding affinities against rhuCD89 were similar (half-maximum binding $EC_{50}\approx20$ ng/mL), whereas CD89/IgA blocking humanized IgG4/kappa anti-human CD89 monoclonal antibody 10E7 versions VH1VL1, VH1VL2, VH1VL3, VH1VL4, VH2VL1, VH2VL2, VH2VL3, VH2VL4, VH3VL1, and VH3VL2 showed significantly lower binding affinities, which were exemplified by lower maximum optical density signals or dissimilar titration curves.

As shown in FIG. 25B, all CD89/IgA blocking humanized IgG4/kappa anti-human CD89 monoclonal antibody 10E7 versions (i.e., VH1VL1, VH1VL2, VH1VL3, VH1VL4, VH2VL1, VH2VL2, VH2VL3, VH2VL4, VH3VL1, VH3VL2, VH3VL3, and VH3VL4) and CD89/IgA blocking chimeric IgG4/kappa anti-human CD89 monoclonal antibody 10E7 dose-dependently bound to membrane human CD89. CD89/IgA blocking chimeric IgG4/kappa anti-human CD89 monoclonal antibody 10E7 (i.e., reference) and CD89/IgA blocking humanized IgG4/kappa anti-human CD89 monoclonal antibody 10E7 versions VH3VL3 and VH3VL4 showed similar S-shaped titration curves, which indicated that their binding affinities against membrane human CD89 were similar (half-maximum binding EC50≈1000 ng/mL), whereas CD89/IgA blocking humanized IgG4/kappa anti-human CD89 monoclonal antibody 10E7 versions VH1VL1, VH1VL2, VH1VL3, VH1VL4, VH2VL1, VH2VL2, VH2VL3, VH2VL4, VH3VL1, and VH3VL2 showed significantly lower binding affinities, which were exemplified by lower maximum fluorescent signals or dissimilar titration curves.

After this supernatant screening, CD89/IgA blocking humanized IgG4/kappa anti-human CD89 monoclonal antibody 10E7 VH3VL3 was selected. However, CDR2 (see SEQ ID NO: 46) in the variable heavy chain of CD89/IgA blocking anti-human CD89 monoclonal antibody 10E7 contains two deamidation 'asparagine-glycine' ('Asn-Gly') motifs, which are prone to be deamidated (Sydow et al. PLoS ONE 2014; 9(6): e100736). Deamidation is a chemical reaction in which an amide functional group in the side chain of amino acid asparagine is converted to another functional group. Typically, asparagine is converted to aspartic acid or iso-aspartic acid. In an antibody, this reaction could form a serious risk factor, because this reaction may alter antibody structure, stability or function (i.e., antibody-antigen binding), and may lead to antibody degradation. Therefore, in silico 'CDR2 deamidation-repaired' humanized variable heavy chain sequences of CD89/IgA blocking mouse anti-human CD89 antibody 10E7 were obtained using an Fv structural model (performed by Applied Protein Services, Lonza Biologics, Cambridge, UK). Based on this detailed assessment, VH:Asn52 and VH:Asn54 were substituted with (1) a (VH3SQ) combination of VH:Ser52 and VH:Gln54, respectively, and with (2) a (VH3ST) combination of VH:Ser52 and VH:Thr54, respectively. For 'CDR2 deamidation-repaired' humanized variable heavy chain amino acid sequences of CD89/IgA blocking mouse anti-human CD89 antibody 10E7, see SEQ ID NO: 138 (VH3SQ) and 139 (VH3ST).

After this design, *Cricetulus griseus*-optimized cDNA sequences, SEQ ID NO: 140, 141 (coding for full length 'CDR2 deamidation-repaired' humanized heavy IgG4 chain 10E7 versions, i.e., VH3SQ, VH3ST, respectively) and SEQ ID NO: 129 (coding for full length humanized light κ chain 10E7 version, i.e., VL3), were ordered at GENEART (Regensburg, Germany), which encoded a human signal peptide followed by either the 'CDR2 deamidation-repaired' humanized variable heavy chain linked to the human stabilized (i.e., S239P; according Angal et al in Mol. Immunol., Vol. 30, No. 1, pp. 105-108, 1993) IgG4 constant region, or followed by the humanized variable light chain linked to the human kappa constant region. Using suitable restriction enzymes, generated cDNAs were subcloned in pcDNA3.1-derived expression plasmids. CD89/IgA blocking humanized anti-human CD89 antibody 10E7 versions were subsequently transiently expressed in 293-F cells (Invitrogen) using the FreeStyle™ 293 Expression System (Invitrogen). After harvesting supernatants, CD89/IgA blocking 'CDR2 deamidation-repaired' humanized anti-human CD89 antibody 10E7 versions VH3SQVL3 and VH3STVL3 were purified using conventional affinity chromatography protein A columns, and were subsequently examined for their binding against rhuCD89 and membrane-bound human CD89 using conventional ELISA and flow cytometry (see Example 10 (b) below), respectively. In addition, LPS levels were determined using the LAL chromogenic endpoint assay (Hycult Biotech), and CD89/IgA blocking 'CDR2 deamidation-repaired' humanized anti-human CD89 antibody 10E7 versions VH3SQVL3 and VH3STVL3 contained <0.002 EU LPS/μg humanized IgG.

In this manner, two 'CDR2 deamidation-repaired' humanized versions of CD89/IgA blocking humanized anti-human CD89 antibody 10E7 were generated, i.e., VH3SQVL3 and VH3STVL3.

For 'CDR2 deamidation-repaired' humanized amino acid sequences of CD89/IgA blocking humanized anti-human CD89 antibody 10E7, see SEQ ID NO: 142, 143 (coding for full length 'CDR2 deamidation-repaired' humanized heavy IgG4 chain 10E7 versions, i.e., VH3SQ, VH3ST, respectively), and SEQ ID NO: 136 (coding for full length humanized light κ chain 10E7 version, i.e., VL3).

(b). Relative Binding Affinity of CD89/IgA Blocking 'CDR2 Deamidation-Repaired' Humanized IgG4/Kappa Anti-Human CD89 Monoclonal Antibody 10E7 Versions VH3SQVL3 and VH3STVL3 for Human CD89

In order to determine the relative binding affinity of CD89/IgA blocking 'CDR2 deamidation-repaired' humanized IgG4/kappa anti-human CD89 monoclonal antibody 10E7 versions VH3SQVL3 and VH3STVL3 for human CD89, ELISA and FACS analysis were used.

ELISA: rhuCD89 (10414-H08H, Sino Biological, Inc) was coated at 0.5 μg/mL in PBS (50 ng/100 μL/well) using 96-wells MaxiSorp plates (NUNC) during 16-24 hours at 4-8° C. After extensive washing with PBS/0.05% Tween 20, plates were blocked with PBS/0.05% Tween 20/1% BSA (Roche) for 1 hour at RT. Subsequently, plates were incubated with and without 100 μL titrated (in PBS/BSA/$NaN_3$) purified 'CDR2 deamidation-repaired' humanized anti-human CD89 antibody 10E7/well for 1 hour at RT. Chimeric anti-human CD89 antibody 10E7 (see Example 6) was run in parallel for reference purposes. After extensive washing in PBS/0.05% Tween 20, binding of antibodies on rhuCD89 was determined with 1:5,000 diluted horseradish peroxidase (HRP)-conjugated goat anti-human IgG Fcy-specific antibodies (Jackson ImmunoResearch) for 1 hour at RT, followed by a ready-to-use solution of TMB substrate (Invitrogen) for colorimetric detection. After adding 1 M HCL, binding (optical density) of antibodies on rhuCD89 was measured at wavelength of 450 nm (reference wavelength of 655 nm) using a microplate reader (Synergy HTX; BioTek).

FACS: stable human full-length CD89-transfected HEK293F cells (clone no. 2; see above Example 1(b) above) were put at $10\times10^6$ cells/mL in ice-chilled PBS containing 0.1% BSA (Sigma)/0.05% $NaN_3$ (PBS/BSA/$NaN_3$) supplemented with 50 μg/mL human IgGs (blocking possible Fcγ receptors; Sigma) for 10 minutes at 4° C. Then, 10 μL/tube (i.e., $0.1\times10^6$ cells) of these cells were incubated with and without 100 μL titrated (in PBS/BSA/$NaN_3$) purified 'CDR2 deamidation-repaired' humanized anti-human CD89 antibody 10E7/tube for 30 minutes at 4° C. Chimeric anti-human CD89 antibody 10E7 (see Example 6) was run in parallel for reference purposes. After extensive washing in PBS/BSA/$NaN_3$, cells were subsequently incubated with 1:200 diluted PE-conjugated goat anti-human IgG Fcy-specific antibodies (Jackson ImmunoResearch) for 30 minutes at 4° C. After extensive washing in PBS/BSA/$NaN_3$, cells were fixed in 4% formaldehyde in PBS/BSA/$NaN_3$ for 30 minutes at 4° C. Binding (geo-mean fluorescence intensity) of antibodies on membrane human CD89 was measured using a flow cytometer (FACSCalibur; BD Biosciences).

As shown in FIG. 26A, both 'CDR2 deamidation-repaired' humanized IgG4/kappa anti-human CD89 monoclonal antibody 10E7 versions VH3SQVL3 and VH3STVL3, and chimeric IgG4/kappa anti-human CD89 monoclonal antibody 10E7 dose-dependently bound to rhuCD89. CD89/IgA blocking chimeric IgG4/kappa anti-human CD89 monoclonal antibody 10E7 (i.e., reference) and CD89/IgA blocking 'CDR2 deamidation-repaired' humanized IgG4/kappa anti-human CD89 monoclonal antibody 10E7 versions VH3SQVL3 and VH3STVL3 showed similar S-shaped titration curves, which indicated that their binding affinities against plate-bound rhuCD89 were similar (half-maximum binding $EC_{50}$≈10 ng/mL).

As shown in FIG. 26B, both 'CDR2 deamidation-repaired' humanized IgG4/kappa anti-human CD89 monoclonal antibody 10E7 versions VH3SQVL3 and VH3STVL3, and chimeric IgG4/kappa anti-human CD89 monoclonal antibody 10E7 dose-dependently bound to membrane human CD89. Surprisingly, CD89/IgA blocking chimeric IgG4/kappa anti-human CD89 monoclonal antibody 10E7 (i.e., reference) and both CD89/IgA blocking 'CDR2 deamidation-repaired' humanized IgG4/kappa anti-human CD89 monoclonal antibody 10E7 versions VH3SQVL3 and VH3STVL3 showed dissimilar S-shaped titration curves, which indicated that binding affinities of both CD89/IgA blocking 'CDR2 deamidation-repaired' humanized IgG4/kappa anti-human CD89 monoclonal antibody 10E7 versions VH3SQVL3 and VH3STVL3 against membrane human CD89 were higher (half-maximum binding EC50≈600 ng/mL) than the binding affinity of CD89/IgA blocking chimeric IgG4/kappa anti-human CD89 monoclonal antibody 10E7 (half-maximum binding EC50≈1300 ng/mL). In summary, both CD89/IgA blocking 'CDR2 deamidation-repaired' humanized IgG4/kappa anti-human CD89 monoclonal antibody 10E7 versions VH3SQVL3 and VH3STVL3 seemed to increase their binding affinity for membrane-bound human CD89 during the 'CDR2 deamidation-repair' process.

(c). Degree of CD89/IgA Blocking Capacity of CD89/IgA Blocking 'CDR2 Deamidation-Repaired' Humanized IgG4/Kappa Anti-Human CD89 Monoclonal Antibody 10E7 Versions VH3SQVL3 and VH3STVL3

In order to analyze the degree of CD89/IgA blocking of purified 'CDR2 deamidation-repaired' humanized IgG4/kappa anti-human CD89 monoclonal antibody 10E7 versions VH3SQVL3 and VH3STVL3, the ability of purified CD89/IgA blocking CDR2 deamidation-repaired' humanized IgG4/kappa anti-human CD89 monoclonal antibody 10E7 versions VH3SQVL3 and VH3STVL3 to sterically hinder the interaction of serum or of secretory human IgA with human CD89 was determined by using FACS analysis.

Stable human full-length CD89-transfected HEK293F cells (clone no. 2; see above Example 1 (b) above) were put at $10\times10^6$ cells/mL in ice-chilled PBS containing 0.1% BSA (Sigma)/0.05% $NaN_3$ (PBS/BSA/$NaN_3$). Then, 10 μL/tube (i.e., $0.1\times10^6$ cells) of these cells were incubated with or without 50 μL titrated (in PBS/BSA/$NaN_3$) purified CD89/IgA blocking 'CDR2 deamidation-repaired' humanized IgG4/kappa anti-human CD89 monoclonal antibody 10E7 versions VH3SQVL3 and VH3STVL3/tube for 30 minutes at 4° C. In parallel, 50 μL titrated (in PBS/BSA/$NaN_3$) purified chimeric anti-human CD89 antibody 10E7 (see Example 6) was run for reference purposes. After this (i.e., without washing), 50 μL purified human serum-derived IgA (Bethyl Laboratories) at 0.20 μM (diluted in PBS/BSA/$NaN_3$) or colostrum-derived IgA (BioRad) at 0.16 μM (diluted in PBS/BSA/$NaN_3$) was added to these cells, and incubated for another 30 minutes at 4° C. After extensive washing in PBS/BSA/$NaN_3$, binding of serum human IgA or secretory human IgA on membrane human CD89 was determined with biotin-conjugated F(ab')2 fragment goat anti-human serum IgA α chain-specific antibodies (Jackson ImmunoResearch) at 5 μg/mL for 30 minutes at 4° C. After extensive washing in PBS/BSA/$NaN_3$, 1:200 diluted PE-conjugated streptavidin (Jackson ImmunoResearch) was added, and incubated for 30 minutes at 4° C. After extensive washing in PBS/BSA/$NaN_3$, cells were fixed in 4% formaldehyde in PBS/BSA/$NaN_3$ for 30 minutes at 4° C. Binding (geo-mean fluorescence intensity) of serum human IgA or secretory human IgA on membrane human CD89 was measured using a flow cytometer (FACSCalibur; BD Biosciences).

As shown in FIGS. 27A and 27B, both 'CDR2 deamidation-repaired' humanized IgG4/kappa anti-human CD89 monoclonal antibody 10E7 versions VH3SQVL3 and VH3STVL3, and CD89/IgA blocking chimeric IgG4/kappa anti-human CD89 monoclonal antibody 10E7 dose-dependently prevented serum and secretory human IgA binding to membrane human CD89. Surprisingly, CD89/IgA blocking chimeric IgG4/kappa anti-human CD89 monoclonal antibody 10E7 (i.e., reference) and both CD89/IgA blocking 'CDR2 deamidation-repaired' humanized IgG4/kappa anti-human CD89 monoclonal antibody 10E7 versions VH3SQVL3 and VH3STVL3 showed dissimilar inhibitory titration curves, which indicated that CD89/IgA inhibition by both 'CDR2 deamidation-repaired' humanized IgG4/kappa anti-human CD89 monoclonal antibody 10E7 versions VH3SQVL3 and VH3STVL3 was stronger (half-maximum inhibition IC50≈900 ng/mL and IC50≈600 ng/mL for serum human IgA and secretory human IgA, respectively) than the CD89/IgA inhibition by chimeric IgG4/kappa anti-human CD89 monoclonal antibody 10E7 (half-maximum inhibition TC50≈1600 ng/mL and TC50≈1000 ng/mL for serum human IgA and secretory human IgA, respectively). In summary, both 'CDR2 deamidation-repaired' humanized IgG4/kappa anti-human CD89 monoclonal antibody 10E7 versions VH3SQVL3 and VH3STVL3 seemed to increase their degree of CD89/IgA blocking capacity during the 'CDR2 deamidation-repair' process, which was in agreement with their increased binding affinity for membrane-bound human CD89 (see Example 10 (b) above).

Collectively, these results demonstrated that CD89/IgA blocking 'CDR2 deamidation-repaired' humanized IgG4/kappa anti-human CD89 monoclonal antibody 10E7 versions VH3SQVL3 and VH3STVL3 prevented the binding of monomeric serum human IgA and dimeric secretory human IgA to membrane human CD89.

(d). Equilibrium Dissociation Constant ($K_D$) of CD89/IgA Blocking 'CDR2 Deamidation-Repaired' Humanized IgG4/Kappa Anti-Human CD89 Monoclonal Antibody 10E7 Versions VH3SQVL3 and VH3STVL3 for Human CD89

In order to determine the equilibrium dissociation constant ($K_D$) of CD89/IgA blocking 'CDR2 deamidation-repaired' humanized IgG4/kappa anti-human CD89 monoclonal antibody 10E7 versions VH3SQVL3 and VH3STVL3 for human CD89, BLI/Octet®-based analysis was used.

Biotinylated (using N-hydroxysuccinimido-biotin from Pierce) purified 'CDR2 deamidation-repaired' humanized anti-human CD89 antibody 10E7 versions VH3SQVL3 and VH3STVL3 were loaded at 2.5 μg/mL in PBS/0.1% BSA/0.02% Tween 20 (pH 7.4) onto streptavidin biosensor tips (ForteBio) during 5 minutes at 30° C. Subsequently, association of monomeric recombinant C-terminal polyhistidine-tagged human (extracellular) CD89 analyte (rhuCD89 (10414-H08H, Sino Biological, Inc)) at 0 nM (reference sample to monitor baseline drift) and at 0.31-20 nM (2-fold dilution steps in PBS/0.1% BSA/0.02% Tween 20) was measured for 5 minutes at 30° C., followed by a dissociation phase of 20 minutes at 30° C. using an Octet® RED96 apparatus (ForteBio). Biotinylated (using N-hydroxysuccinimido-biotin from Pierce) purified mouse and chimeric anti-human CD89 antibody 10E7 counterparts (see Example 2 and Example 6, respectively) were tested for comparative purposes. Equilibrium dissociation constants ($K_D$) were determined using a 1:1 Langmuir binding model in Octet® RED96 software (ForteBio).

Both 'CDR2 deamidation-repaired' humanized IgG4/kappa anti-human CD89 monoclonal antibody 10E7 versions VH3SQVL3 and VH3STVL3, chimeric IgG4/kappa anti-human CD89 monoclonal antibody 10E7, and mouse anti-human CD89 monoclonal antibody 10E7 showed high affinity binding to soluble monomeric rhuCD89. Surprisingly, both CD89/IgA blocking 'CDR2 deamidation-repaired' humanized IgG4/kappa anti-human CD89 monoclonal antibody 10E7 versions VH3SQVL3 and VH3STVL3 showed higher affinity binding to soluble monomeric rhuCD89 (i.e., a $K_D$ value of 0.82 nM and of 0.92 nM, respectively) than binding affinity of CD89/IgA blocking chimeric IgG4/kappa anti-human CD89 monoclonal antibody 10E7 (i.e., a $K_D$ value of 1.28 nM) and of CD89/IgA blocking mouse anti-human CD89 monoclonal antibody 10E7 (i.e., a $K_D$ value of 1.67 nM).

Collectively, both CD89/IgA blocking 'CDR2 deamidation-repaired' humanized IgG4/kappa anti-human CD89 monoclonal antibody 10E7 versions VH3SQVL3 and VH3STVL3 seemed to increase their binding affinity for soluble monomeric rhuCD89 during the 'CDR2 deamidation-repair' process. For summary, see Table 9.

TABLE 9

Results of examined binding kinetic parameters from Octet ® kinetics assays performed with purified CD89/IgA blocking 'CDR2 deamidation repaired' humanized IgG4/kappa anti-human CD89 monoclonal antibody 10E7 versions VH3SQVL3 and VH3STVL3, chimeric IgG4/kappa anti-human CD89 monoclonal antibody 10E7, and mouse anti-human CD89 monoclonal antibody 10E7 on soluble monomeric rhuCD89.

| Anti-CD89 Ab 10E7 version | Binding kinetic parameters $K_{on}$ ($\times10^5$ 1/Ms) | $K_{off}$ ($\times10^{-4}$ 1/s) | $K_D$ (nM) |
|---|---|---|---|
| Mouse* | 6.87 ± 1.61 | 11.10 ± 0.14 | 1.67 ± 0.41 |
| Chimeric* | 8.32 | 10.60 | 1.28 |
| Humanized VH3SQVL3** | 11.50 | 9.41 | 0.82 |
| Humanized VH3STVL3** | 10.60 | 9.74 | 0.92 |

*Results (mean ± SD) from 2 independent experiments,
**results from 1 independent experiment.

Example 11. Biological Characterization of CD89/IgA Blocking 'CDR2 Deamidation-Repaired' Humanized IgG4/Kappa Anti-Human CD89 Monoclonal Antibody 10E7 Versions VH3SQVL3 and VH3STVL3 Using Ex Vivo Human CD89 Expressing Primary Human Neutrophilic Granulocytes (a). Binding of CD89/IgA Blocking 'CDR2 Deamidation-Repaired' Humanized IgG4/Kappa Anti-Human CD89 Monoclonal Antibody 10E7 Versions VH3SQVL3 and VH3STVL3 on Human CD89 Expressing Primary Human Neutrophilic Granulocytes In order to determine the binding of purified CD89/IgA blocking 'CDR2 deamidation-repaired' humanized IgG4/kappa anti-human CD89 monoclonal antibody 10E7 versions VH3SQVL3 and VH3STVL3 on human CD89 expressing primary human neutrophilic granulocytes, FACS analysis was used.

Primary human neutrophilic granulocytes were isolated from healthy donor (after informed consent) peripheral blood using Lymphoprep™ (Axis-Shield) gradient centrifugation followed by lysis of erythrocytes in a $NH_4Cl$ lysis buffer solution—After washing in PBS, granulocytes were put at $10\times10^6$ cells/mL in ice-chilled PBS containing 0.1% BSA (Sigma-Aldrich; PBS/BSA). Then, 10 μL/tube (i.e., $0.1\times10^6$ cells) of these cells were incubated with or without 100 μL purified 'CDR2 deamidation-repaired' humanized anti-human CD89 antibody 10E7 at 10 μg/mL (in PBS/BSA) for 30 minutes at 4° C. In parallel, 100 μL purified human IgG4 isotype control antibody (Sigma-Aldrich) at 10 μg/mL (in PBS/BSA) was run as a negative control. In addition, 100 μL purified chimeric anti-human CD89 antibody 10E7 (see Example 6) at 10 g/mL (in PBS/BSA) was run for reference purposes. After extensive washing in PBS/BSA, cells were subsequently incubated with 1:200 diluted biotin-conjugated mouse anti-human IgG4-specific antibodies (Invitrogen) for 30 minutes at 4° C. After extensive washing in PBS/BSA, cells were incubated with 1:200 diluted PE-conjugated streptavidin (Jackson ImmunoResearch) for 30 minutes at 4° C. After extensive washing in PBS/BSA, cells were fixed in 2% formaldehyde in PBS/BSA for 30 minutes at 4° C. Binding (geo-mean fluorescence intensity) of antibodies on membrane human CD89 from ex vivo human neutrophilic granulocytes was measured using a flow cytometer (Attune; Thermo Fisher).

Figure 28:
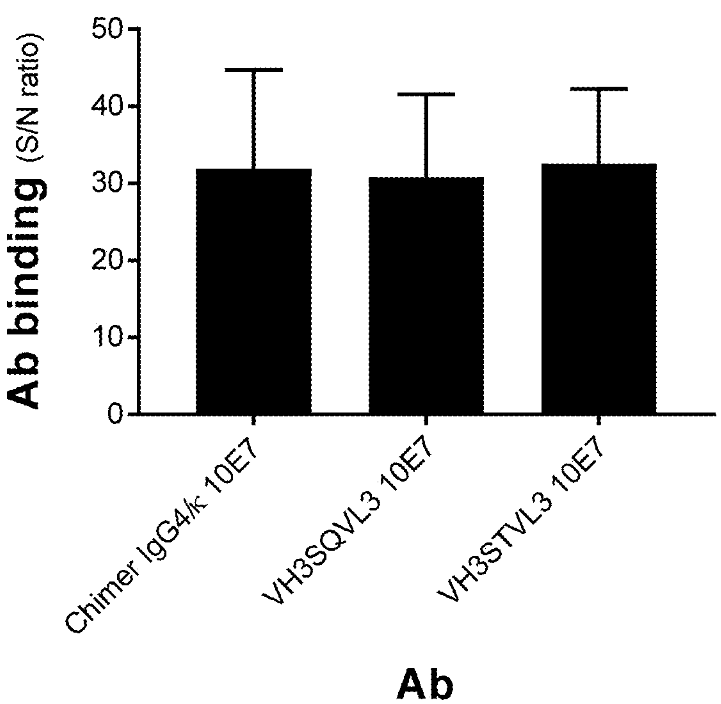
FIG. 28: Binding of purified CD89/IgA blocking 'CDR2 deamidation-repaired' humanized IgG4/kappa anti-human CD89 monoclonal antibody 10E7 versions VH3SQVL3 and VH3STVL3 (at 10 μg/mL) to membrane-bound human CD89 on ex vivo human neutrophilic granulocytes (Mean±SD from 3 different healthy donors).

As shown in FIG. 28, both purified CD89/IgA blocking 'CDR2 deamidation-repaired' humanized IgG4/kappa anti-human CD89 monoclonal antibody 10E7 versions VH3SQVL3 and VH3STVL3 (at 10 μg/mL) bound to membrane human CD89 from ex vivo human neutrophilic granulocytes isolated from multiple donors (n=3).

These results also demonstrated that CD89/IgA blocking 'CDR2 deamidation-repaired' humanized IgG4/kappa anti-human CD89 monoclonal antibody 10E7 versions VH3SQVL3 and VH3STVL3 recognized non-polymorphic epitopes on membrane human CD89 from ex vivo human neutrophilic granulocytes, because these antibodies unambiguously bound to human neutrophilic granulocytes isolated from all 3 examined donors.

(b). Blocking Serum Human IgA-Mediated Phagocytosis by Human CD89 Expressing Primary Human Neutrophilic Granulocytes Using CD89/IgA Blocking 'CDR2 Deamidation-Repaired' Humanized IgG4/Kappa Anti-Human CD89 Monoclonal Antibody 10E7 Versions VH3SQVL3 and VH3STVL3

In order to analyze the biological activity of purified CD89/IgA blocking 'CDR2 deamidation-repaired' humanized IgG4/kappa anti-human CD89 monoclonal antibody 10E7 versions VH3SQVL3 and VH3STVL3, the ability of generated CD89/IgA blocking 'CDR2 deamidation-repaired' humanized IgG4/kappa anti-human CD89 monoclonal antibody 10E7 versions VH3SQVL3 and VH3STVL3 to inhibit phagocytosis of serum human IgA-coated latex beads by human CD89 expressing primary human neutrophilic granulocytes was determined.

Primary human neutrophilic granulocytes were isolated from healthy donors (after informed consent) peripheral blood using Lymphoprep™ (Axis-Shield) gradient centrifugation followed by lysis of erythrocytes in a $NH_4Cl$ lysis buffer solution. After washing in PBS, granulocytes were resuspended at $2.0\times10^6$ cells/mL in RPMI 1640 (Gibco) supplemented with 10% heat-inactivated FCS (Sigma-Aldrich). Then, 100 μL/well (i.e., $0.2\times10^6$ cells in 96-wells flat-bottom plates; Greiner) of these cells were incubated with titrated (in RPMI/10% FCS) purified 'CDR2 deamidation-repaired' humanized anti-human CD89 antibody 10E7 for 20 minutes at 4° C. In parallel, purified human IgG4 isotype control antibody (Sigma-Aldrich) was run as a negative control. In addition, purified chimeric anti-human CD89 antibody 10E7 (see Example 6) at 10 μg/mL (in PBS/BSA) was run for reference purposes. After this (i.e., without washing), 1.2 μL purified human (serum-derived) IgA (MP Biomedicals)-coated fluorescent latex beads (1 μm-sized and carboxylate-modified polystyrene; Sigma-Aldrich) at a cell-to-bead ratio of 1:60 were added to these cells (preparation IgA-beads, see Aleyd et al. J Immunol 2014; 192: 2374-2383), and incubated for another 30 minutes at 37° C. In parallel, BSA (Sigma-Aldrich)-coated fluorescent latex beads at a cell-to-bead ratio of 1:60 were run as a negative control (preparation BSA-beads, see Aleyd et al. J Immunol 2014; 192: 2374-2383). After washing in RPMI/10% FCS and resuspension in PBS/0.1% BSA (Sigma-Aldrich), serum human IgA-mediated phagocytosis of fluorescent latex beads (geo-mean fluorescence intensity used to calculate phagocytic index according to Aleyd et al. J Immunol 2014; 192: 2374-2383) by membrane human CD89 on ex vivo human neutrophilic granulocytes was measured using a flow cytometer (Fortessa; BD Biosciences).

As shown in FIG. 29, both purified CD89/IgA blocking 'CDR2 deamidation-repaired' humanized IgG4/kappa anti-human CD89 monoclonal antibody 10E7 versions VH3SQVL3 and VH3STVL3 dose-dependently inhibited serum human IgA-mediated phagocytosis in membrane human CD89 expressing ex vivo primary human neutrophilic granulocytes isolated from three healthy individuals, although some donor-to-donor variation was observed.

These results demonstrated that CD89/IgA blocking 'CDR2 deamidation-repaired' humanized IgG4/kappa anti-human CD89 monoclonal antibody 10E7 versions VH3SQVL3 and VH3STVL3 inhibited serum human IgA-mediated phagocytotic activity of membrane human CD89 expressing ex vivo primary human neutrophilic granulocytes.

(c). Blocking Serum Human IgA-Mediated Lactoferrin Production from Human CD89 Expressing Primary Human Neutrophilic Granulocytes Using CD89/IgA Blocking 'CDR2 Deamidation-Repaired' Humanized IgG4/Kappa Anti-Human CD89 Monoclonal Antibody 10E7 Versions VH3SQVL3 and VH3STVL3

In order to analyze the biological activity of purified CD89/IgA blocking 'CDR2 deamidation-repaired' humanized IgG4/kappa anti-human CD89 monoclonal antibody 10E7 versions VH3SQVL3 and VH3STVL3, the ability of generated CD89/IgA blocking chimeric mouse/human anti-human CD89 antibodies to inhibit lactoferrin production from human CD89 expressing primary human neutrophilic granulocytes was determined.

Primary human neutrophilic granulocytes were isolated from healthy donors (after informed consent) peripheral blood using Lymphoprep™ (Axis-Shield) gradient centrifugation followed by lysis of erythrocytes in a $NH_4Cl$ lysis buffer solution. Then, these primary human neutrophilic granulocytes were resuspended at $2.0\times10^6$ cells/mL in RPMI 1640 (Gibco) supplemented with 10% heat-inactivated FCS (Sigma-Aldrich), and subsequently 100 μL granulocytes (i.e., $0.2\times10^6$ cells/well) were incubated with titrated (in RPMI/10% FCS) purified CD89/IgA blocking 'CDR2 deamidation-repaired' humanized IgG4/kappa anti-human CD89 monoclonal antibody 10E7 versions VH3SQVL3 and VH3STVL3 for 20 minutes at 4° C. In parallel, titrated (in RPMI/10% FCS) purified human IgG4 isotype control antibody (Sigma-Aldrich) was run as a negative control. In addition, titrated (in RPMI/10% FCS) purified chimeric anti-human CD89 antibody 10E7 (see Example 6) was run for reference purposes. After this (i.e., without washing), 100 μL these cells (i.e., $0.2\times10^6$ cells/well) were added to 96-wells flat-bottom ELISA plates (Nunc-Immuno MaxiSorp), which were previously coated with either 100 μL/well purified human (serum-derived) IgA (MP Biomedicals) at 10 μg/mL or with 100 μL/well BSA (used as a negative control; Sigma-Aldrich) at 10 μg/mL. After incubation for 30 minutes at 37° C., supernatants (180 μL/well) were harvested to remove non-bound granulocytes, and these supernatants were used (after several centrifugal clearance steps) to measure lactoferrin production levels (used as a degranulation marker; see below). For comparison, commercial mouse anti-human CD89 antibodies clone MIP8a was run in parallel, like described in Example 3 (d).

Lactoferrin production was measured in the supernatants of primary human neutrophilic granulocytes (representing the degree of degranulation), which were stimulated with plate-bound serum human IgA (see above). For this, 96-wells flat-bottom ELISA plates (Nunc-Immuno MaxiSorp) were coated with 100 μL/well rabbit anti-human lactoferrin antibodies (1:5000; Sigma-Aldrich) during 16-24 hours at 4-8° C. After extensive washing in PBS/0.05% Tween 20, plates were blocked with 200 μL/well PBS/0.05% Tween 20/0.5% BSA (Sigma-Aldrich) for 1 hour at RT. Plates were then incubated with 100 μL/well supernatant at a 1;2 dilution (in block buffer) for 1 hour at 37° C. After extensive washing in PBS/0.05% Tween 20, plates were incubated with alkaline phosphatase-labeled rabbit anti-human lactoferrin detection antibodies (1:2500; MP Biomedicals) for 1 hour at 37° C. After adding P-nitrophenyl phosphate (Sigma-Aldrich), optical density was measured at wavelength of 405 nm with a microplate reader (iMArk; Bio-Rad). Purified human lactoferrin (Sigma-Aldrich) was used as a standard to calculate the amount of lactoferrin released by serum human IgA-stimulated ex vivo human neutrophilic granulocytes.

As shown in FIG. 30, both purified CD89/IgA blocking 'CDR2 deamidation-repaired' humanized IgG4/kappa anti-human CD89 monoclonal antibody 10E7 versions VH3SQVL3 and VH3STVL3 dose-dependently inhibited serum human IgA-mediated lactoferrin production by human CD89 expressing ex vivo primary human neutrophilic granulocytes isolated from five healthy individuals, although some donor-to-donor variation was observed These results demonstrated that CD89/IgA blocking 'CDR2 deamidation-repaired' humanized IgG4/kappa anti-human CD89 monoclonal antibody 10E7 versions VH3SQVL3 and VH3STVL3 inhibited IgA-mediated lactoferrin production (a degranulation marker) by human CD89 expressing ex vivo primary human neutrophilic granulocytes.

Certain Aspects of the Invention

Aspect 1. An antibody that can bind an extra-cellular part of human CD89 (human FcαRI) on human CD89 expressing cells and that can prevent binding of human IgA to human CD89 when the antibody is bound to said cells and that induces less cell death in said human CD89 expressing cells when compared to the antibody MIP8a.

Aspect 2. An antibody that can bind an extra-cellular part of human CD89 on human CD89 expressing cells and that can prevent binding of human IgA to human CD89 when the antibody is bound to said cells and that does not reduce the cell viability of said cells by more than 60% after overnight incubation at 37° C.

Aspect 3. An antibody that can bind an extra-cellular part of human CD89 on human CD89 expressing cells and that can prevent binding of human IgA to human CD89 when the antibody is bound to said cells and that does not increase phosphatidylserine expression of said cells by more than 20% after overnight incubation at 37° C.

Aspect 4. An antibody that can bind an extra-cellular part of human CD89 on human CD89 expressing cells and that can prevent binding of human IgA to human CD89 when the antibody is bound to said cells and that binds 20% or less to a recombinant human CD89 molecule wherein amino acids 22-46 of human CD89 are exchanged for amino acids 22-46 of cynomolgus CD89.

Aspect 5. An antibody that can bind an extra-cellular part of human CD89 on human CD89 expressing cells and that can prevent binding of human IgA to human CD89 when the antibody is bound to said cells and that binds 20% or less to a chimeric CD89 molecule wherein amino acids 47-71 of human CD89 are exchanged for amino acids 47-71 of cynomolgus CD89.

Aspect 6. An antibody that can bind an extra-cellular part of human CD89 on human CD89 expressing cells and that can prevent binding of human IgA to human CD89 when the antibody is bound to said cells and that binds 20% or less to a chimeric CD89 molecule wherein amino acids 72-96 of human CD89 are exchanged for amino acids 72-96 of cynomolgus CD89.

Aspect 7. An antibody that can bind an extra-cellular part of human CD89 on human CD89 expressing cells and that can prevent binding of human IgA to human CD89 when the antibody is bound to said cells and of which binding is not reduced by 20% or less to a chimeric CD89 molecule wherein amino acids 97-121 of human CD89 are exchanged for amino acids 97-121 of cynomolgus CD89.

Aspect 8. An antibody that can bind an extra-cellular part of human CD89 on human CD89 expressing cells and that can prevent binding of human IgA to human CD89 when the antibody is bound to said cells and that binds 20% or less to a chimeric CD89 molecule wherein amino acids 58; 59; 73; 74; 76; 106 and 107 of human CD89 are exchanged for amino acids 58; 59; 73; 74; 76; 106 and 107 respectively of cynomolgus CD89.

Aspect 9. An antibody according to any one of aspects 1 to 8, wherein the cells are human CD89 expressing HEK293F cells (deposited under number DSM ACC3341).

Aspect 10. An antibody that can bind an extra-cellular part of human CD89 comprising a heavy chain variable region with the CDR1, CDR2 and CDR3 sequence of SEQ ID NO: 29-31 with 0, 1 or 2 amino acid insertions, deletions, substitutions or additions and a light chain variable region with the CDR1, CDR2 and CDR3 sequence of SEQ ID NO: 32-34 with 0, 1 or 2 amino acid insertions, deletions, substitutions or additions.

Aspect 11. An antibody that can bind an extra-cellular part of human CD89 comprising a heavy chain variable region with the amino acid sequence of SEQ ID NO: 27 with 0, 1, 2, 3, 4, 5, 6, 7, 8, 9 or 10 amino acid insertions, deletions, substitutions or additions and a light chain variable region with the amino acid sequence of SEQ ID NO: 28 with 0, 1, 2, 3, 4, 5, 6, 7, 8, 9 or 10 amino acid insertions, deletions, substitutions or additions.

Aspect 12. An antibody that can bind an extra-cellular part of human CD89 comprising a heavy chain variable region with the CDR1, CDR2 and CDR3 sequence of SEQ ID NO: 45-47 with 0, 1 or 2 amino acid insertions, deletions, substitutions or additions and a light chain variable region with the CDR1, CDR2 and CDR3 sequence of SEQ ID NO: 48-50 with 0, 1 or 2 amino acid insertions, deletions, substitutions or additions.

Aspect 13. An antibody that can bind an extra-cellular part of human CD89 comprising a heavy chain variable region with the amino acid sequence of SEQ ID NO: 43 with 0, 1, 2, 3, 4, 5, 6, 7, 8, 9 or 10 amino acid insertions, deletions, substitutions or additions and a light chain variable region with the amino acid sequence of SEQ ID NO: 44 with 0, 1, 2, 3, 4, 5, 6, 7, 8, 9 or 10 amino acid insertions, deletions, substitutions or additions.

Aspect 14. An antibody that can bind an extra-cellular part of human CD89 comprising a heavy chain variable region with the CDR1, CDR2 and CDR3 sequence of SEQ ID NO: 69-71 with 0, 1 or 2 amino acid insertions, deletions, substitutions or additions and a light chain variable region with the CDR1, CDR2 and CDR3 sequence of SEQ ID NO: 72-74 with 0, 1 or 2 amino acid insertions, deletions, substitutions or additions.

Aspect 15. An antibody that can bind an extra-cellular part of human CD89 comprising a heavy chain variable region with the amino acid sequence of SEQ ID NO: 67 with 0, 1, 2, 3, 4, 5, 6, 7, 8, 9 or 10 amino acid insertions, deletions, substitutions or additions and a light chain variable region with the amino acid sequence of SEQ ID NO: 68 with 0, 1, 2, 3, 4, 5, 6, 7, 8, 9 or 10 amino acid insertions, deletions, substitutions or additions.

Aspect 16. An antibody that can bind an extra-cellular part of human CD89 comprising a heavy chain variable region with the CDR1, CDR2 and CDR3 sequence of SEQ ID NO: 77-79 with 0, 1 or 2 amino acid insertions, deletions, substitutions or additions and a light chain variable region with the CDR1, CDR2 and CDR3 sequence of SEQ ID NO: 80-82 with 0, 1 or 2 amino acid insertions, deletions, substitutions or additions.

Aspect 17. An antibody that can bind an extra-cellular part of human CD89 comprising a heavy chain variable region with the amino acid sequence of SEQ ID NO: 75 with 0, 1, 2, 3, 4, 5, 6, 7, 8, 9 or 10 amino acid insertions, deletions, substitutions or additions and a light chain variable region with the amino acid sequence of SEQ ID NO: 76 with 0, 1, 2, 3, 4, 5, 6, 7, 8, 9 or 10 amino acid insertions, deletions, substitutions or additions.

Aspect 18. An antibody that can bind an extra-cellular part of human CD89 comprising a heavy chain variable region with the CDR1, CDR2 and CDR3 sequence of SEQ ID NO: 53-55 with 0, 1 or 2 amino acid insertions, deletions, substitutions or additions and a light chain variable region with the CDR1, CDR2 and CDR3 sequence of SEQ ID NO: 56-58 with 0, 1 or 2 amino acid insertions, deletions, substitutions or additions.

Aspect 19. An antibody that can bind an extra-cellular part of human CD89 comprising a heavy chain variable region with the amino acid sequence of SEQ ID NO: 51 with 0, 1, 2, 3, 4, 5, 6, 7, 8, 9 or 10 amino acid insertions, deletions, substitutions or additions and a light chain variable region with the amino acid sequence of SEQ ID NO: 52 with 0, 1, 2, 3, 4, 5, 6, 7, 8, 9 or 10 amino acid insertions, deletions, substitutions or additions.

Description of Sequences

```
SEQ ID NO: 1:
Amino acid sequence of full-length human CD89
(Swiss-Prot no. P24071.1; aa 287)
MDPKQTTLLCLVLCLGQRIQAQEGDFPMPFISAKSSPVIPLDGSVKIQC

QAIREAYLTQLMIIKNSTYREIGRRLKFWNETDPEFVIDHMDANKAGRY

QCQYRIGHYRFRYSDTLELVVTGLYGKPFLSADRGLVLMPGENISLTCS

SAHIPFDRFSLAKEGELSLPQHQSGEHPANFSLGPVDLNVSGIYRCYGW
```

-continued

YNRSPYLWSFPSNALELVVTDSIHQDYTTQNLIRMAVAGLVLVALLAIL

VENWHSHTALNKEASADVAEPSWSQQMCQPGLTFARTPSVCK

Signal peptide (aa sequence 1-21), extracellular domain (aa sequence 22-227), comprising of an Ig-like EC1 domain (aa sequence 22-121), of a short hinge region (aa sequence 122-125), of an Ig-like EC2 domain (aa sequence 126-220), and of a membrane proximal 'linker' region (aa sequence 221-227), followed by transmembrane domain (aa sequence 228-246), and short cytoplasmic tail (aa sequence 247-287) according to Ding et al. J Biol Chem 2003; 278:27966-27970.

SEQ ID NO: 2:
cDNA sequence coding for full-length human CD89 protein (optimized for mammalian expression)
atggaccccaagcagaccaccctgctgtgcctggtgctgtgtctgggcc agagaatccaggcccaggaaggcgacttccccatgcccttcatcagcgc caagagcagccccgtgatccccctggatggcagcgtgaagatccagtgc caggccatcagagaggcctacctgacccagctgatgatcattaagaaca gcacctaccgcgagatcggcagacggctgaagttctggaacgagacaga ccccgagttcgtgatcgaccacatggacgccaacaaggccggcagatac cagtgtcagtaccggatcggccactaccggttccggtacagcgacaccc tggaactggtcgtgaccggcctgtacggcaagcctttcctgagcgccga tcggggactggtgctgatgcccggcgagaacatcagcctgacctgtagc agcgcccacatccccttcgacagattcagcctggccaaagagggcgagc tgagcctgcctcagcatcagtctggcgagcaccccgccaactttagcct gggccctgtggacctgaacgtgtccggcatctaccggtgctacggctgg tacaaccggtcccccctacctgtggtccttccccagcaacgctctggaac tggtcgtgacagacagcatccaccaggactacaccacccagaacctgat ccggatggccgtggctgggctggtgctggtggctctgctggccattctg gtggaaaactggcacagccacaccgccctgaacaaagaggccagcgccg atgtggccgagccttcttggagccagcagatgtgtcagcccggcctgac cttcgccagaacccccttctgtgtgcaag SEQ ID NO: 3:
Amino acid sequence of chimeric FcR comprising EC1 from human CD89 and EC2 from bovine Fcγ2R (bovine TM & bovine IC)
MDPKQTTLLCLVLCLGQRIQAQEGDFPMPFISAKSSPVIPLDGSVKIQC

QAIREAYLTQLMIIKNSTYREIGRRLKFWNETDPEFVIDHMDANKAGRY

QCQYRIGHYRFRYSDTLELVVTGEEPAGRLRDRPSLSVRPSPSVAPGEN

VTLLCQSGNRTDTFLLSKEGAAHRPLRLRSQDQDGWYQAEFSLSPVTSA

HGGTYRCYRSLSTNPYLLSQPSEPLALLVADYTMQNLIRMGLAASVLLL

LGILLCQARHDHGGAREAARS

Signal peptide from human CD89 (aa sequence 1-21), chimeric human/bovine FcR extracellular domain (aa sequence 22-232), consisting of the EC1 domain from human CD89 (aa sequence 22-121) and of the EC2 domain from bovine Fcγ2R (aa sequence 122-232), transmembrane domain and short cytoplasmic tail from bovine Fcγ2R (aa sequence 233-266).

SEQ ID NO: 4:
Amino acid sequence of chimeric FcR comprising EC1 from human CD89 and EC2 from bovine Fcγ2R (human TM & human IC)
MDPKQTTLLCLVLCLGQRIQAQEGDFPMPFISAKSSPVIPLDGSVKIQC

QAIREAYLTQLMIIKNSTYREIGRRLKFWNETDPEFVIDHMDANKAGRY

QCQYRIGHYRFRYSDTLELVVTGEEPAGRLRDRPSLSVRPSPSVAPGEN

VTLLCQSGNRTDTFLLSKEGAAHRPLRLRSQDQDGWYQAEFSLSPVTSA

HGGTYRCYRSLSTNPYLLSQPSEPLALLVADYTMQNLIRMAVAGLVLVA

LLAILVENWHSHTALNKEASADVAEPSWSQQMCQPGLTFARTPSVCK

Signal peptide from human CD89 (aa sequence 1-21), chimeric human/bovine FcR extracellular domain (aa sequence 22-232), consisting of the EC1 domain from human CD89 (aa sequence 22-121) and of the EC2 domain from bovine Fcγ2R (aa sequence 122-232), transmembrane domain from human CD89 (aa sequence 233-251), and short cytoplasmic tail from human CD89 (aa sequence 252-292).

SEQ ID NO: 5:
cDNA sequence coding for chimeric FcR comprising EC1 from human CD89 and EC2 from bovine Fcγ2R (bovine TM & bovine IC; optimized for mammalian expression)
atggaccccaagcagaccacactgctgtgcctggtgctgtgtctcggcc agagaatccaagctcaagagggcgacttccccatgcctttcatcagcgc caagagcagccctgtgatccctctggatggcagcgtgaagatccagtgc caggccatcagagaggcctacctgacacagctgatgatcattaagaaca gcacctaccgcgagatcggcagacggctgaagttctggaacgagacaga ccccgagttcgtgatcgaccacatggacgccaacaaggccggcagatac cagtgtcagtaccggatcggccactaccggttcagatacagcgacaccc tggaactggtggtcaccggcgaagaacctgctggcagactgagagatag acccagcctgtctgtgcggccttctccttctgttgcccctggcgagaat gtgaccctgctctgtcagagcggcaaccggaccgataccttcctgctgt ctaaagaaggcgccgctcacagacccctgagactgagatcacaggacca ggacggatggtatcaggccgagttctctctgagcccagtgacatctgct cacggcggcacctacagatgctacagaagcctgagcacaaacccctatc tgctgagccagcctagcgagcctctggctctgctggtggccgattacac catgcagaacctgatcagaatgggcctcgccgcctctgttctgctgctg ctgggaatcctgctgtgtcaagccagacacgatcacggcggagccagag aagctgccagatct SEQ ID NO: 6:
cDNA sequence coding for chimeric FcR comprising EC1 from human CD89 and EC2 from bovine Fcγ2R (human TM & human IC; optimized for mammalian expression)
atggaccccaagcagaccacactgctgtgcctggtgctgtgtctcggcc agagaatccaagctcaagagggcgacttccccatgcctttcatcagcgc caagagcagccctgtgatccctctggatggcagcgtgaagatccagtgc caggccatcagagaggcctacctgacacagctgatgatcattaagaaca gcacctaccgcgagatcggcagacggctgaagttctggaacgagacaga -continued ccccgagttcgtgatcgaccacatggacgccaacaaggccggcagatac cagtgtcagtaccggatcggccactaccggttcagatacagcgacaccc tggaactggtggtcaccggcgaagaacctgctggcagactgagagatag acccagcctgtctgtgcggccttctccttctgttgcccctggcgagaat gtgaccctgctctgtcagagcggcaaccggaccgataccttcctgctgt ctaaagaaggcgccgctcacagacccctgagactgagatcacaggacca ggacggatggtatcaggccgagttctctctgagcccagtgacatctgct cacggcggcacctacagatgctacagaagcctgagcacaaacccctatc tgctgagccagcctagcgagcctctggctctgctggtggccgattacac catgcagaacctgatcagaatggccgtggccggactggtgctggttgca ctgctggctatcctggtggaaaactggcacagccacacagccctgaaca aagaggcttctgccgacgtcgccgagccttcttggagtcagcagatgtg tcagcccggcctgaccttcgccagaacacctagcgtgtgcaag SEQ ID NO: 7:
Amino acid sequence of chimeric FcR comprising EC1 from bovine Fcγ2R and EC2 from human CD89 (human TM & human IC)

MAPTLPALLCLGLSVGLRTQVQAGTFPKPIIWAEPSSVVPLGSSVTILC

QGPPNTKSFSLNKEGDSTPWNIHPSLEPWDKANFFISNVREQQAGRYHC

SHFIGVNWSEPSEPLDLLVAGLYGKPFLSADRGLVLMPGENISLTCSSA

HIPFDRFSLAKEGELSLPQHQSGEHPANFSLGPVDLNVSGIYRCYGWYN

RSPYLWSFPSNALELVVTDSIHQDYTTQNLIRMAVAGLVLVALLAILVE

NWHSHTALNKEASADVAEPSWSQQMCQPGLTFARTPSVCK

Signal peptide from bovine Fcγ2R (aa sequence 1-23), chimeric bovine/human FcR extracellular domain (aa sequence 24-225), consisting of the EC1 domain from bovine Fcγ2R (aa sequence 24-119), of the short hinge region from human CD89 (aa sequence aa 120-123), of the EC2 domain from human CD89 (aa sequence 124-218), and of the membrane proximal 'linker' region from human CD89 (aa sequence 219-225), followed transmembrane domain from human CD89 (aa sequence 226-244), and short cytoplasmic tail from human CD89 (aa sequence 245-285) according to Ding et al. J Biol Chem 2003; 278:27966-27970.

SEQ ID NO: 8
cDNA sequence coding for chimeric FcR chimeric FcR comprising EC1 of bovine Fcγ2R and EC2 of human CD89 (optimized for mammalian expression)

atggcccctacactgcctgctctgctgtgtctgggactgtctgtgggcc tgagaacacaggtgcaggccggcacattccccaagcctatcatttgggc cgagcctagctctgtggtgcctctgggaagcagcgtgaccatcctgtgt cagggccctccaaacaccaagagcttcagcctgaacaaagagggcgaca gcacccccttggaacattcaccctagcctggaaccttgggacaaagccaa cttcttcatcagcaacgtgcgcgagcagcaggccggaagataccactgc tctcacttcatcggagtgaattggagcgagcccagcgagcctctggatc tgcttgtggctggcctgtacggcaagcctttttctgtctgccgatagagg cctggtgctgatgcccggcgagaatatcagcctgacctgtagcagcgct -continued cacatccccttcgacagattctccctggccaaagaaggcgagctgagcc tgcctcagcatcagtctggcgaacaccccgccaacttttctctgggccc tgtggacctgaacgtgtccggcatctacagatgctacggctggtacaat cggagcccctacctgtggtctttccccagcaatgccctggaactggtgg tcaccgatagcatccaccaggactacaccacacagaacctgatcagaat ggccgtggccggactggtgctggttgcactgctggctattctggtggaa aactggcacagccacaccgctctcaacaaagaagcctctgccgacgtcg ccgagccttcttggagtcagcagatgtgtcagcccggcctgaccttcgc cagaacacctagcgtgtgcaag SEQ ID NO: 9:
Amino acid sequence of full-length bovine Fcγ2R (Swiss-Prot no. Q28109; aa 264)

MAPTLPALLCLGLSVGLRTQVQAGTFPKPIIWAEPSSVVPLGSSVTILC

QGPPNTKSFSLNKEGDSTPWNIHPSLEPWDKANFFISNVREQQAGRYHC

SHFIGVNWSEPSEPLDLLVAGEEPAGRLRDRPSLSVRPSPSVAPGENVT

LLCQSGNRTDTFLLSKEGAAHRPLRLRSQDQDGWYQAEFSLSPVTSAHG

GTYRCYRSLSTNPYLLSQPSEPLALLVADYTMQNLIRMGLAASVLLLLG

ILLCQARHDHGGAREAARS

Signal peptide (aa sequence 1-23), extracellular domain (aa sequence 24-230), comprising of an Ig-like EC1 domain (aa sequence 24-119) and of an Ig-like EC2 domain (aa sequence 120-230), followed by transmembrane domain and short cytoplasmic tail (aa sequence 231-264).

SEQ ID NO: 10:
cDNA sequence coding for full-length bovine Fcγ2R protein (optimized for mammalian expression)

atggcccctacactgcctgctctgctgtgtctgggactgtctgtgggcc tgagaacacaggtgcaggccggcacattccccaagcctatcatttgggc cgagcctagctctgtggtgcctctgggaagcagcgtgaccatcctgtgt cagggccctccaaacaccaagagcttcagcctgaacaaagagggcgaca gcaccccttggaacattcaccctagcctggaaccttgggacaaagccaa cttcttcatcagcaacgtgcgcgagcagcaggccggaagataccactgc tctcacttcatcggagtgaattggagcgagcccagcgagcctctggatc tgcttgttgctggcgaagaaccagccggcagactgagagatagaccctc tctgagtgtgcggccctctccttctgttgcccctggcgaaaatgtgacc ctgctgtgccagagcggcaacaggaccgataccttcctgctgagcaaag aaggcgccgctcacagacccctgagactgagatcacaggaccaggacgg atggtatcaggccgagttcagcctgtctcctgtgacatctgctcacggc ggcacctacagatgctacagaagcctgagcacaaacccctacctgctgt cccagccttctgagcctttggctctgctggtggccgactacaccatgca gaacctgatcagaatgggcctcgccgcctctgttctgctgctgctggga atcctgctctgtcaggccagacacgatcatggcggagccagagaagccg ccagatct -continued

```
SEQ ID NO: 11:
Amino acid sequence of full-length cynomolgus
monkey CD89 (NCBI Reference Sequence:
XP_005590398.1; aa 287)
MDPKETTLLCLVLCLGQRIQAQEGNFSTPFISTRSSPVVPWGGSVRIQC

QAIPDAYLIWLMMLKNSTYEKRDEKLGFWNDTTPEFVIDHMDANKAGRY

RCRYRIGLSRFRYSDTLELVVTGLYGKPSLSVDRGPVLMPGENISVTCS

SAHIPFDRFSLAKEGELSLPQHQSGEHPANFSLGPVDLNVSGSYRCYGW

YNRSPYLWSFPSNALELVVTDSINRDYTTQNLIRMAMAGLVLVALLAIL

VENWHSHKALNKEASADVAEPSWSHQ

MCQPGWTFARTPSVCK
SEQ ID NO: 12:
cDNA sequence coding for full-length cynomolgus
monkey CD89 (optimized for mammalian expression)
atggaccccaaagaaaccaccctgctgtgcctggtgctgtgtctgggcc

agagaatccaggcccaggaaggcaacttcagcaccccttcatcagcac

cagatccagccccgtggtgccttggggaggctctgtgcggattcagtgc

caggccatccccgacgcctacctgatctggctgatgatgctgaagaaca

gcacctacgagaagcgggacgagaagctgggcttctggaacgacaccac

cccgagttcgtgatcgaccacatggacgccaacaaggccggcagatac

cggtgccggtacagaatcggcctgagccggttcagatacagcgacaccc

tggaactggtcgtgaccggcctgtacggcaagcctagcctgtccgtgga

tagaggccccgtgctgatgcccggcgagaacatcagcgtgacctgtagc

agcgcccacatccccttcgacagattcagcctggccaaagagggcgagc

tgagcctgcctcagcatcagtctggcgagcaccccgccaactttagcct

gggccctgtggacctgaacgtgtccggcagctacagatgctacggctgg

tacaaccggtcccccctacctgtggtccttccccagcaacgctctggaac

tggtcgtgacagacagcatcaaccgggactacaccacccagaacctgat

ccggatggctatggccggactggtgctggtggccctgctggccatcctg

gtggaaaactggcacagccacaaggccctgaacaaagaggccagcgccg

atgtggccgagccttcttggagccaccagatgtgtcagcccggctggac

cttcgccagaaccccttctgtgtgcaag

SEQ ID NO: 13:
Amino acid sequence of chimeric CD89 by exchanging
EC1 part from human CD89 (Gln22 - Lys46) with
EC1 part from cynomolgus monkey CD89 (Gln22 -
Arg46)
MDPKQTTLLCLVLCLGQRIQAQEGNFSTPFISTRSSPVVPWGGSVRIQC

QAIREAYLTQLMIIKNSTYREIGRRLKFWNETDPEFVIDHMDANKAGRY

QCQYRIGHYRFRYSDTLELVVTGLYGKPFLSADRGLVLMPGENISLTCS

SAHIPFDRFSLAKEGELSLPQHQSGEHPANFSLGPVDLNVSGIYRCYGW

YNRSPYLWSFPSNALELVVTDSIHQDYTTQNLIRMAVAGLVLVALLAIL

VENWHSHTALNKEASADVAEPSWSQQMCQPGLTFARTPSVCK
```

Signal peptide from human CD89 (aa sequence 1-21), chimeric human/cynomolgus monkey CD89 extracellular domain (aa sequence 22-227), comprising of an Ig-like EC1 domain part from cynomolgus monkey CD89 (aa sequence 22-46; NCBI Reference Sequence: XP_005590398.1) and an Ig-like EC1 domain part from human CD89 (aa sequence 47-121; Swiss-Prot no. P24071.1), of a short hinge region from human CD89 (aa sequence 122-125), of an Ig-like EC2 domain from human CD89 (aa sequence 126-220), and of a membrane proximal 'linker' region from human CD89 (aa sequence 221-227), followed by transmembrane domain from human CD89 (aa sequence 228-246), and short cytoplasmic tail from human CD89 (aa sequence 247-287) according to Ding et al. J Biol Chem 2003; 278:27966-27970.

```
SEQ ID NO: 14:
cDNA sequence coding for chimeric CD89 by
exchanging EC1 part from human CD89 (Gln22 -
Lys46) with EC1 part from cynomolgus monkey CD89
(Gln22 - Arg46) (optimized for mammalian
expression)
atggaccccaagcagaccacactgctgtgcctggtgctgtgtctcggcc

agagaatccaggctcaagagggcaacttcagcaccccctttcatcagcac

cagatctagccccgtggtgccttggggcggctctgttagaatccagtgc

caggccatcagagaggcctacctgacacagctgatgatcattaagaaca

gcacctaccgcgagatcggcagacggctgaagttctggaacgagacaga

ccccgagttcgtgatcgaccacatggacgccaacaaggccggcagatac

cagtgtcagtaccggatcggccactaccggttcagatacagcgacaccc

tggaactggtggtcaccggcctgtacggcaagcctttttctgagcgccga

tagaggcctggtcctgatgcctggcgagaacatcagcctgacctgtagc

agcgctcacatccccttcgacagattcagcctggccaaagagggcgagc

tgtctctgcctcagcatcagtctggcgagcaccccgccaatttttctct

gggccctgtggacctgaacgtgtccggcatctacagatgctacggctgg

tacaatcggagcccctacctgtggtctttccccagcaatgccctcgaac

tggtcgtgaccgatagcatccaccaggactacaccacacagaacctgat

cagaatggccgtggccggactggtgctggttgctctgctggctattctg

gtggaaaactggcacagccacacagccctgaacaaagaggcttctgccg

acgtcgccgagccttcttggagtcagcagatgtgtcagcccggcctgac

cttcgccagaacacctagcgtgtgcaag

SEQ ID NO: 15:
Amino acid sequence of chimeric CD89 by
exchanging EC1 part from human CD89 (Ile47 -
Ile71) with EC1 part from cynomolgus monkey CD89
(Ile47 - Arg71)
MDPKQTTLLCLVLCLGQRIQAQEGDFPMPFISAKSSPVIPLDGSVKIQC

QAIPDAYLIWLMMLKNSTYEKRGRRLKFWNETDPEFVIDHMDANKAGRY

QCQYRIGHYRFRYSDTLELVVTGLYGKPFLSADRGLVLMPGENISLTCS

SAHIPFDRFSLAKEGELSLPQHQSGEHPANFSLGPVDLNVSGIYRCYGW

YNRSPYLWSFPSNALELVVTDSIHQDYTTQNLIRMAVAGLVLVALLAIL

VENWHSHTALNKEASADVAEPSWSQQMCQPGLTFARTPSVCK
```

Signal peptide from human CD89 (aa sequence 1-21), chimeric human/cynomolgus monkey CD89 extracellular domain (aa sequence 22-227), comprising of an Ig-like EC1 domain part from human CD89 (aa sequence 22-46; Swiss-Prot no. P24071.1), an Ig-like EC1 domain part from cynomolgus monkey CD89 (aa sequence 47-71; NCBI Reference Sequence: XP_005590398.1) and an Ig-like EC1 domain part from human CD89 (aa sequence 48-121; Swiss-Prot no. P24071.1), of a short hinge region from human CD89 (aa sequence 122-125), of an Ig-like EC2 domain from human CD89 (aa sequence 126-220), and of a membrane proximal 'linker' region from human CD89 (aa sequence 221-227), followed by transmembrane domain from human CD89 (aa sequence 228-246), and short cytoplasmic tail from human CD89 (aa sequence 247-287) according to Ding et al. J Biol Chem 2003; 278:27966-27970.

```
SEQ ID NO: 16:
cDNA sequence coding for chimeric CD89 by
exchanging EC1 part from human CD89 (Ile47 -
Ile71) with EC1 part from cynomolgus monkey CD89
(Ile47 - Arg71) (optimized for mammalian
expression)
atggaccccaagcagaccacactgctgtgcctggtgctgtgtctcggcc

agagaatccaagctcaagagggcgacttccccatgcctttcatcagcgc

caagagcagccctgtgatccctctggatggcagcgtgaagatccagtgc

caggccattcctgacgcctacctgatctggctgatgatgctgaagaaca

gcacctacgagaagagaggcagacggctgaagttctggaacgagacaga

ccccgagttcgtgatcgaccacatggacgccaacaaggccggcagatac

cagtgtcagtaccggatcggccactaccggttcagatacagcgacaccc

tggaactggtggtcaccggcctgtacggcaagccttttctgtctgccga

tagaggactggtgctgatgcccggcgagaacatcagcctgacctgtagc

tctgctcacatccccttcgacagattcagcctggccaaagaaggcgagc

tgagcctgcctcagcatcagtctggcgaacaccccgccaacttttctct

gggccctgtggacctgaacgtgtccggcatctacagatgctacggctgg

tacaatcggagcccctacctgtggtctttccccagcaatgccctcgaac

tggtcgtgaccgatagcatccaccaggactacaccacacagaacctgat

cagaatggccgtggccggcctggttctggttgctctgctggctattctg

gtggaaaactggcacagccacacagccctgaacaaagaggcttctgccg

acgtcgccgagccttcttggagtcagcagatgtgtcagcccggcctgac

cttcgccagaacacctagcgtgtgcaag

SEQ ID NO: 17:
Amino acid sequence of chimeric CD89 by
exchanging EC1 part from human CD89 (Gly72 -
Gly96) with EC1 part from cynomolgus monkey CD89
(Asp72 - Gly96)
MDPKQTTLLCLVLCLGQRIQAQEGDFPMPFISAKSSPVIPLDGSVKIQC

QAIREAYLTQLMIIKNSTYREIDEKLGFWNDTTPEFVIDHMDANKAGRY

QCQYRIGHYRFRYSDTLELVVTGLYGKPFLSADRGLVLMPGENISLTCS

SAHIPFDRFSLAKEGELSLPQHQSGEHPANFSLGPVDLNVSGIYRCYGW

YNRSPYLWSFPSNALELVVTDSIHQDYTTQNLIRMAVAGLVLVALLAIL

VENWHSHTALNKEASADVAEPSWSQQMCQPGLTFARTPSVCK
```

Signal peptide from human CD89 (aa sequence 1-21), chimeric human/cynomolgus monkey CD89 extracellular domain (aa sequence 22-227), comprising of an Ig-like EC1 domain part from human CD89 (aa sequence 22-71; Swiss-Prot no. P24071.1), an Ig-like EC1 domain part from cynomolgus monkey CD89 (aa sequence 72-96; NCBI Reference Sequence: XP_005590398.1) and an Ig-like EC1 domain part from human CD89 (aa sequence 97-121; Swiss-Prot no. P24071.1), of a short hinge region from human CD89 (aa sequence 122-125), of an Ig-like EC2 domain from human CD89 (aa sequence 126-220), and of a membrane proximal 'linker' region from human CD89 (aa sequence 221-227), followed by transmembrane domain from human CD89 (aa sequence 228-246), and short cytoplasmic tail from human CD89 (aa sequence 247-287) according to Ding et al. J Biol Chem 2003; 278:27966-27970.

```
SEQ ID NO: 18:
cDNA sequence coding for chimeric CD89 by
exchanging EC1 part from human CD89 (Gly72 -
Gly96) with EC1 part from cynomolgus monkey CD89
(Asp72 - Gly96) (optimized for mammalian
expression)
atggaccccaagcagaccacactgctgtgcctggtgctgtgtctcggcc

agagaatccaagctcaagagggcgacttccccatgcctttcatcagcgc

caagagcagccctgtgatccctctggatggcagcgtgaagatccagtgc

caggccatcagagaggcctacctgacacagctgatgatcattaagaaca

gcacctaccgcgagatcgacgagaagctcggcttctggaacgacaccac

acctgagttcgtgatcgaccacatggacgccaacaaggccggcagatac

cagtgtcagtaccggatcggccactaccggttcagatacagcgacaccc

tggaactggtggtcaccggcctgtacggcaagccttttctgtctgccga

tagaggactggtgctgatgcccggcgagaacatcagcctgacctgtagc

tctgctcacatccccttcgacagattcagcctggccaaagaaggcgagc

tgagcctgcctcagcatcagtctggcgaacaccccgccaacttttctct

gggccctgtggacctgaacgtgtccggcatctacagatgctacggctgg

tacaatcggagcccctacctgtggtctttccccagcaatgccctcgaac

tggtcgtgaccgatagcatccaccaggactacaccacacagaacctgat

cagaatggccgtggccggcctggttctggttgctctgctggctattctg

gtggaaaactggcacagccacacagccctgaacaaagaggcttctgccg

acgtcgccgagccttcttggagtcagcagatgtgtcagcccggcctgac

cttcgccagaacacctagcgtgtgcaag

SEQ ID NO: 19:
Amino acid sequence of chimeric CD89 by
exchanging EC1 part from human CD89 (Arg97 -
Gly121) with EC1 part from cynomolgus monkey CD89
(Arg97- Gly121)
MDPKQTTLLCLVLCLGQRIQAQEGDFPMPFISAKSSPVIPLDGSVKIQC

QAIREAYLTQLMIIKNSTYREIGRRLKFWNETDPEFVIDHMDANKAGRY

RCRYRIGLSRFRYSDTLELVVTGLYGKPFLSADRGLVLMPGENISLTCS

SAHIPFDRFSLAKEGELSLPQHQSGEHPANFSLGPVDLNVSGIYRCYGW

YNRSPYLWSFPSNALELVVTDSIHQDYTTQNLIRMAVAGLVLVALLAIL

VENWHSHTALNKEASADVAEPSWSQQMCQPGLTFARTPSVCK
```

Signal peptide from human CD89 (aa sequence 1-21), chimeric human/cynomolgus monkey CD89 extracellular domain (aa sequence 22-227), comprising of an Ig-like EC1 domain part from human CD89 (aa sequence 22-96; Swiss-Prot no. P24071.1) and an Ig-like EC1 domain part from cynomolgus monkey CD89 (aa sequence 97-121; NCBI Reference Sequence: XP_005590398.1), of a short hinge region from human CD89 (aa sequence 122-125), of an Ig-like EC2 domain from human CD89 (aa sequence 126-220), and of a membrane proximal 'linker' region from human CD89 (aa sequence 221-227), followed by transmembrane domain from human CD89 (aa sequence 228-

246), and short cytoplasmic tail from human CD89 (aa sequence 247-287) according to Ding et al. J Biol Chem 2003; 278:27966-27970.

SEQ ID NO: 20: cDNA sequence coding for chimeric CD89 by exchanging EC1 part from human CD89 (Arg97 - Gly121) with EC1 part from cynomolgus monkey CD89 (Arg97- Gly121) (optimized for mammalian expression)

atggaccccaagcagaccacactgctgtgcctggtgctgtgtctcggcc agagaatccaagctcaagagggcgacttccccatgcctttcatcagcgc caagagcagccctgtgatccctctggatggcagcgtgaagatccagtgc caggccatcagagaggcctacctgacacagctgatgatcattaagaaca gcacctaccgcgagatcggcagacggctgaagttctggaacgagacaga ccccgagttcgtgatcgaccacatggacgccaacaaggccggcagatac cggtgcagatacagaatcggcctgagccggttccggtacagcgatacac tggaactggtggtcaccggcctgtacggcaagccttttctgagcgccga tagaggactggtgctgatgcccggcgagaacatcagcctgacctgtagc tctgctcacatccccttcgacagattcagcctggccaaagaaggcgagc tgagcctgcctcagcatcagtctggcgaacaccccgccaacttttctct gggccctgtggacctgaacgtgtccggcatctacagatgctacggctgg tacaatcggagcccctacctgtggtctttccccagcaatgccctggaac tcgtcgtgaccgatagcatccaccaggactacaccacacagaacctgat cagaatggccgtggccggcctggttctggttgctctgctggctattctg gtggaaaactggcacagccacacagccctgaacaaagaggcttctgccg acgtcgccgagccttcttggagtcagcagatgtgtcagcccggcctgac cttcgccagaacacctagcgtgtgcaag SEQ ID NO: 21:
Amino acid sequence of chimeric CD89 by exchanging human IgA contacting amino acid residues within EC1 part from human CD89 (Thr58, Gln59, Arg73, Arg74, Lys76, His106, and Tyr107) with reciprocal amino acids from EC1 part from cynomolgus monkey CD89 (Ile58, Trp59, Glu73, Lys74, Gly76, Leu106, and Ser107)

MDPKQTTLLCLVLCLGQRIQAQEGDFPMPFISAKSSPVIPLDGSVKIQC

QAIREAYLIWLMIIKNSTYREIGEKLGFWNETDPEFVIDHMDANKAGRY

QCQYRIGLSRFRYSDTLELVVTGLYGKPFLSADRGLVLMPGENISLTCS

SAHIPFDRFSLAKEGELSLPQHQSGEHPANFSLGPVDLNVSGIYRCYGW

YNRSPYLWSFPSNALELVVTDSIHQDYTTQNLIRMAVAGLVLVALLAIL

VENWHSHTALNKEASADVAEPSWSQQMCQPGLTFARTPSVCK

Signal peptide from human CD89 (aa sequence 1-21), chimeric human/cynomolgus monkey CD89 extracellular domain (aa sequence 22-227), comprising of an Ig-like EC1 domain from human CD89 (aa sequence 22-121; Swiss-Prot no. P24071.1), except for Ile58, Trp59, Glu73, Lys74, Gly76, Leu106, and Ser107 from the Ig-like EC1 domain from cynomolgus monkey CD89 (NCBI Reference Sequence: XP_005590398.1), of a short hinge region from human CD89 (aa sequence 122-125), of an Ig-like EC2 domain from human CD89 (aa sequence 126-220), and of a membrane proximal 'linker' region from human CD89 (aa sequence 221-227), followed by transmembrane domain from human CD89 (aa sequence 228-246), and short cytoplasmic tail from human CD89 (aa sequence 247-287) according to Ding et al. J Biol Chem 2003; 278:27966-27970.

SEQ ID NO: 22:
cDNA sequence coding for chimeric CD89 by exchanging human IgA contacting amino acid residues within EC1 part from human CD89 (Thr58, Gln59, Arg73, Arg74, Lys76, His 106, and Tyr107) with reciprocal amino acids from EC1 part from cynomolgus monkey CD89 (Ile58, Trp59, Glu73, Lys74, Gly76, Leu106, and Ser107) (optimized for mammalian expression)

atggaccccaagcagaccacactgctgtgcctggtgctgtgtctcggcc agagaatccaagctcaagagggcgacttccccatgcctttcatcagcgc caagagcagccctgtgatccctctggatggcagcgtgaagatccagtgc caggccatcagagaggcctacctgatctggctgatgatcattaagaaca gcacctaccgcgagatcggcgagaagctcggcttctggaacgagacaga ccccgagttcgtgatcgaccacatggacgccaacaaggccggcagatac cagtgtcagtaccggatcggcctgagccggttcagatacagcgataccc tggaactggtggtcaccggcctgtacggcaagccttttctgtctgccga tagaggactggtgctgatgcccggcgagaacatcagcctgacctgtagc tctgctcacatccccttcgacagattcagcctggccaaagaaggcgagc tgagcctgcctcagcatcagtctggcgaacaccccgccaacttttctct gggccctgtggacctgaacgtgtccggcatctacagatgctacggctgg tacaatcggagcccctacctgtggtctttccccagcaatgccctcgaac tggtcgtgaccgatagcatccaccaggactacaccacacagaacctgat cagaatggccgtggccggcctggttctggttgctctgctggctattctg gtggaaaactggcacagccacacagccctgaacaaagaggcttctgccg acgtcgccgagccttcttggagtcagcagatgtgtcagcccggcctgac cttcgccagaacacctagcgtgtgcaag SEQ ID NO: 23:
Amino acid sequence I within EC1 part of human CD89 (Gln22 - Lys46)

QEGDFPMPFISAKSSPVIPLDGSVK

SEQ ID NO: 24:
Amino acid sequence II within EC1 part of human CD89 (Ile47 - Ile71)

IQCQAIREAYLTQLMIIKNSTYREI

SEQ ID NO: 25:
Amino acid sequence III within EC1 part of human CD89 (Gly72 - Gly96)

GRRLKFWNETDPEFVIDHMDANKAG

SEQ ID NO: 26:
Amino acid sequence IV within EC1 part of human CD89 (Arg97 - Gly121)

RYQCQYRIGHYRFRYSDTLELVVTG

SEQ ID NO: 27:
Consensus amino acid sequence of heavy chain variable region of mouse anti-human CD89-specific antibody 8F3

EVQLVESGGGLVKPGGSLKLSCAASGFTFSNYGMSWVRQTPDKRLEWVA

TMHSGGTYTYYPDNVKGRFTISRDNAKNNLYLQMSSLRSEDTAMYYCAR

ETGLYDGLFDFWGQGTTLTVSS

-continued

SEQ ID NO: 28:
Consensus amino acid sequence of light chain variable region of mouse anti-human CD89-specific antibody 8F3
DVQITQSPSYLAASPGETITINCRASKTISKYLAWYQEKPGKTNMLLIY

SGSTLQSGVPSRFSGSGSGTDFTLTISSLEPEDLAMYYCQQHDEYPWTF

GGGTKLEIK

Complementarity determining regions (CDRs) of mouse anti-human CD89-specific antibody 8F3:
SEQ ID NO: 29-34

SEQ ID NO: 29:
Amino acid sequence heavy chain CDR1 of 8F3
NYGMS

SEQ ID NO: 30:
Amino acid sequence heavy chain CDR2 of 8F3
TMHSGGTYTYYPDNVKG

SEQ ID NO: 31:
Amino acid sequence heavy chain CDR3 of 8F3
ETGLYDGLFDF

SEQ ID NO: 32:
Amino acid sequence light chain CDR1 of 8F3
RASKTISKYLA

SEQ ID NO: 33:
Amino acid sequence light chain CDR2 of 8F3
SGSTLQS

SEQ ID NO: 34:
Amino acid sequence light chain CDR3 of 8F3
QQHDEYPWT

SEQ ID NO: 35:
Consensus amino acid sequence of heavy chain variable region of mouse anti-human CD89-specific antibody 9H7
QIQLVQSGPELKKPGETVKISCKASGYTFKNYGMNWVKQAPGKGLKWMA

WINTYTGEPTHTDDFKGRFVFSLETSASTAYLQINNLKNEDTATYFCAR

WGLGTTEEAARDYWGQGTTLTVSS

SEQ ID NO: 36:
Consensus amino acid sequence of light chain variable region of mouse anti-human CD89-specific antibody 9H7
DVVMTQTPLTLSVTIGQPASMSCKSSQSLLDSDGKTYLNWLLQRPGQSP

KSLIYLVSKQDSGVPDRFTGSGSGTDFTLKISRVEAEDLGVYYCWQGTH

FPQTFGGGTKLEIK

Complementarity determining regions (CDRs) of mouse anti-human CD89-specific antibody 9H7: SEQ ID NO: 37-42

SEQ ID NO: 37:
Amino acid sequence heavy chain CDR1 of 9H7
NYGMN

SEQ ID NO: 38:
Amino acid sequence heavy chain CDR2 of 9H7
WINTYTGEPTHTDDFKG

SEQ ID NO: 39:
Amino acid sequence heavy chain CDR3 of 9H7
WGLGTTEEAARDY

SEQ ID NO: 40:
Amino acid sequence light chain CDR1 of 9H7
KSSQSLLDSDGKTYLN

-continued

SEQ ID NO: 41:
Amino acid sequence light chain CDR2 of 9H7
LVSKQDS

SEQ ID NO: 42:
Amino acid sequence light chain CDR3 of 9H7
WQGTHFPQT

SEQ ID NO: 43:
Consensus amino acid sequence of heavy chain variable region of mouse anti-human CD89-specific antibody 10E7
EVQLVESGGGLVQPGGSLKLSCAASGLTFSSYGMSWVRQTPDKRLELVA

TINGNGDITYYPDSVKGRFTISRDNAKNTLYLQMSSLKSEDTAMYYCAR

DYDYDYAMDYWGQGTSVTVSS

SEQ ID NO: 44:
Consensus amino acid sequence of light chain variable region of mouse anti-human CD89-specific antibody 10E7
DIQMTQSTSSLSASLGDSVTISCRASQDIINYLNWYQQKPDGTVKLLIY

YTSRLHSGVPSRFSGSGSGTEYSLTVSNLEKEDIATYFCQQGKTLPYTF

GGGTKLEIK

Complementarity determining regions (CDRs) of mouse anti-human CD89-specific antibody 10E7: SEQ ID NO: 45-50

SEQ ID NO: 45:
Amino acid sequence heavy chain CDR1 of 10E7
SYGMS

SEQ ID NO: 46:
Amino acid sequence heavy chain CDR2 of 10E7
TINGNGDITYYPDSVKG

SEQ ID NO: 47:
Amino acid sequence heavy chain CDR3 of 10E7
DYDYDYAMDY

SEQ ID NO: 48:
Amino acid sequence light chain CDR1 of 10E7
RASQDIINYLN

SEQ ID NO: 49:
Amino acid sequence light chain CDR2 of 10E7
YTSRLHS

SEQ ID NO: 50:
Amino acid sequence light chain CDR3 of 10E7
QQGKTLPYT

SEQ ID NO: 51:
Consensus amino acid sequence of heavy chain variable region of mouse anti-human CD89-specific antibody 16D6
QVQLQQSGAELMKPGASVKISCKATGYTFSTYWIEWVKQRPGHGLEWIG

EILPGSGSANYNEKFKGKATFTADTSSNTAYMQLSSLTFEDSAVYYCAK

GFGSPYYYAMDYWGQGTSVTVSS

SEQ ID NO: 52:
Consensus amino acid sequence of light chain variable region of mouse anti-human CD89-specific antibody 16D6
EIVLTQSPALMAASPGEKVTITCSVSSSISSSNLHWYQQKSETSPKPWI

YGTSKLASGVPVRFSGSGSGTSYSLTISNMEAEDAATYYCQQWSSFPLT

FGGGTKLEIK

Complementarity determining regions (CDRs) of mouse anti-human CD89-specific antibody 16D6: SEQ ID NO: 53-58

SEQ ID NO: 53:
Amino acid sequence heavy chain CDR1 of 16D6
TYWIE

SEQ ID NO: 54:
Amino acid sequence heavy chain CDR2 of 16D6
EILPGSGSANYNEKFKG

SEQ ID NO: 55:
Amino acid sequence heavy chain CDR3 of 16D6
GFGSPYYYAMDY

SEQ ID NO: 56:
Amino acid sequence light chain CDR1 of 16D6
SVSSSISSSNLH

SEQ ID NO: 57:
Amino acid sequence light chain CDR2 of 16D6
GTSKLAS

SEQ ID NO: 58:
Amino acid sequence light chain CDR3 of 16D6
QQWSSFPLT

SEQ ID NO: 59:
Consensus amino acid sequence of heavy chain variable region of mouse anti-human CD89-specific antibody 26D6
QIQLVQSGPELKKPGETVKISCKASGYTLTKYGMNWVKQAPGKGLKWMG

WINTYTGEPTYADDFKGRFAFSLETSASTAYLQINNLKNEDTATYFCAS

LPLFGRDSFAYWGQGTLVTVSA

SEQ ID NO: 60:
Consensus amino acid sequence of light chain variable region of mouse anti-human CD89-specific antibody 26D6
DVVMTQTPLTLSVTIGQPASISCKSSQSLLDSDGKTYLNWLLQRPGQSP

KRLIYLVSKLDSGVPDRFTGSGSGTDFTLKISRVEAEDLGVYYCWQVTH

FPQTFGGGTKLEIK

Complementarity determining regions (CDRs) of mouse anti-human CD89-specific antibody 26D6: SEQ ID NO: 61-66

SEQ ID NO: 61:
Amino acid sequence heavy chain CDR1 of 26D6
KYGMN

SEQ ID NO: 62:
Amino acid sequence heavy chain CDR2 of 26D6
WINTYTGEPTYADDFKG

SEQ ID NO: 63:
Amino acid sequence heavy chain CDR3 of 26D6
LPLFGRDSFAY

SEQ ID NO: 64:
Amino acid sequence light chain CDR1 of 26D6
KSSQSLLDSDGKTYLN

SEQ ID NO: 65:
Amino acid sequence light chain CDR2 of 26D6
LVSKLDS

SEQ ID NO: 66:
Amino acid sequence light chain CDR3 of 26D6
WQVTHFPQT

-continued

SEQ ID NO: 67:
Consensus amino acid sequence of heavy chain variable region of mouse anti-human CD89-specific antibody 20B4
QVQLKESGPGLVAPSQSLSITCTVSGFSLTSYGVHWVRQPPGKGLEWLG

IIWAGGSTSYNSALMSRLSISKDNSKSQVFLKMNSLQTDDTAMYYCARD

HYDLFAYWGQGTLVTVSA

SEQ ID NO: 68:
Consensus amino acid sequence of light chain variable region of mouse anti-human CD89-specific antibody 20B4
DILMTQSPSSMSVSLGDTVSITCHASQDISRNIGWLQQKPGKSFKGLIY

HGTNLEDGVPSRFSGSGSGADYSLTISSLESEDFADYYCVQYAQFPRTF

GGGTKLEIK

Complementarity determining regions (CDRs) of mouse anti-human CD89-specific antibody 20B4: SEQ ID NO: 69-74

SEQ ID NO: 69:
Amino acid sequence heavy chain CDR1 of 20B4
SYGVH

SEQ ID NO: 70:
Amino acid sequence heavy chain CDR2 of 20B4
IIWAGGSTSYNSALMS

SEQ ID NO: 71:
Amino acid sequence heavy chain CDR3 of 20B4
DHYDLFAY

SEQ ID NO: 72:
Amino acid sequence light chain CDR1 of 20B4
HASQDISRNIG

SEQ ID NO: 73:
Amino acid sequence light chain CDR2 of 20B4
HGTNLED

SEQ ID NO: 74:
Amino acid sequence light chain CDR3 of 20B4
VQYAQFPRT

SEQ ID NO: 75:
Consensus amino acid sequence of heavy chain variable region of mouse anti-human CD89-specific antibody 30C7
QVQLQQSGPELVRPGVSVKISCKGSGYTFTDYVMHWVKQSHAKSLEWIG

VISTYSGNTNYNQKFKGKATMTVDKSSSTAYMELARLTSEDSAIYYCAR

ESDGYYFDYWGQGTTLTVSS

SEQ ID NO: 76:
Consensus amino acid sequence of light chain variable region of mouse anti-human CD89-specific antibody 30C7
DIVMSQSPSSLAVSAGEKVTMSCKSSQSLLNSRTRKNYLAWYQQKPGQS

PKLLIYWASTRESGVPDRFTGSGSGTDFTLTISSVQAEDLAVYYCKQSY

NLMYTFGGGTKLEIK

Complementarity determining regions (CDRs) of mouse anti-human CD89-specific antibody 30C7: SEQ ID NO: 77-82

SEQ ID NO: 77:
Amino acid sequence heavy chain CDR1 of 30C7
DYVMH

SEQ ID NO: 78:
Amino acid sequence heavy chain CDR2 of 30C7
VISTYSGNTNYNQKFKG

SEQ ID NO: 79:
Amino acid sequence heavy chain CDR3 of 30C7
ESDGYYFDY

SEQ ID NO: 80:
Amino acid sequence light chain CDR1 of 30C7
KSSQSLLNSRTRKNYLA

SEQ ID NO: 81:
Amino acid sequence light chain CDR2 of 30C7
WASTRES

SEQ ID NO: 82:
Amino acid sequence light chain CDR3 of 30C7
KQSYNLMYT

SEQ ID NO: 83:
cDNA sequence coding for chimeric mouse VH 8F3 human heavy IgG4 chain
atggagctgggcctgagctggatttttctgctggccatcctgaagggcgtgcagtgcgaagtgcagctggttgaatctggcggcggac tggttaagcctggcggatctctgaagctgagctgtgccgccagcggcttcaccttcagcaattacggcatgagctgggtccgacagac ccctgacaagagactggaatgggtcgccacaatgcacagcggcggcacctacacctactatcccgacaacgtgaagggcagattcacc atcagccgggacaacgccaagaacaacctgtacctgcagatgagcagcctgcggagcgaggataccgccatgtactactgcgccagag aaaccggcctgtacgacggcctgttcgattttggggccagggcaccacactgaccgtgtctagcgcctctacaaagggccctagcgt gttccctctggctccttgtagcagaagcaccagcgagtctacagccgctctgggctgtctggtcaaggactactttcccgagcctgtg acagtgtcctggaactctggcgctctgacaagcggcgtgcacacatttccagccgtgctgcaaagcagcggcctgtattctctgagca gcgtggtcacagtgcccagctctagcctgggcaccaagacctacacatgcaatgtggaccacaagcctagcaacaccaaggtggacaa gcgcgtggaatctaagtacggccctccttgtcctccatgtcctgcacctgagtttctcggcggaccctccgtgttcctgtttcctcca aagcctaaggacaccctgatgatcagcagaacccctgaagtgacctgcgtggtggtggacgtttcccaagaggaccctgaggtgcagt tcaattggtacgtggacggcgtggaagtgcacaatgccaagaccaagcctagagaggaacagttcaacagcacctacagagtggtgtc cgtgctgacagtgctgcaccaggattggctgaacggcaaagagtacaagtgcaaggtgtccaacaagggcctgcctagcagcatcgag aaaaccatcagcaaggccaagggccagccaagagaaccccaggtgtacacactgcctccaagccaagaggaaatgaccaagaaccagg tgtccctgacctgcctggttaagggcttctacccctccgatatcgccgtggaatgggagagcaatggccagcctgagaacaactacaa gaccacacctcctgtgctggacagcgacggctcattcttcctgtacagcaggctgaccgtggacaagagcagatggcaagagggcaac gtgttcagctgcagcgtgatgcacgaggccctgcacaaccactacacccagaagtctctgagcctgtctctgggcaag SEQ ID NO: 84:
cDNA sequence coding for chimeric mouse VH 10E7 human heavy IgG4 chain
atggagctgggcctgagctggatttttctgctggccatcctgaagggcgtgcagtgcgaagtgcagctggttgaatctggcggaggac tggttcagcctggcggatctctgaagctgtcttgtgccgcctctggcctgacctttagcagctacggcatgagctgggtccgacagac ccctgacaagagactggaactggtggccacaatcaacggcaacggcgacatcacctactatcccgacagcgtgaagggcagattcacc atcagccgggacaacgccaagaacaccctgtacctgcagatgagcagcctgaagtccgaggacaccgccatgtactactgcgccagag actacgactacgattacgctatggactactggggccagggcaccagcgtgacagttagctctgcctctacaaagggccctagcgtgtt ccctctggctccttgtagcagaagcaccagcgagtctacagccgctctgggctgtctggtcaaggactactttcccgagcctgtgacc gtgtcctggaattctggcgctctgacaagcggcgtgcacacctttccagctgtgctgcaaagcagcggcctgtactctctgagcagcg tggtcacagtgcctagctctagcctgggcaccaagacctacacctgtaatgtggaccacaagcctagcaacaccaaggtggacaagcg -continued cgtggaatctaagtacggccctccttgtcctccatgtcctgctccagagtttctcggcggaccctccgtgttcctgtttcctccaaag cctaaggacaccctgatgatcagcagaacccctgaagtgacctgcgtggtggtggacgtttcccaagaggaccctgaggtgcagttca attggtacgtggacggcgtggaagtgcacaatgccaagaccaagcctagagaggaacagttcaacagcacctacagagtggtgtccgt gctgaccgtgctgcaccaggattggctgaacggcaaagagtacaagtgcaaggtgtccaacaagggcctgcctagcagcatcgagaaa accatcagcaaggccaagggccagccaagagaaccccaggtgtacacactgcctccaagccaagaggaaatgaccaagaaccaggtgt ccctgacctgcctggttaagggcttctacccctccgatatcgccgtggaatgggagagcaatggccagcctgagaacaactacaagac aacccctcctgtgctggacagcgacggctcattcttcctgtacagcagactgaccgtggacaagagcagatggcaagagggcaacgtg ttcagctgcagcgtgatgcacgaggccctgcacaaccactacacccagaagtctctgagcctgtctctgggcaag SEQ ID NO: 85:
cDNA sequence coding for chimeric mouse VH 16D6 human heavy IgG4 chain
atggagctgggcctgagctggatttttctgctggccatcctgaagggcgtgcagtgtcaggttcagctgcagcagtctggcgccgagc ttatgaagcctggcgcctctgtgaagatcagctgcaaggccaccggctacaccttcagcacctactggatcgagtgggtcaagcagag gcctggccacggactggaatggatcggagagatcctgcctggcagcggcagcgccaactacaacgagaagttcaagggcaaagccacc ttcaccgccgacaccagcagcaacacagcctacatgcagctgagcagcctgaccttcgaggacagcgccgtgtactactgcgccaaag gcttcggcagcccctactactacgctatggattactggggccagggcaccagcgtgacagtgtctagcgcctctacaaagggccctag cgtgttccctctggctccttgtagcagaagcaccagcgagtctacagccgctctgggctgtctggtcaaggactactttcccgagcct gtgaccgtgtcctggaattctggcgctctgacaagcggcgtgcacacctttccagctgtgctgcaaagcagcggcctgtactctctga gcagcgtggtcacagtgcctagctctagcctgggcaccaagacctacacctgtaatgtggaccacaagcctagcaacaccaaggtgga caagcgcgtggaatctaagtacggccctccttgtcctccatgtcctgctccagagtttctcggcggaccctccgtgttcctgtttcct ccaaagcctaaggacaccctgatgatcagcagaacccctgaagtgacctgcgtggtggtggacgtttcccaagaggaccctgaggtgc agttcaattggtacgtggacggcgtggaagtgcacaacgccaagaccaagcctagagaggaacagttcaactccacctacagagtggt gtccgtgctgaccgtgctgcaccaggattggctgaacggcaaagagtacaagtgcaaggtgtccaacaagggcctgcctagcagcatc gagaaaaccatcagcaaggccaagggccagccaagagaaccccaggtgtacacactgcctccaagccaagaggaaatgaccaagaacc aggtgtccctgacctgcctcgtgaagggcttctacccttccgatatcgccgtggaatgggagagcaatggccagcctgagaacaacta caagacaacccctcctgtgctggacagcgacggctcattcttcctgtacagcagactgaccgtggacaagagcagatggcaagagggc aacgtgttctcctgcagcgtgatgcacgaggccctgcacaaccactacacccagaagtctctgagcctgtctctgggcaag SEQ ID NO: 86:
cDNA sequence coding for chimeric mouse VH 20B4 human heavy IgG4 chain
atggagctgggcctgagctggatttttctgctggccatcctgaagggcgtgcagtgcagagtgcagctgaaagagtctggccctggac tggtggccccaagccagtctctgagcatcacctgtaccgtgtccggcttcagcctgacaagctatggcgtgcactgggtccgacagcc tccaggcaaaggactggaatggctgggcatcatttgggctggcggcagcaccagctacaacagcgctctgatgagccggctgagcatc tccaaggacaacagcaagagccaggtgttcctgaagatgaacagcctgcagaccgacgacaccgccatgtactactgcgccagagatc actacgacctgttcgcctattggggccagggcacactggttacagtgtccgccgcctctacaaagggccctagtgtgtttcctctggc tccctgcagcagaagcaccagcgaatctacagccgctctgggctgcctggtcaaggactactttcctgagccagtgaccgtgtcctgg aactctggcgctctgacaagcggcgtgcacacatttccagccgtgctgcaaagcagcggcctgtactctctgtccagcgtggtcacag tgcctagctctagcctgggcaccaagacctacacctgtaatgtggaccacaagcctagcaacaccaaggtggacaagcgcgtggaatc taagtacggccctccttgtcctccatgtcctgcacctgagtttctcggcggaccctccgtgttcctgtttcctccaaagcctaaggac accctgatgatcagcagaacccctgaagtgacctgcgtggtggtggacgtttcccaagaggaccctgaggtgcagttcaattggtacg tggacggcgtggaagtgcacaacgccaagaccaagcctagagaggaacagttcaacagcacctacagagtggtgtccgtgctgacagt gctgcaccaggattggctgaacggcaaagagtacaagtgcaaggtgtccaacaagggcctgcctagcagcatcgagaaaaccatcagc aaggccaagggccagccaagagaaccccaggtgtacacactgcctccaagccaagaggaaatgaccaagaatcaggtgtccctgacct gcctcgtgaagggcttctacccttccgatatcgccgtggaatgggagagcaatggccagcctgagaacaactacaagacaacccctcc -continued tgtgctggacagcgacggctcattcttcctgtacagcagactgaccgtggacaagagcagatggcaagagggcaacgtgttcagctgc tccgtgatgcacgaggccctgcacaaccactacacccagaaaagcctgagcctgtctctgggcaag SEQ ID NO: 87:
cDNA sequence coding for chimeric mouse VH 30C7 human heavy IgG4 chain
atggagctgggcctgagctggatttttctgctggccatcctgaagggcgtgcagtgtcaggttcagctgcagcagtctggccccgaac ttgtcagacctggcgtgtccgtgaagatcagctgtaaaggcagcggctacaccttcaccgactacgtgatgcactgggtcaagcagag ccacgccaagagcctggaatggatcggcgtgatcagcacctacagcggcaacaccaactacaaccagaagttcaagggcaaagccacc atgaccgtggacaagagcagcagcaccgcctacatggaactggccaggctgacctctgaggacagcgccatctactactgcgccagag agagcgacggctactacttcgattattggggccagggcaccacactgaccgtgtctagcgcctctacaaagggccctagcgtgttccc tctggctccttgtagcagaagcaccagcgagtctacagccgctctgggctgtctggtcaaggactactttcccgagcctgtgacagtg tcctggaactctggcgctctgacaagcggcgtgcacacatttccagccgtgctgcaaagcagcggcctgtactctctgagcagcgtgg tcacagtgcctagctctagcctgggcaccaagacctacacctgtaatgtggaccacaagccttccaacaccaaggtggacaagcgcgt ggaatctaagtacggccctccttgtcctccatgtcctgcacctgagtttctcggcggaccctccgtgttcctgtttcctccaaagcct aaggacaccctgatgatcagcagaacccctgaagtgacctgcgtggtggtggacgtttcccaagaggaccctgaggtgcagttcaatt ggtacgtggacggcgtggaagtgcacaacgccaagaccaagcctagagaggaacagttcaactccacctacagagtggtgtccgtgct gacagtgctgcaccaggattggctgaacggcaaagagtacaagtgcaaggtgtccaacaagggcctgcctagcagcatcgagaaaacc atcagcaaggccaagggccagccaagagaaccccaggtgtacacactgcctccaagccaagaggaaatgaccaagaaccaggtgtccc tgacctgcctcgtgaagggcttctacccttccgatatcgccgtggaatgggagagcaatggccagcctgagaacaactacaagacaac ccctcctgtgctggacagcgacggctcattcttcctgtacagcagactgacagtggataagagccggtggcaagagggcaacgtgttc tcctgctctgtgatgcacgaggccctgcacaaccactacacccagaaaagcctgagcctgtctctgggcaag SEQ ID NO: 88:
cDNA sequence coding for chimeric mouse VL 8F3 human light kappa chain
atggacatgagagttcccgctcagctgctgggactgctgctgctttggtttcctggcgctagatgcgacgtgcagatcacacagagcc ctagctacctggctgcctctcctggcgagacaatcaccatcaactgccgggccagcaagaccatcagcaagtacctggcctggtatca agagaagcccggcaagaccaacatgctgctgatctacagcggcagcacactgcagagcggagtgcctagcagattttccggctctggc agcggcaccgatttcaccctgaccataagcagcctggaacctgaggacctggccatgtactactgccagcagcacgacgagtacccct ggacatttggcggaggcaccaagctggaaatcaagcggacagtggccgctcctagcgtgttcatctttccacctagcgacgagcagct gaagtctggcacagcctctgtcgtgtgcctgctgaacaacttctaccccagagaagccaaggtgcagtggaaggtggacaacgccctg cagtccggcaatagccaagagagcgtgaccgagcaggacagcaaggactctacctacagcctgagcagcaccctgacactgagcaagg ccgactacgagaagcacaaagtgtacgcctgcgaagtgacccaccagggcctttctagccctgtgaccaagagcttcaaccggggcga atgt SEQ ID NO: 89:
cDNA sequence coding for chimeric mouse VL 10E7 human light kappa chain
atggacatgagagttcccgctcagctgctgggactgctgctgctttggtttcctggcgctagatgcgacatccagatgacccagagca ccagcagcctgtctgcctctctgggcgatagcgtgaccatcagctgtagagccagccaggacatcatcaactacctgaactggtatca gcagaaacccgacggcaccgtgaagctgctgatctactacaccagcagactgcacagcggcgtgcccagcagattttctggctctgga agcggcaccgagtacagcctgaccgtgtccaacctggaaaaagaggatatcgctacctacttctgccagcaaggcaagaccctgcctt acacctttggcggaggcaccaagctggaaatcaagcggacagtggccgctcctagcgtgttcatctttccacctagcgacgagcagct gaagtctggcacagcctctgtcgtgtgcctgctgaacaacttctaccccagagaagccaaggtgcagtggaaggtggacaacgccctg cagagcggcaatagccaagagagcgtgaccgagcaggacagcaaggactctacctatagcctgagcagcaccctgacactgagcaagg ccgactacgagaagcacaaagtgtacgcctgcgaagtgacccaccagggcctttctagccctgtgaccaagagcttcaaccggggcga atgt -continued SEQ ID NO: 90:
cDNA sequence coding for chimeric mouse VL 16D6 human light kappa chain
atggacatgagagttcccgctcagctgctgggactgctgctgctttggtttcctggcgctagatgcgagatcgtgctgacacagagcc ctgctctgatggctgcttcccctggcgagaaagtgaccatcacctgtagcgtgtccagcagcatcagcagctccaacctgcactggta tcagcagaagtccgagacaagccccaagccttggatctacggcacaagcaaactggccagcggcgtgccagtcagattttctggctct ggcagcggcaccagctacagcctgaccatcagcaacatggaagccgaggatgccgccacctactactgccagcagtggtccagctttc cactgacctttggcggaggcaccaagctggaaatcaagcggacagtggccgctcctagcgtgttcatctttccacctagcgacgagca gctgaagtctggcacagcctctgtcgtgtgcctgctgaacaacttctaccccagagaagccaaggtgcaatggaaggtggacaacgcc ctgcagagcggcaatagccaagagagcgtgaccgagcaggacagcaaggactccacctatagcctgagcagcaccctgacactgagca aggccgactacgagaagcacaaagtgtacgcctgcgaagtgacccaccagggcctttctagccctgtgaccaagagcttcaaccgggg cgaatgt SEQ ID NO: 91:
cDNA sequence coding for chimeric mouse VL 20B4 human light kappa chain
atggacatgagagttcccgctcagctgctgggactgctgctgctttggtttcctggcgctagatgcgacatcctgatgacacagagcc ccagctccatgtccgtgtctctgggcgataccgtgtccatcacatgtcacgccagccaggacatcagccggaatatcggatggctgca gcagaagcccggcaagagctttaagggcctgatctaccacggcaccaacctggaagatggcgtgcccagcagattttccggctctgga tctggcgccgactacagcctgacaatcagcagcctggaaagcgaggacttcgccgattactactgcgtgcagtacgcccagtttcctc ggacatttggcggaggcacaaagctggaaatcaagcggacagtggccgctcctagcgtgttcatctttccacctagcgacgagcagct gaagtctggcacagcctctgtcgtgtgcctgctgaacaacttctaccccagagaagccaaggtgcagtggaaggtggacaacgccctg cagagcggcaatagccaagagagcgtgaccgagcaggacagcaaggactccacctatagcctgagcagcaccctgacactgagcaagg ccgactacgagaagcacaaagtgtacgcctgcgaagtgacccaccagggcctttctagccctgtgaccaagagcttcaaccggggcga atgt SEQ ID NO: 92:
cDNA sequence coding for chimeric mouse VL 30C7 human light kappa chain
atggacatgagagttcccgctcagctgctgggactgctgctgctttggtttcctggcgctagatgcgacatcgtgatgtctcagagcc ctagcagcctggctgtgtctgccggcgagaaagtgaccatgagctgcaagagcagccagagcctgctgaacagccggaccagaaagaa ctacctggcctggtatcagcagaagcccggacagtctcccaagctgctgatctactgggccagcaccagagaaagcggcgtgcccgat agattcacaggcagcggcagcggaaccgacttcaccctgacaatcagctctgtgcaggccgaggatctggccgtgtactactgcaagc agagctacaacctgatgtacaccttcggcggaggcaccaagctggaaatcaagagaacagtggccgctcctagcgtgttcatcttccc accttccgacgagcagctgaagtctggcacagcctctgtcgtgtgcctgctcaacaacttctaccccagagaagccaaggtgcagtgg aaggtggacaacgccctgcagagcggcaatagccaagagagcgtgaccgagcaggacagcaaggactctacctacagcctgagcagca cactgaccctgagcaaggccgactacgagaagcacaaagtgtacgcctgcgaagtgacccaccagggcctttctagccctgtgaccaa gagcttcaaccggggcgaatgt SEQ ID NO: 93:
Amino acid sequence of chimeric mouse VH 8F3 human heavy IgG4 chain
MELGLSWIFLLAILKGVQCEVQLVESGGGLVKPGGSLKLSCAASGFTFSNYGMSWVRQTPDKRLEWV

ATMHSGGTYTYYPDNVKGRFTISRDNAKNNLYLQMSSLRSEDTAMYYCARETGLYDGLFDFWGQGT

TLTVSSASTKGPSVFPLAPCSRSTSESTAALGCLVKDYFPEPVTVSWNSGALTSGVHTFPAVLQSSGLY

SLSSVVTVPSSSLGTKTYTCNVDHKPSNTKVDKRVESKYGPPCPPCPAPEFLGGPSVFLFPPKPKDTL

MISRTPEVTCVVVDVSQEDPEVQFNWYVDGVEVHNAKTKPREEQFNSTYRVVSVLTVLHQDWLNGK

EYKCKVSNKGLPSSIEKTISKAKGQPREPQVYTLPPSQEEMTKNQVSLTCLVKGFYPSDIAVEWESNG

QPENNYKTTPPVLDSDGSFFLYSRLTVDKSRWQEGNVFSCSVMHEALHNHYTQKSLSLSLGK

-continued

SEQ ID NO: 94:
Amino acid sequence of chimeric mouse VH 10E7 human heavy IgG4 chain
MELGLSWIFLLAILKGVQCEVQLVESGGGLVQPGGSLKLSCAASGLTFSSYGMSWVRQTPDKRLELVA

TINGNGDITYYPDSVKGRFTISRDNAKNTLYLQMSSLKSEDTAMYYCARDYDYDYAMDYWGQGTSVT

VSSASTKGPSVFPLAPCSRSTSESTAALGCLVKDYFPEPVTVSWNSGALTSGVHTFPAVLQSSGLYSLSS

VVTVPSSSLGTKTYTCNVDHKPSNTKVDKRVESKYGPPCPPCPAPEFLGGPSVFLFPPKPKDTLMISRT

PEVTCVVVDVSQEDPEVQFNWYVDGVEVHNAKTKPREEQFNSTYRVVSVLTVLHQDWLNGKEYKCK

VSNKGLPSSIEKTISKAKGQPREPQVYTLPPSQEEMTKNQVSLTCLVKGFYPSDIAVEWESNGQPENN

YKTTPPVLDSDGSFFLYSRLTVDKSRWQEGNVFSCSVMHEALHNHYTQKSLSLSLGK

SEQ ID NO: 95:
Amino acid sequence of chimeric mouse VH 16D6 human heavy IgG4 chain
MELGLSWIFLLAILKGVQCQVQLQQSGAELMKPGASVKISCKATGYTFSTYWIEWVKQRPGHGLEWI

GEILPGSGSANYNEKFKGKATFTADTSSNTAYMQLSSLTFEDSAVYYCAKGFGSPYYYAMDYWGQGT

SVTVSSASTKGPSVFPLAPCSRSTSESTAALGCLVKDYFPEPVTVSWNSGALTSGVHTFPAVLQSSGLY

SLSSVVTVPSSSLGTKTYTCNVDHKPSNTKVDKRVESKYGPPCPPCPAPEFLGGPSVFLFPPKPKDTL

MISRTPEVTCVVVDVSQEDPEVQFNWYVDGVEVHNAKTKPREEQFNSTYRVVSVLTVLHQDWLNGK

EYKCKVSNKGLPSSIEKTISKAKGQPREPQVYTLPPSQEEMTKNQVSLTCLVKGFYPSDIAVEWESNG

QPENNYKTTPPVLDSDGSFFLYSRLTVDKSRWQEGNVFSCSVMHEALHNHYTQKSLSLSLGK

SEQ ID NO: 96:
Amino acid sequence of chimeric mouse VH 20B4 human heavy IgG4 chain
MELGLSWIFLLAILKGVQCRVQLKESGPGLVAPSQSLSITCTVSGFSLTSYGVHWVRQPPGKGLEWLGI

IWAGGSTSYNSALMSRLSISKDNSKSQVFLKMNSLQTDDTAMYYCARDHYDLFAYWGQGTLVTVSAA

STKGPSVFPLAPCSRSTSESTAALGCLVKDYFPEPVTVSWNSGALTSGVHTFPAVLQSSGLYSLSSVVT

VPSSSLGTKTYTCNVDHKPSNTKVDKRVESKYGPPCPPCPAPEFLGGPSVFLFPPKPKDTLMISRTPEV

TCVVVDVSQEDPEVQFNWYVDGVEVHNAKTKPREEQFNSTYRVVSVLTVLHQDWLNGKEYKCKVSN

KGLPSSIEKTISKAKGQPREPQVYTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLSLSLGK

SEQ ID NO: 97:
Amino acid sequence of chimeric mouse VH 30C7 human heavy IgG4 chain
MELGLSWIFLLAILKGVQCQVQLQQSGPELVRPGVSVKISCKGSGYTFTDYVMHWVKQSHAKSLEWI

GVISTYSGNTNYNQKFKGKATMTVDKSSSTAYMELARLTSEDSAIYYCARESDGYYFDYWGQGTTLTV

SSASTKGPSVFPLAPCSRSTSESTAALGCLVKDYFPEPVTVSWNSGALTSGVHTFPAVLQSSGLYSLSSV

VTVPSSSLGTKTYTCNVDHKPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQPENNY

KTTPPVLDSDGSFFLYSRLTVDKSRWQEGNVFSCSVMHEALHNHYTQKSLSLSLGK

SEQ ID NO: 98:
Amino acid sequence of chimeric mouse VL 8F3 human light kappa chain
MDMRVPAQLLGLLLLWFPGARCDVQITQSPSYLAASPGETITINCRASKTISKYLAWYQEKPGKTNML

LIYSGSTLQSGVPSRFSGSGSGTDFTLTISSLEPEDLAMYYCQQHDEYPWTFGGGTKLEIKRTVAAPSV

FIFPPSDEQLKSGTASVVCLLNNFYPREAKVQWKVDNALQSGNSQESVTEQDSKDSTYSLSSTLTLSK

ADYEKHKVYACEVTHQGLSSPVTKSFNRGEC

SEQ ID NO: 99:
Amino acid sequence of chimeric mouse VL 10E7 human light kappa chain
MDMRVPAQLLGLLLLWFPGARCDIQMTQSTSSLSASLGDSVTISCRASQDIINYLNWYQQKPDGTVKL

LIYYTSRLHSGVPSRFSGSGSGTEYSLTVSNLEKEDIATYFCQQGKTLPYTFGGGTKLEIKRTVAAPSVF

-continued

IFPPSDEQLKSGTASVVCLLNNFYPREAKVQWKVDNALQSGNSQESVTEQDSKDSTYSLSSTLTLSKA

DYEKHKVYACEVTHQGLSSPVTKSFNRGEC

SEQ ID NO: 100:
Amino acid sequence of chimeric mouse VL 16D6 human light kappa chain
MDMRVPAQLLGLLLLWFPGARCEIVLTQSPALMAASPGEKVTITCSVSSSISSSNLHWYQQKSETSPKP

WIYGTSKLASGVPVRFSGSGSGTSYSLTISNMEAEDAATYYCQQWSSFPLTFGGGTKLEIKRTVAAPSV

FIFPPSDEQLKSGTASVVCLLNNFYPREAKVQWKVDNALQSGNSQESVTEQDSKDSTYSLSSTLTLSK

ADYEKHKVYACEVTHQGLSSPVTKSFNRGEC

SEQ ID NO: 101:
Amino acid sequence of chimeric mouse VL 20B4 human light kappa chain
MDMRVPAQLLGLLLLWFPGARCDILMTQSPSSMSVSLGDTVSITCHASQDISRNIGWLQQKPGKSFKG

LIYHGTNLEDGVPSRFSGSGSGADYSLTISSLESEDFADYYCVQYAQFPRTFGGGTKLEIKRTVAAPSVF

IFPPSDEQLKSGTASVVCLLNNFYPREAKVQWKVDNALQSGNSQESVTEQDSKDSTYSLSSTLTLSKA

DYEKHKVYACEVTHQGLSSPVTKSFNRGEC

SEQ ID NO: 102:
Amino acid sequence of chimeric mouse VL 30C7 human light kappa chain
MDMRVPAQLLGLLLLWFPGARCDIVMSQSPSSLAVSAGEKVTMSCKSSQSLLNSRTRKNYLAWYQQK

PGQSPKLLIYWASTRESGVPDRFTGSGSGTDFTLTISSVQAEDLAVYYCKQSYNLMYTFGGGTKLEIKR

TVAAPSVFIFPPSDEQLKSGTASVVCLLNNFYPREAKVQWKVDNALQSGNSQESVTEQDSKDSTYSLS

STLTLSKADYEKHKVYACEVTHQGLSSPVTKSFNRGEC

SEQ ID NO: 103: PCR primer
ATGAGTGTGC TCACTCAGGT CCTGGSGTTG

SEQ ID NO: 104: PCR primer
ATGAGGRCCC CTGCTCAGWT TYTTGGMWTC TTG

SEQ ID NO: 105: PCR primer
ATGGATTTWC AGGTGCAGAT TWTCAGCTTC

SEQ ID NO: 106: PCR primer
ATGGGCWTCA AAGATGGAGT CACA

SEQ ID NO: 107: PCR primer
ATGGTRTCCW CASCTCAGTT CCTTG

SEQ ID NO: 108: PCR primer
ACTGGATGGT GGGAAGATGG

SEQ ID NO: 109: PCR primer
ATGGGATGGA GCTRTATCAT SYTCTT

SEQ ID NO: 110: PCR primer
ATGRACTTTG GGYTCAGCTT GRTTT

SEQ ID NO: 111: PCR primer
ATGGCTTGTC YTTRGSGCTR CTCTTCTGC

SEQ ID NO: 112: PCR primer
ATGGRATGGA GCKGGGTCTT TMTCTT

SEQ ID NO: 113: PCR primer
ATGGMTTGGG TGTGGAMCTT GCT

SEQ ID NO: 114: PCR primer
CAGTGGATAG ACAGATGGGG G

SEQ ID NO: 115: PCR primer
AAGATGGATA CAGTTGGTGC

SEQ ID NO: 116: PCR primer
GASRTHSTGA TGACCCAGAC NCC

SEQ ID NO: 117:
Amino acid sequence of humanized anti-human-CD89 antibody 10E7 heavy chain variable region VH1
1 EVQLLESGGG LVQPGGSLRL SCAASGLTFS SYGMSWVRQA PGKGLEWVST INGNGDITYY -continued SEQ ID NO: 118:
Amino acid sequence of humanized anti-human-CD89 antibody 10E7 heavy chain variable region VH2

1 EVQLLESGGG LVQPGGSLRL SCAASGLTFS SYGMSWVRQA PGKGLEWVAT INGNGDITYY

61 PDSVKGRFTI SRDNSKNTLY LQMNSLRAED TAVYYCARDY DYDYAMDYWG QGTLVTVSS

SEQ ID NO: 119:
Amino acid sequence of humanized anti-human-CD89 antibody 10E7 heavy chain variable region VH3

1 EVQLLESGGG LVQPGGSLRL SCAASGLTFS SYGMSWVRQA PGKGLELVAT INGNGDITYY

61 PDSVKGRFTI SRDNSKNTLY LQMNSLRAED TAVYYCARDY DYDYAMDYWG QGTLVTVSS

SEQ ID NO: 120:
Amino acid sequence of humanized anti-human-CD89 antibody 10E7 light chain variable region VL1

1 DIQMTQSPSS LSASVGDRVT ITCRASQDII NYLNWYQQKP GKAPKLLIYY TSRLHSGVPS

61 RFSGSGSGTD FTLTISSLQP EDFATYYCQQ GKTLPYTFGQ GTKLEIK

SEQ ID NO: 121:
Amino acid sequence of humanized anti-human-CD89 antibody 10E7 light chain variable region VL2

1 DIQMTQSPSS LSASVGDRVT ITCRASQDII NYLNWYQQKP GKAPKLLIYY TSRLHSGVPS

61 RFSGSGSGTD YTLTISSLQP EDFATYYCQQ GKTLPYTFGQ GTKLEIK

SEQ ID NO: 122:
Amino acid sequence of humanized anti-human-CD89 antibody 10E7 light chain variable region VL3

1 DIQMTQSPSS LSASVGDRVT ITCRASQDII NYLNWYQQKP GKAVKLLIYY TSRLHSGVPS

61 RFSGSGSGTD YTLTISSLQP EDFATYYCQQ GKTLPYTFGQ GTKLEIK

SEQ ID NO: 123:
Amino acid sequence of humanized anti-human-CD89 antibody 10E7 light chain variable region VL4

1 DIQMTQSPSS LSASVGDRVT ITCRASQDII NYLNWYQQKP GKTVKLLIYY TSRLHSGVPS

61 RFSGSGSGTD YTLTISSLQP EDFATYFCQQ GKTLPYTFGQ GTKLEIK

SEQ ID NO: 124:
cDNA sequence coding for humanized IgG4 chain of anti-human-CD89 antibody 10E7 covering humanized VH1

1 atgaaatggg tcacctttat ctccctgctg ttcctgttct ccagcgccta ctctgaggtg 61 cagctgctgg aatctggcgg aggattggtt cagcctggcg gctctctgag actgtcttgt 121 gctgcttctg gcctgacctt ctcctcctac ggcatgtcct gggtccgaca ggctcctgga 181 aaaggcctgg aatgggtgtc caccatcaac ggcaacggcg acatcaccta ctatcccgac 241 tccgtgaagg gcagattcac catctctcgg gacaactcca agaacaccct gtacctgcag 301 atgaactccc tgagagccga ggacaccgcc gtgtactact gcgccagaga ctacgactac 361 gattacgcca tggactactg gggccagggc acactggtta ccgtgtcctc tgcttccacc 421 aagggaccct ctgtgttccc tctggctcct tgctccagat ccacctccga gtctacagct 481 gctctgggct gcctggtcaa ggactacttt cctgagcctg tgaccgtgtc ttggaactct 541 ggcgctctga catccggcgt gcacaccttt ccagctgtgc tgcaatccag cggcctgtac 601 tctctgtcct ccgtcgtgac cgtgccttct agctctctgg gcaccaagac ctacacctgt 661 aatgtggacc acaagccttc caacaccaag gtggacaagc gcgtggaatc taagtacggc 721 cctccttgtc ctccatgtcc tgctccagag tttctcggcg gaccttccgt gtttctgttc 781 cctccaaagc ctaaggacac cctgatgatc tctcggaccc ctgaagtgac ctgcgtggtg 841 gtggatgtgt cccaagagga cccagaggtg cagttcaatt ggtacgtgga cggcgtggaa 901 gtgcacaacg ccaagaccaa gcctagagag gaacagttca actccaccta cagagtggtg 961 tccgtgctga ccgtgctgca ccaggattgg ctgaacggaa aagagtacaa gtgcaaggtg 1021 tccaacaagg gcctgccttc cagcatcgaa aagaccatct ccaaggccaa gggccagcct 1081 agggaacccc aggtttacac cctgcctcca agccaagagg aaatgaccaa gaaccaggtg 1141 tccctgacct gcctcgtgaa gggattctac ccctccgata tcgccgtgga atgggagtct 1201 aatggccagc ctgagaacaa ctacaagaca acccctcctg tgctggactc cgacggcagc -continued

```
1261 ttcttcctgt attcccgcct gaccgtggac aagtccagat ggcaagaggg caacgtgttc

1321 tcctgctccg tgatgcacga ggccctgcac aatcactaca cccagaagtc cctgtctctg

1381 tccctgggca ag
```

SEQ ID NO: 125:
cDNA sequence coding for humanized IgG4 chain of anti-human-CD89 antibody 10E7 covering humanized VH2

```
   1 atgaaatggg tcacctttat ctccctgctg ttcctgttct ccagcgccta ctctgaggtg

  61 cagctgctgg aatctggcgg aggattggtt cagcctggcg gctctctgag actgtcttgt

 121 gctgcttctg gcctgacctt ctcctcctac ggcatgtcct gggtccgaca ggctcctgga

 181 aaaggcctgg aatgggtcgc caccatcaac ggcaacggcg acatcaccta ctatcccgac

 241 tccgtgaagg gcagattcac catctctcgg gacaactcca agaacaccct gtacctgcag

 301 atgaactccc tgagagccga ggacaccgcc gtgtactact gcgccagaga ctacgactac

 361 gattacgcca tggactactg gggccagggc acactggtta ccgtgtcctc tgcttccacc

 421 aagggaccct ctgtgttccc tctggctcct tgctccagat ccacctccga gtctacagct

 481 gctctgggct gcctggtcaa ggactacttt cctgagcctg tgaccgtgtc ttggaactct

 541 ggcgctctga catccggcgt gcacaccttt ccagctgtgc tgcaatccag cggcctgtac

 601 tctctgtcct ccgtcgtgac cgtgccttct agctctctgg gcaccaagac ctacacctgt

 661 aatgtggacc acaagccttc caacaccaag gtggacaagc gcgtggaatc taagtacggc

 721 cctccttgtc ctccatgtcc tgctccagag tttctcggcg gaccttccgt gtttctgttc

 781 cctccaaagc ctaaggacac cctgatgatc tctcggaccc ctgaagtgac ctgcgtggtg

 841 gtggatgtgt cccaagagga cccagaggtg cagttcaatt ggtacgtgga cggcgtggaa

 901 gtgcacaacg ccaagaccaa gcctagagag gaacagttca actccaccta cagagtggtg

 961 tccgtgctga ccgtgctgca ccaggattgg ctgaacggaa aagagtacaa gtgcaaggtg

1021 tccaacaagg gcctgccttc cagcatcgaa aagaccatct ccaaggccaa gggccagcct

1081 agggaacccc aggtttacac cctgcctcca agccaagagg aaatgaccaa gaaccaggtg

1141 tccctgacct gcctcgtgaa gggattctac cctccgata tcgccgtgga atgggagtct

1201 aatggccagc ctgagaacaa ctacaagaca acccctcctg tgctggactc cgacggcagc

1261 ttcttcctgt attcccgcct gaccgtggac aagtccagat ggcaagaggg caacgtgttc

1321 tcctgctccg tgatgcacga ggccctgcac aatcactaca cccagaagtc cctgtctctg

1381 tccctgggca ag
```

SEQ ID NO: 126:
cDNA sequence coding for humanized IgG4 chain of anti-human-CD89 antibody 10E7 covering humanized VH3

```
   1 atgaaatggg tcacctttat ctccctgctg ttcctgttct ccagcgccta ctctgaggtg

  61 cagctgctgg aatctggcgg aggattggtt cagcctggcg gctctctgag actgtcttgt

 121 gctgcttctg gcctgacctt ctcctcctac ggcatgtcct gggtccgaca ggctcctgga

 181 aaaggcctgg aactggtggc taccatcaac ggcaacggcg acatcaccta ctatcccgac

 241 tccgtgaagg gcagattcac catctctcgg gacaactcca agaacaccct gtacctgcag

 301 atgaactccc tgagagccga ggacaccgcc gtgtactact gcgccagaga ctacgactac

 361 gattacgcca tggactactg gggccagggc acactggtta ccgtgtcctc tgcttccacc

 421 aagggaccct ctgtgttccc tctggctcct tgctccagat ccacctccga gtctacagct

 481 gctctgggct gcctggtcaa ggactacttt cctgagcctg tgaccgtgtc ttggaactct

 541 ggcgctctga catccggcgt gcacaccttt ccagctgtgc tgcaatccag cggcctgtac
```

-continued

```
 601 tctctgtcct ccgtcgtgac cgtgccttct agctctctgg gcaccaagac ctacacctgt

 661 aatgtggacc acaagccttc caacaccaag gtggacaagc gcgtggaatc taagtacggc

 721 cctccttgtc ctccatgtcc tgctccagag tttctcggcg gaccttccgt gtttctgttc

 781 cctccaaagc ctaaggacac cctgatgatc tctcggaccc ctgaagtgac ctgcgtggtg

 841 gtggatgtgt cccaagagga cccagaggtg cagttcaatt ggtacgtgga cggcgtggaa

 901 gtgcacaacg ccaagaccaa gcctagagag gaacagttca actccaccta cagagtggtg

 961 tccgtgctga ccgtgctgca ccaggattgg ctgaacggaa aagagtacaa gtgcaaggtg

1021 tccaacaagg gcctgccttc cagcatcgaa aagaccatct ccaaggccaa gggccagcct

1081 agggaacccc aggtttacac cctgcctcca agccaagagg aaatgaccaa gaaccaggtg

1141 tccctgacct gcctcgtgaa gggattctac cctccgata tcgccgtgga atgggagtct

1201 aatggccagc ctgagaacaa ctacaagaca acccctcctg tgctggactc cgacggcagc

1261 ttcttcctgt attcccgcct gaccgtggac aagtccagat ggcaagaggg caacgtgttc

1321 tcctgctccg tgatgcacga ggccctgcac aatcactaca cccagaagtc cctgtctctg

1381 tccctgggca ag
```

SEQ ID NO: 127:
cDNA sequence coding for humanized kappa chain of anti-human-CD89 antibody 10E7 covering humanized VL1

```
   1 atgaaatggg tcacctttat ctccctgctg ttcctgttct cctccgccta ctccgacatc

  61 cagatgaccc agtctccatc ctctctgtcc gcctctgtgg gcgacagagt gaccatcacc

 121 tgtagagcca gccaggacat catcaactac ctgaactggt atcagcagaa gcccggcaag

 181 gcccctaagc tgctgatcta ctacacctct cggctgcact ctggcgtgcc ctctagattt

 241 tctggctccg gctctggcac cgactttacc ctgacaatct ccagcctgca gcctgaggac

 301 ttcgccacct actattgcca gcagggcaag accctgcctt acacctttgg ccagggcacc

 361 aagctggaaa tcaagcggac agtggccgct ccttccgtgt tcatcttccc accttccgac

 421 gagcagctga agtccggcac agcttctgtc gtgtgcctgc tgaacaactt ctaccctcgg

 481 gaagccaagg tgcagtggaa ggtggacaat gccctgcagt ccggcaactc ccaagagtct

 541 gtgaccgagc aggactccaa ggacagcacc tacagcctgt cctccacact gaccctgtcc

 601 aaggccgact acgagaagca caaggtgtac gcctgcgaag tgacccatca gggcctgtct

 661 agccctgtga ccaagtcttt caaccggggc gagtgt
```

SEQ ID NO: 128:
cDNA sequence coding for humanized kappa chain of anti-human-CD89 antibody 10E7 covering humanized VL2

```
   1 atgaaatggg tcacctttat ctccctgctg ttcctgttct cctccgccta ctccgacatc

  61 cagatgaccc agtctccatc ctctctgtcc gcctctgtgg gcgacagagt gaccatcacc

 121 tgtagagcca gccaggacat catcaactac ctgaactggt atcagcagaa gcccggcaag

 181 gcccctaagc tgctgatcta ctacacctct cggctgcact ctggcgtgcc ctctagattt

 241 tctggctccg gctctggcac cgactatacc ctgacaatct ccagcctgca gcctgaggac

 301 ttcgccacct actattgcca gcagggcaag accctgcctt acacctttgg ccagggcacc

 361 aagctggaaa tcaagcggac agtggccgct ccttccgtgt tcatcttccc accttccgac

 421 gagcagctga agtccggcac agcttctgtc gtgtgcctgc tgaacaactt ctaccctcgg

 481 gaagccaagg tgcagtggaa ggtggacaat gccctgcagt ccggcaactc ccaagagtct

 541 gtgaccgagc aggactccaa ggacagcacc tacagcctgt cctccacact gaccctgtcc

 601 aaggccgact acgagaagca caaggtgtac gcctgcgaag tgacccatca gggcctgtct

 661 agccctgtga ccaagtcttt caaccggggc gagtgt
```

-continued

SEQ ID NO: 129:
cDNA sequence coding for humanized kappa chain of anti-human-CD89 antibody 10E7 covering humanized VL3

```
  1 atgaaatggg tcacctttat ctccctgctg ttcctgttct cctccgccta ctccgacatc

 61 cagatgaccc agtctccatc ctctctgtcc gcctctgtgg gcgacagagt gaccatcacc

121 tgtagagcca gccaggacat catcaactac ctgaactggt atcagcagaa acccggcaag

181 gccgtgaagc tgctgatcta ctacacctct cggctgcact ctggcgtgcc ctctagattt

241 tctggctccg gctctggcac cgactatacc ctgacaatct ccagcctgca gcctgaggac

301 ttcgccacct actattgcca gcagggcaag accctgcctt acacctttgg ccagggcacc

361 aagctggaaa tcaagcggac agtggccgct ccttccgtgt tcatcttccc accttccgac

421 gagcagctga agtccggcac agcttctgtc gtgtgcctgc tgaacaactt ctaccctcgg

481 gaagccaagg tgcagtggaa ggtggacaat gccctgcagt ccggcaactc ccaagagtct

541 gtgaccgagc aggactccaa ggacagcacc tacagcctgt cctccacact gaccctgtcc

601 aaggccgact acgagaagca caaggtgtac gcctgcgaag tgacccatca gggcctgtct

661 agccctgtga ccaagtcttt caaccggggc gagtgt
```

SEQ ID NO: 130:
cDNA sequence coding for humanized kappa chain of anti-human-CD89 antibody 10E7 covering humanized VL4

```
  1 atgaaatggg tcacctttat ctccctgctg ttcctgttct cctccgccta ctccgacatc

 61 cagatgaccc agtctccatc ctctctgtcc gcctctgtgg gcgacagagt gaccatcacc

121 tgtagagcca gccaggacat catcaactac ctgaactggt atcagcagaa acccggcaag

181 accgtgaagc tgctgatcta ctacacctct cggctgcact ctggcgtgcc ctctagattt

241 tctggctccg gctctggcac cgactatacc ctgacaatct ccagcctgca gcctgaggac

301 ttcgctacct acttctgcca gcaaggcaag accctgcctt acacctttgg ccagggcacc

361 aagctggaaa tcaagcggac agtggccgct ccttccgtgt tcatcttccc accttccgac

421 gagcagctga agtccggcac agcttctgtc gtgtgcctgc tgaacaactt ctaccctcgg

481 gaagccaagg tgcagtggaa ggtggacaat gccctgcagt ccggcaactc ccaagagtct

541 gtgaccgagc aggactccaa ggacagcacc tacagcctgt cctccacact gaccctgtcc

601 aaggccgact acgagaagca caaggtgtac gcctgcgaag tgacccatca gggcctgtct

661 agccctgtga ccaagtcttt caaccggggc gagtgt
```

SEQ ID NO: 131:
Amino acid sequence coding for humanized IgG4 chain of anti-human-CD89 antibody 10E7 covering humanized VH1

```
  1 MKWVTFISLL FLFSSAYSEV QLLESGGGLV QPGGSLRLSC AASGLTESSY GMSWVRQAPG

 61 KGLEWVSTIN GNGDITYYPD SVKGRFTISR DNSKNTLYLQ MNSLRAEDTA VYYCARDYDY

121 DYAMDYWGQG TLVTVSSAST KGPSVFPLAP CSRSTSESTA ALGCLVKDYF PEPVTVSWNS

181 GALTSGVHTF PAVLQSSGLY SLSSVVTVPS SSLGTKTYTC NVDHKPSNTK VDKRVESKYG

241 PPCPPCPAPE FLGGPSVFLF PPKPKDTLMI SRTPEVTCVV VDVSQEDPEV QFNWYVDGVE

301 VHNAKTKPRE EQFNSTYRVV SVLTVLHQDW LNGKEYKCKV SNKGLPSSIE KTISKAKGQP

361 REPQVYTLPP SQEEMTKNQV SLTCLVKGFY PSDIAVEWES NGQPENNYKT TPPVLDSDGS

421 FFLYSRLTVD KSRWQEGNVF SCSVMHEALH NHYTQKSLSL SLGK
```

SEQ ID NO: 132:
Amino acid sequence coding for humanized IgG4 chain of anti-human-CD89 antibody 10E7 covering humanized VH2

```
  1 MKWVTFISLL FLFSSAYSEV QLLESGGGLV QPGGSLRLSC AASGLTESSY GMSWVRQAPG

 61 KGLEWVATIN GNGDITYYPD SVKGRFTISR DNSKNTLYLQ MNSLRAEDTA VYYCARDYDY
```

-continued

121 DYAMDYWGQG TLVTVSSAST KGPSVFPLAP CSRSTSESTA ALGCLVKDYF PEPVTVSWNS

181 GALTSGVHTF PAVLQSSGLY SLSSVVTVPS SSLGTKTYTC NVDHKPSNTK VDKRVESKYG

241 PPCPPCPAPE FLGGPSVFLF PPKPKDTLMI SRTPEVTCVV VDVSQEDPEV QFNWYVDGVE

301 VHNAKTKPRE EQFNSTYRVV SVLTVLHQDW LNGKEYKCKV SNKGLPSSIE KTISKAKGQP

361 REPQVYTLPP SQEEMTKNQV SLTCLVKGFY PSDIAVEWES NGQPENNYKT TPPVLDSDGS

421 FFLYSRLTVD KSRWQEGNVF SCSVMHEALH NHYTQKSLSL SLGK

SEQ ID NO: 133:
Amino acid sequence coding for humanized IgG4 chain of anti-human-CD89 antibody 10E7 covering humanized VH3

1 MKWVTFISLL FLFSSAYSEV QLLESGGGLV QPGGSLRLSC AASGLTFSSY GMSWVRQAPG

61 KGLELVATIN GNGDITYYPD SVKGRFTISR DNSKNTLYLQ MNSLRAEDTA VYYCARDYDY

121 DYAMDYWGQG TLVTVSSAST KGPSVFPLAP CSRSTSESTA ALGCLVKDYF PEPVTVSWNS

181 GALTSGVHTF PAVLQSSGLY SLSSVVTVPS SSLGTKTYTC NVDHKPSNTK VDKRVESKYG

241 PPCPPCPAPE FLGGPSVFLF PPKPKDTLMI SRTPEVTCVV VDVSQEDPEV QFNWYVDGVE

301 VHNAKTKPRE EQFNSTYRVV SVLTVLHQDW LNGKEYKCKV SNKGLPSSIE KTISKAKGQP

361 REPQVYTLPP SQEEMTKNQV SLTCLVKGFY PSDIAVEWES NGQPENNYKT TPPVLDSDGS

421 FFLYSRLTVD KSRWQEGNVF SCSVMHEALH NHYTQKSLSL SLGK

SEQ ID NO: 134:
Amino acid sequence coding for humanized kappa chain of anti-human-CD89 antibody 10E7 covering humanized VL1

1 MKWVTFISLL FLESSAYSDI QMTQSPSSLS ASVGDRVTIT CRASQDIINY LNWYQQKPGK

61 APKLLIYYTS RLHSGVPSRF SGSGSGTDFT LTISSLQPED FATYYCQQGK TLPYTFGQGT

121 KLEIKRTVAA PSVFIFPPSD EQLKSGTASV VCLLNNFYPR EAKVQWKVDN ALQSGNSQES

181 VTEQDSKDST YSLSSTLTLS KADYEKHKVY ACEVTHQGLS SPVTKSENRG EC

SEQ ID NO: 135:
Amino acid sequence coding for humanized kappa chain of anti-human-CD89 antibody 10E7 covering humanized VL2

1 MKWVTFISLL FLESSAYSDI QMTQSPSSLS ASVGDRVTIT CRASQDIINY LNWYQQKPGK

61 APKLLIYYTS RLHSGVPSRF SGSGSGTDYT LTISSLQPED FATYYCQQGK TLPYTFGQGT

121 KLEIKRTVAA PSVFIFPPSD EQLKSGTASV VCLLNNFYPR EAKVQWKVDN ALQSGNSQES

181 VTEQDSKDST YSLSSTLTLS KADYEKHKVY ACEVTHQGLS SPVTKSENRG EC

SEQ ID NO: 136:
Amino acid sequence coding for humanized kappa chain of anti-human-CD89 antibody 10E7 covering humanized VL3

1 MKWVTFISLL FLFSSAYSDI QMTQSPSSLS ASVGDRVTIT CRASQDIINY LNWYQQKPGK

61 AVKLLIYYTS RLHSGVPSRF SGSGSGTDYT LTISSLQPED FATYYCQQGK TLPYTFGQGT

121 KLEIKRTVAA PSVFIFPPSD EQLKSGTASV VCLLNNFYPR EAKVQWKVDN ALQSGNSQES

181 VTEQDSKDST YSLSSTLTLS KADYEKHKVY ACEVTHQGLS SPVTKSENRG EC

SEQ ID NO: 137:
Amino acid sequence coding for humanized kappa chain of anti-human-CD89 antibody 10E7 covering humanized VL4

1 MKWVTFISLL FLFSSAYSDI QMTQSPSSLS ASVGDRVTIT CRASQDIINY LNWYQQKPGK

61 TVKLLIYYTS RLHSGVPSRF SGSGSGTDYT LTISSLQPED FATYFCQQGK TLPYTFGQGT

121 KLEIKRTVAA PSVFIFPPSD EQLKSGTASV VCLLNNFYPR EAKVQWKVDN ALQSGNSQES

181 VTEQDSKDST YSLSSTLTLS KADYEKHKVY ACEVTHQGLS SPVTKSENRG EC

SEQ ID NO: 138:
Amino acid sequence of 'CDR2 deamidation-repaired' humanized anti-human-CD89 antibody 10E7 heavy chain variable region VH3SQ

1 EVQLLESGGG LVQPGGSLRL SCAASGLTFS SYGMSWVRQA PGKGLELVAT ISGQGDITYY

61 PDSVKGRFTI SRDNSKNTLY LQMNSLRAED TAVYYCARDY DYDYAMDYWG QGTLVTVSS

-continued

SEQ ID NO: 139:
Amino acid sequence of 'CDR2 deamidation-repaired' humanized anti-human-CD89 antibody 10E7 heavy chain variable region VH3ST

```
   1 EVQLLESGGG LVQPGGSLRL SCAASGLTFS SYGMSWVRQA PGKGLELVAT ISGTGDITYY

  61 PDSVKGRFTI SRDNSKNTLY LQMNSLRAED TAVYYCARDY DYDYAMDYWG QGTLVTVSS
```

SEQ ID NO: 140:
cDNA sequence coding for 'CDR2 deamidation-repaired' humanized IgG4 chain of anti-human-CD89 antibody 10E7 covering humanized VH3SQ

```
   1 atgaaatggg tcacctttat ctccctgctg ttcctgttct ccagcgccta ctctgaggtg

  61 cagctgctgg aatctggcgg aggattggtt cagcctggcg gctctctgag actgtcttgt

 121 gctgcttctg gcctgacctt ctcctcctac ggcatgtcct gggtccgaca ggctcctgga

 181 aaaggcctgg aactggtggc taccatctct ggccagggcg acatcaccta ctatcccgac

 241 tctgtgaagg gcagattcac catcagccgg gacaactcca agaacaccct gtacctgcag

 301 atgaactccc tgagagccga ggacaccgcc gtgtactact gcgccagaga ctacgactac

 361 gattacgcca tggactactg gggccagggc acactggtta ccgtgtcctc tgcttccacc

 421 aagggaccct ctgtgttccc tctggctcct tgctccagat ccacctccga gtctacagct

 481 gctctgggct gcctggtcaa ggactacttt cctgagcctg tgaccgtgtc ttggaactct

 541 ggcgctctga catccggcgt gcacaccttt ccagctgtgc tgcaatccag cggcctgtac

 601 tctctgtcct ccgtcgtgac cgtgccttct agctctctgg gcaccaagac ctacacctgt

 661 aatgtggacc acaagccttc caacaccaag gggacaagc gcgtggaatc taagtacggc

 721 cctccttgtc ctccatgtcc tgctccagag tttctcggcg gaccttccgt gtttctgttc

 781 cctccaaagc ctaaggacac cctgatgatc tctcggaccc ctgaagtgac ctgcgtggtg

 841 gtggatgtgt cccaagagga cccagaggtg cagttcaatt ggtacgtgga cggcgtggaa

 901 gtgcacaacg ccaagaccaa gcctagagag gaacagttca actccaccta cagagtggtg

 961 tccgtgctga ccgtgctgca ccaggattgg ctgaacggaa aagagtacaa gtgcaaggtg

1021 tccaacaagg gcctgccttc cagcatcgaa aagaccatct ccaaggccaa gggccagcct

1081 agggaacccc aggtttacac cctgcctcca agccaagagg aaatgaccaa gaaccaggtg

1141 tccctgacct gcctcgtgaa gggcttctac ccttccgata tcgccgtgga atgggagagc

1201 aatggccagc ctgagaacaa ctacaagaca acccctcctg tgctggactc cgacggcagc

1231 ttcttcctgt attctcgcct gaccgtggac aagtccagat ggcaagaggg caacgtgttc

1321 tcctgctccg tgatgcacga ggccctgcac aatcactaca cccagaagtc cctgtctctg

1381 tccctgggca ag
```

SEQ ID NO: 141:
cDNA sequence coding for 'CDR2 deamidation-repaired' humanized IgG4 chain of anti-human-CD89 antibody 10E7 covering humanized VH3ST

```
   1 atgaaatggg tcacctttat ctccctgctg ttcctgttct ccagcgccta ctctgaggtg

  61 cagctgctgg aatctggcgg aggattggtt cagcctggcg gctctctgag actgtcttgt

 121 gctgcttctg gcctgacctt ctcctcctac ggcatgtcct gggtccgaca ggctcctgga

 181 aaaggcctgg aactggtggc taccatctct ggcaccggcg acatcaccta ctatcccgac

 241 tctgtgaagg gcagattcac catcagccgg gacaactcca agaacaccct gtacctgcag

 301 atgaactccc tgagagccga ggacaccgcc gtgtactact gcgccagaga ctacgactac

 361 gattacgcca tggactactg gggccagggc acactggtta ccgtgtcctc tgcttccacc

 421 aagggaccct ctgtgttccc tctggctcct tgctccagat ccacctccga gtctacagct

 481 gctctgggct gcctggtcaa ggactacttt cctgagcctg tgaccgtgtc ttggaactct

 541 ggcgctctga catccggcgt gcacaccttt ccagctgtgc tgcaatccag cggcctgtac
```

-continued

```
 601 tctctgtcct ccgtcgtgac cgtgccttct agctctctgg gcaccaagac ctacacctgt

 661 aatgtggacc acaagccttc caacaccaag gtggacaagc gcgtggaatc taagtacggc

 721 cctccttgtc ctccatgtcc tgctccagag tttctcggcg gaccttccgt gtttctgttc

 781 cctccaaagc ctaaggacac cctgatgatc tctcggaccc ctgaagtgac ctgcgtggtg

 841 gtggatgtgt cccaagagga cccagaggtg cagttcaatt ggtacgtgga cggcgtggaa

 901 gtgcacaacg ccaagaccaa gcctagagag gaacagttca actccaccta cagagtggtg

 961 tccgtgctga ccgtgctgca ccaggattgg ctgaacggaa aagagtacaa gtgcaaggtg

1021 tccaacaagg gcctgccttc cagcatcgaa aagaccatct ccaaggccaa gggccagcct

1081 agggaacccc aggtttacac cctgcctcca agccaagagg aaatgaccaa gaaccaggtg

1141 tccctgacct gcctcgtgaa gggcttctac ccttccgata tcgccgtgga atgggagagc

1201 aatggccagc ctgagaacaa ctacaagaca acccctcctg tgctggactc cgacggcagc

1261 ttcttcctgt attctcgcct gaccgtggac aagtccagat ggcaagaggg caacgtgttc

1321 tcctgctccg tgatgcacga ggccctgcac aatcactaca cccagaagtc cctgtctctg

1381 tccctgggca ag
```

SEQ ID NO: 142:
Amino acid sequence coding for 'CDR2 deamidation-repaired' humanized IgG4 chain of anti-human-CD89 antibody 10E7 covering humanized VH3SQ

1 MKWVTFISLL FLESSAYSEV QLLESGGGLV QPGGSLRLSC AASGLTESSY GMSWVRQAPG

61 KGLELVATIS GQGDITYYPD SVKGRFTISR DNSKNTLYLQ MNSLRAEDTA VYYCARDYDY

121 DYAMDYWGQG TLVTVSSAST KGPSVFPLAP CSRSTSESTA ALGCLVKDYF PEPVTVSWNS

181 GALTSGVHTF PAVLQSSGLY SLSSVVTVPS SSLGTKTYTC NVDHKPSNTK VDKRVESKYG

241 PPCPPCPAPE FLGGPSVFLF PPKPKDTLMI SRTPEVTCVV VDVSQEDPEV QFNWYVDGVE

301 VHNAKTKPRE EQFNSTYRVV SVLTVLHQDW LNGKEYKCKV SNKGLPSSIE KTISKAKGQP

361 REPQVYTLPP SQEEMTKNQV SLTCLVKGFY PSDIAVEWES NGQPENNYKT TPPVLDSDGS

421 FFLYSRLTVD KSRWQEGNVF SCSVMHEALH NHYTQKSLSL SLGK

SEQ ID NO: 143:
Amino acid sequence coding for 'CDR2 deamidation-repaired' humanized IgG4 chain of anti-human-CD89 antibody 10E7 covering humanized VH3ST

1 MKWVTFISLL FLESSAYSEV QLLESGGGLV QPGGSLRLSC AASGLTFSSY GMSWVRQAPG

61 KGLELVATIS GTGDITYYPD SVKGRFTISR DNSKNTLYLQ MNSLRAEDTA VYYCARDYDY

121 DYAMDYWGQG TLVTVSSAST KGPSVFPLAP CSRSTSESTA ALGCLVKDYF PEPVTVSWNS

181 GALTSGVHTF PAVLQSSGLY SLSSVVTVPS SSLGTKTYTC NVDHKPSNTK VDKRVESKYG

241 PPCPPCPAPE FLGGPSVFLF PPKPKDTLMI SRTPEVTCVV VDVSQEDPEV QFNWYVDGVE

301 VHNAKTKPRE EQFNSTYRVV SVLTVLHQDW LNGKEYKCKV SNKGLPSSIE KTISKAKGQP

361 REPQVYTLPP SQEEMTKNQV SLTCLVKGFY PSDIAVEWES NGQPENNYKT TPPVLDSDGS

421 FFLYSRLTVD KSRWQEGNVF SCSVMHEALH NHYTQKSLSL SLGK

---

The invention claimed is:

1. A humanized anti-human CD89 antibody that binds an extracellular part of human CD89, comprising a heavy chain variable region comprising an amino acid sequence:

(SEQ ID NO: 144)
EVQLLESGGG LVQPGGSLRL SCAASGLTFS SYGMSWVRQA

PGKGLE$X_1$V$X_2$T I$X_3$G$X_4$GDITYY PDSVKGRFTI SRDNSKNTLY

TAVYYCARDY LQMNSLRAED DYDYAMDYWG QGTLVTVSS, wherein:

$X_1$ is L or W $X_2$ is A or S $X_3$ is N or S $X_4$ is Q, T or N, wherein said heavy chain variable region comprises 0, 1 or 2 amino acid insertions, deletions or substitutions with respect to SEQ ID NO: 144, or a combination thereof at positions other than $X_1$, $X_2$, $X_3$ and $X_4$, wherein the 0, 1 or 2 amino acid insertions, deletions or substitutions, or the combination thereof, are not within a complementary determining region (CDR), wherein the amino acid sequence of CDR1 is SYGMS (SEQ ID NO: 45), wherein the amino acid sequence of CDR2 is TINGNGDITYYPDSVKG (SEQ ID NO: 46), TISGQGDITYYPDSVKG (SEQ ID NO: 147), or TISGTGDITYYPDSVKG (SEQ ID NO: 148), and wherein the amino acid sequence of CDR3 is DYDYDYAMDY (SEQ ID NO: 47), and a light chain variable region comprising an amino acid sequence:

(SEQ ID NO: 145)
DIQMTQSPSS LSASVGDRVT ITCRASQDII NYLNWYQQKP

GK$Z_1Z_2$KLLIYY TSRLHSGVPS RFSGSGSGTD $Z_3$TLTISSLQP

EDFATY$Z_4$CQQ GKTLPYTFGQ GTKLEIK, wherein:

$Z_1$ is A or T $Z_2$ is V or P $Z_3$ is Y or F $Z_4$ is Y or F, wherein said light chain variable region comprises 0, 1 or 2 amino acid insertions, deletions or substitutions with respect to SEQ ID NO: 145, or a combination thereof at positions other than $Z_1$, $Z_2$, $Z_3$ and $Z_4$, wherein the 0, 1 or 2 amino acid insertions, deletions or substitutions, or the combination thereof, are not within a CDR region, wherein the amino acid sequence of CDR1 is RASQDIINYLN (SEQ ID NO: 48), wherein the amino acid sequence of CDR2 is YTSRLHS (SEQ ID NO: 49), and wherein the amino acid sequence of CDR3 is QQGKTLPYT (SEQ ID NO: 50).

2. The humanized anti-human CD89 antibody of claim 1, wherein the heavy chain variable region comprises the amino acid sequence:

(SEQ ID NO: 149)
EVQLLESGGG LVQPGGSLRL SCAASGLTFS SYGMSWVRQA

PGKGLELVAT ISG$X_4$GDITYY PDSVKGRFTI SRDNSKNTLY

LQMNSLRAED TAVYYCARDY DYDYAMDYWG QGTLVTVSS, wherein $X_4$ is Q, T or N, and a light chain variable region comprising the amino acid sequence of SEQ ID NO: 122 comprising 0, 1 or 2 amino acid insertions, deletions or substitutions with respect to SEQ ID NO: 122, or a combination thereof, and wherein the 0, 1 or 2 amino acid insertions, deletions or substitutions, or the combination thereof are not within a CDR region.

3. The humanized anti-human CD89 antibody of claim 1, wherein the antibody is of an IgG1 or IgG4 isotype.

4. The humanized anti-human CD89 antibody of claim 1, wherein the antibody comprises a heavy chain with the amino acid sequence of SEQ ID NO: 142 or 143 with 0, 1 or 2 amino acid insertions, deletions or substitutions, or a combination thereof, wherein the 0, 1 or 2 amino acid insertions, deletions or substitutions, or the combination thereof, are not within a CDR region, and a light chain with the amino acid sequence of SEQ ID NO: 136 with 0, 1 or 2 amino acid insertions, deletions or substitutions, or the combination thereof, wherein the 0, 1 or 2 amino acid insertions, deletions or substitutions, or the combination thereof, are not within a CDR region.

5. The humanized anti-human CD89 antibody of claim 1, wherein said antibody has a higher affinity for said extracellular part of human CD89 compared to a chimeric antibody comprising a heavy chain with the amino acid sequence of SEQ ID NO: 94 and a light chain with the amino acid sequence of SEQ ID NO: 99.

6. The humanized anti-human CD89 antibody of claim 1, wherein said antibody binds an extracellular part of human CD89 on human CD89 expressing cells, and when the antibody is bound to said cells, the antibody can prevent binding of human IgA to human CD89.

7. The humanized anti-human CD89 antibody of claim 6, wherein said cells are human CD89 expressing HEK293F cells, deposited under number DSM ACC3341.

8. A pharmaceutical composition comprising the humanized anti-human CD89 antibody of claim 1 or an antigen-binding fragment thereof.

9. A method of inhibiting IgA serum level and/or IgA-mediated neutrophil infiltration in a subject comprising administering to the subject in need thereof a therapeutically effective amount of the humanized anti-human CD89 antibody according to claim 1 or an antigen-binding fragment thereof.

10. A pharmaceutical composition comprising a nucleic acid molecule that encodes a variable region of the humanized anti-human CD89 antibody according to claim 1.

11. The pharmaceutical composition of claim 10, wherein the nucleic acid molecule encodes the humanized anti-human CD89 antibody according to claim 1 or an antigen-binding fragment thereof.

12. A pharmaceutical composition comprising a vector comprising a nucleic acid molecule that encodes a variable region of the humanized anti-human CD89 antibody according to claim 1.

13. The pharmaceutical composition of claim 12, wherein the vector comprises a nucleic acid molecule that encodes the humanized anti-human CD89 antibody according to claim 1 or an antigen-binding fragment thereof.

14. The humanized anti-human CD89 antibody of claim 1, wherein the heavy chain variable region and/or the light chain variable region comprise one amino acid insertion, deletion, or substitution relative to SEQ ID NO: 144 and SEQ ID NO: 145, respectively, at a position other than $X_1$, $X_2$, $X_3$, $X_4$ and $Z_1$, $Z_2$, $Z_3$, and $Z_4$, and not within a complementary determining region (CDR).

15. A method for of inhibiting IgA serum level and/or IgA-mediated neutrophil infiltration in a subject comprising administering to the subject in need thereof a therapeutically effective amount of the humanized anti-human CD89 antibody according to claim 14 or an antigen-binding fragment thereof.

16. A pharmaceutical composition comprising a nucleic acid molecule that encodes a variable region of the humanized anti-human CD89 antibody according to claim 14.

17. The pharmaceutical composition of claim 16, wherein the nucleic acid molecule encodes the humanized anti-human CD89 antibody according to claim 14 or an antigen-binding fragment thereof.

18. A pharmaceutical composition comprising a vector comprising a nucleic acid molecule that encodes a variable region of the humanized anti-human CD89 antibody according to claim 14.

19. The pharmaceutical composition of claim 18, wherein the vector comprises a nucleic acid molecule that encodes the humanized anti-human CD89 antibody according to claim 14 or an antigen-binding fragment thereof.

20. The humanized anti-human CD89 antibody of claim 1, wherein the heavy chain variable region and the light chain variable region have the amino sequence depicted in SEQ ID NO: 144 and SEQ ID NO: 145, respectively.

21. A method for of inhibiting IgA serum level and/or IgA-mediated neutrophil infiltration in a subject comprising administering to the subject in need thereof a therapeutically effective amount of the humanized anti-human CD89 antibody according to claim 20 or an antigen-binding fragment thereof.

22. A pharmaceutical composition comprising a nucleic acid molecule that encodes a variable region of the humanized anti-human CD89 antibody according to claim 20 or an antigen binding fragment thereof.

23. A pharmaceutical composition comprising a vector comprising a nucleic acid molecule that encodes a variable region of the humanized anti-human CD89 antibody according to claim 20 or an antigen binding fragment thereof.

24. The method of claim 9, wherein the subject has skin disorder linear IgA bullous disease (LABD).

25. The method of claim 15, wherein the subject has skin disorder linear IgA bullous disease (LABD).

26. The method of claim 21, wherein the subject has skin disorder linear IgA bullous disease (LABD).

* * * * *